(12) United States Patent
Stadlwieser et al.

(10) Patent No.: US 8,445,501 B2
(45) Date of Patent: May 21, 2013

(54) SUBSTITUTED 7-CARBOXAMIDO-PYRROLO[3,2-D]PYRIMIDINES

(75) Inventors: Josef Stadlwieser, Constance (DE); Beate Schmidt, Allensbach (DE); Heiko Bernsmann, Frankfurt (DE); Alexander Sudau, Leichlingen (DE); Torsten Dunkern, Volkertshausen (DE); Degenhard Marx, Moos (DE); Jörg Diefenbach, Stockach-Winterspüren (DE)

(73) Assignee: Takeda GmbH, Constance (DE)

( * ) Notice: Subject to any disclaimer, the term of this patent is extended or adjusted under 35 U.S.C. 154(b) by 252 days.

(21) Appl. No.: 12/918,740

(22) PCT Filed: Feb. 25, 2009

(86) PCT No.: PCT/EP2009/052198
§ 371 (c)(1), (2), (4) Date: Aug. 20, 2010

(87) PCT Pub. No.: WO2009/106531
PCT Pub. Date: Sep. 3, 2009

(65) Prior Publication Data
US 2011/0021479 A1    Jan. 27, 2011

(30) Foreign Application Priority Data
Feb. 27, 2008 (EP) .................. 08102052

(51) Int. Cl.
C07D 487/04 (2006.01)
A61K 31/519 (2006.01)
A61P 9/08 (2006.01)
A61P 11/06 (2006.01)

(52) U.S. Cl.
USPC ...................... 514/265.1; 544/280

(58) Field of Classification Search . 544/280; 514/265.1
See application file for complete search history.

(56) References Cited

U.S. PATENT DOCUMENTS
5,877,190 A    3/1999 Dhainaut et al.
2005/0124623 A1    6/2005 Bender et al.

FOREIGN PATENT DOCUMENTS
WO    2006/095009 A1    9/2006

OTHER PUBLICATIONS

Esper et. al. (Expert. Opin. Investig. Drugs, 2005, 14(5), 633-645).*
MedicineNet.com (Cirrohosis, <http://www.medicinenet.com/cirrhosis/article.htm>, downloaded Aug. 26, 2012.*
Mayo Clinic (<http://www.mayoclinic.com/health/pulmonary-fibrosis/DS00927/DSECTION=treatments-and-drugs >downloaded Aug. 26, 2012.*

Bélanger, et al., "Facile preparations of 4-fluororesorcinol", Can. J. Chem., vol. 66, pp. 1479-1482, (1988).
Freedman, et al., "The Preparation of 3,4-Dihydro-1-benzoxepin-5(2H)-ones", J. Heterocyclic Chem., vol. 26, pp. 1547-1554, (1989).
Murata, et al., "Palladium-Catalyzed Borylation of Aryl Halides or Triflates with Dialkoxyborane: A Novel and Facile Synthetic Route to Arylboronates", J. Org. Chem., vol. 65, pp. 164-168, (2000).
Murata, et al., "Novel Palladium(0)-Catalyzed Coupling Reaction of Dialkoxyborane with Aryl Halides: Convenient Synthetic Route to Arylboronates", J. Org. Chem., vol. 62, No. 19, pp. 6458-6459, (1997).
Stadlwieser, "Notiz zur Herstellung von Chloromethylmethylether aus Methoxyessigsäure", Synthesis, p. 490, (1984).
Yamamoto, et al., "Synthesis of arylboronates via Cp*RuCl-catalyzed cycloaddition of alkynylboronates", Tetrahedron, vol. 62, pp. 4294-4305, (2006).
Kian Fan Chung, "Phosphodiesterase Inhibitors in Airways Disease", European Journal of Pharmacology, vol. 533, 2006, pp. 110-117.
Huzaifa Adamali, et al., "Medical Treatment of Pulmonary Arterial Hypertension", Seminars in Respiratory and Critical Care Medicine, vol. 30, No. 4, 2009, pp. 484-492.
Harold R. Collard, et al., "Sildenafil Improves Walk Distance in Idiopathic Pulmonary Fibrosis", Chest: Official Publication of the American College of Chest Physicians, vol. 131, No. 3, Mar. 2007, pp. 897-899.
S. Alp, et al., "Sildenafil Improves Hemodynamic Parameters in COPD—an Investigation of Six Patients", Pulmonary Pharmacology & Therapeutics, vol. 19, 2006, pp. 386-390.

* cited by examiner

*Primary Examiner* — Susanna Moore
(74) *Attorney, Agent, or Firm* — Nath, Goldberg & Meyer; Sheldon M. McGee

(57) ABSTRACT

The compounds of Formula (I),

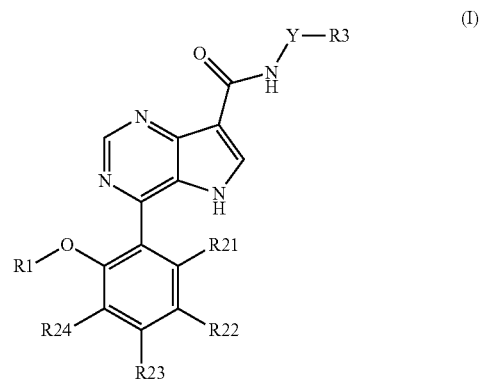

in which R1, R21, R22, R23, R24, Y and R3 have the meanings as given in the description, the salts thereof, the N-oxides of the compounds and the salts thereof and the stereoisomers of the compounds, the salts, the N-oxides of the compounds and the N-oxides of the salts thereof are effective inhibitors of the type 5 phosphodiesterase.

16 Claims, No Drawings

SUBSTITUTED 7-CARBOXAMIDO-PYRROLO [3,2-D]PYRIMIDINES

This application is filed under 35 U.S.C. 371 as the national stage of PCT/EP2009/052198, filed Feb. 25, 2009, which claims priority to EP 08102052.1, filed Feb. 27, 2008.

FIELD OF APPLICATION OF THE INVENTION

The invention relates to pyrrolopyrimidinecarboxamide compounds, processes for their preparation, pharmaceutical compositions comprising said compounds and the use thereof in the treatment or prophylaxis of diseases.

DESCRIPTION OF THE INVENTION

It has now been found that the pyrrolopyrimidinecarboxamide compounds, which are described in detail below, have surprising and advantageous properties.

The invention relates to compounds of formula (I)

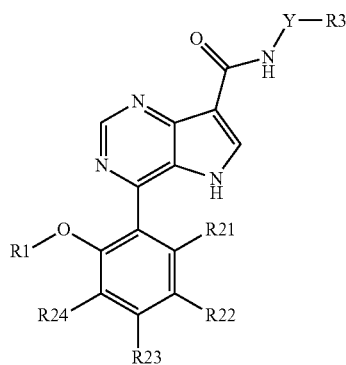

(I)

wherein
R1 is —$CH_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—$CH_2$—O—,
R23 is hydrogen, halogen, 1-4C-alkyl, 1-4C-alkoxy, hydroxy or 1-4C-fluoroalkoxy,
or R22 and R23 combine to form a group —O—$CH_2$—O—,
R24 is hydrogen,
Y is —$(CH_2)_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or $NH_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
salts thereof, an N-oxide of the compound or the salt thereof and a stereoisomer of the compound, the salt, the N-oxide of the compound or the N-oxide of the salt thereof.

1-4C-Alkyl is a straight-chain or branched alkyl group having 1 to 4 carbon atoms. Examples are methyl, ethyl, n-propyl, iso-propyl, n-butyl, iso-butyl, sec-butyl and tert-butyl.

Halogen includes fluorine, chlorine, bromine and iodine. In case of R22 and/or R23 being halogen, fluorine is preferred.

3-6C-Cycloalkyl is a cycloalkyl group having 3 to 6 carbon atoms, examples of which include the cyclopropyl, cyclobutyl, cyclopentyl and cyclohexyl group. In case of R3 being 3-6C-cycloalkyl, cyclohexyl is preferred.

1-4C-Alkoxy represents a group which, in addition to the oxygen atom, contains a straight-chain or branched alkyl moiety having 1 to 4 carbon atoms. Examples are methoxy, ethoxy, n-propoxy, iso-propoxy, n-butoxy, iso-butoxy, sec-butoxy and tert-butoxy.

1-4C-Fluoroalkoxy represents a group which, in addition to the oxygen atom, contains a straight-chain or branched alkyl moiety having 1 to 4 carbon atoms, wherein one or more of the hydrogen atoms of the alkyl moiety are replaced by fluorine. Examples include, but are not limited to, a trifluoromethoxy, difluoromethoxy, fluoromethoxy, perfluoroethoxy, 1,1,1-trifluoro-2-fluoroethoxy, 1,1,1-trifluoroethoxy, 1,1-difluoro-2,2-difluoroethoxy, 1,1-difluoro-2-fluoroethoxy, 1,1-difluoroethoxy, 1-fluoro-2,2-difluoroethoxy, 1-fluoro-2-fluoroethoxy, 1-fluoroethoxy, 2,2-difluoroethoxy, 2-fluoroethoxy, n-perfluoropropoxy, and n-perfluorobutoxy group.

The group —C(O)-1-4C-alkyl represents a group which, in addition to the carbonyl group —C(O)—, contains a straight-chain or branched alkyl moiety having 1 to 4 carbon atoms. Examples are methylcarbonyl, ethylcarbonyl, n-propylcarbonyl, iso-propylcarbonyl, n-butylcarbonyl, iso-butylcarbonyl, sec-butylcarbonyl and tert-butylcarbonyl.

The group —C(O)-3-6C-cycloalkyl represents a group which, in addition to the carbonyl group —C(O)—, contains a cycloalkyl group having 3 to 6 carbon atoms. Examples are cyclopropylcarbonyl, cyclobutylcarbonyl, cyclopentylcarbonyl and cyclohexylcarbonyl.

The group —C(O)—O-1-4C-alkyl represents a group which, in addition to the oxycarbonyl group —C(O)—O—, contains a straight-chain or branched alkyl moiety having 1 to 4 carbon atoms. Examples are methyloxycarbonyl, ethyloxycarbonyl, n-propyloxycarbonyl, iso-propyloxycarbonyl, n-butyloxycarbonyl, iso-butyloxycarbonyl, sec-butyloxycarbonyl and tert-butyloxycarbonyl.

The 4- to 7-membered saturated heterocyclic ring containing one nitrogen atom and optionally one oxygen atom includes, but is not limited to, azetidinyl, oxazetidinyl, pyrrolidinyl, oxazolidinyl, piperidinyl, morpholinyl, azepanyl and oxazepanyl, in particular azetidinyl, 1,3-oxazetidinyl, pyrrolidinyl, 1,3-oxazolidinyl, piperidinyl, morpholinyl, azepanyl and 1,3-oxazepanyl, preferably azetidin-3-yl, pyrrolidin-3-yl, morpholin-2-yl, piperidin-3-yl and piperidin-4-yl.

In a preferred embodiment, the invention relates to compounds of formula (I), wherein
R1 is —CH$_2$-3-4C-cycloalkyl or 2-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 6-membered saturated heterocyclic ring containing one nitrogen atom and optionally one oxygen atom, said heterocyclic ring being optionally substituted by R4,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-4C-cycloalkyl,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is 3-4C-alkyl which is optionally substituted by R11,
R11 is methoxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6, R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43, R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 6-membered saturated heterocyclic ring containing one nitrogen atom, said heterocyclic ring being optionally substituted by R4,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-4C-cycloalkyl or 2-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 3-6C-cycloalkyl group substituted by R6,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-4C-cycloalkyl or 2-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a cyclohexyl group substituted by R6,
R6 is —NH—C(O)—R7, —C(O)—NR8R9 or NH$_2$, R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 6-membered saturated heterocyclic ring containing one nitrogen atom and one oxygen atom, said heterocyclic ring being optionally substituted by R4,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-4C-cycloalkyl or 2-4C-alkyl which is optionally substituted by R11,
R11 is 1-4C-alkoxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 6-membered saturated heterocyclic ring containing one nitrogen atom and one oxygen atom, said heterocyclic ring being substituted by R4,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 5- to 6-membered saturated heterocyclic ring containing one nitrogen atom, said heterocyclic ring being substituted by R4,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 5-membered saturated heterocyclic ring containing one nitrogen atom, said heterocyclic ring being substituted by R4,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy, a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 6-membered saturated heterocyclic ring containing one nitrogen atom, said heterocyclic ring being substituted by R4,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein R1 is —CH$_2$-3-6C-cycloalkyl or 1-4C-alkyl which is optionally substituted by R11,
R11 is 1-4C-alkoxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 6-membered saturated heterocyclic ring containing one nitrogen atom and one oxygen atom, said heterocyclic ring being substituted by R4,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy or —C(O)-1-4C-alkyl,
or R21 and R22 combine to form a group —O—CH$_2$—O—,
R23 is hydrogen, halogen, 1-4C-alkyl, 1-4C-alkoxy or hydroxy,
or R22 and R23 combine to form a group —O—CH$_2$—O—,
R24 is hydrogen,
Y is —(CH$_2$)$_n$—,
n is 0 or 1,
R3 is a 3-6C-cycloalkyl group substituted by R6,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy or —C(O)-1-4C-alkyl,
or R21 and R22 combine to form a group —O—CH$_2$—O—,
R23 is hydrogen, halogen, 1-4C-alkyl, 1-4C-alkoxy or hydroxy,
or R22 and R23 combine to form a group —O—CH$_2$—O—,
R24 is hydrogen,
Y is —(CH$_2$)$_n$—,
n is 0 or 1,
R3 is a cyclohexyl group substituted by R6,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl, or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 and R22 combine to form a group —O—CH$_2$—O—,
R23 is hydrogen, halogen, 1-4C-alkyl, 1-4C-alkoxy, hydroxy or 1-4C-fluoroalkoxy,
R24 is hydrogen, Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21, R22, R23 and R24 are each hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is 1-4C-alkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydroxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy, R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is halogen,
R23 is 1-4C-alkoxy,
R24 is hydrogen,
Y is —(CH$_2$)$_n$—,
n is 0 or 1, R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is —C(O)-1-4C-alkyl,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy, a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is halogen,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is 1-4C-alkoxy,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydroxy,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is 1-4C-fluoroalkoxy,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—, n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is 1-4C-alkoxy,
R23 is halogen,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is 1-4C-alkyl,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 and R22 combine to form a group —O—CH$_2$—O—,
R23 is hydrogen,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$, R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is halogen,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 and R24 are hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is fluorine,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy, a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is methoxy,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is methyl,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is methylcarbonyl,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is fluorine,
R24 is hydrogen, Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is methoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is methoxy,
R23 is fluorine,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is fluorine,
R23 is methoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy, R6 is —NH—C(O)—R7, —C(O)—NR8R9 or $NH_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —$CH_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—$CH_2$—O—,
R23 is hydrogen, halogen, 1-4C-alkyl, 1-4C-alkoxy, hydroxy or 1-4C-fluoroalkoxy,
or R22 and R23 combine to form a group —O—$CH_2$—O—,
R24 is hydrogen,
Y is —$(CH_2)_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H,
R6 is —NH—C(O)—R7, —C(O)—NR8R9 or $NH_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —$CH_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—$CH_2$—O—,
R23 is hydrogen, halogen, 1-4C-alkyl, 1-4C-alkoxy, hydroxy or 1-4C-fluoroalkoxy,
or R22 and R23 combine to form a group —O—$CH_2$—O—,
R24 is hydrogen,
Y is —$(CH_2)_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)-1-4C-alkyl, wherein the 1-4C-alkyl group is optionally substituted by R41,
R41 is 1-4C-alkoxy or hydroxy,
R6 is —NH—C(O)—R7, —C(O)—NR8R9 or $NH_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —$CH_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—$CH_2$—O—,
R23 is hydrogen, halogen, 1-4C-alkyl, 1-4C-alkoxy, hydroxy or 1-4C-fluoroalkoxy,
or R22 and R23 combine to form a group —O—$CH_2$—O—,
R24 is hydrogen,
Y is —$(CH_2)_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)-3-6C-cycloalkyl, wherein the 3-6C-cycloalkyl group is optionally substituted by R42,
R42 is 1-4C-alkoxy or hydroxy,
R6 is —NH—C(O)—R7, —C(O)—NR8R9 or $NH_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —$CH_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—$CH_2$—O—, R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—O-1-4C-alkyl, wherein the 1-4C-alkyl group is optionally substituted by R43,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—O-1-4C-alkyl,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)-1-4C-alkyl, wherein the 1-4C-alkyl group is optionally substituted by R41,
R41 is 1-4C-alkoxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)-2-4C-alkyl, wherein the 2-4C-alkyl group is optionally substituted by R41,
R41 is methoxy,
R6 is —NH—C(O)—R7, —C(O)—NR8R9 or
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy, a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)-2-4C-alkyl, wherein the 2-4C-alkyl group is optionally substituted by R41,
R41 is hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)-cyclopropyl, wherein the cyclopropyl group is optionally substituted by R42,
R42 is 1-4C-alkoxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)-cyclopropyl, wherein the cyclopropyl group is optionally substituted by R42,
R42 is methoxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6, R4 is —C(O)-cyclopropyl, wherein the cyclopropyl group is optionally substituted by R42,
R42 is hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, to the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 —C(O)—O-1-4C-alkyl, which is optionally substituted by R43,
R43 is 1-2C-alkoxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 —C(O)—O-1-4C-alkyl, which is optionally substituted by R43,
R43 is methoxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 —C(O)—O-1-4C-alkyl, which is optionally substituted by R43,
R43 is hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy, R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —C(O)—NR8R9,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7,
R7 is 1-2C-alkyl, which is optionally substituted by R71,
R71 is 1-2C-alkoxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy, R42 is 1-4C-alkoxy or hydroxy,
R43 is 1-4C-alkoxy or hydroxy,
R6 is —NH—C(O)—R7,
R7 is 1-2C-alkyl, which is optionally substituted by R71,
R71 is hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7,
R7 is cyclopropyl, which is optionally substituted by R72,
R72 is hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7,
R7 is cyclopropyl, which is optionally substituted by R72,
R72 is hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7,
R7 is 1-2C-alkoxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—, R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-2C-alkyl, wherein the 1-2C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is 1-4C-alkyl, which is optionally substituted by R71, 3-6C-cycloalkyl, which is optionally substituted by R72, or 1-2C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, or —C(O)-3-6C-cycloalkyl, wherein the 3-6C-cycloalkyl group is optionally substituted by
R42,
R41 is 1-4C-alkoxy or hydroxy,
R42 is 1-4C-alkoxy or hydroxy,
R6 is —NH—C(O)—R7, —C(O)—NR8R9 or NH$_2$,
R7 is 1-4C-alkyl, which is optionally substituted by R71, or 3-6C-cycloalkyl, which is optionally substituted by R72,
R71 is 1-4C-alkoxy or hydroxy,
R72 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
salts thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7 or —C(O)—NR8R9,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
salts thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6, R4 is —C(O)—H, —C(O)-1-4C-alkyl, wherein the 1-4C-alkyl group is optionally substituted by R41, or —C(O)-3-6C-cycloalkyl, wherein the 3-6C-cycloalkyl group is optionally substituted by R42,
R41 is 1-4C-alkoxy or hydroxy,
R42 is 1-4C-alkoxy or hydroxy,
R6 is —NH—C(O)—R7 or —C(O)—NR8R9,
R7 is 1-4C-alkyl, which is optionally substituted by R71, or 3-6C-cycloalkyl, which is optionally substituted by R72,
R71 is 1-4C-alkoxy or hydroxy,
R72 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
salts thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —C(O)—NR8R9,
R8 is hydrogen,
R9 is 1-2C-alkyl, which is optionally substituted by R91,
R91 is 1-2C-alkoxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —C(O)—NR8R9,
R8 is hydrogen,
R9 is 1-2C-alkyl, which is optionally substituted by R91,
R91 is hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —C(O)—NR8R9,
R8 is hydrogen,
R9 is cyclopropyl,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy, or R22 and R23 combine to form a group —O—CH₂—O—,
R24 is hydrogen,
Y is —(CH₂)ₙ—,
n is 0 or 1,
R3 is a 4- to 6-membered saturated heterocyclic ring containing one nitrogen atom and optionally one oxygen atom, said heterocyclic ring being optionally substituted by R4, wherein R4, if present, is bonded to said nitrogen atom,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH₂-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH₂—O—,
R23 is hydrogen, halogen, 1-4C-alkyl, 1-4C-alkoxy, hydroxy or 1-4C-fluoroalkoxy,
or R22 and R23 combine to form a group —O—CH₂—O—,
R24 is hydrogen,
Y is —(CH₂)ₙ—,
n is 0 or 1,
R3 is a 4- to 6-membered saturated heterocyclic ring containing one nitrogen atom and optionally one oxygen atom, said heterocyclic ring being substituted by R4 at said nitrogen atom,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH₂-3-4C-cycloalkyl or 2-4C-alkyl which is optionally substituted by R11,
R11 is 1-4C-alkoxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH₂—O—,
R23 is hydrogen, halogen, 1-4C-alkyl, 1-4C-alkoxy, hydroxy or 1-4C-fluoroalkoxy,
or R22 and R23 combine to form a group —O—CH₂—O—,
R24 is hydrogen,
Y is —(CH₂)ₙ—,
n is 0 or 1, R3 is a 4- to 6-membered saturated heterocyclic ring containing one nitrogen atom and optionally one oxygen atom, said heterocyclic ring being substituted by R4 at said nitrogen atom,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
salts thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH₂-3-4C-cycloalkyl,
R21 is hydrogen,
R22 is hydrogen,
R23 is hydrogen,
R24 is hydrogen,
Y is —(CH₂)ₙ—,
n is 0,
R3 is a 6-membered saturated heterocyclic ring containing one nitrogen atom, said heterocyclic ring being optionally substituted by R4, or a cyclohexyl group substituted by R6,
R4 is —C(O)-1-2C-alkyl, wherein the 1-2C-alkyl group is optionally substituted by R41, —C(O)-cyclopropyl or —C(O)—O-1-4C-alkyl,
R41 is hydroxy,
R6 is —NH—C(O)—R7 or NH₂,
R7 is 1-2C-alkyl, which is optionally substituted by R71, cyclopropyl, which is optionally substituted by R72, or 1-2C-alkoxy, which is optionally substituted by R73,
R71 is 1-2C-alkoxy or hydroxy,
R72 is hydroxy,
R73 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH₂-3-4C-cycloalkyl,
R21 is hydrogen,
R22 is hydrogen,
R23 is 1-4C-alkoxy,
R24 is hydrogen,
Y is —(CH₂)ₙ—,
n is 0,
R3 is a 6-membered saturated heterocyclic ring containing one nitrogen atom, said heterocyclic ring being optionally substituted by R4, or a cyclohexyl group substituted by R6,
R4 is —C(O)-1-2C-alkyl, wherein the 1-2C-alkyl group is optionally substituted by R41, —C(O)-cyclopropyl, wherein cyclopropyl group is optionally substituted by R42, —C(O)—O-1-4C-alkyl,
R41 is 1-2C-alkoxy or hydroxy,
R42 is hydroxy,
R6 is —NH—C(O)—R7, —C(O)—NR8R9 or NH₂,
R7 is 1-2C-alkyl, which is optionally substituted by R71, cyclopropyl, which is optionally substituted by R72, or 1-4C-alkoxy,
R71 is 1-2C-alkoxy or hydroxy,
R72 is hydroxy,
R8 is hydrogen, R9 is 1-2C-alkyl, which is optionally substituted by R91, or cyclopropyl,
R91 is 1-2C-alkoxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-4C-cycloalkyl,
R21 is hydrogen,
R22 is halogen,
R23 is 1-4C-alkoxy,
R24 is hydrogen,
Y is —(CH$_2$)$_n$—,
n is 0,
R3 is a 5- to 6-membered saturated heterocyclic ring containing one nitrogen atom, said heterocyclic ring being optionally substituted by R4, or a cyclohexyl group substituted by R6,
R4 is —C(O)-1-2C-alkyl, wherein the 1-2C-alkyl group is optionally substituted by R41, —C(O)-cyclopropyl, wherein the cyclopropyl group is optionally substituted by R42, or —C(O)—O-1-4C-alkyl,
R41 is 1-2C-alkoxy or hydroxy,
R42 is hydroxy,
R6 is —NH—C(O)—R7 or NH$_2$,
R7 is 1-2C-alkyl, which is optionally substituted by R71, cyclopropyl, which is optionally substituted by R72, or 1-4C-alkoxy,
R71 is 1-2C-alkoxy or hydroxy,
R72 is hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-4C-cycloalkyl,
R21 is hydrogen,
R22 is —C(O)-1-4C-alkyl,
R23 is hydrogen,
R24 is hydrogen,
Y is —(CH$_2$)$_n$—,
n is 0,
R3 is a 6-membered saturated heterocyclic ring containing one nitrogen atom, said heterocyclic ring being optionally substituted by R4,
R4 is —C(O)-1-2C-alkyl, wherein the 1-2C-alkyl group is optionally substituted by R41,
R41 is 1-2C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-4C-cycloalkyl,
R21 is hydrogen,
R22 is halogen,
R23 is hydrogen,
R24 is hydrogen,
Y is —(CH$_2$)$_n$—,
n is 0,
R3 is a 6-membered saturated heterocyclic ring containing one nitrogen atom, said heterocyclic ring being optionally substituted by R4, or a cyclohexyl group substituted by R6,
R4 is —C(O)-1-2C-alkyl, wherein the 1-2C-alkyl group is optionally substituted by R41, or —C(O)—O-1-4C-alkyl,
R41 is 1-2C-alkoxy or hydroxy,
R6 is —NH—C(O)—R7, —C(O)—NR8R9 or NH$_2$,
R7 is 1-2C-alkyl, which is optionally substituted by R71, or 1-4C-alkoxy,
R71 is 1-2C-alkoxy or hydroxy,
R8 is hydrogen,
R9 is 1-2C-alkyl, which is optionally substituted by R91, or cyclopropyl,
R91 is 1-2C-alkoxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-4C-cycloalkyl,
R21 is hydrogen,
R22 is 1-4C-alkoxy,
R23 is hydrogen,
R24 is hydrogen,
Y is —(CH$_2$)$_n$—,
n is 0,
R3 is a 6-membered saturated heterocyclic ring containing one nitrogen atom, said heterocyclic ring being optionally substituted by R4, or a cyclohexyl group substituted by R6,
R4 is —C(O)-1-2C-alkyl, wherein the 1-2C-alkyl group is optionally substituted by R41, —C(O)-cyclopropyl, wherein the cyclopropyl group is optionally substituted by R42, or —C(O)—O-1-4C-alkyl,
R41 is 1-2C-alkoxy or hydroxy,
R42 is hydroxy,
R6 is —NH—C(O)—R7 or NH$_2$,
R7 is 1-2C-alkyl, which is optionally substituted by R71, cyclopropyl, which is optionally substituted by R72, or 1-4C-alkoxy,
R71 is 1-2C-alkoxy or hydroxy,
R72 is hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-4C-cycloalkyl,
R21 is hydrogen,
R22 is 1-4C-fluoroalkoxy,
R23 is hydrogen,
R24 is hydrogen,
Y is —(CH$_2$)$_n$—,
n is 0,
R3 is a 6-membered saturated heterocyclic ring containing one nitrogen atom, said heterocyclic ring being optionally substituted by R4, or a cyclohexyl group substituted by R6,
R4 is —C(O)-1-2C-alkyl, wherein the 1-2C-alkyl group is optionally substituted by R41, —C(O)— cyclopropyl, wherein the cyclopropyl group is optionally substituted by R42, or —C(O)—O-1-4C-alkyl,
R41 is 1-2C-alkoxy or hydroxy,
R42 is hydroxy,
R6 is —NH—C(O)—R7 or NH$_2$,
R7 is 1-2C-alkyl, which is optionally substituted by R71, cyclopropyl, which is optionally substituted by R72, or 1-4C-alkoxy,
R71 is 1-2C-alkoxy or hydroxy,
R72 is hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein R1 is —CH$_2$-3-4C-cycloalkyl,
R21 is hydrogen,
R22 is 1-4C-alkoxy,
R23 is halogen,
R24 is hydrogen,
Y is —(CH$_2$)$_n$—,
n is 0,
R3 is a 5- to 6-membered saturated heterocyclic ring containing one nitrogen atom, said heterocyclic ring being optionally substituted by R4,
R4 is —C(O)-1-2C-alkyl, wherein the 1-2C-alkyl group is optionally substituted by R41, or —C(O)—O-1-4C-alkyl,
R41 is 1-2C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-4C-cycloalkyl,
R21 is hydrogen,
R22 is 1-4C-alkyl,
R23 is hydrogen,
R24 is hydrogen,
Y is —(CH$_2$)$_n$—,
n is 0,
R3 is a 6-membered saturated heterocyclic ring containing one nitrogen atom, said heterocyclic ring being optionally substituted by R4, or a cyclohexyl group substituted by R6,
R4 is —C(O)-1-2C-alkyl, wherein the 1-2C-alkyl group is optionally substituted by R41, —C(O)-cyclopropyl, wherein the cyclopropyl group is optionally substituted by R42, or —C(O)—O-1-4C-alkyl,
R41 is 1-2C-alkoxy or hydroxy,
R42 is hydroxy,
R6 is —NH—C(O)—R7, or NH$_2$,
R7 is 1-2C-alkyl, which is optionally substituted by R71, 3-6C-cycloalkyl, which is optionally substituted by R72, or 1-4C-alkoxy,
R71 is 1-2C-alkoxy or hydroxy,
R72 is hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-4C-cycloalkyl,
R21 and R22 combine to form a group —O—CH$_2$—O—,
R23 is hydrogen,
R24 is hydrogen,
Y is —(CH$_2$)$_n$—,
n is 0 or 1,
R3 is a 4- to 6-membered saturated heterocyclic ring containing one nitrogen atom and optionally one oxygen atom, said heterocyclic ring being optionally substituted by R4, or a cyclohexyl group substituted by R6,
R4 is —C(O)—H, —C(O)-1-2C-alkyl, wherein the 1-2C-alkyl group is optionally substituted by R41, —C(O)-cyclohexyl, wherein the cyclohexyl group is optionally substituted by R42, or —C(O)—O-1-4C-alkyl,
R41 is 1-2C-alkoxy or hydroxy,
R42 is hydroxy,
R6 is —NH—C(O)—R7, —C(O)—NR8R9 or NH$_2$,
R7 is 1-2C-alkyl, which is optionally substituted by R71, cyclopropyl, which is optionally substituted by R72, or 1-4C-alkoxy,
R71 is 1-2C-alkoxy or hydroxy,
R72 is hydroxy,
R8 is hydrogen,
R9 is 1-2C-alkyl, which is optionally substituted by R91, or cyclopropyl,
R91 is 1-2C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-4C-cycloalkyl,
R21 and R22 combine to form a group —O—CH$_2$—O—,
R23 is hydrogen,
R24 is hydrogen,
Y is —(CH$_2$)$_n$—,
n is 0,
R3 is a 4- to 6-membered saturated heterocyclic ring containing one nitrogen atom and optionally one oxygen atom, said heterocyclic ring being optionally substituted by R4, or a cyclohexyl group substituted by R6,
R4 is —C(O)—H, —C(O)-1-2C-alkyl, wherein the 1-2C-alkyl group is optionally substituted by R41, —C(O)-cyclopropyl, wherein the cyclopropyl group is optionally substituted by R42, or —C(O)—-1-4C-alkyl,
R41 is 1-2C-alkoxy or hydroxy,
R42 is hydroxy,
R6 is —NH—C(O)—R7, —C(O)—NR8R9 or NH$_2$,
R7 is 1-2C-alkyl, which is optionally substituted by R71, cyclopropyl, which is optionally substituted by R72, or 1-4C-alkoxy,
R71 is 1-2C-alkoxy or hydroxy,
R72 is hydroxy,
R8 is hydrogen,
R9 is 1-2C-alkyl, which is optionally substituted by R91, or cyclopropyl,
R91 is 1-2C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-4C-cycloalkyl,
R21 and R22 combine to form a group —O—CH$_2$—O—,
R23 is hydrogen,
R24 is hydrogen,
Y is —(CH$_2$)$_n$—,
n is 1,
R3 is a 5- to 6-membered saturated heterocyclic ring containing one nitrogen atom and optionally one oxygen atom, said heterocyclic ring being optionally substituted by R4,
R4 is —C(O)—H, —C(O)-1-2C-alkyl, wherein the 1-2C-alkyl group is optionally substituted by R41, —C(O)-cyclopropyl, wherein the cyclopropyl group is optionally substituted by R42, or —C(O)—-1-4C-alkyl,
R41 is 1-2C-alkoxy or hydroxy,
R42 is hydroxy,
a salt thereof, an N-oxide of the compound or the salt thereof and a stereoisomer of the compound, the salt, the N-oxide of the compound or the N-oxide of the salt thereof.
R1 is —CH$_2$-3-4C-cycloalkyl,
R21 is hydrogen,
R22 is halogen,
R23 is 1-4C-alkoxy,
R24 is hydrogen,
Y is —(CH$_2$)$_n$—,
n is 0 or 1, R3 is a 5- to 6-membered saturated heterocyclic ring containing one nitrogen atom, said heterocyclic ring being substituted by R4,
R4 is —C(O)-1-4C-alkyl, wherein the 1-4C-alkyl group is optionally substituted by R41,
R41 is 1-4C-alkoxy or hydroxy,
salts thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-4C-cycloalkyl,
R21 is hydrogen,
R22 is hydrogen,
R23 is halogen,
R24 is hydrogen,
Y is —(CH$_2$)$_n$—,
n is 0,
R3 is a 6-membered saturated heterocyclic ring containing one nitrogen atom, said heterocyclic ring being optionally substituted by R4, or a cyclohexyl group substituted by R6,
R4 is —C(O)-1-2C-alkyl, wherein the 1-2C-alkyl group is optionally substituted by R41, or —C(O)—O-1-4C-alkyl,
R41 is 1-2C-alkoxy or hydroxy,
R6 is —NH—C(O)—R7 or NH$_2$,
R7 is 1-2C-alkyl, which is optionally substituted by R71, cyclopropyl, which is optionally substituted by R72, or 1-4C-alkoxy,
R71 is 1-2C-alkoxy or hydroxy,
R72 is hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—
R24 is hydrogen,
Y is —(CH$_2$)$_n$—,
n is 0 or 1,
R3 is a 6-membered saturated heterocyclic ring containing one nitrogen atom, said heterocyclic ring being optionally substituted by R4,
R4 is —C(O)-1-4C-alkyl, wherein the 1-4C-alkyl group is optionally substituted by R41,
R41 is 1-2C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—

R24 is hydrogen,
Y is —(CH$_2$)$_n$—,
n is 0,
R3 is a 6-membered saturated heterocyclic ring containing one nitrogen atom, said heterocyclic ring being optionally substituted by R4,
R4 is —C(O)-1-2C-alkyl, wherein the 1-2C-alkyl group is optionally substituted by R41,
R41 is 1-2C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 3-4C-alkyl,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—
R24 is hydrogen,
Y is —(CH$_2$)$_n$—,
n is 0 or 1, R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 3-4C-alkyl,
R21 and R22 combine to form a group —O—CH$_2$—O—,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 3-4C-alkyl,
R21 and R22 combine to form a group —O—CH$_2$—O—,
R23 is hydrogen,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, an N-oxide of the compound or the salt thereof and a stereoisomer of the compound, the salt, the N-oxide of the compound or the N-oxide of the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73, R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
salts thereof, and stereoisomers of the compounds and the salts thereof.

In a preferred embodiment, the invention relates to compounds of formula (I), wherein
R1 is —CH$_2$-3-4C-cycloalkyl or 2-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 6-membered saturated heterocyclic ring containing one nitrogen atom and optionally one oxygen atom, said heterocyclic ring being optionally substituted by R4,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-4C-cycloalkyl,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or the salt thereof.

In a further preferred embodiment, the invention relates to compounds of formula (I), wherein
R1 is 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or the salt thereof.

In a further preferred embodiment, the invention relates to compounds of formula (I), wherein
R1 is 3-4C-alkyl which is optionally substituted by R11,
R11 is methoxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—, R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy 40 or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 6-membered saturated heterocyclic ring containing one nitrogen atom, said heterocyclic ring being optionally substituted by R4,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-4C-cycloalkyl or 2-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 6-membered saturated heterocyclic ring containing one nitrogen atom, said heterocyclic ring being substituted by R4,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-4C-cycloalkyl or 2-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 3-6C-cycloalkyl group substituted by R6,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-4C-cycloalkyl or 2-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a cyclohexyl group substituted by R6, R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 6-membered saturated heterocyclic ring containing one nitrogen atom and one oxygen atom, said heterocyclic ring being optionally substituted by R4,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-4C-cycloalkyl or 2-4C-alkyl which is optionally substituted by R11,
R11 is 1-4C-alkoxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 6-membered saturated heterocyclic ring containing one nitrogen atom and one oxygen atom, said heterocyclic ring being substituted by R4,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 5- to 6-membered saturated heterocyclic ring containing one nitrogen atom, said heterocyclic ring being substituted by R4,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 5-membered saturated heterocyclic ring containing one nitrogen atom, said heterocyclic ring being substituted by R4,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 6-membered saturated heterocyclic ring containing one nitrogen atom, said heterocyclic ring being substituted by R4,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 6-membered saturated heterocyclic ring containing one nitrogen atom and one oxygen atom, said heterocyclic ring being substituted by R4,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy or —C(O)-1-4C-alkyl,
or R21 and R22 combine to form a group —O—CH$_2$—O—,
R23 is hydrogen, halogen, 1-4C-alkyl, 1-4C-alkoxy or hydroxy,
or R22 and R23 combine to form a group —O—CH$_2$—O—,
R24 is hydrogen,
Y is —(CH$_2$)$_n$—,
n is 0 or 1,
R3 is a 3-6C-cycloalkyl group substituted by R6,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy or —C(O)-1-4C-alkyl,
or R21 and R22 combine to form a group —O—CH$_2$—O—,
R23 is hydrogen, halogen, 1-4C-alkyl, 1-4C-alkoxy or hydroxy,
or R22 and R23 combine to form a group —O—CH$_2$—O—,
R24 is hydrogen,
Y is —(CH$_2$)$_n$—,
n is 0 or 1,
R3 is a cyclohexyl group substituted by R6,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0, R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 and R22 combine to form a group —O—CH$_2$—O—,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43, R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21, R22, R23 and R24 are each hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is 1-4C-alkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydroxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein R1 is —CH$_2$-3-6C-cycloalkyl or 1-4C-alkyl which is optionally substituted by R11,
R11 is 1-4C-alkoxy or hydroxy,
R21 is hydrogen,
R22 is halogen,
R23 is 1-4C-alkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein R1 is —CH$_2$-3-6C-cycloalkyl or 1-4C-alkyl which is optionally substituted by R11,
R11 is 1-4C-alkoxy or hydroxy,
R21 is hydrogen,
R22 is —C(O)-1-4C-alkyl,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein R1 is —CH$_2$-3-6C-cycloalkyl or 1-4C-alkyl which is optionally substituted by R11,
R11 is 1-4C-alkoxy or hydroxy,
R21 is hydrogen,
R22 is halogen,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6, R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43, R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein R1 is —CH$_2$-3-6C-cycloalkyl or 1-4C-alkyl which is optionally substituted by R11,
R11 is 1-4C-alkoxy or hydroxy,
R21 is hydrogen,
R22 is 1-4C-alkoxy,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein R1 is —CH$_2$-3-6C-cycloalkyl or 1-4C-alkyl which is optionally substituted by R11,
R11 is 1-4C-alkoxy or hydroxy,
R21 is hydrogen,
R22 is hydroxy,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein R1 is —CH$_2$-3-6C-cycloalkyl or 1-4C-alkyl which is optionally substituted by R11,
R11 is 1-4C-alkoxy or hydroxy,
R21 is hydrogen,
R22 is 1-4C-fluoroalkoxy,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73, R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is 1-4C-alkoxy,
R23 is halogen,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is 1-4C-alkyl,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 and R22 combine to form a group —O—CH$_2$—O—,
R23 is hydrogen,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—, R23 is halogen,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 and R24 are hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is fluorine,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is methoxy,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy, R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is methyl,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is methylcarbonyl,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is fluorine,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is methoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is methoxy,
R23 is fluorine,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is fluorine,
R23 is methoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)-1-4C-alkyl, wherein the 1-4C-alkyl group is optionally substituted by R41,
R41 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)-3-6C-cycloalkyl, wherein the 3-6C-cycloalkyl group is optionally substituted by R42,
R42 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—O-1-4C-alkyl, wherein the 1-4C-alkyl group is optionally substituted by R43,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy, or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—O-1-4C-alkyl,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)-1-4C-alkyl, wherein the 1-4C-alkyl group is optionally substituted by R41,
R41 is 1-4C-alkoxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl, or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)-2-4C-alkyl, wherein the 2-4C-alkyl group is optionally substituted by R41,
R41 is methoxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)-2-4C-alkyl, wherein the 2-4C-alkyl group is optionally substituted by R41,
R41 is hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)-cyclopropyl, wherein the cyclopropyl group is optionally substituted by R42,
R42 is 1-4C-alkoxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)-cyclopropyl, wherein the cyclopropyl group is optionally substituted by R42,
R42 is methoxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)-cyclopropyl, wherein the cyclopropyl group is optionally substituted by R42,
R42 is hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 —C(O)—O-1-4C-alkyl, which is optionally substituted by R43,
R43 is 1-2C-alkoxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy, R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 —C(O)—O-1-4C-alkyl, which is optionally substituted by R43,
R43 is methoxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 —C(O)—O-1-4C-alkyl, which is optionally substituted by R43,
R43 is hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1, R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —C(O)—NR8R9,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7,
R7 is 1-2C-alkyl, which is optionally substituted by R71,
R71 is 1-2C-alkoxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7,
R7 is 1-2C-alkyl, which is optionally substituted by R71,
R71 is hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7,
R7 is cyclopropyl, which is optionally substituted by R72,
R72 is 1-2C-alkoxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7,
R7 is cyclopropyl, which is optionally substituted by R72,
R72 is hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7,
R7 is 1-2C-alkoxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-2C-alkyl, wherein the 1-2C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is 1-4C-alkyl, which is optionally substituted by R71, 3-6C-cycloalkyl, which is optionally substituted by R72, or 1-2C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
salts thereof, and stereoisomers of the compounds and the salts thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy, or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, or —C(O)-3-

6C-cycloalkyl, wherein the 3-6C-cycloalkyl group is optionally substituted by R42,
R41 is 1-4C-alkoxy or hydroxy,
R42 is 1-4C-alkoxy or hydroxy,
R6 is —NH—C(O)—R7, —C(O)—NR8R9 or NH$_2$,
R7 is 1-4C-alkyl, which is optionally substituted by R71, or 3-6C-cycloalkyl, which is optionally substituted by R72,
R71 is 1-4C-alkoxy or hydroxy,
R72 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
salts thereof, and stereoisomers of the compounds and the salts thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7 or —C(O)—NR8R9,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
salts thereof, and stereoisomers of the compounds and the salts thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, or —C(O)-3-6C-cycloalkyl, wherein the 3-6C-cycloalkyl group is optionally substituted by R42,
R41 is 1-4C-alkoxy or hydroxy,
R42 is 1-4C-alkoxy or hydroxy,
R6 is —NH—C(O)—R7 or —C(O)—NR8R9,
R7 is 1-4C-alkyl, which is optionally substituted by R71, or 3-6C-cycloalkyl, which is optionally substituted by R72,
R71 is 1-4C-alkoxy or hydroxy,
R72 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
salts thereof, and stereoisomers of the compounds and the salts thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —C(O)—NR8R9,
R8 is hydrogen,
R9 is 1-2C-alkyl, which is optionally substituted by R91,
R91 is 1-2C-alkoxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy, R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —C(O)—NR8R9,
R8 is hydrogen,
R9 is 1-2C-alkyl, which is optionally substituted by R91,
R91 is hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —C(O)—NR8R9,
R8 is hydrogen,
R9 is cyclopropyl,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 6-membered saturated heterocyclic ring containing one nitrogen atom and optionally one oxygen atom, said heterocyclic ring being optionally substituted by R4, wherein R4, if present, is bonded to said nitrogen atom,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 6-membered saturated heterocyclic ring containing one nitrogen atom and optionally one oxygen atom, said heterocyclic ring being substituted by R4 at said nitrogen atom,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-4C-cycloalkyl or 2-4C-alkyl which is optionally substituted by R11,
R11 is 1-4C-alkoxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—, R24 is hydrogen,
Y is —(CH$_2$)$_n$—,
n is 0 or 1,
R3 is a 4- to 6-membered saturated heterocyclic ring containing one nitrogen atom and optionally one oxygen atom, said heterocyclic ring being substituted by R4 at said nitrogen atom,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
salts thereof, and stereoisomers of the compounds and the salts thereof.

In a further preferred embodiment, the invention relates to compounds of formula (I), wherein
R1 is —CH$_2$-3-4C-cycloalkyl,
R21 is hydrogen,
R22 is hydrogen,
R23 is hydrogen,
R24 is hydrogen,
Y is —(CH$_2$)$_n$—,
n is 0,
R3 is a 6-membered saturated heterocyclic ring containing one nitrogen atom, said heterocyclic ring being optionally substituted by R4, or a cyclohexyl group substituted by R6,
R4 is —C(O)-1-2C-alkyl, wherein the 1-2C-alkyl group is optionally substituted by R41, —C(O)-cyclopropyl or —C(O)—O-1-4C-alkyl,
R41 is hydroxy,
R6 is —NH—C(O)—R7 or NH$_2$,
R7 is 1-2C-alkyl, which is optionally substituted by R71, cyclopropyl, which is optionally substituted by R72, or 1-2C-alkoxy, which is optionally substituted by R73,
R71 is 1-2C-alkoxy or hydroxy,
R72 is hydroxy,
R73 is 1-4C-alkoxy or hydroxy,
a salt thereof, or a stereoisomer of the compound or the salt thereof.

In a further preferred embodiment, the invention relates to compounds of formula (I), wherein
R1 is —CH$_2$-3-4C-cycloalkyl,
R21 is hydrogen,
R22 is hydrogen,
R23 is 1-4C-alkoxy,
R24 is hydrogen,
Y is —(CH$_2$)$_n$—,
n is 0,
R3 is a 6-membered saturated heterocyclic ring containing one nitrogen atom, said heterocyclic ring being optionally substituted by R4, or a cyclohexyl group substituted by R6,
R4 is —C(O)-1-2C-alkyl, wherein the 1-2C-alkyl group is optionally substituted by R41, —C(O)-cyclopropyl, wherein cyclopropyl group is optionally substituted by R42, —C(O)—O-1-4C-alkyl,
R41 is 1-2C-alkoxy or hydroxy,
R42 is hydroxy,
R6 is —NH—C(O)—R7, —C(O)—NR8R9 or NH$_2$,
R7 is 1-2C-alkyl, which is optionally substituted by R71, cyclopropyl, which is optionally substituted by R72, or 1-4C-alkoxy,
R71 is 1-2C-alkoxy or hydroxy,
R72 is hydroxy,
R8 is hydrogen,
R9 is 1-2C-alkyl, which is optionally substituted by R91, or cyclopropyl,
R91 is 1-2C-alkoxy,
a salt thereof, or a stereoisomer of the compound or the salt thereof.

In a further preferred embodiment, the invention relates to compounds of formula (I), wherein
R1 is —CH$_2$-3-4C-cycloalkyl,
R21 is hydrogen,
R22 is halogen,
R23 is 1-4C-alkoxy,
R24 is hydrogen,
Y is —(CH$_2$)$_n$—,
n is 0,
R3 is a 5- to 6-membered saturated heterocyclic ring containing one nitrogen atom, said heterocyclic ring being optionally substituted by R4, or a cyclohexyl group substituted by R6,
R4 is —C(O)-1-2C-alkyl, wherein the 1-2C-alkyl group is optionally substituted by R41, —C(O)-cyclopropyl, wherein the cyclopropyl group is optionally substituted by R42, or —C(O)—O-1-4C-alkyl,
R41 is 1-2C-alkoxy or hydroxy,
R42 is hydroxy,
R6 is —NH—C(O)—R7 or NH$_2$,
R7 is 1-2C-alkyl, which is optionally substituted by R71, cyclopropyl, which is optionally substituted by R72, or 1-4C-alkoxy,
R71 is 1-2C-alkoxy or hydroxy,
R72 is hydroxy,
a salt thereof, or a stereoisomer of the compound or the salt thereof.

In a further preferred embodiment, the invention relates to compounds of formula (I), wherein
R1 is —CH$_2$-3-4C-cycloalkyl,
R21 is hydrogen,
R22 is —C(O)-1-4C-alkyl,
R23 is hydrogen,
R24 is hydrogen,
Y is —(CH$_2$)$_n$—,
n is 0,
R3 is a 6-membered saturated heterocyclic ring containing one nitrogen atom, said heterocyclic ring being optionally substituted by R4,
R4 is —C(O)-1-2C-alkyl, wherein the 1-2C-alkyl group is optionally substituted by R41,
R41 is 1-2C-alkoxy or hydroxy,
a salt thereof, or a stereoisomer of the compound or the salt thereof.

In a further preferred embodiment, the invention relates to compounds of formula (I), wherein
R1 is —CH$_2$-3-4C-cycloalkyl,
R21 is hydrogen,
R22 is halogen,
R23 is hydrogen,
R24 is hydrogen,
Y is —(CH$_2$)$_n$—,
n is 0,
R3 is a 6-membered saturated heterocyclic ring containing one nitrogen atom, said heterocyclic ring being optionally substituted by R4, or a cyclohexyl group substituted by R6,
R4 is —C(O)-1-2C-alkyl, wherein the 1-2C-alkyl group is optionally substituted by R41, or —C(O)—O-1-4C-alkyl,
R41 is 1-2C-alkoxy or hydroxy,
R6 is —NH—C(O)—R7, —C(O)—NR8R9 or NH$_2$, R7 is 1-2C-alkyl, which is optionally substituted by R71, or 1-4C-alkoxy,
R71 is 1-2C-alkoxy or hydroxy,
R8 is hydrogen,
R9 is 1-2C-alkyl, which is optionally substituted by R91, or cyclopropyl,
R91 is 1-2C-alkoxy,
a salt thereof, or a stereoisomer of the compound or the salt thereof.

In a further preferred embodiment, the invention relates to compounds of formula (I), wherein
R1 is —CH$_2$-3-4C-cycloalkyl,
R21 is hydrogen,
R22 is 1-4C-alkoxy,
R23 is hydrogen,
R24 is hydrogen,
Y is —(CH$_2$)$_n$—,
n is 0,
R3 is a 6-membered saturated heterocyclic ring containing one nitrogen atom, said heterocyclic ring being optionally substituted by R4, or a cyclohexyl group substituted by R6,
R4 is —C(O)-1-2C-alkyl, wherein the 1-2C-alkyl group is optionally substituted by R41, —C(O)-cyclopropyl, wherein the cyclopropyl group is optionally substituted by R42, or —C(O)—O-1-4C-alkyl,
R41 is 1-2C-alkoxy or hydroxy,
R42 is hydroxy,
R6 is —NH—C(O)—R7 or NH$_2$,
R7 is 1-2C-alkyl, which is optionally substituted by R71, cyclopropyl, which is optionally substituted by R72, or 1-4C-alkoxy,
R71 is 1-2C-alkoxy or hydroxy,
R72 is hydroxy,
a salt thereof, or a stereoisomer of the compound or the salt thereof.

In a further preferred embodiment, the invention relates to compounds of formula (I), wherein
R1 is —CH$_2$-3-4C-cycloalkyl,
R21 is hydrogen,
R22 is 1-4C-fluoroalkoxy,
R23 is hydrogen,
R24 is hydrogen,
Y is —(CH$_2$)$_n$—,
n is 0,
R3 is a 6-membered saturated heterocyclic ring containing one nitrogen atom, said heterocyclic ring being optionally substituted by R4, or a cyclohexyl group substituted by R6,
R4 is —C(O)-1-2C-alkyl, wherein the 1-2C-alkyl group is optionally substituted by R41, —C(O)-cyclopropyl, wherein the cyclopropyl group is optionally substituted by R42, or —C(O)—O-1-4C-alkyl,
R41 is 1-2C-alkoxy or hydroxy,
R42 is hydroxy,
R6 is —NH—C(O)—R7 or NH$_2$,
R7 is 1-2C-alkyl, which is optionally substituted by R71, cyclopropyl, which is optionally substituted by R72, or 1-4C-alkoxy,
R71 is 1-2C-alkoxy or hydroxy,
R72 is hydroxy,
a salt thereof, or a stereoisomer of the compound or the salt thereof.

In a further preferred embodiment, the invention relates to compounds of formula (I), wherein
R1 is —CH$_2$-3-4C-cycloalkyl,
R21 is hydrogen,
R22 is 1-4C-alkoxy,
R23 is halogen,
R24 is hydrogen,
Y is —(CH$_2$)$_n$—,
n is 0,
R3 is a 5- to 6-membered saturated heterocyclic ring containing one nitrogen atom, said heterocyclic ring being optionally substituted by R4,
R4 is —C(O)-1-2C-alkyl, wherein the 1-2C-alkyl group is optionally substituted by R41, or —C(O)—O-1-4C-alkyl,
R41 is 1-2C-alkoxy or hydroxy,
a salt thereof, or a stereoisomer of the compound or the salt thereof.

In a further preferred embodiment, the invention relates to compounds of formula (I), wherein
R1 is —CH$_2$-3-4C-cycloalkyl,
R21 is hydrogen,
R22 is 1-4C-alkyl,
R23 is hydrogen,
R24 is hydrogen,
Y is —(CH$_2$)$_n$—,
n is 0,
R3 is a 6-membered saturated heterocyclic ring containing one nitrogen atom, said heterocyclic ring being optionally substituted by R4, or a cyclohexyl group substituted by R6,
R4 is —C(O)-1-2C-alkyl, wherein the 1-2C-alkyl group is optionally substituted by R41, —C(O)-cyclopropyl, wherein the cyclopropyl group is optionally substituted by R42, or —C(O)—O-1-4C-alkyl,
R41 is 1-2C-alkoxy or hydroxy,
R42 is hydroxy,
R6 is —NH—C(O)—R7, or NH$_2$,
R7 is 1-2C-alkyl, which is optionally substituted by R71, 3-6C-cycloalkyl, which is optionally substituted by R72, or 1-4C-alkoxy,
R71 is 1-2C-alkoxy or hydroxy,
R72 is hydroxy,
a salt thereof, or a stereoisomer of the compound or the salt thereof.

In a further preferred embodiment, the invention relates to compounds of formula (I), wherein
R1 is —CH$_2$-3-4C-cycloalkyl,
R21 and R22 combine to form a group —O—CH$_2$—O—,
R23 is hydrogen,
R24 is hydrogen,
Y is —(CH$_2$)$_n$—,
n is 0 or 1,
R3 is a 4- to 6-membered saturated heterocyclic ring containing one nitrogen atom and optionally one oxygen atom, said heterocyclic ring being optionally substituted by R4, or a cyclohexyl group substituted by R6,
R4 is —C(O)—H, —C(O)-1-2C-alkyl, wherein the 1-2C-alkyl group is optionally substituted by R41, —C(O)-cyclohexyl, wherein the cyclohexyl group is optionally substituted by R42, or —C(O)—O-1-4C-alkyl,
R41 is 1-2C-alkoxy or hydroxy,
R42 is hydroxy,
R6 is —NH—C(O)—R7, —C(O)—NR8R9 or NH$_2$,
R7 is 1-2C-alkyl, which is optionally substituted by R71, cyclopropyl, which is optionally substituted by R72, or 1-4C-alkoxy,
R71 is 1-2C-alkoxy or hydroxy,
R72 is hydroxy,
R8 is hydrogen,
R9 is 1-2C-alkyl, which is optionally substituted by R91, or cyclopropyl,
R91 is 1-2C-alkoxy or hydroxy,
a salt thereof, or a stereoisomer of the compound or the salt thereof.

In a further preferred embodiment, the invention relates to compounds of formula (I), wherein
R1 is —CH₂-3-4C-cycloalkyl,
R21 and R22 combine to form a group —O—CH₂—O—,
R23 is hydrogen,
R24 is hydrogen,
Y is —(CH₂)$_n$—,
n is 0,
R3 is a 4- to 6-membered saturated heterocyclic ring containing one nitrogen atom and optionally one oxygen atom, said heterocyclic ring being optionally substituted by R4, or a cyclohexyl group substituted by R6,
R4 is —C(O)—H, —C(O)-1-2C-alkyl, wherein the 1-2C-alkyl group is optionally substituted by R41, —C(O)-cyclopropyl, wherein the cyclopropyl group is optionally substituted by R42, or —C(O)—O-1-4C-alkyl,
R41 is 1-2C-alkoxy or hydroxy,
R42 is hydroxy,
R6 is —NH—C(O)—R7, —C(O)—NR8R9 or NH₂,
R7 is 1-2C-alkyl, which is optionally substituted by R71, cyclopropyl, which is optionally substituted by R72, or 1-4C-alkoxy,
R71 is 1-2C-alkoxy or hydroxy,
R72 is hydroxy,
R8 is hydrogen,
R9 is 1-2C-alkyl, which is optionally substituted by R91, or cyclopropyl,
R91 is 1-2C-alkoxy or hydroxy,
a salt thereof, or a stereoisomer of the compound or the salt thereof.

In a further preferred embodiment, the invention relates to compounds of formula (I), wherein
R1 is —CH₂-3-4C-cycloalkyl,
R21 and R22 combine to form a group —O—CH₂—O—,
R23 is hydrogen,
R24 is hydrogen,
Y is —(CH₂)$_n$—,
n is 1,
R3 is a 5- to 6-membered saturated heterocyclic ring containing one nitrogen atom and optionally one oxygen atom, said heterocyclic ring being optionally substituted by R4,
R4 is —C(O)—H, —C(O)-1-2C-alkyl, wherein the 1-2C-alkyl group is optionally substituted by R41, —C(O)-cyclopropyl, wherein the cyclopropyl group is optionally substituted by R42, or —C(O)—O-1-4C-alkyl,
R41 is 1-2C-alkoxy or hydroxy,
R42 is hydroxy,
a salt thereof, or a stereoisomer of the compound or the salt thereof.
R1 is —CH₂-3-4C-cycloalkyl,
R21 is hydrogen,
R22 is halogen,
R23 is 1-4C-alkoxy,
R24 is hydrogen,
Y is —(CH₂)$_n$—,
n is 0 or 1,
R3 is a 5- to 6-membered saturated heterocyclic ring containing one nitrogen atom, said heterocyclic ring being substituted by R4,
R4 is —C(O)-1-4C-alkyl, wherein the 1-4C-alkyl group is optionally substituted by R41,
R41 is 1-4C-alkoxy or hydroxy,
salts thereof, and stereoisomers of the compounds and the salts thereof.

In a further preferred embodiment, the invention relates to compounds of formula (I), wherein
R1 is —CH₂-3-4C-cycloalkyl,
R21 is hydrogen,
R22 is hydrogen,
R23 is halogen,
R24 is hydrogen,
Y is —(CH₂)$_n$—,
n is 0,
R3 is a 6-membered saturated heterocyclic ring containing one nitrogen atom, said heterocyclic ring being optionally substituted by R4, or a cyclohexyl group substituted by R6,
R4 is —C(O)-1-2C-alkyl, wherein the 1-2C-alkyl group is optionally substituted by R41, or —C(O)—O-1-4C-alkyl,
R41 is 1-2C-alkoxy or hydroxy,
R6 is —NH—C(O)—R7 or NH₂,
R7 is 1-2C-alkyl, which is optionally substituted by R71, cyclopropyl, which is optionally substituted by R72, or 1-4C-alkoxy,
R71 is 1-2C-alkoxy or hydroxy,
R72 is hydroxy,
a salt thereof, or a stereoisomer of the compound or the salt thereof.

In a further preferred embodiment, the invention relates to compounds of formula (I), wherein
R1 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH₂—O—,
R23 is hydrogen, halogen, 1-4C-alkyl, 1-4C-alkoxy, hydroxy or 1-4C-fluoroalkoxy,
or R22 and R23 combine to form a group —O—CH₂—O—
R24 is hydrogen,
Y is —(CH₂)$_n$—,
n is 0 or 1,
R3 is a 6-membered saturated heterocyclic ring containing one nitrogen atom, said heterocyclic ring being optionally substituted by R4,
R4 is —C(O)-1-4C-alkyl, wherein the 1-4C-alkyl group is optionally substituted by R41,
R41 is 1-2C-alkoxy or hydroxy,
a salt thereof, or a stereoisomer of the compound or the salt thereof.

In a further preferred embodiment, the invention relates to compounds of formula (I), wherein
R1 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH₂—O—,
R23 is hydrogen, halogen, 1-4C-alkyl, 1-4C-alkoxy, hydroxy or 1-4C-fluoroalkoxy,
or R22 and R23 combine to form a group —O—CH₂—O—
R24 is hydrogen,
Y is —(CH₂)$_n$—,
n is 0,
R3 is a 6-membered saturated heterocyclic ring containing one nitrogen atom, said heterocyclic ring being optionally substituted by R4,
R4 is —C(O)-1-2C-alkyl, wherein the 1-2C-alkyl group is optionally substituted by R41,
R41 is 1-2C-alkoxy or hydroxy,
a salt thereof, or a stereoisomer of the compound or the salt thereof.

In a further preferred embodiment, the invention relates to compounds of formula (I), wherein R1 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 3-4C-alkyl,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 3-4C-alkyl,
R21 and R22 combine to form a group —O—CH$_2$—O—,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), wherein
R1 3-4C-alkyl,
R21 and R22 combine to form a group —O—CH$_2$—O—,
R23 is hydrogen,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43, R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH₂,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl,
R91 is 1-4C-alkoxy or hydroxy,
a salt thereof, or a stereoisomer of the compound or the salt thereof.

In a further preferred embodiment, the invention relates to compounds of formula (I), selected from 4-(5-Cyclopropylmethoxy-1,3-benzodioxol-4-yl)-5H-pyrrolo[3,2-d]pyrimidine-7-carboxylic acid (1-propionyl-piperidin-4-yl)-amid; 4-({1-[4-(5-Cyclopropylmethoxy-benzo[1,3]dioxol-4-yl)-5H-pyrrolo[3,2-d]pyrimidin-7-yl]-methanoyl}-amino)-piperidine-1-carboxylic acid ethyl ester; 4-(5-Cyclopropylmethoxy-benzo[1,3]dioxol-4-yl)-5H-pyrrolo[3,2-d]pyrimidine-7-carboxylic acid [1-(2-methoxy-acetyl)-piperidin-4-yl]-amide; trans-4-(5-Cyclopropylmethoxy-benzo[1,3]dioxol-4-yl)-5H-pyrrolo[3,2-d]pyrimidine-7-carboxylic acid (4-acetylamino-cyclohexyl)-amide; trans-4-(5-Cyclopropylmethoxy-benzo[1,3]dioxol-4-yl)-5H-pyrrolo[3,2-d]pyrimidine-7-carboxylic acid {4-[(1-cyclopropyl-methanoyl)-amino]-cyclohexyl}-amide; trans-[4-({1-[4-(5-Cyclopropylmethoxy-benzo[1,3]dioxol-4-yl)-5H-pyrrolo[3,2-d]pyrimidin-7-yl]-methanoyl}-amino)-cyclohexyl]-carbamic acid ethyl ester; cis-4-(5-Cyclopropylmethoxy-benzo[1,3]dioxol-4-yl)-5H-pyrrolo[3,2-d]pyrimidine-7-carboxylic acid (4-acetylamino-cyclohexyl)-amide; cis-4-(5-Cyclopropylmethoxy-benzo[1,3]dioxol-4-yl)-5H-pyrrolo[3,2-d]pyrimidine-7-carboxylic acid {4-[(1-cyclopropyl-methanoyl)-amino]-cyclohexyl}-amide; cis-4-(5-Cyclopropylmethoxy-benzo[1,3]dioxol-4-yl)-5H-pyrrolo[3,2-d]pyrimidine-7-carboxylic acid [4-(2-methoxy-ethanoylamino)-cyclohexyl]-amide; cis-[4-({1-[4-(5-Cyclopropylmethoxy-benzo[1,3]dioxol-4-yl)-5H-pyrrolo[3,2-d]pyrimidin-7-yl]-methanoyl}-amino)-cyclohexyl]-carbamic acid ethyl ester; 4-(5-Cyclopropylmethoxy-benzo[1,3]dioxol-4-yl)-5H-pyrrolo[3,2-d]pyrimidine-7-carboxylic acid (1-acetyl-piperidin-4-yl)-amide; 4-(5-Cyclopropylmethoxy-benzo[1,3]dioxol-4-yl)-5H-pyrrolo[3,2-d]pyrimidine-7-carboxylic acid [1-(1-cyclopropyl-methanoyl)-piperidin-4-yl]-amide; 4-(5-Cyclopropylmethoxy-benzo[1,3]dioxol-4-yl)-5H-pyrrolo[3,2-d]pyrimidine-7-carboxylic acid [(R)-1-(2-methoxy-acetyl)-pyrrolidin-3-yl]amide; 4-(5-Cyclopropylmethoxy-benzo[1,3]dioxol-4-yl)-5H-pyrrolo[3,2-d]pyrimidine-7-carboxylic acid ((R)-1-formyl-pyrrolidin-3-yl)-amide; 4-(5-Cyclopropylmethoxy-benzo[1,3]dioxol-4-yl)-5H-pyrrolo[3,2-d]pyrimidine-7-carboxylic acid ((R)-1-acetyl-pyrrolidin-3-yl)-amide; 4-(5-Cyclopropylmethoxy-benzo[1,3]dioxol-4-yl)-5H-pyrrolo[3,2-d]pyrimidine-7-carboxylic acid [(R)-1-(1-cyclopropyl-methanoyl)-pyrrolidin-3-yl]amide; (R)-3-({1-[4-(5-Cyclopropylmethoxy-benzo[1,3]dioxol-4-yl)-5H-pyrrolo[3,2-d]pyrimidin-7-yl]-methanoyl}-amino)-pyrrolidine-1-carboxylic acid ethyl ester; 4-(5-Cyclopropylmethoxy-benzo[1,3]dioxol-4-yl)-5H-pyrrolo[3,2-d]pyrimidine-7-carboxylic acid ((S)-1-formyl-pyrrolidin-3-yl)-amide; 4-(5-Cyclopropylmethoxy-benzo[1,3]dioxol-4-yl)-5H-pyrrolo[3,2-d]pyrimidine-7-carboxylic acid ((S)-1-acetyl-pyrrolidin-3-yl)-amide; 4-(5-Cyclopropylmethoxy-benzo[1,3]dioxol-4-yl)-5H-pyrrolo[3,2-d]pyrimidine-7-carboxylic acid [(S)-1-(1-cyclopropyl-methanoyl)-pyrrolidin-3-yl]amide; 4-(5-Cyclopropylmethoxy-benzo[1,3]dioxol-4-yl)-5H-pyrrolo[3,2-d]pyrimidine-7-carboxylic acid [(S)-1-(2-methoxy-ethanoyl)-pyrrolidin-3-yl]amide; (S)-3-({1-[4-(5-Cyclopropylmethoxy-benzo[1,3]dioxol-4-yl)-5H-pyrrolo[3,2-d]pyrimidin-7-yl]-methanoyl}-amino)-pyrrolidine-1-carboxylic acid ethyl ester; 4-(5-Cyclopropylmethoxy-benzo[1,3]dioxol-4-yl)-5H-pyrrolo[3,2-d]pyrimidine-7-carboxylic acid (1-formyl-piperidin-4-ylmethyl)-amide; 4-(5-Cyclopropylmethoxy-benzo[1,3]dioxol-4-yl)-5H-pyrrolo[3,2-d]pyrimidine-7-carboxylic acid (1-acetyl-piperidin-4-ylmethyl)-amide; 4-(5-Cyclopropylmethoxy-benzo[1,3]dioxol-4-yl)-5H-pyrrolo[3,2-d]pyrimidine-7-carboxylic acid [141-cyclopropyl-methanoyl)-piperidin-4-ylmethyl]-amide; 4-(5-Cyclopropylmethoxy-benzo[1,3]dioxol-4-yl)-5H-pyrrolo[3,2-d]pyrimidine-7-carboxylic acid [1-(2-methoxy-ethanoyl)-piperidin-4-ylmethyl]-amide; 4-[({1-[4-(5-Cyclopropylmethoxy-benzo[1,3]dioxol-4-yl)-5H-pyrrolo[3,2-d]pyrimidin-7-yl]-methanoyl}-amino)-methyl]-piperidine-1-carboxylic acid ethyl ester; 4-(5-Cyclopropylmethoxy-benzo[1,3]dioxol-4-yl)-5H-pyrrolo[3,2-d]pyrimidine-7-carboxylic acid (1-formyl-piperidin-3-ylmethyl)-amide; 4-(5-Cyclopropylmethoxy-benzo[1,3]dioxol-4-yl)-5H-pyrrolo[3,2-d]pyrimidine-7-carboxylic acid (1-propionyl-piperidin-3-ylmethyl)-amide; 4-(5-Cyclopropylmethoxy-benzo[1,3]dioxol-4-yl)-5H-pyrrolo[3,2-d]pyrimidine-7-carboxylic acid [1-(2-methoxy-acetyl)piperidin-3-ylmethyl]-amide; 3-({[4-(5-Cyclopropylmethoxy-benzo[1,3]dioxol-4-yl)-5H-pyrrolo[3,2-d]pyrimidine-7-carbonyl]-amino}-methyl)piperidine-1-carboxylic acid ethyl ester; 4-(5-Cyclopropylmethoxy-benzo[1,3]dioxol-4-yl)-5H-pyrrolo[3,2-d]pyrimidine-7-carboxylic acid (1-formyl-pyrrolidin-3-ylmethyl)-amide; 4-(5-Cyclopropylmethoxy-benzo[1,3]dioxol-4-yl)-5H-pyrrolo[3,2-d]pyrimidine-7-carboxylic acid [1-(2-methoxy-acetyl)-pyrrolidin-3-ylmethyl]-amide; 3-({[4-(5-Cyclopropylmethoxy-benzo[1,3]dioxol-4-yl)-5H-pyrrolo[3,2-d]pyrimidine-7-carbonyl]-amino}-methyl)-pyrrolidine-1-carboxylic acid ethyl ester; 4-(5-Cyclopropylmethoxy-benzo[1,3]dioxol-4-yl)-5H-pyrrolo[3,2-d]pyrimidine-7-carboxylic acid (4-formyl-morpholin-2-ylmethyl)-amide; 4-(5-Cyclopropylmethoxy-benzo[1,3]dioxol-4-yl)-5H-pyrrolo[3,2-d]pyrimidine-7-carboxylic acid (4-propionyl-morpholin-2-ylmethyl)-amide; 4-(5-Cyclopropylmethoxy-benzo[1,3]dioxol-4-yl)-5H-pyrrolo[3,2-d]pyrimidine-7-carboxylic acid [4-(2-methoxy-acetyl)-morpholin-2-ylmethyl]-amide; 2-({[4-(5-Cyclopropylmethoxy-benzo[1,3]dioxol-4-yl)-5H-pyrrolo[3,2-d]pyrimidine-7-carbonyl]-amino}-methyl)-morpholine-4-carboxylic acid ethyl ester; 4-(5-Cyclopropylmethoxy-benzo[1,3]dioxol-4-yl)-5H-pyrrolo[3,2-d]pyrimidine-7-carboxylic acid (1-acetyl-azetidin-3-yl)-amide; 4-(5-Cyclopropylmethoxy-benzo[1,3]dioxol-4-yl)-5H-pyrrolo[3,2-d]pyrimidine-7-carboxylic acid (1-propionyl-azetidin-3-yl)-amide; 4-(5-Cyclopropylmethoxy-benzo[1,3]dioxol-4-yl)-5H-pyrrolo[3,2-d]pyrimidine-7-carboxylic acid [1-(2-methoxy-ethanoyl)-azetidin-3-yl]amide; 3-({1-[4-(5-Cyclopropylmethoxy-benzo[1,3]dioxol-4-yl)-5H-pyrrolo[3,2-d]pyrimidin-7-yl]-methanoyl}-amino)-azetidine-1-carboxylic acid ethyl ester; 4-(5-Cyclopropylmethoxy-benzo[1,3]dioxol-4-yl)-5H-pyrrolo[3,2-d]pyrimidine-7-carboxylic acid (1-formyl-piperidin-4-yl)-amide; 4-(5-Cyclopropylmethoxy-benzo[1,3]dioxol-4-yl)-5H-pyrrolo[3,2-d]pyrimidine-7-carboxylic acid ((S)-1-propionyl-piperidin-3-yl)-amide; 4-(5-Cyclopropylmethoxy-benzo[1,3]dioxol-4-yl)-5H-pyrrolo[3,2-d]pyrimidine-7-carboxylic acid [(S)-1-(2-methoxy-ethanoyl)-piperidin-3-yl]-amide; 4-(5-Cyclopropylmethoxy-benzo[1,3]dioxol-4-yl)-5H-pyrrolo[3,2-d]pyrimidine-7-carboxylic acid ((S)-1-acetyl-piperidin-3-yl)-amide; 4-(5-Cyclopropylmethoxy-benzo[1,3]dioxol-4-yl)-5H-pyrrolo[3,2-d]pyrimidine-7-carboxylic acid ((R)-1-propionyl-piperidin-3-yl)-amide; 4-(5-Cyclopropylmethoxy-benzo[1,3]dioxol-4-yl)-5H-pyrrolo[3,2-d]pyrimidine-7-carboxylic acid [(R)-1-(2-methoxy-ethanoyl)-piperidin-3-yl]-amide; 4-(5-Cyclopropylmethoxy-benzo[1,3]dioxol-4-yl)-5H-pyrrolo[3,2-d]pyrimidine-7-carboxylic acid ((R)-1-acetyl-piperidin-3-yl)-amide; trans-4-(5-Cyclopropylmethoxy-benzo[1,3]dioxol-4-yl)-5H-pyrrolo[3,2-d]pyrimidine-7-carboxylic acid [4-(2-methoxy-acetylamino)-cyclohexyl]-amide; trans-4-(2-Cyclopropylmethoxy-4-methoxy-phenyl)-5H-pyrrolo[3,2-d]pyrimidine-7-carboxylic acid (4-acetylamino-cyclohexyl)-amide; trans-4-(2-Cyclopropylmethoxy-4-methoxy-phenyl)-5H-pyrrolo[3,2-d]pyrimidine-7-carboxylic acid [4-(cyclopropanecarbonyl-amino)-cyclohexyl]-amide; trans-4-(2-Cyclopropylmethoxy-4-methoxy-phenyl)-5H-pyrrolo[3,2-d]pyrimidine-7-carboxylic acid [4-(2-methoxy-acetylamino)-cyclohexyl]-amide; trans-(4-{[4-(2-Cyclopropylmethoxy-4-methoxy-phenyl)-5H-pyrrolo[3,2-d]pyrimidine-7-carbonyl]-amino}-cyclohexyl)-carbamic acid ethyl ester; cis-4-(2-Cyclopropylmethoxy-4-methoxy-phenyl)-5H-pyrrolo[3,2-d]pyrimidine-7-carboxylic acid (4-acetylamino-cyclohexyl)-amide; cis-4-(2-Cyclopropylmethoxy-4-methoxy-phenyl)-5H-pyrrolo[3,2-d]pyrimidine-7-carboxylic acid [4-(cyclopropanecarbonyl-amino)-cyclohexyl]-amide; cis-4-(2-Cyclopropylmethoxy-4-methoxy-phenyl)-5H-pyrrolo[3,2-d]pyrimidine-7-carboxylic acid [4-(2-methoxy-acetylamino)-cyclohexyl]-amide; cis-(4-{[4-(2-Cyclopropylmethoxy-4-methoxy-phenyl)-5H-pyrrolo[3,2-d]pyrimidine-7-carbonyl]-amino}-cyclohexyl)-carbamic acid ethyl ester; 4-(2-Cyclopropylmethoxy-4-methoxy-phenyl)-5H-pyrrolo[3,2-d]pyrimidine-7-carboxylic acid (1-acetyl-piperidin-4-yl)-amide; 4-(2-Cyclopropylmethoxy-4-methoxy-phenyl)-5H-pyrrolo[3,2-d]pyrimidine-7-carboxylic acid [1-(1-cyclopropyl-methanoyl)-piperidin-4-yl]-amide; 4-(2-Cyclopropylmethoxy-4-methoxy-phenyl)-5H-pyrrolo[3,2-d]pyrimidine-7-carboxylic acid [1-(2-methoxy-ethanoyl)-piperidin-4-yl]amide; 4-({1-[4-(2-Cyclopropylmethoxy-4-methoxy-phenyl)-5H-pyrrolo[3,2-d]pyrimidin-7-yl]-methanoyl}-amino)-piperidine-1-carboxylic acid ethyl ester; trans-4-(2-Cyclopropylmethoxy-5-methoxy-phenyl)-5H-pyrrolo[3,2-d]pyrimidine-7-carboxylic acid (4-acetylamino-cyclohexyl)-amide; trans-4-(2-Cyclopropylmethoxy-5-methoxy-phenyl)-5H-pyrrolo[3,2-d]pyrimidine-7-carboxylic acid [4-(cyclopropanecarbonyl-amino)cyclohexyl]-amide; trans-4-(2-Cyclopropylmethoxy-5-methoxy-phenyl)-5H-pyrrolo[3,2-d]pyrimidine-7-carboxylic acid [4-(2-methoxy-acetylamino)-cyclohexyl]-amide; trans-(4-{[4-(2-Cyclopropylmethoxy-5-methoxy-phenyl)-5H-pyrrolo[3,2-d]pyrimidine-7-carbonyl]-amino}-cyclohexyl)-carbamic acid ethyl ester; cis-4-(2-Cyclopropylmethoxy-5-methoxy-phenyl)-5H-pyrrolo[3,2-d]pyrimidine-7-carboxylic acid (4-acetylamino-cyclohexyl)-amide; cis-4-(2-Cyclopropylmethoxy-5-methoxy-phenyl)-5H-pyrrolo[3,2-d]pyrimidine-7-carboxylic acid [4-(cyclopropanecarbonyl-amino)cyclohexyl]-amide; cis-4-(2-Cyclopropylmethoxy-5-methoxy-phenyl)-5H-pyrrolo[3,2-d]pyrimidine-7-carboxylic acid [4-(2-methoxy-acetylamino)-cyclohexyl]-amide; cis-(4-{[4-(2-Cyclopropylmethoxy-5-methoxy-phenyl)-5H-pyrrolo[3,2-d]pyrimidine-7-carbonyl]-amino}-cyclohexyl)-carbamic acid ethyl ester; 4-(2-Cyclopropylmethoxy-5-methoxy-phenyl)-5H-pyrrolo[3,2-d]pyrimidine-7-carboxylic acid (1-acetyl-piperidin-4-yl)-amide; 4-(2-Cyclopropylmethoxy-5-methoxy-phenyl)-5H-pyrrolo[3,2-d]pyrimidine-7-carboxylic acid (1-cyclopropanecarbonyl-piperidin-4-yl)-amide; 4-(2-Cyclopropylmethoxy-5-methoxy-phenyl)-5H-pyrrolo[3,2-d]pyrimidine-7-carboxylic acid [1-(2-methoxy-acetyl)-piperidin-4-yl]-amide; 4-{[4-(2-Cyclopropylmethoxy-5-methoxy-phenyl)-5H-pyrrolo[3,2-d]pyrimidine-7-carbonyl]-amino}-piperidine-1-carboxylic acid ethyl ester; cis-4-(2-Cyclopropylmethoxy-4-fluoro-phenyl)-5H-pyrrolo[3,2-d]pyrimidine-7-carboxylic acid (4-acetylamino-cyclohexyl)-amide; cis-4-(2-Cyclopropylmethoxy-4-fluoro-phenyl)-5H-pyrrolo[3,2-d]pyrimidine-7-carboxylic acid [4-(2-methoxy-acetylamino)-cyclohexyl]-amide; cis-(4-{[4-(2-Cyclopropylmethoxy-4-fluoro-phenyl)-5H-pyrrolo[3,2-d]pyrimidine-7-carbonyl]-amino}-cyclohexyl)-carbamic acid ethyl ester; trans-4-(2-Cyclopropylmethoxy-4-fluoro-phenyl)-5H-pyrrolo[3,2-d]pyrimidine-7-carboxylic acid (4-acetylamino-cyclohexyl)-amide; trans-4-(2-Cyclopropylmethoxy-4-fluoro-phenyl)-5H-pyrrolo[3,2-d]pyrimidine-7-carboxylic acid [4-(2-methoxy-acetylamino)-cyclohexyl]-amide; trans-(4-{[4-(2-Cyclopropylmethoxy-4-fluoro-phenyl)-5H-pyrrolo[3,2-d]pyrimidine-7-carbonyl]-amino}-cyclohexyl)-carbamic acid ethyl ester; 4-(2-Cyclopropylmethoxy-4-fluoro-phenyl)-5H-pyrrolo[3,2-d]pyrimidine-7-carboxylic acid (1-acetyl-piperidin-4-yl)-amideter; 4-(2-Cyclopropylmethoxy-4-fluoro-phenyl)-5H-pyrrolo[3,2-d]pyrimidine-7-carboxylic acid (1-propionyl-piperidin-4-yl)-amide; 4-(2-Cyclopropylmethoxy-4-fluoro-phenyl)-5H-pyrrolo[3,2-d]pyrimidine-7-carboxylic acid [1-(2-methoxy-acetyl)-piperidin-4-yl]-amide; 4-(2-Cyclopropylmethoxy-5-fluoro-phenyl)-5H-pyrrolo[3,2-d]pyrimidine-7-carboxylic acid (1-acetyl-piperidin-4-yl)-amide; 4-(2-Cyclopropylmethoxy-5-fluoro-phenyl)-5H-pyrrolo[3,2-d]pyrimidine-7-carboxylic acid (1-propionyl-piperidin-4-yl)-amide; 4-(2-Cyclopropylmethoxy-5-fluoro-phenyl)-5H-pyrrolo[3,2-d]pyrimidine-7-carboxylic acid [1-(2-methoxy-acetyl)-piperidin-4-yl]-amide; trans-4-(2-Cyclopropylmethoxy-5-fluoro-phenyl)-5H-pyrrolo[3,2-d]pyrimidine-7-carboxylic acid (4-acetylamino-cyclohexyl)-amide; trans-4-(2-Cyclopropylmethoxy-5-fluoro-phenyl)-5H-pyrrolo[3,2-d]pyrimidine-7-carboxylic acid (4-propionylamino-cyclohexyl)-amide; trans-4-(2-Cyclopropylmethoxy-5-fluoro-phenyl)-5H-pyrrolo[3,2-d]pyrimidine-7-carboxylic acid [4-(2-methoxy-acetylamino)-cyclohexyl]-amide; trans-4-(2-Cyclopropylmethoxy-phenyl)-5H-pyrrolo[3,2-d]pyrimidine-7-carboxylic acid (4-acetylamino-cyclohexyl)-amide; trans-4-(2-Cyclopropylmethoxy-phenyl)-5H-pyrrolo[3,2-d]pyrimidine-7-carboxylic acid [4-(2-methoxy-acetylamino)-cyclohexyl]-amide; trans-(4-{[4-(2-Cyclopropylmethoxy-phenyl)-5H-pyrrolo[3,2-d]pyrimidine-7-carbonyl]-amino}-cyclohexyl)-carbamic acid ethyl ester; trans-4-(2-Cyclopropylmethoxy-phenyl)-5H-pyrrolo[3,2-d]pyrimidine-7-carboxylic acid [4-(cyclopropanecarbonyl-amino)cyclohexyl]-amide; 4-(2-Cyclopropylmethoxy-phenyl)-5H-pyrrolo[3,2-d]pyrimidine-7-carboxylic acid (1-acetyl-piperidin-4-yl)-amide; 4-{[4-(2-Cyclopropylmethoxy-phenyl)-5H-pyrrolo[3,2-d]pyrimidine-7-carbonyl]-amino}-piperidine-1-carboxylic acid ethyl ester; 4-(2-Cyclopropylmethoxy-phenyl)-5H-pyrrolo[3,2-d]pyrimidine-7-carboxylic acid (1-cyclopropanecarbonyl-piperidin-4-yl)-amide; 4-(2-Cyclopropylmethoxy-4-fluoro-5-methoxy-phenyl)-5H-pyrrolo[3,2-d]pyrimidine-7-carboxylic acid (1-propionyl-piperidin-4-yl)-amide; 4-(2-Cyclopropylmethoxy-4-fluoro-5-methoxy-phenyl)-5H-pyrrolo[3,2-d]pyrimidine-7-carboxylic acid [1-(2-methoxy-ethanoyl)-piperidin-4-yl]amide; 4-(2-Cyclopropylmethoxy- 4-fluoro-5-methoxy-phenyl)-5H-pyrrolo[3,2-d]pyrimidine-7-carboxylic acid (1-acetyl-piperidin-4-yl)-amide; 4-(2-Cyclopropylmethoxy-4-fluoro-5-methoxy-phenyl)-5H-pyrrolo[3,2-d]pyrimidine-7-carboxylic acid ((R)-1-acetyl-piperidin-3-yl)-amide; 4-(2-Cyclopropylmethoxy-4-fluoro-5-methoxy-phenyl)-5H-pyrrolo[3,2-d]pyrimidine-7-carboxylic acid ((R)-1-propionyl-piperidin-3-yl)-amide; 4-(2-Cyclopropylmethoxy-4-fluoro-5-methoxy-phenyl)-5H-pyrrolo[3,2-d]pyrimidine-7-carboxylic acid [(R)-1-(2-methoxy-acetyl)-piperidin-3-yl]-amide; 4-(2-Cyclopropyl-methoxy-4-fluoro-5-methoxy-phenyl)-5H-pyrrolo[3,2-d]pyrimidine-7-carboxylic acid ((R)-1-acetyl-pyrrolidin-3-yl)-amide; 4-(2-Cyclopropylmethoxy-4-fluoro-5-methoxy-phenyl)-5H-pyrrolo[3,2-d]pyrimidine-7-carboxylic acid ((R)-1-propionyl-pyrrolidin-3-yl)-amide; 4-(2-Cyclopropyl-methoxy-4-fluoro-5-methoxy-phenyl)-5H-pyrrolo[3,2-d]pyrimidine-7-carboxylic acid [(R)-1-(2-methoxy-acetyl)-pyrrolidin-3-yl]amide; trans-4-(2-Cyclopropylmethoxy-5-fluoro-4-methoxy-phenyl)-5H-pyrrolo[3,2-d]pyrimidine-7-carboxylic acid (4-acetylamino-cyclohexyl)-amide; trans-4-(2-Cyclopropylmethoxy-5-fluoro-4-methoxy-phenyl)-5H-pyrrolo[3,2-d]pyrimidine-7-carboxylic acid [4-(2-methoxy-acetylamino)-cyclohexyl]-amide; 4-(2-Cyclopropylmethoxy-5-fluoro-4-methoxy-phenyl)-5H-pyrrolo[3,2-d]pyrimidine-7-carboxylic acid (1-acetyl-piperidin-4-yl)-amide; 4-(2-Cyclopropylmethoxy-5-fluoro-4-methoxy-phenyl)-5H-pyrrolo[3,2-d]pyrimidine-7-carboxylic acid [1-(2-methoxy-ethanoyl)-piperidin-4-yl]amide; 4-(2-Cyclopropylmethoxy-5-fluoro-4-methoxy-phenyl)-5H-pyrrolo[3,2-d]pyrimidine-7-carboxylic acid (1-propionyl-piperidin-4-yl)-amide; 4-(2-Cyclopropyl-methoxy-5-fluoro-4-methoxy-phenyl)-5H-pyrrolo[3,2-d]pyrimidine-7-carboxylic acid ((R)-1-propionyl-piperidin-3-yl)-amide; 4-(2-Cyclopropylmethoxy-5-fluoro-4-methoxy-phenyl)-5H-pyrrolo[3,2-d]pyrimidine-7-carboxylic acid [(R)-1-(2-methoxy-ethanoyl)-piperidin-3-yl]-amide; 4-(2-Cyclopropylmethoxy-5-fluoro-4-methoxy-phenyl)-5H-pyrrolo[3,2-d]pyrimidine-7-carboxylic acid ((R)-1-acetyl-piperidin-3-yl)-amide; 4-(2-Cyclopropylmethoxy-5-fluoro-4-methoxy-phenyl)-5H-pyrrolo[3,2-d]pyrimidine-7-carboxylic acid ((S)-1-propionyl-piperidin-3-yl)-amide; 4-(2-Cyclopropylmethoxy-5-fluoro-4-methoxy-phenyl)-5H-pyrrolo[3,2-d]pyrimidine-7-carboxylic acid [(S)-1-(2-methoxy-ethanoyl)-piperidin-3-yl]amide; 4-(2-Cyclopropylmethoxy-5-fluoro-4-methoxy-phenyl)-5H-pyrrolo[3,2-d]pyrimidine-7-carboxylic acid ((S)-1-acetyl-piperidin-3-yl)-amide; 4-(2-Cyclopropylmethoxy-5-fluoro-4-methoxy-phenyl)-5H-pyrrolo[3,2-d]pyrimidine-7-carboxylic acid ((R)-1-acetyl-pyrrolidin-3-yl)-amide; 4-(2-Cyclopropyl-methoxy-5-fluoro-4-methoxy-phenyl)-5H-pyrrolo[3,2-d]pyrimidine-7-carboxylic acid ((R)-1-propionyl-pyrrolidin-3-yl)-amide; 4-(2-Cyclopropylmethoxy-5-fluoro-4-methoxy-phenyl)-5H-pyrrolo[3,2-d]pyrimidine-7-carboxylic acid [(R)-1-(2-methoxy-acetyl)-pyrrolidin-3-yl]amide; trans-4-(2-Cyclopropylmethoxy-5-methyl-phenyl)-5H-pyrrolo[3,2-d]pyrimidine-7-carboxylic acid (4-acetylamino-cyclohexyl)-amide; trans-4-(2-Cyclopropylmethoxy-5-methyl-phenyl)-5H-pyrrolo[3,2-d]pyrimidine-7-carboxylic acid [4-(2-methoxy-acetylamino)-cyclohexyl]-amide; trans-(4-{[4-(2-Cyclopropylmethoxy-5-methyl-phenyl)-5H-pyrrolo[3,2-d]pyrimidine-7-carbonyl]-amino}-cyclohexyl)-carbamic acid ethyl ester; 4-(2-Cyclopropylmethoxy-5-methyl-phenyl)-5H-pyrrolo[3,2-d]pyrimidine-7-carboxylic acid (1-acetyl-piperidin-4-yl)-amide; 4-(2-Cyclopropylmethoxy-5-methyl-phenyl)-5H-pyrrolo[3,2-d]pyrimidine-7-carboxylic acid [1-(2-methoxy-acetyl)-piperidin-4-yl]-amide; 4-{[4-(2-Cyclopropylmethoxy-5-methyl-phenyl)-5H-pyrrolo[3,2-d]pyrimidine-7-carbonyl]-amino}-piperidine-1-carboxylic acid ethyl ester; trans-4-(5-Cyclobutylmethoxy-benzo[1,3]dioxol-4-yl)-5H-pyrrolo[3,2-d]pyrimidine-7-carboxylic acid (4-acetylamino-cyclohexyl)-amide; trans-4-(5-Cyclobutyl-methoxy-benzo[1,3]dioxol-4-yl)-5H-pyrrolo[3,2-d]pyrimidine-7-carboxylic acid [4-(cyclopropanecarbonyl-amino)-cyclohexyl]-amide; trans-4-(5-Cyclobutylmethoxy-benzo[1,3]dioxol-4-yl)-5H-pyrrolo[3,2-d]pyrimidine-7-carboxylic acid [4-(2-methoxy-ethanoylamino)-cyclohexyl]-amide; 4-(5-Cyclobutylmethoxy-benzo[1,3]dioxol-4-yl)-5H-pyrrolo[3,2-d]pyrimidine-7-carboxylic acid (1-acetyl-piperidin-4-yl)-amide; 4-(5-Cyclobutylmethoxy-benzo[1,3]dioxol-4-yl)-5H-pyrrolo[3,2-d]pyrimidine-7-carboxylic acid [1-(1-cyclopropyl-methanoyl)-piperidin-4-yl]amide; 4-(5-Cyclobutylmethoxy-benzo[1,3]dioxol-4-yl)-5H-pyrrolo[3,2-d]pyrimidine-7-carboxylic acid [1-(2-methoxy-ethanoyl)-piperidin-4-yl]-amide; 4-({1-[4-(5-Cyclobutylmethoxy-benzo[1,3]dioxol-4-yl)-5H-pyrrolo[3,2-d]pyrimidin-7-yl]-methanoyl}-amino)-piperidine-1-carboxylic acid ethyl ester; 4-(5-Ethoxy-benzo[1,3]dioxol-4-yl)-5H-pyrrolo[3,2-d]pyrimidine-7-carboxylic acid (1-propionyl-piperidin-4-yl)-amide; 4-{[4-(5-Ethoxy-benzo[1,3]dioxol-4-yl)-5H-pyrrolo[3,2-d]pyrimidine-7-carbonyl]-amino}-piperidine-1-carboxylic acid ethyl ester; 4-(5-Ethoxy-benzo[1,3]dioxol-4-yl)-5H-pyrrolo[3,2-d]pyrimidine-7-carboxylic acid [1-(2-methoxy-acetyl)piperidin-4-yl]amide; 4-(5-Ethoxy-benzo[1,3]dioxol-4-yl)-5H-pyrrolo[3,2-d]pyrimidine-7-carboxylic acid ((R)-1-propionyl-pyrrolidin-3-yl)-amide; (R)-3-{[4-(5-Ethoxy-benzo[1,3]dioxol-4-yl)-5H-pyrrolo[3,2-d]pyrimidine-7-carbonyl]-amino}-pyrrolidine-1-carboxylic acid ethyl ester; 4-(5-Ethoxy-benzo[1,3]dioxol-4-yl)-5H-pyrrolo[3,2-d]pyrimidine-7-carboxylic acid ((R)-1-(2-methoxy-acetyl)-pyrrolidin-amide; 4-(5-Propoxy-benzo[1,3]dioxol-4-yl)-5H-pyrrolo[3,2-d]pyrimidine-7-carboxylic acid (1-propionyl-piperidin-4-yl)-amide; 4-{[4-(5-Propoxy-benzo[1,3]dioxol-4-yl)-5H-pyrrolo[3,2-d]pyrimidine-7-carbonyl]-amino}-piperidine-1-carboxylic acid ethyl ester; 4-(5-Propoxy-benzo[1,3]dioxol-4-yl)-5H-pyrrolo[3,2-d]pyrimidine-7-carboxylic acid ((R)-1-propionyl-pyrrolidin-3-yl)-amide; (R)-3-{[4-(5-Propoxy-benzo[1,3]dioxol-4-yl)-5H-pyrrolo[3,2-d]pyrimidine-7-carbonyl]-amino}-pyrrolidine-1-carboxylic acid ethyl ester; 4-(5-Propoxy-benzo[1,3]dioxol-4-yl)-5H-pyrrolo[3,2-d]pyrimidine-7-carboxylic acid [(R)-1-(2-methoxy-acetyl)-pyrrolidin-3-yl]-amide; 4-(5-Butoxy-benzo[1,3]dioxol-4-yl)-5H-pyrrolo[3,2-d]pyrimidine-7-carboxylic acid (1-propionyl-piperidin-4-yl)-amide; 4-{[4-(5-Butoxy-benzo[1,3]dioxol-4-yl)-5H-pyrrolo[3,2-d]pyrimidine-7-carbonyl]-amino}-piperidine-1-carboxylic acid ethyl ester; 4-(5-Butoxy-benzo[1,3]dioxol-4-yl)-5H-pyrrolo[3,2-d]pyrimidine-7-carboxylic acid (1-formyl-piperidin-4-yl)-amide; 4-(5-Butoxy-benzo[1,3]dioxol-4-yl)-5H-pyrrolo[3,2-d]pyrimidine-7-carboxylic acid (1-propionyl-piperidin-3-yl)-amide; 3-{[4-(5-Butoxy-benzo[1,3]dioxol-4-yl)-5H-pyrrolo[3,2-d]pyrimidine-7-carbonyl]amino}-piperidine-1-carboxylic acid ethyl ester; 4-(5-Butoxy-benzo[1,3]dioxol-4-yl)-5H-pyrrolo[3,2-d]pyrimidine-7-carboxylic acid [1-(2-methoxy-acetyl)piperidin-3-yl]amide; 4-(5-Butoxy-benzo[1,3]dioxol-4-yl)-5H-pyrrolo[3,2-d]pyrimidine-7-carboxylic acid ((R)-1-propionyl-pyrrolidin-3-yl)-amide; (R)-3-{[4-(5-Butoxy-benzo[1,3]dioxol-4-yl)-5H-pyrrolo[3,2-d]pyrimidine-7-carbonyl]-amino}-pyrrolidine-1-carboxylic acid ethyl ester; cis-4-[4-Methoxy-2-(2-methoxy-ethoxy)-phenyl]-5H-pyrrolo[3,2-d]pyrimidine-7-carboxylic acid (4-acetylamino-cyclohexyl)-amide; cis-4-[4-Methoxy-2-(2-methoxy-ethoxy)-phenyl]-5H-pyrrolo[3,2-d]pyrimidine-7-carboxylic acid [4-(cyclopropanecarbonyl-amino)-cyclohexyl]-amide; cis-4-

[4-Methoxy-2-(2-methoxy-ethoxy)-phenyl]-5H-pyrrolo[3,2-d]pyrimidine-7-carboxylic acid [4-(2-methoxy-acetylamino)-cyclohexyl]-amide; trans-4-[4-Methoxy-2-(2-methoxy-ethoxy)-phenyl]-5H-pyrrolo[3,2-d]pyrimidine-7-carboxylic acid (4-acetylamino-cyclohexyl)-amide; trans-4-[4-Methoxy-2-(2-methoxy-ethoxy)-phenyl]-5H-pyrrolo[3,2-d]pyrimidine-7-carboxylic acid [4-(cyclopropanecarbonyl-amino)cyclohexyl]-amide; trans-4-[4-Methoxy-2-(2-methoxy-ethoxy)-phenyl]-5H-pyrrolo[3,2-d]pyrimidine-7-carboxylic acid [4-(2-methoxy-acetylamino)-cyclohexyl]-amide; 4-[4-Methoxy-2-(2-methoxy-ethoxy)-phenyl]-5H-pyrrolo[3,2-d]pyrimidine-7-carboxylic acid (1-acetyl-piperidin-4-yl)-amide; 4-[4-Methoxy-2-(2-methoxy-ethoxy)-phenyl]-5H-pyrrolo[3,2-d]pyrimidine-7-carboxylic acid (1-cyclopropanecarbonyl-piperidin-4-yl)-amide; 4-[4-Methoxy-2-(2-methoxy-ethoxy)-phenyl]-5H-pyrrolo[3,2-d]pyrimidine-7-carboxylic acid [1-(2-methoxy-acetyl)-piperidin-4-yl]-amide; trans-4-[5-(2-Methoxy-ethoxy)-benzo[1,3]dioxol-4-yl]-5H-pyrrolo[3,2-d]pyrimidine-7-carboxylic acid (4-acetylamino-cyclohexyl)-amide; trans-4-[5-(2-Methoxy-ethoxy)-benzo[1,3]dioxol-4-yl]-5H-pyrrolo[3,2-d]pyrimidine-7-carboxylic acid (4-acetylamino-cyclohexyl)-amide; trans-4-[5-(2-Methoxy-ethoxy)-benzo[1,3]dioxol-4-yl]-5H-pyrrolo[3,2-d]pyrimidine-7-carboxylic acid [4-(2-methoxy-acetylamino)-cyclohexyl]-amide; cis-4-[5-(2-Methoxy-ethoxy)-benzo[1,3]dioxol-4-yl]-5H-pyrrolo[3,2-d]pyrimidine-7-carboxylic acid (4-acetylamino-cyclohexyl)-amide; cis-4-[5-(2-Methoxy-ethoxy)-benzo[1,3]dioxol-4-yl]-5H-pyrrolo[3,2-d]pyrimidine-7-carboxylic acid (4-acetylamino-cyclohexyl)-amide; cis-4-[5-(2-Methoxy-ethoxy)-benzo[1,3]dioxol-4-yl]-5H-pyrrolo[3,2-d]pyrimidine-7-carboxylic acid [4-(2-methoxy-acetylamino)-cyclohexyl]-amide; cis-[4-({4-[5-(2-Methoxy-ethoxy)-benzo[1,3]dioxol-4-yl]-5H-pyrrolo[3,2-d]pyrimidine-7-carbonyl}-amino)-cyclohexyl]-carbamic acid ethyl ester; 4-[5-(2-Methoxy-ethoxy)-benzo[1,3]dioxol-4-yl]-5H-pyrrolo[3,2-d]pyrimidine-7-carboxylic acid (1-acetyl-piperidin-4-yl)-amide; 4-[5-(2-Methoxy-ethoxy)-benzo[1,3]dioxol-4-yl]-5H-pyrrolo[3,2-d]pyrimidine-7-carboxylic acid (1-cyclopropanecarbonyl-piperidin-4-yl)-amide; 4-[5-(2-Methoxy-ethoxy)-benzo[1,3]dioxol-4-yl]-5H-pyrrolo[3,2-d]pyrimidine-7-carboxylic acid [1-(2-methoxy-acetyl)-piperidin-4-yl]-amide; 4-(5-Cyclopropylmethoxy-benzo[1,3]dioxol-4-yl)-5H-pyrrolo[3,2-d]pyrimidine-7-carboxylic acid [1-(2-hydroxy-ethanoyl)-piperidin-4-yl]amide; trans-[4-({1-[4-(5-Cyclopropylmethoxy-benzo[1,3]dioxol-4-yl)-5H-pyrrolo[3,2-d]pyrimidine-7-carboxylic acid [4-(2-hydroxy-ethanoylamino)-cyclohexyl]-amide; trans-[4-({1-[4-(5-Cyclopropylmethoxy-benzo[1,3]dioxol-4-yl)-5H-pyrrolo[3,2-d]pyrimidine-7-carboxylic acid [4-((S)-2-hydroxy-propanoylamino)-cyclohexyl]-amide; cis-[4-({1-[4-(5-Cyclopropylmethoxy-benzo[1,3]dioxol-4-yl)-5H-pyrrolo[3,2-d]pyrimidine-7-carboxylic acid [4-(2-hydroxy-ethanoylamino)-cyclohexyl]-amide; cis-[4-({1-[4-(5-Cyclopropylmethoxy-benzo[1,3]dioxol-4-yl)-5H-pyrrolo[3,2-d]pyrimidine-7-carboxylic acid [4-((S)-2-hydroxy-propanoylamino)-cyclohexyl]-amide; 4-(5-Cyclopropylmethoxy-benzo[1,3]dioxol-4-yl)-5H-pyrrolo[3,2-d]pyrimidine-7-carboxylic acid [1-((S)-2-hydroxy-propanoyl)-piperidin-4-yl]-amide; trans-4-(5-Cyclopropylmethoxy-benzo[1,3]dioxol-4-yl)-5H-pyrrolo[3,2-d]pyrimidine-7-carboxylic acid {4-[(1-hydroxy-cyclopropanecarbonyl)-amino]-cyclohexyl}-amide; cis-4-(5-Cyclopropylmethoxy-benzo[1,3]dioxol-4-yl)-5H-pyrrolo[3,2-d]pyrimidine-7-carboxylic acid {4-[(1-hydroxy-cyclopropanecarbonyl)-amino]-cyclohexyl}-amide; 4-(5-Cyclopropylmethoxy-benzo[1,3]dioxol-4-yl)-5H-pyrrolo[3,2-d]pyrimidine-7-carboxylic acid {1-[1-(1-hydroxy-cyclopropyl)-methanoyl]-piperidin-4-yl}-amide; 4-(5-Cyclopropylmethoxy-benzo[1,3]dioxol-4-yl)-5H-pyrrolo[3,2-d]pyrimidine-7-carboxylic acid [(R)-1-(2-hydroxy-ethanoyl)-pyrrolidin-3-yl]-amide; 4-(5-Cyclopropylmethoxy-benzo[1,3]dioxol-4-yl)-5H-pyrrolo[3,2-d]pyrimidine-7-carboxylic acid [(R)-1-((S)-2-hydroxy-propanoyl)-pyrrolidin-3-yl]amide; 4-(5-Cyclopropylmethoxy-benzo[1,3]dioxol-4-yl)-5H-pyrrolo[3,2-d]pyrimidine-7-carboxylic acid {(R)-1-[1-(1-hydroxy-cyclopropyl)-methanoyl]-pyrrolidin-3-yl}-amide; 4-(5-Cyclopropylmethoxy-benzo[1,3]dioxol-4-yl)-5H-pyrrolo[3,2-d]pyrimidine-7-carboxylic acid [(S)-1-(2-hydroxy-ethanoyl)-pyrrolidin-3-yl]-amide; 4-(5-Cyclopropylmethoxy-benzo[1,3]dioxol-4-yl)-5H-pyrrolo[3,2-d]pyrimidine-7-carboxylic acid [(S)-1-((S)-2-hydroxy-propanoyl)-pyrrolidin-3-yl]amide; 4-(5-Cyclopropylmethoxy-benzo[1,3]dioxol-4-yl)-5H-pyrrolo[3,2-d]pyrimidine-7-carboxylic acid {(S)-1-[1-(1-hydroxy-cyclopropyl)-methanoyl]-pyrrolidin-3-yl}-amide; 4-(5-Cyclopropylmethoxy-benzo[1,3]dioxol-4-yl)-5H-pyrrolo[3,2-d]pyrimidine-7-carboxylic acid [1-(2-hydroxy-ethanoyl)-piperidin-4-ylmethyl]-amide; 4-(5-Cyclopropylmethoxy-benzo[1,3]dioxol-4-yl)-5H-pyrrolo[3,2-d]pyrimidine-7-carboxylic acid [1-((S)-2-hydroxy-propanoyl)-piperidin-4-ylmethyl]-amide; 4-(5-Cyclopropylmethoxy-benzo[1,3]dioxol-4-yl)-5H-pyrrolo[3,2-d]pyrimidine-7-carboxylic acid {1-[1-(1-hydroxy-cyclopropyl)-methanoyl]-piperidin-4-ylmethyl}-amide; 4-(5-Cyclopropylmethoxy-benzo[1,3]dioxol-4-yl)-5H-pyrrolo[3,2-d]pyrimidine-7-carboxylic acid [1-(2-hydroxy-acetyl)-piperidin-3-ylmethyl]-amide; 4-(5-Cyclopropylmethoxy-benzo[1,3]dioxol-4-yl)-5H-pyrrolo[3,2-d]pyrimidine-7-carboxylic acid [1-((S)-2-hydroxy-propionyl)-piperidin-3-ylmethyl]-amide; 4-(5-Cyclopropylmethoxy-benzo[1,3]dioxol-4-yl)-5H-pyrrolo[3,2-d]pyrimidine-7-carboxylic acid [1-(2-hydroxy-acetyl)-pyrrolidin-3-ylmethyl]-amide; 4-(5-Cyclopropylmethoxy-benzo[1,3]dioxol-4-yl)-5H-pyrrolo[3,2-d]pyrimidine-7-carboxylic acid [1-((S)-2-hydroxy-propionyl)-pyrrolidin-3-ylmethyl]-amide; 4-(5-Cyclopropylmethoxy-benzo[1,3]dioxol-4-yl)-5H-pyrrolo[3,2-d]pyrimidine-7-carboxylic acid [4-(2-hydroxy-acetyl)-morpholin-2-ylmethyl]-amide; 4-(5-Cyclopropylmethoxy-benzo[1,3]dioxol-4-yl)-5H-pyrrolo[3,2-d]pyrimidine-7-carboxylic acid [4-((S)-2-hydroxy-propionyl)-morpholin-2-ylmethyl]-amide; 4-(5-Cyclopropylmethoxy-benzo[1,3]dioxol-4-yl)-5H-pyrrolo[3,2-d]pyrimidine-7-carboxylic acid [1-(2-hydroxy-ethanoyl)-azetidin-3-yl]amide; 4-(5-Cyclopropylmethoxy-benzo[1,3]dioxol-4-yl)-5H-pyrrolo[3,2-d]pyrimidine-7-carboxylic acid [1-((S)-2-hydroxy-propanoyl)-azetidin-3-yl]-amide; 4-(5-Cyclopropylmethoxy-benzo[1,3]dioxol-4-yl)-5H-pyrrolo[3,2-d]pyrimidine-7-carboxylic acid [(S)-1-((S)-2-hydroxy-propanoyl)piperidin-3-yl]amide; 4-(5-Cyclopropylmethoxy-benzo[1,3]dioxol-4-yl)-5H-pyrrolo[3,2-d]pyrimidine-7-carboxylic acid [(R)-1-((S)-2-hydroxy-propanoyl)piperidin-3-yl]-amide; trans-4-(2-Cyclopropylmethoxy-4-methoxy-phenyl)-5H-pyrrolo[3,2-d]pyrimidine-7-carboxylic acid [4-(2-hydroxy-acetylamino)-cyclohexyl]-amide; trans-4-(2-Cyclopropylmethoxy-4-methoxy-phenyl)-5H-pyrrolo[3,2-d]pyrimidine-7-carboxylic acid [4-((S)-2-hydroxy-propionylamino)-cyclohexyl]-amide; trans-4-(2-Cyclopropylmethoxy-4-methoxy-phenyl)-5H-pyrrolo[3,2-d]pyrimidine-7-carboxylic acid {4-[(1-hydroxy-cyclopropanecarbonyl)-amino]-cyclohexyl}-amide; cis-4-(2-Cyclopropylmethoxy-4-methoxy-phenyl)-5H-pyrrolo[3,2-d]pyrimidine-7-carboxylic acid [4-(2-hydroxyacetylamino)-cyclohexyl]-amide; cis-4-(2-Cyclopropyl-methoxy-4-methoxy-phenyl)-5H-pyrrolo[3,2-d]pyrimidine-7-carboxylic acid [4-((S)-2-hydroxy-propionylamino)-cyclohexyl]-amide; cis-4-(2-Cyclopropylmethoxy-4-methoxy-phenyl)-5H-pyrrolo[3,2-d]pyrimidine-7-carboxylic acid {4-[(1-hydroxy-cyclopropanecarbonyl)-amino]-cyclohexyl}-amide; 4-(2-Cyclopropylmethoxy-4-methoxy-phenyl)-5H-pyrrolo[3,2-d]pyrimidine-7-carboxylic acid [1-(2-hydroxy-ethanoyl)-piperidin-4-yl]amide; 4-(2-Cyclopropylmethoxy-4-methoxy-phenyl)-5H-pyrrolo[3,2-d]pyrimidine-7-carboxylic acid [1-((S)-2-hydroxy-propanoyl)-piperidin-4-yl]-amide; 4-(2-Cyclopropylmethoxy-4-methoxy-phenyl)-5H-pyrrolo[3,2-d]pyrimidine-7-carboxylic acid {1-[1-(1-hydroxy-cyclopropyl)-methanoyl]-piperidin-4-yl}-amide; cis-4-(2-Cyclopropylmethoxy-5-methoxy-phenyl)-5H-pyrrolo[3,2-d]pyrimidine-7-carboxylic acid [4-(2-hydroxy-acetylamino)-cyclohexyl]-amide; cis-4-(2-Cyclopropylmethoxy-5-methoxy-phenyl)-5H-pyrrolo[3,2-d]pyrimidine-7-carboxylic acid {4-[(1-hydroxy-cyclopropanecarbonyl)-amino]-cyclohexyl}-amide; trans-4-(2-Cyclopropylmethoxy-5-methoxy-phenyl)-5H-pyrrolo[3,2-d]pyrimidine-7-carboxylic acid {4-[(1-hydroxy-cyclopropanecarbonyl)-amino]-cyclohexyl}-amide; 4-(2-Cyclopropylmethoxy-5-methoxy-phenyl)-5H-pyrrolo[3,2-d]pyrimidine-7-carboxylic acid [1-(2-hydroxy-acetyl)piperidin-4-yl]amide; 4-(2-Cyclopropylmethoxy-5-methoxy-phenyl)-5H-pyrrolo[3,2-d]pyrimidine-7-carboxylic acid [1-((S)-2-hydroxy-propionyl)-piperidin-4-yl]-amide; 4-(2-Cyclopropylmethoxy-5-methoxy-phenyl)-5H-pyrrolo[3,2-d]pyrimidine-7-carboxylic acid [1-(1-hydroxy-cyclopropanecarbonyl)-piperidin-4-yl]-amide; cis-4-(2-Cyclopropylmethoxy-4-fluoro-phenyl)-5H-pyrrolo[3,2-d]pyrimidine-7-carboxylic acid [4-(2-hydroxy-acetylamino)-cyclohexyl]-amide; cis-4-(2-Cyclopropylmethoxy-4-fluoro-phenyl)-5H-pyrrolo[3,2-d]pyrimidine-7-carboxylic acid [4-((S)-2-hydroxy-propionylamino)-cyclohexyl]-amide; cis-4-(2-Cyclopropylmethoxy-4-fluoro-phenyl)-5H-pyrrolo[3,2-d]pyrimidine-7-carboxylic acid {4-[(1-hydroxy-cyclopropanecarbonyl)-amino]-cyclohexyl}-amide; trans-4-(2-Cyclopropylmethoxy-4-fluoro-phenyl)-5H-pyrrolo[3,2-d]pyrimidine-7-carboxylic acid [4-(2-hydroxy-acetylamino)-cyclohexyl]-amide; trans-4-(2-Cyclopropylmethoxy-4-fluoro-phenyl)-5H-pyrrolo[3,2-d]pyrimidine-7-carboxylic acid [4-((S)-2-hydroxy-propionylamino)-cyclohexyl]-amide; trans-4-(2-Cyclopropylmethoxy-4-fluoro-phenyl)-5H-pyrrolo[3,2-d]pyrimidine-7-carboxylic acid {4-[(1-hydroxy-cyclopropanecarbonyl)-amino]-cyclohexyl}-amide; 4-(2-Cyclopropylmethoxy-5-fluoro-phenyl)-5H-pyrrolo[3,2-d]pyrimidine-7-carboxylic acid [1-(2-hydroxy-acetyl)piperidin-4-yl]amide; 4-(2-Cyclopropylmethoxy-5-fluoro-phenyl)-5H-pyrrolo[3,2-d]pyrimidine-7-carboxylic acid [1-((S)-2-hydroxy-propionyl)-piperidin-4-yl]-amide; trans-4-(2-Cyclopropylmethoxy-5-fluoro-phenyl)-5H-pyrrolo[3,2-d]pyrimidine-7-carboxylic acid [4-(2-hydroxy-acetylamino)-cyclohexyl]-amide; trans-4-(2-Cyclopropylmethoxy-4-fluoro-phenyl)-5H-pyrrolo[3,2-d]pyrimidine-7-carboxylic acid [4-((S)-2-hydroxy-propionylamino)-cyclohexyl]-amide; trans-4-(2-Cyclopropylmethoxy-phenyl)-5H-pyrrolo[3,2-d]pyrimidine-7-carboxylic acid [4-(2-hydroxy-acetylamino)-cyclohexyl]-amide; trans-4-(2-Cyclopropylmethoxy-phenyl)-5H-pyrrolo[3,2-d]pyrimidine-7-carboxylic acid [4-((S)-2-hydroxy-propionylamino)-cyclohexyl]-amide; trans-4-(2-Cyclopropylmethoxy-phenyl)-5H-pyrrolo[3,2-d]pyrimidine-7-carboxylic acid {4-[(1-hydroxy-cyclopropanecarbonyl)-amino]-cyclohexyl}-amide; 4-(2-Cyclopropylmethoxy-phenyl)-5H-pyrrolo[3,2-d]pyrimidine-7-carboxylic acid [1-((S)-2-hydroxy-propionyl)piperidin-4-yl]amide; 4-(2-Cyclopropylmethoxy-4-fluoro-5-methoxy-phenyl)-5H-pyrrolo[3,2-d]pyrimidine-7-carboxylic acid [1-((S)-2-hydroxy-propionyl)piperidin-4-yl]amide; 4-(2-Cyclopropylmethoxy-4-fluoro-5-methoxy-phenyl)-5H-pyrrolo[3,2-d]pyrimidine-7-carboxylic acid [(R)-1-(2-hydroxy-acetyl)-piperidin-3-yl]-amide; 4-(2-Cyclopropylmethoxy-4-fluoro-5-methoxy-phenyl)-5H-pyrrolo[3,2-d]pyrimidine-7-carboxylic acid [(R)-1-((S)-2-hydroxy-propionyl)piperidin-3-yl]amide; 4-(2-Cyclopropylmethoxy-4-fluoro-5-methoxy-phenyl)-5H-pyrrolo[3,2-d]pyrimidine-7-carboxylic acid [(R)-1-(2-hydroxy-acetyl)-pyrrolidin-3-yl]amide; 4-(2-Cyclopropylmethoxy-4-fluoro-5-methoxy-phenyl)-5H-pyrrolo[3,2-d]pyrimidine-7-carboxylic acid [(R)-1-((S)-2-hydroxy-propionyl)-pyrrolidin-3-yl]amide; trans-4-(2-Cyclopropylmethoxy-5-fluoro-4-methoxy-phenyl)-5H-pyrrolo[3,2-d]pyrimidine-7-carboxylic acid [4-(2-hydroxy-acetylamino)-cyclohexyl]-amide; trans-4-(2-Cyclopropylmethoxy-5-fluoro-4-methoxy-phenyl)-5H-pyrrolo[3,2-d]pyrimidine-7-carboxylic acid [4-((S)-2-hydroxy-propionylamino)-cyclohexyl]-amide; trans-4-(2-Cyclopropylmethoxy-5-fluoro-4-methoxy-phenyl)-5H-pyrrolo[3,2-d]pyrimidine-7-carboxylic acid {4-[(1-hydroxy-cyclopropanecarbonyl)-amino]-cyclohexyl}-amide; 4-(2-Cyclopropylmethoxy-5-fluoro-4-methoxy-phenyl)-5H-pyrrolo[3,2-d]pyrimidine-7-carboxylic acid [1-(2-hydroxy-ethanoyl)-piperidin-4-yl]amide; 4-(2-Cyclopropylmethoxy-5-fluoro-4-methoxy-phenyl)-5H-pyrrolo[3,2-d]pyrimidine-7-carboxylic acid [1-((S)-2-hydroxy-propanoyl)-piperidin-4-yl]-amide; 4-(2-Cyclopropylmethoxy-5-fluoro-4-methoxy-phenyl)-5H-pyrrolo[3,2-d]pyrimidine-7-carboxylic acid {1-[1-(1-hydroxy-cyclopropyl)-methanoyl]-piperidin-4-yl}-amide; 4-(2-cyclopropylmethoxy-5-fluoro-4-methoxy-phenyl)-5H-pyrrolo[3,2-d]pyrimidine-7-carboxylic acid [(S)-1-((S)-2-hydroxy-propanoyl)-piperidin-3-yl]-amide; 4-(2-Cyclopropylmethoxy-5-fluoro-4-methoxy-phenyl)-5H-pyrrolo[3,2-d]pyrimidine-7-carboxylic acid [(R)-1-((S)-2-hydroxy-propanoyl)-piperidin-3-yl]-amide; 4-(2-Cyclopropylmethoxy-5-fluoro-4-methoxy-phenyl)-5H-pyrrolo[3,2-d]pyrimidine-7-carboxylic acid [(R)-1-(2-hydroxy-acetyl)-pyrrolidin-3-yl]amide; 4-(2-Cyclopropylmethoxy-5-fluoro-4-methoxy-phenyl)-5H-pyrrolo[3,2-d]pyrimidine-7-carboxylic acid [(R)-1-((S)-2-hydroxy-propionyl)-pyrrolidin-3-yl]-amide; trans-4-(2-Cyclopropylmethoxy-5-methyl-phenyl)-5H-pyrrolo[3,2-d]pyrimidine-7-carboxylic acid [4-(2-hydroxy-acetylamino)-cyclohexyl]-amide; trans-4-(2-Cyclopropylmethoxy-5-methyl-phenyl)-5H-pyrrolo[3,2-d]pyrimidine-7-carboxylic acid [4-((S)-2-hydroxy-propionylamino)-cyclohexyl]-amide; trans-4-(2-Cyclopropylmethoxy-5-methyl-phenyl)-5H-pyrrolo[3,2-d]pyrimidine-7-carboxylic acid {4-[(1-hydroxy-cyclopropanecarbonyl)-amino]-cyclohexyl}-amide; 4-(2-Cyclopropylmethoxy-5-methyl-phenyl)-5H-pyrrolo[3,2-d]pyrimidine-7-carboxylic acid [1-(2-hydroxy-acetyl)piperidin-4-yl]amide; 4-(2-Cyclopropylmethoxy-5-methyl-phenyl)-5H-pyrrolo[3,2-d]pyrimidine-7-carboxylic acid [1-((S)-2-hydroxy-propionyl)-piperidin-4-yl]-amide; 4-(2-Cyclopropylmethoxy-5-methyl-phenyl)-5H-pyrrolo[3,2-d]pyrimidine-7-carboxylic acid [1-(1-hydroxy-cyclopropanecarbonyl)-piperidin-4-yl]-amide; 4-(5-Ethoxy-benzo[1,3]dioxol-4-yl)-5H-pyrrolo[3,2-d]pyrimidine-7-carboxylic acid [1-((S)-2-hydroxy-propionyl)piperidin-4-yl]amide; 4-(5-Ethoxy-benzo[1,3]dioxol-4-yl)-5H-pyrrolo[3,2-d]pyrimidine-7-carboxylic acid [(R)-1-((S)-2- hydroxy-propionyl)-pyrrolidin-3-yl]-amide; 4-(5-Propoxy-benzo[1,3]dioxol-4-yl)-5H-pyrrolo[3,2-d]pyrimidine-7-carboxylic acid [1-((S)-2-hydroxy-propionyl)piperidin-4-yl] amide; 4-(5-Propoxy-benzo[1,3]dioxol-4-yl)-5H-pyrrolo[3,2-d]pyrimidine-7-carboxylic acid [(R)-1-((S)-2-hydroxy-propionyl)-pyrrolidin-3-yl]-amide; 4-(5-Butoxy-benzo[1,3]dioxol-4-yl)-5H-pyrrolo[3,2-d]pyrimidine-7-carboxylic acid [1-((S)-2-hydroxy-propionyl)-piperidin-4-yl]-amide; 4-(5-Butoxy-benzo[1,3]dioxol-4-yl)-5H-pyrrolo[3,2-d]pyrimidine-7-carboxylic acid [(R)-1-((S)-2-hydroxy-propionyl)-pyrrolidin-3-yl]amide; trans-4-[4-Methoxy-2-(2-methoxy-ethoxy)-phenyl]-5H-pyrrolo[3,2-d]pyrimidine-7-carboxylic acid [4-(2-hydroxy-acetylamino)-cyclohexyl]-amide; trans-4-[4-Methoxy-2-(2-methoxy-ethoxy)-phenyl]-5H-pyrrolo[3,2-d]pyrimidine-7-carboxylic acid [4-((S)-2-hydroxy-propionylamino)-cyclohexyl]-amide; trans-4-[4-Methoxy-2-(2-methoxy-ethoxy)-phenyl]-5H-pyrrolo[3,2-d]pyrimidine-7-carboxylic acid {4-[(1-hydroxy-cyclopropanecarbonyl)-amino]-cyclohexyl}-amide; cis-4-[4-Methoxy-2-(2-methoxy-ethoxy)-phenyl]-5H-pyrrolo[3,2-d]pyrimidine-7-carboxylic acid {4-[(1-hydroxy-cyclopropanecarbonyl)-amino]-cyclohexyl}-amide; 4-[4-Methoxy-2-(2-methoxy-ethoxy)-phenyl]-5H-pyrrolo[3,2-d]pyrimidine-7-carboxylic acid [1-(1-hydroxy-cyclopropanecarbonyl)-piperidin-4-yl]-amide; trans-4-[5-(2-Methoxy-ethoxy)-benzo[1,3]dioxol-4-yl]-5H-pyrrolo[3,2-d]pyrimidine-7-carboxylic acid [4-(2-hydroxy-acetylamino)-cyclohexyl]-amide; cis-4-[5-(2-Methoxy-ethoxy)-benzo[1,3]dioxol-4-yl]-5H-pyrrolo[3,2-d]pyrimidine-7-carboxylic acid [4-(2-hydroxy-acetylamino)-cyclohexyl]-amide; cis-4-[5-(2-Methoxy-ethoxy)-benzo[1,3]dioxol-4-yl]-5H-pyrrolo[3,2-d]pyrimidine-7-carboxylic acid [4-((S)-2-hydroxy-propionylamino)-cyclohexyl]-amide; 4-[5-(2-Methoxy-ethoxy)-benzo[1,3]dioxol-4-yl]-5H-pyrrolo[3,2-d]pyrimidine-7-carboxylic acid [1-((S)-2-hydroxy-propionyl)piperidin-4-yl]amide; 4-(5-Acetyl-2-cyclopropylmethoxy-phenyl)-5H-pyrrolo[3,2-d]pyrimidine-7-carboxylic acid [1-((S)-2-hydroxy-propanoyl)-piperidin-4-yl]-amide; 4-(5-Acetyl-2-cyclopropylmethoxy-phenyl)-5H-pyrrolo[3,2-d]pyrimidine-7-carboxylic acid [1-(2-methoxy-acetyl)piperidin-4-yl]amide; 4-(5-Acetyl-2-cyclopropylmethoxy-phenyl)-5H-pyrrolo[3,2-d]pyrimidine-7-carboxylic acid (1-acetyl-piperidin-4-yl)-amide; 4-(5-Acetyl-2-cyclopropylmethoxy-4-methyl-phenyl)-5H-pyrrolo[3,2-d]pyrimidine-7-carboxylic acid [1-((S)-2-hydroxy-propionyl)piperidin-4-yl] amide; 4-(5-Acetyl-2-cyclopropylmethoxy-4-methyl-phenyl)-5H-pyrrolo[3,2-d]pyrimidine-7-carboxylic acid (1-acetyl-piperidin-4-yl)-amide; trans-4-(5-Cyclopropylmethoxy-benzo[1,3]dioxol-4-yl)-5H-pyrrolo[3,2-d]pyrimidine-7-carboxylic acid [4-(2-methoxy-ethylcarbamoyl)-cyclohexyl]-amide; trans-4-(5-Cyclopropylmethoxy-benzo[1,3]dioxol-4-yl)-5H-pyrrolo[3,2-d]pyrimidine-7-carboxylic acid (4-cyclopropylcarbamoyl-cyclohexyl)-amide; trans-4-(2-Cyclopropylmethoxy-4-methoxy-phenyl)-5H-pyrrolo[3,2-d]pyrimidine-7-carboxylic acid (4-cyclopropylcarbamoyl-cyclohexyl)-amide; trans-4-(2-Cyclopropylmethoxy-4-methoxy-phenyl)-5H-pyrrolo[3,2-d]pyrimidine-7-carboxylic acid [4-(2-methoxy-ethylcarbamoyl)-cyclohexyl]-amide; trans-4-(2-Cyclopropylmethoxy-5-fluoro-phenyl)-5H-pyrrolo[3,2-d]pyrimidine-7-carboxylic acid (4-cyclopropylcarbamoyl-cyclohexyl)-amide; trans-4-(2-Cyclopropylmethoxy-5-fluoro-phenyl)-5H-pyrrolo[3,2-d]pyrimidine-7-carboxylic acid [4-(2-methoxy-ethylcarbamoyl)-cyclohexyl]-amide; trans-4-(5-Cyclobutylmethoxy-benzo[1,3]dioxol-4-yl)-5H-pyrrolo[3,2-d]pyrimidine-7-carboxylic acid [4-(2-methoxy-ethylcarbamoyl)-cyclohexyl]-amide; trans-4-(5-Cyclobutylmethoxy-benzo[1,3]dioxol-4-yl)-5H-pyrrolo[3,2-d]pyrimidine-7-carboxylic acid (4-cyclopropylcarbamoyl-cyclohexyl)-amide; 4-(2-Cyclopropylmethoxy-5-fluoro-4-hydroxy-phenyl)-5H-pyrrolo[3,2-d]pyrimidine-7-carboxylic acid (1-acetyl-piperidin-4-yl)-amide; 4-(2-Cyclopropylmethoxy-5-fluoro-4-hydroxy-phenyl)-5H-pyrrolo[3,2-d]pyrimidine-7-carboxylic acid (1-propionyl-piperidin-4-yl)-amide; 4-[2-Cyclopropylmethoxy-4-(1,1-difluoro-methoxy)-5-fluoro-phenyl]-5H-pyrrolo[3,2-d]pyrimidine-7-carboxylic acid (1-acetyl-piperidin-4-yl)-amide; 4-[2-Cyclopropylmethoxy-4-(1,1-difluoro-methoxy)-5-fluoro-phenyl]-5H-pyrrolo[3,2-d]pyrimidine-7-carboxylic acid [1-(2-methoxy-ethanoyl)-piperidin-4-yl]-amide; 4-(2-Cyclopropylmethoxy-5-fluoro-4-hydroxy-phenyl)-5H-pyrrolo[3,2-d]pyrimidine-7-carboxylic acid [1-(2-hydroxy-acetyl)piperidin-4-yl]amide 4-(2-Cyclopropylmethoxy-5-fluoro-4-hydroxy-phenyl)-5H-pyrrolo[3,2-d]pyrimidine-7-carboxylic acid [1-((S)-2-hydroxy-propionyl)piperidin-4-yl]amide; 4-[2-Cyclopropylmethoxy-4-(1,1-difluoro-methoxy)-5-fluoro-phenyl]-5H-pyrrolo[3,2-d]pyrimidine-7-carboxylic acid [1-(2-hydroxy-acetyl)-piperidin-4-yl]-amide; 4-[2-Cyclopropylmethoxy-4-(1,1-difluoro-methoxy)-5-fluoro-phenyl]-5H-pyrrolo[3,2-d]pyrimidine-7-carboxylic acid [1-((S)-2-hydroxy-propionyl)piperidin-4-yl]-amide;

a salt thereof, or a stereoisomer of the compound or the salt thereof.

In a further preferred embodiment, the invention relates to compounds of formula (I), selected from 4-(5-Cyclopropylmethoxy-1,3-benzodioxol-4-yl)-5H-pyrrolo[3,2-d]pyrimidine-7-carboxylic acid (1-propionyl-piperidin-4-yl)-amid; 4-({1-[4-(5-Cyclopropylmethoxy-benzo[1,3]dioxol-4-yl)-5H-pyrrolo[3,2-d]pyrimidin-7-yl]-methanoyl}-amino)-piperidine-1-carboxylic acid ethyl ester; 4-(5-Cyclopropylmethoxy-benzo[1,3]dioxol-4-yl)-5H-pyrrolo[3,2-d]pyrimidine-7-carboxylic acid [1-(2-methoxy-acetyl)-piperidin-4-yl]-amide; trans-4-(5-Cyclopropylmethoxy-benzo[1,3]dioxol-4-yl)-5H-pyrrolo[3,2-d]pyrimidine-7-carboxylic acid (4-acetylamino-cyclohexyl)-amide; trans-4-(5-Cyclopropylmethoxy-benzo[1,3]dioxol-4-yl)-5H-pyrrolo[3,2-d]pyrimidine-7-carboxylic acid {4-[(1-cyclopropyl-methanoyl)-amino]-cyclohexyl}-amide; trans-[4-({1-[4-(5-Cyclopropylmethoxy-benzo[1,3]dioxol-4-yl)-5H-pyrrolo[3,2-d]pyrimidin-7-yl]-methanoyl}-amino)-cyclohexyl]-carbamic acid ethyl ester; cis-4-(5-Cyclopropylmethoxy-benzo[1,3]dioxol-4-yl)-5H-pyrrolo[3,2-d]pyrimidine-7-carboxylic acid (4-acetylamino-cyclohexyl)-amide; cis-4-(5-Cyclopropylmethoxy-benzo[1,3]dioxol-4-yl)-5H-pyrrolo[3,2-d]pyrimidine-7-carboxylic acid {4-[(1-cyclopropyl-methanoyl)-amino]-cyclohexyl}-amide; cis-4-(5-Cyclopropylmethoxy-benzo[1,3]dioxol-4-yl)-5H-pyrrolo[3,2-d]pyrimidine-7-carboxylic acid [4-(2-methoxy-ethanoylamino)-cyclohexyl]-amide; cis-[4-({1-[4-(5-Cyclopropylmethoxy-benzo[1,3]dioxol-4-yl)-5H-pyrrolo[3,2-d]pyrimidin-7-yl]-methanoyl}-amino)-cyclohexyl]-carbamic acid ethyl ester; 4-(5-Cyclopropylmethoxy-benzo[1,3]dioxol-4-yl)-5H-pyrrolo[3,2-d]pyrimidine-7-carboxylic acid (1-acetyl-piperidin-4-yl)-amide; 4-(5-Cyclopropylmethoxy-benzo[1,3]dioxol-4-yl)-5H-pyrrolo[3,2-d]pyrimidine-7-carboxylic acid [1-(1-cyclopropyl-methanoyl)-piperidin-4-yl]-amide; 4-(5-Cyclopropylmethoxy-benzo[1,3]dioxol-4-yl)-5H-pyrrolo[3,2-d]pyrimidine-7-carboxylic acid [(R)-1-(2-methoxy-acetyl)-pyrrolidin-3-yl]amide; 4-(5-Cyclopropylmethoxy-benzo[1,3]dioxol-4-yl)-5H-pyrrolo[3,2-d]pyrimidine-7-carboxylic acid ((R)-1-formyl-pyrrolidin-3-yl)-amide; 4-(5-Cyclopropylmethoxy-benzo[1,3]dioxol-4-yl)-5H-pyrrolo[3,2-d]pyrimidine-7-carboxylic acid ((R)-1-acetyl-pyrrolidin- 3-yl)-amide; 4-(5-Cyclopropylmethoxy-benzo[1,3]dioxol-4-yl)-5H-pyrrolo[3,2-d]pyrimidine-7-carboxylic acid [(R)-1-(1-cyclopropyl-methanoyl)-pyrrolidin-3-yl]amide; (R)-3-({1-[4-(5-Cyclopropylmethoxy-benzo[1,3]dioxol-4-yl)-5H-pyrrolo[3,2-d]pyrimidin-7-yl]-methanoyl}-amino)-pyrrolidine-1-carboxylic acid ethyl ester; 4-(5-Cyclopropylmethoxy-benzo[1,3]dioxol-4-yl)-5H-pyrrolo[3,2-d]pyrimidine-7-carboxylic acid ((S)-1-formyl-pyrrolidin-3-yl)-amide; 4-(5-Cyclopropylmethoxy-benzo[1,3]dioxol-4-yl)-5H-pyrrolo[3,2-d]pyrimidine-7-carboxylic acid ((S)-1-acetyl-pyrrolidin-3-yl)-amide; 4-(5-Cyclopropylmethoxy-benzo[1,3]dioxol-4-yl)-5H-pyrrolo[3,2-d]pyrimidine-7-carboxylic acid [(S)-1-(1-cyclopropyl-methanoyl)-pyrrolidin-3-yl]amide; 4-(5-Cyclopropylmethoxy-benzo[1,3]dioxol-4-yl)-5H-pyrrolo[3,2-d]pyrimidine-7-carboxylic acid [(S)-1-(2-methoxy-ethanoyl)-pyrrolidin-3-yl]-amide; (S)-3-({1-[4-(5-Cyclopropylmethoxy-benzo[1,3]dioxol-4-yl)-5H-pyrrolo[3,2-d]pyrimidin-7-yl]-methanoyl}-amino)-pyrrolidine-1-carboxylic acid ethyl ester; 4-(5-Cyclopropylmethoxy-benzo[1,3]dioxol-4-yl)-5H-pyrrolo[3,2-d]pyrimidine-7-carboxylic acid (1-formyl-piperidin-4-ylmethyl)-amide; 4-(5-Cyclopropylmethoxy-benzo[1,3]dioxol-4-yl)-5H-pyrrolo[3,2-d]pyrimidine-7-carboxylic acid (1-acetyl-piperidin-4-ylmethyl)-amide; 4-(5-Cyclopropylmethoxy-benzo[1,3]dioxol-4-yl)-5H-pyrrolo[3,2-d]pyrimidine-7-carboxylic acid [141-cyclopropyl-methanoyl)-piperidin-4-ylmethyl]-amide; 4-(5-Cyclopropylmethoxy-benzo[1,3]dioxol-4-yl)-5H-pyrrolo[3,2-d]pyrimidine-7-carboxylic acid [1-(2-methoxy-ethanoyl)-piperidin-4-ylmethyl]-amide; 4-[({1-[4-(5-Cyclopropylmethoxy-benzo[1,3]dioxol-4-yl)-5H-pyrrolo[3,2-d]pyrimidin-7-yl]-methanoyl}-amino)-methyl]-piperidine-1-carboxylic acid ethyl ester; 4-(5-Cyclopropylmethoxy-benzo[1,3]dioxol-4-yl)-5H-pyrrolo[3,2-d]pyrimidine-7-carboxylic acid (1-formyl-piperidin-3-ylmethyl)-amide; 4-(5-Cyclopropylmethoxy-benzo[1,3]dioxol-4-yl)-5H-pyrrolo[3,2-d]pyrimidine-7-carboxylic acid (1-propionyl-piperidin-3-ylmethyl)-amide; 4-(5-Cyclopropylmethoxy-benzo[1,3]dioxol-4-yl)-5H-pyrrolo[3,2-d]pyrimidine-7-carboxylic acid [1-(2-methoxy-acetyl)piperidin-3-ylmethyl]-amide; 3-({[4-(5-Cyclopropylmethoxy-benzo[1,3]dioxol-4-yl)-5H-pyrrolo[3,2-d]pyrimidine-7-carbonyl]-amino}-methyl)-piperidine-1-carboxylic acid ethyl ester; 4-(5-Cyclopropylmethoxy-benzo[1,3]dioxol-4-yl)-5H-pyrrolo[3,2-d]pyrimidine-7-carboxylic acid (1-formyl-pyrrolidin-3-ylmethyl)-amide; 4-(5-Cyclopropylmethoxy-benzo[1,3]dioxol-4-yl)-5H-pyrrolo[3,2-d]pyrimidine-7-carboxylic acid [1-(2-methoxy-acetyl)-pyrrolidin-3-ylmethyl]-amide; 3-({[4-(5-Cyclopropylmethoxy-benzo[1,3]dioxol-4-yl)-5H-pyrrolo[3,2-d]pyrimidine-7-carbonyl]-amino}-methyl)-pyrrolidine-1-carboxylic acid ethyl ester; 4-(5-Cyclopropylmethoxy-benzo[1,3]dioxol-4-yl)-5H-pyrrolo[3,2-d]pyrimidine-7-carboxylic acid (4-formyl-morpholin-2-ylmethyl)-amide; 4-(5-Cyclopropylmethoxy-benzo[1,3]dioxol-4-yl)-5H-pyrrolo[3,2-d]pyrimidine-7-carboxylic acid (4-propionyl-morpholin-2-ylmethyl)-amide; 4-(5-Cyclopropylmethoxy-benzo[1,3]dioxol-4-yl)-5H-pyrrolo[3,2-d]pyrimidine-7-carboxylic acid [4-(2-methoxy-acetyl)-morpholin-2-ylmethyl]-amide; 2-({[4-(5-Cyclopropylmethoxy-benzo[1,3]dioxol-4-yl)-5H-pyrrolo[3,2-d]pyrimidine-7-carbonyl]-amino}-methyl)-morpholine-4-carboxylic acid ethyl ester; 4-(5-Cyclopropylmethoxy-benzo[1,3]dioxol-4-yl)-5H-pyrrolo[3,2-d]pyrimidine-7-carboxylic acid (1-acetyl-azetidin-3-yl)-amide; 4-(5-Cyclopropylmethoxy-benzo[1,3]dioxol-4-yl)-5H-pyrrolo[3,2-d]pyrimidine-7-carboxylic acid (1-propionyl-azetidin-3-yl)-amide; 4-(5-Cyclopropylmethoxy-benzo[1,3]dioxol-4-yl)-5H-pyrrolo[3,2-d]pyrimidine-7-carboxylic acid [1-(2-methoxy-ethanoyl)-azetidin-3-yl]-amide; 3-({1-[4-(5-Cyclopropylmethoxy-benzo[1,3]dioxol-4-yl)-5H-pyrrolo[3,2-d]pyrimidin-7-yl]-methanoyl}-amino)-azetidine-1-carboxylic acid ethyl ester; 4-(5-Cyclopropylmethoxy-benzo[1,3]dioxol-4-yl)-5H-pyrrolo[3,2-d]pyrimidine-7-carboxylic acid (1-formyl-piperidin-4-yl)-amide; 4-(5-Cyclopropylmethoxy-benzo[1,3]dioxol-4-yl)-5H-pyrrolo[3,2-d]pyrimidine-7-carboxylic acid ((S)-1-propionyl-piperidin-3-yl)-amide; 4-(5-Cyclopropylmethoxy-benzo[1,3]dioxol-4-yl)-5H-pyrrolo[3,2-d]pyrimidine-7-carboxylic acid [(S)-1-(2-methoxy-ethanoyl)-piperidin-3-yl]-amide; 4-(5-Cyclopropylmethoxy-benzo[1,3]dioxol-4-yl)-5H-pyrrolo[3,2-d]pyrimidine-7-carboxylic acid ((S)-1-acetyl-piperidin-3-yl)-amide; 4-(5-Cyclopropylmethoxy-benzo[1,3]dioxol-4-yl)-5H-pyrrolo[3,2-d]pyrimidine-7-carboxylic acid ((R)-1-propionyl-piperidin-3-yl)-amide; 4-(5-Cyclopropylmethoxy-benzo[1,3]dioxol-4-yl)-5H-pyrrolo[3,2-d]pyrimidine-7-carboxylic acid [(R)-1-(2-methoxy-ethanoyl)-piperidin-3-yl]-amide; 4-(5-Cyclopropylmethoxy-benzo[1,3]dioxol-4-yl)-5H-pyrrolo[3,2-d]pyrimidine-7-carboxylic acid ((R)-1-acetyl-piperidin-3-yl)-amide; trans-4-(5-Cyclopropylmethoxy-benzo[1,3]dioxol-4-yl)-5H-pyrrolo[3,2-d]pyrimidine-7-carboxylic acid [4-(2-methoxy-acetylamino)-cyclohexyl]-amide; trans-4-(2-Cyclopropylmethoxy-4-methoxy-phenyl)-5H-pyrrolo[3,2-d]pyrimidine-7-carboxylic acid (4-acetylamino-cyclohexyl)-amide; trans-4-(2-Cyclopropylmethoxy-4-methoxy-phenyl)-5H-pyrrolo[3,2-d]pyrimidine-7-carboxylic acid [4-(cyclopropanecarbonyl-amino)cyclohexyl]-amide; trans-4-(2-Cyclopropylmethoxy-4-methoxy-phenyl)-5H-pyrrolo[3,2-d]pyrimidine-7-carboxylic acid [4-(2-methoxy-acetylamino)-cyclohexyl]-amide; trans-(4-{[4-(2-Cyclopropylmethoxy-4-methoxy-phenyl)-5H-pyrrolo[3,2-d]pyrimidine-7-carbonyl]-amino}-cyclohexyl)-carbamic acid ethyl ester; cis-4-(2-Cyclopropylmethoxy-4-methoxy-phenyl)-5H-pyrrolo[3,2-d]pyrimidine-7-carboxylic acid (4-acetylamino-cyclohexyl)-amide; cis-4-(2-Cyclopropylmethoxy-4-methoxy-phenyl)-5H-pyrrolo[3,2-d]pyrimidine-7-carboxylic acid [4-(cyclopropanecarbonyl-amino)-cyclohexyl]-amide; cis-4-(2-Cyclopropylmethoxy-4-methoxy-phenyl)-5H-pyrrolo[3,2-d]pyrimidine-7-carboxylic acid [4-(2-methoxy-acetylamino)-cyclohexyl]-amide; cis-(4-{[4-(2-Cyclopropylmethoxy-4-methoxy-phenyl)-5H-pyrrolo[3,2-d]pyrimidine-7-carbonyl]-amino}-cyclohexyl)-carbamic acid ethyl ester; 4-(2-Cyclopropylmethoxy-4-methoxy-phenyl)-5H-pyrrolo[3,2-d]pyrimidine-7-carboxylic acid (1-acetyl-piperidin-4-yl)-amide; 4-(2-Cyclopropylmethoxy-4-methoxy-phenyl)-5H-pyrrolo[3,2-d]pyrimidine-7-carboxylic acid [1-(1-cyclopropyl-methanoyl)-piperidin-4-yl]-amide; 4-(2-Cyclopropylmethoxy-4-methoxy-phenyl)-5H-pyrrolo[3,2-d]pyrimidine-7-carboxylic acid [1-(2-methoxy-ethanoyl)-piperidin-4-yl]amide; 4-({1-[4-(2-Cyclopropylmethoxy-4-methoxy-phenyl)-5H-pyrrolo[3,2-d]pyrimidin-7-yl]-methanoyl}-amino)-piperidine-1-carboxylic acid ethyl ester; trans-4-(2-Cyclopropylmethoxy-5-methoxy-phenyl)-5H-pyrrolo[3,2-d]pyrimidine-7-carboxylic acid (4-acetylamino-cyclohexyl)-amide; trans-4-(2-Cyclopropylmethoxy-5-methoxy-phenyl)-5H-pyrrolo[3,2-d]pyrimidine-7-carboxylic acid [4-(cyclopropanecarbonyl-amino)cyclohexyl]-amide; trans-4-(2-Cyclopropylmethoxy-5-methoxy-phenyl)-5H-pyrrolo[3,2-d]pyrimidine-7-carboxylic acid [4-(2-methoxy-acetylamino)-cyclohexyl]-amide; trans-(4-{[4-(2-Cyclopropylmethoxy-5-methoxy-phenyl)-5H-pyrrolo[3,2-d]pyrimidine-7-carbonyl]-amino}-cyclohexyl)-carbamic acid ethyl ester; cis-4-(2-Cyclopropylmethoxy-5-methoxy-phenyl)-5H-pyrrolo[3,2-d]pyrimidine-7-carboxylic acid (4-acetylamino-cyclohexyl)-amide; cis-4-(2-Cyclopropylmethoxy-5-methoxy-phenyl)-5H-pyrrolo[3,2-d]pyrimidine-7-carboxylic acid [4-(cyclopropanecarbonyl-amino)cyclohexyl]-amide; cis-4-(2-Cyclopropylmethoxy-5-methoxy-phenyl)-5H-pyrrolo[3,2-d]pyrimidine-7-carboxylic acid [4-(2-methoxy-acetylamino)-cyclohexyl]-amide; cis-(4-{[4-(2-Cyclopropylmethoxy-5-methoxy-phenyl)-5H-pyrrolo[3,2-d]pyrimidine-7-carbonyl]-amino}-cyclohexyl)-carbamic acid ethyl ester; 4-(2-Cyclopropylmethoxy-5-methoxy-phenyl)-5H-pyrrolo[3,2-d]pyrimidine-7-carboxylic acid (1-acetyl-piperidin-4-yl)-amide; 4-(2-Cyclopropylmethoxy-5-methoxy-phenyl)-5H-pyrrolo[3,2-d]pyrimidine-7-carboxylic acid (1-cyclopropanecarbonyl-piperidin-4-yl)-amide; 4-(2-Cyclopropylmethoxy-5-methoxy-phenyl)-5H-pyrrolo[3,2-d]pyrimidine-7-carboxylic acid [1-(2-methoxy-acetyl)-piperidin-4-yl]-amide; 4-{[4-(2-Cyclopropylmethoxy-5-methoxy-phenyl)-5H-pyrrolo[3,2-d]pyrimidine-7-carbonyl]-amino}-piperidine-1-carboxylic acid ethyl ester; cis-4-(2-Cyclopropylmethoxy-4-fluoro-phenyl)-5H-pyrrolo[3,2-d]pyrimidine-7-carboxylic acid (4-acetylamino-cyclohexyl)-amide; cis-4-(2-Cyclopropylmethoxy-4-fluoro-phenyl)-5H-pyrrolo[3,2-d]pyrimidine-7-carboxylic acid [4-(2-methoxy-acetylamino)-cyclohexyl]-amide; cis-(4-{[4-(2-Cyclopropylmethoxy-4-fluoro-phenyl)-5H-pyrrolo[3,2-d]pyrimidine-7-carbonyl]-amino}-cyclohexyl)-carbamic acid ethyl ester; trans-4-(2-Cyclopropylmethoxy-4-fluoro-phenyl)-5H-pyrrolo[3,2-d]pyrimidine-7-carboxylic acid (4-acetylamino-cyclohexyl)-amide; trans-4-(2-Cyclopropylmethoxy-4-fluoro-phenyl)-5H-pyrrolo[3,2-d]pyrimidine-7-carboxylic acid [4-(2-methoxy-acetylamino)-cyclohexyl]-amide; trans-(4-{[4-(2-Cyclopropylmethoxy-4-fluoro-phenyl)-5H-pyrrolo[3,2-d]pyrimidine-7-carbonyl]-amino}-cyclohexyl)-carbamic acid ethyl ester; 4-(2-Cyclopropylmethoxy-4-fluoro-phenyl)-5H-pyrrolo[3,2-d]pyrimidine-7-carboxylic acid (1-acetyl-piperidin-4-yl)-amideter; 4-(2-Cyclopropylmethoxy-4-fluoro-phenyl)-5H-pyrrolo[3,2-d]pyrimidine-7-carboxylic acid (1-propionyl-piperidin-4-yl)-amide; 4-(2-Cyclopropylmethoxy-4-fluoro-phenyl)-5H-pyrrolo[3,2-d]pyrimidine-7-carboxylic acid [1-(2-methoxy-acetyl)-piperidin-4-yl]-amide; 4-(2-Cyclopropylmethoxy-5-fluoro-phenyl)-5H-pyrrolo[3,2-d]pyrimidine-7-carboxylic acid (1-acetyl-piperidin-4-yl)-amide; 4-(2-Cyclopropylmethoxy-5-fluoro-phenyl)-5H-pyrrolo[3,2-d]pyrimidine-7-carboxylic acid (1-propionyl-piperidin-4-yl)-amide; 4-(2-Cyclopropylmethoxy-5-fluoro-phenyl)-5H-pyrrolo[3,2-d]pyrimidine-7-carboxylic acid [1-(2-methoxy-acetyl)-piperidin-4-yl]-amide; trans-4-(2-Cyclopropylmethoxy-5-fluoro-phenyl)-5H-pyrrolo[3,2-d]pyrimidine-7-carboxylic acid (4-acetylamino-cyclohexyl)-amide; trans-4-(2-Cyclopropylmethoxy-5-fluoro-phenyl)-5H-pyrrolo[3,2-d]pyrimidine-7-carboxylic acid (4-propionylamino-cyclohexyl)-amide; trans-4-(2-Cyclopropylmethoxy-5-fluoro-phenyl)-5H-pyrrolo[3,2-d]pyrimidine-7-carboxylic acid [4-(2-methoxy-acetylamino)-cyclohexyl]-amide; trans-4-(2-Cyclopropylmethoxy-phenyl)-5H-pyrrolo[3,2-d]pyrimidine-7-carboxylic acid (4-acetylamino-cyclohexyl)-amide; trans-4-(2-Cyclopropylmethoxy-phenyl)-5H-pyrrolo[3,2-d]pyrimidine-7-carboxylic acid [4-(2-methoxy-acetylamino)-cyclohexyl]-amide; trans-(4-{[4-(2-Cyclopropylmethoxy-phenyl)-5H-pyrrolo[3,2-d]pyrimidine-7-carbonyl]-amino}-cyclohexyl)-carbamic acid ethyl ester; trans-4-(2-Cyclopropylmethoxy-phenyl)-5H-pyrrolo[3,2-d]pyrimidine-7-carboxylic acid [4-(cyclopropanecarbonyl-amino)cyclohexyl]-amide; 4-(2-Cyclopropylmethoxy-phenyl)-5H-pyrrolo[3,2-d]pyrimidine-7-carboxylic acid (1-acetyl-piperidin-4-yl)-amide; 4-{[4-(2-Cyclopropylmethoxy-phenyl)-5H-pyrrolo[3,2-d]pyrimidine-7-carbonyl]-amino}-piperidine-1-carboxylic acid ethyl ester; 4-(2-Cyclopropylmethoxy-phenyl)-5H-pyrrolo[3,2-d]pyrimidine-7-carboxylic acid (1-cyclopropanecarbonyl-piperidin-4-yl)-amide; 4-(2-Cyclopropylmethoxy-4-fluoro-5-methoxy-phenyl)-5H-pyrrolo[3,2-d]pyrimidine-7-carboxylic acid (1-propionyl-piperidin-4-yl)-amide; 4-(2-Cyclopropylmethoxy-4-fluoro-5-methoxy-phenyl)-5H-pyrrolo[3,2-d]pyrimidine-7-carboxylic acid [1-(2-methoxy-ethanoyl)-piperidin-4-yl]amide; 4-(2-Cyclopropylmethoxy-4-fluoro-5-methoxy-phenyl)-5H-pyrrolo[3,2-d]pyrimidine-7-carboxylic acid (1-acetyl-piperidin-4-yl)-amide; 4-(2-Cyclopropylmethoxy-4-fluoro-5-methoxy-phenyl)-5H-pyrrolo[3,2-d]pyrimidine-7-carboxylic acid ((R)-1-acetyl-piperidin-3-yl)-amide; 4-(2-Cyclopropylmethoxy-4-fluoro-5-methoxy-phenyl)-5H-pyrrolo[3,2-d]pyrimidine-7-carboxylic acid ((R)-1-propionyl-piperidin-3-yl)-amide; 4-(2-Cyclopropylmethoxy-4-fluoro-5-methoxy-phenyl)-5H-pyrrolo[3,2-d]pyrimidine-7-carboxylic acid [(R)-1-(2-methoxy-acetyl)piperidin-3-yl]amide; 4-(2-Cyclopropylmethoxy-4-fluoro-5-methoxy-phenyl)-5H-pyrrolo[3,2-d]pyrimidine-7-carboxylic acid ((R)-1-acetyl-pyrrolidin-3-yl)-amide; 4-(2-Cyclopropylmethoxy-4-fluoro-5-methoxy-phenyl)-5H-pyrrolo[3,2-d]pyrimidine-7-carboxylic acid ((R)-1-propionyl-pyrrolidin-3-yl)-amide; 4-(2-Cyclopropylmethoxy-4-fluoro-5-methoxy-phenyl)-5H-pyrrolo[3,2-d]pyrimidine-7-carboxylic acid [(R)-1-(2-methoxy-acetyl)-pyrrolidin-3-yl]amide; trans-4-(2-Cyclopropylmethoxy-5-fluoro-4-methoxy-phenyl)-5H-pyrrolo[3,2-d]pyrimidine-7-carboxylic acid (4-acetylamino-cyclohexyl)-amide; trans-4-(2-Cyclopropylmethoxy-5-fluoro-4-methoxy-phenyl)-5H-pyrrolo[3,2-d]pyrimidine-7-carboxylic acid [4-(2-methoxy-acetylamino)-cyclohexyl]-amide; 4-(2-Cyclopropylmethoxy-5-fluoro-4-methoxy-phenyl)-5H-pyrrolo[3,2-d]pyrimidine-7-carboxylic acid (1-acetyl-piperidin-4-yl)-amide; 4-(2-Cyclopropylmethoxy-5-fluoro-4-methoxy-phenyl)-5H-pyrrolo[3,2-d]pyrimidine-7-carboxylic acid [1-(2-methoxy-ethanoyl)-piperidin-4-yl]amide; 4-(2-Cyclopropylmethoxy-5-fluoro-4-methoxy-phenyl)-5H-pyrrolo[3,2-d]pyrimidine-7-carboxylic acid (1-propionyl-piperidin-4-yl)-amide; 4-(2-Cyclopropylmethoxy-5-fluoro-4-methoxy-phenyl)-5H-pyrrolo[3,2-d]pyrimidine-7-carboxylic acid ((R)-1-propionyl-piperidin-3-yl)-amide; 4-(2-Cyclopropylmethoxy-5-fluoro-4-methoxy-phenyl)-5H-pyrrolo[3,2-d]pyrimidine-7-carboxylic acid [(R)-1-(2-methoxy-ethanoyl)-piperidin-3-yl]amide; 4-(2-Cyclopropylmethoxy-5-fluoro-4-methoxy-phenyl)-5H-pyrrolo[3,2-d]pyrimidine-7-carboxylic acid ((R)-1-acetyl-piperidin-3-yl)-amide; 4-(2-Cyclopropylmethoxy-5-fluoro-4-methoxy-phenyl)-5H-pyrrolo[3,2-d]pyrimidine-7-carboxylic acid ((S)-1-propionyl-piperidin-3-yl)-amide; 4-(2-Cyclopropylmethoxy-5-fluoro-4-methoxy-phenyl)-5H-pyrrolo[3,2-d]pyrimidine-7-carboxylic acid [(S)-1-(2-methoxy-ethanoyl)-piperidin-3-yl]amide; 4-(2-Cyclopropylmethoxy-5-fluoro-4-methoxy-phenyl)-5H-pyrrolo[3,2-d]pyrimidine-7-carboxylic acid ((S)-1-acetyl-piperidin-3-yl)-amide; 4-(2-Cyclopropylmethoxy-5-fluoro-4-methoxy-phenyl)-5H-pyrrolo[3,2-d]pyrimidine-7-carboxylic acid ((R)-1-acetyl-pyrrolidin-3-yl)-amide; 4-(2-Cyclopropylmethoxy-5-fluoro-4-methoxy-phenyl)-5H-pyrrolo[3,2-d]pyrimidine-7-carboxylic acid ((R)-1-propionyl-pyrrolidin-3-yl)-amide; 4-(2-Cyclopropylmethoxy-5-fluoro-4-methoxy-phenyl)-5H-pyrrolo[3,2-d]pyrimidine-7-carboxylic acid [(R)-1-(2-methoxy-acetyl)-pyrrolidin-3-yl]-amide; trans-4-(2-Cyclopropylmethoxy-5-methyl-phenyl)-5H-pyrrolo[3,2-d]pyrimidine-7-carboxylic acid (4-acetylamino-cyclohexyl)-amide; trans-4-(2-Cyclopropylmethoxy-5-methyl-phenyl)-5H-pyrrolo[3,2-d]pyrimidine-7-carboxylic acid [4-(2- methoxy-acetylamino)-cyclohexyl]-amide; trans-(4-{[4-(2-Cyclopropylmethoxy-5-methyl-phenyl)-5H-pyrrolo[3,2-d]pyrimidine-7-carbonyl]-amino}-cyclohexyl)-carbamic acid ethyl ester; 4-(2-Cyclopropylmethoxy-5-methyl-phenyl)-5H-pyrrolo[3,2-d]pyrimidine-7-carboxylic acid (1-acetyl-piperidin-4-yl)-amide; 4-(2-Cyclopropylmethoxy-5-methyl-phenyl)-5H-pyrrolo[3,2-d]pyrimidine-7-carboxylic acid [1-(2-methoxy-acetyl)-piperidin-4-yl]-amide; 4-{[4-(2-Cyclopropylmethoxy-5-methyl-phenyl)-5H-pyrrolo[3,2-d]pyrimidine-7-carbonyl]-amino}-piperidine-1-carboxylic acid ethyl ester; trans-4-(5-Cyclobutylmethoxy-benzo[1,3]dioxol-4-yl)-5H-pyrrolo[3,2-d]pyrimidine-7-carboxylic acid (4-acetylamino-cyclohexyl)-amide; trans-4-(5-Cyclobutylmethoxy-benzo[1,3]dioxol-4-yl)-5H-pyrrolo[3,2-d]pyrimidine-7-carboxylic acid [4-(cyclopropanecarbonyl-amino)-cyclohexyl]-amide; trans-4-(5-Cyclobutylmethoxy-benzo[1,3]dioxol-4-yl)-5H-pyrrolo[3,2-d]pyrimidine-7-carboxylic acid [4-(2-methoxy-ethanoylamino)-cyclohexyl]-amide; 4-(5-Cyclobutylmethoxy-benzo[1,3]dioxol-4-yl)-5H-pyrrolo[3,2-d]pyrimidine-7-carboxylic acid (1-acetyl-piperidin-4-yl)-amide; 4-(5-Cyclobutylmethoxy-benzo[1,3]dioxol-4-yl)-5H-pyrrolo[3,2-d]pyrimidine-7-carboxylic acid [1-(1-cyclopropyl-methanoyl)-piperidin-4-yl]amide; 4-(5-Cyclobutylmethoxy-benzo[1,3]dioxol-4-yl)-5H-pyrrolo[3,2-d]pyrimidine-7-carboxylic acid [1-(2-methoxy-ethanoyl)-piperidin-4-yl]amide; 4-({1-[4-(5-Cyclobutylmethoxy-benzo[1,3]dioxol-4-yl)-5H-pyrrolo[3,2-d]pyrimidin-7-yl]-methanoyl}-amino)-piperidine-1-carboxylic acid ethyl ester; 4-(5-Ethoxy-benzo[1,3]dioxol-4-yl)-5H-pyrrolo[3,2-d]pyrimidine-7-carboxylic acid (1-propionyl-piperidin-4-yl)-amide; 4-{[4-(5-Ethoxy-benzo[1,3]dioxol-4-yl)-5H-pyrrolo[3,2-d]pyrimidine-7-carbonyl]-amino}-piperidine-1-carboxylic acid ethyl ester; 4-(5-Ethoxy-benzo[1,3]dioxol-4-yl)-5H-pyrrolo[3,2-d]pyrimidine-7-carboxylic acid [1-(2-methoxy-acetyl)piperidin-4-yl]amide; 4-(5-Ethoxy-benzo[1,3]dioxol-4-yl)-5H-pyrrolo[3,2-d]pyrimidine-7-carboxylic acid ((R)-1-propionyl-pyrrolidin-3-yl)-amide; (R)-3-{[4-(5-Ethoxy-benzo[1,3]dioxol-4-yl)-5H-pyrrolo[3,2-d]pyrimidine-7-carbonyl]-amino}-pyrrolidine-1-carboxylic acid ethyl ester; 4-(5-Ethoxy-benzo[1,3]dioxol-4-yl)-5H-pyrrolo[3,2-d]pyrimidine-7-carboxylic acid ((R)-1-(2-methoxy-acetyl)-pyrrolidin-amide; 4-(5-Propoxy-benzo[1,3]dioxol-4-yl)-5H-pyrrolo[3,2-d]pyrimidine-7-carboxylic acid (1-propionyl-piperidin-4-yl)-amide; 4-{[4-(5-Propoxy-benzo[1,3]dioxol-4-yl)-5H-pyrrolo[3,2-d]pyrimidine-7-carbonyl]-amino}-piperidine-1-carboxylic acid ethyl ester; 4-(5-Propoxy-benzo[1,3]dioxol-4-yl)-5H-pyrrolo[3,2-d]pyrimidine-7-carboxylic acid ((R)-1-propionyl-pyrrolidin-3-yl)-amide; (R)-3-{[4-(5-Propoxy-benzo[1,3]dioxol-4-yl)-5H-pyrrolo[3,2-d]pyrimidine-7-carbonyl]-amino}-pyrrolidine-1-carboxylic acid ethyl ester; 4-(5-Propoxy-benzo[1,3]dioxol-4-yl)-5H-pyrrolo[3,2-d]pyrimidine-7-carboxylic acid [(R)-1-(2-methoxy-acetyl)-pyrrolidin-3-yl]-amide; 4-(5-Butoxy-benzo[1,3]dioxol-4-yl)-5H-pyrrolo[3,2-d]pyrimidine-7-carboxylic acid (1-propionyl-piperidin-4-yl)-amide; 4-{[4-(5-Butoxy-benzo[1,3]dioxol-4-yl)-5H-pyrrolo[3,2-d]pyrimidine-7-carbonyl]-amino}-piperidine-1-carboxylic acid ethyl ester; 4-(5-Butoxy-benzo[1,3]dioxol-4-yl)-5H-pyrrolo[3,2-d]pyrimidine-7-carboxylic acid (1-formyl-piperidin-4-yl)-amide; 4-(5-Butoxy-benzo[1,3]dioxol-4-yl)-5H-pyrrolo[3,2-d]pyrimidine-7-carboxylic acid (1-propionyl-piperidin-3-yl)-amide; 3-{[4-(5-Butoxy-benzo[1,3]dioxol-4-yl)-5H-pyrrolo[3,2-d]pyrimidine-7-carbonyl]-amino}-piperidine-1-carboxylic acid ethyl ester; 4-(5-Butoxy-benzo[1,3]dioxol-4-yl)-5H-pyrrolo[3,2-d]pyrimidine-7-carboxylic acid [1-(2-methoxy-acetyl)piperidin-3-yl]amide; 4-(5-Butoxy-benzo[1,3]dioxol-4-yl)-5H-pyrrolo[3,2-d]pyrimidine-7-carboxylic acid ((R)-1-propionyl-pyrrolidin-3-yl)-amide; (R)-3-{[4-(5-Butoxy-benzo[1,3]dioxol-4-yl)-5H-pyrrolo[3,2-d]pyrimidine-7-carbonyl]-amino}-pyrrolidine-1-carboxylic acid ethyl ester; cis-4-[4-Methoxy-2-(2-methoxy-ethoxy)-phenyl]-5H-pyrrolo[3,2-d]pyrimidine-7-carboxylic acid (4-acetylamino-cyclohexyl)-amide; cis-4-[4-Methoxy-2-(2-methoxy-ethoxy)-phenyl]-5H-pyrrolo[3,2-d]pyrimidine-7-carboxylic acid [4-(cyclopropanecarbonyl-amino)-cyclohexyl]-amide; cis-4-[4-Methoxy-2-(2-methoxy-ethoxy)-phenyl]-5H-pyrrolo[3,2-d]pyrimidine-7-carboxylic acid [4-(2-methoxy-acetylamino)-cyclohexyl]-amide; trans-4-[4-Methoxy-2-(2-methoxy-ethoxy)-phenyl]-5H-pyrrolo[3,2-d]pyrimidine-7-carboxylic acid (4-acetylamino-cyclohexyl)-amide; trans-4-[4-Methoxy-2-(2-methoxy-ethoxy)-phenyl]-5H-pyrrolo[3,2-d]pyrimidine-7-carboxylic acid [4-(cyclopropanecarbonyl-amino)cyclohexyl]-amide; trans-4-[4-Methoxy-2-(2-methoxy-ethoxy)-phenyl]-5H-pyrrolo[3,2-d]pyrimidine-7-carboxylic acid [4-(2-methoxy-acetylamino)-cyclohexyl]-amide; 4-[4-Methoxy-2-(2-methoxy-ethoxy)-phenyl]-5H-pyrrolo[3,2-d]pyrimidine-7-carboxylic acid (1-acetyl-piperidin-4-yl)-amide; 4-[4-Methoxy-2-(2-methoxy-ethoxy)-phenyl]-5H-pyrrolo[3,2-d]pyrimidine-7-carboxylic acid (1-cyclopropanecarbonyl-piperidin-4-yl)-amide; 4-[4-Methoxy-2-(2-methoxy-ethoxy)-phenyl]-5H-pyrrolo[3,2-d]pyrimidine-7-carboxylic acid [1-(2-methoxy-acetyl)piperidin-4-yl]-amide; trans-4-[5-(2-Methoxy-ethoxy)-benzo[1,3]dioxol-4-yl]-5H-pyrrolo[3,2-d]pyrimidine-7-carboxylic acid (4-acetylamino-cyclohexyl)-amide; trans-4-[5-(2-Methoxy-ethoxy)-benzo[1,3]dioxol-4-yl]-5H-pyrrolo[3,2-d]pyrimidine-7-carboxylic acid (4-acetylamino-cyclohexyl)-amide; trans-4-[5-(2-Methoxy-ethoxy)-benzo[1,3]dioxol-4-yl]-5H-pyrrolo[3,2-d]pyrimidine-7-carboxylic acid [4-(2-methoxy-acetylamino)-cyclohexyl]-amide; cis-4-[5-(2-Methoxy-ethoxy)-benzo[1,3]dioxol-4-yl]-5H-pyrrolo[3,2-d]pyrimidine-7-carboxylic acid (4-acetylamino-cyclohexyl)-amide; cis-4-[5-(2-Methoxy-ethoxy)-benzo[1,3]dioxol-4-yl]-5H-pyrrolo[3,2-d]pyrimidine-7-carboxylic acid (4-acetylamino-cyclohexyl)-amide; cis-4-[5-(2-Methoxy-ethoxy)-benzo[1,3]dioxol-4-yl]-5H-pyrrolo[3,2-d]pyrimidine-7-carboxylic acid [4-(2-methoxy-acetylamino)-cyclohexyl]-amide; cis-[4-({4-[5-(2-Methoxy-ethoxy)-benzo[1,3]dioxol-4-yl]-5H-pyrrolo[3,2-d]pyrimidine-7-carbonyl}-amino)-cyclohexyl]-carbamic acid ethyl ester; 4-[5-(2-Methoxy-ethoxy)-benzo[1,3]dioxol-4-yl]-5H-pyrrolo[3,2-d]pyrimidine-7-carboxylic acid (1-acetyl-piperidin-4-yl)-amide; 4-[5-(2-Methoxy-ethoxy)-benzo[1,3]dioxol-4-yl]-5H-pyrrolo[3,2-d]pyrimidine-7-carboxylic acid (1-cyclopropanecarbonyl-piperidin-4-yl)-amide; 4-[5-(2-Methoxy-ethoxy)-benzo[1,3]dioxol-4-yl]-5H-pyrrolo[3,2-d]pyrimidine-7-carboxylic acid [1-(2-methoxy-acetyl)-piperidin-4-yl]-amide; 4-(5-Cyclopropylmethoxy-benzo[1,3]dioxol-4-yl)-5H-pyrrolo[3,2-d]pyrimidine-7-carboxylic acid [1-(2-hydroxy-ethanoyl)-piperidin-4-yl]-amide; trans-[4-({1-[4-(5-Cyclopropylmethoxy-benzo[1,3]dioxol-4-yl)-5H-pyrrolo[3,2-d]pyrimidine-7-carboxylic acid [4-(2-hydroxy-ethanoylamino)-cyclohexyl]-amide; trans-[4-({1-[4-(5-Cyclopropylmethoxy-benzo[1,3]dioxol-4-yl)-5H-pyrrolo[3,2-d]pyrimidine-7-carboxylic acid [4-((S)-2-hydroxy-propanoylamino)-cyclohexyl]-amide; cis-[4-({1-[4-(5-Cyclopropylmethoxy-benzo[1,3]dioxol-4-yl)-5H-pyrrolo[3,2-d]pyrimidine-7-carboxylic acid [4-(2-hydroxy-ethanoylamino)-cyclohexyl]-amide; cis-[4-({1-[4-(5-Cyclopropylmethoxy-benzo[1,3]dioxol-4-yl)-5H-pyrrolo[3,2-d]pyrimidine-7-carboxylic acid [4-((S)-2-hydroxy-propanoylamino)-cyclohexyl]-amide; 4-(5-

Cyclopropylmethoxy-benzo[1,3]dioxol-4-yl)-5H-pyrrolo[3,2-d]pyrimidine-7-carboxylic acid [1-((S)-2-hydroxy-propanoyl)-piperidin-4-yl]-amide; trans-4-(5-Cyclopropylmethoxy-benzo[1,3]dioxol-4-yl)-5H-pyrrolo[3,2-d]pyrimidine-7-carboxylic acid {4-[(1-hydroxy-cyclopropanecarbonyl)-amino]-cyclohexyl}-amide; cis-4-(5-Cyclopropylmethoxy-benzo[1,3]dioxol-4-yl)-5H-pyrrolo[3,2-d]pyrimidine-7-carboxylic acid {4-[(1-hydroxy-cyclopropanecarbonyl)-amino]-cyclohexyl}-amide; 4-(5-Cyclopropylmethoxy-benzo[1,3]dioxol-4-yl)-5H-pyrrolo[3,2-d]pyrimidine-7-carboxylic acid {1-[1-(1-hydroxy-cyclopropyl)-methanoyl]-piperidin-4-yl}-amide; 4-(5-Cyclopropylmethoxy-benzo[1,3]dioxol-4-yl)-5H-pyrrolo[3,2-d]pyrimidine-7-carboxylic acid [(R)-1-(2-hydroxy-ethanoyl)-pyrrolidin-3-yl]-amide; 4-(5-Cyclopropylmethoxy-benzo[1,3]dioxol-4-yl)-5H-pyrrolo[3,2-d]pyrimidine-7-carboxylic acid [(R)-1-((S)-2-hydroxy-propanoyl)-pyrrolidin-3-yl]amide; 4-(5-Cyclopropylmethoxy-benzo[1,3]dioxol-4-yl)-5H-pyrrolo[3,2-d]pyrimidine-7-carboxylic acid {(R)-1-[1-(1-hydroxy-cyclopropyl)-methanoyl]-pyrrolidin-3-yl}-amide; 4-(5-Cyclopropylmethoxy-benzo[1,3]dioxol-4-yl)-5H-pyrrolo[3,2-d]pyrimidine-7-carboxylic acid [(S)-1-(2-hydroxy-ethanoyl)-pyrrolidin-3-yl]-amide; 4-(5-Cyclopropylmethoxy-benzo[1,3]dioxol-4-yl)-5H-pyrrolo[3,2-d]pyrimidine-7-carboxylic acid [(S)-1-((S)-2-hydroxy-propanoyl)-pyrrolidin-3-yl]amide; 4-(5-Cyclopropylmethoxy-benzo[1,3]dioxol-4-yl)-5H-pyrrolo[3,2-d]pyrimidine-7-carboxylic acid {(S)-1-[1-(1-hydroxy-cyclopropyl)-methanoyl]-pyrrolidin-3-yl}-amide; 4-(5-Cyclopropylmethoxy-benzo[1,3]dioxol-4-yl)-5H-pyrrolo[3,2-d]pyrimidine-7-carboxylic acid [1-(2-hydroxy-ethanoyl)-piperidin-4-ylmethyl]-amide; 4-(5-Cyclopropylmethoxy-benzo[1,3]dioxol-4-yl)-5H-pyrrolo[3,2-d]pyrimidine-7-carboxylic acid [1-((S)-2-hydroxy-propanoyl)piperidin-4-ylmethyl]-amide; 4-(5-Cyclopropylmethoxy-benzo[1,3]dioxol-4-yl)-5H-pyrrolo[3,2-d]pyrimidine-7-carboxylic acid {1-[1-(1-hydroxy-cyclopropyl)-methanoyl]-piperidin-4-ylmethyl}-amide; 4-(5-Cyclopropylmethoxy-benzo[1,3]dioxol-4-yl)-5H-pyrrolo[3,2-d]pyrimidine-7-carboxylic acid [1-(2-hydroxy-acetyl)piperidin-3-ylmethyl]-amide; 4-(5-Cyclopropylmethoxy-benzo[1,3]dioxol-4-yl)-5H-pyrrolo[3,2-d]pyrimidine-7-carboxylic acid [1-((S)-2-hydroxy-propionyl)-piperidin-3-ylmethyl]-amide; 4-(5-Cyclopropylmethoxy-benzo[1,3]dioxol-4-yl)-5H-pyrrolo[3,2-d]pyrimidine-7-carboxylic acid [1-(2-hydroxy-acetyl)-pyrrolidin-3-ylmethyl]-amide; 4-(5-Cyclopropylmethoxy-benzo[1,3]dioxol-4-yl)-5H-pyrrolo[3,2-d]pyrimidine-7-carboxylic acid [1-((S)-2-hydroxy-propionyl)-pyrrolidin-3-ylmethyl]-amide; 4-(5-Cyclopropylmethoxy-benzo[1,3]dioxol-4-yl)-5H-pyrrolo[3,2-d]pyrimidine-7-carboxylic acid [4-(2-hydroxy-acetyl)morpholin-2-ylmethyl]-amide; 4-(5-Cyclopropylmethoxy-benzo[1,3]dioxol-4-yl)-5H-pyrrolo[3,2-d]pyrimidine-7-carboxylic acid [4-((S)-2-hydroxy-propionyl)-morpholin-2-ylmethyl]-amide; 4-(5-Cyclopropylmethoxy-benzo[1,3]dioxol-4-yl)-5H-pyrrolo[3,2-d]pyrimidine-7-carboxylic acid [1-(2-hydroxy-ethanoyl)-azetidin-3-yl]amide; 4-(5-Cyclopropylmethoxy-benzo[1,3]dioxol-4-yl)-5H-pyrrolo[3,2-d]pyrimidine-7-carboxylic acid [1-((S)-2-hydroxy-propanoyl)-azetidin-3-yl]amide; 4-(5-Cyclopropylmethoxy-benzo[1,3]dioxol-4-yl)-5H-pyrrolo[3,2-d]pyrimidine-7-carboxylic acid [(S)-1-((S)-2-hydroxy-propanoyl)-piperidin-3-yl]-amide; 4-(5-Cyclopropylmethoxy-benzo[1,3]dioxol-4-yl)-5H-pyrrolo[3,2-d]pyrimidine-7-carboxylic acid [(R)-1-((S)-2-hydroxy-propanoyl)-piperidin-3-yl]-amide; trans-4-(2-Cyclopropylmethoxy-4-methoxy-phenyl)-5H-pyrrolo[3,2-d]pyrimidine-7-carboxylic acid [4-(2-hydroxy-acetylamino)-cyclohexyl]-amide; trans-4-(2-Cyclopropylmethoxy-4-methoxy-phenyl)-5H-pyrrolo[3,2-d]pyrimidine-7-carboxylic acid [4-((S)-2-hydroxy-propionylamino)-cyclohexyl]-amide; trans-4-(2-Cyclopropylmethoxy-4-methoxy-phenyl)-5H-pyrrolo[3,2-d]pyrimidine-7-carboxylic acid {4-[(1-hydroxy-cyclopropanecarbonyl)-amino]-cyclohexyl}-amide; cis-4-(2-Cyclopropylmethoxy-4-methoxy-phenyl)-5H-pyrrolo[3,2-d]pyrimidine-7-carboxylic acid [4-(2-hydroxy-acetylamino)-cyclohexyl]-amide; cis-4-(2-Cyclopropylmethoxy-4-methoxy-phenyl)-5H-pyrrolo[3,2-d]pyrimidine-7-carboxylic acid [4-((S)-2-hydroxy-propionylamino)-cyclohexyl]-amide; cis-4-(2-Cyclopropylmethoxy-4-methoxy-phenyl)-5H-pyrrolo[3,2-d]pyrimidine-7-carboxylic acid {4-[(1-hydroxy-cyclopropanecarbonyl)-amino]-cyclohexyl}-amide; 4-(2-Cyclopropylmethoxy-4-methoxy-phenyl)-5H-pyrrolo[3,2-d]pyrimidine-7-carboxylic acid [1-(2-hydroxy-ethanoyl)-piperidin-4-yl]amide; 4-(2-Cyclopropylmethoxy-4-methoxy-phenyl)-5H-pyrrolo[3,2-d]pyrimidine-7-carboxylic acid [1-((S)-2-hydroxy-propanoyl)-piperidin-4-yl]-amide; 4-(2-Cyclopropylmethoxy-4-methoxy-phenyl)-5H-pyrrolo[3,2-d]pyrimidine-7-carboxylic acid {1-[1-(1-hydroxy-cyclopropyl)-methanoyl]-piperidin-4-yl}-amide; cis-4-(2-Cyclopropylmethoxy-5-methoxy-phenyl)-5H-pyrrolo[3,2-d]pyrimidine-7-carboxylic acid [4-(2-hydroxy-acetylamino)-cyclohexyl]-amide; cis-4-(2-Cyclopropylmethoxy-5-methoxy-phenyl)-5H-pyrrolo[3,2-d]pyrimidine-7-carboxylic acid {4-[(1-hydroxy-cyclopropanecarbonyl)-amino]-cyclohexyl}-amide; trans-4-(2-Cyclopropylmethoxy-5-methoxy-phenyl)-5H-pyrrolo[3,2-d]pyrimidine-7-carboxylic acid {4-[(1-hydroxy-cyclopropanecarbonyl)-amino]-cyclohexyl}-amide; 4-(2-Cyclopropylmethoxy-5-methoxy-phenyl)-5H-pyrrolo[3,2-d]pyrimidine-7-carboxylic acid [1-(2-hydroxy-acetyl)piperidin-4-yl]amide; 4-(2-Cyclopropylmethoxy-5-methoxy-phenyl)-5H-pyrrolo[3,2-d]pyrimidine-7-carboxylic acid [1-((S)-2-hydroxy-propionyl)-piperidin-4-yl]-amide; 4-(2-Cyclopropylmethoxy-5-methoxy-phenyl)-5H-pyrrolo[3,2-d]pyrimidine-7-carboxylic acid [1-(1-hydroxy-cyclopropanecarbonyl)-piperidin-4-yl]-amide; cis-4-(2-Cyclopropylmethoxy-4-fluoro-phenyl)-5H-pyrrolo[3,2-d]pyrimidine-7-carboxylic acid [4-(2-hydroxy-acetylamino)-cyclohexyl]-amide; cis-4-(2-Cyclopropylmethoxy-4-fluoro-phenyl)-5H-pyrrolo[3,2-d]pyrimidine-7-carboxylic acid [4-((S)-2-hydroxy-propionylamino)-cyclohexyl]-amide; cis-4-(2-Cyclopropylmethoxy-4-fluoro-phenyl)-5H-pyrrolo[3,2-d]pyrimidine-7-carboxylic acid {4-[(1-hydroxy-cyclopropanecarbonyl)-amino]-cyclohexyl}-amide; trans-4-(2-Cyclopropylmethoxy-4-fluoro-phenyl)-5H-pyrrolo[3,2-d]pyrimidine-7-carboxylic acid [4-(2-hydroxy-acetylamino)-cyclohexyl]-amide; trans-4-(2-Cyclopropylmethoxy-4-fluoro-phenyl)-5H-pyrrolo[3,2-d]pyrimidine-7-carboxylic acid [4-((S)-2-hydroxy-propionylamino)-cyclohexyl]-amide; trans-4-(2-Cyclopropylmethoxy-4-fluoro-phenyl)-5H-pyrrolo[3,2-d]pyrimidine-7-carboxylic acid {4-[(1-hydroxy-cyclopropanecarbonyl)-amino]-cyclohexyl}-amide; 4-(2-Cyclopropylmethoxy-5-fluoro-phenyl)-5H-pyrrolo[3,2-d]pyrimidine-7-carboxylic acid [1-(2-hydroxy-acetyl)piperidin-4-yl]amide; 4-(2-Cyclopropylmethoxy-5-fluoro-phenyl)-5H-pyrrolo[3,2-d]pyrimidine-7-carboxylic acid [1-((S)-2-hydroxy-propionyl)-piperidin-4-yl]-amide; trans-4-(2-Cyclopropylmethoxy-5-fluoro-phenyl)-5H-pyrrolo[3,2-d]pyrimidine-7-carboxylic acid [4-(2-hydroxy-acetylamino)-cyclohexyl]-amide; trans-4-(2-

Cyclopropylmethoxy-4-fluoro-phenyl)-5H-pyrrolo[3,2-d]pyrimidine-7-carboxylic acid [4-((S)-2-hydroxy-propionylamino)-cyclohexyl]-amide; trans-4-(2-Cyclopropylmethoxy-phenyl)-5H-pyrrolo[3,2-d]pyrimidine-7-carboxylic acid [4-(2-hydroxy-acetylamino)-cyclohexyl]-amide; trans-4-(2-Cyclopropylmethoxy-phenyl)-5H-pyrrolo[3,2-d]pyrimidine-7-carboxylic acid [4-((S)-2-hydroxy-propionylamino)-cyclohexyl]-amide; trans-4-(2-Cyclopropylmethoxy-phenyl)-5H-pyrrolo[3,2-d]pyrimidine-7-carboxylic acid {4-[(1-hydroxy-cyclopropanecarbonyl)-amino]-cyclohexyl}-amide; 4-(2-Cyclopropylmethoxy-phenyl)-5H-pyrrolo[3,2-d]pyrimidine-7-carboxylic acid [1-((S)-2-hydroxy-propionyl)piperidin-4-yl]amide; 4-(2-Cyclopropylmethoxy-4-fluoro-5-methoxy-phenyl)-5H-pyrrolo[3,2-d]pyrimidine-7-carboxylic acid [1-((S)-2-hydroxy-propionyl)-piperidin-4-yl]-amide; 4-(2-Cyclopropylmethoxy-4-fluoro-5-methoxy-phenyl)-5H-pyrrolo[3,2-d]pyrimidine-7-carboxylic acid [(R)-1-(2-hydroxy-acetyl)-piperidin-3-yl]-amide; 4-(2-Cyclopropylmethoxy-4-fluoro-5-methoxy-phenyl)-5H-pyrrolo[3,2-d]pyrimidine-7-carboxylic acid [(R)-1-((S)-2-hydroxy-propionyl)piperidin-3-yl]amide; 4-(2-Cyclopropylmethoxy-4-fluoro-5-methoxy-phenyl)-5H-pyrrolo[3,2-d]pyrimidine-7-carboxylic acid [(R)-1-(2-hydroxy-acetyl)-pyrrolidin-3-yl]-amide; 4-(2-Cyclopropylmethoxy-4-fluoro-5-methoxy-phenyl)-5H-pyrrolo[3,2-d]pyrimidine-7-carboxylic acid [(R)-1-((S)-2-hydroxy-propionyl)-pyrrolidin-3-yl]amide; trans-4-(2-Cyclopropylmethoxy-5-fluoro-4-methoxy-phenyl)-5H-pyrrolo[3,2-d]pyrimidine-7-carboxylic acid [4-(2-hydroxy-acetylamino)-cyclohexyl]-amide; trans-4-(2-Cyclopropylmethoxy-5-fluoro-4-methoxy-phenyl)-5H-pyrrolo[3,2-d]pyrimidine-7-carboxylic acid [4-((S)-2-hydroxy-propionylamino)-cyclohexyl]-amide; trans-4-(2-Cyclopropylmethoxy-5-fluoro-4-methoxy-phenyl)-5H-pyrrolo[3,2-d]pyrimidine-7-carboxylic acid {4-[(1-hydroxy-cyclopropanecarbonyl)-amino]-cyclohexyl}-amide; 4-(2-Cyclopropylmethoxy-5-fluoro-4-methoxy-phenyl)-5H-pyrrolo[3,2-d]pyrimidine-7-carboxylic acid [1-(2-hydroxy-ethanoyl)-piperidin-4-yl]amide; 4-(2-Cyclopropylmethoxy-5-fluoro-4-methoxy-phenyl)-5H-pyrrolo[3,2-d]pyrimidine-7-carboxylic acid [1-((S)-2-hydroxy-propanoyl)-piperidin-4-yl]-amide; 4-(2-Cyclopropylmethoxy-5-fluoro-4-methoxy-phenyl)-5H-pyrrolo[3,2-d]pyrimidine-7-carboxylic acid {1-[1-(1-hydroxy-cyclopropyl)-methanoyl]-piperidin-4-yl}-amide; 4-(2-cyclopropylmethoxy-5-fluoro-4-methoxy-phenyl)-5H-pyrrolo[3,2-d]pyrimidine-7-carboxylic acid [(S)-1-((S)-2-hydroxy-propanoyl)piperidin-3-yl]amide; 4-(2-Cyclopropylmethoxy-5-fluoro-4-methoxy-phenyl)-5H-pyrrolo[3,2-d]pyrimidine-7-carboxylic acid [(R)-1-((S)-2-hydroxy-propanoyl)-piperidin-3-yl]-amide; 4-(2-Cyclopropylmethoxy-5-fluoro-4-methoxy-phenyl)-5H-pyrrolo[3,2-d]pyrimidine-7-carboxylic acid [(R)-1-(2-hydroxy-acetyl)-pyrrolidin-3-yl]amide; 4-(2-Cyclopropylmethoxy-5-fluoro-4-methoxy-phenyl)-5H-pyrrolo[3,2-d]pyrimidine-7-carboxylic acid [(R)-1-((S)-2-hydroxy-propionyl)-pyrrolidin-3-yl]amide; trans-4-(2-Cyclopropylmethoxy-5-methyl-phenyl)-5H-pyrrolo[3,2-d]pyrimidine-7-carboxylic acid [4-(2-hydroxy-acetylamino)-cyclohexyl]-amide; trans-4-(2-Cyclopropylmethoxy-5-methyl-phenyl)-5H-pyrrolo[3,2-d]pyrimidine-7-carboxylic acid [4-((S)-2-hydroxy-propionylamino)-cyclohexyl]-amide; trans-4-(2-Cyclopropylmethoxy-5-methyl-phenyl)-5H-pyrrolo[3,2-d]pyrimidine-7-carboxylic acid {4-[(1-hydroxy-cyclopropanecarbonyl)-amino]-cyclohexyl}-amide; 4-(2-Cyclopropylmethoxy-5-methyl-phenyl)-5H-pyrrolo[3,2-d]pyrimidine-7-carboxylic acid [1-(2-hydroxy-acetyl)-piperidin-4-yl]amide; 4-(2-Cyclopropylmethoxy-5-methyl-phenyl)-5H-pyrrolo[3,2-d]pyrimidine-7-carboxylic acid [1-((S)-2-hydroxy-propionyl)-piperidin-4-yl]-amide; 4-(2-Cyclopropylmethoxy-5-methyl-phenyl)-5H-pyrrolo[3,2-d]pyrimidine-7-carboxylic acid [1-(1-hydroxy-cyclopropanecarbonyl)-piperidin-4-yl]-amide; 4-(5-Ethoxy-benzo[1,3]dioxol-4-yl)-5H-pyrrolo[3,2-d]pyrimidine-7-carboxylic acid [1-((S)-2-hydroxy-propionyl)piperidin-4-yl]amide; 4-(5-Ethoxy-benzo[1,3]dioxol-4-yl)-5H-pyrrolo[3,2-d]pyrimidine-7-carboxylic acid [(R)-1-((S)-2-hydroxy-propionyl)-pyrrolidin-3-yl]-amide; 4-(5-Propoxy-benzo[1,3]dioxol-4-yl)-5H-pyrrolo[3,2-d]pyrimidine-7-carboxylic acid [1-((S)-2-hydroxy-propionyl)piperidin-4-yl]amide; 4-(5-Propoxy-benzo[1,3]dioxol-4-yl)-5H-pyrrolo[3,2-d]pyrimidine-7-carboxylic acid [(R)-1-((S)-2-hydroxy-propionyl)-pyrrolidin-3-yl]-amide; 4-(5-Butoxy-benzo[1,3]dioxol-4-yl)-5H-pyrrolo[3,2-d]pyrimidine-7-carboxylic acid [1-((S)-2-hydroxy-propionyl)-piperidin-4-yl]-amide; 4-(5-Butoxy-benzo[1,3]dioxol-4-yl)-5H-pyrrolo[3,2-d]pyrimidine-7-carboxylic acid [(R)-1-((S)-2-hydroxy-propionyl)-pyrrolidin-3-yl]amide; trans-4-[4-Methoxy-2-(2-methoxy-ethoxy)-phenyl]-5H-pyrrolo[3,2-d]pyrimidine-7-carboxylic acid [4-(2-hydroxy-acetylamino)-cyclohexyl]-amide; trans-4-[4-Methoxy-2-(2-methoxy-ethoxy)-phenyl]-5H-pyrrolo[3,2-d]pyrimidine-7-carboxylic acid [4-((S)-2-hydroxy-propionylamino)-cyclohexyl]-amide; trans-4-[4-Methoxy-2-(2-methoxy-ethoxy)-phenyl]-5H-pyrrolo[3,2-d]pyrimidine-7-carboxylic acid {4-[(1-hydroxy-cyclopropanecarbonyl)-amino]-cyclohexyl}-amide; cis-4-[4-Methoxy-2-(2-methoxy-ethoxy)-phenyl]-5H-pyrrolo[3,2-d]pyrimidine-7-carboxylic acid {4-[(1-hydroxy-cyclopropanecarbonyl)-amino]-cyclohexyl}-amide; 4-[4-Methoxy-2-(2-methoxy-ethoxy)-phenyl]-5H-pyrrolo[3,2-d]pyrimidine-7-carboxylic acid [1-(1-hydroxy-cyclopropanecarbonyl)-piperidin-4-yl]-amide; trans-4-[5-(2-Methoxy-ethoxy)-benzo[1,3]dioxol-4-yl]-5H-pyrrolo[3,2-d]pyrimidine-7-carboxylic acid [4-(2-hydroxy-acetylamino)-cyclohexyl]-amide; cis-4-[5-(2-Methoxy-ethoxy)-benzo[1,3]dioxol-4-yl]-5H-pyrrolo[3,2-d]pyrimidine-7-carboxylic acid [4-(2-hydroxy-acetylamino)-cyclohexyl]-amide; cis-4-[5-(2-Methoxy-ethoxy)-benzo[1,3]dioxol-4-yl]-5H-pyrrolo[3,2-d]pyrimidine-7-carboxylic acid [4-((S)-2-hydroxy-propionylamino)-cyclohexyl]-amide; 4-[5-(2-Methoxy-ethoxy)-benzo[1,3]dioxol-4-yl]-5H-pyrrolo[3,2-d]pyrimidine-7-carboxylic acid [1-((S)-2-hydroxy-propionyl)piperidin-4-yl]amide; 4-(5-Acetyl-2-cyclopropylmethoxy-phenyl)-5H-pyrrolo[3,2-d]pyrimidine-7-carboxylic acid [1-((S)-2-hydroxy-propanoyl)-piperidin-4-yl]amide; 4-(5-Acetyl-2-cyclopropylmethoxy-phenyl)-5H-pyrrolo[3,2-d]pyrimidine-7-carboxylic acid [1-(2-methoxy-acetyl)piperidin-4-yl]amide; 4-(5-Acetyl-2-cyclopropylmethoxy-phenyl)-5H-pyrrolo[3,2-d]pyrimidine-7-carboxylic acid (1-acetyl-piperidin-4-yl)-amide; 4-(5-Acetyl-2-cyclopropylmethoxy-4-methyl-phenyl)-5H-pyrrolo[3,2-d]pyrimidine-7-carboxylic acid [1-((S)-2-hydroxy-propionyl)piperidin-4-yl]amide; 4-(5-Acetyl-2-cyclopropylmethoxy-4-methyl-phenyl)-5H-pyrrolo[3,2-d]pyrimidine-7-carboxylic acid (1-acetyl-piperidin-4-yl)-amide; trans-4-(5-Cyclopropylmethoxy-benzo[1,3]dioxol-4-yl)-5H-pyrrolo[3,2-d]pyrimidine-7-carboxylic acid [4-(2-methoxy-ethylcarbamoyl)-cyclohexyl]-amide; trans-4-(5-Cyclopropylmethoxy-benzo[1,3]dioxol-4-yl)-5H-pyrrolo[3,2-d]pyrimidine-7-carboxylic acid (4-cyclopropylcarbamoyl-cyclohexyl)-amide; trans-4-(2-Cyclopropylmethoxy-4-methoxy-phenyl)-5H-pyrrolo[3,2-d]pyrimidine-7-carboxylic acid (4-cyclopropylcarbamoyl-cyclohexyl)-amide; trans-4-(2-Cyclopropylmethoxy-4-methoxy-phenyl)-5H-pyrrolo[3,2-d]pyrimidine-7-carboxylic acid [4-

(2-methoxy-ethylcarbamoyl)-cyclohexyl]-amide; trans-4-(2-Cyclopropylmethoxy-5-fluoro-phenyl)-5H-pyrrolo[3,2-d]pyrimidine-7-carboxylic acid (4-cyclopropylcarbamoyl-cyclohexyl)-amide; trans-4-(2-Cyclopropylmethoxy-5-fluoro-phenyl)-5H-pyrrolo[3,2-d]pyrimidine-7-carboxylic acid [4-(2-methoxy-ethylcarbamoyl)-cyclohexyl]-amide; trans-4-(5-Cyclobutylmethoxy-benzo[1,3]dioxol-4-yl)-5H-pyrrolo[3,2-d]pyrimidine-7-carboxylic acid [4-(2-methoxy-ethylcarbamoyl)-cyclohexyl]-amide; trans-4-(5-Cyclobutyl-methoxy-benzo[1,3]dioxol-4-yl)-5H-pyrrolo[3,2-d]pyrimidine-7-carboxylic acid (4-cyclopropylcarbamoyl-cyclohexyl)-amide;
a salt thereof, or a stereoisomer of the compound or the salt thereof.

It is to be understood that the invention covers all combinations of substituent groups referred to hereinabove. In particular, the invention covers all combinations of preferred groups described hereinabove.

Salts of the compounds according to the invention and the stereoisomers thereof include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, gluconates including D-gluconates and L-gluconates, glucuronates including D-glucuronates and L-glucuronates, benzoates, 2-(4-hydroxybenzoyl)benzoates, butyrates, salicylates, sulfosalicylates, maleates, laurates, malates including L-malates and D-malates, lactates including L-lactates and D-lactates, fumarates, succinates, oxalates, tartarates including L-tartarates, D-tartarates and meso-tartarates, stearates, benzenesulfonates (besilates), toluenesulfonates (tosilates), methanesulfonates (mesilates), laurylsulfonates, 3-hydroxy-2-naphthoates, lactobionates (salts of 4-O-beta-D-galactopyranosyl-D-gluconic acid), galactarates, embonates and ascorbates.

Examples of salts with bases include, but are not limited to, lithium, sodium, potassium, calcium, aluminum, magnesium, titanium, ammonium, meglumine and guanidinium salts.

The salts include water-insoluble and, particularly, water-soluble salts.

The compounds according to the invention, the salts thereof, the N-oxides of the compounds and the salts thereof and the stereoisomers of the compounds, salts, N-oxides of the compounds and N-oxides of the salts thereof may contain, e.g. when isolated in crystalline form, varying amounts of solvents. Included within the scope of the invention are, therefore, all solvates of the compounds of formula (I), the salts thereof, the N-oxides of the compounds and the salts thereof and the stereoisomers of the compounds, salts, N-oxides of the compounds and N-oxides of the salts thereof. Hydrates are a preferred example of said solvates.

The compounds according to the invention and the salts thereof, the N-oxides of the compounds and the salts thereof include stereoisomers.

Examples of stereoisomers include, but are not limited to, compounds of formula (I) wherein R3 is a 3-6C-cycloalkyl group substituted by R6. Stereoisomers of one exemplified compound of formula (I) wherein R3 is a 3-6C-cycloalkyl group substituted by R6 are shown below (cis/trans stereoisomers):

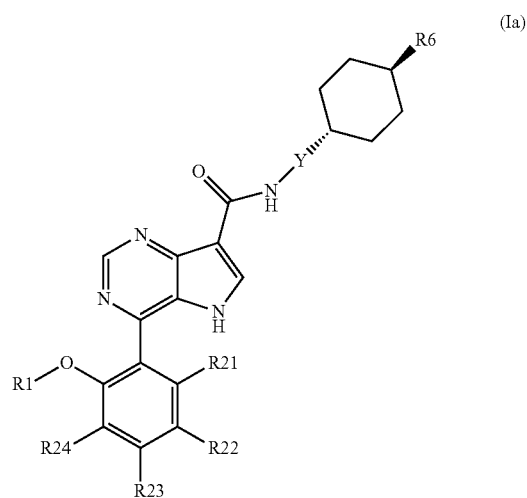

(Ia)

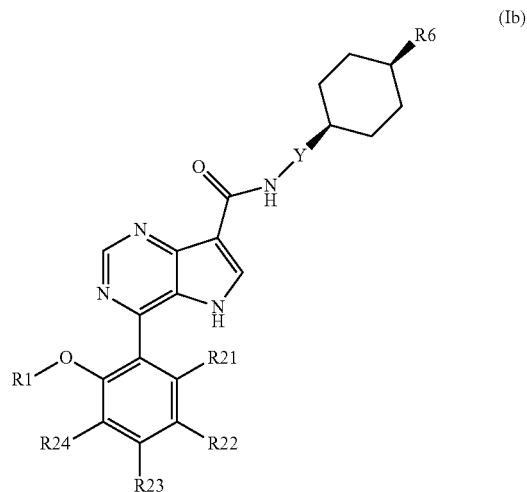

(Ib)

Further examples of stereoisomers include, but are not limited to, compounds of formula (I) wherein R3 is a 4- to 7-membered saturated heterocyclic ring containing one nitrogen atom and optionally one oxygen atom, said heterocyclic ring being optionally substituted by R4 and wherein said heterocyclic ring contains a stereogenic center. Stereoisomers of an exemplified compound of formula (I) wherein R3 is a 4- to 7-membered saturated heterocyclic ring containing one nitrogen atom and optionally one oxygen atom, said heterocyclic ring being optionally substituted by R4 and said heterocyclic ring containing a stereogenic center are shown below:

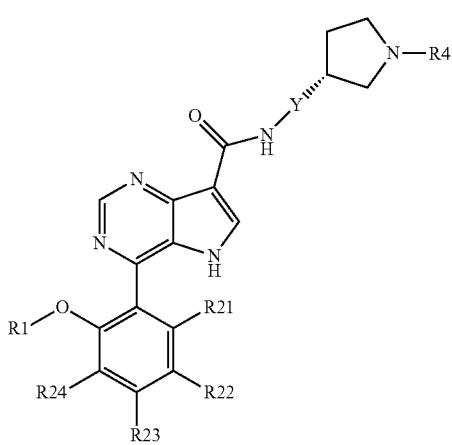

(Ic)

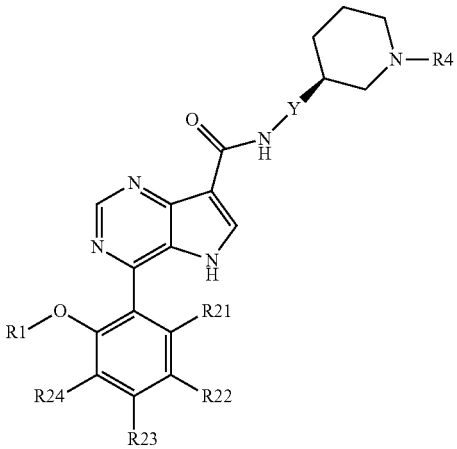

(If)

Stereoisomers of a further exemplified compound of formula (I) wherein R3 is a 4- to 7-membered saturated heterocyclic ring containing one nitrogen atom and optionally one oxygen atom, said heterocyclic ring being optionally substituted by R4 and said heterocyclic ring containing a stereogenic center are shown below:

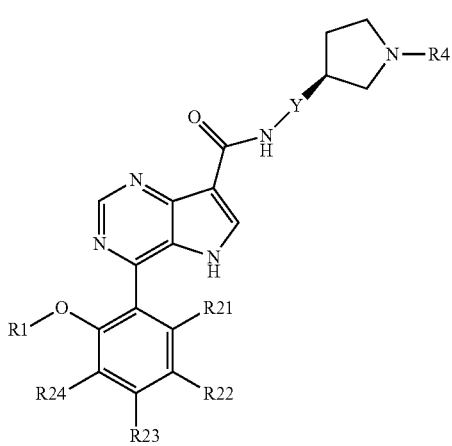

(Id)

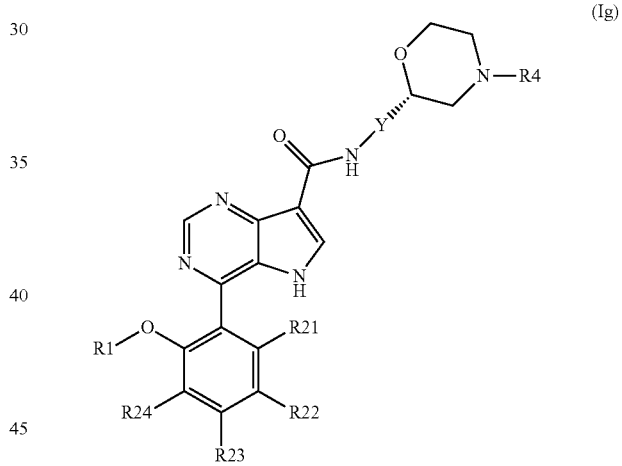

(Ig)

Stereoisomers of a further exemplified compound of formula (I) wherein R3 is a 4- to 7-membered saturated heterocyclic ring containing one nitrogen atom and optionally one oxygen atom, said heterocyclic ring being optionally substituted by R4 and said heterocyclic ring containing a stereogenic center are shown below:

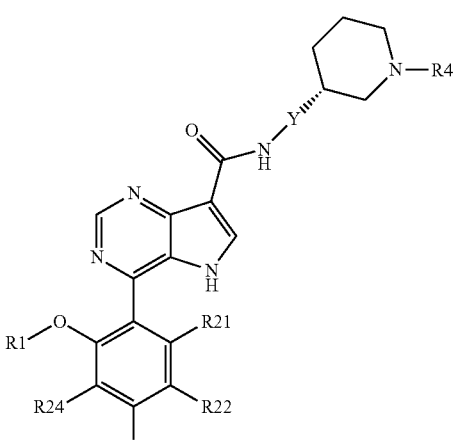

(Ie)

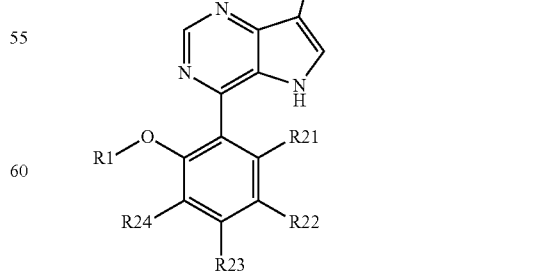

(Ih)

Further examples of stereoisomers include, but are not limited to, compounds of formula (I) wherein R4 is a group having a stereogenic center, such as a group —C(O)—CH(CH₃)—OH. Further examples of stereoisomers include, but are not limited to, compounds of formula (I) wherein R6 is a group having a stereogenic center, such as a group —NH—C(O)—CH(CH₃)—OCH₃.

Each of said stereogenic centers may have the absolute configuration R or the absolute configuration S (according to the rules of Cahn, Ingold and Prelog).

The invention relates to the pure stereoisomers and to mixtures of the stereoisomers independent of the ratio, including the racemates. Accordingly, the invention relates to the pure (cis)-isomers, the pure (trans)-isomers, and mixtures thereof, the pure (R)-isomers, the pure (S)-isomers, and mixtures thereof.

Furthermore, the invention includes the pure (trans,R)-isomers, (trans,S)-isomers, (cis,R)-isomers and (cis,S)-isomers, and mixtures of two or more thereof in any ratio. An example of said isomers is shown below:

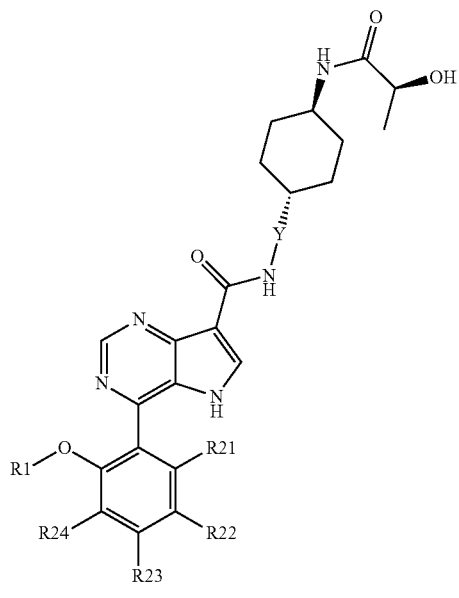

(trans, S)

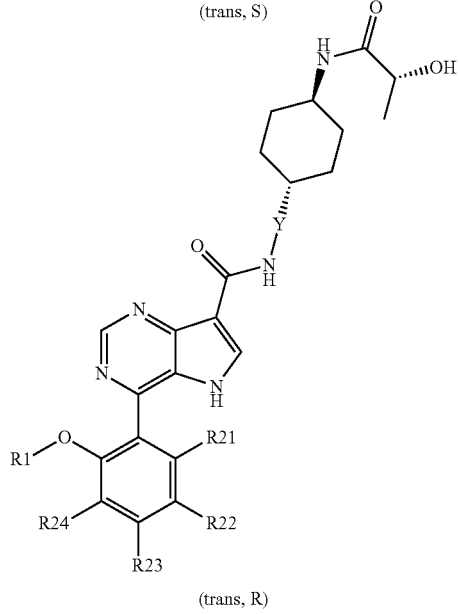

(trans, R)

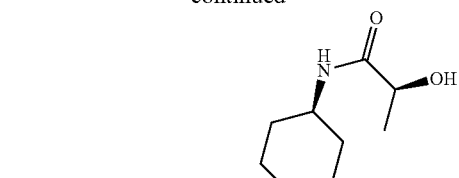

(cis, S)

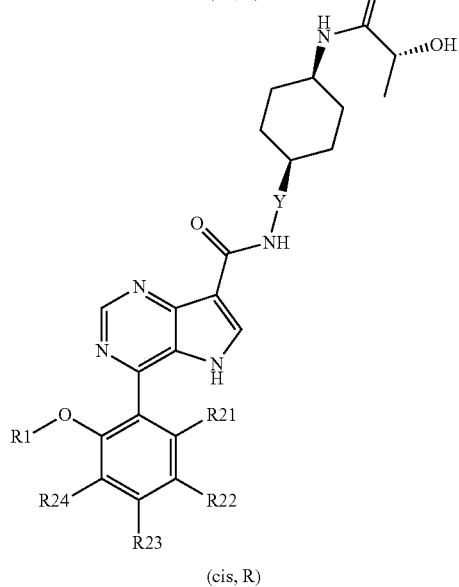

(cis, R)

Furthermore, the invention includes the pure (R,R)-isomers, (R,S)-isomers, (S,R)-isomers and (S,S)-isomers, and mixtures of two or more thereof in any ratio. An example of said isomers is shown below:

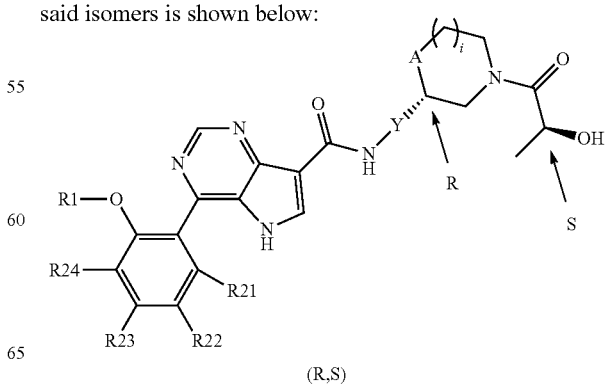

(R,S)

-continued

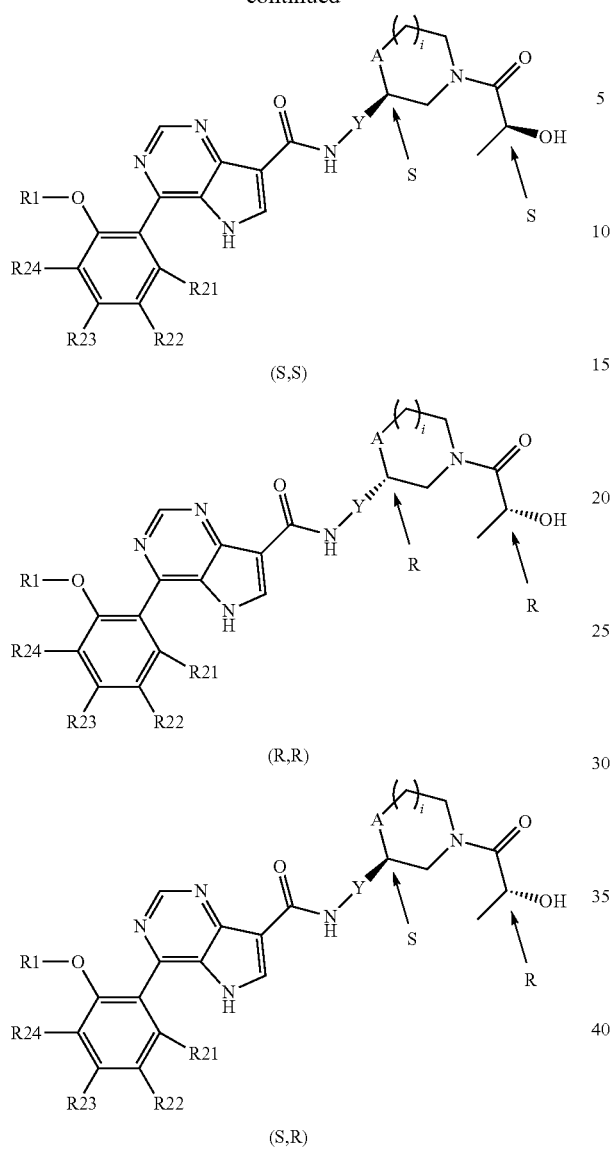

A = —CH₂— or —O—   i = 0, 1 or 2

Furthermore, derivatives of the compounds according to the invention, the salts thereof, the N-oxides of the compounds or the salts thereof, the stereoisomers of the compounds, salts, N-oxides of the compounds or N-oxides of the salts thereof which are converted into compounds according to the invention, the salts thereof, an N-oxide of the compound or the salt thereof, the stereoisomers of the compounds, the salt, the N-oxide of the compound or the N-oxide of the salt thereof in a biological system (bioprecursors or pro-drugs) are covered by the invention. Said biological system is e.g. a mammalian organism, particularly a human subject. The bioprecursor is, for example, converted into the compounds according to the invention, the salts thereof, an N-oxide of the compound or the salt thereof, or a stereoisomers of the compounds, the salt, the N-oxide of the compound or the N-oxide of the salt thereof by metabolic processes.

The compounds according to the invention can be prepared as follows.

Reaction scheme 1

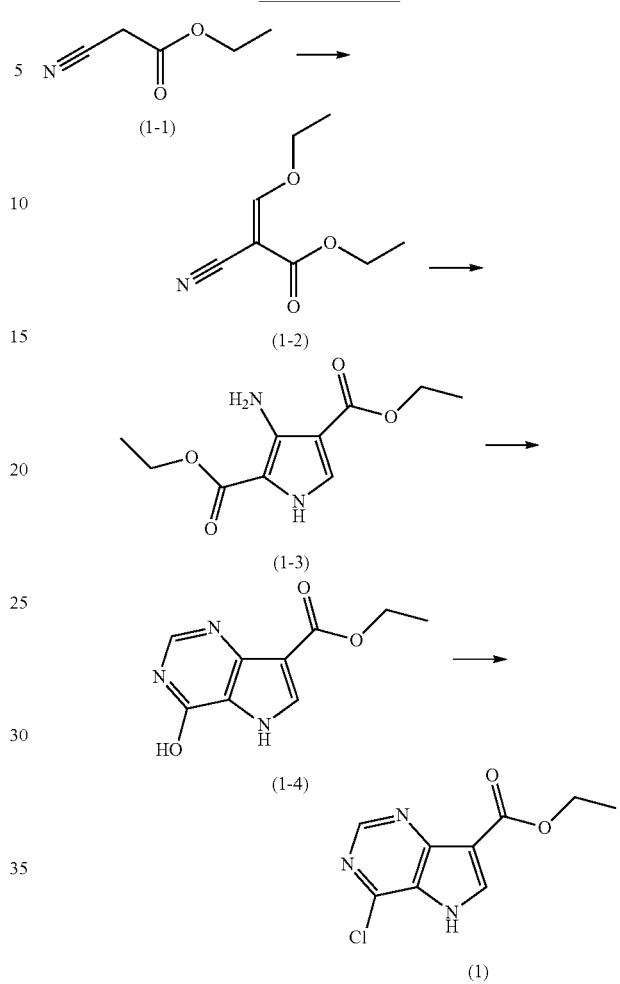

The compound of formula (I) can be obtained as shown in reaction scheme 1 according to the procedures described in US 2005/0124623A1.

Reaction scheme 2

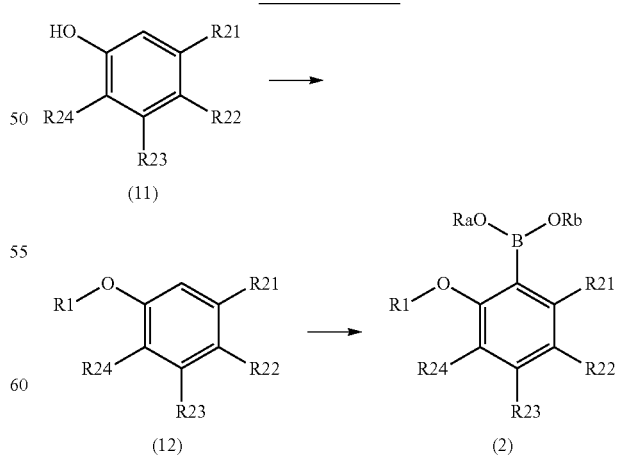

As shown in reaction scheme 2, synthesis of a boronic acid derivative of formula (2) may start from phenols of formula (11) wherein R21, R22, R23 and R24 have the above defined meanings. The phenols of formula (11) are commercially available or can be prepared by methods known to a person skilled in the art. In a first step R1, which has the above defined meaning, may be introduced by alkylation. The alkylation is for example carried out by suspending sodium hydride in an organic solvent, such as dimethylethane (DME) or dimethylsulfoxide (DMSO) or a mixture thereof, adding a solution of compound (II) in an organic solvent, such as DME, at a temperature in the range of from 0 to 40° C., then adding a compound R1-halogen, preferably R1-Br or R1-I, and reacting the mixture at a temperature of from 20 to 80° C. for 1 to 48 h to give a compound of formula (12). In a second step, directed ortho-metalation followed by reaction with a boron electrophile leads to the compounds of formula (2) wherein R1, R21, R22, R23 and R24 have the above defined meanings, and Ra and Rb represent 1-4C-alkyl or hydrogen, preferably Ra and Rb combine to form a straight-chain or branched alkylene group having 2 to 8 carbon atoms, for example without limitation —C(CH$_3$)$_2$—C(CH$_3$)$_2$—. In particular, a solution of compound (12) in an organic solvent, such as tetrahydrofuran (THF), can be reacted with n-butyl lithium (n-BuLi) in an organic solvent, such as hexane, at a temperature of from −78 to 0° C. for 0.5 to 4 h. Subsequently, for example commercially available 2-iso-propoxy-4,4,5,5-tetramethyl-[1,3,2]dioxaborolane is added and the reaction is performed at a temperature of from −78 to 0° C. for 0.5 to 3 h to yield a compound of formula (2).

temperature in the range of from 0 to 40° C., then adding a compound R1-halogen, preferably R1-Br or R1-I, and reacting the mixture at a temperature of from 20 to 80° C. for 1 to 48 h leading to compounds of formula (14). In a third step, halogen-lithium exchange followed by reaction with a boron electrophile yields the compounds of formula (2), wherein R1, R21, R22, R23 and R24 have the above defined meanings, and Ra and Rb represent 1-4C-alkyl or hydrogen, preferably Ra and Rb combine to form a straight-chain or branched alkylene group having 2 to 8 carbon atoms, for example without limitation —C(CH$_3$)$_2$—C(CH$_3$)$_2$—. In particular, a solution of compound (14) in an organic solvent, such as tert-butylmethylether, can be reacted with n-BuLi (n-butyl lithium) in an organic solvent, such as hexane, at a temperature of from −78 to 0° C. for 0.5 to 3 h. Subsequently, for example commercially available 2-iso-propoxy-4,4,5,5-tetramethyl-[1,3,2]dioxaborolane is added and the reaction is performed at a temperature of from −78 to 0° C. for 0.5 to 3 h to yield a compound of formula (2).

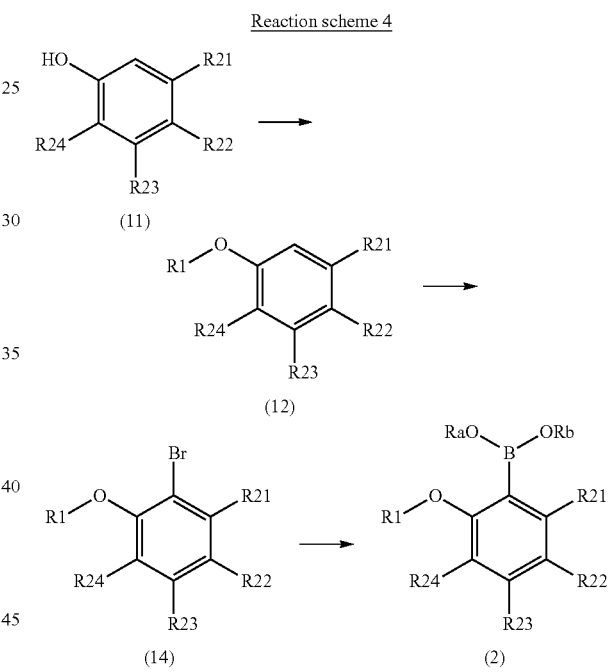

Reaction scheme 4

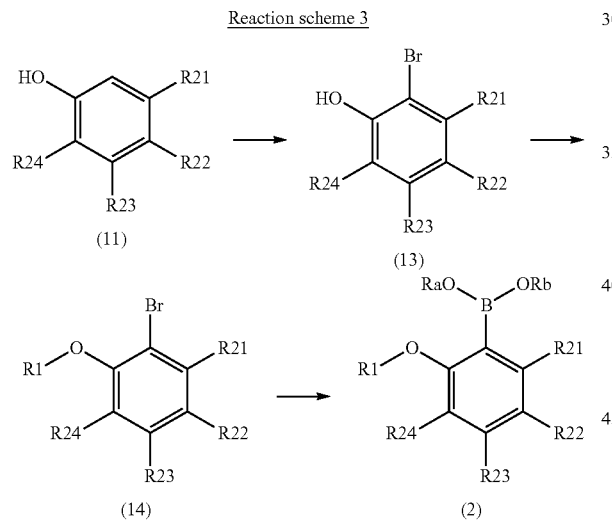

Reaction scheme 3

An alternative preparation of compounds of formula (2) is shown in reaction scheme 3. The preparation may start from phenols of formula (11), wherein R21, R22, R23 and R24 have the above defined meanings and which are commercially available or can be prepared by methods known to a person skilled in the art or as for example described in Yamamoto, Y.; Hattori, K.; Ishii, J.-I.; Nishiyama, H. Tetrahedron, 2006, 62, 4294. The phenols of formula (11) are for example reacted with bromine or N-bromosuccinimide in an organic solvent such as dichloromethane (DCM) at a temperature of from −40 to 20° C. for 0.5 to 4 h to give compounds of formula (13). In a second step R1, which has the above defined meaning, may be introduced by alkylation. The alkylation is for example carried out by suspending sodium hydride in an organic solvent, such as dimethylethane (DME) or dimethylsulfoxide (DMSO) or a mixture thereof, adding a solution of compound (13) in an organic solvent, such as DME, at a According to a further alternative preparation method shown in reaction scheme 4, synthesis of boronic acid derivatives of formula (2) may start from phenols of formula (11) wherein R21, R22, R23 and R24 have the above defined meanings and which are commercially available or can be prepared by methods known to a person skilled in the art. In a first step R1, which has the above defined meaning, is introduced by alkylation. The alkylation is for example carried out by suspending sodium hydride in an organic solvent, such as dimethylethane (DME) or dimethylsulfoxide (DMSO) or a mixture thereof, adding a solution of compound (II) in an organic solvent, such as DME, at a temperature in the range of from 0 to 40° C., then adding a compound R1-halogen, preferably R1-Br or R1-I, and reacting the mixture at a temperature of from 20 to 80° C. for 1 to 48 h to give a compound of formula (12). In a second step, compound (14) may be prepared for example from compound (12) by reaction with N-bromosuccinimide in an organic solvent, such as dimethylformamide, at a temperature of from 0 to 60° C. for 0.5 to 5 h. In a third step, halogen-lithium exchange followed by reaction with a boron electrophile yields the compounds of formula (2), wherein R1, R21, R22, R23 and R24 have the above defined meanings, and Ra and Rb represent 1-4C-alkyl or hydrogen, preferably Ra and Rb combine to form a straight-chain or branched alkylene group having 2 to 8 carbon atoms, for example without limitation —C(CH$_3$)$_2$—C(CH$_3$)$_2$—. In particular, a solution of compound (14) in an organic solvent, such as tert-butylmethylether, can be reacted with n-BuLi (n-butyl lithium) in an organic solvent, such as hexane, at a temperature of from −78 to 0° C. for 0.5 to 3 h. Subsequently, for example commercially available 2-iso-propoxy-4,4,5,5-tetramethyl-[1,3,2]dioxaborolane is added and the reaction is performed at a temperature of from −78 to 0° C. for 0.5 to 3 h to yield a compound of formula (2). Alternatively, compounds of formula (2) may be synthesized from compounds of formula (14) and an appropriate boron compound, such as bis(pinacolato)diboron, in the presence of a Pd catalyst, such as 1,1'-bis(diphenylphosphino)ferrocene palladium-(II)-chloride, and a base, such as potassium acetate, in an organic solvent, such as dioxane, at a temperature of from 20 to 100° C. for 1 to 24 h. The Pd catalyzed preparation of boronic acid derivatives is, for example, described in Murata et al, J Org Chem 1997 62, 6458 and J Org Chem 1997, 65, 164.

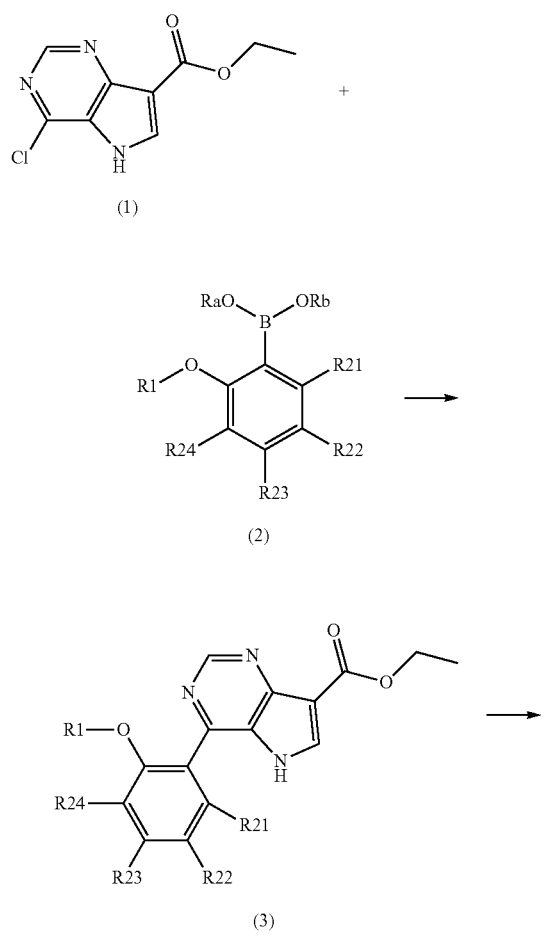

Reaction Scheme 5

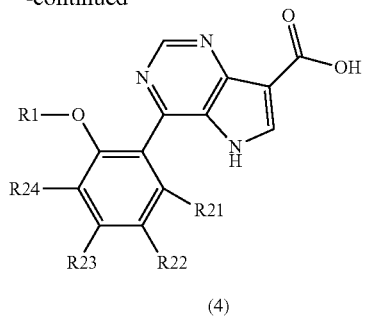

(4)

Reaction scheme 5 illustrates the synthesis of compounds of formula (4) in which R1, R21, R22, R23 and R24 have the above defined meanings. In a first step, compound (1) prepared according to reaction scheme 1 can be reacted with a compound of formula (2) prepared according to any of reaction scheme 2, 3 or 4, wherein R1, R21, R22, R23, R24, Ra and Rb have the above defined meanings, to obtain a compound of formula (3). In particular, the compound of formula (I), a base, such as K$_2$CO$_3$, Cs$_2$CO$_3$ or K$_3$PO$_4$, a solvent, such as dimethoxyethane, and a Pd catalyst, such as PdCl$_2$(PCy$_3$)$_2$ (Cy=cyclohexyl), are preferably heated at a temperature in the range of from 60 to 160° C. for 5 to 10 min, more preferably under microwave irradiation. After cooling to ambient temperature (e.g. 20 to 25° C.), a compound of formula (2) can be added to the reaction mixture which is then preferably heated to a temperature in the range of from 60 to 160° C. for 10 to 120 min, more preferably under microwave irradiation. The compound of formula (3) thus obtained can then be reacted with an alkali hydroxide, such as LiOH, in a solvent, preferably a mixture of an organic solvent, such as dioxane, and water, at a temperature in the range of from 20 to 100° C. for 1 to 48 h to yield a compound of formula (4).

Reaction scheme 6

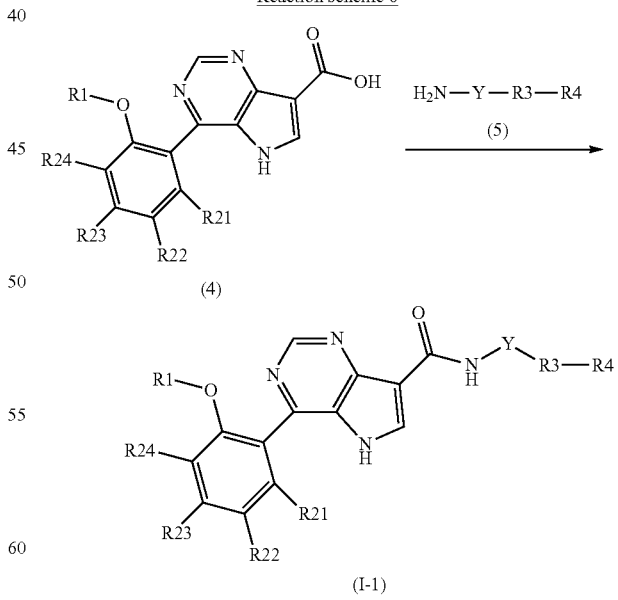

As shown in reaction scheme 6, starting from compounds of formula (4) prepared according to above reaction scheme 5, compounds of formula (I-1), wherein R1, R21, R22, R23, R24 and Y have the above defined meanings and R3 is a 4- to 7-membered saturated heterocyclic ring containing one nitrogen atom and optionally one oxygen atom, said heterocyclic ring being substituted by R4 with R4 being —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43, with R41, R42 and R43 having the above defined meanings, can be prepared by reaction with compounds of formula (5), wherein Y has the above defined meaning and R3 is a 4- to 7-membered saturated heterocyclic ring containing one nitrogen atom and optionally one oxygen atom, said heterocyclic ring being substituted by R4 with R4 being —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43, with R41, R42 and R43 having the above defined meanings, under standard amide bond forming conditions. The compounds of formula (5) are commercially available or can be prepared by methods known to a person skilled in the art. An exemplified method for preparing compounds of formula (5) is shown in reaction scheme 15 below. In particular, a dehydrating agent, such as 1-(3-dimethylaminopropyl)-3-ethylcarbodiimide hydrochloride, a base, such as triethylamine, and a catalyst, such as 1-hydroxybenzotriazole, can be added to a compound of formula (4) which is preferably dissolved or suspended in an organic solvent, e.g. dichloromethane. After stirring the mixture e.g. for 0.3 to 2 h, preferably at ambient temperature (e.g. 20 to 25° C.), a compound of formula (5) can be added and the reaction is preferably performed at ambient temperature (e.g. 20 to 25° C.) for 1 to 48 h to yield the compound of formula (I-1).

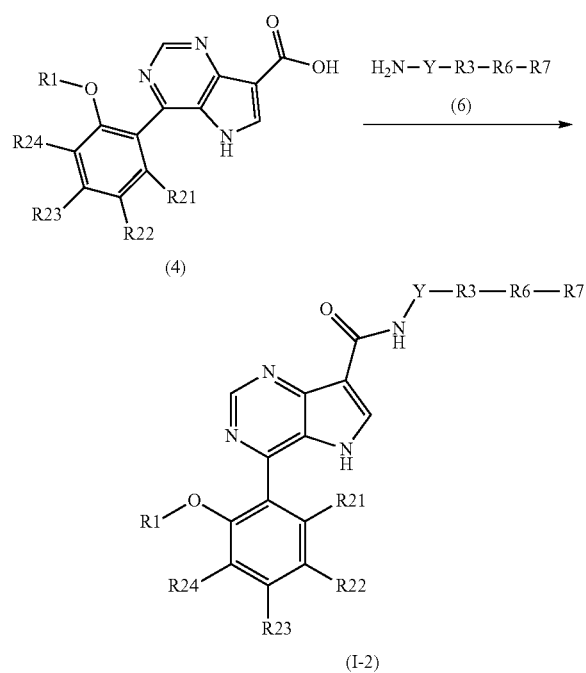

(I-2)

As shown in reaction scheme 7, compounds of formula (I-2), wherein R1, R21, R22, R23, R24 and Y have the above defined meanings and R3 is a 3-6C-cycloalkyl group substituted by R6, with R6 being —NH—C(O)—R7 and R7 being 1-4C-alkyl, which is optionally substituted by R71, 3-6C-cycloalkyl, which is optionally substituted by R72, or 1-4C-alkoxy, which is optionally substituted by R73, with R71, R72 and R73 having the above defined meanings, can be synthesized by reaction of compounds of formula (4) prepared according to above reaction scheme 5, with compounds of formula (6), wherein Y has the above defined meaning and R3 is a 3-6C-cycloalkyl group substituted by R6, with R6 being —NH—C(O)—R7 and R7 being 1-4C-alkyl, which is optionally substituted by R71, 3-6C-cycloalkyl, which is optionally substituted by R72, or 1-4C-alkoxy, which is optionally substituted by R73, with R71, R72 and R73 having the above defined meanings. The compounds of formula (6) are commercially available or can be prepared by methods known to a person skilled in the art. In particular, a dehydrating agent, such as 1-(3-dimethylaminopropyl)-3-ethylcarbodiimide hydrochloride, a base, such as triethylamine, and a catalyst, such as 1-hydroxybenzotriazole, can be added to a compound of formula (4) which is preferably dissolved or suspended in an organic solvent, such as dichloromethane. After stirring the mixture e.g. for 0.3 to 2 h preferably at ambient temperature (e.g. 20 to 25° C.), a compound of formula (6) can be added and the reaction is preferably performed at ambient temperature (e.g. 20 to 25° C.) for 1 to 48 h to yield the compound of formula (I-2).

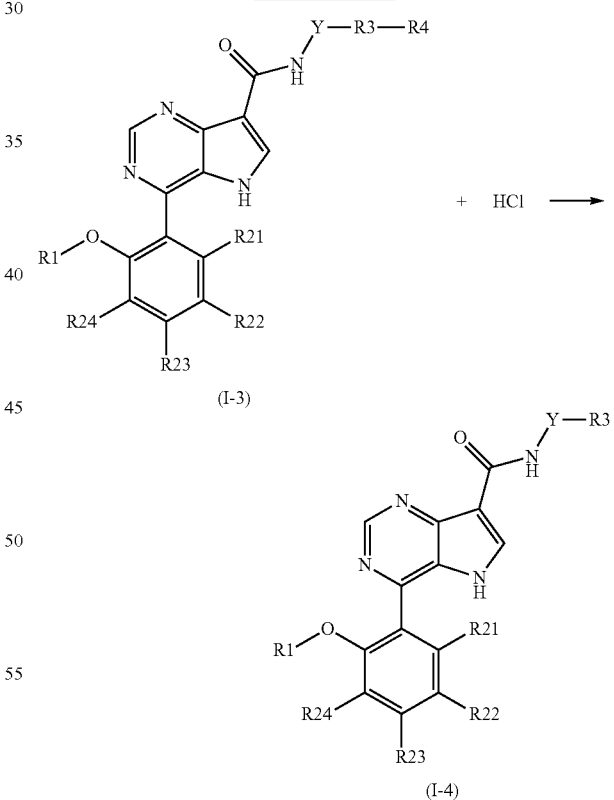

Compounds of formula (I-3), wherein R1, R21, R22, R23, R24 and Y have the above defined meanings and R3 is a 4- to 7-membered saturated heterocyclic ring containing one nitrogen atom and optionally one oxygen atom, said heterocyclic ring being substituted by R4 with R4 being —C(O)—O—C(CH$_3$)$_3$, prepared according to reaction scheme 6 can be converted into compounds of formula (I-4), wherein R1, R21, R22, R23, R24 and Y have the above defined meanings and R3 is a non-substituted 4- to 7-membered saturated heterocyclic ring containing one nitrogen atom and optionally one oxygen atom, as shown in reaction scheme 8. In particular, HCl preferably dissolved in an organic solvent, such as dioxane, can be added to the compound of formula (I-3) which is preferably dissolved in an organic solvent, such as an alcohol, e.g. 2-propanol. The reaction mixture is then preferably heated at 40 to 80° C. for 1 to 4 h to yield the hydrochloride of the compound of formula (I-4). The compound of formula (I-4) can be prepared from said hydrochloride as known to a person skilled in the art, such as by treatment with a base, e.g. aqueous potassium carbonate or aqueous ammonia.

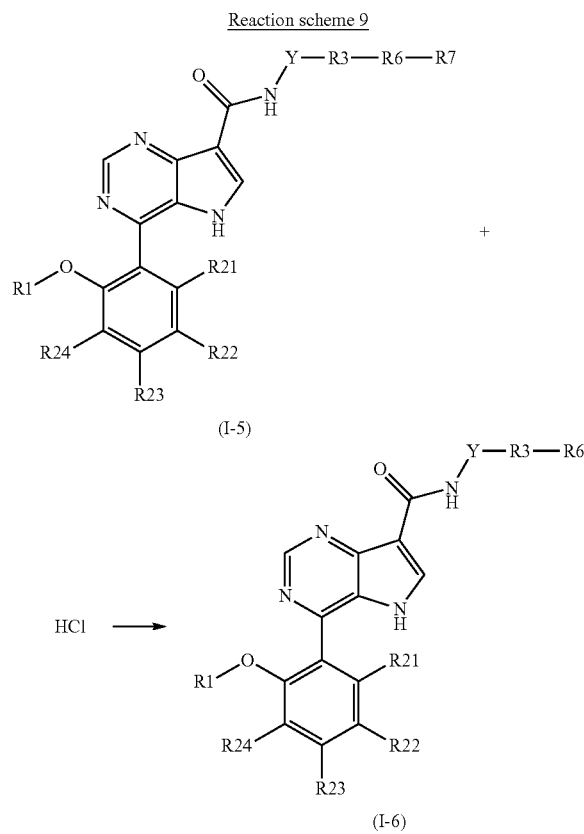

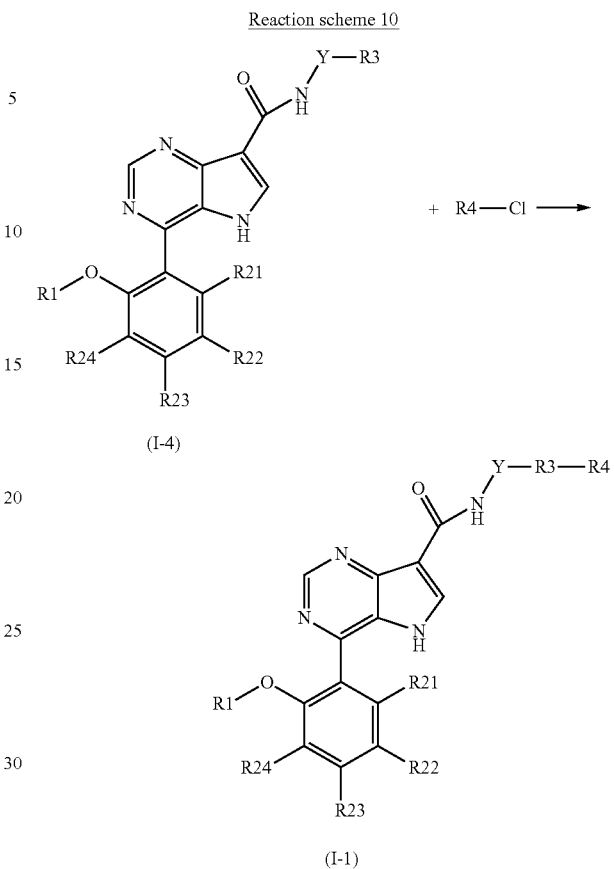

Compounds of formula (I-5), wherein R1, R21, R22, R23, R24 and Y have the above defined meanings and R3 is a 3-6C-cycloalkyl group substituted by R6 with R6 being —NH—C(O)—R7 and R7 being —O—C(CH$_3$)$_3$, prepared according to reaction scheme 7 can be converted into compounds of formula (I-6), wherein R1, R21, R22, R23, R24 and Y have the above defined meanings and R3 is a 3-6C-cycloalkyl group substituted by R6 with R6 being —NH$_2$ as shown in reaction scheme 9. In particular, HCl preferably dissolved in an organic solvent, such as dioxane, can be added to the compound of formula (I-5) which is preferably dissolved in an organic solvent, such as an alcohol, e.g. 2-propanol. The reaction mixture is then preferably heated at 40 to 80° C. for 1 to 4 h to yield the hydrochloride of the compound of formula (I-6). The compound of formula (I-6) can be prepared from said hydrochloride as known to a person skilled in the art, such as by treatment with a base, e.g. aqueous potassium carbonate or aqueous ammonia.

Alternatively, as shown in reaction scheme 10, compounds of formula (I-1), wherein R1, R21, R22, R23, R24 and Y have the above defined meanings and R3 is a 4- to 7-membered saturated heterocyclic ring containing one nitrogen atom and optionally one oxygen atom, with R4 being —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43, and R41, R42 and R43 are as defined above, may be prepared from compounds of formula (I-4), wherein R1, R21, R22, R23, R24 and Y have the above defined meanings and R3 is a non-substituted 4- to 7-membered saturated heterocyclic ring containing one nitrogen atom and optionally one oxygen atom prepared according to reaction scheme 8. In particular, a compound R4-Cl can be added to the compound of formula (I-4) which is preferably dissolved in an organic solvent, such as dichloromethane, in the presence of a base, such as diazabicycloundecene (DBU). The compound of formula R4-Cl is commercially available or can be prepared by methods known to a person skilled in the art. The addition is preferably carried out at a temperature of from 0 to 20° C. After complete addition, the reaction is preferably continued at ambient temperature (e.g. 20 to 25° C.) for 1 to 24 h. In case R41, R42 or R43 represent hydroxy, it is known to a person skilled in the art that the hydroxy group is preferably to be protected by a suitable protecting group, such as an acetate group or a silyl protective group, e.g. a tert-butyl-dimethylsilyl group or a tert-butyl-diphenylsilyl group. Said protective groups can be removed by methods known to a person skilled in the art with or without prior isolation of the protected intermediate (i.e. the compound of formula (I-1) in its protected form).

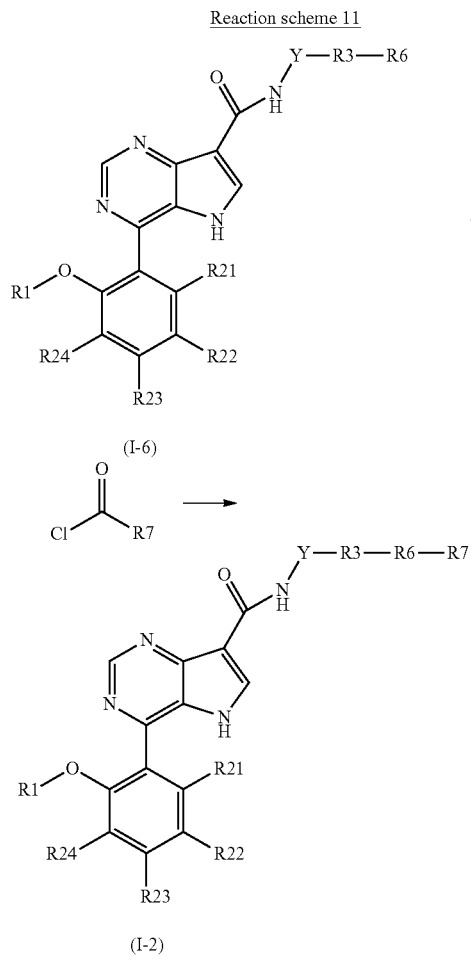

protective group, e.g. a tert-butyl-dimethylsilyl group or tert-butyl-diphenylsilyl group. Said protective groups can be removed by methods known to a person skilled in the art with or without prior isolation of the protected intermediate (i.e. the compound of formula (I-2) in its protected form).

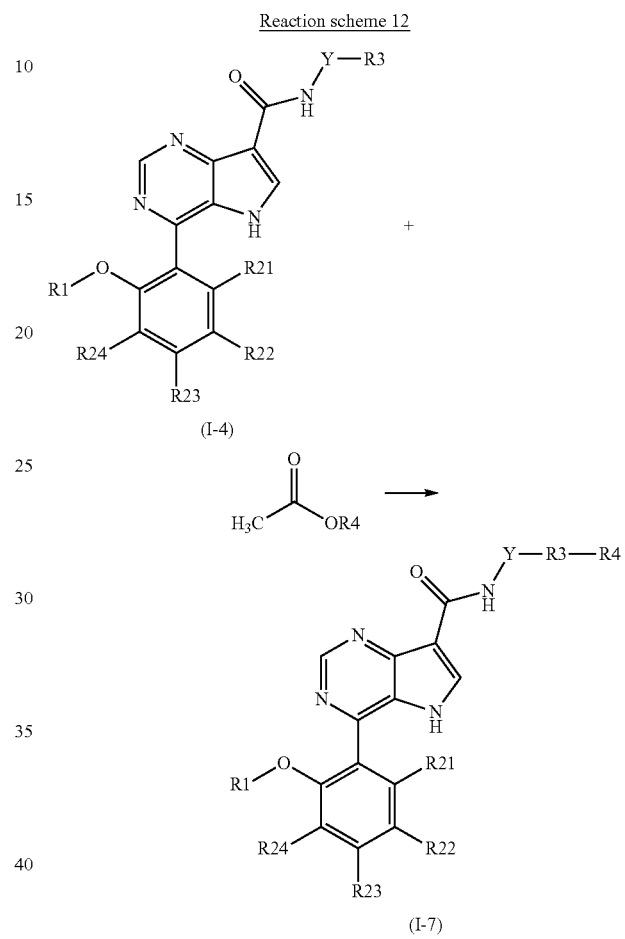

Alternatively, as shown in reaction scheme 11, compounds of formula (I-2), wherein R1, R21, R22, R23, R24 and Y have the above defined meanings and R3 is a 3-6C-cycloalkyl group substituted by R6, with R6 being —NH—C(O)—R7, with R7 being 1-4C-alkyl, which is optionally substituted by R71, 3-6C-cycloalkyl, which is optionally substituted by R72, or 1-4C-alkoxy, which is optionally substituted by R73, and R71, R72 and R73 are as defined above, may be prepared from compounds of formula (I-6), wherein R1, R21, R22, R23, R24 and Y have the above defined meanings and R3 is a 3-6C-cycloalkyl group substituted by R6 with R6 being NH$_2$ prepared according to reaction scheme 9. In particular, a compound R7-C(O)—Cl can be added to the compound of formula (I-6) which is preferably dissolved in an organic solvent, such as dichloromethane, in the presence of a base, such as diazabicycloundecene (DBU). The compound of formula R7-C(O)—Cl is commercially available or can be prepared by methods known to a person skilled in the art. The addition is preferably carried out at a temperature of from 0 to 20° C. After complete addition, the reaction is preferably continued at ambient temperature (e.g. 20 to 25° C.) for 1 to 24 h to yield the compound of formula (I-2). In case R71, R72 or R73 represent hydroxy, it is known to a person skilled in the art that the hydroxy group is preferably to be protected by a suitable protecting group, such as an acetate group or a silyl As shown in reaction scheme 12, compounds of formula (I-7), wherein R1, R21, R22, R23, R24 and Y have the above defined meanings and R3 is a 4- to 7-membered saturated heterocyclic ring containing one nitrogen atom and optionally one oxygen atom, said heterocyclic ring being substituted by R4, with R4 being —C(O)—H can be prepared from compounds of formula (I-4), wherein R1, R21, R22, R23, R24 and Y have the above defined meanings and R3 is a non-substituted 4- to 7-membered saturated heterocyclic ring containing one nitrogen atom and optionally one oxygen atom prepared according to reaction scheme 8. In particular, the compound R4-O—C(O)—CH$_3$, which can be prepared by methods known to a person skilled in the art, can be added to the compound of formula (I-4) which is preferably dissolved in an organic solvent, such as dichloromethane, in the presence of a base, such as diazabicycloundecene (DBU). The addition is preferably carried out at a temperature of from 0 to 20° C. After completion of addition, the reaction is preferably continued at ambient temperature (e.g. 20 to 25° C.) for 1 to 24 h to yield the compound of formula (I-7).

Reaction scheme 13

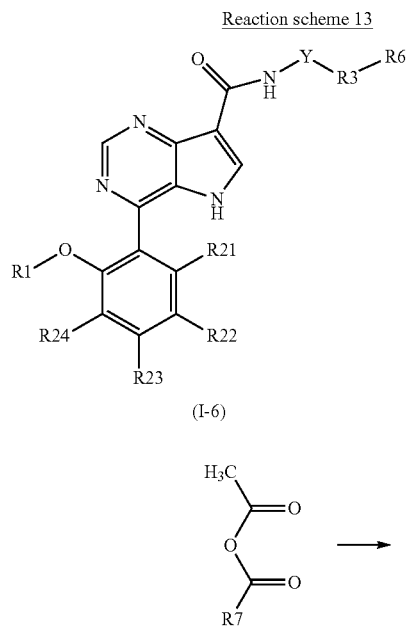

(I-6)

(I-8)

As shown in reaction scheme 13, compounds of formula (I-8), wherein R1, R21, R22, R23, R24 and Y have the above defined meanings and R3 is a 3-6C-cycloalkyl group substituted by R6 with R6 being —NH—C(O)—R7 with R7 being hydrogen can be prepared from compounds of formula (I-6), wherein R1, R21, R22, R23, R24 and Y have the above defined meanings and R3 is a 3-6C-cycloalkyl group substituted by R6 with R6 being —NH$_2$, obtained according to reaction scheme 9. In particular, the compound R7-C(O)—O—C(O)—CH$_3$ with R7 being hydrogen, which can be prepared by methods known to a person skilled in the art, can be added to the compound of formula (I-6) which is preferably dissolved in an organic solvent, such as dichloromethane, in the presence of a base, such as diazabicycloundecene (DBU). The addition is preferably carried out at a temperature of from 0 to 20° C. After completion of addition, the reaction is preferably continued at ambient temperature (e.g. 20 to 25° C.) for 1 to 24 h to yield a compound of formula (I-8).

Reaction scheme 14

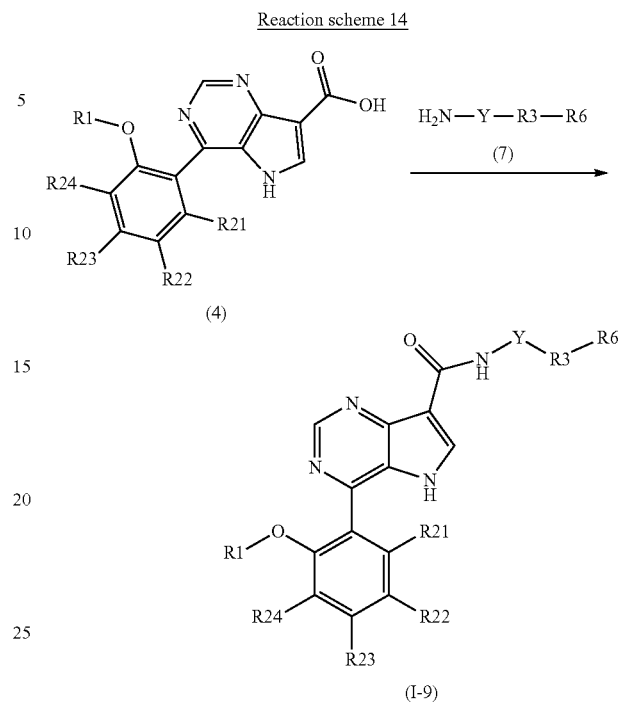

(4)

(I-9)

As shown in reaction scheme 14, compounds of formula (I-9), wherein R1, R21, R22, R23, R24 and Y have the above defined meanings and R3 is a 3-6C-cycloalkyl group substituted by R6, with R6 being —C(O)—NR8R9, with R8 and R9 having the above defined meanings, can be synthesized by reaction of compounds of formula (4) prepared according to above reaction scheme 5, with compounds of formula (7), wherein Y has the above defined meaning and R3 is a 3-6C-cycloalkyl group substituted by R6, with R6 being —C(O)—NR8R9, with R8 and R9 having the above defined to meanings. The compounds of formula (7) are commercially available or can be prepared by methods known to a person skilled in the art. An exemplified method for preparing compounds of formula (7) is shown in reaction scheme 16 below. In particular, a dehydrating agent, such as 1-(3-dimethylaminopropyl)-3-ethylcarbodiimide hydrochloride, a base, such as triethylamine, and a catalyst, such as 1-hydroxybenzotriazole, can be added to a compound of formula (4) which is preferably dissolved or suspended in an organic solvent, such as dichloromethane. After stirring the mixture e.g. for 0.3 to 2 h preferably at ambient temperature (e.g. 20 to 25° C.), a compound of formula (7) can be added and the reaction is preferably performed at ambient temperature (e.g. 20 to 25° C.) for 1 to 48 h to yield the compound of formula (I-9).

Reaction scheme 15

(5)

A compound of formula (5) with Y having the above defined meaning and R3 being a 4- to 7-membered saturated heterocyclic ring containing one nitrogen atom and optionally one oxygen atom substituted by R4 with R4 being —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43, with R41, R42 and R43 having the above defined meanings, can be prepared by reacting a compound of formula NH$_2$—Y—R3 with Y having the above defined meaning and R3 being a non-substituted 4- to 7-membered saturated heterocyclic ring containing one nitrogen atom and optionally one oxygen atom, in which compound the —NH$_2$ group is protected by a suitable protecting group, such as a tert-butoxycarbonyl group, with a compound of formula Cl—R4 with R4 being —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43, with R41, R42 and R43 having the above defined meanings, and subsequent removal of the protective group. In particular, a compound of the formula Cl—R4 can be added to a solution of a compound of formula NH$_2$—Y—R3 in an organic solvent, such as dichloromethane, containing a base, such as Huenigs base at a temperature of from 0 to 25° C. The mixture is then stirred for 1 to 48 h at ambient temperature (e.g. 20 to 25° C.). The protective group can be removed by methods known to a person skilled in the art, such as by treatment with hydrochloric acid in an organic solvent, such as dioxane or an alcohol, e.g. iso-propanol. The hydrochloride of the compound of formula (5) thus obtained can be converted into the compound of formula (5) by methods known to a person skilled in the art, such as treatment with a base, e.g. potassium carbonate or aqueous ammonia. In case R41, R42 or R43 represent hydroxy, it is known to a person skilled in the art to protect the hydroxy group by a suitable protecting group, such as an acetate group or a silyl protective group, e.g. a tert-butyl-dimethylsilyl group or tert-butyl-diphenylsilyl group. Said protective group can be removed by methods known to a person skilled in the art with or without prior isolation of the protected intermediate (i.e. the compound of formula (5) in its protected form).

Reaction scheme 16

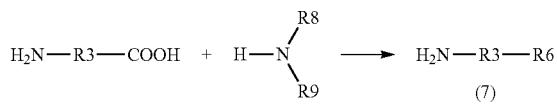

(7)

As shown in reaction scheme 16, a compound of formula (7) with R3 being a 3-6C-cycloalkyl group substituted by R6 and R6 being —C(O)—NR8R9 can be prepared by reacting a compound of formula NH$_2$—R3-COOH, in which R3 is a 3-6C-cycloalkyl group and wherein the —NH$_2$ group is protected by a suitable protecting group, such as a tert-butoxycarbonyl group, with a compound of formula NHR8R9, in which R8 and R9 have the above defined meanings, and subsequent removal of the protective group. In particular, a dehydrating agent, such as 1-(3-dimethylaminopropyl)-3-ethylcarbodiimide hydrochloride (EDCI) can be added to a mixture of a compound of formula NH$_2$—R3-COON, wherein the —NH$_2$ group is protected by a suitable protecting group, and a compound of formula NHR8R9 in an organic solvent, such as dichloromethane. The reaction is preferably performed at ambient temperature (e.g. 20 to 25° C.) for 1 to 48 hours. The protective group can be removed by methods known to a person skilled in the art, such as by treatment with hydrochloric acid in an organic solvent, such as dioxane or an alcohol, e.g. iso-propanol. The hydrochloride of the compound of formula (7) thus obtained can be converted into the compound of formula (7) by methods known to a person skilled in the art, such as by treatment with a base, e.g. potassium carbonate or aqueous ammonia. In case R9 is substituted by R91 or R92 with R91 or R92 being hydroxy, it is known to a person skilled in the art to protect the hydroxy group by a suitable protecting group, such as an acetate group or a silyl protective group, e.g. a tert-butyl-dimethylsilyl group or tert-butyl-diphenylsilyl group. Said protective group can be removed by methods known to a person skilled in the art with or without prior isolation of the protected intermediate (i.e. the compound of formula (7) in its protected form).

It is known to the person skilled in the art that, if there are a number of reactive centers on a starting or intermediate compound, it may be necessary to block one or more reactive centers temporarily by protective groups in order to allow a reaction to proceed specifically at the desired reaction center.

The compounds according to the invention are isolated and purified in a manner known per se, e.g. by distilling off the solvent in vacuo and recrystallizing the residue obtained from a suitable solvent or subjecting them to one of the customary purification methods, such as column chromatography on a suitable support material.

Salts of the compounds of formula (I), the N-oxides thereof and the stereoisomers of the compounds and the N-oxides thereof can be obtained by dissolving the free compound in a suitable solvent (for example a ketone such as acetone, methylethylketone or methylisobutylketone, an ether such as diethyl ether, tetrahydrofurane or dioxane, a chlorinated hydrocarbon such as methylene chloride or chloroform, a low molecular weight aliphatic alcohol such as methanol, ethanol or isopropanol, a low molecular weight aliphatic ester such as ethyl acetate or isopropyl acetate, or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

The compounds of formula (I), the salts thereof and the stereoisomers of the compounds and the salts according to the invention can be converted into their N-oxides, for example, by reaction with peracids, such as m-chloroperbenzoic acid or peracetic acid. The person skilled in the art is familiar with the reaction conditions for carrying out the N-oxidation.

Pure diastereomers and pure enantiomers of the compounds of formula (I) and the salts thereof, the N-oxides of the compounds and the N-oxides of the salts can be obtained e.g. by asymmetric synthesis, by using chiral starting compounds in synthesis and/or by splitting up enantiomeric and diasteriomeric mixtures obtained in synthesis. Preferably, the pure diastereomeric and pure enantiomeric compounds of the invention are obtainable by using chiral starting compounds in synthesis and/or by splitting up enantiomeric and diasteriomeric mixtures obtained in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

All patents, patent applications, publications, test methods and other materials cited herein are incorporated by reference in their entireties.

The following examples illustrate the invention in greater detail, without restricting it. Further compounds according to the invention, of which the preparation is not explicitly described, can be prepared in an analogous way.

The compounds, salts and stereoisomers which are mentioned in the examples, and the salts of the compounds which are mentioned in the examples, and the stereoisomers of the compounds mentioned in the examples, the stereoisomers of the salts which are mentioned in the examples and the stereoisomers of the salts of the compounds which are mentioned in the examples represent preferred embodiments of the invention.

The compounds which are mentioned in the examples, the salts thereof, N-oxides of the compounds and the salts thereof and stereoisomers of the compounds, salts, N-oxides of the compounds and N-oxides of the salts thereof represent preferred embodiments of the invention.

EXAMPLES

The following abbreviations are used: min: minutes, h: hour(s), DCM: dichloromethane, DCE: dichloroethane, THF: tetrahydrofuran, EA: ethyl acetate, sesamol: 3,4-methylenedioxyphenol, brine: saturated sodium chloride solution, DBU: 1,8-diazabicyclo[5.4.0]undec-7-ene, Huenigs base: N-ethyl-diisopropylamine, mp.: melting point, bp: boiling point, RT: room temperature (20 to 25° C.), ambient temperature: 20 to 25° C., TLC: thin layer chromatography, HPLC: high performance liquid chromatography, GC-MS (EI): gas chromatography coupled to mass spectrometry with electron impact ionization, MS (ESI): mass spectrometry with electron spray ionization, $^1$H-NMR: $^1$H nuclear magnetic resonance spectroscopy (chemical shifts are reported as ppm against tetramethylsilane as internal standard, coupling constants J are reported in Hz).

Example A1

4-Fluoro-3-methoxymethoxy-phenol

Under an atmosphere of argon a stirred solution of 4-bromo-1-fluoro-2-methoxymethoxy-benzene from example A25 (47.0 g; 0.200 mol) in dry tert-BuOMe (1000.0 mL) is cooled to −78° C. before tert-BuLi (1.7 M solution in pentane; 247.0 mL; 0.420 mol) is added via syringe within 30 min. After complete addition stirring is continue at −78° C. for one hour. 2-Isopropoxy-4,4,5,5-tetramethyl-1,3,2-dioxaborolane (91.6 mL; 0.440 mol) is slowly syringed into the reaction mixture. After complete addition the mixture is stirred at −78° C. for 30 min. Stirring is continued without external cooling. At 0° C. internal temperature the reaction mixture is quenched with 1 M citric acid (400.0 mL). The mixture is vigorously stirred for 30 min. The organic layer is separated. The aqueous layer is extracted with tert-BuOMe (2×100 mL). The combined organic layers are washed with saturated Na—HCO$_3$ (250 mL) and concentrated to about 500 mL under reduced pressure.

To the well stirred solution of the crude product H$_2$O$_2$ (30% aqueous solution; 51.5 mL; 0.500 mol) is slowly added at 0° C. and the reaction mixture is stirred at ambient temperature over night. The aqueous layer is separated. The organic layer is washed with water (2×100 mL), 1M aqueous Na$_2$SO$_3$ solution (several small portions) till free of peroxide and dried over MgSO$_4$. After filtration the solvent is removed under reduced pressure. The residual oil is chromatographed on silica gel (cyclohexane:AcOEt/9:1) to give the title compound as colorless oil. Yield: 29.8 g.

GC-MS (EI): m/z=172 (M$^+$); 45 (100%).

$^1$H-NMR (300 MHz, DMSO-d$_6$): 9.35 (s, 1H, —OH); 6.99 (dd, J$_1$=11.3, J$_2$=8.9, 1H); 6.64 (dd, J$_1$=7.1, J$_2$=2.9, 1H); 6.36 (ddd, J$_1$=8.9, J$_2$=3.4, J$_3$=2.9, 1H); 5.15 (s, 2H); 3.40 (s, 3H).

The following compounds are obtained analogously to the procedure described in the above example A1.

Example A2

3-(1,1-Difluoro-methoxy)-4-fluoro-phenol

Starting from 4-bromo-2-(1,1-difluoro-methoxy)-1-fluoro-benzene (example A26) the title compound is obtained as colorless oil.

GC-MS (EI): m/z=178 (M$^+$); 128 (100%).

$^1$H-NMR (300 MHz, DMSO-d$_6$): 9.72 (s, 1H, —OH); 7.18 (t, J=74.0, 1H); 7.17 (dd, J$_1$=10.8, J$_2$=8.9, 1H); 6.70 (dd, J$_1$=6.8, J$_2$=2.8, 1H); 6.63 (ddd, J$_1$=8.9, J$_2$=3.7, J$_3$=2.8).

Example A3

2-Bromo-5-fluoro-4-methoxy-phenol

3-Fluoro-4-methoxy-phenol (21.32 g; 0.15 mol) prepared according to literature [Freedman, J.; Stewart, K. T.; J. Heterocycl. Chem. 1989, 26, 1547-1554] is dissolved in dry dichloromethane (300 mL). The well stirred reaction mixture is cooled to −15° C. (ice/salt). A solution of bromine (23.97 g; 0.15 mol) in dry dichloromethane (75 mL) is slowly dropped into the reaction mixture. After complete addition stirring is continued for one hour. Water (150 mL) containing sodium sulfite (3.0 g) is added to the reaction mixture. Stirring is continued at ambient temperature for 30 min. The organic layer is separated, washed with water (100 mL) and dried over MgSO$_4$ in the presence of decolorizing charcoal. After filtration the solvent is completely removed under reduced pressure. The residue is crystallized from tert-butylmethylether/hexane to give the title compound as a colorless solid. Yield: 30.74 g.

GC-MS (EI): m/z=222, 220 (M$^+$); 207, 205 (M$^+$-CH$_3$, 100%); 179, 177.

$^1$H-NMR (300 MHz, DMSO-d$_6$): 10.06 (s, 1H, —OH); 7.28 (d, J=9.2, 1H); 6.81 (d, J=12.6, 1H); 3.76 (s, 3H).

The following compound is obtained analogously to the procedure described in above example A3.

Example A4

2-Bromo-4-fluoro-5-methoxy-phenol

Starting from 4-fluoro-3-methoxy-phenol prepared according to literature [Belanger, P. C.; Lau, C. K.; Williams, H. W. R.; Dufresne, C.; Scheigetz, J. Can. J. Chem. 1988, 66, 1479-1482] the title compound is obtained as colorless solid.

GC-MS (EI): m/z=222, 220 ($M^+$, 100%); 207, 205 ($M$-$CH_3^+$); 179, 177.

$^1$H-NMR (300 MHz, CDCl$_3$): 7.16 (d, J=10.2, 1H); 6.67 (d, J=7.7, 1H); 5.29 (s, 1H, —OH); 3.85 (s, 3H)

Example A5

2-Bromo-5-(1,1-difluoro-methoxy)-4-fluoro-phenol

Starting from 3-(1,1-difluoro-methoxy)-4-fluoro-phenol (example A2) the title compound is obtained as colorless oil.

GC-MS (EI): m/z=256, 258 ($M^+$); 206, 208 (100%).

$^1$H-NMR (300 MHz, DMSO-d$_6$): 10.55 (s, 1H, —OH); 7.65 (d, J=10.0, 1H); 7.19 (t, J=73.0, 1H); 6.90 (d, J=7.3, 1H).

Example A6

1-(5-Bromo-4-cyclopropylmethoxy-2-methyl-phenyl)ethanone

A suspension of 1-(4-cyclopropylmethoxy-2-methyl-phenyl)-ethanone from example A24 (6.4 g, 31.3 mmol) and N-bromosuccinimide (6.20 g, 34.5 mmol) in dry dimethylformamide (50 mL) is heated for 3 h at 50° C. After cooling to ambient temperature, water (200 mL) is added and the mixture is extracted with ethyl acetate (3×60 mL). The combined organic extracts are dried over sodium sulfate. The solvent is removed under reduced pressure. The crude is purified by column chromatography on silica gel using dichloromethane as eluent to give the title compound as a off-white solid. Yield: 4.80 g.

MS (ESI): m/z=282 (MH$^+$).

$^1$H-NMR (300 MHz, DMSO-d$_6$): 8.05 (s, 1H); 7.02 (m, 1H); 4.02 (d, J=6.0, 2H); 2.50 (s, 3H); 2.45 (s, 3H); 1.30 (m, 1H); 0.62 (m, 2H); 0.40 (m, 2H).

Example A7

2-Bromo-4-fluoro-5-methoxymethoxy-phenol

4-Fluoro-3-methoxymethoxy-phenol from example A1 (6.89 g; 40.0 mmol) is dissolved in dry di-chloromethane (160.0 mL). The stirred solution is cooled to −15° C. N-bromosuccinimide (7.12 g; 40.0 mmol) is added in small portions over one hour. After complete addition the reaction mixture is stirred for another 30 min at −15° C.

The reaction mixture is extracted with 2% aqueous sodium sulfite solution (25.0 mL). The organic layer is separated. The aqueous layer is extracted with dichloromethane (2×25.0 mL). The combined organic layers are dried over MgSO$_4$. The crude material is chromatographed on silica gel (dichloromethane:MeOH/99:01) to give the title compound as a colorless solid. Yield: 8.33 g.

GC-MS (EI): m/z=250, 252 ($M^+$); 45 (100%).

$^1$H-NMR (300 MHz, DMSO-d$_6$): 10.14 (s, 1H, —OH); 7.41 (d, J=10.8, 1H); 6.87 (d, J=7.8, 1H); 5.17 (s, 2H); 3.41 (s, 3H).

Example A8

5-Cyclopropylmethoxy-benzo[1,3]dioxole

Sodium hydride (60 wt % dispersion in mineral oil; 11.0 g; 275.0 mmol) is freed from oil by washing with hexane (2×50 mL) and suspended in dry DME (375 mL) and dry DMSO (37.5 mL). Under an atmosphere of nitrogen a solution of commercially available sesamol (3,4-methylenedioxy-phenol) (34.53 g; 250.0 mmol) in dry DME (250 mL) is dropped into the well-stirred suspension at a rate to keep the internal temperature below 40° C. After complete addition stirring is continued at ambient temperature for one hour.

Neat commercially available bromomethyl-cyclopropane (37.13 g; 275.0 mmol) is added in one portion and the reaction mixture is stirred at 80° C. over night. Ice-cold water (125 mL) is drop wise added and the reaction mixture is stirred for 30 min at ambient temperature. After addition of brine (125 mL) the organic layer is separated and concentrated in vacuo. The aqueous layer is extracted with tert-butylmethylether (3×200 mL). All organic phases are combined, washed with brine (200 mL), dried over MgSO$_4$ and filtered through a plug of neutral alumina containing 5 wt % of water. The product is completely eluted with several portions of tert-butylmethylether. The solvent is removed under reduced pressure. The remaining crude product is purified by short path distillation at 3×10$^{-3}$ mbar (117° C.) to give the title compound as colorless oil that solidifies at ambient temperature. Yield: 47.28 g.

GC-MS (EI): m/z=192 ($M^+$); 138 ($M^+$-$C_4H_6$, 100%).

$^1$H-NMR (200 MHz, DMSO-d$_6$): 6.77 (d, J=8.5, 1H); 6.59 (d, J=2.5, 1H); 6.32 (dd, J$_1$=8.5, J$_2$=2.5, 1H); 5.93 (s, 2H); 3.71 (d, J=6.9, 2H); 1.15 (m, 1H); 0.53 (m, 2H); 0.27 (m, 2H).

The following compounds are obtained analogously to the procedure described in above example A8.

Example A9

5-Cyclobutylmethoxy-benzo[1,3]dioxole

Starting from commercially available bromomethyl-cyclobutane and sesamol the title compound is obtained as colorless solid.

GC-MS (EI): m/z=206 (M+); 138 (100%).

$^1$H-NMR (300 MHz, DMSO-d$_6$): 6.78 (d, J=8.4, 1H); 5.59 (d, J=2.5, 1H); 6.34 (dd, J$_1$=8.4, J$_2$=2.5, 1H); 5.94 (s, 2H); 3.85 (d, J=6.7, 2H); 2.66 (m, 1H); 2.05 (m, 2H); 1.93-1.76 (m, 4H).

Example A10

5-Ethoxy-benzo[1,3]dioxole

Starting from commercially available iodoethane and sesamol the title compound is obtained as colorless oil.

GC-MS (EI): m/z=166 ($M^+$); 138 ($M^+$-$C_2H_4$); 137 ($M^+$-$C_2H_6$, 100%).

$^1$H-NMR (300 MHz, DMSO-d$_6$): 6.78 (d, J=8.4, 1H); 6.59 (d, J=2.5, 1H); 6.33 (dd, J$_1$=8.4, J$_2$=2.5, 1H); 5.94 (s, 2H); 3.93 (qu, J=7.0, 2H); 1.28 (t, J=7.0, 3H).

Example A11

5-Propoxy-benzo[1,3]dioxole

Starting from commercially available iodopropane and sesamol the title compound is obtained as colorless oil.

GC-MS (EI): m/z=180 (M$^+$); 138 (M$^+$-C$_3$H$_6$, 100%); 137 (M$^+$-C$_3$H$_7$).
$^1$H-NMR (300 MHz, DMSO-d$_6$): 6.78 (d, J=8.4, 1H); 6.59 (d, J=2.5, 1H); 6.34 (dd, J$_1$=8.4, J$_2$=2.5, 1H); 5.94 (s, 2H); 3.83 (t, J=6.5, 2H); 1.68 (m, 2H); 0.95 (t, J=7.4, 3H).

Example A12

5-Butoxy-benzo[1,3]dioxole

Starting from commercially available bromobutane and sesamol the title compound is obtained as colorless oil.
GC-MS (EI): m/z=194 (M$^+$); 138 (M$^+$-C$_4$H$_8$, 100%); 137 (M$^+$-C$_4$H$_9$).
$^1$H-NMR (300 MHz, DMSO-d$_6$): 6.78 (d, J=8.4, 1H); 6.59 (d, J=2.5, 1H); 6.34 (dd, J$_1$=8.4, J$_2$=2.5, 1H); 5.94 (s, 2H); 3.87 (t, J=6.5, 2H); 1.65 (m, 2H); 1.41 (m, 2H); 0.92 (t, J=7.4, 3H).

Example A13

5-(2-Methoxy-ethoxy)benzo[1,3]dioxole

Starting from commercially available 1-bromo-2-methoxy-ethane and sesamol the title compound is obtained as colorless oil.
GC-MS (EI): m/z=196 (M$^+$); 138 (M$^+$-C$_3$H$_6$O, 100%); 59.
$^1$H-NMR (300 MHz, DMSO-d$_6$): 6.09 (d, J=8.5, 1H); 6.53 (d, J=2.5, 1H); 6.33 (dd, J$_1$=8.5, J$_2$=2.5, 1H); 5.90 (s, 2H); 4.04 (m, 2H); 3.71 (m, 2H); 3.44 (s, 3H).

Example A14

1-Bromo-2-cyclopropylmethoxy-4-methoxy-benzene

Starting from commercially available 2-bromo-5-methoxy-phenol and bromomethyl-cyclopropane the title compound is obtained as colorless solid.
GC-MS (EI): m/z=258, 256 (M$^+$).
$^1$H-NMR (200 MHz, DMSO-d$_6$): 7.41 (d, J=7.9, 1H); 6.48 (dd, J$_1$=7.9, J$_2$=2.2, 1H); 6.45 (d, J=2.2, 1H); 3.87 (d, J=5.6, 2H); 3.76 (s, 3H); 1.26 (m, 1H); 0.63 (m, 2H); 0.36 (m, 2H).

Example A15

1-Bromo-4-methoxy-2-(2-methoxy-ethoxy)-benzene

Starting from commercially available 2-bromo-5-methoxy-phenol and 1-bromo-2-methoxy-ethane the title compound is obtained as colorless solid.
GC-MS (EI): m/z=260, 262 (M$^+$); 202, 204 (M$^+$-C$_3$H$_6$O, 100%).
$^1$H-NMR (200 MHz, DMSO-d$_6$): 7.40 (d, J=8.7, 1H); 6.51 (d, J=2.8, 1H); 6.41 (dd, J$_1$=8.7, J$_2$=2.8, 1H); 4.15 (t, J=4.8, 2H), 3.80 (t, J=4.8, 2H); 3.78 (s, 3H); 3.48 (s, 3H).

Example A16

1-Bromo-2-cyclopropylmethoxy-5-methoxy-benzene

Starting from commercially available 2-bromo-4-methoxy-phenol and bromomethyl-cyclopropane the title compound is obtained as colorless oil.
GC-MS (EI): m/z=256, 258 (M$^+$); 202, 204 (100%).
$^1$H-NMR (200 MHz, CDCl$_3$): 7.11 (d, J=2.8, 1H); 6.86 (d, J=8.9, 1H); 6.78 (dd, J$_1$=8.9, J$_2$=2.8, 1H); 3.82 (d, J=6.8, 2H); 3.75 (s, 3H); 1.16 (m, 1H); 0.51 (m, 2H); 0.44 (m, 2H).

Example A17

1-Bromo-2-cyclopropylmethoxy-4-fluoro-benzene

Starting from commercially available 2-bromo-5-fluorophenol and bromomethyl-cyclopropane the title compound is prepared as colorless oil
GC-MS (EI): m/z=244, 246 (M$^+$); 190, 192 (M$^+$-C4H6); 55 (100%).
$^1$H-NMR (300 MHz, DMSO-d$_6$): 7.58 (dd, J$_1$=8.7, J$_2$=6.4, 1H); 7.02 (dd, J$_1$=11.2, J$_2$=2.8, 1H); 6.75 (ddd, J$_1$=J$_2$=8.7, J$_3$=2.8, 1H); 3.93 (d, J=6.8, 2H); 1.24 (m, 1H); 0.56 (m, 2H); 0.38 (m, 2H).

Example A18

1-Bromo-2-cyclopropylmethoxy-5-fluoro-benzene

Starting from commercially available 2-bromo-4-fluorophenol and bromomethyl-cyclopropane the title compound is obtained as colorless oil.
GC-MS (EI): m/z=244, 246 (M$^+$); 190, 192; (M$^+$-C$_4$H$_6$); 55 (100%).
$^1$H-NMR (400 MHz, DMSO-d$_6$): 7.52 (dd, J$_1$=8.2, J$_2$=3.1, 1H); 7.19 (ddd, J$_1$=9.1, J$_2$=8.2, J$_3$=3.1, 1H); 7.10 (dd, J1=9.1, J2=5.0, 1H); 3.89 (d, J=6.8, 2H); 1.22 (m, 2H); 0.57 (m, 2H); 0.35 (m, 2H).

Example A19

1-Bromo-2-cyclopropylmethoxy-4-fluoro-5-methoxy-benzene

Starting from 2-bromo-5-fluoro-4-methoxy-phenol (example A3) and bromomethyl-cyclopropane the title compound is obtained as colorless solid.
GC-MS (EI): m/z=276, 274 (M$^+$); 222, 220 (M$^+$-C$_4$H$_6$, 100%); 206, 204.
$^1$H-NMR (400 MHz, DMSO-d$_6$): 7.38 (d, J=9.2, 1H); 7.13 (d, J=13.1, 1H); 3.85 (d, J=6.9, 2H); 3.80 (s, 3H); 1.20 (m, 1H); 0.57 (m, 2H); 0.33 (m, 2H).

Example A20

1-Bromo-2-cyclopropylmethoxy-5-fluoro-4-methoxy-benzene

Starting from commercially available 2-bromo-4-fluoro-5-methoxy-phenol (example A4) and bromomethyl-cyclopropane the title compound is obtained as colorless solid.
GC-MS (EI): m/z=276, 274 (M$^+$); 222, 219 (M$^+$-C$_4$H$_6$, 100%).
$^1$H-NMR (400 MHz, DMSO-d$_6$): 7.48 (d, J=10.8, 1H); 6.90 (d, J=7.9, 1H); 3.93 (d, J=6.8, 2H); 3.85 (s, 3H); 1.24 (m, 1H); 0.58 (m, 2H); 0.36 (m, 2H).

Example A21

1-Bromo-2-cyclopropylmethoxy-benzene

Starting from commercially available 2-bromo-phenol and bromomethyl-cyclopropane the title compound is obtained as colorless oil.
GC-MS (EI): m/z=226, 228 (M$^+$); 172, 174 (M$^+$-C$_4$H$_6$), 55 (100%).
$^1$H-NMR (400 MHz, DMSO-d$_6$): 7.56 (dd, J$_1$=7.9, J$_2$=1.6, 1H); 7.31 (ddd, J$_1$=8.3, J$_2$=7.3, J$_3$=1.6, 1H); 7.08 (dd, J$_1$=8.3, $J_2$=1.3, 1H); 6.87 (ddd, $J_1$=7.9, $J_2$=7.3, $J_3$=1.3, 1H); 3.91 (d, J=6.8, 2H); 1.24 (m, 1H); 0.58 (m, 2H); 0.35 (m, 2H).

Example A22

2-Bromo-1-cyclopropylmethoxy-4-methyl-benzene

Starting from commercially available 2-bromo-4-methyl-phenol and bromomethyl-cyclopropane the title compound is obtained as colorless oil.

GC-MS (EI): m/z=240, 242 (M$^+$); 186, 188 (M$^+$-C$_4$H$_6$); 107.

$^1$H-NMR (300 MHz, CDCl3): 7.34 (d, J=2.1, 1H); 7.01 (dd, $J_1$=8.2, $J_2$=2.1, 1H); 6.78 (d, J=8.2, 1H); 3.86 (d, J=6.8, 2H); 2.28 (s, 3H); 1.30 (m, 1H); 0.63 (m, 2H); 0.39 (m, 2H).

Example A23

1-(3-Bromo-4-cyclopropylmethoxy-phenyl)-ethanone

Starting from 1-(3-bromo-4-hydroxy-phenyl)-ethanone prepared according to literature (Heravi et al, Tetrahedron Letters 2005, 46, 8959) and bromomethyl-cyclopropane the title compound is obtained as colorless solid.

$^1$H-NMR (300 MHz, DMSO-d$_6$): 8.10 (d, J=2.0, 1H); 7.91 (dd, $J_1$=8.0, $J_2$=2.0, 1H); 7.18 (d, J=8.0, 1H); 4.03 (d, J=6.0, 2H); 2.50 (s, 3H); 1.30 (m, 1H); 0.62 (m, 2H); 0.40 (m, 2H).

Example A24

1-(4-Cyclopropylmethoxy-2-methyl-phenyl)-ethanone

Starting from commercially available 1-(4-hydroxy-2-methyl-phenyl)-ethanone and bromomethyl-cyclopropane the title compound is obtained as pale yellow oil.

$^1$H-NMR (300 MHz, DMSO-d$_6$): 7.78 (d, J=2.0, 1H), 6.80 (m, 2H), 3.88 (d, J=6.0, 2H), 2.50 (s, 3H), 2.45 (s, 3H), 1.25 (m, 1H), 0.55 (m, 2H), 0.32 (m, 2H).

Example A25

4-Bromo-1-fluoro-2-methoxymethoxy-benzene

Starting from commercially available 5-bromo-2-fluoro-phenol and 1-chloro-1-methoxy-methane prepared according to literature (Stadlwieser, J. Synthesis 1985, 490) the title compound is obtained as colorless oil.

GC-MS (EI): m/z=234, 236 (M$^+$); 45 (100%).

$^1$H-NMR (300 MHz, DMSO-d$_6$): 7.45 (dd, $J_1$=7.5, $J_2$=2.2, 1H); 7.28-7.17 (m, 2H); 5.28 (s, 2H); 3.41 (s, 3H).

Example A26

4-Bromo-2-(1,1-difluoro-methoxy)-1-fluoro-benzene

A pressure reactor is charged with commercially available 5-bromo-2-fluoro-phenol (95.50 g; 0.50 mol), 6N NaOH (500 mL; 3.0 mol) and dioxane (500 mL). The reactor is pressurized with 1-chloro-1,1-difluoro-methane to 6.0 bar and heated to 80° C. for 72 hours.

The cooled reaction mixture is acidified to pH 2 by careful addition of 6N HCl and extracted with tert.-BuOMe (1000 mL+2×200 mL). The combined organic layers are washed with brine (300 mL) and dried over MgSO$_4$. After filtration the solvent is removed under reduced pressure. The product is separated from remaining starting material by column chromatography on silica gel (cyclohexane) to give the title compound as colorless oil. Yield: 54.1 g.

GC-MS (EI): m/z=240, 242 (M$^+$); 190, 192 (100%).

$^1$H-NMR (300 MHz, DMSO-d$_6$): 7.64 (dd, $J_1$=7.1, $J_2$=2.4, 1H); 7.52 (ddd, $J_1$=8.8, $J_2$=4.2, $J_3$=2.4, 1); 7.41 (dd, $J_1$=10.4, $J_2$=8.8, 1H); 7.3 (T, J=73.0, 1H).

Example A27

1-Bromo-2-cyclopropylmethoxy-5-fluoro-4-methoxymethoxy-benzene

Starting from 2-bromo-4-fluoro-5-methoxymethoxy-phenol (example A7) and bromomethyl-cyclopropane the title compound is obtained as colorless oil.

GC-MS (EI): m/z=304, 306 (M$^+$); 45 (100%).

$^1$H-NMR (300 MHz, DMSO-d$_6$): 7.54 (d, J=10.4, 1H); 6.99 (d, J=7.7, 1H); 5.26 (s, 2H); 3.88 (d, J=6.9, 2H); 3.41 (s, 3H); 1.22 (m, 1H); 0.57 (m, 2H); 0.34 (m, 2H).

Example A28

1-Bromo-2-cyclopropylmethoxy-4-(1,1-difluoro-methoxy)-5-fluoro-benzene

Starting from 2-bromo-5-(1,1-difluoro-methoxy)-4-fluoro-phenol (example A5) and bromomethyl-cyclopropane the title compound is obtained as colorless oil.

GC-MS (EI): m/z=310, 312 (M$^+$); 256, 258; 206, 208; 177, 179; 55 (100%).

$^1$H-NMR (300 MHz, DMSO-d$_6$): 7.78 (d, J=6.9, 1H); 7.25 (t, J=74.0, 1H); 7.13 (d, J=7.3, 1H); 3.92 (d, J=6.9, 2H); 1.23 (m, 1H); 0.58 (m, 2H); 0.35 (m, 2H).

Example A29

5-Cyclopropylmethoxy-4-(4,4,5,5-tetramethyl-[1,3,2]dioxaborolan-2-yl)-benzo[1,3]dioxole The reaction is performed in flame-dried glassware under an atmosphere of argon.

A stirred solution of 5-cyclopropylmethoxy-benzo[1,3]dioxole from example A8 (38.44 g; 200.0 mmol) in dry THF (500 mL) is cooled to −40° C. before n-butyl lithium (138.0 mL; 1.6 M solution in hexane; 220 mmol) is slowly added via syringe. After complete addition, stirring is continued at −40° C. for two hours. At −78° C. neat 2-iso-propoxy-4,4,5,5-tetramethyl-[1,3,2]dioxaborolane (40.95 g; 220.0 mmol) is added via syringe and stirring is continued at −78° C. for two hours.

At −15° C. the reaction mixture is quenched with saturated NH$_4$Cl-solution (200 mL) and stirred at ambient temperature for 30 min. The organic layer is separated and concentrated under reduced pressure. The aqueous layer is extracted with tert-butylmethylether (3×200 mL). All organic phases are combined, washed with saturated NaCl-solution (200 mL), dried over MgSO$_4$ and filtered through a plug of neutral alumina containing 5 wt % of water. The product is completely eluted with several small portions of tert-butylmethylether.

The solvent is removed under reduced pressure. The crude is treated with ice-cold methanol (50 mL) to deliver the title compound as colorless solid. Yield 54.32 g.

GC-MS (EI): m/z=318 (M$^+$); 264 (M$^+$-C$_4$H$_6$); 207; 164 (100%).

¹H-NMR (200 MHz, DMSO-d₆): 6.78 (d, J=8.4, 1H); 6.29 (d, J=8.4; 1H); 5.92 (s, 2H); 3.71 (d, J=6.3, 2H); 1.29 (s, 12H); 1.14 (m, 1H); 0.50 (m, 2H); 0.34 (m, 2H).

The following compounds are obtained analogously to the procedure described in above example A29.

Example A30

5-Cyclobutylmethoxy-4-(4,4,5,5-tetramethyl-[1,3,2]dioxaborolan-2-yl)-benzo[1,3]dioxole Starting from 5-cyclobutylmethoxy-benzo[1,3]dioxole (example A9) the title compound is prepared as colorless solid.

GC-MS (EI): m/z=332 (M⁺); 164 (100%);
¹H-NMR (400 MHz, DMSO-d₆): 6.81 (d, J=8.4, 1H); 6.29 (d, J=8.4; 1H); 5.92 (s, 2H); 3.76 (d, J=6.0, 2H); 2.64 (m, 1H); 2.07-1.76 (m, 6H); 1.27 (s, 12H).

Example A31

5-Ethoxy-4-(4,4,5,5-tetramethyl-[1,3,2]dioxaborolan-2-yl)-benzo[1,3]dioxole

Starting from 5-ethoxy-benzo[1,3]dioxole (example A10) the title compound is prepared as color-less solid.

GC-MS (EI): m/z=292 (M⁺, 100%); 207; 164.
¹H-NMR (300 MHz, DMSO-d₆): 6.80 (d, J=8.4, 1H); 6.30 (d, J=8.4; 1H); 5.92 (s, 2H); 3.86 (qu, J=7.0, 2H); 1.27 (s, 12H); 1.25 (t, J=7.0, 3H).

Example A32

5-Propoxy-4-(4,4,5,5-tetramethyl-[1,3,2]dioxaborolan-2-yl)-benzo[1,3]dioxole

Starting from 5-propoxy-benzo[1,3]dioxole (example A11) the title compound is prepared as color-less solid.

GC-MS (EI): m/z=306 (M⁺); 207 (100%); 164.
¹H-NMR (300 MHz, DMSO-d₆): 6.80 (d, J=8.4, 1H); 6.28 (d, J=8.4; 1H); 5.92 (s, 2H); 3.77 (t, J=6.2, 2H); 1.66 (m, 2H); 1.27 (s, 12H); 0.98 (t, J=7.4, 3H).

Example A33

5-Butoxy-4-(4,4,5,5-tetramethyl-[1,3,2]dioxaborolan-2-yl)-benzo[1,3]dioxole

Starting from 5-butoxy-benzo[1,3]dioxole (example A12) the title compound is prepared as color-less solid.

GC-MS (EI): m/z=320 (M⁺); 207 (100%); 164.
¹H-NMR (300 MHz, DMSO-d₆): 6.80 (d, J=8.5, 1H); 6.29 (d, J=8.5; 1H); 5.92 (s, 2H); 3.81 (t, J=6.1, 2H); 1.62 (m, 2H); 1.46 (m, 2H); 1.26 (s, 12H); 0.91 (t, J=7.3, 3H).

Example A34

5-(2-Methoxy-ethoxy)-4-(4,4,5,5-tetramethyl-[1,3,2]dioxaborolan-2-yl)-benzo[1,3]dioxole Starting from 5-(2-methoxy-ethoxy)-benzo[1,3]dioxole (example A13) the title compound is pre-pared as colorless solid.

GC-MS (EI): m/z=322 (M⁺); 207 (100%); 164.
¹H-NMR (200 MHz, CDCl₃): 6.81 (d, J=8.5, 1H); 6.31 (d, J=8.5, 1H); 5.93 (s, 2H); 3.93 (m, 2H); 3.59 (m, 2H); 3.30 (s, 3H); 1.27 (s, 12H).

Example A35

2-(2-Cyclopropylmethoxy-4-fluoro-5-methoxy-phenyl)-4,4,5,5-tetramethyl-[1,3,2]dioxaborolane The reaction is performed in flame-dried glassware under an atmosphere of argon.

A stirred solution of 1-bromo-2-cyclopropylmethoxy-4-fluoro-5-methoxy-benzene from example A19 (27.51 g; 0.10 mol) in dry tert-butylmethylether (500 mL) is cooled to −20° C. before addition of n-butyl lithium (1.6 M in hexane; 68.8 mL; 0.11 mol) via syringe. After complete addition stirring is continued for one hour. Neat 2-iso-propoxy-4,4,5,5-tetramethyl-[1,3,2]dioxaborolane is added via syringe into the reaction mixture at −40° C. After 30 min the reaction is quenched with 1M citric acid (200 mL) at 0° C. and stirred for one hour at ambient temperature. The organic layer is separated. The aqueous layer is extracted with tert-butylmethylether (100 mL). The combined organic layers are washed with brine (200 mL) dried over MgSO₄ and filtered through a plug of neutral alumina containing 5 wt % of water. The product is completely eluted with several small portions of tert-butylmethylether. The solvent is removed under reduced pressure. The crude is purified by short path distillation at 3×10⁻³ mbar (160° C.) to give the title compound as a colorless oil that solidifies at ambient temperature. Yield: 22.65 g.

GC-MS (EI): m/z=322 (M⁺, 100%); 211, 168. Purity: >99.8%.
¹H-NMR (300 MHz, DMSO-d₆): 7.14 (d, J=10.5, 1H); 6.91 (d, J=13.6, 1H); 3.81 (d, J=6.0, 2H); 3.77 (s, 3H); 1.28 (s, 12H); 1.16 (m, 1H); 0.48 (m, 2H); 0.38 (m, 2H).

The following compounds are obtained analogously to the procedure described in above example A35.

Example A36

2-(2-Cyclopropylmethoxy-4-methoxy-phenyl)-4,4,5,5-tetramethyl-[1,3,2]dioxaborolane Starting from 1-bromo-2-cyclopropylmethoxy-4-methoxy-benzene (example A14) the title compound is prepared as colorless solid after crystallization from hexane.

GC-MS (EI): m/z=304 (M⁺); 276; 250; 193; 164 (100%); 150.
¹H-NMR (200 MHz, DMSO-d₆): 7.41 (d, J=7.9, 1H); 6.48 (dd, J₁=7.9, J₂=2.2, 1H); 6.45 (d, J=2.2, 1H); 3.87 (d, J=5.6, 2H); 3.75 (s, 3H); 1.25 (s, 12H); 1.16 (m, 1H); 0.49 (m, 2H); 0.44 (m, 2H).

Example A37

2-(2-Cyclopropylmethoxy-5-methoxy-phenyl)-4,4,5,5-tetramethyl-[1,3,2]dioxaborolane Starting from 1-bromo-2-cyclopropylmethoxy-5-methoxy-benzene (example A16) the title compound is obtained as colorless oil after short path distillation at 3×10⁻³ mbar (160° C.).

GC-MS (EI): m/z=304 (M⁺); 276; 250; 193 (100%); 150.
¹H-NMR (200 MHz, CDCl₃): 7.15 (d, J=3.1, 1H); 6.90 (dd, J₁=9.0, J₂=3.1, 1H); 6.81 (d, J=9.0, 1H); 3.80 (d, J=6.3, 2H); 3.78 (s, 3H); 1.35 (s, 12H); 1.17 (m, 1H); 0.55 (m, 2H); 0.38 (m, 2H).

Example A38

2-(2-Cyclopropylmethoxy-4-fluoro-phenyl)-4,4,5,5-tetramethyl-[1,3,2]dioxaborolane Starting from 1-bromo-2-cyclopropylmethoxy-4-fluoro-benzene (example A17) the title compound is obtained as colorless solid after short path distillation at $3\times10^{-3}$ mbar (130° C.).

GC-MS (EI): m/z=292 (M$^+$); 181, 55 (100%).
$^1$H-NMR (300 MHz, DMSO-d$_6$): 7.48 (dd, J1=J2=8.0, 1H); 6.80 (dd, J1=12.0, J2=2.2, 1H); 6.71 (ddd, J1=8.4, J2=8.0, J3=2.2, 1H); 3.89 (d, J=5.8, 2H); 1.27 (s, 12H); 1.17 (m, 1H); 0.51 (m, 2H); 0.46 (m, 2H).

Example A39

2-(2-Cyclopropylmethoxy-5-fluoro-phenyl)-4,4,5,5-tetramethyl-[1,3,2]dioxaborolane Starting from 1-bromo-2-cyclopropylmethoxy-5-fluoro-benzene (example A18) the title compound is obtained as colorless solid after short path distillation at $3\times10^{-3}$ mbar (100° C.).

GC-MS (EI): m/z=292 (M+); 181 (100%); 55.
$^1$H-NMR (300 MHz, DMSO-d$_6$): 7.22-7.13 (m, 2H); 6.95 (dd, J1=8.9, J2=4.2, 1H); 3.85 (d, J=6.4, 2H); 1.28 (s, 12H); 1.17 (m, 1H); 0.52 (m, 2H); 0.46 (m, 2H).

Example A40

2-(2-Cyclopropylmethoxy-phenyl)-4,4,5,5-tetramethyl-[1,3,2]dioxaborolane

Starting from 1-bromo-2-cyclopropylmethoxy-benzene (example A21) the title compound is obtained as colorless viscous oil.

GC-MS (EI): m/z=274 (M+); 163; 120; 83; 55 (100%).
$^1$H-NMR (300 MHz, DMSO-d$_6$): 7.45 (dd, J$_1$=7.4, J$_2$=1.7, 1H); 7.37 (ddd, J$_1$=7.8, J$_2$=6.9, J$_3$=1.7, 1H); 6.91 (d, J=7.8, 1H); 6.89 (d, J=6.9, 1H); 3.86 (d, J=5.8, 2H); 1.28 (s, 12H); 1.20 (m, 1H); 0.50 (m, 2H); 0.44 (m, 2H).

Example A41

2-(2-Cyclopropylmethoxy-5-methyl-phenyl)-4,4,5,5-tetramethyl-[1,3,2]dioxaborolane Starting from 1-bromo-2-cyclopropylmethoxy-5-methyl-benzene (example A22) the title compound is obtained as colorless solid.

$^1$H-NMR 400 MHz, DMSO-d$_6$): 7.26 (d, J=2.1, 1H); 7.16 (dd, J$_1$=8.3, J$_2$=2.1, 1H); 6.81 (d, J=8.3, 1H); 3.81 (d, J=5.9, 2H); 2.21 (s, 3H); 1.27 (s, 12H); 1.15 (m, 1H); 0.47 (m, 2H); 0.40 (m, 2H).

Example A42

2-(2-Cyclopropylmethoxy-5-fluoro-4-methoxy-phenyl)-4,4,5,5-tetramethyl-[1,3,2]dioxaborolane Starting from 1-bromo-2-cyclopropylmethoxy-5-fluoro-4-methoxy-benzene (example A20) the title compound is obtained as colorless solid after crystallization from methanol.

GC-MS (EI): m/z=322 (M$^+$); 211; 182; 168 (100%); 55.
$^1$H-NMR (300 MHz, DMSO-d$_6$): 7.15 (d, J=11.7, 1H); 6.73 (d, J=7.0, 1H); 3.88 (d, J=6.0, 2H); 3.85 (s, 3H); 1.26 (s, 12H); 1.16 (m, 1H); 0.50 (m, 2H); 0.30 (m, 2H).

Example A43

2-[4-Methoxy-2-(2-methoxy-ethoxy)-phenyl]-4,4,5,5-tetramethyl-[1,3,2]dioxaborolane Starting from 1-bromo-4-methoxy-2-(2-methoxy-ethoxy)-benzene (example A15) the title compound is obtained as colorless solid after crystallization from methanol.

GC-MS (EI): m/z=308 (M+); 250 (M+-C$_3$H$_6$O); 164 (100%).
$^1$H-NMR (200 MHz, CDCl$_3$): 7.61 (d, J=8.2, 1H); 6.49 (dd, J$_1$=8.2, J$_2$=2.2, 1H); 6.41 (d, J=2.2 1H); 4.10 (t, J=5.4, 2H); 3.80 (s, 3H); 3.78 (t, J=5.4, 2H); 3.50 (s, 3H); 1.32 (s, 12H).

Example A44

2-(2-Cyclopropylmethoxy-5-fluoro-4-methoxymethoxy-phenyl)-4,4,5,5-tetramethyl-[1,3,2]dioxaborolane Starting from 1-bromo-2-cyclopropylmethoxy-5-fluoro-4-methoxymethoxy-benzene (example A27) the title compound is obtained as colorless oil that solidified on standing at ambient temperature after short path distillation at $3\times10^{-3}$ mbar (150° C.).

GC-MS (EI): m/z=352 (M$^+$); 45 (100%).
$^1$H-NMR (300 MHz, DMSO-d$_6$): 7.19 (d, J=11.3, 1H); 6.82 (d, J=6.8, 1H); 5.28 (s, 2H); 3.83 (d, J=6.0, 2H); 3.41 (s, 3H); 1.26 (s, 12H); 1.16 (m, 1H); 0.49 (m, 2H); 0.40 (m, 2H).

Example A45

2-[2-Cyclopropylmethoxy-4-(1,1-difluoro-methoxy)-5-fluoro-phenyl]-4,4,5,5-tetramethyl-[1,3,2]-dioxabolane Starting from 1-bromo-2-cyclopropylmethoxy-4-(1,1-difluoro-methoxy)-5-fluoro-benzene (example A28) the title compound is obtained as colorless oil after short path distillation at $2\times10^{-3}$ mbar (130° C.)

GC-MS (EI): 358 (M+); 330, 247, 204, 154, 83, 55 (100%).
$^1$H-NMR (300 MHz, DMSO-d$_6$): 7.41 (d, J=10.6, 1h); 6.69 (d, J=6.0, 1H); 6.55 (t, J=74.0, 1H); 3.83 (d, J=6.0, 2H); 1.34 (s, 12H); 1.23 (m, 1H); 0.57 (m, 2H); 0.42 (m, 2H).

Example A46

1-[4-Cyclopropylmethoxy-3-(4,4,5,5-tetramethyl-[1,3,2]dioxaborolan-2-yl)-phenyl]-ethanone A suspension of 1-(3-Bromo-4-cyclopropylmethoxy-phenyl)-ethanone from example A23 (3.00 g, 11.1 mmol), potassium acetate (3.30 g, 33.3 mmol), bis(pinacolato)diboron (5.70 g, 22.2 mmol) and 1,1'-bis(diphenyl-phosphino)ferrocene palladium-Op-chloride (0.90 g, 1.1 mmol) in 1,4-dioxane (50 mL) is heated under a nitrogen atmosphere for 4 h at 100° C. After cooling to ambient temperature the solvent is evaporated. The mixture is purified by column chromatography on silica gel (n-hexane/ethyl acetate (65:35 v/v) to give the title compound as a off white solid.

Yield: 3.13 g.
MS (ESI): m/z=317 (MH$^+$, 100%).

¹H-NMR (300 MHz, DMSO-$d_6$) 8.02 (m, 2H); 7.00 (m, 1H); 3.97 (d, J=6.0, 2H); 2.50 (s, 3H); 1.30 (s, 12H); 1.23 (m, 1H); 0.50 (m, 4H).

The following compound is obtained analogously to the procedure described in above example A46.

Example A47

1-[4-Cyclopropylmethoxy-2-methyl-5-(4,4,5,5-tetramethyl-[1,3,2]dioxaborolan-2-yl)-phenyl]-ethanone Starting from 1-(5-bromo-4-cyclopropylmethoxy-2-methyl-phenyl)-ethanone (example A6) the title compound is obtained as off-white solid after column chromatography on silica gel.

MS (ESI): m/z=331 (MH⁺, 100%).

¹H-NMR (300 MHz, DMSO-$d_6$): 7.95 (s, 1H); 6.83 (s, 1H); 3.98 (d, J=6.0, 2H); 2.50 (m, 6H); 1.35 (m, 1H); 1.30 (s, 12H); 0.60-0.30 (m, 4H).

Example A48

4-(5-Cyclopropylmethoxy-1,3 benzodioxol-4-yl)-5H-pyrrolo[3,2-d]pyrimidine-7-carboxylic acid ethyl ester A 25 ml pressure vial is charged with 4-chloro-5H-pyrrolo[3,2-d]pyrimidine-7-carboxylic acid ethyl ester (0.90 g; 4.0 mmol) prepared according to the procedure described in US 2005/124623A1, 2M aqueous $Cs_2CO_3$ solution (6.0 mL), dimethoxyethane (10.0 mL) and $PdCl_2(PCy_3)_2$ (236 mg, 0.32 mmol) (Cy=cyclohexyl). The mixture is heated to 150° C. for 5 min under microwave irradiation. After cooling to ambient temperature, 5-cyclopropylmethoxy-4-(4,4,5,5-tetramethyl-[1,3,2]dioxaborolan-2-yl)-benzo[1,3]dioxole from example A29 (1.91 g; 5.0 mmol) is added to the reaction vial and the mixture is heated to 150° C. for 30 min under microwave irradiation.

After cooling to ambient temperature, water (10.0 mL) is added. The precipitated crude product is collected by suction filtration and washed with several small portions (10 to 25 mL) of DME/water (1:2 v/v). Crude products from ten reactions are combined and dissolved in hot DME. The hot solution is filtered through a short column of neutral alumina containing 5 wt % of water. The column is washed with several portions of hot DME. The combined filtrates are evaporated to dryness. The crude is crystallized from DME/toluene to give the title compound as colorless solid. Yield 11.58 g MS (ESI): m/z=404 (MNa⁺); 382 (MH⁺, 100%).

¹H-NMR (200 MHz, DMSO-$d_6$): 12.36 (s, 1H, —NH); 9.01 (s, 1H); 8.39 (s, 1H); 7.00 (d, J=8.6, 1H); 6.56 (d, J=8.6, 1H); 5.99 (s, 2H); 4.31 (qu, J=7.1, 2H); 3.75 (d, J=6.7, 2H); 1.33 (t, J=7.1, 3H); 0.87 (m, 1H); 0.29 (m, 2H); 0.08 (m, 2H).

The following compounds are obtained analogously to the procedure described in above example A48.

Example A49

4-(5-Cyclobutylmethoxy-benzo[1,3]dioxol-4-yl)-5H-pyrrolo[3,2-d]pyrimidine-7-carboxylic acid ethyl ester Starting from 4-chloro-5H-pyrrolo[3,2-d]pyrimidine-7-carboxylic acid ethyl ester and 5-cyclobutylmethoxy-4-(4,4,5,5-tetramethyl-[1,3,2]dioxaborolan-2-yl)-benzo[1,3]dioxole (example A30) the title compound is obtained as colorless solid.

MS (ESI): m/z=396 (MH⁺, 100%); 382 (MH⁺—$CH_2$).

¹H-NMR (400 MHz, DMSO-$d_6$): 12.42 (br.s, 1H, —NH); 9.00 (s, 1H); 8.37 (d, J=3.0, 1H); 7.01 (d, J=8.6, 1H); 6.59 (d, J=8.6, 1H); 6.00 (s, 2H); 4.31 (qu, J=7.1, 2H); 3.84 (d, J=6.1, 2H); 2.36 (m, 1H); 1.65 (m, 3H); 1.50 (m, 3H); 1.33 (t, J=7.1, 3H).

Example A50

4-(2-Cyclopropylmethoxy-4-methoxy-phenyl)-5H-pyrrolo[3,2-d]pyrimidine-7-carboxylic acid ethyl ester Starting from 4-chloro-5H-pyrrolo[3,2-d]pyrimidine-7-carboxylic acid ethyl ester and 2-(2-cyclopropylmethoxy-4-methoxy-phenyl)-4,4,5,5-tetramethyl-[1,3,2]dioxaborolane (example A36) the title compound is obtained as colorless solid.

MS (ESI): m/z=390 (MNa⁺); 368 (MH⁺, 100%); 354 (MH⁺—$CH_2$).

¹H-NMR (200 MHz, DMSO-$d_6$): 12.03 (br.s, 1H, —NH); 8.98 (s, 1H); 8.32 (s, 1H); 7.59 (d, J=8.2, 1H); 6.72 (dd, $J_1$=8.2, $J_2$=2.3, 1H); 6.69 (d, J=2.3, 1H); 4.31 (qu, J=7.1, 2H); 3.91 (d, J=6.9, 2H); 3.86 (s, 3H); 1.33 (t, J=7.1, 3H); 0.96 (m, 1H); 0.35 (m, 2H); 0.23 (m, 2H).

Example A51

4-(2-Cyclopropylmethoxy-5-methoxy-phenyl)-5H-pyrrolo[3,2-d]pyrimidine-7-carboxylic acid ethyl ester Starting from 4-chloro-5H-pyrrolo[3,2-d]pyrimidine-7-carboxylic acid ethyl ester and 2-(2-Cyclopropylmethoxy-5-methoxy-phenyl)-4,4,5,5-tetramethyl-[1,3,2]dioxaborolane (example A37) the title compound is obtained as colorless solid.

MS (ESI): m/z=390 (MNa⁺); 368 (MH⁺, 100%); 354 (MH⁺—$CH_2$).

¹H-NMR (200 MHz, DMSO-$d_6$): 12.10 (br.s, 1H, —NH); 9.04 (s, 1H); 8.36 (d, J=3.2, 1H); 7.19 (t, J=1.7, 1H); 7.11 (t, J=1.7, 2H); 6.69 (d, J=2.3, 1H); 4.31 (qu, J=7.0, 2H); 3.81 (d, J=6.8, 2H); 3.77 (s, 3H); 1.34 (t, J=7.0, 3H); 0.91 (m, 1H); 0.32 (m, 2H); 0.15 (m, 2H).

Example A52

4-(2-Cyclopropylmethoxy-4-fluoro-phenyl)-5H-pyrrolo[3,2-d]pyrimidine-7-carboxylic acid ethyl ester Starting from 4-chloro-5H-pyrrolo[3,2-d]pyrimidine-7-carboxylic acid ethyl ester and 2-(2-cyclopropylmethoxy-4-fluoro-phenyl)-4,4,5,5-tetramethyl-[1,3,2]dioxaborolane (example A38) the title compound is obtained as colorless solid.

MS (ESI): m/z=378 (MNa⁺); 356 (MH⁺, 100%).

¹H-NMR (400 MHz, DMSO-$d_6$): 12.18 (br.s, 1H, —NH); 9.02 (s, 1H); 8.39 (s, 1H); 7.65 (dd, $J_1$=8.4, $J_2$=2.3, 1H); 7.08 (dd, $J_1$=11.5, $J_2$=2.3, 1H); 6.96 (ddd, $J_1$=$J_2$=8.4, $J_3$=2.3); 4.31 (qu, J=7.1, 2H); 3.91 (d, J=7.0, 2H); 1.33 (t, J=7.1, 3H); 0.95 (m, 1H); 0.35 (m, 2H); 0.21 (m, 2H).

Example A53

4-(2-Cyclopropylmethoxy-5-fluoro-phenyl)-5H-pyrrolo[3,2-d]pyrimidine-7-carboxylic acid ethyl ester Starting from 4-chloro-5H-pyrrolo[3,2-d]pyrimidine-7-carboxylic acid ethyl ester and 2-(2-cyclopropylmethoxy-5-fluoro-phenyl)-4,4,5,5-tetramethyl-[1,3,2]dioxaborolane (example A39) the title compound is obtained as colorless solid.

MS (ESI): m/z=378 (MNa$^+$); 356 (MH$^+$, 100%); 342 (MH$^+$—CH$_2$).

$^1$H-NMR (200 MHz, DMSO-d$_6$): 12.20 (br.s, 1H, —NH); 9.04 (s, 1H); 8.41 (s, 1H); 7.46-7.32 (m, 2H); 7.18 (dd, J$_1$=8.9, J$_2$=4.4, 1H); 4.32 (qu, J=7.1, 2H); 3.87 (d, J=6.9, 2H); 1.34 (t, J=7.1, 3H); 0.93 (m, 1H); 0.33 (m, 2H); 0.17 (m, 2H).

Example A54

4-(2-Cyclopropylmethoxy-phenyl)-5H-pyrrolo[3,2-d]pyrimidine-7-carboxylic acid ethyl ester Starting from 4-chloro-5H-pyrrolo[3,2-d]pyrimidine-7-carboxylic acid ethyl ester and 2-(2-cyclopropylmethoxy-phenyl)-4,4,5,5-tetramethyl-[1,3,2]dioxaborolane (example A40) the title compound is obtained as colorless solid.

MS (ESI): m/z=360 (MNa$^+$); 338 (MH$^+$); 324 (MH$^+$—CH$_2$, 100%).

$^1$H-NMR (400 MHz, DMSO-d$_6$): 12.17 (br.s, 1H, —NH); 9.04 (s, 1H); 8.38 (d, J=3.4, 1H); 7.62 (dd, =7.5 J$_2$=1.2, 1H); 7.53 (ddd, J$_1$=8.6, J$_2$=7.5, J$_3$=1.2, 1H); 7.17 (d, J=8.6, 1H); 7.12 (d, J=7.5, 1H); 4.32 (qu, J=7.1, 2H); 3.90 (d, J=6.9, 2H); 1.32 (t, J=7.1, 3H); 0.95 (m, 1H); 0.34 (m, 2H); 0.22 (m, 2H).

Example A55

4-(2-Cyclopropylmethoxy-4-fluoro-5-methoxy-phenyl)-5H-pyrrolo[3,2-d]pyrimidine-7-carboxylic acid ethyl ester Starting from 4-chloro-5H-pyrrolo[3,2-d]pyrimidine-7-carboxylic acid ethyl ester and 2-(2-cyclopropylmethoxy-4-fluoro-5-methoxy-phenyl)-4,4,5,5-tetramethyl-[1,3,2]dioxaborolane (example A35) the title compound is obtained as colorless solid.

MS (ESI): m/z=389 (MH$^+$, 100%)

$^1$H-NMR (300 MHz, DMSO-d$_6$): 12.11 (br.s, 1H, —NH); 9.03 (s, 1H); 8.38 (d, J=3.2, 1H, —NH); 7.39 (d, J=9.8, 1H); 7.18 (d, J=13.4, 1H); 4.31 (qu, J=7.1, 2H); 3.84 (s, 3H & d, J=5.1, 2H); 1.34 (t, J=7.1, 3H); 0.92 (m, 1H); 0.33 (m, 2H); 0.15 (m, 2H).

Example A56

4-(2-Cyclopropylmethoxy-5-fluoro-4-methoxy-phenyl)-5H-pyrrolo[3,2-d]pyrimidine-7-carboxylic acid ethyl ester Starting from 4-chloro-5H-pyrrolo[3,2-d]pyrimidine-7-carboxylic acid ethyl ester and 2-(2-cyclopropylmethoxy-5-fluoro-4-methoxy-phenyl)-4,4,5,5-tetramethyl-[1,3,2]dioxaborolane (example A42) the title compound is obtained as pale yellow solid.

MS (ESI): m/z=408 (MNa$^+$); 386 (MH$^+$, 100%).

$^1$H-NMR (400 MHz, DMSO-d$_6$): 12.06 (br.s, 1H, —NH); 9.00 (s, 1H); 8.37 (d, J=2.7, 1H); 7.48 (d, J=11.9, 1H); 6.92 (d, J=7.3, 1H); 4.32 (qu, J=7.1, sH); 3.97 (s, 3H); 3.94 (d, J=6.9, 2H); 1.34 (t, J=7.1, 3H); 0.96 (m, 1H); 0.37 (m, 2H), 0.21 (m, 2H).

Example A57

4-(5-Acetyl-2-cyclopropylmethoxy-phenyl)-5H-pyrrolo[3,2-d]pyrimidine-7-carboxylic acid ethyl ester Starting from 4-chloro-5H-pyrrolo[3,2-d]pyrimidine-7-carboxylic acid ethyl ester and 1-[4-cyclopropylmethoxy-3-(4,4,5,5-tetramethyl-[1,3,2]dioxaborolan-2-yl)-phenyl]-ethanone (example A46) the title compound is obtained as colorless solid.

MS (ESI): m/z=386 (MH$^+$, 100%).

$^1$H-NMR (400 MHz, DMSO-d$_6$): 12.30 (s, 1H, —NH); 9.08 (s, 1H), 8.42 (d, J=3.5, 1H); 8.20 (d, J=1.5 Hz, 1H); 8.12 (dd, J$_1$=9.0, J$_2$=1.5, 1H); 7.25 (d, J=9.0, 1H); 4.34 (q, J=7.0, 2H); 4.05 (d, J=7.0, 2H); 2.60 (s, 3H); 1.33 (t, J=7.0, 3H); 1.00 (m, 1H); 0.35 (m, 2H); 0.24 (m, 2H).

Example A58

4-(5-Acetyl-4-methyl-2-cyclopropylmethoxy-phenyl)-5H-pyrrolo[3,2-d]pyrimidine-7-carboxylic acid ethyl ester Starting from 4-chloro-5H-pyrrolo[3,2-d]pyrimidine-7-carboxylic acid ethyl ester and 1-[4-cyclopropylmethoxy-2-methyl-5-(4,4,5,5-tetramethyl-[1,3,2]dioxaborolan-2-yl)-phenyl]-ethanone (example A47) the title compound is obtained as colorless solid.

MS (ESI): m/z=394 (MH$^+$, 100%).

$^1$H-NMR (400 MHz, DMSO-d$_6$): 12.20 (s, 1H, —NH); 9.05 (s, 1H), 8.40 (s, 1H), 8.12 (s, 1H); 7.10 (s, 1H); 4.34 (q, J=7.0, 2H); 3.95 (d, J=7.0, 2H); 2.60 (s, 3H); 2.55 (s, 3H); 1.33 (t, J=7.0, 3H), 0.95 (m, 1H); 0.38 (m, 2H); 0.24 (m, 2H).

Example A59

4-(2-Cyclopropylmethoxy-5-methyl-phenyl)-5H-pyrrolo[3,2-d]pyrimidine-7-carboxylic acid ethyl ester Starting from 4-chloro-5H-pyrrolo[3,2-d]pyrimidine-7-carboxylic acid ethyl ester and 2-(2-cyclopropylmethoxy-5-methyl-phenyl)-4,4,5,5-tetramethyl-[1,3,2]dioxaborolane (example A41) the title compound is obtained as colorless solid.

MS (ESI): m/z=352 (MNH$^+$, 100%); 338 (MH$^+$—CH$_2$).

$^1$H-NMR (400 MHz, DMSO-d$_6$): 12.09 (br.s, 1H, —NH); 9.02 (s, 1H); 8.35 (s, 1H); 7.43 (s, 1H); 7.33 (d, J=8.5, 1H); 7.05 (d, J=8.5, 1H); 4.32 (qu, J=7.1, 2H); 3.86 (d, J=6.9, 2H); 2.33 (s, 3H); 1.34 (t, J=7.1, 3H); 0.94 (m, 1H); 0.34 (m, 2H); 0.18 (m, 2H).

Example A60

4-(5-Ethoxy-benzo[1,3]dioxol-4-yl)-5H-pyrrolo[3,2-d]pyrimidine-7-carboxylic acid ethyl ester Starting from 4-chloro-5H-pyrrolo[3,2-d]pyrimidine-7-carboxylic acid ethyl ester and 5-ethoxy-4-(4,4,5,5-tetramethyl-[1,3,2]dioxaborolan-2-yl)-benzo[1,3]dioxole (example A31) the title compound is obtained as colorless solid.

MS (ESI): m/z=356 (MH+, 100%).
¹H-NMR (400 MHz, DMSO-d₆): 12.37 (s, 1H, —NH); 9.01 (s, 1H); 8.39 (s, 1H); 7.01 (d, J=8.6, 1H); 6.58 (d, J=8.6, 1H); 6.00 (s, 2H); 4.32 (qu, J=7.1, 2H); 3.95 (qu, J=6.9, 2H); 1.33 (t, J=7.1, 3H); 1.03 (t, J=6.9, 3H).

Example A61

4-(5-Propoxy-benzo[1,3]dioxol-4-yl)-5H-pyrrolo[3,2-d]pyrimidine-7-carboxylic acid ethyl ester Starting from 4-chloro-5H-pyrrolo[3,2-d]pyrimidine-7-carboxylic acid ethyl ester and 5-propoxy-4-(4,4,5,5-tetramethyl-[1,3,2]dioxaborolan-2-yl)-benzo[1,3]dioxole (example A32) the title compound is obtained as colorless solid.
MS (ESI): m/z=370 (MH+, 100%).
¹H-NMR (400 MHz, DMSO-d₆): 12.40 (s, 1H, —NH); 9.01 (s, 1H); 8.38 (d, J=3.5, 1H); 7.01 (d, J=8.6, 1H); 6.58 (d, J=8.6, 1H); 6.00 (s, 2H); 4.31 (qu, J=7.1, 2H); 3.84 (t, J=6.4, 2H); 1.42 (m, 2H); 1.33 (t, J=7.1, 3H); 0.61 (t, J=7.4, 3H).

Example A62

4-(5-Butoxy-benzo[1,3]dioxol-4-yl)-5H-pyrrolo[3,2-d]pyrimidine-7-carboxylic acid ethyl ester Starting from 4-chloro-5H-pyrrolo[3,2-d]pyrimidine-7-carboxylic acid ethyl ester and 5-butoxy-4-(4,4,5,5-tetramethyl-[1,3,2]dioxaborolan-2-yl)-benzo[1,3]dioxole (example A33) the title compound is obtained as colorless solid.
MS (ESI): m/z=384 (MH+, 100%).
¹H-NMR (300 MHz, DMSO-d₆): 12.40 (s, 1H, —NH); 9.00 (s, 1H); 8.38 (s, 1H); 7.01 (d, J=8.6, 1H); 6.59 (d, J=8.6, 1H); 6.00 (s, 2H); 4.31 (qu, J=7.1, 2H); 3.88 (t, J=6.3, 2H); 1.38 (m, 2H); 1.33 (t, J=7.1, 3H); 1.05 (m, 2H); 0.68 (t, J=7.4, 3H).

Example A63

4-[5-(2-Methoxy-ethoxy)-benzo[1,3]dioxol-4-yl]-5H-pyrrolo[3,2-d]pyrimidine-7-carboxylic acid ethyl ester Starting from 4-chloro-5H-pyrrolo[3,2-d]pyrimidine-7-carboxylic acid ethyl ester and 5-(2-methoxy-ethoxy)-4-(4,4,5,5-tetramethyl-[1,3,2]dioxaborolan-2-yl)-benzo[1,3]dioxole (example A34) the title compound is obtained as colorless solid.
MS (ESI): m/z=386 (MH+, 100%); 372 (MH+—CH₂).
¹H-NMR (200 MHz, DMSO-d₆): 12.32 (br.s, 1H, —NH); 9.01 (s, 1H); 8.39 (s, 1H); 7.02 (d, J=8.5, 1H); 6.61 (d, J=8.5, 1H); 6.01 (s, 1H); 4.31 (qu, J=7.1, 2H); 4.02 (t, J=4.6, 2H); 3.38 (t, J=4.6, 2H); 3.00 (s, 3H); 1.33 (t, J=7.1, 3H).

Example A64

4-[4-Methoxy-2-(2-methoxy-ethoxy)-phenyl]-5H-pyrrolo[3,2-d]pyrimidine-7-carboxylic acid ethyl ester Starting from 4-chloro-5H-pyrrolo[3,2-d]pyrimidine-7-carboxylic acid ethyl ester and 2-[4-methoxy-2-(2-methoxy-ethoxy)-phenyl]-4,4,5,5-tetramethyl-[1,3,2]dioxaborolane (example A43) the title compound is obtained as colorless solid.

MS (ESI): m/z=372 (MH+, 100%); 358 (MH+—CH₂).
¹H-NMR (200 MHz, DMSO-d₆): 11.87 (br.s, 1H, —NH); 8.98 (s, 1H); 8.33 (s, 1H); 7.65 (d, J=8.1, 1H); 6.77 (s, 1H); 6.75 (dd, J₁=8.1, J₂=2.2, 1H); 4.31 (qu, J=7.1, 2H); 4.21 (m, 2H); 3.87 (s, 3H); 3.52 (m, 2H); 3.10 (s, 3H); 1.33 (t, J=7.1, 3H).

Example A65

4-(2-Cyclopropylmethoxy-5-fluoro-4-methoxymethoxy-phenyl)-5H-pyrrolo[3,2-d]pyrimidine-7-carboxylic acid ethyl ester Under an atmosphere of argon Pd(OAc)₂ (0.26 g; 1.14 mmol) and tricyclohexylphosphine (0.64 g; 2.28 mmol) is added to oxygen free dioxane (117.0 mL). The mixture is stirred for 15 min at ambient temperature. 2M Cs₂CO₃ solution in oxygen free water (38.9 mL; 77.8 mmol) is added followed by 4-chloro-5H-pyrrolo[3,2-d]pyrimidine-7-carboxylic acid ethyl ester prepared according to the procedure described in US 2005/124623A1 (5.85 g; 25.95 mmol). The mixture is heated to 80° C. before addition of 2-(2-Cyclopropylmethoxy-5-fluoro-4-methoxymethoxy-phenyl)-4,4,5,5-tetramethyl-[1,3,2]dioxaborolane from example A44 (10.05 g; 28.53 mmol). Afterwards the stirred reaction mixture is heated at 100° C. over night.

After addition of decolorizing charcoal (one spatula) the cooled reaction mixture is filtered through a plug of celite. The filtrate is concentrated under reduced pressure. The residue is distributed between water (100 mL) and dichloromethane (250 mL). The organic layer is separated the aqueous layer is extracted with dichloromethane (2×50 mL) and the combined organic layers are dried over MgSO₄. The crud material is chromatographed on silica gel (dichloromethane: MeOH/97:03) to give the title compound as colorless solid after triturating with tert-BuOMe. Yield: 7.30 g.
MS (ESI): m/z=416 (MH+, 100%).
¹H-NMR (300 MHz, DMSO-d₆): 12.14 (br.s, 1H, —NH); 9.02 (s, 1H); 8.38 (d, J=3.3, 1H); 7.50 (d, J=11.5, 1H); 7.03 (d, J=6.9, 1H); 5.40 (s, 2H); 4.32 (qu J=7.1, 2H); 3.88 (d, J=6.9, 2H); 3.47 (s, 3H); 1.34 (t, J=7.1, 3H); 0.95 (m, 1H); 0.35 (m, 2H); 0.20 (m, 2H).

The following compounds are obtained analogously to the procedure described in the above example A65.

Example A66

4-[2-Cyclopropylmethoxy-4-(1,1-difluoro-methoxy)-5-fluoro-phenyl]-5H-pyrrolo[3,2-d]pyrimidine-7-carboxylic acid ethyl ester Starting from 4-chloro-5H-pyrrolo[3,2-d]pyrimidine-7-carboxylic acid ethyl ester prepared according to the procedure described in US 2005/124623A1 and 2-[2-cyclopropylmethoxy-4-(1,1-difluoro-methoxy)-5-fluoro-phenyl]-4,4,5,5-tetramethyl-[1,3,2]-dioxabolane (example A45) the title compound is obtained as colorless solid.
MS (ESI-): m/z=420 (MH-, 100%).
¹H-NMR (300 MHz, DMSO-d₆): 12.15 (br.s, 1H, —NH); 9.04 (s, 1H); 8.44 (d, J=3.5, 1H); 7.63 (d, J=9.7, 1H); 7.40 (t, J=73.0, 1H); 7.18 (d, J=6.6, 1H); 4.32 (qu, J=7.1, 2H); 3.90 (d, J=6.9, 2H); 1.33 (t, J=7.1, 3H); 0.94 (m, 1H); 0.35 (m, 2H); 0.20 (m, 2H).

Example A67

4-(5-Cyclopropylmethoxy-1,3-benzodioxol-4-yl)-5H-pyrrolo[3,2-d]pyrimidine-7-carboxylic acid 4-(5-Cyclopropylmethoxy-1,3-benzodioxol-4-yl)-5H-pyrrolo[3,2-d]pyrimidine-7-carboxylic acid ethyl ester (9.53 g; 25.0 mmol) from example A48 is suspended in dioxane (170 mL) and water (100 mL). After addition of LiOH (2.99 g; 125.0 mmol) the reaction mixture is stirred at 100° C. over night. The resulting solution is evaporated to dryness. The residue is dissolved in hot (60-90° C.) water (250 mL) and pH is adjusted to 2-3 by addition of 2M citric acid while still hot. After cooling to ambient temperature the precipitated product is collected by suction filtration, washed with water, ethanol and dried in high vacuo at 50° C. to yield 8.22 g of the title compound as pale yellow solid.

MS (ESI): m/z=354 (MH$^+$, 100%).

$^1$H-NMR (300 MHz, DMSO-d$_6$): 12.28 (br.s, 1H, —NH); 12.19 (br.s, 1H, —OH); 8.99 (s, 1H); 8.34 (d, J=3.4, 1H); 7.00 (d, J=8.6, 1H); 6.56 (d, J=8.6, 1H); 6.00 (s, 2H); 3.76 (d, J=6.7, 2H); 0.88 (m, 1H); 0.29 (m, 2H); 0.09 (m, 2H).

The following compounds are obtained analogously to the procedure described in above example A67.

Example A68

4-(5-Cyclobutylmethoxy-1,3-benzodioxol-4-yl)-5H-pyrrolo[3,2-d]pyrimidine-7-carboxylic acid 4-(5-Cyclobutylmethoxy-1,3-benzodioxol-4-yl)-5H-pyrrolo[3,2-d]pyrimidine-7-carboxylic acid ethyl ester (example A49) is used as starting material to give the title compound as pale yellow solid.

MS (ESI): m/z=324 (MH$^+$—CO$_2$, 100%); 256 (MH$^+$—CO$_2$—C$_5$H$_8$).

$^1$H-NMR (200 MHz, DMSO-d$_6$): 12.32 (br.s, 1H, —OH); 12.10 (br.s, 1H, —NH); 8.97 (s, 1H); 8.31 (d, J=3.2, 1H); 7.01 (d, J=8.5, 1H); 6.58 (d, J=8.5, 1H); 6.00 (s, 2H); 3.83 (d, J=6.1, 2H); 2.38 (m, 1H); 1.67 (m, 3H); 1.49 (m, 3H).

Example A69

4-(5-Ethoxy-benzo[1,3]dioxol-4-yl)-5H-pyrrolo[3,2-d]pyrimidine-7-carboxylic acid 4-(5-Ethoxy-benzo[1,3]dioxol-4-yl)-5H-pyrrolo[3,2-d]pyrimidine-7-carboxylic acid ethyl ester (example A60) was used as starting material to give the title compound as pale yellow solid.

MS (ESI): m/z=356 (MH$^+$, 100%).

$^1$H-NMR (400 MHz, DMSO-d$_6$): 12.37 (s, 1H, —NH); 9.01 (s, 1H); 8.39 (s, 1H); 7.01 (d, J=8.6, 1H); 6.58 (d, J=8.6, 1H); 6.00 (s, 2H); 4.32 (qu, J=7.1, 2H); 3.95 (qu, J=6.9, 2H); 1.33 (t, J=7.1, 3H); 1.03 (t, J=6.9, 3H).

Example A70

4-(5-Propoxy-benzo[1,3]dioxol-4-yl)-5H-pyrrolo[3,2-d]pyrimidine-7-carboxylic acid 4-(5-Propoxy-benzo[1,3]dioxol-4-yl)-5H-pyrrolo[3,2-d]pyrimidine-7-carboxylic acid ethyl ester (example A61) was used as starting material to give the title compound as pale yellow solid.

MS (ESI): m/z=342 (MH$^+$, 100%).

$^1$H-NMR (400 MHz, DMSO-d$_6$): 12.31 (s, 1H, —NH); 12.19 (br.s, 1H, —OH); 8.98 (s, 1H); 8.33 (d, J=3.4, 1H); 7.01 (d, J=8.6, 1H); 6.59 (d, J=8.6, 1H); 6.00 (s, 2H); 3.84 (t, J=6.4, 2H); 1.42 (m, 2H); 0.61 (t, J=7.4, 3H).

Example A71

4-(5-Butoxy-benzo[1,3]dioxol-4-yl)-5H-pyrrolo[3,2-d]pyrimidine-7-carboxylic acid 4-(5-Butoxy-benzo[1,3]dioxol-4-yl)-5H-pyrrolo[3,2-d]pyrimidine-7-carboxylic acid ethyl ester (example A62) was used as starting material to give the title compound as pale yellow solid.

MS (ESI): m/z=356 (MH$^+$, 100%).

$^1$H-NMR (300 MHz, DMSO-d$_6$): 12.31 (s, 1H, —NH); 12.06 (br.s, 1H, —OH); 8.99 (s, 1H); 8.33 (d, J=2.3, 1H); 7.01 (d, J=8.6, 1H); 6.59 (d, J=8.6, 1H); 6.00 (s, 2H); 3.89 (t, J=6.4, 2H); 1.48 (m, 2H); 1.03 (m, 2H); 0.68 (t, J=7.4, 3H).

Example A72

4-[5-(2-Methoxy-ethoxy)-benzo[1,3]dioxol-4-yl]-5H-pyrrolo[3,2-d]pyrimidine-7-carboxylic acid 4-[5-(2-Methoxy-ethoxy)-benzo[1,3]dioxol-4-yl]-5H-pyrrolo[3,2-d]pyrimidine-7-carboxylic acid ethyl ester (example A63) was used as starting material to give the title compound as pale yellow solid.

MS (ESI): m/z=358 (MH$^+$, 100%).

$^1$H-NMR (200 MHz, DMSO-d$_6$): 12.22 (br.s, 2H, —NH & —OH); 8.98 (s, 1H); 8.34 (s, 1H); 7.02 (d, J=8.6, 1H); 6.61 (d, J=8.6, 1H); 6.01 (s, 1H); 4.02 (t, J=4.7, 2H); 3.39 (t, J=4.7, 2H); 3.00 (s, 3H).

Example A73

4-(2-Cyclopropylmethoxy-4-methoxy-phenyl)-5H-pyrrolo[3,2-d]pyrimidine-7-carboxylic acid 4-(2-Cyclopropylmethoxy-4-methoxy-phenyl)-5H-pyrrolo[3,2-d]pyrimidine-7-carboxylic acid ethyl ester (example A50) is used as starting material to give the title compound as pale yellow solid.

MS (ESI): m/z=340 (MH$^+$, 100%).

$^1$H-NMR (200 MHz, DMSO-d$_6$): 11.95 (br.s, 2H, —NH, —OH); 8.96 (s, 1H); 8.28 (d, J=2.6, 1H); 7.59 (d, J=8.3, 1H); 6.72 (dd, J$_1$=8.3, J$_2$=2.2, 1H); 6.69 (d, J=2.2, 1H); 3.91 (d, J=6.9, 2H); 3.86 (s, 3H); 0.97 (m, 1H); 0.35 (m, 2H); 0.23 (m, 2H).

Example A74

4-[4-Methoxy-2-(2-methoxy-ethoxy)-phenyl]-5H-pyrrolo[3,2-d]pyrimidine-7-carboxylic acid 4-[4-Methoxy-2-(2-methoxy-ethoxy)-phenyl]-5H-pyrrolo[3,2-d]pyrimidine-7-carboxylic acid ethyl ester (example A64) was used as starting material to give the title compound as pale yellow solid.

MS (ESI): m/z=344 (MH$^+$, 100%).

$^1$H-NMR (200 MHz, DMSO-d$_6$): 12.11 (br.s, 1H, .OH); 11.80 (br.s, 1H, —NH); 8.96 (s, 1H); 8.30 (d, J=3.4, 1H); 7.66

(d, J=8.1, 1H); 6.77 (s, 1H); 6.75 (dd, $J_1$=8.1, $J_2$=2.2, 1H); 4.22 (t, J=4.6, 2H); 3.87 (s, 3H); 3.53 (t, J=4.6, 2H); 3.10 (s, 3H).

Example A75

4-(2-Cyclopropylmethoxy-5-methoxy-phenyl)-5H-pyrrolo[3,2-d]pyrimidine-7-carboxylic acid 4-(2-Cyclopropylmethoxy-5-methoxy-phenyl)-5H-pyrrolo[3,2-d]pyrimidine-7-carboxylic acid ethyl ester (example A51) is used as starting material to give the title compound as pale yellow solid.

MS (ESI): m/z=340 (MH$^+$, 100%).

$^1$H-NMR (200 MHz, DMSO-d$_6$): 12.06 (br.s, 2H, —NH, —OH); 9.01 (s, 1H); 8.31 (s, 1H); 7.17 (d, J=1.8, 1H); 7.11 (t, J=1.8, 2H); 3.82 (d, J=6.8, 2H); 3.77 (s, 3H); 0.92 (m, 1H); 0.32 (m, 2H); 0.14 (m, 2H).

Example A76

4-(2-Cyclopropylmethoxy-4-fluoro-phenyl)-5H-pyrrolo[3,2-d]pyrimidine-7-carboxylic acid 4-(2-Cyclopropylmethoxy-4-fluoro-phenyl)-5H-pyrrolo[3,2-d]pyrimidine-7-carboxylic acid ethyl ester (example A52) is used as starting material to give the title compound as pale yellow solid.

MS (ESI): m/z=328 (MH$^+$ 100%).

$^1$H-NMR (400 MHz, DMSO-d$_6$): 12.10 (br.s, 2H, —NH, —OH); 8.99 (s, 1H); 8.34 (s, 1H); 7.65 (dd, $J_1$=8.4, $J_2$=7.0, 1H); 7.07 (dd, $J_1$=11.5, $J_2$=2.3, 1H); 6.95 (ddd, $J_1$=$J_2$=9.9, $J_3$=2.3, 1H); 3.92 (d, J=7.0, 2H); 0.96 (m, 1H); 0.36 (m, 2H); 0.21 (m, 2H).

Example A77

4-(2-Cyclopropylmethoxy-5-fluoro-phenyl)-5H-pyrrolo[3,2-d]pyrimidine-7-carboxylic acid 4-(2-Cyclopropylmethoxy-5-fluoro-phenyl)-5H-pyrrolo[3,2-d]pyrimidine-7-carboxylic acid ethyl ester (example A53) is used as starting material to give the title compound as pale yellow solid.

MS (ESI): m/z=328 (MH$^+$, 100%).

$^1$H-NMR (200 MHz, DMSO-d$_6$): 12.15 (br.s, 2H, —NH, —OH); 9.02 (s, 1H); 8.36 (s, 1H); 7.45-7.31 (m, 2H); 7.18 (dd, $J_1$=9.0, $J_2$=5.4, 1H); 3.87 (d, J=6.1, 2H); 0.94 (m, 1H); 0.34 (m, 3H); 0.17 (m, 3H).

Example A78

4-(2-Cyclopropylmethoxy-phenyl)-5H-pyrrolo[3,2-d]pyrimidine-7-carboxylic acid 4-(2-Cyclopropylmethoxy-phenyl)-5H-pyrrolo[3,2-d]pyrimidine-7-carboxylic acid ethyl ester (example A54) is used as starting material to give the title compound as pale yellow solid.

MS (ESI): m/z=310 (MH$^+$, 100%); 266 (MH$^+$—CO$_2$).

$^1$H-NMR (400 MHz, DMSO-d$_6$): 12.18 (br.s, 1H, —NH/—OH); 12.09 (br.s, 1H, —NH/—OH); 9.01 (s, 1H); 8.32 (s, 1H); 7.62 (dd, $J_1$=7.5, $J_2$=1.5, 1H); 7.52 (ddd, $J_1$=8.4, $J_2$=7.5, $J_3$=1.5, 1H); 7.17 (d, J=8.4, 1H); 7.12 (d, J=7.5, 1H); 3.91 (d, J=6.9, 2H); 0.95 (m, 1H); 0.35 (m, 2H); 0.21 (m, 2H).

Example A79

4-(2-Cyclopropylmethoxy-4-fluoro-5-methoxy-phenyl)-5H-pyrrolo[3,2-d]pyrimidine-7-carboxylic acid 4-(2-Cyclopropylmethoxy-4-fluoro-5-methoxy-phenyl)-5H-pyrrolo[3,2-d]pyrimidine-7-carboxylic acid ethyl ester (example A55) is used as starting material to give the title compound as pale yellow solid.

MS (ESI): m/z=358 (MH$^+$, 100%); 314 (MH$^+$—CO$_2$).

$^1$H-NMR (300 MHz, DMSO-d$_6$): 12.04 (br.s, 2H, —NH, —OH); 9.01 (s, 1H); 8.34 (s, 1H); 7.39 (d, J=9.8, 1H); 7.17 (d, J=13.4, 1H); 4.84 (d, J=6.8, 2H & s, 3H); 0.93 (m, 1H); 0.33 (m, 2H); 0.16 (m, 2H).

Example A80

4-(2-Cyclopropylmethoxy-5-fluoro-4-methoxy-phenyl)-5H-pyrrolo[3,2-d]pyrimidine-7-carboxylic acid 4-(2-Cyclopropylmethoxy-5-fluoro-4-methoxy-phenyl)-5H-pyrrolo[3,2-d]pyrimidine-7-carboxylic acid ethyl ester (example A56) is used as starting material to give the title compound as pale yellow solid.

MS (ESI): m/z=358.0 (MH$^+$, 100%).

$^1$H-NMR (200 MHz, DMSO-d$_6$): 12.17 (br.s, 1H, —OH); 12.02 (br.s, 1H, —NH); 8.98 (s, 1H); 8.34 (s, 1H); 7.49 (d, J=11.9, 1H); 6.92 (d, J=7.3, 1H); 3.97 (s, 3H); 3.95 (d, J=7.0, 2H); 0.96 (m, 1H); 0.36 (m, 2H); 0.22 (m, 2H).

Example A81

4-(5-Acetyl-2-cyclopropylmethoxy-phenyl)-5H-pyrrolo[3,2-d]pyrimidine-7-carboxylic acid 4-(5-Acetyl-2-cyclopropylmethoxy-phenyl)-5H-pyrrolo[3,2-d]pyrimidine-7-carboxylic acid ethyl ester (example A57) is used as starting material to give the title compound as pale yellow solid.

MS (ESI): m/z=352 (MH$^+$, 100%).

$^1$H-NMR (400 MHz, DMSO-d$_6$): 12.40 (s, 1H, —NH); 9.10 (s, 1H); 8.48 (d, J=3.0, 1H); 8.19 (d, J=2.0, 1H); 8.13 (dd, $J_1$=9.0, $J_2$=3.0 1H); 7.27 (d, J=9.0, 1H); 4.00 (d, J=7.0, 2H); 2.60 (s, 3H); 0.95 (m); 0.37 (m, 2H); 0.23 (m, 2H).

Example A82

4-(5-Acetyl-4-methyl-2-cyclopropylmethoxy-phenyl)-5H-pyrrolo[3,2-d]pyrimidine-7-carboxylic acid 4-(5-Acetyl-4-methyl-2-cyclopropylmethoxy-phenyl)-5H-pyrrolo[3,2-d]pyrimidine-7-carboxylic acid ethyl ester (example A58) is used as starting material to give the title compound as pale yellow solid.

MS (ESI): m/z=366 (MH$^+$, 100%).

$^1$H-NMR (400 MHz, DMSO-d$_6$): 12.10 (s, 1H, —NH); 9.05 (s, 1H); 8.36 (d, J=3.0, 1H); 8.10 (s, 1H); 7.10 (s, 1H); 4.00 (d, J=7.0 2H); 2.60 (s, 3H); 2.55 (s, 3H); 1.00 (m, 1H); 0.38 (m, 2H); 0.24 (m, 2H).

Example A83

4-(2-Cyclopropylmethoxy-5-methyl-phenyl)-5H-pyrrolo[3,2-d]pyrimidine-7-carboxylic acid 4-(2-Cyclopropylmethoxy-5-methyl-phenyl)-5H-pyrrolo[3,2-d]pyrimidine-7-carboxylic acid ethyl ester (example A59) is used as starting material to give the title compound as pale yellow solid.

MS (ESI): m/z=324 (MH+ 100%).

¹H-NMR (400 MHz, DMSO-d₆): 12.10 (br.s, 2H, —NH, —OH); 8.99 (s, 1H); 8.30 (s, 1H); 7.43 (d, J=1.8, 1H); 7.32 (dd, J₁=8.4 J₂=1.8, 1H); 7.06 (d, J=8.4, 1H); 3.86 (d, J=6.9, 2H); 2.33 (s, 3H); 0.94 (m, 1H); 0.33 (m, 2H); 0.18 (m, 2H).

Example A84

4-(2-Cyclopropylmethoxy-5-fluoro-4-methoxymethoxy-phenyl)-5H-pyrrolo[3,2-d]pyrimidine-7-carboxylic acid Starting from 4-(2-cyclopropylmethoxy-5-fluoro-4-methoxymethoxy-phenyl)-5H-pyrrolo[3,2-d]pyrimidine-7-carboxylic acid ethyl ester (example A65) the title compound is obtained as color-less solid.

MS (ESI): m/z=388 (MH+, 100%).

¹H-NMR (300 MHz, DMSO-d₆): 12.06 (br.s, 2H, —NH, —OH); 8.98 (s, 1H); 8.33 (s, 1H); 7.49 (d, J=11.5, 1H); 7.02 (d, J=7.1, 1H); 5.39 (s, 2H); 3.87 (d, J=6.9, 2H); 3.47 (s, 3H); 0.94 (m, 1H); 0.34 (m, 2H); 0.20 (m, 2H).

Example A85

4-[2-Cyclopropylmethoxy-4-(1,1-difluoro-methoxy)-5-fluoro-phenyl]-5H-pyrrolo[3,2-d]pyrimidine-7-carboxylic acid Starting from 4-[2-cyclopropylmethoxy-4-(1,1-difluoro-methoxy)-5-fluoro-phenyl]-5H-pyrrolo[3,2-d]pyrimidine-7-carboxylic acid ethyl ester (example A66) the title compound is obtained as color-less solid.

MS (ESI): 394 (MH+, 100%).

¹H-NMR (300 MHz, DMSO-d₆): ¹H-NMR (300 MHz, DMSO-d₆): 12.16 (br.s, 2H, —NH, —OH); 9.02 (s, 1H); 8.38 (s, 1H); 7.63 (d, J=10.8, 1H); 7.40 (t, J=73.2, 1H); 7.18 (d, J=6.9, 1H); 3.90 (d, J=6.9, 2H); 0.95 (m, 1H); 0.35 (m, 2H); 0.20 (m, 2H).

Example A86

4-({1-[4-(5-Cyclopropylmethoxy-1,3-benzodioxol-4-yl)-5H-pyrrolo[3,2-d]pyrimidin-7-yl]-methanoyl}-amino)-piperidine-1-carboxylic acid tert-butyl ester To a suspension of 4-(5-cyclopropylmethoxy-1,3-benzodioxol-4-yl)-5H-pyrrolo[3,2-d]pyrimidine-7-carboxylic acid (3.53 g; 10.0 mmol) from example A67 in dry dichloromethane (50 mL) is added 1-(3-dimethylaminopropyl)-3-ethylcarbodiimide hydrochloride (12.0 mmol), triethylamine (15.0 mmol) and 1-hydroxybenzotriazole (10.0 mmol). The suspension is stirred at ambient temperature for one hour. To the resulting solution, 4-amino-piperidine-1-carboxylic acid tert-butyl ester (12.0 mmol) is added and stirring is continued overnight at ambient temperature. The reaction mixture is loaded onto a silica gel column and purified by flash chromatography using acetic acid ethyl ester/2-propanol (98:2 v/v). The eluate containing the product fraction is collected and evaporated. The product is triturated with n-hexane and dried in high vacuo at 50° C. to yield 3.85 g of the title compound as white solid.

MS (ESI): m/z=558 (MNa+); 536 (MH+, 100%); 480 (MH+—C₄H₈).

¹H-NMR (400 MHz, DMSO-d₆): 12.28 (s, 1H, —NH); 9.03 (s, 1H); 8.44 (d, J=7.7, 1H, —NH); 8.29 (s, 3.2, 1H); 7.01 (d, J=8.6, 1H); 6.56 (d, J=8.6, 1H); 6.00 (s, 2H); 4.07 (m, 1H); 3.87 (~d, J 13.5, 2H); 3.76 (d, J=6.8, 2H); 1.94 (~dd, J₁~12.8, J₂~3.4, 2H); 1.46 (m, 2H); 1.42 (s 9H); 0.87 (m, 1H); 0.27 (m, 2H); 0.12 (m, 2H).

The following compounds are obtained analogously to the procedure described in above example A86.

Example A87 trans-(4-{[4-(5-Cyclopropylmethoxy-benzo[1,3]dioxol-4-yl)-5H-pyrrolo[3,2-d]pyrimidine-7-carbonyl]-amino}-cyclohexyl)-carbamic acid tert-butyl ester Starting from 4-(5-cyclopropylmethoxy-1,3-benzodioxol-4-yl)-5H-pyrrolo[3,2-d]pyrimidine-7-carboxylic acid (example A67) and trans-(4-amino-cyclohexyl)-carbamic acid tert-butyl ester the title compound is obtained as colorless solid.

MS (ESI): m/z=550 (MH+, 100%); 494 (MH+—C₄H₈).

¹H-NMR (400 MHz, DMSO-d₆): 12.26 (br.s, 1H, —NH); 9.02 (s, 1H); 8.29 (d, J=8.1, 1H, —NH); 8.27 (s, 1H); 7.00 (d, J=8.6, 1H); 6.74 (d, J=7.7, 1H, —NH); 6.56 (d, J=8.6, 1H); 6.00 (s, 2H); 3.76 (d, J=6.7, 2H & m, 1H); 1.99 (m, 2H); 1.85 (m, 2H); 1.39 (s, 9H); 1.43-1.26 (m, 4H); 0.85 (m, 1H); 0.29 (m, 2H); 0.10 (m, 2H).

Example A88 cis-(4-{[4-(5-Cyclopropylmethoxy-benzo[1,3]dioxol-4-yl)-5H-pyrrolo[3,2-d]pyrimidine-7-carbonyl]-amino}-cyclohexyl)-carbamic acid tert-butyl ester Starting from 4-(5-cyclopropylmethoxy-1,3-benzodioxol-4-yl)-5H-pyrrolo[3,2-d]pyrimidine-7-carboxylic acid (example A67) and cis-(4-amino-cyclohexyl)-carbamic acid tert-butyl ester the title compound is obtained as colorless solid.

MS (ESI): m/z=550 (MH+, 100%); 494 (MH+—C₄H₈); 450 (MH+—C₆H₈O₂).

¹H-NMR (400 MHz, DMSO-d₆): 12.27 (br.s, 1H, —NH); 9.06 (s, 1H); 8.60 (d, J=7.8, 1H, —NH); 8.27 (s, 1H); 7.00 (d, J=8.6, 1H); 6.94 (d, J=6.7, 1H, —NH); 6.56 (d, J=8.6, 1H); 6.00 (s, 2H); 4.02 (m, 1H); 3.77 (d, J=6.7, 2H); 3.45 (m, 1H); 1.78 (m, 2H); 1.69-1.56 (m, 6H); 1.39 (s, 9H); 0.86 (m, 1H); 0.30 (m, 2H); 0.11 (m, 2H).

Example A89

(S)-3-{[4-(5-Cyclopropylmethoxy-benzo[1,3]dioxol-4-yl)-5H-pyrrolo[3,2-d]pyrimidine-7-carbonyl]-amino}-pyrrolidine-1-carboxylic acid tert-butyl ester Starting from 4-(5-cyclopropylmethoxy-1,3-benzodioxol-4-yl)-5H-pyrrolo[3,2-d]pyrimidine-7-carboxylic acid (example A67) and (S)-3-amino-pyrrolidine-1-carboxylic acid tert-butyl ester the title compound is obtained as colorless solid.

MS (ESI): m/z=522 (MH+, 100%); 466 (MH+—C₄H₈).

¹H-NMR (300 MHz, DMSO-d₆): 12.31 (br.s, 1H, —NH); 9.02 (s, 1H); 8.55 (d, J=6.9, 1H, —NH); 8.31 (s, 1H); 7.01 (d, J=8.6, 1H); 6.56 (d, J=8.6, 1H); 6.01 (s, 2H); 4.50 (m, 1H);

3.76 (d, J=6.7, 2H); 3.64 (m, 1H); 3.44 (m, 2H); 3.24 (m, 2H); 2.21 (m, 1H); 1.96 (m, 1H); 1.42 (s, 9H); 0.87 (m, 1H); 0.29 (m, 2H); 0.11 (m, 2H).

Example A90

(R)-3-{[4-(5-Cyclopropylmethoxy-benzo[1,3]dioxol-4-yl)-5H-pyrrolo[3,2-d]pyrimidine-7-carbonyl]-amino}-pyrrolidine-1-carboxylic acid tert-butyl ester Starting from 4-(5-cyclopropylmethoxy-1,3-benzodioxol-4-yl)-5H-pyrrolo[3,2-d]pyrimidine-7-carboxylic acid (example A67) and (R)-3-amino-pyrrolidine-1-carboxylic acid tert-butyl ester the title compound is obtained as colorless solid.

MS (ESI): m/z=522 (MH$^+$, 100%); 466 (MH$^+$—C$_4$H$_8$).

$^1$H-NMR (300 MHz, DMSO-d$_6$): 12.31 (br.s, 1H, —NH); 9.02 (s, 1H); 8.55 (d, J=6.9, 1H, —NH); 8.31 (s, 1H); 7.01 (d, J=8.6, 1H); 6.56 (d, J=8.6, 1H); 6.01 (s, 2H); 4.50 (m, 1H); 3.76 (d, J=6.7, 2H); 3.64 (m, 1H); 3.44 (m, 2H); 3.24 (m, 2H); 2.21 (m, 1H); 1.96 (m, 1H); 1.42 (s, 9H); 0.87 (m, 1H); 0.29 (m, 2H); 0.11 (m, 2H).

Example A91

4-({[4-(5-Cyclopropylmethoxy-benzo[1,3]dioxol-4-yl)-5H-pyrrolo[3,2-d]pyrimidine-7-carbonyl]-amino}-methyl)-piperidine-1-carboxylic acid tert-butyl ester Starting from 4-(5-cyclopropylmethoxy-1,3-benzodioxol-4-yl)-5H-pyrrolo[3,2-d]pyrimidine-7-carboxylic acid (example A67) and 4-aminomethyl-piperidine-1-carboxylic acid tert-butyl ester the title compound is obtained as colorless solid.

Example A92

3-({[4-(5-Cyclopropylmethoxy-benzo[1,3]dioxol-4-yl)-5H-pyrrolo[3,2-d]pyrimidine-7-carbonyl]amino}-methyl)-piperidine-1-carboxylic acid tert-butyl ester Starting from 4-(5-cyclopropylmethoxy-1,3-benzodioxol-4-yl)-5H-pyrrolo[3,2-d]pyrimidine-7-carboxylic acid (example A67) and 3-aminomethyl-piperidine-1-carboxylic acid tert-butyl ester the title compound is obtained as colorless solid.

Example A93

3-({[4-(5-Cyclopropylmethoxy-benzo[1,3]dioxol-4-yl)-5H-pyrrolo[3,2-d]pyrimidine-7-carbonyl]-amino}-methyl)-pyrrolidine-1-carboxylic acid tert-butyl ester Starting from 4-(5-cyclopropylmethoxy-1,3-benzodioxol-4-yl)-5H-pyrrolo[3,2-d]pyrimidine-7-carboxylic acid (example A67) and 3-aminomethyl-pyrrolidine-1-carboxylic acid tert-butyl ester the title compound is obtained as colorless solid.

Example A94

2-({[4-(5-Cyclopropylmethoxy-benzo[1,3]dioxol-4-yl)-5H-pyrrolo[3,2-d]pyrimidine-7-carbonyl]-amino}-methyl)-morpholine-4-carboxylic acid tert-butyl ester Starting from 4-(5-cyclopropylmethoxy-1,3-benzodioxol-4-yl)-5H-pyrrolo[3,2-d]pyrimidine-7-carboxylic acid (example A67) and 2-aminomethyl-morpholine-4-carboxylic acid tert-butyl ester the title compound is obtained as colorless solid.

Example A95

2-({[4-(5-Cyclopropylmethoxy-benzo[1,3]dioxol-4-yl)-5H-pyrrolo[3,2-d]pyrimidine-7-carbonyl]-amino}-methyl)-morpholine-4-carboxylic acid tert-butyl ester Starting from 4-(5-cyclopropylmethoxy-1,3-benzodioxol-4-yl)-5H-pyrrolo[3,2-d]pyrimidine-7-carboxylic acid (example A67) and 3-amino-azetidine-1-carboxylic acid tert-butyl ester the title compound is obtained as colorless solid.

Example A96

(S)-3-{[4-(5-Cyclopropylmethoxy-benzo[1,3]dioxol-4-yl)-5H-pyrrolo[3,2-d]pyrimidine-7-carbonyl]-amino}-piperidine-1-carboxylic acid tert-butyl ester Starting from 4-(5-cyclopropylmethoxy-1,3-benzodioxol-4-yl)-5H-pyrrolo[3,2-d]pyrimidine-7-carboxylic acid (example A67) and (S)-3-amino-piperidine-1-carboxylic acid tert-butyl ester the title compound is obtained as colorless solid.

Example A97

(R)-3-{[4-(5-Cyclopropylmethoxy-benzo[1,3]dioxol-4-yl)-5H-pyrrolo[3,2-d]pyrimidine-7-carbonyl]-amino}-piperidine-1-carboxylic acid tert-butyl ester Starting from 4-(5-cyclopropylmethoxy-1,3-benzodioxol-4-yl)-5H-pyrrolo[3,2-d]pyrimidine-7-carboxylic acid (example A67) and (R)-3-amino-piperidine-1-carboxylic acid tert-butyl ester the title compound is obtained as colorless solid.

Example A98

4-{[4-(2-Cyclopropylmethoxy-4-methoxy-phenyl)-5H-pyrrolo[3,2-d]pyrimidine-7-carbonyl]-amino}-piperidine-1-carboxylic acid tert-butyl ester Starting from 4-(2-Cyclopropylmethoxy-4-methoxy-phenyl)-5H-pyrrolo[3,2-d]pyrimidine-7-carboxylic acid (example A73) and 4-amino-piperidine-1-carboxylic acid tert-butyl ester the title compound is obtained as colorless solid.

MS (ESI): m/z=522 (MH$^+$, 100%); 466 (MH$^+$—C$_4$H$_8$); 422 (MH$^+$—C$_5$H$_8$O$_2$).

$^1$H-NMR (200 MHz, DMSO-d$_6$): 11.89 (br.s, 1H, —NH); 9.00 (s, 1H); 8.51 (d, J=7.8, 1H, —NH); 8.22 (s, 1H); 7.62 (d, J=8.3, 1H); 6.72 (dd, J$_1$=8.3, J$_2$=2.2, 1H); 6.69 (d, J=2.2, 1H & br.s, 1H, —NH); 3.92 (d, J=6.8, 2H); 3.86 (s, 3H & m, 2H);

3.03 (m, 2H); 1.94 (m, 2H); 1.42 (m, 4H & s, 9H); 0.97 (m, 1H); 0.35 (m, 2H); 0.24 (m, 2H).

Example A99 cis-(4-{[4-(2-Cyclopropylmethoxy-4-methoxy-phenyl)-5H-pyrrolo[3,2-d]pyrimidine-7-carbonyl]-amino}-cyclohexyl)-carbamic acid tert-butyl ester Starting from 4-(2-cyclopropylmethoxy-4-methoxy-phenyl)-5H-pyrrolo[3,2-d]pyrimidine-7-carboxylic acid (example A73) and cis-(4-amino-cyclohexyl)-carbamic acid tert-butyl ester the title compound is obtained as colorless solid.

MS (ESI): m/z=536 (MH$^+$, 100%); 480 (MH$^+$—C$_4$H$_8$); 436 (MH$^+$—C$_6$H$_8$O$_2$).

$^1$H-NMR (200 MHz, DMSO-d$_6$): 11.88 (br.s, 1H, —NH); 9.03 (s, 1H); 8.68 (d, J=7.7, 1H, —NH); 8.20 (s, 1H); 7.62 (d, J=8.3, 1H); 6.92 (br.s, 1H, —NH); 6.72 (dd, J$_1$=8.3, J$_2$=2.2, 1H); 6.69 (d, J=2.2, 1H); 4.04 (m, 1H); 3.92 (d, J=6.9, 2H); 3.86 (s, 3H); 3.45 (m, 1H); 1.90-1.48 (m, 8H); 1.40 (s, 9H); 0.98 (m, 1H); 0.35 (m, 2H); 0.24 (m, 2H).

Example A100 trans-(4-{[4-(2-Cyclopropylmethoxy-4-methoxy-phenyl)-5H-pyrrolo[3,2-d]pyrimidine-7-carbonyl]-amino}-cyclohexyl)-carbamic acid tert-butyl ester Starting from 4-(2-cyclopropylmethoxy-4-methoxy-phenyl)-5H-pyrrolo[3,2-d]pyrimidine-7-carboxylic acid (example A73) and trans-(4-amino-cyclohexyl)-carbamic acid tert-butyl ester the title compound is obtained as colorless solid.

MS (ESI): m/z=536 (MH$^+$, 100%); 480 (MH$^+$—C$_4$H$_8$).

$^1$H-NMR (200 MHz, DMSO-d$_6$): 11.89 (br.s, 1H, —NH); 9.00 (s, 1H); 8.36 (d, J=7.8, 1H, —NH); 8.19 (s, 1H); 7.62 (d, J=8.3, 1H); 6.92 (br.s, 1H, —NH); 6.72 (dd, J$_1$=8.3, J$_2$=2.2, 1H); 6.69 (d, J=2.2, 1H); 3.91 (d, J=6.9, 2H); 3.86 (s, 3H); 3.78 (m, 1H); 3.28 (m, 1H); 2.00 (m, 2H); 1.86 (m, 2H); 1.34 (m, 4H & s, 9H); 0.97 (m, 1H); 0.34 (m, 2H); 0.24 (m, 2H).

Example A101 trans-(4-{[4-(2-Cyclopropylmethoxy-5-methoxy-phenyl)-5H-pyrrolo[3,2-d]pyrimidine-7-carbonyl]-amino}-cyclohexyl)-carbamic acid tert-butyl ester Starting from 4-(2-cyclopropylmethoxy-5-methoxy-phenyl)-5H-pyrrolo[3,2-d]pyrimidine-7-carboxylic acid (example A75) and trans-(4-amino-cyclohexyl)-carbamic acid tert-butyl ester the title compound is obtained as colorless solid.

MS (ESI): m/z=536 (MH$^+$, 100%); 480 (MH$^+$—C$_4$H$_8$).

$^1$H-NMR (400 MHz, DMSO-d$_6$): 12.00 (br.s, 1H, —NH); 9.05 (s, 1H); 8.34 (d, J=7.7, 1H, —NH); 8.23 (s, 1H); 7.20 (t, J=1.6, 1H); 7.12 (d, J=1.6, 2H); 6.74 (d, J=7.7, 1H, —NH); 3.87 (d, J=6.9, 2H); 3.77 (s, 3H &m, 1H); 3.31 (m, 1H); 2.00 (m, 2H); 1.85 (m, 2H); 1.43-1.22 (m, 4H); 1.39 (s, 9H); 0.84 (m, 1H); 0.32 (m, 2H); 0.15 (m, 2H).

Example A102 cis-(4-{[4-(2-Cyclopropylmethoxy-5-methoxy-phenyl)-5H-pyrrolo[3,2-d]pyrimidine-7-carbonyl]-amino}-cyclohexyl)-carbamic acid tert-butyl ester Starting from 4-(2-cyclopropylmethoxy-5-methoxy-phenyl)-5H-pyrrolo[3,2-d]pyrimidine-7-carboxylic acid (example A75) and cis-(4-amino-cyclohexyl)-carbamic acid tert-butyl ester the title compound is obtained as colorless solid.

MS (ESI): m/z=536 (MH$^+$, 100%); 480 (MH$^+$—C$_4$H$_8$).

$^1$H-NMR (400 MHz, DMSO-d$_6$): 11.99 (br.s, 1H, —NH); 9.08 (s, 1H); 8.65 (d, J=7.7, 1H, —NH); 8.24 (d, J=3.3, 1H); 7.19 (t, J=1.6, 1H); 7.11 (d, J=1.6, 2H); 6.95 (d, J=6.1, 1H, —NH); 4.04 (m, 1H); 3.83 (d, J=6.8, 2H); 3.78 (s, 3H); 3.45 (m, 1H); 1.79 (m, 2H); 1.70-1.56 (m, 6H); 1.40 (s, 9H); 0.90 (m, 1H); 0.33 (m, 2H); 0.16 (m, 2H).

Example A103

4-{[4-(2-Cyclopropylmethoxy-5-methoxy-phenyl)-5H-pyrrolo[3,2-d]pyrimidine-7-carbonyl]-amino}-piperidine-1-carboxylic acid tert-butyl ester Starting from 4-(2-cyclopropylmethoxy-5-methoxy-phenyl)-5H-pyrrolo[3,2-d]pyrimidine-7-carboxylic acid (example A75) and 4-amino-piperidine-1-carboxylic acid tert-butyl ester the title compound is obtained as colorless solid.

MS (ESI): m/z=522 (MH$^+$, 100%); 466 (MH$^+$—C$_4$H$_8$).

$^1$H-NMR (200 MHz, DMSO-d$_6$): 12.00 (br.s, 1H, —NH); 9.05 (s, 1H); 8.50 (d, J=7.8, 1H, —NH); 8.26 (s, 1H); 7.19 (t, J=1.7, 1H); 7.11 (d, J=1.7, 2H); 4.09 (m, 1H); 3.86 (m, 2H); 3.83 (d, J=6.9, 2H); 3.77 (s, 3H); 3.04 (m, 2H); 1.94 (m, 2H); 1.47 (m, 2H); 1.43 (s, 9H); 0.93 (m, 1H); 0.32 (m, 2H); 0.15 (m, 2H).

Example A104 trans-(4-{[4-(2-Cyclopropylmethoxy-4-fluoro-phenyl)-5H-pyrrolo[3,2-d]pyrimidine-7-carbonyl]-amino}-cyclohexyl)-carbamic acid tert-butyl ester Starting from 4-(2-cyclopropylmethoxy-4-fluoro-phenyl)-5H-pyrrolo[3,2-d]pyrimidine-7-carboxylic acid (example A76) and trans-(4-amino-cyclohexyl)-carbamic acid tert-butyl ester the title compound is obtained as colorless solid.

MS (ESI): m/z=524 (MH$^+$, 100%); 468 (MH$^+$—C$_4$H$_8$); 424 (MH$^+$—C$_5$H$_8$O$_2$).

$^1$H-NMR (300 MHz, DMSO-d$_6$): 12.05 (br.s, 1H, —NH); 9.06 (s, 1H); 8.34 (d, J=7.9, 1H; —NH); 8.26 (s, 1H); 7.67 (dd, J$_1$=8.4, J$_2$=7.2, 1H); 7.08 (dd, J$_1$=11.6, J$_2$=2.4, 1H); 6.96 (ddd, J$_1$=J2=8.5, J$_3$=2.4, 1H); 6.72 (d, J=7.6, 1H, —NH); 3.92 (d, J=7.0, 2H); 3.79 (m, 1H); 3.13 (m, 1H); 2.00 (m, 2H); 1.85 (m, 2H); 1.39 (s, 9H & m, 4H); 0.96 (m, 1H); 0.36 (m, 2H); 0.22 (m, 2H).

Example A105 cis-(4-{[4-(2-Cyclopropylmethoxy-4-fluoro-phenyl)-5H-pyrrolo[3,2-d]pyrimidine-7-carbonyl]-amino}-cyclohexyl)-carbamic acid tert-butyl ester Starting from 4-(2-cyclopropylmethoxy-4-fluoro-phenyl)-5H-pyrrolo[3,2-d]pyrimidine-7-carboxylic acid (example A76) and cis-(4-amino-cyclohexyl)-carbamic acid tert-butyl ester the title compound is obtained as colorless solid.

MS (ESI): m/z=524 (MH$^+$, 100%); 468 (MH$^+$—C$_4$H$_8$); 424 (MH$^+$—C$_5$H$_8$O$_2$).

$^1$H-NMR (300 MHz, DMSO-d$_6$): 12.05 (br.s, 1H, —NH); 9.06 (s, 1H); 8.65 (d, J=7.7, 1H; —NH); 8.26 (d, J=2.0, 1H); 7.67 (dd, J$_1$=8.5, J$_2$=7.0, 1H); 7.08 (dd, J$_1$=11.6, J$_2$=2.4, 1H); 6.96 (ddd, J=J$_2$=8.5, J$_3$=2.4, 1H); 6.91 (br.s, 1H, —NH); 4.05

(m, 1H); 3.92 (d, J=7.0, 2H); 3.45 (m, 1H); 1.79 (m, 2H); 1.73-1.51 (m, 6H); 1.40 (s, 9H); 0.97 (m, 1H); 0.36 (m, 2H); 0.22 (m, 2H).

Example A106

4-{[4-(2-Cyclopropylmethoxy-4-fluoro-phenyl)-5H-pyrrolo[3,2-d]pyrimidine-7-carbonyl]-amino}-piperidine-1-carboxylic acid tert-butyl ester Starting from 4-(2-cyclopropylmethoxy-4-fluoro-phenyl)-5H-pyrrolo[3,2-d]pyrimidine-7-carboxylic acid (example A76) and 4-amino-piperidine-1-carboxylic acid tert-butyl ester the title compound is obtained as colorless solid.

MS (ESI): m/z=510 (MH$^+$); 454 (MH$^+$—C$_4$H$_8$. 100%); 410 (MH$^+$—C$_5$H$_8$O$_2$).

$^1$H-NMR (300 MHz, DMSO-d$_6$): 12.07 (br.s, 1H, —NH); 9.03 (s, 1H); 8.49 (d, J=7.8, 1H, —NH); 8.29 (d, J=2.4, 1H); 7.67 (dd, J$_1$=8.5, J$_2$=7.0, 1H); 7.08 (dd, J$_1$=11.6, J$_2$=2.4, 1H); 6.96 (ddd, J$_1$=J$_2$=8.5, J$_3$=2.4, 1H); 4.06 (m, 2H); 3.92 (d, J=7.0, 2H); 3.87 (m, 1H); 3.03 (m, 2H); 1.94 (m, 2H); 1.44 (m, 2H); 1.42 (s, 9H); 0.96 (m, 1H); 0.36 (m, 2H); 0.22 (m, 2H).

Example A107 trans-(4-{[4-(2-Cyclopropylmethoxy-5-fluoro-phenyl)-5H-pyrrolo[3,2-d]pyrimidine-7-carbonyl]-amino}-cyclohexyl)-carbamic acid tert-butyl ester Starting from 4-(2-cyclopropylmethoxy-5-fluoro-phenyl)-5H-pyrrolo[3,2-d]pyrimidine-7-carboxylic acid (example A77) and trans-(4-amino-cyclohexyl)-carbamic acid tert-butyl ester the title compound is obtained as colorless solid.

MS (ESI): m/z=524 (MH$^+$, 100%); 468 (MH$^+$—C$_4$H$_8$).

$^1$H-NMR (300 MHz, DMSO-d$_6$): 12.08 (br.s, 1H, —NH); 9.06 (s, 1H); 8.33 (d, J=7.9, 1H, —NH); 8.28 (d, J=3.0, 1H); 7.45-7.34 (m, 2H); 7.18 (dd, J$_1$=9.1, J$_2$=4.5, 1H); 6.72 (d, J=7.3, 1H, —NH); 3.88 (d, J=6.9, 2H); 3.79 (m, 1H); 3.29 (m, 1H); 2.00 (m, 2H); 1.85 (m, 2H); 1.39 (s, 9H & m, 4H); 0.94 (m, 1H); 0.33 (m, 2H); 0.18 (m, 2H).

Example A108

4-{[4-(2-Cyclopropylmethoxy-5-fluoro-phenyl)-5H-pyrrolo[3,2-d]pyrimidine-7-carbonyl]-amino}-piperidine-1-carboxylic acid tert-butyl ester Starting from 4-(2-cyclopropylmethoxy-5-fluoro-phenyl)-5H-pyrrolo[3,2-d]pyrimidine-7-carboxylic acid (example A77) and 4-amino-piperidine-1-carboxylic acid tert-butyl ester the title compound is obtained as colorless solid.

MS (ESI): m/z=510 (MH$^+$, 100%); 454 (MH$^+$—C$_4$H$_8$); 410 (MH$^+$—C$_5$H$_8$O$_2$).

$^1$H-NMR (300 MHz, DMSO-d$_6$): 12.11 (br.s, 1H, —NH); 9.06 (s, 1H); 8.37 (d, J=3.4, 1H); 8.48 (d, J=7.8, 1H, —NH); 8.30 (s, 1H); 7.46-7.34 (m, 2H); 7.19 (dd, J$_1$=9.1, J$_2$=4.4, 1H); 4.09 (m, 1H); 3.88 (d, J=6.9, 2H & m, 2H); 3.03 (m, 2H); 1.94 (m, 2H); 1.46 (m, 2H); 1.42 (s, 9H); 0.94 (m, 1H); 0.34 (m, 2H); 0.18 (m, 2H).

Example A109 trans-(4-{[4-(2-Cyclopropylmethoxy-phenyl)-5H-pyrrolo[3,2-d]pyrimidine-7-carbonyl]-amino}-cyclohexyl)-carbamic acid tert-butyl ester Starting from 4-(2-cyclopropylmethoxy-phenyl)-5H-pyrrolo[3,2-d]pyrimidine-7-carboxylic acid (example A78) and trans-(4-amino-cyclohexyl)-carbamic acid tert-butyl ester the title compound is obtained as colorless solid.

MS (ESI): m/z=506 (MH$^+$, 100%); 450 (MH$^+$—C$_4$H$_8$).

$^1$H-NMR (3000 MHz, DMSO-d$_6$): 12.02 (s, 1H, —NH); 9.05 (s, 1H); 8.34 (d, J=7.8, 1H, —NH); 8.26 (s, 1H); 7.63 (dd, J$_1$=7.6, J$_2$=1.7, 1H); 7.53 (ddd, J$_1$=8.0, J$_2$=7.6, J$_3$=1.7, 1H); 7.17 (dd, J$_1$=8.0, J$_2$=0.9, 1H); 7.13 (ddd, J$_1$=J2=7.6, J$_3$=0.9, 1H); 6.73 (d, J=7.5, 1H, —NH); 3.91 (d, J=6.9, 2H); 3.78 (m, 1H); 3.41 (m, 1H); 2.00 (m, 2H); 1.86 (m, 2H); 1.40 (s, 9H); 1.34 (m, 4H); 0.97 (m, 1H); 0.34 (m, 2H); 0.21 (m, 2H).

Example A110

4-{[4-(2-Cyclopropylmethoxy-phenyl)-5H-pyrrolo[3,2-d]pyrimidine-7-carbonyl]-amino}-piperidine-1-carboxylic acid tert-butyl ester Starting from 4-(2-cyclopropylmethoxy-phenyl)-5H-pyrrolo[3,2-d]pyrimidine-7-carboxylic acid (example A78) and 4-amino-piperidine-1-carboxylic acid tert-butyl ester the title compound is obtained as colorless solid.

MS (ESI): m/z=492 (MH$^+$, 100%); 436 (MH$^+$—C$_4$H$_8$).

$^1$H-NMR (300 MHz, DMSO-d$_6$): 12.06 (s, 1H, —NH); 9.05 (s, 1H); 8.51 (d, J=7.8, 1H, —NH); 8.26 (s, 1H); 7.63 (dd, J$_1$=7.6, J$_2$=1.7, 1H); 7.53 (ddd, J1=8.0, J$_2$=7.6, J$_3$=1.7, 1H); 7.17 (dd, J$_1$=8.0, J$_2$=0.9, 1H); 7.13 (ddd, J$_1$=J$_2$=7.6, J$_3$=0.9, 1H); 4.09 (m, 1H); 3.91 (d, J=6.9, 2H); 3.88 (m, 2H); 3.04 (m, 1H); 1.93 (m, 2H); 1.47 (m, 2H); 1.42 (s, 9H); 0.96 (m, 1H); 0.34 (m, 2H); 0.21 (m, 2H).

Example A111

4-{[4-(2-Cyclopropylmethoxy-4-fluoro-5-methoxy-phenyl)-5H-pyrrolo[3,2-d]pyrimidine-7-carbonyl]-amino}-piperidine-1-carboxylic acid tert-butyl ester Starting from 4-(2-Cyclopropylmethoxy-4-fluoro-5-methoxy-phenyl)-5H-pyrrolo[3,2-d]pyrimidine-7-carboxylic acid (example A79) and 4-amino-piperidine-1-carboxylic acid tert-butyl ester the title compound is obtained as colorless solid.

MS (ESI): m/z=540 (MH$^+$, 100%); 484 (MH$^+$—C$_4$H$_8$).

$^1$H-NMR (300 MHz, DMSO-d$_6$): 12.02 (br.s, 1H, —NH); 9.05 (s, 1H); 8.49 (d, J=7.8, 1H, —NH); 8.28 (s, 1H); 7.41 (d, J=9.8, 1H); 7.18 (d, J=13.3, 1H); 4.09 (m, 1H); 3.98 (m, 2H); 3.85 (s, 3H); 3.84 (d, J=6.7, 2H); 3.03 (m, 1H); 1.96 (m, 2H); 1.46 (m, 2H); 1.42 (s, 9H); 0.93 (m, 1H); 0.34 (m, 2H); 0.17 (m, 2H).

Example A112

(R)-3-{[4-(2-Cyclopropylmethoxy-4-fluoro-5-methoxy-phenyl)-5H-pyrrolo[3,2-d]pyrimidine-7-carbonyl]-amino}-piperidine-1-carboxylic acid tert-butyl ester Starting from 4-(2-cyclopropylmethoxy-4-fluoro-5-methoxy-phenyl)-5H-pyrrolo[3,2-d]pyrimidine-7-carboxylic acid (example A79) and (R)-3-amino-piperidine-1-carboxylic acid tert-butyl ester the title compound is obtained as colorless solid.

MS (ESI): m/z=540 (MH$^+$, 100%); 484 (MH$^+$—C$_4$H$_8$); 440 (MH$^+$—C$_5$H$_8$O$_2$).

$^1$H-NMR (300 MHz, DMSO-d$_6$): 12.02 (br.s, 1H, —NH); 9.02 (s, 1H); 8.58 (d, J=7.9, 1H, —NH); 8.30 (s, 1H); 7.41 (d, J=9.9, 1H); 7.19 (d, J=13.4, 1H); 3.99 (m, 1H); 3.88 (s, 3H & d, J=6.8, 2H); 3.62 (m, 1H); 3.38 (m, 3H); 1.92 (m, 1H); 1.72 (m, 2H); 1.53 (m, 1H); 1.29 (br.s, 9H); 0.92 (m, 1H); 0.32 (m, 2H); 0.18 (m, 2H).

Example A113

(R)-3-{[4-(2-Cyclopropylmethoxy-4-fluoro-5-methoxy-phenyl)-5H-pyrrolo[3,2-d]pyrimidine-7-carbonyl]-amino}-pyrrolidine-1-carboxylic acid tert-butyl ester Starting from 4-(2-cyclopropylmethoxy-4-fluoro-5-methoxy-phenyl)-5H-pyrrolo[3,2-d]pyrimidine-7-carboxylic acid (example A79) and (R)-3-amino-pyrrolidine-1-carboxylic acid tert-butyl ester the title compound is obtained as colorless solid.

MS (ESI): m/z=526 (MH$^+$, 100%); 470 (MH$^+$—C$_4$H$_8$).

$^1$H-NMR (300 MHz, DMSO-d$_6$): 12.06 (br.s, 1H, —NH); 9.04 (s, 1H); 8.60 (d, J=6.9, 1H, —NH); 8.31 (d, J=2.2, 1H); 7.41 (d, J=9.9, 1H); 7.18 (d, J=13.4, 1H); 4.51 (m, 1H); 3.85 (s, 3H & d, J=6.7, 2H); 3.62 (m, 1H); 3.44 (m, 2H); 3.26 (m, 1H); 2.22 (m, 1H); 1.99 (m, 2H); 1.42 (s, 9H); 0.93 (m, 1H); 0.34 (m, 2H); 0.17 (m, 2H).

Example A114 trans-(4-{[4-(2-Cyclopropylmethoxy-5-fluoro-4-methoxy-phenyl)-5H-pyrrolo[3,2-d]pyrimidine-7-carbonyl]-amino}-cyclohexyl)-carbamic acid tert-butyl ester Starting from 4-(2-Cyclopropylmethoxy-5-fluoro-4-methoxy-phenyl)-5H-pyrrolo[3,2-d]pyrimidine-7-carboxylic acid (example A80) and trans-(4-amino-cyclohexyl)-carbamic acid tert-butyl ester the title compound is obtained as colorless solid.

MS (ESI): m/z=554 (MH$^+$, 100%); 498 (MH$^+$—C$_4$H$_8$).

$^1$H-NMR (400 MHz, DMSO-d$_6$): 11.96 (br.s, 1H, —NH); 9.01 (s, 1H); 8.35 (d, J=7.8, 1H, —NH); 8.24 (s, 1H); 7.49 (d, J=11.8, 1H); 6.92 (d, J=7.3, 1H); 6.74 (d, J=7.8, 1H, —NH); 3.97 (s, 1H); 3.94 (d, J=7.0, 2H); 3.77 (m, 1H); 1.99 (m, 2H); 1.85 (m, 2H); 1.43-1.24 (m, 4H); 1.39 (s, 9H); 0.96 (m, 1H); 0.36 (m, 2H); 0.22 (m, 2H).

Example A115

4-{[4-(2-Cyclopropylmethoxy-5-fluoro-4-methoxy-phenyl)-5H-pyrrolo[3,2-d]pyrimidine-7-carbonyl]-amino}-piperidine-1-carboxylic acid tert-butyl ester Starting from 4-(2-Cyclopropylmethoxy-5-fluoro-4-methoxy-phenyl)-5H-pyrrolo[3,2-d]pyrimidine-7-carboxylic acid (example A80) and 4-amino-piperidine-1-carboxylic acid tert-butyl ester the title compound is obtained as colorless solid.

MS (ESI): m/z=540 (MH$^+$, 100%); 484 (MH$^+$—C$_4$H$_8$).

$^1$H-NMR (300 MHz, DMSO-d$_6$): 11.97 (br.s, 1H, —NH); 9.01 (s, 1H); 8.50 (d, J=7.8, 1H, —NH); 8.26 (s, 1H); 7.49 (d, J=11.8, 1H); 6.93 (d, J=7.3, 1H); 4.07 (m, 1H); 3.97 (s, 1H); 3.95 (d, J=7.3, 2H); 3.87 (m, 1H); 3.03 (m, 2H); 1.93 (m, 2H); 1.46 (m, 2H); 1.42 (s, 9H); 0.97 (m, 1H); 0.36 (m, 2H); 0.21 (m, 2H).

Example A116

(R)-3-{[4-(2-Cyclopropylmethoxy-5-fluoro-4-methoxy-phenyl)-5H-pyrrolo[3,2-d]pyrimidine-7-carbonyl]-amino}-piperidine-1-carboxylic acid tert-butyl ester Starting from 4-(2-Cyclopropylmethoxy-5-fluoro-4-methoxy-phenyl)-5H-pyrrolo[3,2-d]pyrimidine-7-carboxylic acid (example A80) and (R)-3-amino-piperidine-1-carboxylic acid tert-butyl ester the title compound is obtained as colorless solid.

MS (ESI): m/z=540 (MH$^+$, 100%); 484 (MH$^+$—C$_4$H$_8$); 440 (MH$^+$—C$_6$H$_8$O$_2$).

$^1$H-NMR (300 MHz, DMSO-d$_6$): 11.97 (br.s, 1H, —NH); 8.98 (s, 1H); 8.59 (d, J=7.8, 1H, —NH); 8.28 (s, 1H); 7.50 (d, J=11.9, 1H); 6.93 (d, J=7.3, 1H); 3.97 (s, 3H & m, 1H); 3.95 (d, J=7.0, 2H); 3.63 (m, 1H); 3.36 (m, 3H); 1.91 (m, 2H); 1.73 (m, 2H); 1.55 (m, 1H); 0.96 (m, 1H); 0.36 (m, 2H); 0.22 (m, 2H).

Example A117

(S)-3-{[4-(2-Cyclopropylmethoxy-5-fluoro-4-methoxy-phenyl)-5H-pyrrolo[3,2-d]pyrimidine-7-carbonyl]-amino}-piperidine-1-carboxylic acid tert-butyl ester Starting from 4-(2-cyclopropylmethoxy-5-fluoro-4-methoxy-phenyl)-5H-pyrrolo[3,2-d]pyrimidine-7-carboxylic acid (example A80) and (S)-3-amino-piperidine-1-carboxylic acid tert-butyl ester the title compound is obtained as colorless solid.

MS (ESI): m/z=540 (MH$^+$, 100%); 484 (MH$^+$—C$_4$H$_8$); 440 (MH$^+$—C$_6$H$_8$O$_2$).

$^1$H-NMR (300 MHz, DMSO-d$_6$): 11.97 (br.s, 1H, —NH); 8.98 (s, 1H); 8.59 (d, J=7.8, 1H, —NH); 8.28 (s, 1H); 7.50 (d, J=11.9, 1H); 6.93 (d, J=7.3, 1H); 3.97 (s, 3H & m, 1H); 3.95 (d, J=7.0, 2H); 3.63 (m, 1H); 3.36 (m, 3H); 1.91 (m, 2H); 1.73 (m, 2H); 1.55 (m, 1H); 0.96 (m, 1H); 0.36 (m, 2H); 0.22 (m, 2H).

Example A118

(R)-3-{[4-(2-Cyclopropylmethoxy-5-fluoro-4-methoxy-phenyl)-5H-pyrrolo[3,2-d]pyrimidine-7-carbonyl]-amino}-pyrrolidine-1-carboxylic acid tert-butyl ester Starting from 4-(2-cyclopropylmethoxy-5-fluoro-4-methoxy-phenyl)-5H-pyrrolo[3,2-d]pyrimidine-7-carboxylic acid (example A80) and (R)-3-amino-pyrrolidine-1-carboxylic acid tert-butyl ester the title compound is obtained as colorless solid.

MS (ESI): m/z=548 (MNa$^+$); 526 (MH$^+$, 100%).

$^1$H-NMR (300 MHz, DMSO-d$_6$): 12.00 (br.s, 1H, —NH); 9.00 (s, 1H); 8.61 (d, J=6.9, 1H; —NH); 8.28 (s, 1H); 7.50 (d, J=11.9, 1H); 6.93 (d, J=7.3, 1H); 4.51 (m, 1H); 3.96 (s, 3H); 3.95 (d, J=7.1, 2H); 3.61 (m, 1H); 3.43 (m, 2H); 3.24 (m, 1H); 2.21 (m, 1H); 1.96 (m, 1H); 1.42 (s, 9H); 0.97 (m, 1H); 0.36 (m, 2H), 0.21 (m, 2H).

Example A119

4-{[4-(2-Cyclopropylmethoxy-5-methyl-phenyl)-5H-pyrrolo[3,2-d]pyrimidine-7-carbonyl]-amino}-piperidine-1-carboxylic acid tert-butyl ester Starting from 4-(2-cyclopropylmethoxy-5-methyl-phenyl)-5H-pyrrolo[3,2-d]pyrimidine-7-carboxylic acid (example A83) and 4-amino-piperidine-1-carboxylic acid tert-butyl ester the title compound is obtained as colorless solid.
MS (ESI): m/z=506 (MH+, 100%); 450 (MH+—C4H8).
1H-NMR 400 MHz, DMSO-d6): 11.98 (br.s, 1H, —NH); 9.03 (s, 1H); 8.50 (d, J=7.7, 1H, —NH); 8.24 (s, 1H); 7.44 (d, J=2.0, 1H); 7.33 (dd, J1=8.4, J2=2.0, 1H); 7.06 (d, J=8.4, 1H); 4.09 (m, 1H); 3.86 (d, J=6.9, 2H & m, 2H); 3.04 (m, 2H); 2.33 (s, 3H); 1.94 (m, 2H); 1.46 (m, 2H); 1.43 (s, 9H); 0.94 (m, 1H); 0.33 (m, 2H); 0.19 (m, 2H).

Example A120 trans-(4-{[4-(2-Cyclopropylmethoxy-5-methyl-phenyl)-5H-pyrrolo[3,2-d]pyrimidine-7-carbonyl]-amino}-cyclohexyl)-carbamic acid tert-butyl ester Starting from 4-(2-cyclopropylmethoxy-5-methyl-phenyl)-5H-pyrrolo[3,2-d]pyrimidine-7-carboxylic acid (example A83) and trans-(4-amino-cyclohexyl)-carbamic acid tert-butyl ester the title compound is obtained as colorless solid.
MS (ESI): m/z=520 (MH+, 100%); 464 (MH+—C4H8).
1H-NMR 400 MHz, DMSO-d6): 11.95 (br.s, 1H, —NH); 9.03 (s, 1H); 8.35 (d, J=7.8, 1H, —NH); 8.21 (s, 1H); 7.44 (s, 1H); 7.33 (d, J=8.4, 1H); 7.06 (d, J=8.4, 1H); 6.72 (d, J=7.3, 1H, —NH); 3.86 (d, J=6.9, 2H); 3.77 (m, 1H); 3.29 (m, 1H); 2.33 (s, 3H); 2.00 (m, 2H); 1.85 (m, 2H); 1.44-1.23 (m, 4H); 1.39 (s, 9H); 0.94 (m, 1H); 0.33 (m, 2H); 0.18 (m, 2H).

Example A121 trans-[4-({1-[4-(5-Cyclobutylmethoxy-benzo[1,3]dioxol-4-yl)-5H-pyrrolo[3,2-d]pyrimidin-7-yl]-methanoyl}-amino)-cyclohexyl]-carbamic acid tert-butyl ester Starting from 4-(5-Cyclobutylmethoxy-benzo[1,3]dioxol-4-yl)-5H-pyrrolo[3,2-d]pyrimidine-7-carboxylic acid (example A68) and trans-(4-amino-cyclohexyl)-carbamic acid tert-butyl ester the title compound is obtained as colorless solid.
MS (ESI): m/z=564 (MH+); 508 (MH+—C4H8).
1H-NMR (400 MHz, DMSO-d6): 12.28 (br.s, 1H, —NH); 9.02 (s, 1H); 8.28 (d, J=7.9, 1H, —NH); 8.24 (d, J=3.2, 1H); 7.50 (s, 1H); 7.02 (d, J=8.6, 1H); 6.56 (d, J=8.6, 1H); 6.00 (s, 2H); 4.30 (m, 1H); 3.76 (d, J=6.8, 2H); 3.50 (m, 1H); 3.30 (m, 1H); 2.30 (m, 2H); 2.00 (m, 2H); 0.95 (m, 1H); 0.30 (m, 2H); 0.10 (m, 2H).

Example A122

4-({1-[4-(5-Cyclobutylmethoxy-benzo[1,3]dioxol-4-yl)-5H-pyrrolo[3,2-d]pyrimidin-7-yl]methanoyl}-amino)-piperidine-1-carboxylic acid tert-butyl ester Starting from 4-(5-cyclobutylmethoxy-benzo[1,3]dioxol-4-yl)-5H-pyrrolo[3,2-d]pyrimidine-7-carboxylic acid (example A68) and 4-amino-piperidine-1-carboxylic acid tert-butyl ester the title compound is obtained as colorless solid.
MS (ESI): m/z=550 (MH+); 494 (MH+—C4H8); 450 (MH+—C6H8O2).
1H-NMR (400 MHz, DMSO-d6): 12.32 (br.s, 1H, —NH); 9.02 (s, 1H); 8.42 (d, J=7.7, 1H, —NH); 8.28 (d, J=1.8, 1H); 7.01 (d, J=8.6, 1H); 6.72 (d, J=7.5, 1H, —NH); 6.59 (d, J=8.6, 1H); 6.01 (s, 2H); 3.85 (d, J=6.2, 2H); 3.77 (m, 1H); 3.30 (m, 1H); 2.38 (m, 1H); 2.00 (m, 2H); 1.85 (m, 2H); 1.67 (m, 3H); 1.50 (m, 3H); 1.40 (s, 9H); 1.34 (m, 4H).

Example A123

4-{[4-(5-Ethoxy-benzo[1,3]dioxol-4-yl)-5H-pyrrolo[3,2-d]pyrimidine-7-carbonyl]-amino}-piperidine-1-carboxylic acid tert-butyl ester Starting from 4-(5-ethoxy-benzo[1,3]dioxol-4-yl)-5H-pyrrolo[3,2-d]pyrimidine-7-carboxylic acid (example A69) and commercially available 4-amino-piperidine-1-carboxylic acid tert-butyl ester the title compound was obtained as colorless solid.
MS (ESI): m/z=510 (MH+, 100%); 454 (MH+—C4H8).
1H-NMR (400 MHz, DMSO-d6): 12.28 (s, 1H, —NH); 9.02 (s, 1H); 8.43 (d, J=7.8, 1H, —NH); 8.29 (s, 1H); 7.01 (d, J=8.6, 1H); 6.59 (d, J=8.6, 1H); 6.01 (s, 2H); 4.07 (m, 1H); 3.96 (qu, J=7.0, 2H); 3.87 (m, 2H); 3.03 (m, 2H); 1.92 (m, 2H); 1.43 (m, 2H & s, 9H); 1.03 (t, J=7.0, 3H).

Example A124

(R)-3-{[4-(5-Ethoxy-benzo[1,3]dioxol-4-yl)-5H-pyrrolo[3,2-d]pyrimidine-7-carbonyl]-amino}-pyrrolidine-1-carboxylic acid tert-butyl ester Starting from 4-(5-ethoxy-benzo[1,3]dioxol-4-yl)-5H-pyrrolo[3,2-d]pyrimidine-7-carboxylic acid (example A69) and commercially available (R)-3-amino-pyrrolidine-1-carboxylic acid tert-butyl ester the title compound was obtained as colorless solid.
MS (ESI): m/z=496 (MH+, 100%); 440 (MH+—C4H8).
1H-NMR (300 MHz, DMSO-d6): 12.32 (s, 1H, —NH); 9.02 (s, 1H); 8.56 (d, J=6.9, 1H, —NH); 8.32 (s, 1H); 7.02 (d, J=8.6, 1H); 6.59 (d, J=8.6, 1H); 6.01 (s, 2H); 4.52 (m, 1H); 3.96 (qu, J=6.9, 2H); 3.62 (m, 1H); 3.50-3.37 (m, 2H); 3.25 (m, 1H); 2.22 (m, 1H); 1.98 (m, 2H); 1.42 (s, 9H); 1.04 (t, J=6.9, 3H).

Example A125

4-{[4-(5-Propoxy-benzo[1,3]dioxol-4-yl)-5H-pyrrolo[3,2-d]pyrimidine-7-carbonyl]-amino}-piperidine-1-carboxylic acid tert-butyl ester Starting from 4-(5-propoxy-benzo[1,3]dioxol-4-yl)-5H-pyrrolo[3,2-d]pyrimidine-7-carboxylic acid (example A70) and commercially available 4-amino-piperidine-1-carboxylic acid tert-butyl ester the title compound was obtained as colorless solid.
MS (ESI): m/z=524 (MH+, 100%); 468 (MH+—C4H8).
1H-NMR (400 MHz, DMSO-d6): 12.31 (s, 1H, —NH); 9.02 (s, 1H); 8.43 (d, J=7.8, 1H, —NH); 7.95 (s, 1H); 7.01 (d, J=8.6, 1H); 6.58 (d, J=8.6, 1H); 6.00 (s, 2H); 4.04 (m, 1H); 3.85 (t, J=6.4, 2H & m, 2H); 3.03 (m, 2H); 1.97 (m, 2H); 1.52-1.37 (s, 9H & m, 4H); 0.61 (t, J=7.4, 3H).

Example A126

(R)-3-{[4-(5-Propoxy-benzo[1,3]dioxol-4-yl)-5H-pyrrolo[3,2-d]pyrimidine-7-carbonyl]-amino}-pyrrolidine-1-carboxylic acid tert-butyl ester Starting from 4-(5-propoxy-benzo[1,3]dioxol-4-yl)-5H-pyrrolo[3,2-d]pyrimidine-7-carboxylic acid (example A70)

and commercially available (R)-3-amino-pyrrolidine-1-carboxylic acid tert-butyl ester the title compound was obtained as colorless solid.

MS (ESI): m/z=510 (MH$^+$, 100%); 454 (MH$^+$—C$_4$H$_8$).

$^1$H-NMR (300 MHz, DMSO-d$_6$): 12.34 (s, 1H, —NH); 9.01 (s, 1H); 8.55 (d, J=6.9, 1H, —NH); 8.30 (s, 1H); 7.02 (d, J=8.6, 1H); 6.58 (d, J=8.6, 1H); 6.01 (s, 2H); 4.51 (m, 1H); 3.85 (t, J=6.4, 2H); 3.62 (m, 1H); 3.42 (m, 2H); 3.24 (m, 1H); 2.21 (m, 1H); 1.98 (m, 1H); 1.42 (s, 9H & m, 2H); 0.62 (t, J=7.4, 3H).

Example A127

4-{[4-(5-Butoxy-benzo[1,3]dioxol-4-yl)-5H-pyrrolo[3,2-d]pyrimidine-7-carbonyl]-amino}-piperidine-1-carboxylic acid tert-butyl ester Starting from 4-(5-butoxy-benzo[1,3]dioxol-4-yl)-5H-pyrrolo[3,2-d]pyrimidine-7-carboxylic acid (example A71) and commercially available 4-amino-piperidine-1-carboxylic acid tert-butyl ester the title compound was obtained as colorless solid.

MS (ESI): m/z=538 (MH$^+$, 100%); 482 (MH$^+$—C$_4$H$_8$).

$^1$H-NMR 300 MHz, DMSO-d$_6$): 12.31 (br.s, 1H, —NH); 9.02 (s, 1H); 8.43 (d, J=7.8, 1H, —NH); 8.28 (s, 1H); 7.01 (d, J=8.6, 1H); 6.59 (d, J=8.6, 1H); 6.01 (s, 2H); 4.07 (m, 1H); 3.88 (t, J=6.4, 2H & m, 2H); 3.03 (m, 2H); 1.94 (m, 2H); 1.52-1.34 (m, 4H); 1.42 (s, 9H); 1.04 (m, 2H); 0.69 (t, J=7.4, 3H).

Example A128

3-{[4-(5-Butoxy-benzo[1,3]dioxol-4-yl)-5H-pyrrolo[3,2-d]pyrimidine-7-carbonyl]-amino}-1-carboxylic acid tert-butyl ester Starting from 4-(5-butoxy-benzo[1,3]dioxol-4-yl)-5H-pyrrolo[3,2-d]pyrimidine-7-carboxylic acid (example A70) and commercially available 3-amino-piperidine-1-carboxylic acid tert-butyl ester the title compound was obtained as colorless solid.

MS (ESI): m/z=538 (MH$^+$, 100%); 482 (MH$^+$—C$_4$H$_8$).

$^1$H-NMR 300 MHz, DMSO-d$_6$): 12.31 (br.s, 1H, —NH); 9.00 (s, 1H); 8.54 (d, J=7.8, 1H, —NH); 8.29 (s, 1H); 7.01 (d, J=8.6, 1H); 6.59 (d, J=8.6, 1H); 6.01 (s, 2H); 3.99 (m, 1H); 3.88 (t, J=6.4, 2H); 3.61 (m, 2H); 3.38 (m, 2H); 1.92 (m, 1H); 1.72 (m, 2H); 1.56 (m, 2H); 1.38 (m, 2H); 1.28 (br.s, 9H); 1.04 (m, 2H); 0.69 (t, J=7.4, 3H).

Example A129

(R)-3-{[4-(5-Butoxy-benzo[1,3]dioxol-4-yl)-5H-pyrrolo[3,2-d]pyrimidine-7-carbonyl]amino}-pyrrolidine-1-carboxylic acid tert-butyl ester Starting from 4-(5-butoxy-benzo[1,3]dioxol-4-yl)-5H-pyrrolo[3,2-d]pyrimidine-7-carboxylic acid (example A71) and commercially available (R)-3-amino-pyrrolidine-1-carboxylic acid tert-butyl ester the title compound was obtained as colorless solid.

MS (ESI): m/z=524 (MH$^+$, 100%); 468 (MH$^+$—C$_4$H$_8$).

$^1$H-NMR (300 MHz, DMSO-d$_6$): 12.33 (br.s, 1H, —NH); 9.01 (s, 1H); 8.54 (d, J=6.9, 1H, —NH); 8.30 (s, 1H); 7.01 (d, J=8.6, 1H); 6.59 (d, J=8.6, 1H); 6.01 (s, 2H); 4.01 (m, 1H); 3.89 (t, J=6.4, 2H); 3.62 (m, 1H); 3.43 (m, 2H); 3.26 (m, 1H); 2.21 (m, 1H); 1.98 (m, 1H); 1.43 (s, 9H); 1.39 (m, 2H); 1.05 (m, 2H); 0.69 (t, J=7.4, 3H).

Example A130 trans-[4-({4-[4-Methoxy-2-(2-methoxy-ethoxy)-phenyl]-5H-pyrrolo[3,2-d]pyrimidine-7-carbonyl}-amino)-cyclohexyl]-carbamic acid tert-butyl ester Starting from 4-[4-methoxy-2-(2-methoxy-ethoxy)-phenyl]-5H-pyrrolo[3,2-d]pyrimidine-7-carboxylic acid (example A74) and commercially available trans-(4-amino-cyclohexyl)-carbamic acid tert-butyl ester the title compound was obtained as colorless solid.

MS (ESI): m/z=540 (MH$^+$); 484 (MH$^+$—C$_4$H$_8$).

$^1$H-NMR (400 MHz, DMSO-d$_6$): 11.73 (br.s, 1H, —NH); 9.00 (s, 1H); 8.38 (d, J=7.7, 1H, —NH); 8.22 (d, J=3.1, 1H); 7.69 (d, J=8.2, 1H); 6.77 (s, 1H); 6.75 (dd, J$_1$=8.2, J$_2$=2.2, 1H); 6.71 (d, J=7.5, 1H, —NH); 4.23 (t, J=4.6, 2H); 3.87 (s, 3H); 3.77 (m, 1H); 3.54 (t, J=4.6, 2H); 3.31 (m, 1H); 3.13 (s, 3H); 1.99 (m, 2H); 1.85 (m, 2H); 1.39 (s, 9H); 1.33 (m, 4H).

Example A131 cis-[4-({4-[4-Methoxy-2-(2-methoxy-ethoxy)-phenyl]-5H-pyrrolo[3,2-d]pyrimidine-7-carbonyl}-amino)-cyclohexyl]-carbamic acid tert-butyl ester Starting from 4-[4-methoxy-2-(2-methoxy-ethoxy)-phenyl]-5H-pyrrolo[3,2-d]pyrimidine-7-carboxylic acid (example A74) and commercially available cis-(4-amino-cyclohexyl)-carbamic acid tert-butyl ester the title compound was obtained as colorless solid.

MS (ESI): m/z=540 (MH+); 484 (MH$^+$—C$_4$H$_8$); 440 (MH$^+$—C$_6$H$_8$O$_2$).

$^1$H-NMR (400 MHz, DMSO-d$_6$): 11.73 (br.s, 1H, —NH); 9.03 (s, 1H); 8.69 (d, J=7.7, 1H, —NH); 8.22 (d, J=3.3, 1H); 7.69 (d, J=8.3, 1H); 6.93 (br.s, 1H, —NH); 6.77 (s, 1H); 6.76 (d, J=8.3, 1H); 4.24 (t, J=4.6, 2H); 4.04 (br.s, 1H); 3.87 (s, 3H); 3.55 (t, J=4.6, 2H); 3.44 (br.s, 1H); 3.13 (s, 3H); 1.77 (m, 2H); 1.63 (m, 4H+2H); 1.40 (s, 9H).

Example A132

4-({4-[4-Methoxy-2-(2-methoxy-ethoxy)-phenyl]-5H-pyrrolo[3,2-d]pyrimidine-7-carbonyl}-amino) piperidine-1-carboxylic acid tert-butyl ester Starting from 4-[4-methoxy-2-(2-methoxy-ethoxy)-phenyl]-5H-pyrrolo[3,2-d]pyrimidine-7-carboxylic acid (example A74) and commercially available 4-amino-piperidine-1-carboxylic acid tert-butyl ester the title compound was obtained as colorless solid.

MS (ESI): m/z=548 (MNa$^+$); 526 (MH$^+$); 470 (MH$^+$—C$_4$H$_8$).

$^1$H-NMR (400 MHz, DMSO-d$_6$): 11.76 (br.s, 1H, —NH); 9.00 (s, 1H); 8.53 (d, J=7.8, 1H, —NH); 8.24 (d, J=3.3, 1H); 7.69 (d, J=8.3, 1H); 6.77 (s, 1H); 6.75 (dd, J$_1$=8.3, J$_2$=2.2, 1H); 4.23 (t, J=4.6, 2H); 4.06 (m, 1H); 3.87 (s, 3H+m, 2H); 3.54 (t, J=4.6, 2H); 3.13 (s, 3H); 3.03 (m, 2H); 1.93 (m, 2H); 1.42 (s, 9H+m, 2H).

Example A133 trans-[4-({4-[5-(2-Methoxy-ethoxy)-benzo[1,3]dioxol-4-yl]-5H-pyrrolo[3,2-d]pyrimidine-7-carbonyl}-amino)-cyclohexyl]-carbamic acid tert-butyl ester Starting from 4-[5-(2-methoxy-ethoxy)-benzo[1,3]dioxol-4-yl]-5H-pyrrolo[3,2-d]pyrimidine-7-carboxylic acid (example A72) and commercially available trans-(4-amino-cyclohexyl)-carbamic acid tert-butyl ester the title compound was obtained as colorless solid.

MS (ESI): m/z=554 (MH$^+$, 100%); 498 (MH$^+$—C$_4$H$_8$).

$^1$H-NMR (200 MHz, DMSO-d$_6$): 12.20 (br. s, 1H, —NH); 9.02 (s, 1H); 8.28 (d, J=7.9, 1H, —NH); 8.27 (s, 1H); 7.02 (d, J=8.6, 1H); 6.93 (d, J=7.6, 1H, —NH); 6.62 (d, J=8.6, 1H); 6.02 (s, 2H); 4.04 (t, J=4.7, 2H & m, 1H); 3.44 (m, 1H); 3.40 (t, J=4.7, 2H); 3.03 (s, 3H); 1.90-1.56 (m, 8H); 1.40 (s, 9H).

Example A134 cis-[4-({4-[5-(2-Methoxy-ethoxy)-benzo[1,3]dioxol-4-yl]-5H-pyrrolo[3,2-d]pyrimidine-7-carbonyl}-amino)-cyclohexyl]-carbamic acid tert-butyl ester Starting from 4-[5-(2-methoxy-ethoxy)-benzo[1,3]dioxol-4-yl]-5H-pyrrolo[3,2-d]pyrimidine-7-carboxylic acid (example A72) and commercially available cis-(4-amino-cyclohexyl)-carbamic acid tert-butyl ester the title compound was obtained as colorless solid.

MS (ESI): m/z=554 (MH$^+$, 100%); 498 (MH$^+$—C$_4$H$_8$); 454 (MH$^+$—C$_6$H$_8$O$_2$).

$^1$H-NMR (200 MHz, DMSO-d$_6$): 12.21 (br. s, 1H, —NH); 9.05 (s, 1H); 8.60 (d, J=7.8, 1H, —NH); 8.28 (d, J=3.3, 1H); 7.02 (d, J=8.6, 1H); 6.72 (d, J=7.6, 1H, —NH); 6.61 (d, J=8.6, 1H); 6.01 (s, 2H); 4.03 (t, J=4.7, 2H); 3.78 (m, 1H); 3.38 (t, J=4.7, 2H); 3.30 (m, 1H); 3.02 (s, 3H); 2.00 (m, 2H); 1.85 (m, 2H); 1.50-1.28 (s, 9H & m, 4H).

Example A135

4-({4-[5-(2-Methoxy-ethoxy)-benzo[1,3]dioxol-4-yl]-5H-pyrrolo[3,2-d]pyrimidine-7-carbonyl}-amino)-piperidine-1-carboxylic acid tert-butyl ester Starting from 4-[5-(2-methoxy-ethoxy)-benzo[1,3]dioxol-4-yl]-5H-pyrrolo[3,2-d]pyrimidine-7-carboxylic acid (example A72) and commercially available 4-amino-piperidine-1-carboxylic acid tert-butyl ester the title compound was obtained as colorless solid.

MS (ESI): m/z=540 (MH$^+$, 100%); 484 (MH$^+$—C$_4$H$_8$); 440 (MH$^+$—C$_6$H$_8$O$_2$).

$^1$H-NMR (200 MHz, DMSO-d$_6$): 12.23 (br.s, 1H, —NH); 9.02 (s, 1H); 8.43 (d, J=7.8, 1H; —NH); 8.29 (s, 1H); 7.02 (d, J=8.6, 1H); 6.61 (d, J=8.6, 1H); 6.01 (s, 2H); 4.08 (m, 1H); 4.03 (t, J=4.7, 2H); 3.87 (m, 2H); 3.39 (t, J=4.7, 2H); 3.02 (s, 3H & m, 2H); 1.94 (m, 2H); 1.42 (s, 9H & m, 2H).

Example A136

4-{[4-(2-Cyclopropylmethoxy-5-fluoro-4-methoxymethoxy-phenyl)-5H-pyrrolo[3,2-d]pyrimidine-7-carbonyl]-amino}-piperidine-1-carboxylic acid tert-butyl ester Starting from 4-(2-cyclopropylmethoxy-5-fluoro-4-methoxymethoxy-phenyl)-5H-pyrrolo[3,2-d]pyrimidine-7-carboxylic acid (example A84) and commercially available 4-amino-piperidine-1-carboxylic acid the title compound is obtained as colorless foam.

MS (ESI): m/z=570 (MH$^+$, 100%).

$^1$H-NMR (300 MHz, DMSO-d$_6$): 12.04 (br.s, 1H, —NH); 9.02 (s, 1H); 8.49 (d, J=7.9, 1H, —NH); 8.27 (s, 1H); 7.51 (d, J=11.5, 1H); 7.02 (d, J=6.9, 1H); 5.39 (s, 2H); 4.07 (m, 1H); 3.88 (d, J=6.9, 2H); 3.87 (m, 2H); 3.47 (s, 3H); 3.03 (m, 2H); 1.93 (m, 2H); 1.46 (m, 2H); 1.42 (s, 9H); 0.95 (m, 1H); 0.35 (m, 2H); 0.21 (m, 2H).

Example A137

4-[2-Cyclopropylmethoxy-4-(1,1-difluoro-methoxy)-5-fluoro-phenyl]-5H-pyrrolo[3,2-d]pyrimidine-7-carbonyl]-amino}-piperidine-1-carboxylic acid tert-butyl ester Starting from 4-[2-cyclopropylmethoxy-4-(1,1-difluoro-methoxy)-5-fluoro-phenyl]-5H-pyrrolo[3,2-d]pyrimidine-7-carboxylic acid (example A85) and commercially available 4-amino-piperidine-1-carboxylic acid the title compound is obtained as colorless foam.

MS (ESI): m/z=576 (MH$^+$); 520 (MH$^+$—C$_4$H$_8$); 476 (MH$^+$—C$_5$H$_8$O$_2$).

$^1$H-NMR (300 MHz, DMSO-d$_6$): 12.16 (br.s, 1H, —NH); 9.06 (s, 1H); 8.47 (d, J=7.7, 1H, —NH); 8.33 (s, 1H); 7.64 (d, J=10.8, 1H); 7.40 (t, J=73.1, 1H); 7.18 (d, J=6.6, 1H); 4.07 (m, 1H); 3.91 (d, J=6.9, 2H); 3.87 (m, 2H); 3.03 (m, 2H); 1.93 (m, 2H); 1.46 (m, 2H); 1.42 (s, 9H); 0.95 (m, 1H); 0.35 (m, 2H); 0.21 (m, 2H).

Example A138

4-(5-Cyclopropylmethoxy-1,3-benzodioxol-4-yl)-5H-pyrrolo[3,2-d]pyrimidine-7-carboxylic acid piperidin-4-ylamide hydrochloride 4-({1-[4-(5-Cyclopropylmethoxy-1,3-benzodioxol-4-yl)-5H-pyrrolo[3,2-d]pyrimidin-7-yl]-methanoyl}-amino)-piperidine-1-carboxylic acid tert-butyl ester from example A86 (4.02 g; 7.5 mmol) is dissolved in warm (40-70° C.) 2-propanol (37.5 mL). After addition of 4M HCl in dioxane (7.5 mL) the stirred reaction mixture is heated to 80° C. for two hours. Tert-butylmethylether (150 mL) is added to the reaction mixture while still warm (40-70° C.). After cooling in an ice bath the precipitated product is collected, washed with tert-butylmethylether and dried in high vacuo at 50° C. to yield 3.35 g of the title compound as bright yellow solid.

MS (ESI): m/z=438 (MH$^+$, 100%).

$^1$H-NMR (400 MHz, DMSO-d$_6$): 12.56 (br.s, 1H, —NH); 9.10 (s, 1H); 9.03 (br.s, 2H, —NH$_2^+$); 8.44 (d, J=7.3, 1H, —NH); 8.42 (2, 1H); 7.03 (d, J=8.6, 1H); 6.58 (d, J=8.6, 1H); 6.03 (s, 2H); 4.17 (m, 1H); 3.78 (d, J=6.7, 2H); 3.32 (m, 2H); 3.07 (m, 2H); 2.13 (m, 2H); 1.83 (m, 2H); 0.88 (m, 1H); 0.30 (m, 2H); 0.12 (m, 2H).

Example A139 trans-4-(2-Cyclopropylmethoxy-5-fluoro-4-methoxy-phenyl)-5H-pyrrolo[3,2-d]pyrimidine-7-carboxylic acid (4-amino-cyclohexyl)-amide Trans-[4-({1-[4-(2-cyclopropylmethoxy-5-fluoro-4-methoxy-phenyl)-5H-pyrrolo[3,2-d]pyrimidin-7-yl]-methanoyl}-amino)-cyclohexyl]-carbamic acid tert-butyl ester from example A114 (3.05 g; 5.51 mmol) is dissolved in 2-propanol (27.5 mL). After addition of 4M HCl in dioxane (5.5 mL) the stirred reaction mixture is heated to 80° C. for two hours. Tert-butylmethylether (100 mL) is added to the reaction mixture while still warm (40-70° C.). After cooling in an ice bath the precipitated product is collected, washed with tert-butylmethylether and dried in high vacuo at 50° C. to yield the bright yellow hydrochloric acid salt of the title compound.

The salt is dissolved in hot (60-90° C.) water (25 mL). The pH of the well stirred solution is adjusted to 9.0 by dropwise addition of 25% NH$_4$OH. After stirring for one hour in an ice bath the precipitated product is collected, washed with ice-cold water and dried in high vacuo at 50° C. to yield 2.18 g of the title compound as colorless solid.

MS (ESI): m/z=454 (MH$^+$, 100%).

$^1$H-NMR (400 MHz, DMSO-d$_6$, MeOH-d$_4$): 9.00 (s, 1H); 8.39 (d, J=7.8, 1H, —NH); 8.24 (s, 1H); 7.50 (d, J=11.8, 1H); 6.92 (d, J=7.3, 1H); 3.97 (s, 1H); 3.94 (d, J=7.1, 2H); 3.80 (m, 1H); 2.74 (m, 1H); 2.01 (m, 2H); 1.88 (m, 2H); 1.40 (m, 2H); 1.26 (m, 2H); 0.97 (m, 1H); 0.37 (m, 2H); 0.22 (m, 2H).

The following compounds are obtained analogously to the procedures described in above example A138 or A139.

Example A140 trans-4-(5-Cyclopropylmethoxy-benzo[1,3]dioxol-4-yl)-5H-pyrrolo[3,2-d]pyrimidine-7-carboxylic acid (4-amino-cyclohexyl)-amide Starting from trans-(4-{[4-(5-Cyclopropylmethoxy-benzo[1,3]dioxol-4-yl)-5H-pyrrolo[3,2-d]pyrimidine-7-carbonyl]-amino}-cyclohexyl)-carbamic acid tert-butyl ester (example A87) the title compound is obtained as colorless solid.

MS (ESI): m/z=450 (MH$^+$, 100%).

$^1$H-NMR (200 MHz, DMSO-d$_6$/MeOH-d$_4$): 9.02 (s, 1H); 8.29 (d, J=8.8, 1H, —NH); 8.29 (s, 1H); 8.27 (s, 1H); 7.00 (d, J=8.6, 1H); 6.56 (d, J=8.6, 1H); 6.00 (s, 2H); 3.76 (d, J=6.7, 2H & m, 1H); 2.80 (m, 1H); 2.04 (m, 2H); 1.89 (m, 2H); 1.51-1.19 (m, 4H); 0.87 (m, 1H); 0.29 (m, 2H); 0.09 (m, 2H).

Example A141 cis-4-(5-Cyclopropylmethoxy-benzo[1,3]dioxol-4-yl)-5H-pyrrolo[3,2-d]pyrimidine-7-carboxylic acid (4-amino-cyclohexyl)-amide Starting from cis-(4-{[4-(5-cyclopropylmethoxy-benzo[1,3]dioxol-4-yl)-5H-pyrrolo[3,2-d]pyrimidine-7-carbonyl]-amino}-cyclohexyl)-carbamic acid tert-butyl ester (example A88) the title compound is obtained as colorless solid.

MS (ESI): m/z=450 (MH$^+$, 100%).

$^1$H-NMR (400 MHz, DMSO-d$_6$): 12.33 (br.s, 1H, —NH); 9.06 (s, 1H); 8.62 (d, J=7.2, 1H, —NH); 8.30 (s, 1H); 7.89 (br.s, 2H, —NH$_2^+$); 7.02 (d, J=8.6, 1H); 6.57 (d, J=8.6, 1H); 6.00 (s, 2H); 4.11 (m, 1H); 3.77 (d, J=6.8, 2H); 3.23 (m, 1H); 1.87 (m, 4H); 1.73 (m, 4H); 0.88 (m, 1H); 0.30 (m, 2H); 0.11 (m, 2H).

Example A142

4-(5-Cyclopropylmethoxy-benzo[1,3]dioxol-4-yl)-5H-pyrrolo[3,2-d]pyrimidine-7-carboxylic acid (R)-pyrrolidin-3-ylamide hydrochloride Starting from (R)-3-{[4-(5-Cyclopropylmethoxy-benzo[1,3]dioxol-4-yl)-5H-pyrrolo[3,2-d]pyrimidine-7-carbonyl]-amino}-pyrrolidine-1-carboxylic acid tert-butyl ester (example A90) the title compound is obtained as bright yellow solid.

Example A143

4-(5-Cyclopropylmethoxy-benzo[1,3]dioxol-4-yl)-5H-pyrrolo[3,2-d]pyrimidine-7-carboxylic acid (S)-pyrrolidin-3-ylamide hydrochloride Starting from (S)-3-{[4-(5-cyclopropylmethoxy-benzo[1,3]dioxol-4-yl)-5H-pyrrolo[3,2-d]pyrimidine-7-carbonyl]-amino}-pyrrolidine-1-carboxylic acid tert-butyl ester (example A89) the title compound is obtained as bright yellow solid.

Example A144

4-(5-Cyclopropylmethoxy-benzo[1,3]dioxol-4-yl)-5H-pyrrolo[3,2-d]pyrimidine-7-carboxylic acid (piperidin-4-ylmethyl)-amide Starting from 4-({[4-(5-cyclopropylmethoxy-benzo[1,3]dioxol-4-yl)-5H-pyrrolo[3,2-d]pyrimidine-7-carbonyl]-amino}-methyl)-piperidine-1-carboxylic acid tert-butyl ester (example A91) the title compound is obtained as colorless solid.

Example A145

4-(5-Cyclopropylmethoxy-benzo[1,3]dioxol-4-yl)-5H-pyrrolo[3,2-d]pyrimidine-7-carboxylic acid (piperidin-3-ylmethyl)-amide Starting from 3-({[4-(5-cyclopropylmethoxy-benzo[1,3]dioxol-4-yl)-5H-pyrrolo[3,2-d]pyrimidine-7-carbonyl]-amino}-methyl)-piperidine-1-carboxylic acid tert-butyl ester (example A92) the title compound is obtained as colorless solid.

Example A146

4-(5-Cyclopropylmethoxy-benzo[1,3]dioxol-4-yl)-5H-pyrrolo[3,2-d]pyrimidine-7-carboxylic acid (pyrrolidin-3-ylmethyl)-amide Starting from 3-({[4-(5-cyclopropylmethoxy-benzo[1,3]dioxol-4-yl)-5H-pyrrolo[3,2-d]pyrimidine-7-carbonyl]-amino}-methyl)-pyrrolidine-1-carboxylic acid tert-butyl ester (example A93) the title compound is obtained as colorless solid.

Example A147

4-(5-Cyclopropylmethoxy-benzo[1,3]dioxol-4-yl)-5H-pyrrolo[3,2-d]pyrimidine-7-carboxylic acid (morpholin-2-ylmethyl)-amide Starting from 2-({[4-(5-cyclopropylmethoxy-benzo[1,3]dioxol-4-yl)-5H-pyrrolo[3,2-d]pyrimidine-7-carbonyl]- amino}-methyl)-morpholine-4-carboxylic acid tert-butyl ester (example A94) the title compound is obtained as colorless solid.

Example A148

4-(5-Cyclopropylmethoxy-benzo[1,3]dioxol-4-yl)-5H-pyrrolo[3,2-d]pyrimidine-7-carboxylic acid (S)-piperidin-3-ylamide Starting from (S)-3-{[4-(5-cyclopropylmethoxy-benzo[1,3]dioxol-4-yl)-5H-pyrrolo[3,2-d]pyrimidine-7-carbonyl]-amino}-piperidine-1-carboxylic acid tert-butyl ester (example A96) the title compound is obtained as colorless solid.
MS (ESI): m/z=436 (MH$^+$, 100%).
$^1$H-NMR (300 MHz, DMSO-d$_6$/MeOH-d$_4$): 9.03 (s, 1H); 8.51 (d, J=8.1, 1H, —NH); 8.26 (s, 1H); 7.00 (d, J=8.6, 1H); 6.56 (d, J=8.6, 1H); 6.00 (s, 2H); 3.96 (m, 1H); 3.76 (d, J=6.7, 2H); 3.02 (m, 1H); 2.73 (m, 1H); 2.63 (m, 1H); 2.54 (m, 1H); 1.87 (m, 1H); 1.66 (m, 1H); 1.50 (m, 1H); 0.88 (m, 1H); 0.29 (m, 2H); 0.10 (m, 2H).

Example A149

4-(5-Cyclopropylmethoxy-benzo[1,3]dioxol-4-yl)-5H-pyrrolo[3,2-d]pyrimidine-7-carboxylic acid (R)-piperidin-3-ylamide Starting from (R)-3-{[4-(5-cyclopropylmethoxy-benzo[1,3]dioxol-4-yl)-5H-pyrrolo[3,2-d]pyrimidine-7-carbonyl]-amino}-piperidine-1-carboxylic acid tert-butyl ester (example A97) the title compound is obtained as colorless solid.
MS (ESI): m/z=436 (MH$^+$, 100%).
$^1$H-NMR (300 MHz, DMSO-d$_6$): 12.85 (br.s, 1H, —NH); 9.38 (br.m, 2H, —NH$_2^+$); 9.13 (s, 1H); 8.60 (s, 1H); 8.51 (d, J=7.6, 1H, —NH); 7.06 (d, J=8.6, 1H); 6.58 (d, J=8.6, 1H); 6.05 (s, 2H); 4.31 (m, 1H); 3.79 (d, J=6.7, 2H); 3.38 (m, 1H); 3.18 (m, 1H); 2.97 (m, 1H); 2.91 (m, 1H); 2.04-11.71 (m, 4H); 0.90 (m, 1H); 0.31 (m, 2H); 0.14 (m, 2H).

Example A150 trans-4-(2-Cyclopropylmethoxy-4-methoxy-phenyl)-5H-pyrrolo[3,2-d]pyrimidine-7-carboxylic acid (4-amino-cyclohexyl)-amide Starting from trans-(4-{[4-(2-cyclopropylmethoxy-4-methoxy-phenyl)-5H-pyrrolo[3,2-d]pyrimidine-7-carbonyl]-amino}-cyclohexyl)-carbamic acid tert-butyl ester (example A100) the title compound is obtained as colorless solid.
MS (ESI): m/z=436 (MH$^+$, 100%).
$^1$H-NMR (400 MHz, DMSO-d$_6$/MeOH-d$_4$): 9.09 (s, 1H); 8.39 (d, J=7.9, 1H, —NH); 8.21 (s, 1H); 7.61 (d, J=8.5, 1H); 6.70 (dd, J$^1$=8.5, J$_2$=2.2, 1H); 6.68 (d, J=2.2, 1H); 3.92 (d, J=6.9, 2H); 3.86 (s, 3H); 3.81 (m, 1H); 3.08 (m, 1H); 2.05 (m, 4H); 1.48 (m, 4H); 0.97 (m, 1H); 0.36 (m, 2H); 0.23 (m, 2H).

Example A151 cis-4-(2-Cyclopropylmethoxy-4-methoxy-phenyl)-5H-pyrrolo[3,2-d]pyrimidine-7-carboxylic acid (4-amino-cyclohexyl)-amide Starting from cis-(4-{[4-(2-cyclopropylmethoxy-4-methoxy-phenyl)-5H-pyrrolo[3,2-d]pyrimidine-7-carbonyl]-amino}-cyclohexyl)-carbamic acid tert-butyl ester (example A99) the title compound is obtained as colorless solid.
MS (ESI): m/z=436 (MH$^+$, 100%).
$^1$H-NMR (400 MHz, DMSO-d$_6$/MeOH-d$_4$): 9.01 (s, 1H); 8.74 (d, J=7.7, 1H, —NH); 8.19 (s, 1H); 7.63 (d, J=8.5, 1H); 6.73 (dd, J$_1$=8.5, J$_2$=2.2, 1H); 6.69 (d, J=2.2, 1H); 4.04 (m, 1H); 3.93 (d, J=6.9, 2H); 3.86 (s, 3H); 2.79 (m, 1H); 1.80 (m, 2H); 1.66 (m, 4H); 1.47 (m, 2H); 0.99 (m, 1H); 0.37 (m, 2H); 0.24 (m, 2H).

Example A152

4-(2-Cyclopropylmethoxy-4-methoxy-phenyl)-5H-pyrrolo[3,2-d]pyrimidine-7-carboxylic acid piperidin-4-ylamide Starting from 4-{[4-(2-cyclopropylmethoxy-4-methoxy-phenyl)-5H-pyrrolo[3,2-d]pyrimidine-7-carbonyl]-amino}-piperidine-1-carboxylic acid tert-butyl ester (example A98) the title compound is obtained as colorless solid.
MS (ESI): m/z=422 (MH$^+$, 100%).
$^1$H-NMR (400 MHz, DMSO-d$_6$/MeOH-d$_4$): 9.02 (s, 1H); 8.57 (d, J=7.5, 1H, —NH); 8.25 (s, 1H); 7.63 (d, J=8.5, 1H); 6.73 (dd, J$_1$=8.5, J$_2$=2.2, 1H); 6.69 (d, J=2.2, 1H); 4.18 (m, 1H); 3.93 (d, J=6.9, 2H); 3.86 (s, 3H); 3.37 (m, 2H); 3.11 (m, 2H); 2.16 (m, 2H); 1.80 (m, 2H); 0.98 (m, 1H); 0.37 (m, 2H); 0.24 (m, 2H).

Example A153 trans-4-(2-Cyclopropylmethoxy-5-methoxy-phenyl)-5H-pyrrolo[3,2-d]pyrimidine-7-carboxylic acid (4-amino-cyclohexyl)-amide Starting from trans-(4-{[4-(2-cyclopropylmethoxy-5-methoxy-phenyl)-5H-pyrrolo[3,2-d]pyrimidine-7-carbonyl]-amino}-cyclohexyl)-carbamic acid tert-butyl ester (example A101) the title compound is obtained as colorless solid.
MS (ESI): m/z=436 (MH$^+$, 100%).
$^1$H-NMR (400 MHz, DMSO-d$_6$/MeOH-d$_4$): 9.04 (s, 1H); 8.41 (d, J=7.9, 1H, —NH); 8.25 (s, 1H); 7.20 (t, J=1.6, 1H); 7.12 (d, J=1.6, 2H); 3.83 (d, J=6.9, 2H & m, 1H); 3.77 (s, 3H); 3.11 (m, 1H); 2.08 (m, 2H); 2.01 (m, 2H); 1.49 (m, 4H); 0.92 (m, 1H); 0.32 (m, 2H); 0.16 (m, 2H).

Example A154 cis-4-(2-Cyclopropylmethoxy-5-methoxy-phenyl)-5H-pyrrolo[3,2-d]pyrimidine-7-carboxylic acid (4-amino-cyclohexyl)-amide Starting from cis-(4-{[4-(2-cyclopropylmethoxy-5-methoxy-phenyl)-5H-pyrrolo[3,2-d]pyrimidine-7-carbonyl]-amino}-cyclohexyl)-carbamic acid tert-butyl ester (example A102) the title compound is obtained as colorless solid.
MS (ESI): m/z=436 (MH$^+$, 100%).
$^1$H-NMR (200 MHz, DMSO-d$_6$/MeOH-d$_4$): 9.06 (s, 1H); 8.65 (d, J=7.8, 1H, —NH); 8.23 (s, 1H); 7.19 (t, J=1.7, 1H); 7.11 (d, J=1.7, 2H); 4.04 (m, 1H); 3.83 (d, J=6.8, 2H); 3.77 (s, 3H); 2.82 (m, 1H); 1.88-1.54 (m, 6H); 1.54-1.32 (m, 2H); 0.93 (m, 1H); 0.33 (m, 2H); 0.11 (m, 2H).

Example A155

4-(2-Cyclopropylmethoxy-5-methoxy-phenyl)-5H-pyrrolo[3,2-d]pyrimidine-7-carboxylic acid piperidin-4-ylamide Starting from 4-{[4-(2-cyclopropylmethoxy-5-methoxy-phenyl)-5H-pyrrolo[3,2-d]pyrimidine-7-carbonyl]-amino}- piperidine-1-carboxylic acid tert-butyl ester (example A103) the title compound is obtained as colorless solid.

MS (ESI): m/z=422 (MH+, 100%).

$^1$H-NMR (400 MHz, DMSO-d$_6$/MeOH-d$_4$): 9.06 (s, 1H); 8.47 (d, J=8.0, 1H, —NH); 8.24 (s, 1H); 7.19 (t, J=1.6, 1H); 7.11 (d, J=1.6, 2H); 3.97 (m, 1H); 3.83 (d, J=6.9, 2H); 3.77 (s, 3H); 3.11 (m, 1H); 2.97 (m, 2H); 2.59 (m, 2H); 1.90 (m, 2H); 1.41 (m, 2H); 0.92 (m, 1H); 0.32 (m, 2H); 0.16 (m, 2H).

Example A156 cis-4-(2-Cyclopropylmethoxy-4-fluoro-phenyl)-5H-pyrrolo[3,2-d]pyrimidine-7-carboxylic acid (4-amino-cyclohexyl)-amide Starting from cis-(4-{[4-(2-cyclopropylmethoxy-4-fluoro-phenyl)-5H-pyrrolo[3,2-d]pyrimidine-7-carbonyl]-amino}-cyclohexyl)-carbamic acid tert-butyl ester (example A105) the title compound is obtained as colorless solid.

MS (ESI): m/z=424 (MH+, 100%).

$^1$H-NMR (300 MHz, DMSO-d$_6$/MeOH-d$_4$): 9.05 (s, 1H); 8.66 (d, J=7.8, 1H; —NH); 8.26 (s, 1H); 7.86 (d, J=7.6, 1H, —NH); 7.65 (dd, J$_1$=8.5, J$_2$=7.0, 1H); 7.08 (dd, J$_1$=12.6, J$_2$=2.3, 1H); 6.96 (ddd, J$_1$=J$_2$=8.5, J$_3$=2.3, 1H); 4.04 (m, 1H); 3.93 (d, J=7.0, 2H); 2.82 (m, 1H); 1.83 (s, 3H); 1.88-1.74 (m, 2H); 1.74-1.58 (m, 4H); 1.52-1.39 (m, 2H); 0.97 (m, 1H); 0.36 (m, 2H); 0.22 (m, 2H).

Example A157 trans-4-(2-Cyclopropylmethoxy-4-fluoro-phenyl)-5H-pyrrolo[3,2-d]pyrimidine-7-carboxylic acid (4-amino-cyclohexyl)-amide Starting from trans-(4-{[4-(2-cyclopropylmethoxy-4-fluoro-phenyl)-5H-pyrrolo[3,2-d]pyrimidine-7-carbonyl]-amino}-cyclohexyl)-carbamic acid tert-butyl ester (example A104) the title compound is obtained as colorless solid.

MS (ESI): m/z=424 (MH+, 100%).

$^1$H-NMR (300 MHz, DMSO-d$_6$/MeOH-d$_4$): 9.01 (s, 1H); 8.33 (d, J=7.9, 1H; —NH); 8.25 (s, 1H); 7.66 (dd, J$_1$=8.5, J$_2$=7.0, 1H); 7.07 (dd, J$_1$=12.6, J$_2$=2.3, 1H); 6.95 (ddd, J$_1$=J$_2$=8.5, J$_3$=2.3, 1H); 3.92 (d, J=6.9, 2H); 3.79 (m, 1H); 2.63 (m, 1H); 1.97 (m, 2H); 1.82 (m, 2H); 1.36 (m, 2H); 1.18 (m, 2H); 0.95 (m, 1H); 0.36 (m, 2H); 0.22 (m, 2H).

Example A158

4-(2-Cyclopropylmethoxy-4-fluoro-phenyl)-5H-pyrrolo[3,2-d]pyrimidine-7-carboxylic acid piperidin-4-ylamide Starting from 4-{[4-(2-cyclopropylmethoxy-4-fluoro-phenyl)-5H-pyrrolo[3,2-d]pyrimidine-7-carbonyl]-amino}-piperidine-1-carboxylic acid tert-butyl ester (example A106) the title compound is obtained as colorless solid.

MS (ESI): m/z=410 (MH+, 100%).

$^1$H-NMR (300 MHz, DMSO-d$_6$): 12.45 (br.s, 1H, —NH); 9.11 (s, 1H); 9.10 (br.s, 2H, NH$_2$+); 8.51 (d, J=7.7, 1H —NH); 8.48 (s, 1H); 7.70 (dd, J$_1$=8.5, J$_2$=7.0, 1H); 7.11 (dd, J$_1$=11.6, J$_2$=2.4, 1H); 6.99 (ddd, J$_1$=J$_2$=8.5, J$_3$=2.4, 1H); 4.17 (m, 1H); 3.94 (d, J=7.0, 2H); 3.32 (m, 2H); 3.08 (m, 2H); 2.12 (m, 2H); 1.83 (m, 2H); 0.97 (m, 1H); 0.36 (m, 2H); 0.24 (m, 2H).

Example A159

4-(2-Cyclopropylmethoxy-5-fluoro-phenyl)-5H-pyrrolo[3,2-d]pyrimidine-7-carboxylic acid piperidin-4-ylamide hydrochloride Starting from 4-{[4-(2-cyclopropylmethoxy-5-fluoro-phenyl)-5H-pyrrolo[3,2-d]pyrimidine-7-carbonyl]-amino}-piperidine-1-carboxylic acid tert-butyl ester (example A108) the title compound is obtained as bright yellow solid.

MS (ESI): m/z=410 (MH+, 100%).

$^1$H-NMR (300 MHz, DMSO-d$_6$): 12.28 (br.s, 1H, —NH); 9.08 (s, 1H); 8.37 (d, J=3.4, 1H); 8.34 (s, 1H, —NH); 8.09 (br.s, 3H, —NH$_3$+); 7.47-7.36 (m, 2H); 7.20 (dd, J$_1$=9.1, J$_2$=4.4, 1H); 3.90 (d, J=6.9, 2H); 3.81 (m, 1H); 3.08 (m, 1H); 2.04 (m, 4H); 1.49 (m, 4H); 0.94 (m, 1H); 0.34 (m, 2H); 0.19 (m, 2H).

Example A160 trans-4-(2-Cyclopropylmethoxy-5-fluoro-phenyl)-5H-pyrrolo[3,2-d]pyrimidine-7-carboxylic acid (4-amino-cyclohexyl)-amide hydrochloride Starting from trans-(4-{[4-(2-cyclopropylmethoxy-5-fluoro-phenyl)-5H-pyrrolo[3,2-d]pyrimidine-7-carbonyl]-amino}-cyclohexyl)-carbamic acid tert-butyl ester (example A107) the title compound is obtained as bright yellow solid.

MS (ESI): m/z=424 (MH+, 100%).

$^1$H-NMR (300 MHz, DMSO-d$_6$): 12.37 (br.s, 1H, —NH); 9.11 (s, 1H); 9.07 (br.s, 2H, —NH$_2$); 8.49 (d, J=7.6, 1H, —NH); 8.44 (d, J=3.3, 1H); 7.47-7.37 (m, 2H); 7.20 (dd, J$_1$=9.1, J$_2$=4.4, 1H); 4.17 (m, 1H); 3.89 (d, J=6.9, 2H); 3.31 (m, 2H); 3.08 (m, 2H); 2.12 (m, 2H); 1.82 (m, 2H); 0.94 (m, 1H); 0.33 (m, 2H); 0.19 (m, 2H).

Example A161 trans-4-(2-Cyclopropylmethoxy-phenyl)-5H-pyrrolo[3,2-d]pyrimidine-7-carboxylic acid (4-amino-cyclohexyl)-amide Starting from trans-(4-{[4-(2-cyclopropylmethoxy-phenyl)-5H-pyrrolo[3,2-d]pyrimidine-7-carbonyl]-amino}-cyclohexyl)-carbamic acid tert-butyl ester (example A109) the title compound is obtained as colorless solid.

MS (ESI): m/z=406 (MH+, 100%).

$^1$H-NMR (300 MHz, DMSO-d$_6$, MeOH-d$_4$): 9.02 (s, 1H); 8.34 (d, J=8.0, 1H, —NH); 8.22 (s, 1H); 7.63 (dd, J$_1$=7.6, J$_2$=1.7, 1H); 7.53 (ddd, J$_1$=8.0, J$_2$=7.6, J$_3$=1.7, 1H); 7.17 (dd, J$_1$=8.0, J$_2$=0.9, 1H); 7.13 (ddd, J$_1$=J$_2$=7.6, J$_3$=0.9, 1H); 3.91 (d, J=6.9, 2H); 3.80 (m, 1H); 2.62 (m, 1H); 1.98 (m, 2H); 1.92 (m, 2H); 1.36 (m, 2H); 1.18 (m, 2H); 0.96 (m, 1H); 0.35 (m, 2H); 0.21 (m, 2H).

Example A162

4-(2-Cyclopropylmethoxy-phenyl)-5H-pyrrolo[3,2-d]pyrimidine-7-carboxylic acid piperidin-4-ylamide Starting from 4-{[4-(2-cyclopropylmethoxy-phenyl)-5H-pyrrolo[3,2-d]pyrimidine-7-carbonyl]-amino}-piperidine-1- carboxylic acid tert-butyl ester (example A110) the title compound is obtained as colorless solid.

MS (ESI): m/z=392 (MH⁺, 100%).

¹H-NMR (300 MHz, DMSO-d₆, MeOH-d₄): 9.06 (s, 1H); 8.48 (d, J=7.9, 1H, —NH); 8.23 (s, 1H); 7.63 (dd, J₁=7.6, J₂=1.7, 1H); 7.53 (ddd, J₁=8.0, J₂=7.6, J₃=1.7, 1H); 7.17 (dd, J₁=8.0, J2=0.9, 1H); 7.13 (ddd, J₁=J₂=7.6, J₃=0.9, 1H); 3.98 (m, 1H); 3.91 (d, J=6.9, 2H); 2.98 (m, 2H); 2.60 (m, 2H); 1.89 (m, 2H); 1.42 (m, 2H); 0.97 (m, 1H); 0.34 (m, 2H); 0.21 (m, 2H).

Example A163

4-(2-Cyclopropylmethoxy-4-fluoro-5-methoxy-phenyl)-5H-pyrrolo[3,2-d]pyrimidine-7-carboxylic acid piperidin-4-ylamide hydrochloride Starting from 4-{[4-(2-cyclopropylmethoxy-4-fluoro-5-methoxy-phenyl)-5H-pyrrolo[3,2-d]pyrimidine-7-carbonyl]-amino}-piperidine-1-carboxylic acid tert-butyl ester (example A111) the title compound is obtained as bright yellow solid.

MS (ESI): m/z=440 (MH⁺, 100%).

¹H-NMR (300 MHz, DMSO-d₆): 12.44 (br.s, 1H, —NH); 9.13 (s, 1H & br.s, 2H, —NH₂⁺); 8.51 (d, J=5.6, 1H, —NH); 8.49 (s, 1H); 7.45 (d, J=9.8, 1H); 7.22 (d, J=13.4, 1H); 4.17 (m, 1H); 3.87 (d, J=7.2, 2H & s, 3H); 3.32 (m, 2H); 3.07 (m, 2H); 2.13 (m, 2H); 1.83 (m, 2H); 0.93 (m, 1H); 0.34 (m, 2H); 0.19 (m, 2H).

Example A164

4-(2-Cyclopropylmethoxy-4-fluoro-5-methoxy-phenyl)-5H-pyrrolo[3,2-d]pyrimidine-7-carboxylic acid (R)-piperidin-3-ylamide hydrochloride Starting from (R)-3-{[4-(2-cyclopropylmethoxy-4-fluoro-5-methoxy-phenyl)-5H-pyrrolo[3,2-d]pyrimidine-7-carbonyl]-amino}-piperidine-1-carboxylic acid tert-butyl ester (example A112) the title compound is obtained as bright yellow solid.

MS (ESI): m/z=440 (MH⁺, 100%).

¹H-NMR (300 MHz, DMSO-d₆): 12.46 (br.s, 1H, —NH); 9.29 (br.s, 1H, —NH); 9.19 (br.s, 1H, —NH); 9.11 (s, 1H); 8.55 (s, 1H); 8.53 (br.s, 1H, —NH); 7.45 (d, J=9.8, 1H); 7.22 (d, J=13.3, 1H); 4.28 (m, 1H); 3.87 (d, J=6.7, 2H); 3.86 s, 3H); 3.38 (m, 1H); 3.20 (m, 1H); 2.97 (m, 2H); 2.04-1.71 (m, 4H); 0.94 (m, 1H); 0.34 (m, 2H); 0.19 (m, 2H).

Example A165

4-(2-Cyclopropylmethoxy-4-fluoro-5-methoxy-phenyl)-5H-pyrrolo[3,2-d]pyrimidine-7-carboxylic acid (R)-pyrrolidin-3-ylamide hydrochloride Starting from (R)-3-{[4-(2-cyclopropylmethoxy-4-fluoro-5-methoxy-phenyl)-5H-pyrrolo[3,2-d]pyrimidine-7-carbonyl]-amino}-pyrrolidine-1-carboxylic acid tert-butyl ester (example A113) the title compound is obtained as bright yellow solid.

MS (ESI): m/z=426 (MH⁺, 100%).

¹H-NMR (300 MHz, DMSO-d₆): 12.41 (br.s, 1H, —NH); 9.39 (br.s, 1H, —NH₂); 9.11 (s, 1H); 8.69 (d, J=6.7, 1H, —NH); 8.51 (d, J=3.3, 1H); 7.45 (d, J=9.8, 1H); 7.21 (d, J=13.3, 1H); 4.65 (m, 1H); 3.87 (d, J=6.8, 2H); 3.86 s, 3H); 3.52-3.46 (m, 1H); 3.30-3.14 (m, 1H); 2.32 (m, 1H); 2.04 (m, 1H); 0.93 (m, 1H); 0.33 (m, 2H); 0.19 (m, 2H). solid.

Example A166

4-(2-Cyclopropylmethoxy-5-fluoro-4-methoxy-phenyl)-5H-pyrrolo[3,2-d]pyrimidine-7-carboxylic acid piperidin-4-ylamide hydrochloride Starting from 4-{[4-(2-cyclopropylmethoxy-5-fluoro-4-methoxy-phenyl)-5H-pyrrolo[3,2-d]pyrimidine-7-carbonyl]-amino}-piperidine-1-carboxylic acid tert-butyl ester (example A115) the title compound is obtained as bright yellow solid.

MS (ESI): m/z=440 (MH⁺, 100%).

¹H-NMR (300 MHz, DMSO-d₆): 12.53 (br.s, 1H, —NH); 9.16 (br.s, 2H, —NH₂); 9.11 (s, 1H); 8.57 (d, J=3.2, 1H); 8.53 (d, J=7.6, 1H); 7.55 (d, J=11.7, 1H); 6.96 (d, J=7.3, 1H); 4.17 (m, 1H); 4.00 (s, 3H); 3.99 (d, J=5.2, 2H); 3.31 (m, 2H); 3.06 (m, 2H); 2.12 (m, 2H); 1.82 (m, 2H); 0.97 (m, 1H); 0.37 (m, 2H); 0.24 (m, 2H).

Example A167

4-(2-Cyclopropylmethoxy-5-fluoro-4-methoxy-phenyl)-5H-pyrrolo[3,2-d]pyrimidine-7-carboxylic acid (R)-piperidin-3-ylamide hydrochloride Starting from (R)-3-{[4-(2-cyclopropylmethoxy-5-fluoro-4-methoxy-phenyl)-5H-pyrrolo[3,2-d]pyrimidine-7-carbonyl]-amino}-piperidine-1-carboxylic acid tert-butyl ester (example A116) the title compound is obtained as bright yellow solid.

MS (ESI): m/z=440 (MH⁺, 100%).

¹H-NMR (300 MHz, DMSO-d₆): 12.48 (br.s, 1H, —NH); 9.28 (br.m, 2H, —NH₂); 9.08 (s, 1H); 8.59 (d, J=6.8, 1H, —NH); 8.57 (s, 1H); 7.57 (d, J=11.7, 1H); 6.96 (d, J=7.3, 1H); 4.30 (m, 1H); 4.00 (s, 3H); 3.99 (d, J=5.2, 2H); 3.39 (m, 1H); 3.20 (m, 1H); 2.99 (m, 1H); 2.97 (m, 1H); 1.98 (m, 2H); 1.76 (m, 2H); 0.98 (m, 1H); 0.38 (m, 2H); 0.25 (m, 2H).

Example A168

4-(2-Cyclopropylmethoxy-5-fluoro-4-methoxy-phenyl)-5H-pyrrolo[3,2-d]pyrimidine-7-carboxylic acid (S)-piperidin-3-ylamide hydrochloride Starting from (S)-3-{[4-(2-cyclopropylmethoxy-5-fluoro-4-methoxy-phenyl)-5H-pyrrolo[3,2-d]pyrimidine-7-carbonyl]-amino}-piperidine-1-carboxylic acid tert-butyl ester (example A117) the title compound is obtained as bright yellow solid.

MS (ESI): m/z=440 (MH⁺, 100%).

¹H-NMR (300 MHz, DMSO-d₆): 12.48 (br.s, 1H, —NH); 9.28 (br.m, 2H, —NH₂); 9.08 (s, 1H); 8.59 (d, J=6.8, 1H, —NH); 8.57 (s, 1H); 7.57 (d, J=11.7, 1H); 6.96 (d, J=7.3, 1H); 4.30 (m, 1H); 4.00 (s, 3H); 3.99 (d, J=5.2, 2H); 3.39 (m, 1H); 3.20 (m, 1H); 2.99 (m, 1H); 2.97 (m, 1H); 1.98 (m, 2H); 1.76 (m, 2H); 0.98 (m, 1H); 0.38 (m, 2H); 0.25 (m, 2H).

Example A169

4-(2-Cyclopropylmethoxy-5-fluoro-4-methoxy-phenyl)-5H-pyrrolo[3,2-d]pyrimidine-7-carboxylic acid (R)-pyrrolidin-3-ylamide hydrochloride Starting from (R)-3-{[4-(2-cyclopropylmethoxy-5-fluoro-4-methoxy-phenyl)-5H-pyrrolo[3,2-d]pyrimidine-7-carbonyl]-amino}-pyrrolidine-1-carboxylic acid tert-butyl ester (example A118) the title compound is obtained as bright yellow solid.

MS (ESI): m/z=426 (MH$^+$, 100%).
$^1$H-NMR (300 MHz, DMSO-d$_6$): 12.39 (br.s, 1H, —NH); 9.37 (br.s, 2H, —NH$_2$); 9.08 (s, 1H); 8.73 (d, J=6.7, 1H, —NH); 8.53 (d, J=3.2, 1H); 7.54 (d, J=11.8, 1H); 6.95 (d, J=7.2, 1H); 4.65 (m, 1H); 3.98 (s, 3H); 3.96 (d, J=6.2, 2H); 3.57-3.39 (m, 2H); 3.30-3.17 (m, 2H); 2.33 (m, 1H); 2.03 (m, 1H); 0.97 (m, 1H); 0.37 (m, 2H), 0.23 (m, 2H).

Example A170 trans-4-(2-Cyclopropylmethoxy-5-methyl-phenyl)-5H-pyrrolo[3,2-d]pyrimidine-7-carboxylic acid (4-amino-cyclohexyl)-amide Starting from trans-(4-{[4-(2-cyclopropylmethoxy-5-methyl-phenyl)-5H-pyrrolo[3,2-d]pyrimidine-7-carbonyl]-amino}-cyclohexyl)-carbamic acid tert-butyl ester (example A120) the title compound is obtained as colorless solid.

MS (ESI): m/z=420 (MH$^+$, 100%).
$^1$H-NMR 400 MHz, DMSO-d$_6$/MeOH-d$_4$): 9.01 (s, 1H); 8.38 (d, J=7.9, 1H, —NH); 8.21 (s, 1H); 7.45 (d, J=1.9, 1H); 7.33 (dd, J$_1$=8.4, J$_2$=1.9, 1H); 7.06 (d, J=8.4, 1H); 3.87 (d, J=6.8, 2H); 3.80 (m, 1H); 2.63 (m, 1H); 2.17 (s, 3H); 2.00 (m, 2H); 1.84 (m, 2H); 1.38 (m, 2H); 1.20 (m, 2H); 0.95 (m, 1H); 0.34 (m, 2H); 0.19 (m, 2H).

Example A171

4-(2-Cyclopropylmethoxy-5-methyl-phenyl)-5H-pyrrolo[3,2-d]pyrimidine-7-carboxylic acid piperidin-4-ylamide Starting from 4-{[4-(2-cyclopropylmethoxy-5-methyl-phenyl)-5H-pyrrolo[3,2-d]pyrimidine-7-carbonyl]-amino}-piperidine-1-carboxylic acid tert-butyl ester (example A119) the title compound is obtained as colorless solid.

MS (ESI): m/z=406 (MH$^+$, 100%).
$^1$H-NMR 400 MHz, DMSO-d$_6$/MeOH-d$_4$): 9.04 (s, 1H); 8.53 (d, J=7.7, 1H, —NH); 8.24 (s, 1H); 7.46 (d, J=1.9, 1H); 7.34 (dd, J$_1$=8.4, J$_2$=1.9, 1H); 7.07 (d, J=8.4, 1H); 4.03 (m, 1H) 3.87 (d, J=6.8, 2H); 3.13 (m, 2H); 2.80 (m, 2H); 2.34 (s, 3H); 2.01 (m, 2H); 1.57 (m, 2H); 0.95 (m, 1H); 0.34 (m, 2H); 0.20 (m, 2H).

Example A172

4-(5-Cyclopropylmethoxy-benzo[1,3]dioxol-4-yl)-5H-pyrrolo[3,2-d]pyrimidine-7-carboxylic acid azetidin-3-ylamide Starting from 3-{[4-(5-Cyclopropylmethoxy-benzo[1,3]dioxol-4-yl)-5H-pyrrolo[3,2-d]pyrimidine-7-carbonyl]-amino}-azetidine-1-carboxylic acid tert-butyl ester (example A95) the title compound is obtained as colorless solid.

Example A173 trans-4-(5-Cyclobutylmethoxy-benzo[1,3]dioxol-4-yl)-5H-pyrrolo[3,2-d]pyrimidine-7-carboxylic acid (4-amino-cyclohexyl)-amide hydrochloride Starting from trans-[4-({1-[4-(5-cyclobutylmethoxy-benzo[1,3]dioxol-4-yl)-5H-pyrrolo[3,2-d]pyrimidin-7-yl]-methanoyl}-amino)-cyclohexyl]-carbamic acid tert-butyl ester (example A121) the title compound is obtained as bright yellow solid.

MS (ESI): m/z=464 (MH$^+$, 100%).
$^1$H-NMR (300 MHz, DMSO-d$_6$): 12.88 (br.s, 1H, —NH); 9.12 (s, 1H); 8.52 (d, J=3.1, 1H); 8.29 (d, J=7.4, 1H, —NH & br.s, 3H, —NH$_3^+$); 7.07 (d, J=8.6, 1H); 6.62 (d, J=8.6, 1H); 6.06 (s, 2H); 3.88 (d, J=6.3, 2H); 3.82 (m, 2H); 3.07 (m, 1H); 2.41 (m, 1H); 2.06 (m, 4H); 1.70 (m, 3H); 1.63-1.40 (m, 7H).

Example A174

4-(5-Cyclobutylmethoxy-benzo[1,3]dioxol-4-yl)-5H-pyrrolo[3,2-d]pyrimidine-7-carboxylic acid piperidin-4-ylamide hydrochloride Starting from 4-({1-[4-(5-cyclobutylmethoxy-benzo[1,3]dioxol-4-yl)-5H-pyrrolo[3,2-d]pyrimidin-7-yl]-methanoyl}-amino)-piperidine-1-carboxylic acid tert-butyl ester (example A122) the title compound is obtained as bright yellow solid.

MS (ESI): m/z=450 (MH$^+$, 100%).
$^1$H-NMR (300 MHz, DMSO-d$_6$): 12.74 (br.s, 1H, —NH); 9.17 (br.s, 2H, —NH$_2^+$); 9.12 (s, 1H); 8.48 (d, J=3.1, 1H); 8.43 (d, J=7.5, 1H, —NH); 7.06 (d, J=8.6, 1H); 6.61 (d, J=8.6, 1H); 6.05 (s, 2H); 4.16 (m, 1H); 3.87 (d, J=6.3, 2H); 3.31 (m, 2H); 3.07 (m, 2H); 2.40 (m, 1H); 2.12 (m, 2H); 1.83 (m, 2H); 1.70 (m, 3H); 1.52 (m, 3H).

Example A175

4-(5-Ethoxy-benzo[1,3]dioxol-4-yl)-5H-pyrrolo[3,2-d]pyrimidine-7-carboxylic acid piperidin-4-ylamide Starting from 4-{[4-(5-ethoxy-benzo[1,3]dioxol-4-yl)-5H-pyrrolo[3,2-d]pyrimidine-7-carbonyl]-amino}-piperidine-1-carboxylic acid tert-butyl ester (example A123) the title compound was obtained as colorless solid.

MS (ESI): m/z=410 (MH$^+$, 100%).
$^1$H-NMR (400 MHz, DMSO-d$_6$/MeOH-d$_4$): 9.04 (s, 1H); 8.47 (d, J=7.8, 1H, —NH); 8.29 (s, 1H); 7.01 (d, J=8.6, 1H); 6.59 (d, J=8.6, 1H); 6.01 (s, 2H); 4.03 (m, 1H); 3.96 (qu, J=6.9, 2H); 3.09 (m, 1H); 2.93 (m, 1H); 2.76 (m, 1H); 2.21 (m, 1H); 1.98 (m, 2H); 1.57 (m, 2H); 1.03 (t, J=6.9, 3H).

Example A176

4-(5-Ethoxy-benzo[1,3]dioxol-4-yl)-5H-pyrrolo[3,2-d]pyrimidine-7-carboxylic acid (R)-pyrrolidin-3-ylamide Starting from (R)-3-{[4-(5-ethoxy-benzo[1,3]dioxol-4-yl)-5H-pyrrolo[3,2-d]pyrimidine-7-carbonyl]-amino}-pyrrolidine-1-carboxylic acid tert-butyl ester (example A124) the title compound was obtained as colorless solid.

MS (ESI): m/z=396 (MH$^+$, 100%).
$^1$H-NMR (400 MHz, DMSO-d$_6$/MeOH-d$_4$): 9.04 (s, 1H); 8.49 (d, J=7.3, 1H, —NH); 8.30 (s, 1H); 7.02 (d, J=8.6, 1H); 6.59 (d, J=8.6, 1H); 6.01 (s, 2H); 4.45 (m, 1H); 3.96 (qu, J=6.9, 2H); 3.17 (m, 1H); 3.02 (m, 1H); 2.89 (m, 1H); 2.75 (m, 1H); 2.13 (m, 1H); 1.70 (m, 1H); 1.03 (t, J=6.9, 3H).

Example A177

4-(5-Propoxy-benzo[1,3]dioxol-4-yl)-5H-pyrrolo[3,2-d]pyrimidine-7-carboxylic acid piperidin-4-ylamide Starting from 4-{[4-(5-propoxy-benzo[1,3]dioxol-4-yl)-5H-pyrrolo[3,2-d]pyrimidine-7-carbonyl]-amino}-piperidine-1-carboxylic acid tert-butyl ester (example A125) the title compound was obtained as colorless solid.

MS (ESI): m/z=424 (MH+, 100%).

$^1$H-NMR (400 MHz, DMSO-$d_6$/MeOH-$d_4$): 9.03 (s, 1H); 8.49 (d, J=8.0, 1H, —NH); 8.27 (s, 1H); 7.01 (d, J=8.6, 1H); 6.58 (d, J=8.6, 1H); 6.01 (s, 2H); 4.03 (m, 1H); 3.86 (t, J=6.4, 2H); 3.11 (m, 1H); 2.87 (m, 1H); 2.69 (m, 2H); 1.92 (m, 1H); 1.72 (m, 1H); 1.57 (m, 2H); 1.40 (m, 2H); 0.62 (t, J=7.4, 3H).

Example A178

4-(5-Propoxy-benzo[1,3]dioxol-4-yl)-5H-pyrrolo[3,2-d]pyrimidine-7-carboxylic acid (R)-pyrrolidin-3-ylamide Starting from (R)-3-{[4-(5-propoxy-benzo[1,3]dioxol-4-yl)-5H-pyrrolo[3,2-d]pyrimidine-7-carbonyl]-amino}-pyrrolidine-1-carboxylic acid tert-butyl ester (example A126) the title compound was obtained as colorless solid.

MS (ESI): m/z=410 (MH+, 100%).

$^1$H-NMR (400 MHz, DMSO-$d_6$/MeOH-$d_4$): 9.02 (s, 1H); 8.48 (d, J=7.3, 1H, —NH); 8.26 (s, 1H); 7.01 (d, J=8.6, 1H); 6.58 (d, J=8.6, 1H); 6.01 (s, 2H); 4.43 (m, 1H); 3.86 (t, J=6.4, 2H); 3.15 (m, 1H); 3.01 (m, 1H); 2.87 (m, 1H); 2.73 (m, 1H); 2.12 (m, 1H); 1.69 (m, 1H); 1.42 (m, 2H); 0.62 (t, J=7.4, 3H).

Example A179

4-(5-Butoxy-benzo[1,3]dioxol-4-yl)-5H-pyrrolo[3,2-d]pyrimidine-7-carboxylic acid piperidin-4-ylamide Starting from 4-{[4-(5-butoxy-benzo[1,3]dioxol-4-yl)-5H-pyrrolo[3,2-d]pyrimidine-7-carbonyl]-amino}-piperidine-1-carboxylic acid tert-butyl ester (example A127) the title compound was obtained as colorless solid.

MS (ESI): m/z=438 (MH+, 100%).

$^1$H-NMR (300 MHz, DMSO-$d_6$/MeOH-$d_4$): 9.03 (s, 1H); 8.50 (d, J=8.0, 1H, —NH); 8.26 (s, 1H); 7.01 (d, J=8.6, 1H); 6.59 (d, J=8.6, 1H); 6.01 (s, 2H); 4.00 (m, 1H); 3.89 (t, J=6.4, 2H); 3.08 (m, 1H); 2.80 (m, 1H); 2.70-2.55 (m, 2H); 1.90 (m, 1H); 1.70 (m, 1H); 1.61-1.47 (m, 2H); 1.40 (m, 2H); 1.04 (m, 2H); 0.69 (t, J=7.4, 3H).

Example A180

4-(5-Butoxy-benzo[1,3]dioxol-4-yl)-5H-pyrrolo[3,2-d]pyrimidine-7-carboxylic acid piperidin-3-ylamide Starting from 3-{[4-(5-butoxy-benzo[1,3]dioxol-4-yl)-5H-pyrrolo[3,2-d]pyrimidine-7-carbonyl]-amino}-piperidine-1-carboxylic acid tert-butyl ester (example A128) the title compound was obtained as colorless solid.

MS (ESI): m/z=438 (MH+, 100%).

$^1$H-NMR (300 MHz, DMSO-$d_6$/MeOH-$d_4$): 9.03 (s, 1H); 8.46 (d, J=7.8, 0.5H, —NH); 8.42 (d, J=7.8, 0.5H, —NH); 8.27 (s, 1H); 7.01 (d, J=8.6, 1H); 6.59 (d, J=8.6, 1H); 6.01 (s, 2H); 4.09-3.91 (m, 1H); 3.89 (t, J=6.4, 2H); 3.08 (m, 1H); 2.92 (m, 1H); 2.73 (m, 2H); 2.22 (m, 1H); 1.97 (m, 2H); 1.54 (m, 2H); 1.40 (m, 2H); 1.08 (m, 2H); 0.69 (t, J=7.4, 3H).

Example A181

4-(5-Butoxy-benzo[1,3]dioxol-4-yl)-5H-pyrrolo[3,2-d]pyrimidine-7-carboxylic acid (R)-pyrrolidin-3-ylamide Starting from (R)-3-{[4-(5-butoxy-benzo[1,3]dioxol-4-yl)-5H-pyrrolo[3,2-d]pyrimidine-7-carbonyl]-amino}-pyrrolidine-1-carboxylic acid tert-butyl ester (example A129) the title compound was obtained as colorless solid.

MS (ESI): m/z=424 (MH+, 100%).

$^1$H-NMR 300 MHz, DMSO-$d_6$/MeOH-$d_4$): 9.02 (s, 1H); 8.84 (d, J=7.3, 1H, —NH); 8.26 (s, 1H); 7.01 (d, J=8.6, 1H); 6.59 (d, J=8.6, 1H); 6.00 (s, 2H); 4.43 (m, 1H); 3.89 (t, J=6.4, 2H); 3.14 (m, 1H); 3.01 (m, 1H); 2.89 (m, 1H); 2.74 (m, 1H); 2.12 (m, 1H); 1.69 (m, 1H); 1.40 (m, 2H); 1.07 (m, 2H); 0.69 (t, J=7.4, 3H).

Example A182 trans-4-[4-Methoxy-2-(2-methoxy-ethoxy)-phenyl]-5H-pyrrolo[3,2-d]pyrimidine-7-carboxylic acid (4-amino-cyclohexyl)-amide Starting from trans-[4-({4-[4-methoxy-2-(2-methoxy-ethoxy)-phenyl]-5H-pyrrolo[3,2-d]pyrimidine-7-carbonyl}-amino)-cyclohexyl]-carbamic acid tert-butyl ester (example A130) the title compound was obtained as colorless solid.

MS (ESI): m/z=440 (MH+, 100%).

$^1$H-NMR (400 MHz, DMSO-$d_6$/MeOH-$d_4$): 8.99 (s, 1H); 8.45 (d, J=7.9, 1H, —NH); 8.23 (s, 1H); 7.70 (d, J=8.3, 1H); 6.77 (s, 1H); 6.75 (dd, $J_1$=8.3, $J_2$=2.1, 1H); 4.25 (t, J=4.6, 2H); 3.88 (s, 3H); 3.84 (m, 1H); 3.55 (t, J=4.6, 2H); 3.14 (s, 3H); 3.13 (m, 1H); 2.12-1.97 (m, 4H); 1.49 (m, 4H).

Example A183 cis-4-[4-Methoxy-2-(2-methoxy-ethoxy)-phenyl]-5H-pyrrolo[3,2-d]pyrimidine-7-carboxylic acid (4-amino-cyclohexyl)-amide Starting from cis-[4-({4-[4-methoxy-2-(2-methoxy-ethoxy)-phenyl]-5H-pyrrolo[3,2-d]pyrimidine-7-carbonyl}-amino)-cyclohexyl]-carbamic acid tert-butyl ester (example A131) the title compound was obtained as colorless solid.

MS (ESI): m/z=440 (MH+, 100%).

$^1$H-NMR (400 MHz, DMSO-$d_6$/MeOH-$d_4$): 9.03 (s, 1H); 8.76 (d, J=7.4, 1H, —NH); 8.23 (s, 1H); 7.71 (d, J=8.3, 1H); 6.78 (s, 1H); 6.75 (dd, $J_1$=8.3, $J_2$=2.1, 1H); 4.25 (t, J=4.6, 2H); 3.88 (s, 3H); 3.56 (t, J=4.6, 2H); 3.41 (m, 1H); 3.15 (s, 3H); 3.05 (m, 1H); 2.12-1.97 (m, 4H); 1.49 (m, 4H).

Example A184

4-[4-Methoxy-2-(2-methoxy-ethoxy)-phenyl]-5H-pyrrolo[3,2-d]pyrimidine-7-carboxylic acid piperidin-4-ylamide Starting from 4-({4-[4-methoxy-2-(2-methoxy-ethoxy)-phenyl]-5H-pyrrolo[3,2-d]pyrimidine-7-carbonyl}-amino)-piperidine-1-carboxylic acid tert-butyl ester (example A132) the title compound was obtained as colorless solid.

MS (ESI): m/z=426 (MH+).

$^1$H-NMR (400 MHz, DMSO-$d_6$/MeOH-$d_4$): 9.02 (s, 1H); 8.57 (d, J=7.7, 1H, —NH); 8.24 (s, 1H); 7.72 (d, J=8.2, 1H); 6.77 (s, 1H); 6.75 (dd, $J_1$=8.2, $J_2$=2.2, 1H); 4.25 (t, J=4.6, 2H); 4.06 (m, 1H); 3.88 (s, 3H); 3.55 (t, J=4.6, 2H); 3.15 (s, 3H & m, 2H); 1.92-1.87 (m, 4H); 1.73 (m, 2H); 1.61 (m, 2H).

Example A185 trans-4-[5-(2-Methoxy-ethoxy)-benzo[1,3]dioxol-4-yl]-5H-pyrrolo[3,2-d]pyrimidine-7-carboxylic acid (4-amino-cyclohexyl)-amide Starting from trans-[4-({4-[5-(2-methoxy-ethoxy)-benzo[1,3]dioxol-4-yl]-5H-pyrrolo[3,2-d]pyrimidine-7-carbonyl}-amino)-cyclohexyl]-carbamic acid tert-butyl ester (example A133) the title compound was obtained as colorless solid.

MS (ESI): m/z=454 (MH$^+$, 100%).

$^1$H-NMR (200 MHz, DMSO-d$_6$/MeOH-d$_4$): 9.00 (s, 1H); 8.31 (d, J=7.9, 1H, —NH); 8.24 (s, 1H); 7.01 (d, J=8.6, 1H); 6.60 (d, J=8.6, 1H); 6.01 (s, 2H); 4.02 (t, J=4.7, 2H); 3.82 (m, 1H); 3.39 (t, J=4.7, 2H); 3.03 (s, 3H); 2.81 (m, 1H); 1.92-1.38 (m, 8H).

Example A186 cis-4-[5-(2-Methoxy-ethoxy)-benzo[1,3]dioxol-4-yl]-5H-pyrrolo[3,2-d]pyrimidine-7-carboxylic acid (4-amino-cyclohexyl)-amide Starting from cis-[4-({4-[5-(2-methoxy-ethoxy)-benzo[1,3]dioxol-4-yl]-5H-pyrrolo[3,2-d]pyrimidine-7-carbonyl}-amino)-cyclohexyl]-carbamic acid tert-butyl ester (example A134) the title compound was obtained as colorless solid.

MS (ESI): m/z=454 (MH$^+$, 100%).

$^1$H-NMR (200 MHz, DMSO-d$_6$/MeOH-d$_4$): 9.02 (s, 1H); 8.64 (d, J=7.9, 1H, —NH); 8.27 (s, 1H); 7.01 (d, J=8.6, 1H); 6.62 (d, J=8.6, 1H); 6.01 (s, 2H); 4.02 (t, J=4.7, 2H & m, 1H); 3.40 (t, J=4.7, 2H); 3.03 (s, 3H); 2.64 (m, 1H); 2.00 (m, 2H); 1.86 (m, 2H); 1.52-1.16 (m, 4H).

Example A187

4-[5-(2-Methoxy-ethoxy)-benzo[1,3]dioxol-4-yl]-5H-pyrrolo[3,2-d]pyrimidine-7-carboxylic acid piperidin-4-ylamide Starting from 4-({4-[5-(2-methoxy-ethoxy)-benzo[1,3]dioxol-4-yl]-5H-pyrrolo[3,2-d]pyrimidine-7-carbonyl}-amino)-piperidine-1-carboxylic acid tert-butyl ester (example A135) the title compound was obtained as colorless solid.

MS (ESI): m/z=440 (MH$^+$, 100%).

$^1$H-NMR (200 MHz, DMSO-d$_6$/MeOH-d$_4$): 9.02 (s, 1H); 8.40 (d, J=8.0, 1H, —NH); 8.27 (s, 1H); 7.01 (d, J=8.6, 1H); 6.61 (d, J=8.6, 1H); 6.01 (s, 2H); 4.03 (t, J=4.7, 2H); 3.96 (m, 1H); 3.39 (t, J=4.7, 2H); 3.02 (s, 3H); 2.98 (m, 2H); 2.60 (m, 2H); 1.90 (m, 2H); 1.41 (m, 2H).

Example A188

4-(2-Cyclopropylmethoxy-5-fluoro-4-hydroxy-phenyl)-5H-pyrrolo[3,2-d]pyrimidine-7-carboxylic acid piperidin-4-ylamide hydrochloride Starting from 4-{[4-(2-cyclopropylmethoxy-5-fluoro-4-methoxymethoxy-phenyl)-5H-pyrrolo[3,2-d]pyrimidine-7-carbonyl]amino}-piperidine-1-carboxylic acid tert-butyl ester (example A136) the title compound is obtained as pale yellow solid.

MS (ESI): m/z=426 (MH$^+$, 100%).

$^1$H-NMR (300 MHz, DMSO-d$_6$): 12.66 (br.s, 1H, —NH); 10.91 (br.s, 1H, —OH); 9.19 (br.s, 2H, —NH$_2^+$); 9.12 (s, 1H); 8.64 (d, J=2.9, 1H); 8.53 (d, J=7.5, 1H, —NH); 7.53 (d, J=11.5, 1H); 6.85 (d, J=7.3, 1H); 4.17 (m, 1H); 3.85 (d, J=6.9, 2H); 3.32 (m, 2H); 3.06 (m, 2H); 2.11 (m, 2H); 1.85 (m, 2H); 0.99 (m, 1H); 0.36 (m, 2H); 0.26 (m, 2H).

Example A189

4-[2-Cyclopropylmethoxy-4-(1,1-difluoro-methoxy)-5-fluoro-phenyl]-5H-pyrrolo[3,2-d]pyrimidine-7-carboxylic acid piperidin-4-ylamide hydrochloride Starting from 4-{[4-(2-cyclopropylmethoxy-5-fluoro-4-methoxymethoxy-phenyl)-5H-pyrrolo[3,2-d]pyrimidine-7-carbonyl]-amino}-piperidine-1-carboxylic acid tert-butyl ester (example A136) the title compound is obtained as pale yellow solid.

MS (ESI): m/z=476 (MH$^+$, 100%).

$^1$H-NMR (300 MHz, DMSO-d$_6$): 12.47 (br.s, 1H, —NH); 9.16 (br.s, 2H, —NH$_2^+$); 9.12 (s, 1H); 8.51 (d, J=7.5, 1H, —NH); 8.50 (s, 1H); 7.67 (d, J=10.9, 1H); 7.45 (t, J=72.5, 1H); 7.21 (d, J=6.0, 1H); 4.14 (m, 1H); 3.93 (d, J=7.1, 2H); 3.31 (m, 2H); 3.07 (m, 2H); 2.13 (m, 2H); 1.83 (m, 2H); 0.96 (m, 1H); 0.35 (m, 2H); 0.23 (m, 2H).

Example A190

(S)-1-(4-Amino-piperidin-1-yl)-2-hydroxy-propan-1-one hydrochloride

To a solution of 4-amino-piperidine-4-carboxylic acid tert-butyl ester (2.50 g, 12.48 mmol) and Huenigs base (3.2 mL; 18.7 mmol) in dichloromethane (15 mL) is added (S)-2-acetoxypropionyl chloride (1.9 mL; 15.0 mmol) under ice-cooling. The mixture is stirred overnight at ambient temperature. The solvent is evaporated and the obtained crude product is partitioned between ethyl acetate and saturated sodium bicarbonate solution. Drying and evaporation of the solvent gave an orange oil (4.14 g) which is dissolved in methanol (30 mL). A 4M HCl in 1,4-dioxane (30 mL) is added and the mixture is stirred for 20 min at ambient temperature. The volatiles are evaporated and the obtained solid is triturated with diethyl ether. Recrystallization from methanol/1,4-dioxane gave 1.63 g of the title compound as white solid.

MS (ESI): m/z=173 (MH$^+$, 100%).

$^1$H-NMR (400 MHz, DMSO-d$_6$): 8.20 (br.s, 3H, —NH$_3^+$); 4.85 (br.s, 1H, —OH); 4.30 (m, 2H); 4.00 (m, 1H); 3.10 (m, 2H); 2.30 (m, 1H); 2.00 (m, 2H); 1.40 (m, 2H); 1.18 (d, 3H, J=6.0).

Example A191

1-(4-Amino-piperidin-1-yl)-ethanone

To a solution of 4-amino-piperidine-4-carboxylic acid tert-butyl ester (2.50 g; 12.5 mmol) and Huenigs base (3.2 mL) in dichloromethane (15 mL) is added acetyl chloride (1.1 mL; 15.0 mmol) under ice-cooling. The mixture is stirred overnight at ambient temperature. The solvent is evaporated and the obtained crude is partitioned between ethyl acetate and 1M aqueous HCl. Drying and evaporation of the solvent gave an orange oil which is dissolved in dichloromethane (38 mL). Trifluoroacetic acid (19 mL) is added and the mixture is stirred for 20 min at ambient temperature. The volatiles are completely evaporated at 35° C. bath temperature and the obtained residue is dissolved in a mixture of dichloromethane/methanol (95:5 v/v). Solid sodium carbonate is added and the suspension is stirred at ambient temperature overnight. Filtration and evaporation of the solvent gave 0.98 g of the title compound as slightly brown oil.

MS (ESI): m/z=142 (MH+, 100%).
1H-NMR (400 MHz, DMSO-$d_6$): 4.12 (m, 1H); 3.65 (m, 1H); 3.35 (br.s, 2H, —NH); 3.00 (m, 1H); 2.74 (m, 1H); 2.57 (m, 1H); 1.95 (s, 3H); 1.68 (m, 2H); 0.98 (m, 2H).

The following compound is obtained analogously to the procedure described in above example A191.

Example A192

1-(4-Amino-piperidin-1-yl)-2-methoxy-ethanone

Starting from 4-amino-piperidine-4-carboxylic acid tert-butyl ester and methoxy-acetyl chloride the title compound is obtained as slightly brown oil.
MS (ESI): m/z=173 (MH+, 100%).

Example A193 trans-(4-Cyclopropylcarbamoyl-cyclohexyl)-carbamic acid tert-butyl ester

To a stirred mixture of trans-4-tert-butoxycarbonylamino-cyclohexanecarboxylic acid (6.1 g, 25.0 mmol) and cyclopropylamine (1.9 mL, 27.5 mmol) in dichloromethane (125 mL), 1-(3-dimethylaminopropyl)-3-ethylcarbodiimide hydrochloride (5.3 g; 27.5 mmol) is added in one portion. The reaction is stirred at ambient temperature for 48 hours. The solvent is evaporated and the crude is stirred in ice-cold 1N hydrochloric acid (100 mL) for 30 min. The solid product is isolated by suction filtration, washed with small portions of water and recrystallized from ethanol/water to deliver 5.2 g of the title compound as colorless solid.
MS (ESI): m/z=305 (MNa+); 283 (MH+); 227 (MH+—$C_4H_8$, 100%).
1H-NMR (200 MHz, DMSO-$d_6$): 7.70 (d, J=4.1, 1H, —NH); 6.64 (d, J=7.6, 1H, —NH); 3.13 (m, 1H); 2.57 (m, 1H); 1.91 (m, 1H); 1.86-1.58 (m, 4H); 1.37 (m, 9H); 1.33 (m, 2H); 1.09 (m, 2H); 0.57 (m, 2H); 0.34 (m, 2H).

The following compound is obtained analogously to the procedure described in above example A193.

Example A194 trans-[4-(2-Methoxy-ethylcarbamoyl)-cyclohexyl]-carbamic acid tert-butyl ester

Starting from trans-4-tert-butoxycarbonylamino-cyclohexanecarboxylic acid and 2-methoxy-ethylamine the title compound is obtained as colorless solid.
MS (ESI): m/z=323 (MNa+); 301 (MH+, 100%); 245 (MH+—$C_4H_8$).
1H-NMR (200 MHz, DMSO-$d_6$): 7.72 (t, J=5.4, 1H, —NH); 6.65 (d, J=7.7, 1H, —NH); 3.30 (t, J=5.3, 2H); 3.23 (s, 3H); 3.18 (m, 2H & m, 1H); 2.01 (m, 1H); 1.73 (m, 4H); 1.37 (m, 9H); 1.34 (m, 2H); 1.11 (m, 2H).

Example A195 trans-4-Amino-cyclohexanecarboxylic acid cyclopropylamide hydrochloride

Trans-(4-Cyclopropylcarbamoyl-cyclohexyl)-carbamic acid tert-butyl ester from example A193 (5.0 g; 17.7 mmol) is suspended in 1,4-dioxane (72 mL). 4N hydrochloric acid in 1,4-dioxane (18.0 mL) is added and the mixture is stirred at 80° C. for six hours. The product is precipitated with tert-butylmethylether at ice bath temperature, isolated by suction filtration, washed with small portions of tert-butylmethylether and dried under reduced pressure to deliver 3.8 g of the title compound as colorless solid.
MS (ESI): m/z=183 (MH+, 100%); 166 MH+—$NH_3$).
1H-NMR (200 MHz, DMSO-$d_6$): 8.07 (br.s, 1H, —$NH_3^+$); 7.84 (d, J=4.0, 1H, —NH); 2.93 (m, 1H); 2.59 (m, 1H); 1.97 (m, 3H); 1.73 (m, 2H); 1.34 (m, 4H); 0.58 (m, 2H); 0.35 (m, 2H).

The following compound is obtained analogously to the procedure described in above example A195.

Example A196 trans-4-Amino-cyclohexanecarboxylic acid (2-methoxy-ethyl)-amide hydrochloride

Starting from trans-[4-(2-methoxy-ethylcarbamoyl)-cyclohexyl]-carbamic acid tert-butyl ester (example A194) the title compound is obtained as colorless solid.
MS (ESI): m/z=201 (MH+, 100%); 183 MH+—$NH_3$).
1H-NMR (200 MHz, DMSO-$d_6$): 8.19 (br.s, 1H, —$NH_3^+$); 7.87 (br.s, 1H, —NH); 3.31 (t, J=5.4, 2H); 3.23 (s, 3H); 3.16 (t, J=5.4, 2H); 2.91 (m, 1H); 2.08 (m, 1H); 1.99 (m, 2H); 1.76 (m, 2H); 1.38 (m, 2H).

Example 1

4-(5-Cyclopropylmethoxy-1,3-benzodioxol-4-yl)-5H-pyrrolo[3,2-d]pyrimidine-7-carboxylic acid (1-propionyl-piperidin-4-yl)-amide 4-(5-Cyclopropylmethoxy-1,3-benzodioxol-4-yl)-5H-pyrrolo[3,2-d]pyrimidine-7-carboxylic acid piperidin-4-ylamide hydrochloride from example A138 (472 mg; 1.0 mmol) and DBU (2.5 mmol) is dissolved in dry dichloromethane (5 mL). Propionyl chloride (1.1 mmol) is syringed into the reaction mixture at ice bath temperature. After complete addition stirring is continued at ambient temperature over night. Methanol (1 mL) is added and stirring is continued for two hours. The volatiles are evaporated. The residue is purified by reversed phase preparative HPLC. The collected product fraction is freeze-dried to yield 375 mg of the title compound as colorless solid.
MS (ESI): m/z=492.1 (MH+).
1H-NMR (400 MHz, DMSO-$d_6$): 12.28 (br.s, 1H, —NH); 9.02 (s, 1H); 8.45 (d, J=7.8, 1H, —NH); 8.29 (s, 1H); 7.00 (d, J=8.6, 1H); 6.56 (d, J=8.6, 1H); 6.00 (s, 2H); 4.23 (m, 1H); 4.14 (m, 1H); 3.83 (m, 1H); 3.76 (d, J=6.8, 2H); 3.24 (m, 1H); 2.92 (m, 1H); 2.35 (qu, J=7.4, 2H); 1.97 (m, 2H); 1.53 (m, 1H); 1.40 (m, 1H); 1.01 (t, J=7.4, 3H); 0.87 (m, 1H); 0.29 (m, 2H); 0.10 (m, 2H).

The following compounds are obtained analogously to the procedure described in above example 1.

Example 2

4-({1-[4-(5-Cyclopropylmethoxy-benzo[1,3]dioxol-4-yl)-5H-pyrrolo[3,2-d]pyrimidin-7-yl]-methanoyl}-amino)-piperidine-1-carboxylic acid ethyl ester Starting from 4-(5-cyclopropylmethoxy-1,3-benzodioxol-4-yl)-5H-pyrrolo[3,2-d]pyrimidine-7-carboxylic acid piperidin-4-ylamide hydrochloride (example A138) and ethyl chloroformate the title compound is obtained as colorless solid.
MS (ESI): m/z=494 (MH+).
1H-NMR (400 MHz, DMSO-$d_6$): 12.27 (br.s, 1H, —NH); 9.03 (s, 1H); 8.44 (d, J=7.8, 1H, —NH); 8.29 (s, 1H); 7.01 (d, J=8.6, 1H); 6.56 (d, J=8.6, 1H); 6.00 (s, 2H); 4.08 (m, 1H & qu, J=7.1, 2H); 3.91 (m, 2H); 3.76 (d, J=6.8, 2H); 3.08 (m, 2H); 1.95 (m, 2H); 1.47 (m, 2H); 1.20 (t, J=7.1, 3H); 0.87 (m, 1H); 0.29 (m, 2H); 0.10 (m, 2H).

Example 3

4-(5-Cyclopropylmethoxy-benzo[1,3]dioxol-4-yl)-5H-pyrrolo[3,2-d]pyrimidine-7-carboxylic acid [1-(2-methoxy-acetyl)piperidin-4-yl]-amide Starting from 4-(5-cyclopropylmethoxy-1,3-benzodioxol-4-yl)-5H-pyrrolo[3,2-d]pyrimidine-7-carboxylic acid piperidin-4-ylamide hydrochloride (example A138) and methoxyacetyl chloride the title compound is obtained as colorless solid.

MS (ESI): m/z=508 (MH$^+$).

$^1$H-NMR (400 MHz, DMSO-d$_6$): 11.99 (br.s, 1H, —NH); 9.03 (s, 1H); 8.45 (d, J=7.8, 1H, —NH); 8.30 (s, 1H); 7.01 (d, J=8.6, 1H); 6.56 (d, J=8.6, 1H); 6.00 (s, 2H); 4.15 (m, 2H); 4.12 (s, 2H); 3.76 (m, 1H & d, J=6.8, 2H); 3.31 (s, 3H); 3.21 (m, 1H); 2.94 (m, 1H); 1.97 (m, 2H); 1.55 (m, 1H); 1.42 (m, 1H); 0.87 (m, 1H); 0.29 (m, 2H); 0.10 (m, 2H).

Example 4 trans-4-(5-Cyclopropylmethoxy-benzo[1,3]dioxol-4-yl)-5H-pyrrolo[3,2-d]pyrimidine-7-carboxylic acid (4-acetylamino-cyclohexyl)-amide Starting from trans-4-(5-cyclopropylmethoxy-benzo[1,3]dioxol-4-yl)-5H-pyrrolo[3,2-d]pyrimidine-7-carboxylic acid (4-amino-cyclohexyl)-amide (example A140) and acetyl chloride the title compound is obtained as colorless solid.

MS (ESI): m/z=492 (MH$^+$).

$^1$H-NMR (400 MHz, DMSO-d$_6$): 11.42 (br. S, 1H, —NH); 9.03 (s, 1H); 8.30 (d, J=7.9, 1H, —NH); 8.27 (s, 1H); 7.74 (d, J=7.7, 1H, —NH); 7.00 (d, J=8.5, 1H); 6.56 (d, J=8.5, 1H); 6.00 (s, 2H); 3.82 (m, 1H); 3.76 (d, J=6.7, 2H); 3.58 (m, 1H); 2.01 (~d; J ~10.0, 2H); 1.86 (~d, J ~10.2, 2H); 1.63 (s, 3H); 1.42 (m, 2H); 1.31 (m, 2H), 0.87 (m, 1H); 0.29 (m, 2H); 0.11 (m, 2H).

Example 5 trans-4-(5-Cyclopropylmethoxy-benzo[1,3]dioxol-4-yl)-5H-pyrrolo[3,2-d]pyrimidine-7-carboxylic acid {4-[(1-cyclopropyl-methanoyl)-amino]-cyclohexyl}-amide Starting from trans-4-(5-cyclopropylmethoxy-benzo[1,3]dioxol-4-yl)-5H-pyrrolo[3,2-d]pyrimidine-7-carboxylic acid (4-amino-cyclohexyl)-amide (example A140) and cyclopropanecarbonyl chloride the title compound is obtained as colorless solid.

MS (ESI): m/z=518 (MH$^+$).

$^1$H-NMR (400 MHz, DMSO-d$_6$): 12.23 (br. S, 1H, —NH); 9.03 (s, 1H); 8.31 (d, J=7.8, 1H, —NH); 8.27 (s, 1H); 7.96 (d, J=7.7, 1H, —NH); 7.00 (d, J=8.5, 1H); 6.56 (d, J=8.5, 1H); 6.00 (s, 2H); 3.82 (m, 1H); 3.76 (d, J=6.8, 2H); 3.61 (m, 1H); 2.02 (~d; J ~10.0, 2H); 1.87 (~d, J ~10.2, 2H); 1.54 (m, 1H); 1.38 (m, 4H); 0.87 (m, 1H); 0.64 (m, 4H); 0.31 (m, 2H); 0.11 (m, 2H).

Example 6 trans-[4-({1-[4-(5-Cyclopropylmethoxy-benzo[1,3]dioxol-4-yl)-5H-pyrrolo[3,2-d]pyrimidin-7-yl]-methanoyl}-amino)-cyclohexyl]-carbamic acid ethyl ester Starting from trans-4-(5-cyclopropylmethoxy-benzo[1,3]dioxol-4-yl)-5H-pyrrolo[3,2-d]pyrimidine-7-carboxylic acid (4-amino-cyclohexyl)-amide (example A140) and ethyl chloroformate the title compound is obtained as colorless solid.

MS (ESI): m/z=522 (MH$^+$).

$^1$H-NMR (400 MHz, DMSO-d$_6$): 12.25 (br. s, 1H, —NH); 9.03 (s, 1H); 8.29 (d, J=7.9, 1H, —NH); 8.27 (s, 1H); 7.02 (d, J=9.2, 1H, —NH); 7.00 (d, J=8.5, 1H); 6.56 (d, J=8.5, 1H); 6.00 (s, 2H); 3.98 (qu, J=7.0, 2H); 3.79 (m, 1H); 3.76 (d, J=6.7, 2H); 3.31 (m, 1H); 2.00 (~d, J ~10.3, 2H); 1.87 (~d, J ~11.4, 2H); 1.37 (m, 4H); 1.16 (t, J=7.0, 3H); 0.86 (m, 1H); 0.29 (m, 2H); 0.10 (m, 2H).

Example 7 cis-4-(5-Cyclopropylmethoxy-benzo[1,3]dioxol-4-yl)-5H-pyrrolo[3,2-d]pyrimidine-7-carboxylic acid (4-acetylamino-cyclohexyl)-amide Starting from cis-4-(5-cyclopropylmethoxy-benzo[1,3]dioxol-4-yl)-5H-pyrrolo[3,2-d]pyrimidine-7-carboxylic acid (4-amino-cyclohexyl)-amide (example A141) and acetyl chloride the title compound is obtained as colorless solid.

MS (ESI): m/z=492 (MH$^+$).

$^1$H-NMR (400 MHz, DMSO-d$_6$): 12.24 (br.s, 1H, —NH); 9.06 (s, 1H); 8.56 (d, J=7.6, 1H, —NH); 8.28 (s, 1H); 7.86 (d, J=7.4, 1H, —NH); 7.01 (d, J=8.6, 1H); 6.56 (d, J=8.6, 1H); 6.01 (s, 2H); 4.03 (m, 1H); 3.77 (m, 1H & d, J=6.7, 2H); 1.84 (s, 3H); 1.73 (m, 6H); 1.59 (m, 2H); 0.88 (m, 1H); 0.30 (m, 2H); 0.11 (m, 2H).

Example 8 cis-4-(5-Cyclopropylmethoxy-benzo[1,3]dioxol-4-yl)-5H-pyrrolo[3,2-d]pyrimidine-7-carboxylic acid {4-[(1-cyclopropyl-methanoyl)-amino]-cyclohexyl}-amide Starting from cis-4-(5-cyclopropylmethoxy-benzo[1,3]dioxol-4-yl)-5H-pyrrolo[3,2-d]pyrimidine-7-carboxylic acid (4-amino-cyclohexyl)-amide (example A141) and cyclopropanecarbonyl chloride the title compound is obtained as colorless solid.

MS (ESI): m/z=518 (MH$^+$).

$^1$H-NMR (400 MHz, DMSO-d$_6$): 12.24 (br.s, 1H, —NH); 9.07 (s, 1H); 8.58 (d, J=7.5, 1H, —NH); 8.29 (s, 1H); 8.07 (d, J=7.4, 1H, —NH); 7.01 (d, J=8.6, 1H); 6.56 (d, J=8.6, 1H); 6.01 (s, 2H); 4.03 (m, 1H); 3.77 (m, 1H & d, J=6.7, 2H); 1.79 (m, 1H); 1.67 (m, 8H); 0.87 (m, 1H); 0.65 (m, 4H); 0.31 (m, 2H); 0.11 (m, 2H).

Example 9 cis-4-(5-Cyclopropylmethoxy-benzo[1,3]dioxol-4-yl)-5H-pyrrolo[3,2-d]pyrimidine-7-carboxylic acid [4-(2-methoxy-ethanoylamino)-cyclohexyl]-amide Starting from cis-4-(5-cyclopropylmethoxy-benzo[1,3]dioxol-4-yl)-5H-pyrrolo[3,2-d]pyrimidine-7-carboxylic acid (4-amino-cyclohexyl)-amide (example A141) and methoxy-acetyl chloride the title compound is obtained as colorless solid.

MS (ESI): m/z=522 (MH$^+$).

$^1$H-NMR (400 MHz, DMSO-d$_6$): 12.22 (br.s, 1H, —NH); 9.06 (s, 1H); 8.59 (d, J=7.4, 1H, —NH); 8.28 (s, 1H); 7.70 (d, J=7.7, 1H, —NH); 7.01 (d, J=8.6, 1H); 6.56 (d, J=8.6, 1H); 6.01 (s, 2H); 4.06 (m, 1H); 3.82 (s, 2H); 3.77 (m, 1H & d, J=6.8, 2H); 3.31 (s, 3H); 1.80 (m, 3H); 1.74 (m, 2H); 1.69 (m, 4H); 0.86 (m, 1H); 0.30 (m, 2H); 0.11 (m, 2H).

Example 10 cis-[4-({1-[4-(5-Cyclopropylmethoxy-benzo[1,3]dioxol-4-yl)-5H-pyrrolo[3,2-d]pyrimidin-7-yl]-methanoyl}-amino)-cyclohexyl]-carbamic acid ethyl ester Starting from cis-4-(5-cyclopropylmethoxy-benzo[1,3]dioxol-4-yl)-5H-pyrrolo[3,2-d]pyrimidine-7-carboxylic acid (4-amino-cyclohexyl)-amide (example A141) and ethyl chloroformate the title compound is obtained as colorless solid.

MS (ESI): m/z=522 (MH$^+$).

$^1$H-NMR (400 MHz, DMSO-d$_6$): 12.26 (br.s, 1H, —NH); 9.05 (s, 1H); 8.60 (d, J=7.7, 1H, —NH); 8.27 (s, 1H); 7.23 (d, J=7.7, 1H, —NH); 7.01 (d, J=8.6, 1H); 6.56 (d, J=8.6, 1H); 6.01 (s, 2H); 3.99 (m, 1H & qu, J=7.1, 2H); 3.50 (m, 1H); 1.80 (m, 3H); 1.78 (m, 2H); 1.67 (m, 6H); 1.17 (t, J=7.1, 3H); 0.88 (m, 1H); 0.30 (m, 2H); 0.11 (m, 2H).

Example 11

4-(5-Cyclopropylmethoxy-benzo[1,3]dioxol-4-yl)-5H-pyrrolo[3,2-d]pyrimidine-7-carboxylic acid (1-acetyl-piperidin-4-yl)-amide Starting from 4-(5-cyclopropylmethoxy-1,3-benzodioxol-4-yl)-5H-pyrrolo[3,2-d]pyrimidine-7-carboxylic acid piperidin-4-ylamide hydrochloride (example A138) and acetyl chloride the title compound is obtained as colorless solid.

MS (ESI): m/z=478 (MH$^+$).

$^1$H-NMR (400 MHz, DMSO-d$_6$): 11.91 (br.s, 1H, —NH); 9.03 (s, 1H); 8.45 (d, J=7.8, 1H, —NH); 8.30 (s, 1H); 7.01 (d, J=8.6, 1H); 6.56 (d, J=8.6, 1H); 6.00 (s, 2H); 4.21 (m, 1H); 4.13 (m, 1H); 3.81 (m, 1H); 3.76 (d, J=6.8, 2H); 3.24 (m, 1H); 2.91 (m, 1H); 2.04 (s, 3H); 1.97 (m, 2H); 1.56 (m, 1H); 1.40 (m, 1H); 0.87 (m, 1H); 0.29 (m, 2H); 0.10 (m, 2H).

Example 12

4-(5-Cyclopropylmethoxy-benzo[1,3]dioxol-4-yl)-5H-pyrrolo[3,2-d]pyrimidine-7-carboxylic acid [1-(1-cyclopropyl-methanoyl)-piperidin-4-yl]amide Starting from 4-(5-cyclopropylmethoxy-1,3-benzodioxol-4-yl)-5H-pyrrolo[3,2-d]pyrimidine-7-carboxylic acid piperidin-4-ylamide hydrochloride (example A138) and cyclopropanecarbonyl chloride the title compound is obtained as colorless solid.

MS (ESI): m/z=504 (MH$^+$).

$^1$H-NMR (400 MHz, DMSO-d$_6$): 12.16 (br.s, 1H, —NH); 9.03 (s, 1H); 8.46 (d, J=7.8, 1H, —NH); 8.30 (s, 1H); 7.01 (d, J=8.6, 1H); 6.56 (d, J=8.6, 1H); 6.00 (s, 2H); 4.18 (m, 3H); 3.76 (d, J=6.8, 2H); 3.31 (m, 1H); 2.96 (m, 1H); 2.01 (m, 3H); 1.54 (m, 1H); 1.42 (m, 1H); 0.87 (m, 1H); 0.72 (m, 4H); 0.29 (m, 2H); 0.13 (m, 2H).

Example 13

4-(5-Cyclopropylmethoxy-benzo[1,3]dioxol-4-yl)-5H-pyrrolo[3,2-d]pyrimidine-7-carboxylic acid [(R)-1-(2-methoxy-acetyl)pyrrolidin-3-yl]-amide Starting from 4-(5-Cyclopropylmethoxy-benzo[1,3]dioxol-4-yl)-5H-pyrrolo[3,2-d]pyrimidine-7-carboxylic acid (R)-pyrrolidin-3-ylamide hydrochloride (example A142) and methoxy-acetyl chloride the title compound is obtained as colorless solid.

MS (ESI): m/z=494 (MH$^+$).

$^1$H-NMR (300 MHz, DMSO-d$_6$): 12.31 (br.s, 1H, —NH); 9.02 (s, 0.5H); 9.01 (s, 0.5H); 8.57 (d, J=6.7, 0.5H, —NH); 8.55 (d, J=6.0, 0.5H, —NH); 8.31 (s, 1H); 7.00 (d, J=8.6, 1H); 6.56 (d, J=8.6, 1H); 6.00 (s, 2H); 4.61 (m, 0.5H); 4.51 (m, 0.5H); 4.06 (d, J=4.0, 1H); 4.01 (d, J=1.5, 1H); 3.82-3.67 (m, 1H); 3.76 (d, J=6.7, 2H); 3.61-3.45 (m, 2H); 3.38 (m, 1H); 3.32 (s, 1.5H); 3.30 (s, 1.5H); 2.31-2.17 (m, 1H); 2.06 (m, 0.5H); 1.93 (m, 0.5H); 0.87 (m, 1H); 0.29 (m, 2H); 0.10 (m, 2H).

Example 14

4-(5-Cyclopropylmethoxy-benzo[1,3]dioxol-4-yl)-5H-pyrrolo[3,2-d]pyrimidine-7-carboxylic acid ((R)-1-formyl-pyrrolidin-3-yl)-amide Starting from 4-(5-Cyclopropylmethoxy-benzo[1,3]dioxol-4-yl)-5H-pyrrolo[3,2-d]pyrimidine-7-carboxylic acid (R)-pyrrolidin-3-ylamide hydrochloride (example A142) and acetic formic anhydride the title compound is obtained as colorless solid.

MS (ESI): m/z=450 (MH$^+$).

$^1$H-NMR (300 MHz, DMSO-d$_6$): 12.31 (br.s, 1H, —NH); 9.03 (s, 0.5H); 9.02 (s, 0.5H); 8.57 (d, J=6.9, 0.5H, —NH); 8.53 (d, J=6.9, 0.5H, —NH); 8.32 (s, 1H); 8.22 (s, 1H); 7.01 (d, J=8.6, 1H); 6.56 (d, J=8.6, 1H); 6.00 (s, 2H); 4.56 (m, 1H); 3.85 (m, 0.5H); 3.76 (d, J=6.8, 2H); 3.66 (m, 1H & 0.5H); 3.47 (m, 1H & 0.5H); 3.27 (m, 0.5H); 2.26 (m, 1H); 2.01 (m, 1H); 0.87 (m, 1H); 0.29 (m, 2H); 0.10 (m, 2H).

Example 15

4-(5-Cyclopropylmethoxy-benzo[1,3]dioxol-4-yl)-5H-pyrrolo[3,2-d]pyrimidine-7-carboxylic acid ((R)-1-acetyl-pyrrolidin-3-yl)-amide Starting from 4-(5-Cyclopropylmethoxy-benzo[1,3]dioxol-4-yl)-5H-pyrrolo[3,2-d]pyrimidine-7-carboxylic acid (R)-pyrrolidin-3-ylamide hydrochloride (example A142) and acetyl chloride the title compound is obtained as colorless solid.

MS (ESI): m/z=464 (MH$^+$).

$^1$H-NMR (300 MHz, DMSO-d$_6$): 12.31 (br.s, 1H, —NH); 9.03 (s, 1H); 8.58 (d, J=6.9, 0.5H, —NH); 8.55 (d, J=6.9, 0.5H, —NH); 8.31 (d, J=1.6, 1H); 7.01 (d, J=8.6, 1H); 6.56 (d, J=8.6, 1H); 6.00 (s, 2H); 4.61 (m, 0.5H); 4.51 (m, 0.5H); 3.84 (m, 0.5H); 3.76 (d, J=6.7, 2H); 3.64 (m, 1H & 0.5H); 3.46 (m, 1H & 0.5H); 3.31 (m, 0.5H); 2.25 (m, 1H); 2.06 (m, 0.5H); 1.98 (s, 1.5H); 1.96 (s, 1.5H); 1.95 (m, 0.5H); 0.87 (m, 1H); 0.29 (m, 2H); 0.10 (m, 2H).

Example 16

4-(5-Cyclopropylmethoxy-benzo[1,3]dioxol-4-yl)-5H-pyrrolo[3,2-d]pyrimidine-7-carboxylic acid [(R)-1-(1-cyclopropyl-methanoyl)-pyrrolidin-3-yl]amide Starting from 4-(5-Cyclopropylmethoxy-benzo[1,3]dioxol-4-yl)-5H-pyrrolo[3,2-d]pyrimidine-7-carboxylic acid (R)-pyrrolidin-3-ylamide hydrochloride (example A142) and cyclopropanecarbonyl chloride the title compound is obtained as colorless solid.

MS (ESI): m/z=490 (MH$^+$).
$^1$H-NMR (300 MHz, DMSO-d$_6$): 12.31 (br.s, 1H, —NH); 9.03 (s, 1H); 8.61 (d, J=6.9, 0.5H, —NH); 8.55 (d, J=6.9, 0.5H, —NH); 8.32 (d, J=2.6, 1H); 7.01 (d, J=8.6, 1H); 6.56 (d, J=8.6, 1H); 6.00 (s, 2H); 4.65 (m, 0.5H); 4.54 (m, 0.5H); 4.02 (m, 0.5H); 3.82 (m, 1H); 3.76 (d, J=6.7, 2H); 3.65 (m, 1H); 3.51 (m, 1H); 3.35 (m, 0.5H); 2.33 (m, 0.5H); 2.21 (m, 0.5H); 2.10 (m, 0.5H); 1.98 (m, 0.5H); 1.79 (m, 1H); 0.87 (m, 1H); 0.73 (m, 4H); 0.29 (m, 2H); 0.11 (m, 2H).

Example 17

(R)-3-({1-[4-(5-Cyclopropylmethoxy-benzo[1,3]dioxol-4-yl)-5H-pyrrolo[3,2-d]pyrimidin-7-yl]-methanoyl}-amino)-pyrrolidine-1-carboxylic acid ethyl ester Starting from 4-(5-Cyclopropylmethoxy-benzo[1,3]dioxol-4-yl)-5H-pyrrolo[3,2-d]pyrimidine-7-carboxylic acid (R)-pyrrolidin-3-ylamide hydrochloride (example A142) and ethyl chloroformate the title compound is obtained as colorless solid.

MS (ESI): m/z=494.1 (MH$^+$).
$^1$H-NMR (300 MHz, DMSO-d$_6$): 12.31 (br.s, 1H, —NH); 9.02 (s, 1H); 8.56 (d, J=6.8, 1H, —NH); 8.31 (s, 1H); 7.01 (d, J=8.6, 1H); 6.56 (d, J=8.6, 1H); 6.00 (s, 2H); 4.52 (m, 1H); 4.05 (qu, J=7.0, 2H); 3.76 (d, J=6.7, 2H); 3.65 (m, 1H); 3.48 (m, 2H); 3.29 (m, 1H); 2.22 (m, 1H); 1.99 (m, 1H); 1.79 (m, 1H); 1.19 (t, J=7.0, 3H); 0.87 (m, 1H); 0.29 (m, 2H); 0.10 (m, 2H).

Example 18

4-(5-Cyclopropylmethoxy-benzo[1,3]dioxol-4-yl)-5H-pyrrolo[3,2-d]pyrimidine-7-carboxylic acid ((S)-1-formyl-pyrrolidin-3-yl)-amide Starting from 4-(5-Cyclopropylmethoxy-benzo[1,3]dioxol-4-yl)-5H-pyrrolo[3,2-d]pyrimidine-7-carboxylic acid (S)-pyrrolidin-3-ylamide hydrochloride (example A143) and acetic formic anhydride the title compound is obtained as colorless solid.

MS (ESI): m/z=450 (MH$^+$).
$^1$H-NMR (300 MHz, DMSO-d$_6$): 12.31 (br.s, 1H, —NH); 9.03 (s, 0.5H); 9.02 (s, 0.5H); 8.57 (d, J=6.9, 0.5H, —NH); 8.53 (d, J=6.9, 0.5H, —NH); 8.32 (s, 1H); 8.22 (s, 1H); 7.01 (d, J=8.6, 1H); 6.56 (d, J=8.6, 1H); 6.00 (s, 2H); 4.56 (m, 1H); 3.85 (m, 0.5H); 3.76 (d, J=6.8, 2H); 3.66 (m, 1H & 0.5H); 3.47 (m, 1H & 0.5H); 3.27 (m, 0.5H); 2.26 (m, 1H); 2.01 (m, 1H); 0.87 (m, 1H); 0.29 (m, 2H); 0.10 (m, 2H).

Example 19

4-(5-Cyclopropylmethoxy-benzo[1,3]dioxol-4-yl)-5H-pyrrolo[3,2-d]pyrimidine-7-carboxylic acid ((S)-1-acetyl-pyrrolidin-3-yl)-amide Starting from 4-(5-Cyclopropylmethoxy-benzo[1,3]dioxol-4-yl)-5H-pyrrolo[3,2-d]pyrimidine-7-carboxylic acid (S)-pyrrolidin-3-ylamide hydrochloride (example A143) and acetyl chloride the title compound is obtained as colorless solid.

MS (ESI): m/z=464 (MH$^+$).
$^1$H-NMR (300 MHz, DMSO-d$_6$): 12.31 (br.s, 1H, —NH); 9.03 (s, 1H); 8.58 (d, J=6.9, 0.5H, —NH); 8.55 (d, J=6.9, 0.5H, —NH); 8.31 (d, J=1.6, 1H); 7.01 (d, J=8.6, 1H); 6.56 (d, J=8.6, 1H); 6.00 (s, 2H); 4.61 (m, 0.5H); 4.51 (m, 0.5H); 3.84 (m, 0.5H); 3.76 (d, J=6.7, 2H); 3.64 (m, 1H & 0.5H); 3.46 (m, 1H & 0.5H); 3.31 (m, 0.5H); 2.25 (m, 1H); 2.06 (m, 0.5H); 1.98 (s, 1.5H); 1.96 (s, 1.5H); 1.95 (m, 0.5H); 0.87 (m, 1H); 0.29 (m, 2H); 0.10 (m, 2H).

Example 20

4-(5-Cyclopropylmethoxy-benzo[1,3]dioxol-4-yl)-5H-pyrrolo[3,2-d]pyrimidine-7-carboxylic acid [(S)-1-(1-cyclopropyl-methanoyl)-pyrrolidin-3-yl]amide Starting from 4-(5-Cyclopropylmethoxy-benzo[1,3]dioxol-4-yl)-5H-pyrrolo[3,2-d]pyrimidine-7-carboxylic acid (S)-pyrrolidin-3-ylamide hydrochloride (example A143) and cyclopropanecarbonyl chloride the title compound is obtained as colorless solid.

MS (ESI): m/z=490 (MH$^+$).
$^1$H-NMR (300 MHz, DMSO-d$_6$): 12.31 (br.s, 1H, —NH); 9.03 (s, 1H); 8.61 (d, J=6.9, 0.5H, —NH); 8.55 (d, J=6.9, 0.5H, —NH); 8.32 (d, J=2.6, 1H); 7.01 (d, J=8.6, 1H); 6.56 (d, J=8.6, 1H); 6.00 (s, 2H); 4.65 (m, 0.5H); 4.54 (m, 0.5H); 4.02 (m, 0.5H); 3.82 (m, 1H); 3.76 (d, J=6.7, 2H); 3.65 (m, 1H); 3.51 (m, 1H); 3.35 (m, 0.5H); 2.33 (m, 0.5H); 2.21 (m, 0.5H); 2.10 (m, 0.5H); 1.98 (m, 0.5H); 1.79 (m, 1H); 0.87 (m, 1H); 0.73 (m, 4H); 0.29 (m, 2H); 0.11 (m, 2H).

Example 21

4-(5-Cyclopropylmethoxy-benzo[1,3]dioxol-4-yl)-5H-pyrrolo[3,2-d]pyrimidine-7-carboxylic acid [(S)-1-(2-methoxy-ethanoyl)-pyrrolidin-3-yl]amide Starting from 4-(5-Cyclopropylmethoxy-benzo[1,3]dioxol-4-yl)-5H-pyrrolo[3,2-d]pyrimidine-7-carboxylic acid (S)-pyrrolidin-3-ylamide hydrochloride (example A143) and methoxy-acetyl chloride the title compound is obtained as colorless solid.

MS (ESI): m/z=494 (MH$^+$).
$^1$H-NMR (300 MHz, DMSO-d$_6$): 12.31 (br.s, 1H, —NH); 9.02 (s, 0.5H); 9.01 (s, 0.5H); 8.57 (d, J=6.7, 0.5H, —NH); 8.55 (d, J=6.0, 0.5H, —NH); 8.31 (s, 1H); 7.00 (d, J=8.6, 1H); 6.56 (d, J=8.6, 1H); 6.00 (s, 2H); 4.61 (m, 0.5H); 4.51 (m, 0.5H); 4.06 (d, J=4.0, 1H); 4.01 (d, J=1.5, 1H); 3.82-3.67 (m, 1H); 3.76 (d, J=6.7, 2H); 3.61-3.45 (m, 2H); 3.38 (m, 1H); 3.32 (s, 1.5H); 3.30 (s, 1.5H); 2.31-2.17 (m, 1H); 2.06 (m, 0.5H); 1.93 (m, 0.5H); 0.87 (m, 1H); 0.29 (m, 2H); 0.10 (m, 2H).

Example 22

(S)-3-({1-[4-(5-Cyclopropylmethoxy-benzo[1,3]dioxol-4-yl)-5H-pyrrolo[3,2-d]pyrimidin-7-yl]-methanoyl}-amino)-pyrrolidine-1-carboxylic acid ethyl ester Starting from 4-(5-Cyclopropylmethoxy-benzo[1,3]dioxol-4-yl)-5H-pyrrolo[3,2-d]pyrimidine-7-carboxylic acid (S)-pyrrolidin-3-ylamide hydrochloride (example A143) and ethyl chloroformate the title compound is obtained as colorless solid.

MS (ESI): m/z=494.1 (MH$^+$).

$^1$H-NMR (300 MHz, DMSO-d$_6$): 12.31 (br.s, 1H, —NH); 9.02 (s, 1H); 8.56 (d, J=6.8, 1H, —NH); 8.31 (s, 1H); 7.01 (d, J=8.6, 1H); 6.56 (d, J=8.6, 1H); 6.00 (s, 2H); 4.52 (m, 1H); 4.05 (qu, J=7.0, 2H); 3.76 (d, J=6.7, 2H); 3.65 (m, 1H); 3.48 (m, 2H); 3.29 (m, 1H); 2.22 (m, 1H); 1.99 (m, 1H); 1.79 (m, 1H); 1.19 (t, J=7.0, 3H); 0.87 (m, 1H); 0.29 (m, 2H); 0.10 (m, 2H).

Example 23

4-(5-Cyclopropylmethoxy-benzo[1,3]dioxol-4-yl)-5H-pyrrolo[3,2-d]pyrimidine-7-carboxylic acid (1-formyl-piperidin-4-ylmethyl)-amide Starting from 4-(5-Cyclopropylmethoxy-benzo[1,3]dioxol-4-yl)-5H-pyrrolo[3,2-d]pyrimidine-7-carboxylic acid (piperidin-4-ylmethyl)-amide (example A144) and acetic formic anhydride the title compound is obtained as colorless solid.

MS (ESI): m/z=478 (MH$^+$).

$^1$H-NMR (400 MHz, DMSO-d$_6$): 12.27 (br.s, 1H, —NH); 9.04 (s, 1H); 8.51 (t, J=5.9, 1H, —NH); 8.28 (s, 1H); 7.97 (s, 1H); 7.01 (d, J=8.5, 1H); 6.57 (d, J=8.5, 1H); 6.00 (s, 2H); 4.18 (m, 1H); 3.77 (d, J=6.7, 2H); 3.69 (m, 1H); 3.35 (dd, J$_1$=J$_2$=6.2, 2H); 3.02 (m, 1H); 2.60 (m, 1H); 1.87 (m, 1H); 1.77 (m, 2H); 1.15 (m, 1H); 1.06 (m, 1H); 0.88 (m, 1H); 0.30 (m, 2H); 0.11 (m, 2H).

Example 24

4-(5-Cyclopropylmethoxy-benzo[1,3]dioxol-4-yl)-5H-pyrrolo[3,2-d]pyrimidine-7-carboxylic acid (1-acetyl-piperidin-4-ylmethyl)-amide Starting from 4-(5-Cyclopropylmethoxy-benzo[1,3]dioxol-4-yl)-5H-pyrrolo[3,2-d]pyrimidine-7-carboxylic acid (piperidin-4-ylmethyl)-amide (example A144) and acetyl chloride the title compound is obtained as colorless solid.

MS (ESI): m/z=492 (MH$^+$).

$^1$H-NMR (400 MHz, DMSO-d$_6$): 12.27 (br.s, 1H, —NH); 9.03 (s, 1H); 8.50 (t, J=6.1, 1H, —NH); 8.27 (s, 1H); 7.01 (d, J=8.6, 1H); 6.57 (d, J=8.6, 1H); 6.00 (s, 2H); 4.38 (m, 1H); 3.82 (m, 1H); 3.77 (d, J=6.8, 2H); 3.35 (dd, J$_1$=J$_2$=6.0, 2H); 3.01 (m, 1H); 2.50 (m, 1H); 1.98 (s, 3H); 1.82 (m, 1H); 1.74 (m, 2H); 1.20 (m, 1H); 1.06 (m, 1H); 0.88 (m, 1H); 0.30 (m, 2H); 0.11 (m, 2H).

Example 25

4-(5-Cyclopropylmethoxy-benzo[1,3]dioxol-4-yl)-5H-pyrrolo[3,2-d]pyrimidine-7-carboxylic acid [1-(1-cyclopropyl-methanoyl)-piperidin-4-ylmethyl]-amide Starting from 4-(5-Cyclopropylmethoxy-benzo[1,3]dioxol-4-yl)-5H-pyrrolo[3,2-d]pyrimidine-7-carboxylic acid (piperidin-4-ylmethyl)-amide (example A144) and cyclopropanecarbonyl chloride the title compound is obtained as colorless solid.

MS (ESI): m/z=518 (MH$^+$).

$^1$H-NMR (400 MHz, DMSO-d$_6$): 12.27 (br.s, 1H, —NH); 9.03 (s, 1H); 8.51 (t, J=6.1, 1H, —NH); 8.27 (d, J=2.2, 1H); 7.01 (d, J=8.6, 1H); 6.57 (d, J=8.6, 1H); 6.00 (s, 2H); 4.36 (m, 1H); 4.28 (m, 1H); 3.77 (d, J=6.7, 2H); 3.35 (dd, J$_1$=J$_2$=6.2, 2H); 3.08 (m, 1H); 2.58 (m, 1H); 1.97 (m, 1H); 1.86 (m, 2H); 1.74 (m, 1H); 1.20 (m, 1H); 1.09 (m, 1H); 0.88 (m, 1H); 0.68 (m, 4H); 0.30 (m, 2H); 0.10 (m, 2H).

Example 26

4-(5-Cyclopropylmethoxy-benzo[1,3]dioxol-4-yl)-5H-pyrrolo[3,2-d]pyrimidine-7-carboxylic acid [1-(2-methoxy-ethanoyl)-piperidin-4-ylmethyl]-amide Starting from 4-(5-Cyclopropylmethoxy-benzo[1,3]dioxol-4-yl)-5H-pyrrolo[3,2-d]pyrimidine-7-carboxylic acid (piperidin-4-ylmethyl)-amide (example A144) and methoxyacetyl chloride the title compound is obtained as colorless solid.

MS (ESI): m/z=522 (MH$^+$).

$^1$H-NMR (400 MHz, DMSO-d$_6$): 12.26 (br.s, 1H, —NH); 9.03 (s, 1H); 8.50 (t, J=6.1, 1H, —NH); 8.27 (d, J=2.3, 1H); 7.01 (d, J=8.6, 1H); 6.57 (d, J=8.6, 1H); 6.00 (s, 2H); 4.35 (m, 1H); 4.09 (d, J=13.6, 1H); 4.02 (d, J=13.6, 1H); 3.80 (m, 1H); 3.77 (d, J=6.7, 2H); 3.34 (dd, J$_1$=J$_2$=6.2, 2H); 3.27 (s, 3H); 2.96 (m, 1H); 2.57 (m, 1H); 1.84 (m, 1H); 1.75 (m, 2H); 1.20 (m, 1H); 1.09 (m, 1H); 0.87 (m, 1H); 0.30 (m, 2H); 0.10 (m, 2H).

Example 27

4-[({1-[4-(5-Cyclopropylmethoxy-benzo[1,3]dioxol-4-yl)-5H-pyrrolo[3,2-d]pyrimidin-7-yl]-methanoyl}-amino)-methyl]-piperidine-1-carboxylic acid ethyl ester Starting from 4-(5-Cyclopropylmethoxy-benzo[1,3]dioxol-4-yl)-5H-pyrrolo[3,2-d]pyrimidine-7-carboxylic acid (piperidin-4-ylmethyl)-amide (example A144) and ethyl chloroformate the title compound is obtained as colorless solid.

MS (ESI): m/z=522 (MH$^+$).

$^1$H-NMR (400 MHz, DMSO-d$_6$): 12.27 (br.s, 1H, —NH); 9.03 (s, 1H); 8.50 (t, J=6.0, 1H, —NH); 8.27 (s, 1H); 7.01 (d, J=8.6, 1H); 6.56 (d, J=8.6, 1H); 6.00 (s, 2H); 4.03 (qu, J=7.1, 2H); 3.98 (m, 2H); 3.77 (d, J=6.7, 2H); 3.34 (dd, J$_1$=J$_2$=6.2, 2H); 2.77 (m, 2H); 1.77 (m, 1H); 1.73 (m, 2H); 1.17 (t, J=7.1, 3H); 1.10 (m, 2H); 0.88 (m, 1H); 0.30 (m, 2H); 0.10 (m, 2H).

Example 28

4-(5-Cyclopropylmethoxy-benzo[1,3]dioxol-4-yl)-5H-pyrrolo[3,2-d]pyrimidine-7-carboxylic acid (1-formyl-piperidin-3-ylmethyl)-amide Starting from 4-(5-cyclopropylmethoxy-benzo[1,3]dioxol-4-yl)-5H-pyrrolo[3,2-d]pyrimidine-7-carboxylic acid (piperidin-3-ylmethyl)-amide (example A145) and acetic formic anhydride the title compound is obtained as colorless solid.

MS (ESI): m/z=478 (MH$^+$).

$^1$H-NMR (400 MHz, DMSO-d$_6$): 12.28 (br.s, 1H, —NH); 9.05 (s, 0.5H); 9.04 (s, 0.5H); 8.52 (br.s, 1H, —NH); 8.29 (s, 0.5H); 8.28 (s, 0.5H); 7.98 (s, 0.5H); 7.97 (s, 0.5H); 7.00 (d, J=8.6, 1H); 6.57 (d, J=8.6, 1H); 6.00 (s, 2H); 4.13 (m, 0.5H); 3.90 (m, 0.5H); 3.77 (d, J=6.7, 2H); 3.64 (m, 0.5H); 3.56 (m, 0.5H); 3.36 (m, 2H); 3.02 (m, 0.5H); 2.92 (m, 0.5H); 2.78 (m, 0.5H); 2.54 (m, 0.5H); 1.87 (m, 1H); 1.71 (m, 2H); 1.33 (m, 2H); 0.89 (m, 1H); 0.30 (m, 2H); 0.11 (m, 2H).

Example 29

4-(5-Cyclopropylmethoxy-benzo[1,3]dioxol-4-yl)-5H-pyrrolo[3,2-d]pyrimidine-7-carboxylic acid (1-propionyl-piperidin-3-ylmethyl)-amide Starting from 4-(5-Cyclopropylmethoxy-benzo[1,3]dioxol-4-yl)-5H-pyrrolo[3,2-d]pyrimidine-7-carboxylic acid (piperidin-3-ylmethyl)-amide (example A145) and propionyl chloride the title compound is obtained as colorless solid.

MS (ESI): m/z=506 (MH$^+$).
$^1$H-NMR (400 MHz, DMSO-d$_6$): 12.28 (br.s, 1H, —NH); 9.03 (s, 1H); 8.51 (t, J=6.9, 1H, —NH); 8.29 (s, 0.5H); 8.28 (s, 0.5H); 7.00 (d, J=8.6, 1H); 6.57 (d, J=8.6, 1H); 6.00 (s, 2H); 4.34 (m, 0.5H); 4.13 (m, 0.5H); 3.84 (m, 0.5H); 3.77 (d, J=6.8, 2H); 3.74 (m, 0.5H); 3.34 (m, 2H); 2.99 (m, 0.5H); 2.92 (m, 0.5H); 2.71 (m, 0.5H); 2.47 (m, 0.5H); 2.30 (qu, J=7.3, 2H); 1.86 (m, 1H); 1.70 (m, 2H); 1.33 (m, 2H); 0.96 (t, J=7.3, 3H); 0.89 (m, 1H); 0.29 (m, 2H); 0.10 (m, 2H).

Example 30

4-(5-Cyclopropylmethoxy-benzo[1,3]dioxol-4-yl)-5H-pyrrolo[3,2-d]pyrimidine-7-carboxylic acid [1-(2-methoxy-acetyl)piperidin-3-ylmethyl]-amide Starting from 4-(5-Cyclopropylmethoxy-benzo[1,3]dioxol-4-yl)-5H-pyrrolo[3,2-d]pyrimidine-7-carboxylic acid (piperidin-3-ylmethyl)-amide (example A145) and methoxy-acetyl chloride the title compound is obtained as colorless solid.

MS (ESI): m/z=522 (MH$^+$).
$^1$H-NMR (400 MHz, DMSO-d$_6$): 12.28 (br.s, 1H, —NH); 9.04 (s, 1H); 8.51 (br.s, 1H, —NH); 8.28 (s, 1H); 7.00 (d, J=8.6, 1H); 6.56 (d, J=8.6, 1H); 6.00 (s, 2H); 4.28 (m, 0.5H); 4.02 (m, 2H); 3.77 (d, J=6.8, 2H); 3.65 (m, 0.5H); 3.34 (m, 3H); 3.27 (m, 1.5H); 3.17 (m, 1.5H); 2.97 (m, 0.5H); 2.87 (m, 0.5H); 2.74 (m, 0.5H); 2.50 (m, 0.5H); 1.83 (m, 1.5H); 1.68 (m, 1.5H); 1.33 (m, 2H); 0.89 (m, 1H); 0.29 (m, 2H); 0.10 (m, 2H).

Example 31

3-({[4-(5-Cyclopropylmethoxy-benzo[1,3]dioxol-4-yl)-5H-pyrrolo[3,2-d]pyrimidine-7-carbonyl]-amino}-methyl)-piperidine-1-carboxylic acid ethyl ester Starting from 4-(5-Cyclopropylmethoxy-benzo[1,3]dioxol-4-yl)-5H-pyrrolo[3,2-d]pyrimidine-7-carboxylic acid (piperidin-3-ylmethyl)-amide (example A145) and ethyl chloroformate the title compound is obtained as colorless solid.

MS (ESI): m/z=522 (MH$^+$).
$^1$H-NMR (400 MHz, DMSO-d$_6$): 12.28 (br.s, 1H, —NH); 9.03 (s, 1H); 8.50 (t, J=6.1, 1H, —NH); 8.28 (s, 1H); 7.00 (d, J=8.6, 1H); 6.57 (d, J=8.6, 1H); 6.00 (s, 2H); 4.00 (qu, J=7.1, 2H); 3.97 (m, 1H); 3.83 (m, 1H); 3.77 (d, J=6.9, 2H); 2.86 (m, 1H); 2.68 (m, 1H); 1.81 (m, 1H); 1.67 (m, 2H); 1.30 (m, 2H); 1.12 (br.s, 3H); 0.88 (m, 1H); 0.29 (m, 2H); 0.11 (m, 2H).

Example 32

4-(5-Cyclopropylmethoxy-benzo[1,3]dioxol-4-yl)-5H-pyrrolo[3,2-d]pyrimidine-7-carboxylic acid (1-formyl-pyrrolidin-3-ylmethyl)-amide Starting from 4-(5-Cyclopropylmethoxy-benzo[1,3]dioxol-4-yl)-5H-pyrrolo[3,2-d]pyrimidine-7-carboxylic acid (pyrrolidin-3-ylmethyl)-amide (example A146) and ethyl chloroformate the title compound is obtained as colorless solid.

MS (ESI): m/z=464 (MH$^+$).
$^1$H-NMR (400 MHz, DMSO-d$_6$): 12.28 (br.s, 1H, —NH); 9.04 (s, 1H); 8.55 (br.s, 1H, —NH); 8.29 (s, 1H); 8.16 (s, 0.5H); 8.15 (s, 0.5H); 7.01 (d, J=8.6, 1H); 6.57 (d, J=8.6, 1H); 6.00 (s, 2H); 3.77 (d, J=6.7, 2H); 3.65 (m, 1H); 3.46 (m, 3H); 3.39 (m, 0.5H); 3.26 (m, 1H); 3.07 (m, 0.5H); 2.51 (m, 1H); 2.00 (m, 1H); 1.70 (m, 1H); 0.88 (m, 1H); 0.30 (m, 2H); 0.10 (m, 2H).

Example 33

4-(5-Cyclopropylmethoxy-benzo[1,3]dioxol-4-yl)-5H-pyrrolo[3,2-d]pyrimidine-7-carboxylic acid [1-(2-methoxy-acetyl)-pyrrolidin-3-ylmethyl]-amide Starting from 4-(5-Cyclopropylmethoxy-benzo[1,3]dioxol-4-yl)-5H-pyrrolo[3,2-d]pyrimidine-7-carboxylic acid (pyrrolidin-3-ylmethyl)-amide (example A146) and methoxy-acetyl chloride the title compound is obtained as colorless solid.

MS (ESI): m/z=508 (MH$^+$).
$^1$H-NMR (400 MHz, DMSO-d$_6$): 12.28 (br.s, 1H, —NH); 9.04 (s, 1H); 8.55 (m, 1H, —NH); 8.29 (s, 1H); 7.00 (d, J=8.6, 1H); 6.57 (d, J=8.6, 1H); 6.00 (s, 2H); 3.99 (s, 1H); 3.98 (s, 1H); 3.77 (d, J=6.7, 2H); 3.50 (m, 4H); 3.37 (m, 0.5H); 3.29 (m, 0.5H); 3.28 (s, 1.5H); 3.27 (s, 1.5H); 3.21 (m, 0.5H); 3.13 (m, 0.5H); 2.56 (m, 0.5H); 2.44 (m, 0.5H); 2.05 (m, 0.5H); 1.95 (m, 0.5H); 1.75 (m, 0.5H); 1.65 (m, 0.5H); 0.88 (m, 1H); 0.30 (m, 2H); 0.10 (m, 2H).

Example 34

3-({[4-(5-Cyclopropylmethoxy-benzo[1,3]dioxol-4-yl)-5H-pyrrolo[3,2-d]pyrimidine-7-carbonyl]-amino}-methyl)-pyrrolidine-1-carboxylic acid ethyl ester Starting from 4-(5-Cyclopropylmethoxy-benzo[1,3]dioxol-4-yl)-5H-pyrrolo[3,2-d]pyrimidine-7-carboxylic acid (pyrrolidin-3-ylmethyl)-amide (example A146) and ethyl chloroformate the title compound is obtained as colorless solid.

MS (ESI): m/z=508 (MH$^+$).
$^1$H-NMR (400 MHz, DMSO-d$_6$): 12.28 (br.s, 1H, —NH); 9.04 (s, 1H); 8.54 (t, J=6.0, 1H, —NH); 8.29 (s, 1H); 7.00 (d, J=8.6, 1H); 6.57 (d, J=8.6, 1H); 6.00 (s, 2H); 4.01 (qu, J=7.1, 2H); 3.77 (d, J=6.7, 2H); 3.46 (m, 4H); 3.29 (m, 1H); 3.09 (s, 1H); 2.50 (m, 1H); 1.99 (m, 1H); 1.69 (m, 1H); 0.88 (m, 1H); 0.30 (m, 2H); 0.10 (m, 2H).

Example 35

4-(5-Cyclopropylmethoxy-benzo[1,3]dioxol-4-yl)-5H-pyrrolo[3,2-d]pyrimidine-7-carboxylic acid (4-formyl-morpholin-2-ylmethyl)-amide Starting from 4-(5-Cyclopropylmethoxy-benzo[1,3]dioxol-4-yl)-5H-pyrrolo[3,2-d]pyrimidine-7-carboxylic acid (morpholin-2-ylmethyl)-amide (example A147) and acetic formic anhydride the title compound is obtained as colorless solid.

MS (ESI): m/z=480 (MH$^+$).
$^1$H-NMR (400 MHz, DMSO-d$_6$): 12.30 (br.s, 1H, —NH); 9.04 (s, 0.5H); 9.03 (s, 0.5H); 8.59 (br.s, 1H, —NH); 8.30 (s,

1H); 8.05 (s, 0.5H); 8.04 (s, 0.5H); 7.01 (d, J=8.6, 1H); 6.56 (d, J=8.6, 1H); 6.00 (s, 2H); 4.13 (m, 0.5H); 3.98 (m, 0.5H); 3.94 (m, 1H); 3.77 (d, J=6.7, 2H); 3.72 (m, 0.5H); 3.61 (m, 1.5H); 3.50 (m, 2H); 3.39 (m, 0.5H); 3.18 (m, 0.5H); 3.00 (m, 0.5H); 2.80 (m, 0.5H); 2.62 (m, 0.5H); 0.88 (m, 1H); 0.30 (m, 2H); 0.10 (m, 2H).

Example 36

4-(5-Cyclopropylmethoxy-benzo[1,3]dioxol-4-yl)-5H-pyrrolo[3,2-d]pyrimidine-7-carboxylic acid (4-propionyl-morpholin-2-ylmethyl)-amide Starting from 4-(5-Cyclopropylmethoxy-benzo[1,3]dioxol-4-yl)-5H-pyrrolo[3,2-d]pyrimidine-7-carboxylic acid (morpholin-2-ylmethyl)-amide (example A147) and propionyl chloride the title compound is obtained as colorless solid.

MS (ESI): m/z=508 (MH$^+$).

$^1$H-NMR (400 MHz, DMSO-d$_6$): 12.29 (br.s, 1H, —NH); 9.04 (s, 1H); 8.58 (br.s, 1H, —NH); 8.30 (s, 1H); 7.01 (d, J=8.6, 1H); 6.56 (d, J=8.6, 1H); 6.00 (s, 2H); 4.32 (m, 0.5H); 4.16 (m, 0.5H); 3.89 (m, 1.5H); 3.76 (d, J=6.7, 2H); 3.70 (m, 0.5H); 3.63 (m, 0.5H); 3.57 (m, 1H); 3.49 (m, 2H); 3.40 (m, 0.5H); 3.13 (m, 0.5H); 2.97 (m, 0.5H); 2.66 (m, 0.5H); 2.50 (m, 0.5H); 2.35 (m, 1H); 2.28 (m, 1H); 0.98 (t, J=7.4, 3H); 0.88 (m, 1H); 0.29 (m, 2H); 0.10 (m, 2H).

Example 37

4-(5-Cyclopropylmethoxy-benzo[1,3]dioxol-4-yl)-5H-pyrrolo[3,2-d]pyrimidine-7-carboxylic acid [4-(2-methoxy-acetyl)morpholin-2-ylmethyl]-amide Starting from 4-(5-Cyclopropylmethoxy-benzo[1,3]dioxol-4-yl)-5H-pyrrolo[3,2-d]pyrimidine-7-carboxylic acid (morpholin-2-ylmethyl)-amide (example A147) and methoxy-acetyl chloride the title compound is obtained as colorless solid.

MS (ESI): m/z=524 (MH$^+$).

$^1$H-NMR (400 MHz, DMSO-d$_6$): 12.29 (br.s, 1H, —NH); 9.04 (s, 1H); 8.58 (t, J=5.6, 1H, —NH); 8.30 (s, 1H); 7.01 (d, J=8.6, 1H); 6.56 (d, J=8.6, 1H); 6.00 (s, 2H); 4.27 (m, 0.5H); 4.11 (m, 1.5H); 4.05 (m, 1H), 3.91 (m, 1H); 3.76 (d, J=6.7, 2H & m, 1H); 3.61 (m, 2H); 3.48 (m, 2H); 3.27 (s, 1.5H); 3.25 (s, 1.5H); 3.12 (m, 0.5H); 2.97 (m, 0.5H); 2.76 (m, 0.5H); 2.56 (m, 0.5H); 0.88 (m, 1H); 0.29 (m, 2H); 0.10 (m, 2H).

Example 38

2-({[4-(5-Cyclopropylmethoxy-benzo[1,3]dioxol-4-yl)-5H-pyrrolo[3,2-d]pyrimidine-7-carbonyl]-amino}-methyl)-morpholine-4-carboxylic acid ethyl ester Starting from 4-(5-Cyclopropylmethoxy-benzo[1,3]dioxol-4-yl)-5H-pyrrolo[3,2-d]pyrimidine-7-carboxylic acid (morpholin-2-ylmethyl)-amide (example A147) and ethyl chloroformate the title compound is obtained as colorless solid.

MS (ESI): m/z=524 (MH$^+$).

$^1$H-NMR (400 MHz, DMSO-d$_6$): 12.30 (br.s, 1H, —NH); 9.04 (s, 1H); 8.57 (t, J=6.1, 1H, —NH); 8.30 (s, 1H); 7.01 (d, J=8.6, 1H); 6.56 (d, J=8.6, 1H); 6.00 (s, 2H); 4.05 (qu, J=7.1, 2H); 3.90 (m, 2H); 3.76 (d, J=6.7, 2H &m, 1H); 3.58 (m, 2H); 3.46 (m, 2H); 2.93 (m, 1H); 2.75 (m, 1H); 1.17 (t, J=7.1, 3H); 0.88 (m, 1H); 0.29 (m, 2H); 0.10 (m, 2H).

Example 39

4-(5-Cyclopropylmethoxy-benzo[1,3]dioxol-4-yl)-5H-pyrrolo[3,2-d]pyrimidine-7-carboxylic acid (1-acetyl-azetidin-3-yl)-amide Starting from 4-(5-Cyclopropylmethoxy-benzo[1,3]dioxol-4-yl)-5H-pyrrolo[3,2-d]pyrimidine-7-carboxylic acid azetidin-3-ylamide (example A172) and acetyl chloride the title compound is obtained as colorless solid.

MS (ESI): m/z=450 (MH$^+$).

$^1$H-NMR (400 MHz, DMSO-d$_6$): 12.33 (br.s, 1H, —NH); 9.06 (s, 1H); 8.84 (d, J=7.2, 1H, —NH); 8.32 (s, 1H); 7.01 (d, J=8.6, 1H); 6.57 (d, J=8.6, 1H); 6.01 (s, 2H); 4.78 (m, 1H); 4.47 (m, 1H); 4.20 (m, 1H); 4.16 (m, 1H); 3.85 (m, 1H); 3.76 (d, J=6.7, 2H); 1.80 (s, 3H); 0.86 (m, 1H); 0.29 (m, 2H); 0.09 (m, 2H).

Example 40

4-(5-Cyclopropylmethoxy-benzo[1,3]dioxol-4-yl)-5H-pyrrolo[3,2-d]pyrimidine-7-carboxylic acid (1-propionyl-azetidin-3-yl)-amide Starting from 4-(5-Cyclopropylmethoxy-benzo[1,3]dioxol-4-yl)-5H-pyrrolo[3,2-d]pyrimidine-7-carboxylic acid azetidin-3-ylamide (example A172) and propionyl chloride the title compound is obtained as colorless solid.

MS (ESI): m/z=463 (MH$^+$).

$^1$H-NMR (400 MHz, DMSO-d$_6$): 12.32 (br.s, 1H, —NH); 9.06 (s, 1H); 8.84 (d, J=7.2, 1H, —NH); 8.32 (s, 1H); 7.01 (d, J=8.6, 1H); 6.57 (d, J=8.6, 1H); 6.01 (s, 2H); 4.79 (m, 1H); 4.46 (m, 1H); 4.21 (m, 1H); 4.14 (m, 1H); 3.86 (m, 1H); 3.76 (d, J=6.8, 2H); 2.10 (qu, J=7.5, 2H); 0.98 (t, J=7.5, 3H); 0.86 (m, 1H); 0.29 (m, 2H); 0.09 (m, 2H).

Example 41

4-(5-Cyclopropylmethoxy-benzo[1,3]dioxol-4-yl)-5H-pyrrolo[3,2-d]pyrimidine-7-carboxylic acid [1-(2-methoxy-ethanoyl)-azetidin-3-yl]amide Starting from 4-(5-Cyclopropylmethoxy-benzo[1,3]dioxol-4-yl)-5H-pyrrolo[3,2-d]pyrimidine-7-carboxylic acid azetidin-3-ylamide (example A172) and methoxy-acetyl chloride the title compound is obtained as colorless solid.

MS (ESI): m/z=479 (MH$^+$).

$^1$H-NMR (400 MHz, DMSO-d$_6$): 12.33 (br.s, 1H, —NH); 9.06 (s, 1H); 8.85 (d, J=7.1, 1H, —NH); 8.32 (s, 1H); 7.01 (d, J=8.6, 1H); 6.57 (d, J=8.6, 1H); 6.01 (s, 2H); 4.82 (m, 1H); 4.52 (m, 1H); 4.27 (m, 1H); 4.20 (m, 1H); 3.94 (s, 2H); 3.92 (m, 1H); 3.76 (d, J=6.8, 2H); 3.30 (s, 3H); 0.87 (m, 1H); 0.28 (m, 2H); 0.09 (m, 2H).

Example 42

3-({1-[4-(5-Cyclopropylmethoxy-benzo[1,3]dioxol-4-yl)-5H-pyrrolo[3,2-d]pyrimidin-7-yl]-methanoyl}-amino)-azetidine-1-carboxylic acid ethyl ester Starting from 4-(5-Cyclopropylmethoxy-benzo[1,3]dioxol-4-yl)-5H-pyrrolo[3,2-d]pyrimidine-7-carboxylic acid azetidin-3-ylamide (example A172) and ethyl chloroformate the title compound is obtained as colorless solid.

MS (ESI): m/z=479 (MH$^+$).

$^1$H-NMR (400 MHz, DMSO-d$_6$): 12.32 (br.s, 1H, —NH); 9.06 (s, 1H); 8.84 (d, J=7.1, 1H, —NH); 8.31 (s, 1H); 7.01 (d,

J=8.6, 1H); 6.57 (d, J=8.6, 1H); 6.01 (s, 2H); 4.79 (m, 1H); 4.26 (m, 2H); 4.04 (qu, J=7.1, 2H), 3.96 (m, 2H); 3.76 (d, J=6.8, 2H); 1.19 (t, J=7.1, 3H); 0.87 (m, 1H); 0.28 (m, 2H); 0.09 (m, 2H).

Example 43

4-(5-Cyclopropylmethoxy-benzo[1,3]dioxol-4-yl)-5H-pyrrolo[3,2-d]pyrimidine-7-carboxylic acid (1-formyl-piperidin-4-yl)-amide Starting from 4-(5-cyclopropylmethoxy-1,3-benzodioxol-4-yl)-5H-pyrrolo[3,2-d]pyrimidine-7-carboxylic acid piperidin-4-ylamide hydrochloride (example A138) and acetic formic anhydride the title compound is obtained as colorless solid.

MS (ESI): m/z=464 (MH$^+$).

$^1$H-NMR (400 MHz, DMSO-d$_6$): 12.29 (br.s, 1H, —NH); 9.03 (s, 1H); 8.46 (d, J=7.8, 1H, —NH); 8.30 (s, 1H); 8.03 (s, 1H); 7.00 (d, J=8.6, 1H); 6.56 (d, J=8.6, 1H); 6.00 (s, 2H); 4.17 (m, 1H); 4.06 (m, 1H); 3.76 (d, J=6.7, 2H); 3.70 (m, 1H); 3.24 (m, 1H); 2.95 (m, 1H); 2.01 (m, 2H); 1.52 (m, 1H); 1.41 (m, 1H); 0.86 (m, 1H); 0.30 (m, 2H); 0.10 (m, 2H).

Example 44

4-(5-Cyclopropylmethoxy-benzo[1,3]dioxol-4-yl)-5H-pyrrolo[3,2-d]pyrimidine-7-carboxylic acid ((S)-1-propionyl-piperidin-3-yl)-amide Starting from 4-(5-Cyclopropylmethoxy-benzo[1,3]dioxol-4-yl)-5H-pyrrolo[3,2-d]pyrimidine-7-carboxylic acid (S)-piperidin-3-ylamide (example A148) and propionyl chloride the title compound is obtained as colorless solid.

MS (ESI): m/z=492 (MH$^+$, 100%).

$^1$H-NMR (300 MHz, DMSO-d$_6$): 12.29 (br.s, 1H, —NH); 9.00 (s, 1H); 8.56 (d, J=7.8, 0.5H, —NH); 8.51 (d, J=7.8, 0.5H); 8.30 (s, 0.5H); 8.29 (s, 0.5H); 7.00 (d, J=8.6, 1H); 6.56 (d, J=8.6, 1H); 6.00 (s, 2H); 4.00 (m, 1H); 3.94 (m, 0.5H); 3.76 (d, J=6.8, 2H & m, 0.5H); 3.57 (m, 1H); 3.40 (m, 1.5H); 3.26 (m, 0.5H); 2.38 (m, 1H); 2.31 (m, 1H); 1.97 (m, 1H); 1.74 (m, 2H); 1.53 (m, 1H); 1.01 (t, J=7.3, 1.5H); 0.95 (t, J=7.3, 1.5H); 0.87 (m, 1H); 0.29 (m, 2H); 0.10 (m, 2H).

Example 45

4-(5-Cyclopropylmethoxy-benzo[1,3]dioxol-4-yl)-5H-pyrrolo[3,2-d]pyrimidine-7-carboxylic acid [(S)-1-(2-methoxy-ethanoyl)-piperidin-3-yl]amide Starting from 4-(5-Cyclopropylmethoxy-benzo[1,3]dioxol-4-yl)-5H-pyrrolo[3,2-d]pyrimidine-7-carboxylic acid (S)-piperidin-3-ylamide (example A148) and methoxyacetyl chloride the title compound is obtained as colorless solid.

MS (ESI): m/z=508.0 (MH$^+$).

$^1$H-NMR (300 MHz, DMSO-d$_6$): 12.30 (br.s, 1H, —NH); 9.00 (s, 1H); 8.55 (m, 1H, —NH); 8.31 (s, 0.5H); 8.29 (s, 0.5H); 7.00 (d, J=8.6, 1H); 6.56 (d, J=8.6, 1H); 6.00 (s, 2H); 4.13-4.00 (m, 3H); 3.91 (m, 0.5H); 3.76 (d, J=6.8, 2H); 3.68 (m, 0.5H); 3.50 (m, 1.5H); 3.35 (m, 1.5H); 3.29 (br.s, 0.5H); 3.17 (br.s, 1.5H); 1.98 (m, 1H); 1.75 (m, 2H); 1.58 (m, 1H); 0.87 (m, 1H); 0.29 (m, 2H); 0.10 (m, 2H).

Example 46

4-(5-Cyclopropylmethoxy-benzo[1,3]dioxol-4-yl)-5H-pyrrolo[3,2-d]pyrimidine-7-carboxylic acid ((S)-1-acetyl-piperidin-3-yl)-amide Starting from 4-(5-Cyclopropylmethoxy-benzo[1,3]dioxol-4-yl)-5H-pyrrolo[3,2-d]pyrimidine-7-carboxylic acid (S)-piperidin-3-ylamide (example A148) and acetyl chloride the title compound is obtained as colorless solid.

MS (ESI): m/z=478.1 (MH$^+$).

$^1$H-NMR (300 MHz, DMSO-d$_6$): 12.26 (br.s, 1H, —NH); 9.01 (s, 0.5H); 9.00 (s, 0.5H); 8.58 (d, J=7.8, 0.5H, —NH); 8.52 (d, J=7.8, 0.5H); 8.31 (s, 0.5H); 8.28 (s, 0.5H); 7.01 (d, J=8.6, 1H); 6.56 (d, J=8.6, 1H); 6.01 (s, 2H); 3.99 (m, 1H); 3.95 (m, 0.5H); 3.76 (d, J=6.8, 2H); 3.71 (m, 0.5H); 3.48 (m, 2H); 3.42 (m, 0.5H); 3.23 (m, 0.5H); 2.06 (s, 1.5H); 1.97 (s, 1.5H); 1.94 (m, 1H); 1.71 (m, 2H); 1.54 (m, 1H); 0.87 (m, 1H); 0.29 (m, 2H); 0.10 (m, 2H).

Example 47

4-(5-Cyclopropylmethoxy-benzo[1,3]dioxol-4-yl)-5H-pyrrolo[3,2-d]pyrimidine-7-carboxylic acid ((R)-1-propionyl-piperidin-3-yl)-amide Starting from 4-(5-Cyclopropylmethoxy-benzo[1,3]dioxol-4-yl)-5H-pyrrolo[3,2-d]pyrimidine-7-carboxylic acid (R)-piperidin-3-ylamide hydrochloride (example A149) and propionyl chloride the title compound is obtained as colorless solid.

MS (ESI): m/z=436 (MH$^+$, 100%).

$^1$H-NMR (300 MHz, DMSO-d$_6$): 12.85 (br.s, 1H, —NH); 9.38 (br.m, 2H, —NH$_2^+$); 9.13 (s, 1H); 8.60 (s, 1H); 8.51 (d, J=7.6, 1H, —NH); 7.06 (d, J=8.6, 1H); 6.58 (d, J=8.6, 1H); 6.05 (s, 2H); 4.31 (m, 1H); 3.79 (d, J=6.7, 2H); 3.38 (m, 1H); 3.18 (m, 1H); 2.97 (m, 1H); 2.91 (m, 1H); 2.04-11.71 (m, 4H); 0.90 (m, 1H); 0.31 (m, 2H); 0.14 (m, 2H).

Example 48

4-(5-Cyclopropylmethoxy-benzo[1,3]dioxol-4-yl)-5H-pyrrolo[3,2-d]pyrimidine-7-carboxylic acid [(R)-1-(2-methoxy-ethanoyl)-piperidin-3-yl]amide Starting from 4-(5-Cyclopropylmethoxy-benzo[1,3]dioxol-4-yl)-5H-pyrrolo[3,2-d]pyrimidine-7-carboxylic acid (R)-piperidin-3-ylamide hydrochloride (example A149) and methoxy-acetyl chloride the title compound is obtained as colorless solid.

MS (ESI): m/z=508.0 (MH$^+$).

$^1$H-NMR (300 MHz, DMSO-d$_6$): 12.30 (br.s, 1H, —NH); 9.00 (s, 1H); 8.55 (m, 1H, —NH); 8.31 (s, 0.5H); 8.29 (s, 0.5H); 7.00 (d, J=8.6, 1H); 6.56 (d, J=8.6, 1H); 6.00 (s, 2H); 4.13-4.00 (m, 3H); 3.91 (m, 0.5H); 3.76 (d, J=6.8, 2H); 3.68 (m, 0.5H); 3.50 (m, 1.5H); 3.35 (m, 1.5H); 3.29 (br.s, 0.5H); 3.17 (br.s, 1.5H); 1.98 (m, 1H); 1.75 (m, 2H); 1.58 (m, 1H); 0.87 (m, 1H); 0.29 (m, 2H); 0.10 (m, 2H).

Example 49

4-(5-Cyclopropylmethoxy-benzo[1,3]dioxol-4-yl)-5H-pyrrolo[3,2-d]pyrimidine-7-carboxylic acid ((R)-1-acetyl-piperidin-3-yl)-amide Starting from 4-(5-Cyclopropylmethoxy-benzo[1,3]dioxol-4-yl)-5H-pyrrolo[3,2-d]pyrimidine-7-carboxylic acid (R)-piperidin-3-ylamide hydrochloride (example A149) and acetyl chloride the title compound is obtained as colorless solid.

MS (ESI): m/z=478.1 (MH$^+$).

$^1$H-NMR (300 MHz, DMSO-d$_6$): 12.26 (br.s, 1H, —NH); 9.01 (s, 0.5H); 9.00 (s, 0.5H); 8.58 (d, J=7.8, 0.5H, —NH); 8.52 (d, J=7.8, 0.5H); 8.31 (s, 0.5H); 8.28 (s, 0.5H); 7.01 (d, J=8.6, 1H); 6.56 (d, J=8.6, 1H); 6.01 (s, 2H); 3.99 (m, 1H); 3.95 (m, 0.5H); 3.76 (d, J=6.8, 2H); 3.71 (m, 0.5H); 3.48 (m, 2H); 3.42 (m, 0.5H); 3.23 (m, 0.5H); 2.06 (s, 1.5H); 1.97 (s, 1.5H); 1.94 (m, 1H); 1.71 (m, 2H); 1.54 (m, 1H); 0.87 (m, 1H); 0.29 (m, 2H); 0.10 (m, 2H).

Example 50 trans-4-(5-Cyclopropylmethoxy-benzo[1,3]dioxol-4-yl)-5H-pyrrolo[3,2-d]pyrimidine-7-carboxylic acid [4-(2-methoxy-acetylamino)-cyclohexyl]-amide Starting from trans-4-(5-Cyclopropylmethoxy-benzo[1,3]dioxol-4-yl)-5H-pyrrolo[3,2-d]pyrimidine-7-carboxylic acid (4-amino-cyclohexyl)-amide (example A140) and methoxyacetyl chloride the title compound is obtained as colorless solid.

MS (ESI): m/z=522 (MH$^+$).

$^1$H-NMR (400 MHz, DMSO-d$_6$): 12.27 (br.s, 1H, —NH); 9.03 (s, 1H); 8.30 (d, J=7.9, 1H, —NH); 8.27 (s, 1H); 7.58 (d, J=8.2, 1H, —NH); 7.01 (d, J=8.6, 1H); 6.56 (d, J=8.6, 1H); 6.00 (s, 2H); 3.82 (m, 1H); 3.79 (s, 2H); 3.76 (d, J=6.7, 2H); 3.70 (m, 1H); 3.31 (s, 3H); 2.00 (m, 2H); 1.81 (m, 2H); 1.44 (m, 4H); 0.86 (m, 1H); 0.29 (m, 2H); 0.10 (m, 2H).

Example 51 trans-4-(2-Cyclopropylmethoxy-4-methoxy-phenyl)-5H-pyrrolo[3,2-d]pyrimidine-7-carboxylic acid (4-acetylamino-cyclohexyl)-amide Starting from trans-4-(2-cyclopropylmethoxy-4-methoxy-phenyl)-5H-pyrrolo[3,2-d]pyrimidine-7-carboxylic acid (4-amino-cyclohexyl)-amide (example A150) and acetyl chloride the title compound is obtained as colorless solid.

MS (ESI): m/z=478 (MH$^+$, 100%).

$^1$H-NMR (400 MHz, DMSO-d$_6$): 11.90 (br.s, 1H, —NH); 9.00 (s, 1H); 8.38 (d, J=7.8, 1H, —NH); 8.20 (s, 1H); 7.74 (d, J=7.7, 1H); 7.61 (d, J=8.5, 1H); 6.72 (dd, J$_1$=8.5, J$_2$=2.1, 1H); 6.69 (d, J=2.1, 1H); 3.92 (d, J=6.9, 2H); 3.86 (s, 3H); 3.80 (m, 1H); 3.59 (m, 1H); 2.01 (m, 2H); 1.87 (m, 2H); 1.80 (s, 3H); 1.42 (m, 2H); 1.31 (m, 2H); 0.97 (m, 1H); 0.36 (m, 2H); 0.23 (m, 2H).

Example 52 trans-4-(2-Cyclopropylmethoxy-4-methoxy-phenyl)-5H-pyrrolo[3,2-d]pyrimidine-7-carboxylic acid [4-(cyclopropanecarbonyl-amino)cyclohexyl]-amide Starting from trans-4-(2-cyclopropylmethoxy-4-methoxy-phenyl)-5H-pyrrolo[3,2-d]pyrimidine-7-carboxylic acid (4-amino-cyclohexyl)-amide (example A150) and cyclopropanecarbonyl chloride the title compound is obtained as colorless solid.

MS (ESI): m/z=504 (MH$^+$, 100%).

$^1$H-NMR 400 MHz, DMSO-d$_6$): 11.90 (br.s, 1H, —NH); 9.00 (s, 1H); 8.39 (d, J=7.8, 1H, —NH); 8.20 (s, 1H); 7.96 (d, J=7.8, 1H); 7.62 (d, J=8.5, 1H); 6.72 (dd, J$_1$=8.5, J$_2$=2.2, 1H); 6.69 (d, J=2.2, 1H); 3.92 (d, J=6.9, 2H); 3.86 (s, 3H); 3.81 (m, 1H); 3.61 (m, 1H); 2.01 (m, 2H); 1.88 (m, 2H); 1.53 (m, 1H); 1.38 (m, 4H); 0.97 (m, 1H); 0.62 (m, 4H); 0.36 (m, 2H); 0.23 (m, 2H).

Example 53 trans-4-(2-Cyclopropylmethoxy-4-methoxy-phenyl)-5H-pyrrolo[3,2-d]pyrimidine-7-carboxylic acid [4-(2-methoxy-acetylamino)-cyclohexyl]-amide Starting from trans-4-(2-cyclopropylmethoxy-4-methoxy-phenyl)-5H-pyrrolo[3,2-d]pyrimidine-7-carboxylic acid (4-amino-cyclohexyl)-amide (example A150) and methoxyacetyl chloride the title compound is obtained as colorless solid.

MS (ESI): m/z=508 (MH$^+$, 100%).

$^1$H-NMR 400 MHz, DMSO-d$_6$): 11.90 (br.s, 1H, —NH); 9.00 (s, 1H); 8.38 (d, J=7.8, 1H, —NH); 8.21 (s, 1H); 7.61 (d, J=8.5, 1H); 7.59 (d, J=8.3, 1H, —NH); 6.72 (dd, J$_1$=8.5, J$_2$=2.2, 1H); 6.69 (d, J=2.2, 1H); 3.91 (d, J=6.9, 2H); 3.85 (s, 3H & m, 1H); 3.78 (s, 2H); 3.68 (m, 1H); 3.31 (s, 3H); 2.01 (m, 2H); 1.81 (m, 2H); 1.44 (m, 4H); 0.97 (m, 1H); 0.36 (m, 2H); 0.23 (m, 2H).

Example 54 trans-(4-{[4-(2-Cyclopropylmethoxy-4-methoxy-phenyl)-5H-pyrrolo[3,2-d]pyrimidine-7-carbonyl]-amino}-cyclohexyl)-carbamic acid ethyl ester Starting from trans-4-(2-cyclopropylmethoxy-4-methoxy-phenyl)-5H-pyrrolo[3,2-d]pyrimidine-7-carboxylic acid (4-amino-cyclohexyl)-amide (example A150) and ethyl chloroformate the title compound is obtained as colorless solid.

MS (ESI): m/z=508 (MH$^+$, 100%).

$^1$H-NMR 400 MHz, DMSO-d$_6$): 11.90 (br.s, 1H, —NH); 9.00 (s, 1H); 8.38 (d, J=7.9, 1H, —NH); 8.21 (s, 1H); 7.62 (d, J=8.5, 1H); 7.03 (d, J=7.6, 1H, —NH); 6.73 (dd, J$_1$=8.5, J$_2$=2.1, 1H); 6.69 (d, J=2.1, 1H); 3.98 (qu, J=7.0, 2H); 3.92 (d, J=6.9, 2H); 3.86 (s, 3H); 3.79 (m, 1H); 3.69 (m, 1H); 2.01 (m, 2H, 1.82 (m, 2H); 1.46 (m, 4H); 0.97 (m, 1H); 0.37 (m, 2H); 0.23 (m, 2H).

Example 55 cis-4-(2-Cyclopropylmethoxy-4-methoxy-phenyl)-5H-pyrrolo[3,2-d]pyrimidine-7-carboxylic acid (4-acetylamino-cyclohexyl)-amide Starting from cis-4-(2-cyclopropylmethoxy-4-methoxy-phenyl)-5H-pyrrolo[3,2-d]pyrimidine-7-carboxylic acid (4-amino-cyclohexyl)-amide (example A151) and acetyl chloride the title compound is obtained as colorless solid.

MS (ESI): m/z=478 (MH$^+$, 100%).

$^1$H-NMR 400 MHz, DMSO-d$_6$): 11.91 (br.s, 1H, —NH); 9.03 (s, 1H); 8.63 (d, J=7.7, 1H, —NH); 8.21 (s, 1H); 7.87 (d, J=7.6, 1H, —NH); 7.61 (d, J=8.5, 1H); 6.72 (dd, J$_1$=8.5, J$_2$=2.1, 1H); 6.69 (d, J=2.1, 1H); 4.02 (m, 1H); 3.91 (d, J=6.9, 2H); 3.86 (s, 3H); 3.76 (m, 1H); 1.87-1.55 (m, 9H); 0.97 (m, 1H); 0.65 (m, 4H); 0.37 (m, 2H); 0.23 (m, 2H).

Example 56 cis-4-(2-Cyclopropylmethoxy-4-methoxy-phenyl)-5H-pyrrolo[3,2-d]pyrimidine-7-carboxylic acid [4-(cyclopropanecarbonyl-amino)cyclohexyl]-amide Starting from cis-4-(2-cyclopropylmethoxy-4-methoxy-phenyl)-5H-pyrrolo[3,2-d]pyrimidine-7-carboxylic acid (4-amino-cyclohexyl)-amide (example A151) and cyclopropanecarbonyl chloride the title compound is obtained as colorless solid.

MS (ESI): m/z=504 (MH⁺, 100%).

$^1$H-NMR 400 MHz, DMSO-$d_6$): 11.91 (br.s, 1H, —NH); 9.03 (s, 1H); 8.68 (d, J=7.6, 1H, —NH); 8.21 (s, 1H); 8.08 (d, J=7.6, 1H, —NH); 7.61 (d, J=8.5, 1H); 6.72 (dd, $J_1$=8.5, $J_2$=2.1, 1H); 6.69 (d, J=2.1, 1H); 4.03 (m, 1H); 3.91 (d, J=6.9, 2H); 3.86 (s, 3H); 3.79 (m, 1H); 1.83 (s, 1H); 1.82-1.55 (m, 8H); 0.97 (m, 1H); 0.37 (m, 2H); 0.23 (m, 2H).

Example 57 cis-4-(2-Cyclopropylmethoxy-4-methoxy-phenyl)-5H-pyrrolo[3,2-d]pyrimidine-7-carboxylic acid [4-(2-methoxy-acetylamino)-cyclohexyl]-amide Starting from cis-4-(2-cyclopropylmethoxy-4-methoxy-phenyl)-5H-pyrrolo[3,2-d]pyrimidine-7-carboxylic acid (4-amino-cyclohexyl)-amide (example A151) and methoxyacetyl chloride the title compound is obtained as colorless solid.

MS (ESI): m/z=508 (MH⁺, 100%).

$^1$H-NMR 400 MHz, DMSO-$d_6$): 11.90 (br.s, 1H, —NH); 9.03 (s, 1H); 8.68 (d, J=7.5, 1H, —NH); 8.20 (s, 1H); 7.70 (d, J=7.7, 1H, —NH); 7.61 (d, J=8.5, 1H); 6.72 (dd, $J_1$=8.5, $J_2$=2.1, 1H); 6.69 (d, J=2.1, 1H); 4.06 (m, 1H); 3.91 (d, J=7.0, 2H); 3.86 (s, 3H); 3.81 (s, 2H & m, 1H); 3.31 (s, 3H); 1.86-1.59 (m, 8H); 0.97 (m, 1H); 0.37 (m, 2H); 0.23 (m, 2H).

Example 58 cis-(4-{[4-(2-Cyclopropylmethoxy-4-methoxy-phenyl)-5H-pyrrolo[3,2-d]pyrimidine-7-carbonyl]-amino}-cyclohexyl)-carbamic acid ethyl ester Starting from cis-4-(2-cyclopropylmethoxy-4-methoxy-phenyl)-5H-pyrrolo[3,2-d]pyrimidine-7-carboxylic acid (4-amino-cyclohexyl)-amide (example A151) and ethyl chloroformate the title compound is obtained as colorless solid.

MS (ESI): m/z=508 (MH⁺, 100%).

$^1$H-NMR 400 MHz, DMSO-$d_6$): 11.90 (br.s, 1H, —NH); 9.03 (s, 1H); 8.67 (d, J=7.7, 1H, —NH); 8.20 (d, J=3.3, 1H); 7.61 (d, J=8.5, 1H); 7.22 (d, J=6.5, 1H, —NH); 6.72 (dd, $J_1$=8.5, $J_2$=2.1, 1H); 6.69 (d, J=2.1, 1H); 4.00 (qu, J=7.1, 2H & m, 1H); 3.91 (d, J=6.9, 2H); 3.86 (s, 3H); 3.50 (m, 1H); 1.87-1.56 (m, 8H); 1.18 (t, J=7.1, 3H); 0.97 (m, 1H); 0.37 (m, 2H); 0.23 (m, 2H).

Example 59

4-(2-Cyclopropylmethoxy-4-methoxy-phenyl)-5H-pyrrolo[3,2-d]pyrimidine-7-carboxylic acid (1-acetyl-piperidin-4-yl)-amide Starting from 4-(2-cyclopropylmethoxy-4-methoxy-phenyl)-5H-pyrrolo[3,2-d]pyrimidine-7-carboxylic acid piperidin-4-ylamide (example A152) and acetyl chloride the title compound is obtained as colorless solid.

MS (ESI): m/z=464 (MH⁺, 100%).

$^1$H-NMR 400 MHz, DMSO-$d_6$): 11.92 (br.s, 1H, —NH); 9.00 (s, 1H); 8.54 (d, J=7.7, 1H, —NH); 8.23 (d, J=3.2, 1H); 7.61 (d, J=8.5, 1H); 6.72 (dd, $J_1$=8.5, $J_2$=2.1, 1H); 6.69 (d, J=2.1, 1H); 4.20 (m, 1H); 4.12 (m, 1H); 3.91 (d, J=7.0, 2H); 3.86 (s, 3H); 3.79 (m, 1H); 3.27 (m, 1H); 2.92 (m, 1H); 1.96 (m, 2H); 1.55 (m, 1H); 1.39 (m 1H); 0.98 (m, 1H); 0.37 (m, 2H); 0.23 (m, 2H).

Example 60

4-(2-Cyclopropylmethoxy-4-methoxy-phenyl)-5H-pyrrolo[3,2-d]pyrimidine-7-carboxylic acid [1-(1-cyclopropyl-methanoyl)-piperidin-4-yl]-amide Starting from 4-(2-cyclopropylmethoxy-4-methoxy-phenyl)-5H-pyrrolo[3,2-d]pyrimidine-7-carboxylic acid piperidin-4-ylamide (example A152) and cyclopropanecarbonyl chloride the title compound is obtained as colorless solid.

MS (ESI): m/z=490 (MH⁺, 100%).

$^1$H-NMR 400 MHz, DMSO-$d_6$): 11.93 (br.s, 1H, —NH); 9.00 (s, 1H); 8.56 (d, J=7.8, 1H, —NH); 8.23 (d, J=2.2, 1H); 7.61 (d, J=8.5, 1H); 6.72 (dd, $J_1$=8.5, $J_2$=2.1, 1H); 6.69 (d, J=2.1, 1H); 4.15 (m, 2H); 4.12 (d, J=4.4, 2H); 3.92 (d, J=7.0, 2H); 3.86 (s, 3H); 3.75 (m, 1H); 3.31 (s, 3H); 3.21 (m, 1H); 2.96 (m, 1H); 1.97 (m, 2H); 1.54 (m, 1H); 1.41 (m 1H); 0.98 (m, 1H); 0.37 (m, 2H); 0.23 (m, 2H).

Example 61

4-(2-Cyclopropylmethoxy-4-methoxy-phenyl)-5H-pyrrolo[3,2-d]pyrimidine-7-carboxylic acid [1-(2-methoxy-ethanoyl)-piperidin-4-yl]amide Starting from 4-(2-cyclopropylmethoxy-4-methoxy-phenyl)-5H-pyrrolo[3,2-d]pyrimidine-7-carboxylic acid piperidin-4-ylamide (example A152) and methoxy-acetyl chloride the title compound is obtained as colorless solid.

MS (ESI): m/z=494 (MH⁺, 100%).

$^1$H-NMR 400 MHz, DMSO-$d_6$): 11.92 (br.s, 1H, —NH); 9.00 (s, 1H); 8.53 (d, J=7.8, 1H, —NH); 8.23 (d, J=3.0, 1H); 7.61 (d, J=8.5, 1H); 6.72 (dd, $J_1$=8.5, $J_2$=2.1, 1H); 6.69 (d, J=2.1, 1H); 4.30-4.10 (m, 3H); 3.92 (d, J=7.0, 2H); 3.86 (s, 3H); 3.39 (m, 1H); 2.97 (m, 1H); 2.10-1.89 (m, 2H); 1.53 (m, 1H); 1.41 (m, 1H); 0.98 (m, 1H); 0.74 (m, 4H); 0.38 (m, 2H); 0.23 (m, 2H).

Example 62

4-({1-[4-(2-Cyclopropylmethoxy-4-methoxy-phenyl)-5H-pyrrolo[3,2-d]pyrimidin-7-yl]-methanoyl}-amino)-piperidine-1-carboxylic acid ethyl ester Starting from 4-(2-cyclopropylmethoxy-4-methoxy-phenyl)-5H-pyrrolo[3,2-d]pyrimidine-7-carboxylic acid piperidin-4-ylamide (example A152) and ethyl chloroformate the title compound is obtained as colorless solid.

MS (ESI): m/z=494 (MH⁺, 100%).

$^1$H-NMR 400 MHz, DMSO-$d_6$): 11.91 (br.s, 1H, —NH); 9.00 (s, 1H); 8.57 (d, J=7.6, 1H, —NH); 8.21 (s, 1H); 7.62 (d, J=8.4, 1H); 6.73 (dd, $J_1$=8.4, $J_2$=2.1, 1H); 6.69 (d, J=2.1, 1H); 4.07 (qu, J=7.1, 2H & m, 1H); 3.92 (d, J=7.1, 2H & m, 2H); 3.86 (s, 3H); 3.10 (m, 2H); 1.96 (m, 2H); 1.49 (m, 2H); 1.20 (t, J=7.1, 1H); 0.98 (m, 1H); 0.37 (m, 2H); 0.24 (m, 2H).

Example 63 trans-4-(2-Cyclopropylmethoxy-5-methoxy-phenyl)-5H-pyrrolo[3,2-d]pyrimidine-7-carboxylic acid (4-acetylamino-cyclohexyl)-amide Starting from trans-4-(2-cyclopropylmethoxy-5-methoxy-phenyl)-5H-pyrrolo[3,2-d]pyrimidine-7-carboxylic acid (4-amino-cyclohexyl)-amide (example A153) and acetyl chloride the title compound is obtained as colorless solid.

MS (ESI): m/z=478 (MH+, 100%).

¹H-NMR 200 MHz, DMSO-d₆): 11.98 (br.s, 1H, —NH); 9.05 (s, 1H); 8.36 (d, J=7.8, 1H, —NH); 8.23 (s, 1H); 7.73 (d, J=7.7, 1H, —NH); 7.19 (t, J=1.7, 1H); 7.11 (d, J=1.7, 2H); 3.82 (d, J=6.9, 2H & m, 1H); 3.77 (s, 3H); 3.57 (m, 1H); 2.02 (m, 2H); 1.87 (m, 2H); 1.79 (s, 3H); 1.53-1.20 (m, 4H); 0.92 (m, 1H); 0.32 (m, 2H); 0.15 (m, 2H).

Example 64 trans-4-(2-Cyclopropylmethoxy-5-methoxy-phenyl)-5H-pyrrolo[3,2-d]pyrimidine-7-carboxylic acid [4-(cyclopropanecarbonyl-amino)cyclohexyl]-amide Starting from trans-4-(2-cyclopropylmethoxy-5-methoxy-phenyl)-5H-pyrrolo[3,2-d]pyrimidine-7-carboxylic acid (4-amino-cyclohexyl)-amide (example A153) and cyclopropanecarbonyl chloride the title compound is obtained as colorless solid.

MS (ESI): m/z=504 (MH+, 100%).

¹H-NMR 200 MHz, DMSO-d₆): 11.98 (br.s, 1H, —NH); 9.05 (s, 1H); 8.36 (d, J=7.8, 1H, —NH); 8.23 (s, 1H); 7.94 (d, J=7.7, 1H, —NH); 7.18 (t, J=1.7, 1H); 7.11 (d, J=1.7, 2H); 3.82 (d, J=6.9, 2H & m, 1H); 3.77 (s, 3H); 3.60 (m, 1H); 2.02 (m, 2H); 1.87 (m, 2H); 1.53 (m, 1H); 1.52-1.20 (m, 4H); 0.92 (m, 1H); 0.63 (m, 4H); 0.32 (m, 2H); 0.15 (m, 2H).

Example 65 trans-4-(2-Cyclopropylmethoxy-5-methoxy-phenyl)-5H-pyrrolo[3,2-d]pyrimidine-7-carboxylic acid [4-(2-methoxy-acetylamino)-cyclohexyl]-amide Starting from trans-4-(2-cyclopropylmethoxy-5-methoxy-phenyl)-5H-pyrrolo[3,2-d]pyrimidine-7-carboxylic acid (4-amino-cyclohexyl)-amide (example A153) and methoxyacetyl chloride the title compound is obtained as colorless solid.

MS (ESI): m/z=508 (MH+, 100%).

¹H-NMR 200 MHz, DMSO-d₆): 11.98 (br.s, 1H, —NH); 9.05 (s, 1H); 8.35 (d, J=7.8, 1H, —NH); 8.23 (s, 1H); 7.57 (d, J=8.2, 1H, —NH); 7.19 (t, J=1.7, 1H); 7.11 (d, J=1.7, 2H); 3.82 (d, J=6.9, 2H & m, 1H & s, 2H); 3.77 (s, 3H); 3.66 (m, 1H); 3.31 (s, 3H); 2.04 (m, 2H); 1.81 (m, 2H); 1.58-1.32 (m, 4H); 0.92 (m, 1H); 0.32 (m, 2H); 0.15 (m, 2H).

Example 66 trans-(4-{[4-(2-Cyclopropylmethoxy-5-methoxy-phenyl)-5H-pyrrolo[3,2-d]pyrimidine-7-carbonyl]-amino}-cyclohexyl)-carbamic acid ethyl ester Starting from trans-4-(2-cyclopropylmethoxy-5-methoxy-phenyl)-5H-pyrrolo[3,2-d]pyrimidine-7-carboxylic acid (4-amino-cyclohexyl)-amide (example A153) and ethyl chloroformate the title compound is obtained as colorless solid.

MS (ESI): m/z=508 (MH+, 100%).

¹H-NMR 200 MHz, DMSO-d₆): 11.97 (br.s, 1H, —NH); 9.05 (s, 1H); 8.35 (d, J=7.9, 1H, —NH); 8.23 (s, 1H); 7.18 (t, J=1.7, 1H); 7.11 (d, J=1.7, 2H); 7.01 (d, J=7.8, 1H, —NH); 3.98 (qu, J=7.1, 2H); 3.82 (d, J=6.8, 2H & m, 1H); 3.77 (s, 3H); 3.38 (m, 1H); 2.02 (m, 2H); 1.89 (m, 2H); 1.52-1.23 (m, 4H); 1.16 (t, J=7.1, 3H); 0.92 (m, 1H); 0.32 (m, 2H); 0.16 (m, 2H).

Example 67 cis-4-(2-Cyclopropylmethoxy-5-methoxy-phenyl)-5H-pyrrolo[3,2-d]pyrimidine-7-carboxylic acid (4-acetylamino-cyclohexyl)-amide Starting from cis-4-(2-cyclopropylmethoxy-5-methoxy-phenyl)-5H-pyrrolo[3,2-d]pyrimidine-7-carboxylic acid (4-amino-cyclohexyl)-amide (example A154) and acetyl chloride the title compound is obtained as colorless solid.

MS (ESI): m/z=478 (MH+, 100%).

¹H-NMR 200 MHz, DMSO-d₆): 12.00 (br.s, 1H, —NH); 9.08 (s, 1H); 8.61 (d, J=7.6, 1H, —NH); 8.25 (s, 1H); 7.86 (d, J=7.6, 1H, —NH); 7.19 (t, J=1.7, 1H); 7.12 (d, J=1.7, 2H); 4.02 (m, 1H); 3.83 (d, J=6.8, 2H); 3.77 (s, 3H & m, 1H); 1.84 (s, 3H); 1.81-1.53 (m, 8H); 0.92 (m, 1H); 0.33 (m, 2H); 0.17 (m, 2H).

Example 68 cis-4-(2-Cyclopropylmethoxy-5-methoxy-phenyl)-5H-pyrrolo[3,2-d]pyrimidine-7-carboxylic acid [4-(cyclopropanecarbonyl-amino)cyclohexyl]-amide Starting from cis-4-(2-cyclopropylmethoxy-5-methoxy-phenyl)-5H-pyrrolo[3,2-d]pyrimidine-7-carboxylic acid (4-amino-cyclohexyl)-amide (example A154) and cyclopropanecarbonyl chloride the title compound is obtained as colorless solid.

MS (ESI): m/z=504 (MH+, 100%).

¹H-NMR 200 MHz, DMSO-d₆): 12.01 (br.s, 1H, —NH); 9.09 (s, 1H); 8.63 (d, J=7.5, 1H, —NH); 8.25 (s, 1H); 8.07 (d, J=7.5, 1H, —NH); 7.20 (t, J=1.7, 1H); 7.12 (d, J=1.7, 2H); 4.04 (m, 1H); 3.83 (d, J=6.8, 2H); 3.78 (s, 3H & m, 1H); 1.84 (s, 3H); 1.91-1.50 (m, 9H); 0.93 (m, 1H); 0.65 (m, 4H); 0.33 (m, 2H); 0.17 (m, 2H).

Example 69 cis-4-(2-Cyclopropylmethoxy-5-methoxy-phenyl)-5H-pyrrolo[3,2-d]pyrimidine-7-carboxylic acid [4-(2-methoxy-acetylamino)-cyclohexyl]-amide Starting from cis-4-(2-cyclopropylmethoxy-5-methoxy-phenyl)-5H-pyrrolo[3,2-d]pyrimidine-7-carboxylic acid (4-amino-cyclohexyl)-amide (example A154) and methoxyacetyl chloride the title compound is obtained as colorless solid.

MS (ESI): m/z=508 (MH+, 100%).

¹H-NMR 200 MHz, DMSO-d₆): 12.00 (br.s, 1H, —NH); 9.08 (s, 1H); 8.64 (d, J=7.5, 1H, —NH); 8.24 (s, 1H); 7.69 (d, J=7.6, 1H, —NH); 7.19 (t, J=1.7, 1H); 7.12 (d, J=1.7, 2H); 4.06 (m, 1H); 3.83 (d, J=6.8, 2H & s, 2H); 3.78 (s, 3H & m, 1H); 3.31 (s, 3H); 1.90-1.58 (m, 8H); 0.92 (m, 1H); 0.31 (m, 2H); 0.17 (m, 2H).

Example 70 cis-(4-{[4-(2-Cyclopropylmethoxy-5-methoxy-phenyl)-5H-pyrrolo[3,2-d]pyrimidine-7-carbonyl]-amino}-cyclohexyl)-carbamic acid ethyl ester Starting from cis-4-(2-cyclopropylmethoxy-5-methoxy-phenyl)-5H-pyrrolo[3,2-d]pyrimidine-7-carboxylic acid (4-amino-cyclohexyl)-amide (example A154) and ethyl chloroformate the title compound is obtained as colorless solid.

MS (ESI): m/z=508 (MH+, 100%).

$^1$H-NMR 200 MHz, DMSO-$d_6$): 12.00 (br.s, 1H, —NH); 9.08 (s, 1H); 8.64 (d, J=7.8, 1H, —NH); 8.24 (s, 1H); 7.19 (t, J=1.7, 1H & br.s, 1H, —NH); 7.12 (d, J=1.7, 2H); 4.00 (qu, J=7.1, 2H & m, 1H); 3.83 (d, J=6.8, 2H); 3.78 (s, 3H); 3.51 (m, 1H); 1.88-1.58 (m, 8H); 1.18 (t, J=7.1, 3H); 0.93 (m, 1H); 0.33 (m, 2H); 0.17 (m, 2H).

Example 71

4-(2-Cyclopropylmethoxy-5-methoxy-phenyl)-5H-pyrrolo[3,2-d]pyrimidine-7-carboxylic acid (1-acetyl-piperidin-4-yl)-amide Starting from 4-(2-cyclopropylmethoxy-5-methoxy-phenyl)-5H-pyrrolo[3,2-d]pyrimidine-7-carboxylic acid piperidin-4-ylamide (example A155) and acetyl chloride the title compound is obtained as colorless solid.

MS (ESI): m/z=464 (MH+, 100%).

$^1$H-NMR 400 MHz, DMSO-$d_6$): 12.03 (br.s, 1H, —NH); 9.05 (s, 1H); 8.51 (d, J=7.8, 1H, —NH); 8.27 (s, 1H); 7.19 (t, J=1.6, 1H); 7.11 (d, J=1.6, 2H); 4.21 (m, 1H); 4.14 (m, 1H); 3.83 (d, J=6.8, 2H & m, 1H); 3.77 (s, 3H); 3.27 (m, 1H); 2.92 (m, 1H); 2.04 (s, 3H); 1.97 (m, 2H); 1.56 (m, 1H); 1.40 (m, 1H); 0.92 (m, 1H); 0.32 (m, 2H); 0.16 (m, 2H).

Example 72

4-(2-Cyclopropylmethoxy-5-methoxy-phenyl)-5H-pyrrolo[3,2-d]pyrimidine-7-carboxylic acid (1-cyclopropanecarbonyl-piperidin-4-yl)-amide Starting from 4-(2-cyclopropylmethoxy-5-methoxy-phenyl)-5H-pyrrolo[3,2-d]pyrimidine-7-carboxylic acid piperidin-4-ylamide (example A155) and cyclopropanecarbonyl chloride the title compound is obtained as colorless solid.

MS (ESI): m/z=490 (MH+, 100%).

$^1$H-NMR 400 MHz, DMSO-$d_6$): 12.03 (br.s, 1H, —NH); 9.05 (s, 1H); 8.51 (d, J=7.8, 1H, —NH); 8.27 (s, 1H); 7.19 (t, J=1.6, 1H); 7.11 (d, J=1.6, 2H); 4.20 (m, 3H); 3.83 (d, J=6.8, 2H); 3.77 (s, 3H); 3.39 (m, 1H); 2.98 (m, 1H); 2.01 (m, 1H); 1.99 (m, 2H); 1.56 (m, 1H); 1.42 (m, 1H); 0.92 (m, 1H); 0.73 (m, 4H); 0.32 (m, 2H); 0.16 (m, 2H).

Example 73

4-(2-Cyclopropylmethoxy-5-methoxy-phenyl)-5H-pyrrolo[3,2-d]pyrimidine-7-carboxylic acid [1-(2-methoxy-acetyl)piperidin-4-yl]-amide Starting from 4-(2-cyclopropylmethoxy-5-methoxy-phenyl)-5H-pyrrolo[3,2-d]pyrimidine-7-carboxylic acid piperidin-4-ylamide (example A155) and methoxy-acetyl chloride the title compound is obtained as colorless solid.

MS (ESI): m/z=494 (MH+, 100%).

$^1$H-NMR 400 MHz, DMSO-$d_6$): 12.03 (br.s, 1H, —NH); 9.05 (s, 1H); 8.51 (d, J=7.8, 1H, —NH); 8.27 (s, 1H); 7.19 (t, J=1.6, 1H); 7.11 (d, J=1.6, 2H); 4.17 (m, 2H); 4.11 (d, J=4.7, 2H); 3.83 (d, J=6.9, 2H); 3.77 (s, 3H & m, 1H); 3.31 (s, 3H); 3.21 (m, 1H); 2.94 (m, 1H); 1.97 (m, 2H); 1.56 (m, 1H); 1.41 (m, 1H); 0.91 (m, 1H); 0.32 (m, 2H); 0.17 (m, 2H).

Example 74

4-{[4-(2-Cyclopropylmethoxy-5-methoxy-phenyl)-5H-pyrrolo[3,2-d]pyrimidine-7-carbonyl]-amino}-piperidine-1-carboxylic acid ethyl ester Starting from 4-(2-cyclopropylmethoxy-5-methoxy-phenyl)-5H-pyrrolo[3,2-d]pyrimidine-7-carboxylic acid piperidin-4-ylamide (example A155) and ethyl chloroformate the title compound is obtained as colorless solid.

MS (ESI): m/z=494 (MH+, 100%).

$^1$H-NMR 400 MHz, DMSO-$d_6$): 12.03 (br.s, 1H, —NH); 9.05 (s, 1H); 8.51 (d, J=7.8, 1H, —NH); 8.27 (s, 1H); 7.19 (t, J=1.6, 1H); 7.11 (d, J=1.6, 2H); 4.08 (qu, J=7.1, 2H & m, 1H); 3.91 (m, 2H); 3.83 (d, J=6.8, 2H); 3.78 (s, 3H); 3.09 (m, 2H); 1.97 (m, 2H); 1.48 (m, 2H); 0.92 (m, 1H); 0.32 (m, 2H); 0.17 (m, 2H).

Example 75 cis-4-(2-Cyclopropylmethoxy-4-fluoro-phenyl)-5H-pyrrolo[3,2-d]pyrimidine-7-carboxylic acid (4-acetylamino-cyclohexyl)-amide Starting from cis-4-(2-Cyclopropylmethoxy-4-fluoro-phenyl)-5H-pyrrolo[3,2-d]pyrimidine-7-carboxylic acid (4-amino-cyclohexyl)-amide (example A156) and acetyl chloride the title compound is obtained as colorless solid.

MS (ESI): m/z=466 (MH+, 100%).

$^1$H-NMR (300 MHz, DMSO-$d_6$): 12.06 (br.s, 1H, —NH); 9.07 (s, 1H); 8.62 (d, J=7.6, 1H; —NH); 8.28 (s, 1H); 7.86 (d, J=7.6, 1H, —NH); 7.68 (dd, J$_1$=8.5, J$_2$=7.0, 1H); 7.08 (dd, J$_1$=11.6, J$_2$=2.3, 1H); 6.96 (ddd, J$_1$=J$_2$=8.5, J$_3$=2.3, 1H); 4.03 (m, 1H); 3.92 (d, J=6.9, 2H); 3.78 (m, 1H); 1.83 (s, 3H); 1.81-1.50 (m, 8H); 0.98 (m, 1H); 0.36 (m, 2H); 0.22 (m, 2H).

Example 76 cis-4-(2-Cyclopropylmethoxy-4-fluoro-phenyl)-5H-pyrrolo[3,2-d]pyrimidine-7-carboxylic acid [4-(2-methoxy-acetylamino)-cyclohexyl]-amide Starting from cis-4-(2-Cyclopropylmethoxy-4-fluoro-phenyl)-5H-pyrrolo[3,2-d]pyrimidine-7-carboxylic acid (4-amino-cyclohexyl)-amide (example A156) and methoxy-acetyl chloride the title compound is obtained as colorless solid.

MS (ESI): m/z=496 (MH+, 100%).

$^1$H-NMR (300 MHz, DMSO-$d_6$): 12.06 (br.s, 1H, —NH); 9.07 (s, 1H); 8.65 (d, J=7.4, 1H; —NH); 8.28 (s, 1H); 7.68 (dd, J$_1$=8.5, J$_2$=7.0, 1H & br.s, 1H, —NH); 7.08 (dd, J$_1$=12.6, J$_2$=2.3, 1H); 6.96 (ddd, J$_1$=J$_2$=8.5, J$_3$=2.3, 1H); 4.05 (m, 1H); 3.92 (d, J=7.0, 2H); 3.82 (m, 1H & s, 2H); 3.31 (s, 3H); 1.89-1.58 (m, 8H); 0.98 (m, 1H); 0.36 (m, 2H); 0.22 (m, 2H).

Example 77 cis-(4-{[4-(2-Cyclopropylmethoxy-4-fluoro-phenyl)-5H-pyrrolo[3,2-d]pyrimidine-7-carbonyl]-amino}-cyclohexyl)-carbamic acid ethyl ester Starting from cis-4-(2-Cyclopropylmethoxy-4-fluoro-phenyl)-5H-pyrrolo[3,2-d]pyrimidine-7-carboxylic acid (4-amino-cyclohexyl)-amide (example A156) and ethyl chloroformate the title compound is obtained as colorless solid.

MS (ESI): m/z=496 (MH+, 100%).

$^1$H-NMR (300 MHz, DMSO-d$_6$): 12.05 (br.s, 1H, —NH); 9.06 (s, 1H); 8.65 (d, J=7.8, 1H; —NH); 8.27 (s, 1H); 7.68 (dd, J$_1$=8.5, J$_2$=7.0, 1H); 7.20 (br.s, 1H, —NH); 7.08 (dd, J$_1$=12.6, J$_2$=2.3, 1H); 6.96 (ddd, J$_1$=J$_2$=8.5, J$_3$=2.3, 1H); 4.03 (m, 1H); 4.00 (qu, J=7.1, 2H); 3.92 (d, J=7.0, 2H); 3.50 (m, 1H); 1.88-1.53 (m, 8H); 1.17 (t, J=7.1, 3H); 0.98 (m, 1H); 0.36 (m, 2H); 0.22 (m, 2H).

Example 78 trans-4-(2-Cyclopropylmethoxy-4-fluoro-phenyl)-5H-pyrrolo[3,2-d]pyrimidine-7-carboxylic acid (4-acetylamino-cyclohexyl)-amide Starting from trans-4-(2-Cyclopropylmethoxy-4-fluoro-phenyl)-5H-pyrrolo[3,2-d]pyrimidine-7-carboxylic acid (4-amino-cyclohexyl)-amide (example A157) and acetyl chloride the title compound is obtained as colorless solid.

MS (ESI): m/z=466 (MH+, 100%).

$^1$H-NMR (400 MHz, DMSO-d$_6$): 12.05 (br.s, 1H, —NH); 9.03 (s, 1H); 8.35 (d, J=7.9, 1H; —NH); 8.26 (s, 1H); 7.72 (d, J=7.6, 1H, —NH); 7.67 (dd, J$_1$=8.4, J$_2$=7.1, 1H); 7.08 (dd, J$_1$=11.5, J$_2$=2.2, 1H); 6.96 (ddd, J$_1$=J$_2$=8.4, J$_3$=2.2, 1H); 3.92 (d, J=7.0, 2H); 3.82 (m, 1H); 3.58 (m, 1H); 2.01 (m, 2H); 1.87 (m, 2H); 1.79 (s, 3H); 1.42 (m, 2H); 1.31 (m, 2H); 0.96 (m, 1H); 0.36 (m, 2H); 0.22 (m, 2H).

Example 79 trans-4-(2-Cyclopropylmethoxy-4-fluoro-phenyl)-5H-pyrrolo[3,2-d]pyrimidine-7-carboxylic acid [4-(2-methoxy-acetylamino)-cyclohexyl]-amide Starting from trans-4-(2-Cyclopropylmethoxy-4-fluoro-phenyl)-5H-pyrrolo[3,2-d]pyrimidine-7-carboxylic acid (4-amino-cyclohexyl)-amide (example A157) and methoxyacetyl chloride the title compound is obtained as colorless solid.

MS (ESI): m/z=496 (MH+, 100%).

$^1$H-NMR (400 MHz, DMSO-d$_6$): 12.05 (br.s, 1H, —NH); 9.04 (s, 1H); 8.35 (d, J=7.8, 1H; —NH); 8.27 (s, 1H); 7.67 (dd, J$_1$=8.4, J$_2$=7.1, 1H); 7.56 (d, J=8.2, 1H, —NH); 7.08 (dd, J$_1$=11.5, J$_2$=2.2, 1H); 6.96 (ddd, J$_1$=J$_2$=8.4, J$_3$=2.2, 1H); 3.92 (d, J=6.9, 2H); 3.79 (m, 1H & s, 2H); 3.70 (m, 1H); 3.31 (s, 3H); 2.01 (m, 2H); 1.87 (m, 2H); 1.43 (m, 4H); 0.96 (m, 1H); 0.36 (m, 2H); 0.22 (m, 2H).

Example 80 trans-(4-{[4-(2-Cyclopropylmethoxy-4-fluoro-phenyl)-5H-pyrrolo[3,2-d]pyrimidine-7-carbonyl]-amino}-cyclohexyl)-carbamic acid ethyl ester Starting from trans-4-(2-Cyclopropylmethoxy-4-fluoro-phenyl)-5H-pyrrolo[3,2-d]pyrimidine-7-carboxylic acid (4-amino-cyclohexyl)-amide (example A157) and ethyl chloroformate the title compound is obtained as colorless solid.

MS (ESI): m/z=496 (MH+, 100%).

$^1$H-NMR (400 MHz, DMSO-d$_6$): 12.04 (br.s, 1H, —NH); 9.03 (s, 1H); 8.34 (d, J=7.8, 1H; —NH); 8.26 (s, 1H); 7.67 (dd, J$_1$=8.4, J$_2$=7.2, 1H); 7.07 (dd, J$_1$=11.5, J$_2$=2.2, 1H); 7.01 (d, J=7.2, 1H, —NH); 6.96 (ddd, J$_1$=J$_2$=8.5, J$_3$=2.2, 1H); 3.98 (qu, J=7.0, 2H); 3.92 (d, J=7.0, 2H); 3.79 (m, 1H); 3.35 (m, 1H); 2.04 (m, 2H); 1.88 (m, 2H); 1.37 (m, 4H); 1.16 (t, J=7.0, 3H); 0.96 (m, 1H); 0.36 (m, 2H); 0.22 (m, 2H).

Example 81

4-(2-Cyclopropylmethoxy-4-fluoro-phenyl)-5H-pyrrolo[3,2-d]pyrimidine-7-carboxylic acid (1-acetyl-piperidin-4-yl)-amide Starting from 4-(2-Cyclopropylmethoxy-4-fluoro-phenyl)-5H-pyrrolo[3,2-d]pyrimidine-7-carboxylic acid piperidin-4-ylamide hydrochloride (example A158) and acetyl chloride the title compound is obtained as colorless solid.

MS (ESI): m/z=452 (MH+, 100%).

$^1$H-NMR (300 MHz, DMSO-d$_6$): 11.98 (br.s, 1H, —NH); 9.03 (s, 1H); 8.50 (d, J=7.8, 1H; —NH); 8.29 (s, 1H); 7.67 (dd, J$_1$=8.5, J$_2$=7.0, 1H); 7.08 (dd, J$_1$=11.6, J$_2$=2.3, 1H); 6.96 (ddd, J$_1$=J2=8.5, J$_3$=2.3, 1H); 4.27-4.06 (m, 2H); 3.92 (d, J=6.9, 2H); 3.79 (m, 1H); 3.28 (m, 1H); 2.91 (m, 1H); 2.04 (s, 3H); 1.97 (m, 2H); 1.57 (m, 1H); 1.40 (m, 1H); 0.96 (m, 1H); 0.36 (m, 2H); 0.22 (m, 2H).

Example 82

4-(2-Cyclopropylmethoxy-4-fluoro-phenyl)-5H-pyrrolo[3,2-d]pyrimidine-7-carboxylic acid (1-propionyl-piperidin-4-yl)-amide Starting from 4-(2-Cyclopropylmethoxy-4-fluoro-phenyl)-5H-pyrrolo[3,2-d]pyrimidine-7-carboxylic acid piperidin-4-ylamide hydrochloride (example A158) and propionyl chloride the title compound is obtained as colorless solid.

MS (ESI): m/z=466 (MH+, 100%).

$^1$H-NMR (300 MHz, DMSO-d$_6$): 12.07 (br.s, 1H, —NH); 9.02 (s, 1H); 8.50 (d, J=7.8, 1H; —NH); 8.29 (s, 1H); 7.67 (dd, J$_1$=8.5, J$_2$=7.0, 1H); 7.08 (dd, J$_1$=11.6, J$_2$=2.3, 1H); 6.96 (ddd, J$_1$=J$_2$=8.5, J$_3$=2.3, 1H); 4.23 (m, 1H); 4.14 (m, 1H); 3.92 (d, J=7.0, 2H); 3.82 (m, 1H); 3.25 (m, 1H); 2.93 (m, 1H); 2.36 (qu, J=7.4, 2H); 1.97 (m, 2H); 1.52 (m, 1H); 1.40 (m, 1H); 1.01 (t, J=7.4, 3H); 0.96 (m, 1H); 0.37 (m, 2H); 0.22 (m, 2H).

Example 83

4-(2-Cyclopropylmethoxy-4-fluoro-phenyl)-5H-pyrrolo[3,2-d]pyrimidine-7-carboxylic acid [1-(2-methoxy-acetyl)piperidin-4-yl]-amide Starting from 4-(2-Cyclopropylmethoxy-4-fluoro-phenyl)-5H-pyrrolo[3,2-d]pyrimidine-7-carboxylic acid piperidin-4-ylamide hydrochloride (example A158) and methoxyacetyl chloride the title compound is obtained as colorless solid.

MS (ESI): m/z=482 (MH+, 100%).

$^1$H-NMR (300 MHz, DMSO-d$_6$): 11.99 (br.s, 1H, —NH); 9.01 (s, 1H); 8.50 (d, J=7.8, 1H; —NH); 8.29 (s, 1H); 7.67 (dd, J=8.5, J$_2$=7.0, 1H); 7.08 (dd, J=11.6, J$_2$=2.4, 1H); 6.96 (ddd, J=J$_2$=8.5, J$_3$=2.4, 1H); 4.17 (m, 1H); 4.12 (d, J=2.3, 2H); 3.92 (d, J=7.0, 2H); 3.76 (m, 1H); 3.29 (s, 3H); 3.22 (m, 1H); 2.95 (m, 1H); 1.98 (m, 2H); 1.59 (m, 1H); 1.41 (m, 1H); 0.96 (m, 1H); 0.37 (m, 2H); 0.22 (m, 2H).

Example 84

4-(2-Cyclopropylmethoxy-5-fluoro-phenyl)-5H-pyrrolo[3,2-d]pyrimidine-7-carboxylic acid (1-acetyl-piperidin-4-yl)-amide Starting from 4-(2-cyclopropylmethoxy-5-fluoro-phenyl)-5H-pyrrolo[3,2-d]pyrimidine-7-carboxylic acid piperidin-4- ylamide hydrochloride (example A159) and acetyl chloride the title compound is obtained as colorless solid.

MS (ESI): m/z=452 (MH$^+$, 100%).

$^1$H-NMR (300 MHz, DMSO-d$_6$): 12.11 (br.s, 1H, —NH); 9.05 (s, 1H); 8.49 (d, J=7.8, 1H, —NH); 8.31 (s, 1H); 7.44 (dd, J$_1$=9.0, J$_2$=3.2, 1H); 7.38 (ddd, J$_1$=J$_2$=9.1, J$_3$=3.2, 1H); 7.19 (dd, J$_1$=9.1, J$_2$=4.4, 1H); 4.28-4.07 (m, 2H); 3.88 (d, J=6.9, 2H); 3.80 (m, 1H); 3.27 (m, 1H); 2.92 (m, 1H); 2.04 (s, 3H); 1.97 (m, 2H); 1.56 (m, 1H); 1.42 (m, 1H); 0.94 (m, 1H); 0.34 (m, 2H); 0.19 (m, 2H).

Example 85

4-(2-Cyclopropylmethoxy-5-fluoro-phenyl)-5H-pyrrolo[3,2-d]pyrimidine-7-carboxylic acid (1-propionyl-piperidin-4-yl)-amide Starting from 4-(2-Cyclopropylmethoxy-5-fluoro-phenyl)-5H-pyrrolo[3,2-d]pyrimidine-7-carboxylic acid piperidin-4-ylamide hydrochloride (example A159) and propionyl chloride the title compound is obtained as colorless solid.

MS (ESI): m/z=466 (MH$^+$, 100%).

$^1$H-NMR (300 MHz, DMSO-d$_6$): 12.11 (br.s, 1H, —NH); 9.05 (s, 1H); 8.49 (d, J=7.9, 1H, —NH); 8.31 (s, 1H); 7.44 (dd, J$_1$=8.9, J$_2$=3.2, 1H); 7.38 (ddd, J$_1$=J$_2$=9.1, J$_3$=3.2, 1H); 7.19 (dd, J$_1$=9.1, J$_2$=4.4, 1H); 4.23 (m, 1H); 4.14 (m, 1H); 3.88 (d, J=6.9, 2H); 3.82 (m, 1H); 3.25 (m, 1H); 2.92 (m, 1H); 2.36 (qu, J=7.3, 2H); 1.97 (m, 2H); 1.54 (m, 1H); 1.40 (m, 1H); 1.01 (t, J=7.3, 3H); 0.94 (m, 1H); 0.34 (m, 2H); 0.19 (m, 2H).

Example 86

4-(2-Cyclopropylmethoxy-5-fluoro-phenyl)-5H-pyrrolo[3,2-d]pyrimidine-7-carboxylic acid [1-(2-methoxy-acetyl)piperidin-4-yl]-amide Starting from 4-(2-Cyclopropylmethoxy-5-fluoro-phenyl)-5H-pyrrolo[3,2-d]pyrimidine-7-carboxylic acid piperidin-4-ylamide hydrochloride (example A159) and methoxy-acetyl chloride the title compound is obtained as colorless solid.

MS (ESI): m/z=482 (MH$^+$, 100%).

$^1$H-NMR (300 MHz, DMSO-d$_6$): 12.11 (br.s, 1H, —NH); 9.05 (s, 1H); 8.49 (d, J=7.7, 1H, —NH); 8.31 (s, 1H); 7.44 (dd, J$_1$=9.0, J$_2$=3.2, 1H); 7.38 (ddd, J$_1$=J$_2$=9.1, J$_3$=3.2, 1H); 7.19 (dd, J$_1$=9.1, J$_2$=4.4, 1H); 4.16 (m, 2H); 4.12 (d, J=2.6, 2H); 3.88 (d, J=6.9, 2H); 3.76 (m, 1H); 3.31 (s, 3H); 3.21 (m, 1H); 2.95 (m, 1H); 1.98 (m, 2H); 1.56 (m, 1H); 1.42 (m, 1H); 0.94 (m, 1H); 0.34 (m, 2H); 0.19 (m, 2H).

Example 87 trans-4-(2-Cyclopropylmethoxy-5-fluoro-phenyl)-5H-pyrrolo[3,2-d]pyrimidine-7-carboxylic acid (4-acetylamino-cyclohexyl)-amide Starting from trans-4-(2-Cyclopropylmethoxy-5-fluoro-phenyl)-5H-pyrrolo[3,2-d]pyrimidine-7-carboxylic acid (4-amino-cyclohexyl)-amide hydrochloride (example A160) and acetyl chloride the title compound is obtained as colorless solid.

MS (ESI): m/z=466 (MH$^+$, 100%).

$^1$H-NMR (300 MHz, DMSO-d$_6$): 12.08 (br.s, 1H, —NH); 9.06 (s, 1H); 8.34 (d, J=7.7, 1H, —NH); 8.28 (s, 1H); 7.73 (d, J=7.7, 1H, —NH); 7.44 (dd, J$_1$=8.9, J$_2$=3.2, 1H); 7.38 (ddd, J$_1$=J$_2$=9.1, J$_3$=3.2, 1H); 7.19 (dd, J$_1$=9.1, J$_2$=4.4, 1H); 3.88 (d, J=6.9, 2H); 3.82 (m, 1H); 3.57 (m, 1H); 2.02 (m, 2H); 1.86 (m, 2H); 1.79 (s, 3H); 1.37 (m, 4H); 0.94 (m, 1H); 0.34 (m, 2H); 0.18 (m, 2H).

Example 88 trans-4-(2-Cyclopropylmethoxy-5-fluoro-phenyl)-5H-pyrrolo[3,2-d]pyrimidine-7-carboxylic acid (4-propionylamino-cyclohexyl)-amide Starting from trans-4-(2-Cyclopropylmethoxy-5-fluoro-phenyl)-5H-pyrrolo[3,2-d]pyrimidine-7-carboxylic acid (4-amino-cyclohexyl)-amide hydrochloride (example A160) and propionyl chloride the title compound is obtained as colorless solid.

MS (ESI): m/z=480 (MH$^+$, 100%).

$^1$H-NMR (300 MHz, DMSO-d$_6$): 12.08 (br.s, 1H, —NH); 9.06 (s, 1H); 8.34 (d, J=7.8, 1H, —NH), 8.28 (s, 1H); 7.63 (d, J=7.8, 1H, —NH); 7.44 (dd, J$_1$=8.9, J$_2$=3.2, 1H); 7.38 (ddd, J$_1$=J$_2$=9.2, J$_3$=3.2, 1H); 7.19 (dd, J$_1$=9.2, J$_2$=4.4, 1H); 3.88 (d, J=6.9, 2H); 3.82 (m, 1H); 3.58 (m, 1H); 2.06 (qu, J=7.5, 2H); 2.02 (m, 2H); 1.86 (m, 2H); 1.37 (m, 4H); 0.94 (m, 1H); 0.34 (m, 2H); 0.18 (m, 2H).

Example 89 trans-4-(2-Cyclopropylmethoxy-5-fluoro-phenyl)-5H-pyrrolo[3,2-d]pyrimidine-7-carboxylic acid [4-(2-methoxy-acetylamino)-cyclohexyl]-amide Starting from trans-4-(2-Cyclopropylmethoxy-5-fluoro-phenyl)-5H-pyrrolo[3,2-d]pyrimidine-7-carboxylic acid (4-amino-cyclohexyl)-amide hydrochloride (example A160) and methoxy-acetyl chloride the title compound is obtained as colorless solid.

MS (ESI): m/z=496 (MH$^+$, 100%).

$^1$H-NMR (300 MHz, DMSO-d$_6$): 12.08 (br.s, 1H, —NH); 9.06 (s, 1H); 8.33 (d, J=7.9, 1H, —NH); 8.28 (s, 1H); 7.56 (d, J=8.2, 1H, —NH); 7.43 (dd, J$_1$=9.0, J$_2$=3.3, 1H); 7.38 (ddd, J$_1$=J$_2$=9.1, J$_3$=3.3, 1H); 7.19 (dd, J$_1$=9.1, J$_2$=4.4, 1H); 3.88 (d, J=6.9, 2H); 3.82 (m, 1H & s, 2H); 3.71 (m, 1H); 3.31 (s, 3H); 2.02 (m, 2H); 1.82 (m, 2H); 1.45 (m, 4H); 0.94 (m, 1H); 0.34 (m, 2H); 0.18 (m, 2H).

Example 90 trans-4-(2-Cyclopropylmethoxy-phenyl)-5H-pyrrolo[3,2-d]pyrimidine-7-carboxylic acid (4-acetylamino-cyclohexyl)-amide Starting from trans-4-(2-cyclopropylmethoxy-phenyl)-5H-pyrrolo[3,2-d]pyrimidine-7-carboxylic acid (4-amino-cyclohexyl)-amide (example A161) and acetyl chloride the title compound is obtained as colorless solid.

MS (ESI): m/z=448 (MH$^+$, 100%).

$^1$H-NMR (300 MHz, DMSO-d$_6$): 12.02 (s, 1H, —NH); 9.05 (s, 1H); 8.37 (d, J=7.9, 1H, —NH); 8.24 (s, 1H); 7.73 (d, J=7.7, 1H, —NH); 7.64 (dd, J$_1$=7.6, J$_2$=1.7, 1H); 7.53 (ddd, J$_1$=8.0, J$_2$=7.6, J$_3$=1.7, 1H); 7.17 (dd, J$_1$=8.0, J$_2$=0.9, 1H); 7.13 (ddd, J$_1$=J$_2$=7.6, J$_3$=0.9, 1H); 3.91 (d, J=6.9, 2H); 3.82 (m, 1H); 3.69 (m, 1H); 2.01 (m, 2H); 1.83 (m, 2H); 1.80 (s, 3H); 1.48-1.24 (m, 4H); 0.96 (m, 1H); 0.36 (m, 2H); 0.22 (m, 2H).

Example 91 trans-4-(2-Cyclopropylmethoxy-phenyl)-5H-pyrrolo[3,2-d]pyrimidine-7-carboxylic acid [4-(2-methoxy-acetylamino)-cyclohexyl]-amide Starting from trans-4-(2-Cyclopropylmethoxy-phenyl)-5H-pyrrolo[3,2-d]pyrimidine-7-carboxylic acid (4-amino-cyclohexyl)-amide (example A161) and methoxy-acetyl chloride the title compound is obtained as colorless solid.

MS (ESI): m/z=478 (MH$^+$, 100%).
$^1$H-NMR (300 MHz, DMSO-d$_6$): 12.03 (s, 1H, —NH); 9.05 (s, 1H); 8.36 (d, J=7.8, 1H, —NH); 8.24 (s, 1H); 7.64 (dd, J$_1$=7.6, J$_2$=1.7, 1H); 7.57 (, J=8.3, 1H, —NH); 7.53 (ddd, J$_1$=8.0, J$_2$=7.6, J$_3$=1.7, 1H); 7.17 (dd, J$_1$=8.0, J$_2$=0.9, 1H); 7.13 (ddd, J$_1$=J$_2$=7.6, J$_3$=0.9, 1H); 6.20 (s, 1H, —OH); 3.91 (d, J=6.9, 2H); 3.80 (s, 2H & m, 1H); 3.71 (m, 1H); 3.30 (s, 3H); 2.03 (m, 2H); 1.82 (m, 2H); 1.47 (m, 4H); 0.96 (m, 1H); 0.36 (m, 2H); 0.22 (m, 2H).

Example 92 trans-(4-{[4-(2-Cyclopropylmethoxy-phenyl)-5H-pyrrolo[3,2-d]pyrimidine-7-carbonyl]-amino}-cyclohexyl)-carbamic acid ethyl ester Starting from trans-4-(2-Cyclopropylmethoxy-phenyl)-5H-pyrrolo[3,2-d]pyrimidine-7-carboxylic acid (4-amino-cyclohexyl)-amide (example A161) and ethyl chloroformate the title compound is obtained as colorless solid.

MS (ESI): m/z=478 (MH$^+$, 100%).
$^1$H-NMR (300 MHz, DMSO-d$_6$): 12.02 (s, 1H, —NH); 9.05 (s, 1H); 8.36 (d, J=7.8, 1H, —NH); 8.24 (s, 1H); 7.64 (dd, J$_1$=7.6, J$_2$=1.7, 1H); 7.53 (ddd, J$_1$=8.0, J$_2$=7.6, J$_3$=1.7, 1H); 7.17 (dd, J$_1$=8.0, J$_2$=0.9, 1H); 7.13 (ddd, J$_1$=J$_2$=7.6, J$_3$=0.9, 1H); 7.02 (d, J=7.4, 1H, —NH); 3.98 (qu, J=7.0, 2H); 3.91 (d, J=6.8, 2H); 3.80 (m, 1H); 3.34 (m, 1H); 2.01 (m, 2H); 1.89 (m, 2H); 1.80 (s, 3H); 1.48 (m, 4H); 1.18 (t, J=7.0, 3H); 0.96 (m, 1H); 0.36 (m, 2H); 0.22 (m, 2H).

Example 93 trans-4-(2-Cyclopropylmethoxy-phenyl)-5H-pyrrolo[3,2-d]pyrimidine-7-carboxylic acid [4-(cyclopropanecarbonyl-amino)cyclohexyl]-amide Starting from trans-4-(2-Cyclopropylmethoxy-phenyl)-5H-pyrrolo[3,2-d]pyrimidine-7-carboxylic acid (4-amino-cyclohexyl)-amide (example A161) and cyclopropanecarbonyl chloride the title compound is obtained as colorless solid.

MS (ESI): m/z=474 (MH$^+$, 100%).
$^1$H-NMR (300 MHz, DMSO-d$_6$): 12.03 (s, 1H, —NH); 9.05 (s, 1H); 8.37 (d, J=7.8, 1H, —NH); 8.24 (s, 1H); 7.95 (d, J=7.8, 1H, —NH); 7.64 (dd, J$_1$=7.6, J$_2$=1.7, 1H); 7.53 (ddd, J$_1$=8.0, J$_2$=7.6, J$_3$=1.7, 1H); 7.17 (dd, J$_1$=8.0, J$_2$=0.9, 1H); 7.13 (ddd, J$_1$=J$_2$=7.6, J$_3$=0.9, 1H); 3.91 (d, J=6.8, 2H); 3.84 (m, 1H); 3.61 (m, 1H); 2.01 (m, 2H); 1.89 (m, 2H); 1.05 (m, 1H); 1.39 (m, 4H); 0.96 (m, 1H); 0.67 (m, 4H); 0.36 (m, 2H); 0.22 (m, 2H).

Example 94

4-(2-Cyclopropylmethoxy-phenyl)-5H-pyrrolo[3,2-d]pyrimidine-7-carboxylic acid (1-acetyl-piperidin-4-yl)-amide Starting from 4-(2-cyclopropylmethoxy-phenyl)-5H-pyrrolo[3,2-d]pyrimidine-7-carboxylic acid piperidin-4-ylamide (example A162) and acetyl chloride the title compound is obtained as colorless solid.

MS (ESI): m/z=434 (MH$^+$, 100%).
$^1$H-NMR (300 MHz, DMSO-d$_6$): 12.06 (s, 1H, —NH); 9.05 (s, 1H); 8.52 (d, J=7.8, 1H, —NH); 8.26 (s, 1H); 7.64 (dd, J$_1$=7.6, J$_2$=1.7, 1H); 7.53 (ddd, J$_1$=8.0, J$_2$=7.6, J$_3$=1.7, 1H); 7.17 (dd, J$_1$=8.0, J$_2$=0.9, 1H); 7.13 (ddd, J$_1$=J$_2$=7.6, J$_3$=0.9, 1H); 4.21 (m, 1H); 4.17 (m, 1H); 3.91 (d, J=6.8, 2H); 3.80 (m, 1H); 3.28 (m, 1H); 2.92 (m, 1H); 2.04 (s, 3H); 1.98 (m, 2H); 1.57 (m, 1H); 1.40 (m, 1H); 0.96 (m, 1H); 0.36 (m, 2H); 0.22 (m, 2H).

Example 95

4-{[4-(2-Cyclopropylmethoxy-phenyl)-5H-pyrrolo[3,2-d]pyrimidine-7-carbonyl]-amino}-piperidine-1-carboxylic acid ethyl ester Starting from 4-(2-cyclopropylmethoxy-phenyl)-5H-pyrrolo[3,2-d]pyrimidine-7-carboxylic acid piperidin-4-ylamide (example A162) and ethyl chloroformate the title compound is obtained as colorless solid.

MS (ESI): m/z=464 (MH$^+$, 100%).
$^1$H-NMR (300 MHz, DMSO-d$_6$): 12.05 (s, 1H, —NH); 9.05 (s, 1H); 8.51 (d, J=7.8, 1H, —NH); 8.27 (s, 1H); 7.64 (dd, J$_1$=7.6, J$_2$=1.7, 1H); 7.53 (ddd, J$_1$=8.0, J$_2$=7.6, J$_3$=1.7, 1H); 7.17 (dd, J$_1$=8.0, J$_2$=0.9, 1H); 7.13 (ddd, J$_1$=J$_2$=7.6, J$_3$=0.9, 1H); 4.13 (m, 1H); 4.08 (qu, J=7.1, 1H); 3.91 (d, J=6.8, 2H & m, 2H); 3.10 (m, 2H); 1.97 (m, 2H); 1.50 (m, 2H); 1.21 (t, J=7.1, 3H); 0.97 (m, 1H); 0.36 (m, 2H); 0.22 (m, 2H).

Example 96

4-(2-Cyclopropylmethoxy-phenyl)-5H-pyrrolo[3,2-d]pyrimidine-7-carboxylic acid (1-cyclopropanecarbonyl-piperidin-4-yl)-amide Starting from 4-(2-cyclopropylmethoxy-phenyl)-5H-pyrrolo[3,2-d]pyrimidine-7-carboxylic acid piperidin-4-ylamide (example A162) and cyclopropanecarbonyl chloride the title compound is obtained as colorless solid.

MS (ESI): m/z=460 (MH$^+$, 100%).
$^1$H-NMR (300 MHz, DMSO-d$_6$): 12.05 (s, 1H, —NH); 9.05 (s, 1H); 8.54 (d, J=7.8, 1H, —NH); 8.27 (s, 1H); 7.64 (dd, J$_1$=7.6, J$_2$=1.7, 1H); 7.53 (ddd, J$_1$=8.0, J$_2$=7.6, J$_3$=1.7, 1H); 7.17 (dd, J$_1$=8.0, J$_2$=0.9, 1H); 7.13 (ddd, J$_1$=J$_2$=7.6, J$_3$=0.9, 1H); 4.27-4.10 (m, 3H); 3.91 (d, J=6.8, 2H); 3.40 (m, 1H); 2.98 (m, 1H); 2.10-1.90 (m, 3H); 1.69-1.34 (m, 2H); 0.96 (m, 1H); 0.72 (m, 4H); 0.35 (m, 2H); 0.22 (m, 2H).

Example 97

4-(2-Cyclopropylmethoxy-4-fluoro-5-methoxy-phenyl)-5H-pyrrolo[3,2-d]pyrimidine-7-carboxylic acid (1-propionyl-piperidin-4-yl)-amide Starting from 4-(2-cyclopropylmethoxy-4-fluoro-5-methoxy-phenyl)-5H-pyrrolo[3,2-d]pyrimidine-7-carboxylic acid piperidin-4-ylamide hydrochloride (example A163) and propionyl chloride the title compound is obtained as colorless solid.

MS (ESI): m/z=496 (MH$^+$, 100%).
$^1$H-NMR (300 MHz, DMSO-d$_6$): 12.03 (br.s, 1H, —NH); 9.05 (s, 1H); 8.50 (d, J=7.8, 1H; —NH); 8.29 (s, 1H); 7.41 (d, J=9.8, 1H); 7.18 (d, J=13.4, 1H); 4.23 (m, 1H); 4.14 (m, 1H); 3.85 (s, 3H & d, J=6.8, 2H); 3.84 (m, 1H); 3.24 (m, 1H); 2.93

(m, 1H); 2.36 (qu, J=7.4, 2H); 1.97 (m, 2H); 1.53 (m, 1H); 1.40 (m, 1H); 1.01 (t, J=7.4, 3H); 0.93 (m, 1H); 0.34 (m, 2H), 0.18 (m, 2H).

Example 98

4-(2-Cyclopropylmethoxy-4-fluoro-5-methoxy-phenyl)-5H-pyrrolo[3,2-d]pyrimidine-7-carboxylic acid [1-(2-methoxy-ethanoyl)-piperidin-4-yl]-amide Starting from 4-(2-cyclopropylmethoxy-4-fluoro-5-methoxy-phenyl)-5H-pyrrolo[3,2-d]pyrimidine-7-carboxylic acid piperidin-4-ylamide hydrochloride (example A163) and methoxy-acetyl chloride the title compound is obtained as colorless solid.

MS (ESI): m/z=512 (MH$^+$, 100%).
$^1$H-NMR (300 MHz, DMSO-d$_6$): 12.03 (br.s, 1H, —NH); 9.05 (s, 1H); 8.50 (d, J=7.8, 1H; —NH); 8.29 (s, 1H); 7.41 (d, J=9.8, 1H); 7.18 (d, J=13.4, 1H); 4.16 (m, 1H); 4.12 (d, J=2.7, 2H)); 3.85 (s, 3H & d, J=6.8, 2H); 3.77 (m, 1H); 3.31 (s, 3H); 3.22 (m, 1H); 2.95 (m, 1H); 1.98 (m, 2H); 1.54 (m, 1H); 1.44 (m, 1H); 0.92 (m, 1H); 0.34 (m, 2H), 0.17 (m, 2H).

Example 99

4-(2-Cyclopropylmethoxy-4-fluoro-5-methoxy-phenyl)-5H-pyrrolo[3,2-d]pyrimidine-7-carboxylic acid (1-acetyl-piperidin-4-yl)-amide Starting from 4-(2-cyclopropylmethoxy-4-fluoro-5-methoxy-phenyl)-5H-pyrrolo[3,2-d]pyrimidine-7-carboxylic acid piperidin-4-ylamide hydrochloride (example A163) and acetyl chloride the title compound is obtained as colorless solid.

MS (ESI): m/z=482 (MH$^+$, 100%).
$^1$H-NMR (300 MHz, DMSO-d$_6$): 12.03 (br.s, 1H, —NH); 9.05 (s, 1H); 8.50 (d, J=7.8, 1H; —NH); 8.29 (s, 1H); 7.41 (d, J=9.8, 1H); 7.18 (d, J=13.4, 1H); 4.18 (m, 1H); 4.13 (m, 1H)); 3.85 (s, 3H & d, J=6.8, 2H); 3.81 (m, 1H); 3.27 (m, 1H); 2.92 (m, 1H); 2.04 (s, 3H); 1.97 (m, 2H); 1.56 (m, 1H); 1.40 (m, 1H); 0.93 (m, 1H); 0.34 (m, 2H), 0.17 (m, 2H).

Example 100

4-(2-Cyclopropylmethoxy-4-fluoro-5-methoxy-phenyl)-5H-pyrrolo[3,2-d]pyrimidine-7-carboxylic acid ((R)-1-acetyl-piperidin-3-yl)-amide Starting from 4-(2-cyclopropylmethoxy-4-fluoro-5-methoxy-phenyl)-5H-pyrrolo[3,2-d]pyrimidine-7-carboxylic acid (R)-piperidin-3-ylamide hydrochloride (example A164) and acetyl chloride the title compound is obtained as colorless solid.

MS (ESI): m/z=482 (MH$^+$, 100%).
$^1$H-NMR (300 MHz, DMSO-d$_6$): 11.89 (br.s, 1H, —NH); 9.03 (s, 0.5H); 9.02 (s, 0.5H); 8.63 (d, J=7.2, 0.5H, —NH); 8.57 (d, J=8.3, 0.5H, —NH); 8.30 (s, 0.5H); 8.28 (s, 0.5H); 7.41 (d, J=9.9, 1H); 7.18 (d, J=13.4, 1H); 4.08-3.90 (m, 1.5H); 3.87 (s, 3H & d, J=6.8, 2H); 3.72 (m, 0.5H); 3.60-3.19 (m, 3H); 2.06 (s, 1.5H); 1.97 (s, 1.5H & m, 1H); 1.86-1.45 (m, 3H); 0.94 (m, 1H); 0.33 (m, 2H); 0.17 (m, 2H).

Example 101

4-(2-Cyclopropylmethoxy-4-fluoro-5-methoxy-phenyl)-5H-pyrrolo[3,2-d]pyrimidine-7-carboxylic acid ((R)-1-propionyl-piperidin-3-yl)-amide Starting from 4-(2-Cyclopropylmethoxy-4-fluoro-5-methoxy-phenyl)-5H-pyrrolo[3,2-d]pyrimidine-7-carboxylic acid (R)-piperidin-3-ylamide hydrochloride (example A164) and propionyl chloride the title compound is obtained as colorless solid.

MS (ESI): m/z=496 (MH$^+$, 100%).
$^1$H-NMR (300 MHz, DMSO-d$_6$): 12.31 (br.s, 1H, —NH); 9.01 (s, 1H); 8.61 (d, J=7.5, 0.5H, —NH); 8.57 (d, J=7.5, 0.5H, —NH); 8.30 (s, 0.5H); 8.29 (s, 0.5H); 7.41 (d, J=9.9, 1H); 7.18 (d, J=13.4, 1H); 4.08-3.91 (m, 1.5H); 3.85 (s, 3H & d, J=6.7, 2H); 3.76 (m, 0.5H); 3.57 (m, 1H); 3.48-3.21 (m, 2H); 2.45-2.23 (m, 2H); 1.98 (m, 1H); 1.75 (m, 2H); 1.53 (m, 1H); 1.05-0.89 (m, 4H); 0.32 (m, 2H); 0.18 (m, 2H).

Example 102

4-(2-Cyclopropylmethoxy-4-fluoro-5-methoxy-phenyl)-5H-pyrrolo[3,2-d]pyrimidine-7-carboxylic acid [(R)-1-(2-methoxy-acetyl)piperidin-3-yl]-amide Starting from 4-(2-Cyclopropylmethoxy-4-fluoro-5-methoxy-phenyl)-5H-pyrrolo[3,2-d]pyrimidine-7-carboxylic acid (R)-piperidin-3-ylamide hydrochloride (example A164) and methoxy-acetyl chloride the title compound is obtained as colorless solid.

MS (ESI): m/z=512 (MH$^+$, 100%).
$^1$H-NMR (300 MHz, DMSO-d$_6$): 11.90 (br.s, 1H, —NH); 9.02 (s, 1H); 8.60 (br.m, 1H, —NH); 8.31 (m, 1H); 7.41 (d, J=9.8, 1H); 7.18 (d, J=13.3, 1H); 4.16-3.95 (m, 3H); 3.92 (m, 0.5H); 3.84 (s, 3H & d, J=6.8, 2H); 3.69 (m, 0.5H); 3.55-3.21 (m, 3H); 3.30 (s, 1H); 3.17 (s, 1H); 1.98 (m, 1H); 1.75 (m, 2H); 1.57 (m, 1H); 0.93 (m, 1H); 0.33 (m, 2H); 0.17 (m, 2H).

Example 103

4-(2-Cyclopropylmethoxy-4-fluoro-5-methoxy-phenyl)-5H-pyrrolo[3,2-d]pyrimidine-7-carboxylic acid ((R)-1-acetyl-pyrrolidin-3-yl)-amide Starting from 4-(2-Cyclopropylmethoxy-4-fluoro-5-methoxy-phenyl)-5H-pyrrolo[3,2-d]pyrimidine-7-carboxylic acid (R)-pyrrolidin-3-ylamide hydrochloride (example A165) and acetyl chloride the title compound is obtained as colorless MS (ESI): m/z=426 (MH$^+$, 100%).
$^1$H-NMR (300 MHz, DMSO-d$_6$): 12.41 (br.s, 1H, —NH); 9.39 (br.s, 1H, —NH$_2$); 9.11 (s, 1H); 8.69 (d, J=6.7, 1H, —NH); 8.51 (d, J=3.3, 1H); 7.45 (d, J=9.8, 1H); 7.21 (d, J=13.3, 1H); 4.65 (m, 1H); 3.87 (d, J=6.8, 2H); 3.86 s, 3H); 3.52-3.46 (m, 1H); 3.30-3.14 (m, 1H); 2.32 (m, 1H); 2.04 (m, 1H); 0.93 (m, 1H); 0.33 (m, 2H); 0.19 (m, 2H). solid.

Example 104

4-(2-Cyclopropylmethoxy-4-fluoro-5-methoxy-phenyl)-5H-pyrrolo[3,2-d]pyrimidine-7-carboxylic acid ((R)-1-propionyl-pyrrolidin-3-yl)-amide Starting from 4-(2-Cyclopropylmethoxy-4-fluoro-5-methoxy-phenyl)-5H-pyrrolo[3,2-d]pyrimidine-7-carboxylic acid (R)-pyrrolidin-3-ylamide hydrochloride (example A165) and propionyl chloride the title compound is obtained as colorless solid.

MS (ESI): m/z=482 (MH$^+$, 100%).
$^1$H-NMR (400 MHz, DMSO-d$_6$): 11.98 (br.s, 1H, —NH); 9.04 (s, 1H); 8.62 (d, J=7.0, 1H, —NH); 8.59 (d, J=7.0, 0.5H, —NH); 8.31 (d, J=1.8, 1H); 7.41 (d, J=9.6, 1H); 7.18 (d, J=13.3, 1H); 4.59 (m, 0.5H); 4.51 (m, 0.5H); 3.84 (s, 3H & d, J=4.4, 2H & m, 0.5H); 3.70-3.58 (m, 1.5H); 3.56-3.38 (m, 1.5H); 3.30 (m, 0.5H); 2.33-2.18 (m, 1H & m, 2H); 2.06 (m, 0.5H); 1.94 (m, 0.5H); 1.00 (m, 3H); 0.92 (m, 1H); 0.33 (m, 2H); 0.17 (m, 2H).

Example 105

4-(2-Cyclopropylmethoxy-4-fluoro-5-methoxy-phenyl)-5H-pyrrolo[3,2-d]pyrimidine-7-carboxylic acid [(R)-1-(2-methoxy-acetyl)-pyrrolidin-3-yl]amide Starting from 4-(2-Cyclopropylmethoxy-4-fluoro-5-methoxy-phenyl)-5H-pyrrolo[3,2-d]pyrimidine-7-carboxylic acid (R)-pyrrolidin-3-ylamide hydrochloride (example A165) and methoxy-acetyl chloride the title compound is obtained as colorless solid.

MS (ESI): m/z=498 (MH$^+$, 100%).

$^1$H-NMR (400 MHz, DMSO-d$_6$): 11.95 (br.s, 1H, —NH); 9.04 (s, 1H); 8.61 (d, J=7.2, 1H, —NH); 8.59 (d, J=7.2, 0.5H, —NH); 8.31 (s, 1H); 7.41 (d, J=9.7, 1H); 7.18 (d, J=13.2, 1H); 4.59 (m, 0.5H); 4.51 (m, 0.5H); 4.10-3.97 (m, 2H); 3.84 (s, 3H & d, J=4.4, 2H); 3.79 (m, 0.5H); 3.70 (m, 0.5H); 3.57 (m, 1H); 3.48 (m, 0.5H); 3.41-3.30 (m, 1.5H); 3.31 (s, 1.5H); 3.29 (s, 1.5H); 2.33-2.17 (m, 1H); 2.10 (m, 0.5H); 1.93 (m, 0.5H); 0.92 (m, 1H); 0.33 (m, 2H); 0.17 (m, 2H).

Example 106 trans-4-(2-Cyclopropylmethoxy-5-fluoro-4-methoxy-phenyl)-5H-pyrrolo[3,2-d]pyrimidine-7-carboxylic acid (4-acetylamino-cyclohexyl)-amide Starting from trans-4-(2-cyclopropylmethoxy-5-fluoro-4-methoxy-phenyl)-5H-pyrrolo[3,2-d]pyrimidine-7-carboxylic acid (4-amino-cyclohexyl)-amide (example A139) and acetyl chloride the title compound is obtained as colorless solid.

MS (ESI): m/z=496 (MH$^+$, 100%).

$^1$H-NMR (300 MHz, DMSO-d$_6$): 11.95 (br.s, 1H, —NH); 9.01 (s, 1H); 8.36 (d, J=7.8, 1H, —NH); 8.24 (s, 1H); 7.73 (d, J=7.7, 1H, —NH); 7.49 (d, J=11.8, 1H); 6.93 (d, J=7.3, 1H); 3.97 (s, 3H); 3.95 (d, J=7.1, 2H); 3.81 (m, 1H); 3.58 (m, 1H); 2.01 (m, 2H); 1.86 (m, 2H); 1.79 (s, 3H); 1.36 (m, 4H); 0.97 (m, 1H); 0.36 (m, 2H); 0.21 (m, 2H).

Example 107 trans-4-(2-Cyclopropylmethoxy-5-fluoro-4-methoxy-phenyl)-5H-pyrrolo[3,2-d]pyrimidine-7-carboxylic acid [4-(2-methoxy-acetylamino)-cyclohexyl]-amide Starting from trans-4-(2-cyclopropylmethoxy-5-fluoro-4-methoxy-phenyl)-5H-pyrrolo[3,2-d]pyrimidine-7-carboxylic acid (4-amino-cyclohexyl)-amide (example A139) and methoxy-acetyl chloride the title compound is obtained as colorless solid.

MS (ESI): m/z=526 (MH$^+$, 100%).

$^1$H-NMR (300 MHz, DMSO-d$_6$): 11.94 (br.s, 1H, —NH); 9.01 (s, 1H); 8.35 (d, J=7.8, 1H, —NH); 8.24 (s, 1H); 7.57 (d, J=8.2, 1H, —NH); 7.49 (d, J=11.9, 1H); 6.93 (d, J=7.3, 1H); 3.97 (s, 3H); 3.95 (d, J=7.0, 2H); 3.79 (m, 1H & s, 2H); 3.54 (m, 1H); 3.31 (s, 3H); 2.03 (m, 2H); 1.80 (m, 2H); 1.45 (m, 4H); 0.96 (m, 1H); 0.36 (m, 2H); 0.21 (m, 2H).

Example 108

4-(2-Cyclopropylmethoxy-5-fluoro-4-methoxy-phenyl)-5H-pyrrolo[3,2-d]pyrimidine-7-carboxylic acid (1-acetyl-piperidin-4-yl)-amide Starting from 4-(2-cyclopropylmethoxy-5-fluoro-4-methoxy-phenyl)-5H-pyrrolo[3,2-d]pyrimidine-7-carboxylic acid piperidin-4-ylamide hydrochloride (example A166) and acetyl chloride the title compound is obtained as colorless solid.

MS (ESI): m/z=482 (MH$^+$, 100%).

$^1$H-NMR (300 MHz, DMSO-d$_6$): 11.98 (br.s, 1H, —NH); 9.01 (s, 1H); 8.51 (d, J=7.8, 1H; —NH); 8.27 (s, 1H); 7.50 (d, J=11.9, 1H); 6.93 (d, J=7.3, 1H); 4.20 (m, 1H); 4.13 (m, 1H); 3.97 (s, 3H); 3.95 (d, J=7.1, 2H); 3.79 (m, 1H); 3.27 (m, 1H); 2.92 (m, 1H); 2.04 (s, 3H); 1.97 (m, 2H); 1.56 (m, 1H); 1.40 (m, 1H); 0.95 (m, 1H); 0.36 (m, 2H), 0.22 (m, 2H).

Example 109

4-(2-Cyclopropylmethoxy-5-fluoro-4-methoxy-phenyl)-5H-pyrrolo[3,2-d]pyrimidine-7-carboxylic acid [1-(2-methoxy-ethanoyl)-piperidin-4-yl]amide Starting from 4-(2-cyclopropylmethoxy-5-fluoro-4-methoxy-phenyl)-5H-pyrrolo[3,2-d]pyrimidine-7-carboxylic acid piperidin-4-ylamide hydrochloride (example A166) and methoxy-acetyl chloride the title compound is obtained as colorless solid.

MS (ESI): m/z=512 (MH$^+$, 100%).

$^1$H-NMR (300 MHz, DMSO-d$_6$): 11.98 (br.s, 1H, —NH); 9.01 (s, 1H); 8.51 (d, J=7.8, 1H; —NH); 8.27 (s, 1H); 7.50 (d, J=11.9, 1H); 6.93 (d, J=7.3, 1H); 4.16 (m, 1H); 4.12 (d, J=2.5, 2H); 3.97 (s, 3H); 3.95 (d, J=7.1, 2H); 3.76 (m, 1H); 3.31 (s, 3H); 3.22 (m, 1H); 2.95 (m, 1H); 1.98 (m, 2H); 1.55 (m, 1H); 1.40 (m, 1H); 0.96 (m, 1H); 0.36 (m, 2H), 0.22 (m, 2H).

Example 110

4-(2-Cyclopropylmethoxy-5-fluoro-4-methoxy-phenyl)-5H-pyrrolo[3,2-d]pyrimidine-7-carboxylic acid (1-propionyl-piperidin-4-yl)-amide Starting from 4-(2-cyclopropylmethoxy-5-fluoro-4-methoxy-phenyl)-5H-pyrrolo[3,2-d]pyrimidine-7-carboxylic acid piperidin-4-ylamide hydrochloride (example A166) and propionyl chloride the title compound is obtained as colorless solid.

MS (ESI): m/z=496 (MH$^+$, 100%).

$^1$H-NMR (300 MHz, DMSO-d$_6$): 11.97 (br.s, 1H, —NH); 9.00 (s, 1H); 8.51 (d, J=7.8, 1H; —NH); 8.27 (s, 1H); 7.49 (d, J=11.8, 1H); 6.93 (d, J=7.3, 1H); 4.23 (m, 1H); 4.13 (m, 1H); 3.97 (s, 3H); 3.95 (d, J=7.1, 2H); 3.83 (m, 1H); 3.24 (m, 1H); 2.93 (m, 1H); 2.36 (qu, J=7.4, 3H); 1.96 (m, 2H); 1.53 (m, 1H); 1.40 (m, 1H); 1.01 (t, J=7.4, 3H); 0.97 (m, 1H); 0.36 (m, 2H), 0.22 (m, 2H).

Example 111

4-(2-Cyclopropylmethoxy-5-fluoro-4-methoxy-phenyl)-5H-pyrrolo[3,2-d]pyrimidine-7-carboxylic acid ((R)-1-propionyl-piperidin-3-yl)-amide Starting from 4-(2-cyclopropylmethoxy-5-fluoro-4-methoxy-phenyl)-5H-pyrrolo[3,2-d]pyrimidine-7-carboxylic acid (R)-piperidin-3-ylamide hydrochloride (example A167) and propionyl chloride the title compound is obtained as colorless solid.

MS (ESI): m/z=496 (MH$^+$, 100%).

$^1$H-NMR (300 MHz, DMSO-d$_6$): 11.98 (br.s, 1H, —NH); 8.97 (s, 1H); 8.61 (d, J=7.3, 0.5H; —NH); 8.56 (d, J=7.3, 0.5H, —NH); 8.28 (s, 0.5H); 8.27 (s, 0.5H); 7.50 (d, J=11.9, 1H); 6.93 (d, J=7.3, 1H); 4.16 (m, 1H); 4.12 (d, J=2.5, 2H); 3.97 (s, 3H & m, 1.5H); 3.95 (d, J=7.1, 2H); 3.77 (m, 0.5H); 3.57 (m, 1H); 3.40 (m, 1.5H); 3.27 (m, 0.5H); 2.38 (m, 1H); 2.32 (m, 1H); 1.96 (m, 1H); 1.74 (m, 2H); 1.53 (m, 1H); 0.99 (m, 3H & m, 1H); 0.36 (m, 2H), 0.21 (m, 2H).

Example 112

4-(2-Cyclopropylmethoxy-5-fluoro-4-methoxy-phenyl)-5H-pyrrolo[3,2-d]pyrimidine-7-carboxylic acid [(R)-1-(2-methoxy-ethanoyl)-piperidin-3-yl]amide Starting from 4-(2-cyclopropylmethoxy-5-fluoro-4-methoxy-phenyl)-5H-pyrrolo[3,2-d]pyrimidine-7-carboxylic acid (R)-piperidin-3-ylamide hydrochloride (example A167) and methoxy-acetyl chloride the title compound is obtained as colorless solid.

Example 113

4-(2-Cyclopropylmethoxy-5-fluoro-4-methoxy-phenyl)-5H-pyrrolo[3,2-d]pyrimidine-7-carboxylic acid ((R)-1-acetyl-piperidin-3-yl)-amide Starting from 4-(2-cyclopropylmethoxy-5-fluoro-4-methoxy-phenyl)-5H-pyrrolo[3,2-d]pyrimidine-7-carboxylic acid (R)-piperidin-3-ylamide hydrochloride (example A167) and acetyl chloride the title compound is obtained as colorless solid.

MS (ESI): m/z=482 (MH$^+$, 100%).

$^1$H-NMR (300 MHz, DMSO-d$_6$): 11.98 (br.s, 1H, —NH); 8.99 (s, 0.5H); 8.98 (s, 0.5H); 8.64 (d, J=7.3, 0.5H; —NH); 8.56 (d, J=7.3, 0.5H, —NH); 8.28 (s, 0.5H); 8.26 (s, 0.5H); 7.50 (d, J=11.8, 1H); 6.93 (d, J=7.3, 1H); 3.97 (s, 3H & m, 1.5H); 3.94 (d, J=7.3, 2H); 3.73 (m, 0.5H); 3.49 (m, 2H); 3.41 (m, 0.5H); 3.22 (m, 0.5H); 2.05 (s, 1.5H); 1.98 (s, 1.5H & m, 1H); 1.71 (m, 2H); 1.54 (m, 1H); 0.97 (m, 1H); 0.36 (m, 2H), 0.22 (m, 2H).

Example 114

4-(2-Cyclopropylmethoxy-5-fluoro-4-methoxy-phenyl)-5H-pyrrolo[3,2-d]pyrimidine-7-carboxylic acid ((S)-1-propionyl-piperidin-3-yl)-amide Starting from 4-(2-cyclopropylmethoxy-5-fluoro-4-methoxy-phenyl)-5H-pyrrolo[3,2-d]pyrimidine-7-carboxylic acid (S)-piperidin-3-ylamide hydrochloride (example A168) and propionyl chloride the title compound is obtained as colorless solid.

MS (ESI): m/z=496 (MH$^+$, 100%).

$^1$H-NMR (300 MHz, DMSO-d$_6$): 11.98 (br.s, 1H, —NH); 8.97 (s, 1H); 8.61 (d, J=7.3, 0.5H; —NH); 8.56 (d, J=7.3, 0.5H, —NH); 8.28 (s, 0.5H); 8.27 (s, 0.5H); 7.50 (d, J=11.9, 1H); 6.93 (d, J=7.3, 1H); 4.16 (m, 1H); 4.12 (d, J=2.5, 2H); 3.97 (s, 3H & m, 1.5H); 3.95 (d, J=7.1, 2H); 3.77 (m, 0.5H); 3.57 (m, 1H); 3.40 (m, 1.5H); 3.27 (m, 0.5H); 2.38 (m, 1H); 2.32 (m, 1H); 1.96 (m, 2H); 1.74 (m, 2H); 1.53 (m, 1H); 0.99 (m, 3H & m, 1H); 0.36 (m, 1H), 0.21 (m, 2H).

Example 115

4-(2-Cyclopropylmethoxy-5-fluoro-4-methoxy-phenyl)-5H-pyrrolo[3,2-d]pyrimidine-7-carboxylic acid [(S)-1-(2-methoxy-ethanoyl)-piperidin-3-yl]amide Starting from 4-(2-cyclopropylmethoxy-5-fluoro-4-methoxy-phenyl)-5H-pyrrolo[3,2-d]pyrimidine-7-carboxylic acid (S)-piperidin-3-ylamide hydrochloride (example A168) and methoxy-acetyl chloride the title compound is obtained as colorless solid.

Example 116

4-(2-Cyclopropylmethoxy-5-fluoro-4-methoxy-phenyl)-5H-pyrrolo[3,2-d]pyrimidine-7-carboxylic acid ((S)-1-acetyl-piperidin-3-yl)-amide Starting from 4-(2-cyclopropylmethoxy-5-fluoro-4-methoxy-phenyl)-5H-pyrrolo[3,2-d]pyrimidine-7-carboxylic acid (S)-piperidin-3-ylamide hydrochloride (example A168) and acetyl chloride the title compound is obtained as colorless solid.

MS (ESI): m/z=482 (MH$^+$, 100%).

$^1$H-NMR (300 MHz, DMSO-d$_6$): 11.98 (br.s, 1H, —NH); 8.99 (s, 0.5H); 8.98 (s, 0.5H); 8.64 (d, J=7.3, 0.5H; —NH); 8.56 (d, J=7.3, 0.5H, —NH); 8.28 (s, 0.5H); 8.26 (s, 0.5H); 7.50 (d, J=11.8, 1H); 6.93 (d, J=7.3, 1H); 3.97 (s, 3H & m, 1.5H); 3.94 (d, J=7.3, 2H); 3.73 (m, 0.5H); 3.49 (m, 2H); 3.41 (m, 0.5H); 3.22 (m, 0.5H); 2.05 (s, 1.5H); 1.98 (s, 1.5H & m, 1H); 1.71 (m, 2H); 1.54 (m, 1H); 0.97 (m, 1H); 0.36 (m, 2H), 0.22 (m, 2H).

Example 117

4-(2-Cyclopropylmethoxy-5-fluoro-4-methoxy-phenyl)-5H-pyrrolo[3,2-d]pyrimidine-7-carboxylic acid ((R)-1-acetyl-pyrrolidin-3-yl)-amide Starting from 4-(2-cyclopropylmethoxy-5-fluoro-4-methoxy-phenyl)-5H-pyrrolo[3,2-d]pyrimidine-7-carboxylic acid (R)-pyrrolidin-3-ylamide hydrochloride (example A169) and acetyl chloride the title compound is obtained as colorless solid.

MS (ESI): m/z=468.1 (MH$^+$, 100%).

$^1$H-NMR (300 MHz, DMSO-d$_6$): 11.93 (br.s, 1H, —NH); 9.01 (s, 1H); 8.64 (d, J=7.1, 0.5H; —NH); 8.61 (d, J=8.6, 0.5H, —NH); 8.29 (d, J=2.3, 1H); 7.50 (dd, J$_1$=11.8, J$_2$=1.3, 1H); 6.93 (d, J=7.2, 1H); 4.61 (m, 0.5H); 4.51 (m, 0.5H); 3.97 (s, 3H); 3.95 (d, J=7.0, 2H); 3.85 (m, 0.5H); 3.67-3.56 (m, 1.5H); 3.54-3.30 (m, 1.5H); 3.32 (m, 0.5H); 2.30 (m, 0.5H); 2.22 (m, 0.5H); 2.10 (m, 0.5H); 1.98 (m, 1.5H); 1.96 (m, 1.5H); 1.95 (m, 0.5H); 0.96 (m, 1H); 0.36 (m, 2H), 0.22 (m, 2H).

Example 118

4-(2-Cyclopropylmethoxy-5-fluoro-4-methoxy-phenyl)-5H-pyrrolo[3,2-d]pyrimidine-7-carboxylic acid ((R)-1-propionyl-pyrrolidin-3-yl)-amide Starting from 4-(2-cyclopropylmethoxy-5-fluoro-4-methoxy-phenyl)-5H-pyrrolo[3,2-d]pyrimidine-7-carboxylic acid (R)-pyrrolidin-3-ylamide hydrochloride (example A169) and propionyl chloride the title compound is obtained as colorless solid.

MS (ESI): m/z=482 (MH+, 100%).

¹H-NMR (300 MHz, DMSO-d₆): 11.97 (br.s, 1H, —NH); 9.00 (s, 0.5H); 8.99 (s, 0.5H); 8.64 (d, J=7.1, 0.5H; —NH); 8.61 (d, J=8.6, 0.5H, —NH); 8.29 (d, J=1.8, 1H); 7.50 (dd, J₁=11.9, J₂=1.1, 1H); 6.93 (d, J=7.3, 1H); 4.61 (m, 0.5H); 4.51 (m, 0.5H); 3.97 (s, 3H); 3.95 (d, J=6.9, 2H); 3.82 (m, 0.5H); 3.65 (m, 0.5H); 3.51 (m, 0.5H); 3.42 (m, 1H); 3.33 (m, 0.5H); 2.33-2.17 (m, 3H); 2.05 (m, 0.5H); 1.93 (m, 0.5H); 0.98 (m, 1H); 0.36 (m, 2H), 0.23 (m, 2H).

Example 119

4-(2-Cyclopropylmethoxy-5-fluoro-4-methoxy-phenyl)-5H-pyrrolo[3,2-d]pyrimidine-7-carboxylic acid [(R)-1-(2-methoxy-acetyl)-pyrrolidin-3-yl]amide Starting from 4-(2-cyclopropylmethoxy-5-fluoro-4-methoxy-phenyl)-5H-pyrrolo[3,2-d]pyrimidine-7-carboxylic acid (R)-pyrrolidin-3-ylamide hydrochloride (example A169) and methoxy-acetyl chloride the title compound is obtained as colorless solid.

MS (ESI): m/z=498 (MH+, 100%).

¹H-NMR (300 MHz, DMSO-d₆): 11.21 (br.s, 1H, —NH); 9.00 (s, 0.5H); 8.99 (s, 0.5H); 8.63 (d, J=7.3, 0.5H; —NH); 8.61 (d, J=7.3, 0.5H, —NH); 8.29 (s, 1H); 7.50 (dd, J₁=11.8, J₂=1.0, 1H); 6.93 (d, J=7.3, 1H); 4.61 (m, 0.5H); 4.51 (m, 0.5H); 4.07-4.01 (m, 2H); 3.97 (s, 3H); 3.95 (d, J=7.0, 2H); 3.79 (m, 0.5H); 3.69 (m, 0.5H); 3.58 (m, 1H); 3.47 (m, 0.5H); 3.41-3.30 (m, 1.5H); 3.32 (m, 1.5H); 3.30 (m, 1.5H); 2.29 (m, 0.5H); 2.20 (m, 0.5H); 2.06 (m, 0.5H); 1.93 (m, 0.5H); 0.95 (m, 1H); 0.33 (m, 2H), 0.21 (m, 2H).

Example 120 trans-4-(2-Cyclopropylmethoxy-5-methyl-phenyl)-5H-pyrrolo[3,2-d]pyrimidine-7-carboxylic acid (4-acetylamino-cyclohexyl)-amide Starting from trans-4-(2-cyclopropylmethoxy-5-methyl-phenyl)-5H-pyrrolo[3,2-d]pyrimidine-7-carboxylic acid (4-amino-cyclohexyl)-amide (example A170) and acetyl chloride the title compound is obtained as colorless solid.

MS (ESI): m/z=462 (MH+, 100%).

¹H-NMR (400 MHz, DMSO-d₆): 11.96 (br.s, 1H, —NH); 9.03 (s, 1H); 8.36 (d, J=7.8, 1H, —NH); 8.22 (s, 1H); 7.73 (d, J=7.7, 1H, —NH); 7.44 (d, J=1.9, 1H); 7.33 (dd, J₁=8.4, J₂=1.9, 1H); 7.06 (d, J=8.4, 1H); 3.86 (d, J=6.8, 2H); 3.82 (m, 1H); 3.59 (m, 1H); 2.33 (s, 3H); 2.02 (m, 2H); 1.87 (m, 2H); 1.63 (s, 3H); 1.46-1.27 (m, 4H); 0.93 (m, 1H); 0.34 (m, 2H); 0.19 (m, 2H).

Example 121 trans-4-(2-Cyclopropylmethoxy-5-methyl-phenyl)-5H-pyrrolo[3,2-d]pyrimidine-7-carboxylic acid [4-(2-methoxy-acetylamino)-cyclohexyl]-amide Starting from trans-4-(2-cyclopropylmethoxy-5-methyl-phenyl)-5H-pyrrolo[3,2-d]pyrimidine-7-carboxylic acid (4-amino-cyclohexyl)-amide (example A170) and methoxy-acetyl chloride the title compound is obtained as colorless solid.

MS (ESI): m/z=492 (MH+, 100%).

¹H-NMR (400 MHz, DMSO-d₆): 11.96 (br.s, 1H, —NH); 9.03 (s, 1H); 8.36 (d, J=7.8, 1H, —NH); 8.22 (s, 1H); 7.56 (d, J=8.2, 1H, —NH); 7.44 (d, J=1.9, 1H); 7.33 (dd, J₁=8.4, J₂=1.9, 1H); 7.06 (d, J=8.4, 1H); 3.86 (d, J=6.8, 2H); 3.78 (s, 2H & m, 1H); 3.71 (m, 1H); 3.31 (s, 3H); 2.33 (s, 3H); 2.02 (m, 2H); 1.87 (m, 2H); 1.32 (m, 4H); 0.93 (m, 1H); 0.34 (m, 2H); 0.19 (m, 2H).

Example 122 trans-(4-{[4-(2-Cyclopropylmethoxy-5-methyl-phenyl)-5H-pyrrolo[3,2-d]pyrimidine-7-carbonyl]-amino}-cyclohexyl)-carbamic acid ethyl ester Starting from trans-4-(2-cyclopropylmethoxy-5-methyl-phenyl)-5H-pyrrolo[3,2-d]pyrimidine-7-carboxylic acid (4-amino-cyclohexyl)-amide (example A170) and ethyl chloroformate the title compound is obtained as colorless solid.

MS (ESI): m/z=492 (MH+, 100%).

¹H-NMR 400 MHz, DMSO-d₆): 11.96 (br.s, 1H, —NH); 9.03 (s, 1H); 8.36 (d, J=7.8, 1H, —NH); 8.22 (s, 1H); 7.44 (d, J=1.9, 1H); 7.33 (dd, J₁=8.4, J₂=1.9, 1H); 7.06 (d, J=8.4, 1H); 7.01 (d, J=7.1, 1H, —NH); 3.98 (qu, J=7.0, 1H); 3.86 (d, J=6.8, 2H); 3.79 (m, 1H); 3.34 (m, 1H); 2.33 (s, 3H); 2.01 (m, 2H); 1.88 (m, 2H); 1.46-1.26 (m, 4H); 1.16 (t, J=7.0, 3H); 0.93 (m, 1H); 0.34 (m, 2H); 0.19 (m, 2H).

Example 123

4-(2-Cyclopropylmethoxy-5-methyl-phenyl)-5H-pyrrolo[3,2-d]pyrimidine-7-carboxylic acid (1-acetyl-piperidin-4-yl)-amide Starting from 4-(2-cyclopropylmethoxy-5-methyl-phenyl)-5H-pyrrolo[3,2-d]pyrimidine-7-carboxylic acid piperidin-4-ylamide (example A172) and acetyl chloride the title compound is obtained as colorless solid.

MS (ESI): m/z=448 (MH+, 100%).

¹H-NMR 300 MHz, DMSO-d₆): 11.99 (br.s, 1H, —NH); 9.03 (s, 1H); 8.52 (d, J=7.8, 1H, —NH); 8.25 (s, 1H); 7.44 (d, J=2.0, 1H); 7.33 (dd, J₁=8.5, J₂=2.0, 1H); 7.06 (d, J=8.5, 1H); 4.23-4.10 (m, 2H); 3.87 (d, J=6.8, 2H); 3.80 (m, 1H); 3.27 (m, 1H); 2.92 (m, 1H); 2.33 (s, 3H); 2.04 (s, 3H); 1.97 (m, 2H); 1.56 (m, 1H); 1.39 (m, 1H); 0.93 (m, 1H); 0.34 (m, 2H); 0.19 (m, 2H).

Example 124

4-(2-Cyclopropylmethoxy-5-methyl-phenyl)-5H-pyrrolo[3,2-d]pyrimidine-7-carboxylic acid [1-(2-methoxy-acetyl)piperidin-4-yl]-amide Starting from 4-(2-cyclopropylmethoxy-5-methyl-phenyl)-5H-pyrrolo[3,2-d]pyrimidine-7-carboxylic acid piperidin-4-ylamide (example A172) and methoxy-acetyl chloride the title compound is obtained as colorless solid.

MS (ESI): m/z=478 (MH+, 100%).

¹H-NMR 300 MHz, DMSO-d₆): 11.99 (br.s, 1H, —NH); 9.03 (s, 1H); 8.51 (d, J=7.9, 1H, —NH); 8.25 (s, 1H); 7.44 (d, J=1.9, 1H); 7.33 (dd, J₁=8.5, J₂=1.9, 1H); 7.06 (d, J=8.5, 1H); 4.16 (m, 2H); 4.12 (d, J=2.7, 2H); 3.87 (d, J=6.9, 2H); 3.76 (m, 1H); 3.31 (s, 3H); 3.22 (m, 1H); 2.96 (m, 1H); 2.33 (s, 3H); 1.97 (m, 2H); 1.56 (m, 1H); 1.41 (m, 1H); 0.93 (m, 1H); 0.34 (m, 2H); 0.19 (m, 2H).

Example 125

4-{[4-(2-Cyclopropylmethoxy-5-methyl-phenyl)-5H-pyrrolo[3,2-d]pyrimidine-7-carbonyl]-amino}-piperidine-1-carboxylic acid ethyl ester Starting from 4-(2-cyclopropylmethoxy-5-methyl-phenyl)-5H-pyrrolo[3,2-d]pyrimidine-7-carboxylic acid piperidin-4-ylamide (example A172) and ethyl chloroformate the title compound is obtained as colorless solid.

MS (ESI): m/z=478 (MH+, 100%).

¹H-NMR 400 MHz, DMSO-d₆): 11.98 (br.s, 1H, —NH); 9.03 (s, 1H); 8.51 (d, J=7.8, 1H, —NH); 8.24 (s, 1H); 7.44 (d, J=2.1, 1H); 7.33 (dd, J₁=8.5, J₂=2.1, 1H); 7.06 (d, J=8.5, 1H); 4.15-4.03 (m, 2H); 4.06 (qu, J=7.1, 2H); 3.89 (m, 2H); 3.87 (d, J=6.9, 2H); 2.67 (m, 1H); 2.33 (s, 3H); 1.96 (m, 2H); 1.48 (m, 2H); 1.20 (t, J=7.1, 3H); 0.93 (m, 1H); 0.34 (m, 2H); 0.19 (m, 2H).

Example 126 trans-4-(5-Cyclobutylmethoxy-benzo[1,3]dioxol-4-yl)-5H-pyrrolo[3,2-d]pyrimidine-7-carboxylic acid (4-acetylamino-cyclohexyl)-amide Starting from trans-4-(5-cyclobutylmethoxy-benzo[1,3]dioxol-4-yl)-5H-pyrrolo[3,2-d]pyrimidine-7-carboxylic acid (4-amino-cyclohexyl)-amide hydrochloride (example A173) and acetyl chloride the title compound is obtained as colorless solid.

MS (ESI): m/z=506 (MH+).

¹H-NMR (400 MHz, DMSO-d₆): 12.29 (br.s, 1H, —NH); 9.02 (s, 1H); 8.29 (d, J=7.8, 1H, —NH); 8.24 (s, 1H); 7.73 (d, J=7.7, 1H, —NH); 7.01 (d, J=8.6, 1H); 6.59 (d, J=8.6, 1H); 6.01 (s, 2H); 3.84 (d, J=6.3, 2H); 3.80 (m, 1H); 3.58 (m, 1H); 2.38 (m, 1H); 2.01 (m, 2H); 1.86 (m, 2H); 1.79 (s, 3H); 1.68 (m, 3H); 1.53 (m, 3H); 1.36 (m, 4H).

Example 127 trans-4-(5-Cyclobutylmethoxy-benzo[1,3]dioxol-4-yl)-5H-pyrrolo[3,2-d]pyrimidine-7-carboxylic acid [4-(cyclopropanecarbonyl-amino)cyclohexyl]-amide Starting from trans-4-(5-cyclobutylmethoxy-benzo[1,3]dioxol-4-yl)-5H-pyrrolo[3,2-d]pyrimidine-7-carboxylic acid (4-amino-cyclohexyl)-amide hydrochloride (example A173) and cyclopropanecarbonyl chloride the title compound is obtained as colorless solid.

MS (ESI): m/z=532 (MH+).

¹H-NMR (400 MHz, DMSO-d₆): 12.29 (br.s, 1H, —NH); 9.02 (s, 1H); 8.29 (d, J=7.8, 1H, —NH); 8.24 (s, 1H); 7.94 (d, J=7.7, 1H, —NH); 7.01 (d, J=8.6, 1H); 6.59 (d, J=8.6, 1H); 6.01 (s, 2H); 3.84 (d, J=6.2, 2H); 3.80 (m, 1H); 3.60 (m, 1H); 2.39 (m, 1H); 2.02 (m, 2H); 1.88 (m, 2H); 1.69 (m, 3H); 1.51 (m, 4H); 1.39 (m, 4H); 0.63 (m, 4H).

Example 128 trans-4-(5-Cyclobutylmethoxy-benzo[1,3]dioxol-4-yl)-5H-pyrrolo[3,2-d]pyrimidine-7-carboxylic acid [4-(2-methoxy-ethanoylamino)-cyclohexyl]-amide Starting from trans-4-(5-cyclobutyl methoxy-benzo[1,3]dioxol-4-yl)-5H-pyrrolo[3,2-d]pyrimidine-7-carboxylic acid (4-amino-cyclohexyl)-amide hydrochloride (example A173) and methoxy-acetyl chloride the title compound is obtained as colorless solid.

MS (ESI): m/z=536 (MH+).

¹H-NMR (400 MHz, DMSO-d₆): 12.28 (br.s, 1H, —NH); 9.01 (s, 1H); 8.28 (d, J=7.8, 1H, —NH); 8.24 (s, 1H); 7.56 (d, J=8.2, 1H, —NH); 7.01 (d, J=8.6, 1H); 6.59 (d, J=8.6, 1H); 6.00 (s, 2H); 3.84 (d, J=6.2, 2H); 3.78 (s, 2H & m, 1H); 3.70 (m, 1H); 3.31 (s, 3H); 2.38 (m, 1H); 2.01 (m, 2H); 1.82 (m, 2H); 1.68 (m, 3H); 1.50 (m, 3H); 1.44 (m, 4H).

Example 129

4-(5-Cyclobutylmethoxy-benzo[1,3]dioxol-4-yl)-5H-pyrrolo[3,2-d]pyrimidine-7-carboxylic acid (1-acetyl-piperidin-4-yl)-amide Starting from 4-(5-cyclobutylmethoxy-benzo[1,3]dioxol-4-yl)-5H-pyrrolo[3,2-d]pyrimidine-7-carboxylic acid piperidin-4-ylamide hydrochloride (example A174) and acetyl chloride the title compound is obtained as colorless solid.

MS (ESI): m/z=492 (MH+).

¹H-NMR (400 MHz, DMSO-d₆): 12.31 (br.s, 1H, —NH); 9.01 (s, 1H); 8.43 (d, J=7.7, 1H, —NH); 8.27 (s, 1H); 7.01 (d, J=8.6, 1H); 6.59 (d, J=8.6, 1H); 6.00 (s, 2H); 4.20 (m, 1H); 4.12 (m, 1H); 3.85 (d, J=6.2, 2H); 3.79 (m, 1H); 3.28 (m, 1H); 2.90 (m, 1H); 2.37 (m, 1H); 2.03 (s, 3H); 1.96 (m, 2H); 1.68 (m, 3H); 1.59-1.34 (m, 5H).

Example 130

4-(5-Cyclobutylmethoxy-benzo[1,3]dioxol-4-yl)-5H-pyrrolo[3,2-d]pyrimidine-7-carboxylic acid [1-(1-cyclopropyl-methanoyl)-piperidin-4-yl]-amide Starting from 4-(5-cyclobutylmethoxy-benzo[1,3]dioxol-4-yl)-5H-pyrrolo[3,2-d]pyrimidine-7-carboxylic acid piperidin-4-ylamide hydrochloride (example A174) and cyclopropanecarbonyl chloride the title compound is obtained as colorless solid.

MS (ESI): m/z=518 (MH+).

¹H-NMR (400 MHz, DMSO-d₆): 12.31 (br.s, 1H, —NH); 9.01 (s, 1H); 8.45 (d, J=7.8, 1H, —NH); 8.27 (s, 1H); 7.01 (d, J=8.6, 1H); 6.59 (d, J=8.6, 1H); 6.00 (s, 2H); 4.27-4.10 (m, 3H); 3.85 (d, J=6.3, 2H); 3.38 (m, 1H); 2.95 (m, 1H); 2.37 (m, 1H); 2.09-1.90 (m, 3H); 1.69 (m, 3H); 1.59-1.36 (m, 5H); 0.72 (m, 4H).

Example 131

4-(5-Cyclobutylmethoxy-benzo[1,3]dioxol-4-yl)-5H-pyrrolo[3,2-d]pyrimidine-7-carboxylic acid [1-(2-methoxy-ethanoyl)-piperidin-4-yl]amide Starting from 4-(5-cyclobutylmethoxy-benzo[1,3]dioxol-4-yl)-5H-pyrrolo[3,2-d]pyrimidine-7-carboxylic acid piperidin-4-ylamide hydrochloride (example A174) and methoxyacetyl chloride the title compound is obtained as colorless solid.

MS (ESI): m/z=522 (MH+).

¹H-NMR (400 MHz, DMSO-d₆): 12.31 (br.s, 1H, —NH); 9.01 (s, 1H); 8.43 (d, J=7.8, 1H, —NH); 8.27 (s, 1H); 7.01 (d, J=8.6, 1H); 6.59 (d, J=8.6, 1H); 6.00 (s, 2H); 4.24-4.08 (m, 2H); 4.11 (d, J=4.5, 2H); 3.85 (d, J=6.2, 2H); 3.76 (m, 1H); 3.31 (s, 3H); 3.21 (m, 1H); 2.93 (m, 1H); 2.37 (m, 1H); 1.98 (m, 1H); 1.68 (m, 3H); 1.58-1.37 (m, 5H).

Example 132

4-({1-[4-(5-Cyclobutylmethoxy-benzo[1,3]dioxol-4-yl)-5H-pyrrolo[3,2-d]pyrimidin-7-yl]-methanoyl}-amino)-piperidine-1-carboxylic acid ethyl ester Starting from 4-(5-cyclobutylmethoxy-benzo[1,3]dioxol-4-yl)-5H-pyrrolo[3,2-d]pyrimidine-7-carboxylic acid piperidin-4-ylamide hydrochloride (example A174) and ethyl chloroformate the title compound is obtained as colorless solid.

MS (ESI): m/z=522 (MH$^+$).

$^1$H-NMR (400 MHz, DMSO-d$_6$): 12.31 (br.s, 1H, —NH); 9.01 (s, 1H); 8.42 (d, J=7.8, 1H, —NH); 8.26 (s, 1H); 7.01 (d, J=8.6, 1H); 6.59 (d, J=8.6, 1H); 6.00 (s, 2H); 4.06 (qu, J=7.1, 2H & m, 1H); 3.90 (m, 2H); 3.83 (d, J=6.2, 2H); 3.09 (m, 2H); 2.38 (m, 1H); 1.95 (m, 2H); 1.69 (m, 3H); 1.58-1.43 (m, 5H); 1.21 (t, J=7.1, 3H).

Example 133

4-(5-Ethoxy-benzo[1,3]dioxol-4-yl)-5H-pyrrolo[3,2-d]pyrimidine-7-carboxylic acid (1-propionyl-piperidin-4-yl)-amide Starting from 4-(5-ethoxy-benzo[1,3]dioxol-4-yl)-5H-pyrrolo[3,2-d]pyrimidine-7-carboxylic acid piperidin-4-ylamide (example A175) and propionyl chloride the title compound was obtained as colorless solid.

MS (ESI): m/z=466 (MH$^+$, 100%).

$^1$H-NMR (400 MHz, DMSO-d$_6$): 12.25 (s, 1H, —NH); 9.02 (s, 1H); 8.44 (d, J=7.8, 1H, —NH); 8.29 (s, 1H); 7.02 (d, J=8.6, 1H); 6.58 (d, J=8.6, 1H); 6.00 (s, 2H); 4.23 (m, 1H); 4.12 (m, 1H); 3.95 (qu, J=7.0, 2H); 3.72 (m, 1H); 3.23 (m, 1H); 2.92 (m, 1H); 2.36 (qu, J=7.3, 2H); 1.95 (m, 2H); 1.60-1.31 (m, 2H); 1.03 (t, J=7.0, 3H); 1.01 (t, J=7.3, m, 3H).

Example 134

4-{[4-(5-Ethoxy-benzo[1,3]dioxol-4-yl)-5H-pyrrolo[3,2-d]pyrimidine-7-carbonyl]-amino}-piperidine-1-carboxylic acid ethyl ester Starting from 4-(5-ethoxy-benzo[1,3]dioxol-4-yl)-5H-pyrrolo[3,2-d]pyrimidine-7-carboxylic acid piperidin-4-ylamide (example A175) and ethyl chloroformate the title compound was obtained as colorless solid.

MS (ESI): m/z=482 (MH$^+$, 100%).

$^1$H-NMR (400 MHz, DMSO-d$_6$): 12.28 (s, 1H, —NH); 9.02 (s, 1H); 8.44 (d, J=7.8, 1H, —NH); 8.29 (s, 1H); 7.02 (d, J=8.6, 1H); 6.58 (d, J=8.6, 1H); 6.00 (s, 2H); 4.06 (qu, J=7.1, 2H & m, 1H); 3.95 (qu, J=6.9, 2H & m, 2H); 3.09 (m, 2H); 1.95 (m, 2H); 1.48 (m, 2H); 1.20 (t, J=7.1, 3H); 1.03 (t, J=6.9, 3H).

Example 135

4-(5-Ethoxy-benzo[1,3]dioxol-4-yl)-5H-pyrrolo[3,2-d]pyrimidine-7-carboxylic acid [1-(2-methoxy-acetyl)piperidin-4-yl]-amide Starting from 4-(5-ethoxy-benzo[1,3]dioxol-4-yl)-5H-pyrrolo[3,2-d]pyrimidine-7-carboxylic acid piperidin-4-ylamide (example A175) and methoxy-acetyl chloride the title compound was obtained as colorless solid.

MS (ESI): m/z=482 (MH$^+$, 100%).

$^1$H-NMR (400 MHz, DMSO-d$_6$): 11.99 (s, 1H, —NH); 9.02 (s, 1H); 8.45 (d, J=7.8, 1H, —NH); 8.30 (s, 1H); 7.02 (d, J=8.6, 1H); 6.58 (d, J=8.6, 1H); 6.00 (s, 2H); 4.17 (m, 2H); 4.12 (d, J=2.6, 2H); 3.95 (qu, J=6.9, 2H); 3.76 (m, 1H); 3.31 (s, 3H); 3.22 (m, 1H); 2.95 (m, 1H); 1.98 (m, 2H); 1.63-1.37 (m, 2H); 1.03 (t, J=6.9, 3H).

Example 136

4-(5-Ethoxy-benzo[1,3]dioxol-4-yl)-5H-pyrrolo[3,2-d]pyrimidine-7-carboxylic acid ((R)-1-propionyl-pyrrolidin-3-yl)-amide Starting from 4-(5-ethoxy-benzo[1,3]dioxol-4-yl)-5H-pyrrolo[3,2-d]pyrimidine-7-carboxylic acid (R)-pyrrolidin-3-ylamide (example A176) and propionyl chloride the title compound was obtained as colorless solid.

MS (ESI): m/z=452 (MH$^+$, 100%).

$^1$H-NMR (300 MHz, DMSO-d$_6$): 12.19 (s, 1H, —NH); 9.02 (s, 1H); 8.58 (d, J=7.2, 0.5H, —NH); 8.55 (d, J=6.9, 0.5H, —NH); 8.32 (s, 1H); 7.02 (d, J=8.6, 1H); 6.58 (d, J=8.6, 1H); 6.01 (s, 2H); 4.61 (m, 0.5H); 4.51 (m, 0.5H); 3.96 (qu, J=6.9, 2H); 3.82 (m, 0.5H); 3.71-3.32 (m, 3.5H); 2.36-2.16 (m, 3H); 2.07 (m, 0.5H); 1.94 (m, 0.5H); 1.03 (m, 6H).

Example 137

(R)-3-{[4-(5-Ethoxy-benzo[1,3]dioxol-4-yl)-5H-pyrrolo[3,2-d]pyrimidine-7-carbonyl]-amino}-pyrrolidine-1-carboxylic acid ethyl ester Starting from 4-(5-ethoxy-benzo[1,3]dioxol-4-yl)-5H-pyrrolo[3,2-d]pyrimidine-7-carboxylic acid (R)-pyrrolidin-3-ylamide (example A176) and ethyl chloroformate the title compound was obtained as colorless solid.

MS (ESI): m/z=468 (MH$^+$, 100%).

$^1$H-NMR (300 MHz, DMSO-d$_6$): 12.26 (s, 1H, —NH); 9.02 (s, 1H); 8.56 (d, J=7.0, 1H, —NH); 8.31 (s, 1H); 7.02 (d, J=8.6, 1H); 6.58 (d, J=8.6, 1H); 6.01 (s, 2H); 4.53 (m, 1H); 4.05 (qu, J=7.0, 2H); 3.95 (qu, J=6.9, 2H); 3.67 (m, 1H); 3.48 (m, 2H); 3.31 (m, 1H); 2.23 (m, 1H); 1.98 (m, 1H); 1.19 (t, J=7.0, 3H); 1.03 (t, J=6.9, 3H).

Example 138

4-(5-Ethoxy-benzo[1,3]dioxol-4-yl)-5H-pyrrolo[3,2-d]pyrimidine-7-carboxylic acid [(R)-1-(2-methoxy-acetyl)-pyrrolidin-amide Starting from 4-(5-ethoxy-benzo[1,3]dioxol-4-yl)-5H-pyrrolo[3,2-d]pyrimidine-7-carboxylic acid (R)-pyrrolidin-3-ylamide (example A176) and methoxy-acetyl chloride the title compound was obtained as colorless solid.

MS (ESI): m/z=468 (MH$^+$, 100%).

$^1$H-NMR (300 MHz, DMSO-d$_6$): 11.89 (s, 1H, —NH); 9.02 (s, 1H); 8.57 (d, J=6.7, 0.5H, —NH); 8.54 (d, J=6.3, 0.5H); 8.31 (s, 1H); 7.02 (d, J=8.6, 1H); 6.58 (d, J=8.6, 1H); 6.00 (s, 2H); 4.61 (m, 0.5H); 4.51 (m, 0.5H); 4.08 (d, J=3.8, 1H); 4.01 (d, J=1.4, 2H); 3.97 (qu, J=6.9, 2H); 3.80 (m, 0.5H); 3.70 (m, 0.5H); 3.62-3.33 (m, 3H); 3.32 (s, 1.5H); 3.30 (s, 1.5H); 2.32-2.14 (m, 1H); 2.07 (m, 0.5H); 1.92 (m, 0.5H); 1.03 (t, J=6.9, 3H).

Example 139

4-(5-Propoxy-benzo[1,3]dioxol-4-yl)-5H-pyrrolo[3,2-d]pyrimidine-7-carboxylic acid (1-propionyl-piperidin-4-yl)-amide Starting from 4-(5-propoxy-benzo[1,3]dioxol-4-yl)-5H-pyrrolo[3,2-d]pyrimidine-7-carboxylic acid piperidin-4-ylamide (example A177) and propionyl chloride the title compound was obtained as colorless solid.

MS (ESI): m/z=480 (MH+, 100%).

¹H-NMR (300 MHz, DMSO-$d_6$): 12.28 (s, 1H, —NH); 9.02 (s, 1H); 8.44 (d, J=7.7, 1H, —NH); 8.28 (s, 1H); 7.01 (d, J=8.6, 1H); 6.58 (d, J=8.6, 1H); 6.00 (s, 2H); 4.24 (m, 1H); 4.14 (m, 1H); 3.85 (t, J=6.3, 2H & m, 1H); 3.24 (m, 1H); 2.92 (m, 1H); 2.36 (qu, J=7.4, 2H); 1.97 (m, 2H); 1.53 (m, 1H); 1.42 (m, 2H & m, 1H); 1.01 (t, J=7.4, 3H); 0.63 (t, J=7.4, 3H).

Example 140

4-{[4-(5-Propoxy-benzo[1,3]dioxol-4-yl)-5H-pyrrolo[3,2-d]pyrimidine-7-carbonyl]-amino}-piperidine-1-carboxylic acid ethyl ester Starting from 4-(5-propoxy-benzo[1,3]dioxol-4-yl)-5H-pyrrolo[3,2-d]pyrimidine-7-carboxylic acid piperidin-4-ylamide (example A177) and ethyl chloroformate the title compound was obtained as colorless solid.

MS (ESI): m/z=496 (MH+, 100%).

¹H-NMR (300 MHz, DMSO-$d_6$): 12.31 (s, 1H, —NH); 9.02 (s, 1H); 8.43 (d, J=7.8, 1H, —NH); 8.27 (s, 1H); 7.02 (d, J=8.6, 1H); 6.58 (d, J=8.6, 1H); 6.00 (s, 2H); 4.47 (m, 1H); 4.06 (qu, J=7.0, 2H & m, 1H); 3.91 (m, 2H); 3.85 (t, J=6.4, 2H); 3.09 (m, 2H); 1.95 (m, 2H); 1.49 (m, 2H); 1.42 (m, 2H); 1.20 (t, J=7.0, 3H); 0.63 (t, J=7.4, 3H).

Example 141

4-(5-Propoxy-benzo[1,3]dioxol-4-yl)-5H-pyrrolo[3,2-d]pyrimidine-7-carboxylic acid ((R)-1-propionyl-pyrrolidin-3-yl)-amide Starting from 4-(5-propoxy-benzo[1,3]dioxol-4-yl)-5H-pyrrolo[3,2-d]pyrimidine-7-carboxylic acid (R)-pyrrolidin-3-ylamide (example A178) and propionyl chloride the title compound was obtained as colorless solid.

MS (ESI): m/z=466 (MH+, 100%).

¹H-NMR (300 MHz, DMSO-$d_6$): 12.25 (s, 1H, —NH); 9.02 (s, 1H); 8.57 (d, J=7.2, 0.5H, —NH); 8.54 (d, J=6.9, 0.5H, —NH); 8.30 (s, 1H); 7.02 (d, J=8.6, 1H); 6.58 (d, J=8.6, 1H); 6.01 (s, 2H); 4.61 (m, 0.5H); 4.51 (m, 0.5H); 3.86 (t, J=6.4, 2H); 3.71-3.32 (m, 4H); 2.37-2.15 (m, 3H); 2.07 (m, 0.5H); 1.94 (m, 0.5H); 1.41 (m, 2H); 1.00 (m, 3H); 0.62 (t, J=7.4, 3H).

Example 142

(R)-3-{[4-(5-Propoxy-benzo[1,3]dioxol-4-yl)-5H-pyrrolo[3,2-d]pyrimidine-7-carbonyl]amino}-pyrrolidine-1-carboxylic acid ethyl ester Starting from 4-(5-propoxy-benzo[1,3]dioxol-4-yl)-5H-pyrrolo[3,2-d]pyrimidine-7-carboxylic acid (R)-pyrrolidin-3-ylamide (example A178) and ethyl chloroformate the title compound was obtained as colorless solid.

MS (ESI): m/z=482 (MH+, 100%).

¹H-NMR (300 MHz, DMSO-$d_6$): 12.32 (s, 1H, —NH); 9.02 (s, 1H); 8.55 (d, J=7.8, 1H, —NH); 8.30 (s, 1H); 7.02 (d, J=8.6, 1H); 6.58 (d, J=8.6, 1H); 6.01 (s, 2H); 4.52 (m, 1H); 4.05 (qu, J=7.0, 2H); 3.84 (t, J=6.4, 2H); 3.67 (m, 1H); 3.47 (m, 2H); 3.30 (m, 1H); 2.23 (m, 1H); 2.00 (m, 1H); 1.41 (m, 2H); 1.19 (t, J=7.0, 3H); 0.62 (t, J=7.4, 3H).

Example 143

4-(5-Propoxy-benzo[1,3]dioxol-4-yl)-5H-pyrrolo[3,2-d]pyrimidine-7-carboxylic acid [(R)-1-(2-methoxy-acetyl)-pyrrolidin-3-yl]amide Starting from 4-(5-propoxy-benzo[1,3]dioxol-4-yl)-5H-pyrrolo[3,2-d]pyrimidine-7-carboxylic acid (R)-pyrrolidin-3-ylamide (example A178) and methoxy-acetyl chloride the title compound was obtained as colorless solid.

MS (ESI): m/z=482 (MH+, 100%).

¹H-NMR (300 MHz, DMSO-$d_6$): 12.15 (s, 1H, —NH); 9.02 (s, 0.5H); 9.01 (s, 0.5H); 8.57 (d, J=6.8, 0.5H, —NH); 8.54 (d, J=6.3, 0.5H, —NH); 8.30 (s, 1H); 7.02 (d, J=8.6, 1H); 6.58 (d, J=8.6, 1H); 6.00 (s, 2H); 4.61 (m, 0.5H); 4.52 (m, 0.5H); 4.07 (d, J=4.0, 1H); 4.01 (d, J=1.5, 1H); 3.85 (t, J=6.4, 2H); 3.80 (m, 0.5H); 3.70 (m, 0.5H); 3.62-3.34 (m, 3H); 3.32 (s, 1.5H); 3.30 (s, 1.5H); 2.34-2.15 (m, 1H); 2.07 (m, 0.5H); 1.92 (m, 0.5H); 1.41 (m, 2H); 0.62 (t, J=7.4, 3H).

Example 144

4-(5-Butoxy-benzo[1,3]dioxol-4-yl)-5H-pyrrolo[3,2-d]pyrimidine-7-carboxylic acid (1-propionyl-piperidin-4-yl)-amide Starting from 4-(5-butoxy-benzo[1,3]dioxol-4-yl)-5H-pyrrolo[3,2-d]pyrimidine-7-carboxylic acid piperidin-4-ylamide (example A179) and propionyl chloride the title compound was obtained as colorless solid.

MS (ESI): m/z=494 (MH+, 100%).

¹H-NMR (300 MHz, DMSO-$d_6$): 12.29 (s, 1H, —NH); 9.01 (s, 1H); 8.43 (d, J=7.8, 1H, —NH); 8.28 (s, 1H); 7.01 (d, J=8.6, 1H); 6.58 (d, J=8.6, 1H); 6.00 (s, 2H); 4.24 (m, 1H); 4.14 (m, 1H); 3.88 (t, J=6.4, 2H); 3.86 (m, 1H); 3.24 (m, 1H); 2.92 (m, 1H); 2.36 (qu, J=7.4, 2H); 1.97 (m, 2H); 1.53 (m, 1H); 1.42 (m, 2H & m, 1H); 1.07 (m, 2H); 1.01 (t, J=7.4, 3H); 0.69 (t, J=7.4, 3H).

Example 145

4-{[4-(5-Butoxy-benzo[1,3]dioxol-4-yl)-5H-pyrrolo[3,2-d]pyrimidine-7-carbonyl]-amino}-piperidine-1-carboxylic acid ethyl ester Starting from 4-(5-butoxy-benzo[1,3]dioxol-4-yl)-5H-pyrrolo[3,2-d]pyrimidine-7-carboxylic acid piperidin-4-ylamide (example A179) and ethyl chloroformate the title compound was obtained as colorless solid.

MS (ESI): m/z=510 (MH+, 100%).

¹H-NMR (300 MHz, DMSO-$d_6$): 12.31 (s, 1H, —NH); 9.02 (s, 1H); 8.43 (d, J=7.7, 1H, —NH); 8.28 (s, 1H); 7.02 (d, J=8.6, 1H); 6.58 (d, J=8.6, 1H); 6.00 (s, 2H); 4.06 (qu, J=7.0, 2H & m, 1H); 3.90 (t, J=6.4, 2H & m, 2H); 3.09 (m, 2H); 1.95 (m, 2H); 1.48 (m, 1H); 1.36 (m, 2H); 1.20 (t, J=7.0, 3H); 1.05 (m, 2H); 0.69 (t, J=7.4, 3H).

Example 146

4-(5-Butoxy-benzo[1,3]dioxol-4-yl)-5H-pyrrolo[3,2-d]pyrimidine-7-carboxylic acid (1-formyl-piperidin-4-yl)-amide Starting from 4-(5-butoxy-benzo[1,3]dioxol-4-yl)-5H-pyrrolo[3,2-d]pyrimidine-7-carboxylic acid piperidin-4-ylamide (example A179) and acetic formic anhydride the title compound was obtained as colorless solid.

MS (ESI): m/z=466 (MH+, 100%).

¹H-NMR (300 MHz, DMSO-d₆): 12.25 (s, 1H, —NH); 9.02 (s, 1H); 8.44 (d, J=7.8, 1H); 8.29 (s, 1H); 8.03 (s, 1H); 7.01 (d, J=8.6, 1H); 6.58 (d, J=8.6, 1H); 6.00 (s, 2H); 4.17 (m, 1H); 4.10 (m, 1H); 3.88 (t, J=6.4, 2H); 3.53 (m, 1H); 3.26 (m, 1H); 2.95 (m, 1H); 2.00 (m, 1H); 1.52 (m, 1H); 1.39 (m, 2H & m, 1H); 1.05 (m, 2H); 0.69 (t, J=7.4, 3H).

Example 147

4-(5-Butoxy-benzo[1,3]dioxol-4-yl)-5H-pyrrolo[3,2-d]pyrimidine-7-carboxylic acid (1-propionyl-piperidin-3-yl)-amide Starting from 4-(5-butoxy-benzo[1,3]dioxol-4-yl)-5H-pyrrolo[3,2-d]pyrimidine-7-carboxylic acid piperidin-3-ylamide (example A180) and propionyl chloride the title compound was obtained as colorless solid.

MS (ESI): m/z=494 (MH+, 100%).

¹H-NMR (300 MHz, DMSO-d₆): 12.31 (s, 1H, —NH); 8.98 (s, 1H); 8.56 (d, J=7.3, 0.5H, —NH); 8.51 (d, J=7.9, 0.5H, —NH); 8.29 (s, 0.5H); 8.28 (s, 0.5H); 7.01 (d, J=8.6, 1H); 6.59 (d, J=8.6, 1H); 6.01 (s, 2H); 4.08-3.93 (m, 1.5H); 3.88 (t, J=6.4, 2H); 3.75 (m, 0.5H); 3.54 (m, 1H); 3.50-3.35 (m, 1.5H); 3.30 (m, 0.5H); 2.37 (m, 1H); 2.30 (m, 1H); 1.97 (m, 1H); 1.74 (m, 2H); 1.56 (m, 1H); 1.39 (m, 2H); 0.99 (m, 2H & m, 3H); 0.68 (t, J=7.4, 3H).

Example 148

3-{[4-(5-Butoxy-benzo[1,3]dioxol-4-yl)-5H-pyrrolo[3,2-d]pyrimidine-7-carbonyl]-amino}-piperidine-1-carboxylic acid ethyl ester Starting from 4-(5-butoxy-benzo[1,3]dioxol-4-yl)-5H-pyrrolo[3,2-d]pyrimidine-7-carboxylic acid piperidin-3-ylamide (example A180) and ethyl chloroformate the title compound was obtained as colorless solid.

MS (ESI): m/z=510 (MH+, 100%).

¹H-NMR (300 MHz, DMSO-d₆): 12.31 (s, 1H, —NH); 8.99 (s, 1H); 8.53 (d, J=7.9, 1H, —NH); 8.28 (s, 1H); 7.01 (d, J=8.6, 1H); 6.59 (d, J=8.6, 1H); 6.01 (s, 2H); 4.01-3.92 (m, 3H); 3.88 (t, J=6.4, 2H); 3.75 (m, 1H); 3.48 (m, 1H); 3.32 (m, 2H); 1.94 (m, 1H); 1.73 (m, 2H); 1.56 (m, 1H); 1.39 (m, 2H); 1.05 (m, 2H & m, 3H); 0.69 (t, J=7.4, 3H).

Example 149

4-(5-Butoxy-benzo[1,3]dioxol-4-yl)-5H-pyrrolo[3,2-d]pyrimidine-7-carboxylic acid [1-(2-methoxy-acetyl)piperidin-3-yl]-amide Starting from 4-(5-butoxy-benzo[1,3]dioxol-4-yl)-5H-pyrrolo[3,2-d]pyrimidine-7-carboxylic acid piperidin-3-ylamide (example A180) and methoxy-acetyl chloride the title compound was obtained as colorless solid.

MS (ESI): m/z=510 (MH+, 100%).

¹H-NMR (300 MHz, DMSO-d₆): 12.28 (s, 1H, —NH); 8.98 (s, 1H); 8.55 (br.s, 1H, —NH); 8.29 (s, 0.5H); 8.27 (s, 0.5H); 7.01 (d, J=8.6, 1H); 6.59 (d, J=8.6, 1H); 6.01 (s, 2H); 4.12-3.97 (m, 3H); 3.88 (t, J=6.4, 2H & m, 3H); 3.68 (m, 0.5H); 3.49 (m, 1H); 3.31 (m, 2H); 3.28 (s, 1.5H); 3.16 (s, 1.5H); 1.97 (m, 1H); 1.76 (m, 2H); 1.57 (m, 1H); 1.39 (m, 2H); 1.05 (m, 2H); 0.69 (t, J=7.4, 3H).

Example 150

4-(5-Butoxy-benzo[1,3]dioxol-4-yl)-5H-pyrrolo[3,2-d]pyrimidine-7-carboxylic acid ((R)-1-propionyl-pyrrolidin-3-yl)-amide Starting from 4-(5-butoxy-benzo[1,3]dioxol-4-yl)-5H-pyrrolo[3,2-d]pyrimidine-7-carboxylic acid (R)-pyrrolidin-3-ylamide (example A181) and propionyl chloride the title compound was obtained as colorless solid.

MS (ESI): m/z=480 (MH+, 100%).

¹H-NMR (300 MHz, DMSO-d₆): 12.29 (br.s, 1H, —NH); 9.01 (s, 1H); 8.57 (d, J=7.1, 1H, —NH); 8.54 (d, J=7.1, 0.5H, —NH); 8.30 (s, 1H); 7.01 (d, J=8.6, 1H); 6.59 (d, J=8.6, 1H); 6.00 (s, 2H); 4.61 (m, 0.5H); 4.50 (m, 0.5H); 3.89 (t, J=6.4, 2H); 3.82 (m, 0.5H); 3.68 (m, 0.5H); 3.63-3.31 (m, 3H); 2.35-2.17 (m, 3H); 2.07 (m, 0.5H); 1.94 (m, 0.5H); 1.40 (m, 2H); 1.10-0.98 (m, 4H); 0.69 (t, J=7.4, 3H).

Example 151

(R)-3-{[4-(5-Butoxy-benzo[1,3]dioxol-4-yl)-5H-pyrrolo[3,2-d]pyrimidine-7-carbonyl]amino}-pyrrolidine-1-carboxylic acid ethyl ester Starting from 4-(5-butoxy-benzo[1,3]dioxol-4-yl)-5H-pyrrolo[3,2-d]pyrimidine-7-carboxylic acid (R)-pyrrolidin-3-ylamide (example A181) and ethyl chloroformate the title compound was obtained as colorless solid.

MS (ESI): m/z=496 (MH+, 100%).

¹H-NMR 300 MHz, DMSO-d₆): 12.32 (br.s, 1H, —NH); 9.02 (s, 1H); 8.56 (d, J=6.7, 1H, —NH); 8.30 (s, 1H); 7.02 (d, J=8.6, 1H); 6.59 (d, J=8.6, 1H); 6.01 (s, 2H); 4.53 (m, 1H); 4.05 (qu, J=7.0, 2H); 3.88 (t, J=6.4, 2H); 3.67 (m, 1H); 3.48 (m, 2H); 3.30 (m, 1H); 2.22 (m, 1H); 1.99 (m, 1H); 1.39 (m, 2H); 1.19 (t, J=7.0, 2H); 1.05 (m, 2H); 0.69 (t, J=7.4, 3H).

Example 152 cis-4-[4-Methoxy-2-(2-methoxy-ethoxy)-phenyl]-5H-pyrrolo[3,2-d]pyrimidine-7-carboxylic acid (4-acetylamino-cyclohexyl)-amide Starting from cis-4-[4-methoxy-2-(2-methoxy-ethoxy)-phenyl]-5H-pyrrolo[3,2-d]pyrimidine-7-carboxylic acid (4-amino-cyclohexyl)-amide (example A183) and acetyl chloride the title compound was obtained as colorless solid.

MS (ESI): m/z=482 (MH+).

¹H-NMR (400 MHz, DMSO-d₆): 11.75 (br.s, 1H, —NH); 9.03 (s, 1H); 8.65 (d, J=7.6, 1H, —NH); 8.23 (d, J=3.2, 1H); 7.86 (d, J=7.6, 1H, —NH); 7.70 (d, J=8.3, 1H); 6.77 (s, 1H); 6.76 (dd, J₁=8.3, J₂=2.2, 1H); 4.24 (t, J=4.6, 2H); 4.03 (m, 1H); 3.88 (s, 3H); 3.76 (m, 1H); 3.55 (t, J=4.6, 2H); 3.13 (s, 3H); 1.83 (s, 3H); 1.80-1.63 (m, 6H); 1.60 (s, 2H).

Example 153 cis-4-[4-Methoxy-2-(2-methoxy-ethoxy)-phenyl]-5H-pyrrolo[3,2-d]pyrimidine-7-carboxylic acid [4-(cyclopropanecarbonyl-amino)cyclohexyl]-amide Starting from cis-4-[4-methoxy-2-(2-methoxy-ethoxy)-phenyl]-5H-pyrrolo[3,2-d]pyrimidine-7-carboxylic acid (4-amino-cyclohexyl)-amide (example A183) and cyclopropanecarbonyl chloride the title compound was obtained as colorless solid.

MS (ESI): m/z=508 (MH$^+$).

$^1$H-NMR (400 MHz, DMSO-d$_6$): 11.75 (br.s, 1H, —NH); 9.04 (s, 1H); 8.67 (d, J=7.6, 1H, —NH); 8.23 (s, 1H); 8.07 (d, J=7.6, 1H, —NH); 7.70 (d, J=8.3, 1H); 6.77 (s, 1H); 6.76 (dd, J$_1$=8.3, J$_2$=2.2, 1H); 4.24 (t, J=4.6, 2H); 4.04 (m, 1H); 3.88 (s, 3H); 3.78 (m, 1H); 3.55 (t, J=4.6, 2H); 3.13 (s, 3H); 1.86-1.54 (m, 9H); 0.65 (m, 4H).

Example 154 cis-4-[4-Methoxy-2-(2-methoxy-ethoxy)-phenyl]-5H-pyrrolo[3,2-d]pyrimidine-7-carboxylic acid [4-(2-methoxy-acetylamino)-cyclohexyl]-amide Starting from cis-4-[4-methoxy-2-(2-methoxy-ethoxy)-phenyl]-5H-pyrrolo[3,2-d]pyrimidine-7-carboxylic acid (4-amino-cyclohexyl)-amide (example A183) and methoxyacetyl chloride the title compound was obtained as colorless solid.

MS (ESI): m/z=512 (MH$^+$).

$^1$H-NMR (400 MHz, DMSO-d$_6$): 11.74 (br.s, 1H, —NH); 9.03 (s, 1H); 8.61 (d, J=7.3, 1H, —NH); 8.22 (s, 1H); 7.69 (d, J=8.2, 1H & d, J=5.4, 1H, —NH); 6.77 (s, 1H); 6.76 (dd, J$_1$=8.2, J$_2$=2.2, 1H); 4.24 (t, J=4.6, 2H); 4.05 (m, 1H); 3.88 (s, 3H); 3.82 (s, 2H & m, 1H); 3.55 (t, J=4.6, 2H); 3.29 (s, 3H); 3.13 (s, 3H); 1.79 (m, 2H); 1.77-1.60 (m, 6H).

Example 155 trans-4-[4-Methoxy-2-(2-methoxy-ethoxy)-phenyl]-5H-pyrrolo[3,2-d]pyrimidine-7-carboxylic acid (4-acetylamino-cyclohexyl)-amide Starting from trans-4-[4-methoxy-2-(2-methoxy-ethoxy)-phenyl]-5H-pyrrolo[3,2-d]pyrimidine-7-carboxylic acid (4-amino-cyclohexyl)-amide (example A182) and acetyl chloride the title compound was obtained as colorless solid.

MS (ESI): m/z=482 (MH$^+$).

$^1$H-NMR (400 MHz, DMSO-d$_6$): 11.73 (br.s, 1H, —NH); 9.00 (s, 1H); 8.39 (d, J=7.8, 1H, —NH); 8.22 (d, J=3.4, 1H); 7.74 (d, J=7.6, 1H, —NH); 7.69 (d, J=8.2, 1H); 6.77 (s, 1H); 6.76 (dd, J$_1$=8.2, J$_2$=2.2, 1H); 4.24 (t, J=4.6, 2H); 3.87 (s, 3H); 3.82 (m, 1H); 3.58 (m, 1H); 3.54 (t, J=4.6, 2H); 3.13 (s, 3H); 2.01 (m, 2H); 1.88 (m, 2H); 1.63 (s, 3H); 1.42 (m, 2H); 1.31 (m, 2H).

Example 156 trans-4-[4-Methoxy-2-(2-methoxy-ethoxy)-phenyl]-5H-pyrrolo[3,2-d]pyrimidine-7-carboxylic acid [4-(cyclopropanecarbonyl-amino)cyclohexyl]-amide Starting from trans-4-[4-methoxy-2-(2-methoxy-ethoxy)-phenyl]-5H-pyrrolo[3,2-d]pyrimidine-7-carboxylic acid (4-amino-cyclohexyl)-amide (example A182) and cyclopropanecarbonyl chloride the title compound was obtained as colorless solid.

MS (ESI): m/z=508 (MH$^+$).

$^1$H-NMR (400 MHz, DMSO-d$_6$): 11.73 (br.s, 1H, —NH); 9.00 (s, 1H); 8.40 (d, J=7.8, 1H, —NH); 8.22 (s, 1H); 7.95 (d, J=7.7, 1H, —NH); 7.69 (d, J=8.3, 1H); 6.77 (s, 1H); 6.76 (dd, J$_1$=8.3, J$_2$=2.2, 1H); 4.24 (t, J=4.6, 2H); 3.87 (s, 3H); 3.82 (m, 1H); 3.61 (m, 1H); 3.54 (t, J=4.6, 2H); 3.13 (s, 3H); 2.01 (m, 2H); 1.88 (m, 2H); 1.52 (m, 1H); 1.48 (m, 4H); 0.65 (m, 4H).

Example 157 trans-4-[4-Methoxy-2-(2-methoxy-ethoxy)-phenyl]-5H-pyrrolo[3,2-d]pyrimidine-7-carboxylic acid [4-(2-methoxy-acetylamino)-cyclohexyl]-amide Starting from trans-4-[4-methoxy-2-(2-methoxy-ethoxy)-phenyl]-5H-pyrrolo[3,2-d]pyrimidine-7-carboxylic acid (4-amino-cyclohexyl)-amide (example A182) and methoxyacetyl chloride the title compound was obtained as colorless solid.

MS (ESI): m/z=512 (MH$^+$).

$^1$H-NMR (400 MHz, DMSO-d$_6$): 11.73 (br.s, 1H, —NH); 9.00 (s, 1H); 8.39 (d, J=7.8, 1H, —NH); 8.22 (s, 1H); 7.69 (d, J=8.3, 1H); 7.58 (d, J=8.2, 1H, —NH); 6.77 (s, 1H); 6.76 (dd, J$_1$=8.3, J$_2$=2.2, 1H); 4.24 (t, J=4.6, 2H); 3.87 (s, 3H); 3.79 (s, 2H & m, 1H); 3.70 (m, 1H); 3.54 (t, J=4.6, 2H); 3.31 (s, 3H); 3.13 (s, 3H); 2.01 (m, 2H); 1.81 (m, 2H); 1.44 (m, 4H).

Example 158

4-[4-Methoxy-2-(2-methoxy-ethoxy)-phenyl]-5H-pyrrolo[3,2-d]pyrimidine-7-carboxylic acid (1-acetyl-piperidin-4-yl)-amide Starting from 4-[4-methoxy-2-(2-methoxy-ethoxy)-phenyl]-5H-pyrrolo[3,2-d]pyrimidine-7-carboxylic acid piperidin-4-ylamide (example A184) and acetyl chloride the title compound was obtained as colorless solid.

MS (ESI): m/z=468 (MH$^+$).

$^1$H-NMR (400 MHz, DMSO-d$_6$): 11.76 (br.s, 1H, —NH); 9.00 (s, 1H); 8.56 (d, J=7.8, 1H, —NH); 8.25 (s, 1H); 7.69 (d, J=8.3, 1H); 6.77 (s, 1H); 6.76 (dd, J$_1$=8.3, J$_2$=2.2, 1H); 4.24 (t, J=4.6, 2H); 4.20-4.09 (m, 3H); 3.87 (s, 3H); 3.79 (m, 1H); 3.54 (t, J=4.6, 2H); 3.27 (m, 1H); 3.13 (s, 3H); 2.91 (m, 1H); 1.97 (m, 2H); 1.56 (m, 1H); 1.40 (m, 1H).

Example 159

4-[4-Methoxy-2-(2-methoxy-ethoxy)-phenyl]-5H-pyrrolo[3,2-d]pyrimidine-7-carboxylic acid (1-cyclopropanecarbonyl-piperidin-4-yl)-amide Starting from 4-[4-methoxy-2-(2-methoxy-ethoxy)-phenyl]-5H-pyrrolo[3,2-d]pyrimidine-7-carboxylic acid piperidin-4-ylamide (example A184) and cyclopropanecarbonyl chloride the title compound was obtained as colorless solid.

MS (ESI): m/z=494 (MH$^+$).

$^1$H-NMR (400 MHz, DMSO-d$_6$): 11.76 (br.s, 1H, —NH); 9.00 (s, 1H); 8.57 (d, J=7.7, 1H, —NH); 8.25 (d, J=3.4, 1H); 7.69 (d, J=8.2, 1H); 6.77 (s, 1H); 6.76 (dd, J$_1$=8.2, J$_2$=2.3, 1H); 4.24 (t, J=4.6, 2H); 4.24-4.10 (m, 3H); 3.87 (s, 3H); 3.54 (t, J=4.6, 2H); 3.39 (m, 1H); 3.13 (s, 3H); 2.97 (m, 1H); 2.09-1.90 (m, 3H); 1.53 (m, 1H); 1.42 (m, 1H); 0.73 (m, 4H).

Example 160

4-[4-Methoxy-2-(2-methoxy-ethoxy)-phenyl]-5H-pyrrolo[3,2-d]pyrimidine-7-carboxylic acid [1-(2-methoxy-acetyl)-piperidin-4-yl]-amide Starting from 4-[4-methoxy-2-(2-methoxy-ethoxy)-phenyl]-5H-pyrrolo[3,2-d]pyrimidine-7-carboxylic acid piperidin-4-ylamide (example A184) and methoxy-acetyl chloride the title compound was obtained as colorless solid.

MS (ESI): m/z=498 (MH$^+$).

$^1$H-NMR (400 MHz, DMSO-d$_6$): 11.76 (br.s, 1H, —NH); 8.99 (s, 1H); 8.55 (d, J=7.8, 1H, —NH); 8.25 (s, 1H); 7.69 (d, J=8.2, 1H); 6.77 (s, 1H); 6.75 (dd, J$_1$=8.2, J$_2$=2.2, 1H); 4.22 (t, J=4.6, 2H & m, 1H); 4.15 (m, 1H); 4.12 (d, J=4.3, 2H); 3.87 (s, 3H); 3.75 (m, 1H); 3.54 (t, J=4.6, 2H); 3.31 (s, 3H); 3.21 (m, 1H); 3.12 (s, 3H); 2.95 (m, 1H); 1.98 (m, 2H); 1.57 (m, 1H); 1.42 (m, 1H).

Example 161 trans-4-[5-(2-Methoxy-ethoxy)-benzo[1,3]dioxol-4-yl]-5H-pyrrolo[3,2-d]pyrimidine-7-carboxylic acid (4-acetylamino-cyclohexyl)-amide Starting from trans-4-[5-(2-methoxy-ethoxy)-benzo[1,3]dioxol-4-yl]-5H-pyrrolo[3,2-d]pyrimidine-7-carboxylic acid (4-amino-cyclohexyl)-amide (example A185) and acetyl chloride the title compound was obtained as colorless solid.

MS (ESI): m/z=496 (MH$^+$).

$^1$H-NMR (200 MHz, DMSO-d$_6$): 12.13 (br. s, 1H, —NH); 9.02 (s, 1H); 8.34 (d, J=7.9, 1H, —NH); 8.26 (s, 1H); 7.73 (d, J=7.7, —NH); 7.02 (d, J=8.5, 1H); 6.61 (d, J=8.5, 1H); 6.01 (s, 2H); 4.03 (t, J=4.7, 2H); 3.83 (m, 1H); 3.56 (m, 1H); 3.39 (t, J=4.7, 2H); 3.02 (s, 3H); 2.04 (m, 2H); 1.83 (m, 2H); 1.77 (s, 3H); 1.36 (m, 4H).

Example 162 trans-4-[5-(2-Methoxy-ethoxy)-benzo[1,3]dioxol-4-yl]-5H-pyrrolo[3,2-d]pyrimidine-7-carboxylic acid (4-(cyclopropanecarbonyl-amino)-cyclohexyl]-amide Starting from trans-4-[5-(2-methoxy-ethoxy)-benzo[1,3]dioxol-4-yl]-5H-pyrrolo[3,2-d]pyrimidine-7-carboxylic acid (4-amino-cyclohexyl)-amide (example A185) and cyclopropanecarbonyl chloride the title compound was obtained as colorless solid.

MS (ESI): m/z=522 (MH$^+$).

$^1$H-NMR (200 MHz, DMSO-d$_6$): 12.20 (br. s, 1H, —NH); 9.02 (s, 1H); 8.34 (d, J=7.8, 1H, —NH); 8.27 (s, 1H); 7.90 (d, J=7.6, —NH); 7.02 (d, J=8.6, 1H); 6.61 (d, J=8.6, 1H); 6.01 (s, 2H); 4.03 (t, J=4.7, 2H); 3.84 (m, 1H); 3.59 (m, 1H); 3.39 (t, J=4.7, 2H); 3.02 (s, 3H); 2.04 (m, 2H); 1.83 (m, 2H); 1.53 (m, 1H); 1.38 (m, 4H); 0.64 (m, 4H).

Example 163 trans-4-[5-(2-Methoxy-ethoxy)-benzo[1,3]dioxol-4-yl]-5H-pyrrolo[3,2-d]pyrimidine-7-carboxylic acid [4-(2-methoxy-acetylamino)-cyclohexyl]-amide Starting from trans-4-[5-(2-methoxy-ethoxy)-benzo[1,3]dioxol-4-yl]-5H-pyrrolo[3,2-d]pyrimidine-7-carboxylic acid (4-amino-cyclohexyl)-amide (example A185) and methoxy-acetyl chloride the title compound was obtained as colorless solid.

MS (ESI): m/z=526 (MH$^+$).

$^1$H-NMR (200 MHz, DMSO-d$_6$): 12.15 (br. s, 1H, —NH); 9.02 (s, 1H); 8.33 (d, J=7.8, 1H, —NH); 8.27 (s, 1H); 7.57 (d, J=7.6, —NH); 7.02 (d, J=8.6, 1H); 6.62 (d, J=8.6, 1H); 6.01 (s, 2H); 4.03 (t, J=4.7, 2H); 3.78 (s, 2H & m); 3.39 (t, J=4.7, 2H); 3.31 (s, 3H); 3.02 (s, 3H); 2.03 (m, 2H); 1.80 (m, 2H); 1.44 (m, 4H).

Example 164 cis-4-[5-(2-Methoxy-ethoxy)-benzo[1,3]dioxol-4-yl]-5H-pyrrolo[3,2-d]pyrimidine-7-carboxylic acid (4-acetylamino-cyclohexyl)-amide Starting from cis-4-[5-(2-methoxy-ethoxy)-benzo[1,3]dioxol-4-yl]-5H-pyrrolo[3,2-d]pyrimidine-7-carboxylic acid (4-amino-cyclohexyl)-amide (example A186) and acetyl chloride the title compound was obtained as colorless solid.

MS (ESI): m/z=496 (MH$^+$).

$^1$H-NMR (200 MHz, DMSO-d$_6$): 12.10 (br.s, 1H, —NH); 9.05 (s, 1H); 8.55 (d, J=7.6, 1H; —NH); 8.28 (s, 1H); 7.85 (d, J=7.6, 1H, —NH); 7.03 (d, J=8.6, 1H); 6.62 (d, J=8.6, 1H); 6.02 (s, 2H); 4.04 (t, J=4.7, 2H); 3.76 (m, 1H); 3.39 (t, J=4.7, 2H & m, 1H); 3.02 (s, 3H); 1.83 (s, 3H); 1.73 (m. 4H), 1.66 (m, 4H).

Example 165 cis-4-[5-(2-Methoxy-ethoxy)-benzo[1,3]dioxol-4-yl]-5H-pyrrolo[3,2-d]pyrimidine-7-carboxylic acid [4-(cyclopropanecarbonyl-amino)-cyclohexyl]-amide Starting from cis-4-[5-(2-methoxy-ethoxy)-benzo[1,3]dioxol-4-yl]-5H-pyrrolo[3,2-d]pyrimidine-7-carboxylic acid (4-amino-cyclohexyl)-amide (example A186) and cyclopropanecarbonyl chloride the title compound was obtained as colorless solid.

MS (ESI): m/z=522 (MH$^+$).

$^1$H-NMR (200 MHz, DMSO-d$_6$): 12.18 (br.s, 1H, —NH); 9.06 (s, 1H); 8.57 (d, J=7.6, 1H; —NH); 8.29 (s, 1H); 8.06 (d, J=7.6, 1H, —NH); 7.03 (d, J=8.6, 1H); 6.62 (d, J=8.6, 1H); 6.02 (s, 2H); 4.04 (t, J=4.7, 2H); 3.76 (m, 1H); 3.79 (m, 1H); 3.40 (t, J=4.7, 2H); 3.03 (s, 3H); 1.75 (m. 4H), 1.66 (m, 5H); 0.65 (m, 4H).

Example 166 cis-4-[5-(2-Methoxy-ethoxy)-benzo[1,3]dioxol-4-yl]-5H-pyrrolo[3,2-d]pyrimidine-7-carboxylic acid [4-(2-methoxy-acetylamino)-cyclohexyl]-amide Starting from cis-4-[5-(2-methoxy-ethoxy)-benzo[1,3]dioxol-4-yl]-5H-pyrrolo[3,2-d]pyrimidine-7-carboxylic acid (4-amino-cyclohexyl)-amide (example A186) and methoxy-acetyl chloride the title compound was obtained as colorless solid.

MS (ESI): m/z=526 (MH$^+$).

$^1$H-NMR (200 MHz, DMSO-d$_6$): 12.13 (br.s, 1H, —NH); 9.05 (s, 1H); 8.58 (d, J=7.4, 1H; —NH); 8.28 (s, 1H); 7.69 (d, J=7.6, 1H, —NH); 7.03 (d, J=8.6, 1H); 6.62 (d, J=8.6, 1H); 6.02 (s, 2H); 4.04 (t, J=4.7, 2H & m, 1H); 3.82 (s, 2H & m, 1H); 3.39 (t, J=4.7, 2H); 3.31 (s, 3H); 3.03 (s, 3H); 1.73 (m. 8H).

Example 167 cis-[4-({4-[5-(2-Methoxy-ethoxy)-benzo[1,3]dioxol-4-yl]-5H-pyrrolo[3,2-d]pyrimidine-7-carbonyl}-amino)-cyclohexyl]-carbamic acid ethyl ester Starting from cis-4-[5-(2-methoxy-ethoxy)-benzo[1,3]dioxol-4-yl]-5H-pyrrolo[3,2-d]pyrimidine-7-carboxylic acid (4-amino-cyclohexyl)-amide (example A186) and ethyl chloroformate the title compound was obtained as colorless solid.

MS (ESI): m/z=526 (MH⁺).
¹H-NMR (200 MHz, DMSO-d₆): 12.20 (br.s, 1H, —NH); 9.05 (s, 1H); 8.59 (d, J=7.8, 1H; —NH); 8.27 (s, 1H); 7.19 (d, J=7.6, 1H, —NH); 7.03 (d, J=8.6, 1H); 6.62 (d, J=8.6, 1H); 6.02 (s, 2H); 4.04 (t, J=4.7, 2H & m, 1H); 3.99 (qu, J=7.1, 2H); 3.50 (m, 1H); 3.39 (t, J=4.7, 2H); 3.03 (s, 3H); 1.67 (m. 8H); 1.17 (t, J=7.1, 3H).

Example 168

4-[5-(2-Methoxy-ethoxy)-benzo[1,3]dioxol-4-yl]-5H-pyrrolo[3,2-d]pyrimidine-7-carboxylic acid (1-acetyl-piperidin-4-yl)-amide Starting from 4-[5-(2-methoxy-ethoxy)-benzo[1,3]dioxol-4-yl]-5H-pyrrolo[3,2-d]pyrimidine-7-carboxylic acid piperidin-4-ylamide (example A187) and acetyl chloride the title compound was obtained as colorless solid.

MS (ESI): m/z=482 (MH⁺).
¹H-NMR (200 MHz, DMSO-d₆): 12.17 (br.s, 1H, —NH); 9.02 (s, 1H); 8.45 (d, J=7.8, 1H; —NH); 8.30 (s, 1H); 7.02 (d, J=8.6, 1H); 6.61 (d, J=8.6, 1H); 6.01 (s, 2H); 4.17 (m, 2H); 4.03 (t, J=4.7, 2H); 3.80 (m, 1H); 3.39 (t, J=4.7, 2H); 3.27 (m, 1H); 3.03 (s, 3H); 2.93 (m, 1H); 2.05 (s, 3H); 1.97 (m, 2H); 1.47 (m, 2H).

Example 169

4-[5-(2-Methoxy-ethoxy)-benzo[1,3]dioxol-4-yl]-5H-pyrrolo[3,2-d]pyrimidine-7-carboxylic acid (1-cyclopropanecarbonyl-piperidin-4-yl)-amide Starting from 4-[5-(2-methoxy-ethoxy)-benzo[1,3]dioxol-4-yl]-5H-pyrrolo[3,2-d]pyrimidine-7-carboxylic acid piperidin-4-ylamide (example A187) and cyclopropanecarbonyl chloride the title compound was obtained as colorless solid.

MS (ESI): m/z=508 (MH⁺).
¹H-NMR (200 MHz, DMSO-d₆): 12.16 (br.s, 1H, —NH); 9.02 (s, 1H); 8.46 (d, J=7.8, 1H; —NH); 8.30 (s, 1H); 7.02 (d, J=8.6, 1H); 6.61 (d, J=8.6, 1H); 6.01 (s, 2H); 4.20 (m, 3H); 4.03 (t, J=4.7, 2H); 3.39 (t, J=4.7, 2H & m, 1H); 3.02 (s, 3H & m, 2H); 2.00 (m, 3H); 1.49 (m, 2H); 0.73 (m, 4H).

Example 170

4-[5-(2-Methoxy-ethoxy)-benzo[1,3]dioxol-4-yl]-5H-pyrrolo[3,2-d]pyrimidine-7-carboxylic acid [1-(2-methoxy-acetyl)piperidin-4-yl]-amide Starting from 4-[5-(2-methoxy-ethoxy)-benzo[1,3]dioxol-4-yl]-5H-pyrrolo[3,2-d]pyrimidine-7-carboxylic acid piperidin-4-ylamide (example A187) and methoxy-acetyl chloride the title compound was obtained as colorless solid.

MS (ESI): m/z=512 (MH⁺).
¹H-NMR (200 MHz, DMSO-d₆): 12.18 (br.s, 1H, —NH); 9.02 (s, 1H); 8.44 (d, J=7.8, 1H; —NH); 8.30 (s, 1H); 7.02 (d, J=8.6, 1H); 6.61 (d, J=8.6, 1H); 6.01 (s, 2H); 4.12 (m, 2H & s, 2H); 4.03 (t, J=4.7, 2H); 3.73 (m, 1H); 3.38 (t, J=4.7, 2H); 3.31 (s, 1H); 3.28 (m, 1H); 3.02 (s, 3H); 2.95 (m, 1H); 1.98 (m, 2H); 1.52 (m, 2H).

Example 171

4-(5-Cyclopropylmethoxy-benzo[1,3]dioxol-4-yl)-5H-pyrrolo[3,2-d]pyrimidine-7-carboxylic acid [1-(2-hydroxy-ethanoyl)-piperidin-4-yl]amide 4-(5-Cyclopropylmethoxy-1,3-benzodioxol-4-yl)-5H-pyrrolo[3,2-d]pyrimidine-7-carboxylic acid piperidin-4-ylamide hydrochloride from example A138 (472 mg; 1.0 mmol) is dissolved in dry dichloromethane (5 mL) and DBU (2.5 mmol). Acetic acid chlorocarbonylmethyl ester (1.1 mmol) is dropped into the reaction mixture at ice bath temperature. After complete addition stirring is continued at ambient temperature overnight. Methanol (1 mL) is added and stirring is continued for two hours. The volatiles are evaporated.

The residue is dissolved in methanol (5 mL), treated with 5M KOH (1.5 mmol) and stirred overnight at ambient temperature. The pH of the reaction mixture is adjusted to 6-7 by addition of 2M citric acid. The volatiles are evaporated. The residue is purified by reversed phase preparative HPLC. The collected product fraction is freeze-dried to yield 364 mg of the title compound as colorless solid.

MS (ESI): m/z=494 (MH⁺, 100%).
¹H-NMR (400 MHz, DMSO-d₆): 9.02 (s, 1H); 8.45 (d, J=7.8, 1H, —NH); 8.30 (s, 1H); 7.01 (d, J=8.6, 1H); 6.56 (d, J=8.6, 1H); 6.01 (s, 2H); 4.52 (br.s, 1H, —OH); 4.16 (m, 2H & d, J=7.9, 2H); 3.76 (d, J=6.8, 2H); 3.69 (m, 1H); 3.19 (m, 1H); 2.98 (m, 1H); 1.98 (m, 2H); 1.56 (m, 1H); 1.43 (m, 1H); 0.87 (m, 1H); 0.29 (m, 2H); 0.10 (m, 2H).

The following compounds are obtained analogously to the procedure described in above example 171.

Example 172 trans-[4-({1-[4-(5-Cyclopropylmethoxy-benzo[1,3]dioxol-4-yl)-5H-pyrrolo[3,2-d]pyrimidine-7-carboxylic acid [4-(2-hydroxy-ethanoylamino)-cyclohexyl]-amide Starting from trans-4-(5-cyclopropylmethoxy-benzo[1,3]dioxol-4-yl)-5H-pyrrolo[3,2-d]pyrimidine-7-carboxylic acid (4-amino-cyclohexyl)-amide (example A140) and acetic acid chlorocarbonyl-methyl ester the title compound is obtained as colorless solid.

MS (ESI): m/z=508 (MH⁺, 100%)
¹H-NMR (400 MHz, DMSO-d₆): 12.27 (br.s, 1H, —NH); 9.03 (s, 1H); 8.30 (d, J=7.9, 1H, —NH); 8.27 (s, 1H); 7.49 (d, J=8.3, 1H, —NH); 7.01 (d, J=8.6, 1H); 6.56 (d, J=8.6, 1H); 6.00 (s, 2H); 5.42 (t, J=5.5, 1H, —OH); 3.79 (m, 1H &d, J=5.5, 2H); 3.76 (d, J=6.8, 2H); 3.69 (m, 1H); 2.02 (~d, J~8.9, 2H); 1.82 (~d, J ~8.8, 2H); 1.46 (m, 4H); 0.86 (m, 1H); 0.29 (m, 2H); 0.11 (m, 2H).

Example 173 trans-[4-({1-[4-(5-Cyclopropylmethoxy-benzo[1,3]dioxol-4-yl)-5H-pyrrolo[3,2-d]pyrimidine-7-carboxylic acid [4-((S)-2-hydroxy-propanoylamino)-cyclohexyl]-amide Starting from trans-4-(5-cyclopropylmethoxy-benzo[1,3]dioxol-4-yl)-5H-pyrrolo[3,2-d]pyrimidine-7-carboxylic acid (4-amino-cyclohexyl)-amide (example A140) and acetic acid (S)-1-chlorocarbonyl-ethyl ester the title compound is obtained as colorless solid.

MS (ESI): m/z=522 (MH⁺).
¹H-NMR (400 MHz, DMSO-d₆): 9.03 (s, 1H); 8.30 (d, J=7.9, 1H, —NH); 8.27 (s, 1H); 7.44 (d, J=8.3, 1H, —NH); 7.00 (d, J=8.6, 1H); 6.56 (d, J=8.6, 1H); 6.00 (s, 2H); 5.45 (br.s, 1H, —OH); 3.94 (qu, J=6.7, 1H); 3.81 (m, 1H); 3.76 (d, J=6.7, 2H); 3.63 (m, 1H); 2.02 (m, 2H); 1.81 (m, 2H); 1.44 (m, 4H); 1.22 (d, J=6.7, 3H); 0.87 (m, 1H); 0.29 (m, 2H); 0.10 (m, 2H).

Example 174 cis-[4-({1-[4-(5-Cyclopropylmethoxy-benzo[1,3] dioxol-4-yl)-5H-pyrrolo[3,2-d]pyrimidine-7-carboxylic acid [4-(2-hydroxy-ethanoylamino)-cyclohexyl]-amide Starting from cis-4-(5-cyclopropylmethoxy-benzo[1,3]dioxol-4-yl)-5H-pyrrolo[3,2-d]pyrimidine-7-carboxylic acid (4-amino-cyclohexyl)-amide (example A141) and acetic acid chlorocarbonyl-methyl ester the title compound is obtained as colorless solid.

MS (ESI): m/z=508 (MH$^+$, 100%).
$^1$H-NMR (400 MHz, DMSO-d$_6$): 9.06 (s, 1H); 8.59 (d, J=7.4, 1H, —NH); 8.28 (s, 1H); 7.57 (d, J=7.7, 1H, —NH); 7.01 (d, J=8.6, 1H); 6.56 (d, J=8.6, 1H); 6.01 (s, 2H); 5.34 (br.s, 1H, —OH); 4.06 (m, 1H); 3.82 (s, 2H & m, 1H); 3.77 (d, J=6.7, 2H); 1.76 (m, 4H); 1.67 (m, 4H); 0.88 (m, 1H); 0.30 (m, 2H); 0.11 (m, 2H).

Example 175 cis-[4-({1-[4-(5-Cyclopropylmethoxy-benzo[1,3] dioxol-4-yl)-5H-pyrrolo[3,2-d]pyrimidine-7-carboxylic acid [4-((S)-2-hydroxy-propanoylamino)-cyclohexyl]-amide Starting from cis-4-(5-cyclopropylmethoxy-benzo[1,3]dioxol-4-yl)-5H-pyrrolo[3,2-d]pyrimidine-7-carboxylic acid (4-amino-cyclohexyl)-amide (example A141) and acetic acid (S)-1-chlorocarbonyl-ethyl ester the title compound is obtained as colorless solid.

MS (ESI): m/z=522 (MH$^+$, 100%).
$^1$H-NMR (400 MHz, DMSO-d$_6$): 12.16 (br.s, 1H, —NH); 9.06 (s, 1H); 8.58 (d, J=7.4, 1H, —NH); 8.28 (s, 1H); 7.52 (d, J=7.8, 1H, —NH); 7.01 (d, J=8.6, 1H); 6.56 (d, J=8.6, 1H); 6.01 (s, 2H); 5.37 (d, J=5.3, 1H, —OH); 4.05 (m, 1H); 3.99 (m, 1H); 3.77 (m, 1H & d, J=6.7, 2H); 1.75 (m, 4H); 1.66 (m, 4H); 1.22 (d, J=6.7, 3H); 0.87 (m, 1H); 0.30 (m, 2H); 0.11 (m, 2H).

Example 176

4-(5-Cyclopropylmethoxy-benzo[1,3]dioxol-4-yl)-5H-pyrrolo[3,2-d]pyrimidine-7-carboxylic acid [1-((S)-2-hydroxy-propanoyl)-piperidin-4-yl]amide Starting from 4-(5-cyclopropylmethoxy-benzo[1,3]dioxol-4-yl)-5H-pyrrolo[3,2-d]pyrimidine-7-carboxylic acid piperidin-4-ylamide hydrochloride (example A138) and acetic acid (S)-1-chlorocarbonyl-ethyl ester the title compound is obtained as colorless solid.

MS (ESI): m/z=508 (MH$^+$, 100%).
$^1$H-NMR (400 MHz, DMSO-d$_6$): 11.91 (br.s, 1H, —NH); 9.03 (s, 1H); 8.45 (d, J=7.7, 1H, —NH); 8.30 (s, 1H); 7.01 (d, J=8.6, 1H); 6.56 (d, J=8.6, 1H); 6.00 (s, 2H); 4.88 (br.s, 1H, —OH); 4.46 (m, 1H); 4.25 (m, 1H); 4.16 (m, 1H); 3.84 (m, 1H); 3.76 (d, J=6.8, 2H); 3.16 (m, 1H); 2.96 (m, 1H); 1.99 (m, 2H); 1.56 (m, 1H); 1.42 (m, 1H); 1.21 (dd, J$_1$=6.9, J$_2$=6.6, 3H); 0.87 (m, 1H); 0.29 (m, 2H); 0.11 (m, 2H).

Example 177 trans-4-(5-Cyclopropylmethoxy-benzo[1,3]dioxol-4-yl)-5H-pyrrolo[3,2-d]pyrimidine-7-carboxylic acid {4-[(1-hydroxy-cyclopropanecarbonyl)-amino]-cyclohexyl}-amide Starting from trans-4-(5-cyclopropylmethoxy-benzo[1,3]dioxol-4-yl)-5H-pyrrolo[3,2-d]pyrimidine-7-carboxylic acid (4-amino-cyclohexyl)-amide (example A140) and acetic acid 1-chlorocarbonyl-cyclopropyl ester the title compound is obtained as colorless solid.

Example 178 cis-4-(5-Cyclopropylmethoxy-benzo[1,3]dioxol-4-yl)-5H-pyrrolo[3,2-d]pyrimidine-7-carboxylic acid {4-[(1-hydroxy-cyclopropanecarbonyl)-amino]-cyclohexyl}-amide Starting from cis-4-(5-cyclopropylmethoxy-benzo[1,3]dioxol-4-yl)-5H-pyrrolo[3,2-d]pyrimidine-7-carboxylic acid (4-amino-cyclohexyl)-amide (example A141) and acetic acid 1-chlorocarbonyl-cyclopropyl ester the title compound is obtained as colorless solid.

Example 179

4-(5-Cyclopropylmethoxy-benzo[1,3]dioxol-4-yl)-5H-pyrrolo[3,2-d]pyrimidine-7-carboxylic acid {1-[1-(1-hydroxy-cyclopropyl)methanoyl]-piperidin-4-yl}-amide Starting from 4-(5-cyclopropylmethoxy-benzo[1,3]dioxol-4-yl)-5H-pyrrolo[3,2-d]pyrimidine-7-carboxylic acid piperidin-4-ylamide hydrochloride (example A138) and acetic acid 1-chlorocarbonyl-cyclopropyl ester the title compound is obtained as colorless solid.

Example 180

4-(5-Cyclopropylmethoxy-benzo[1,3]dioxol-4-yl)-5H-pyrrolo[3,2-d]pyrimidine-7-carboxylic acid [(R)-1-(2-hydroxy-ethanoyl)-pyrrolidin-3-yl]amide Starting from 4-(5-cyclopropylmethoxy-benzo[1,3]dioxol-4-yl)-5H-pyrrolo[3,2-d]pyrimidine-7-carboxylic acid (R)-pyrrolidin-3-ylamide hydrochloride (example A142) and acetic acid chlorocarbonyl-methyl ester the title compound is obtained as colorless solid.

MS (ESI): m/z=480.0 (MH$^+$).
$^1$H-NMR (300 MHz, DMSO-d$_6$): 12.31 (br.s, 1H, —NH); 9.03 (s, 1H); 8.57 (d, J=7.1, 0.5H, —NH); 8.54 (d, J=7.1, 0.5H, —NH); 8.31 (s, 1H); 7.01 (d, J=8.6, 1H); 6.56 (d, J=8.6, 1H); 6.00 (s, 2H); 4.62 (m, 0.5H); 4.56 (t, J=5.6, 1H, —OH & m, 0.5H); 4.06 (d, J=5.6, 1H); 4.01 (d, J=5.6, 1H); 3.76 (m, 1H); 3.53 (m, 2H); 3.37 (m, 1H); 2.32-2.18 (m, 1H); 2.07 (m, 0.5H); 1.94 (m, 0.5H); 0.87 (m, 1H); 0.29 (m, 2H); 0.10 (m, 2H).

Example 181

4-(5-Cyclopropylmethoxy-benzo[1,3]dioxol-4-yl)-5H-pyrrolo[3,2-d]pyrimidine-7-carboxylic acid [(R)-1-((S)-2-hydroxy-propanoyl)-pyrrolidin-3-yl]amide Starting from 4-(5-cyclopropylmethoxy-benzo[1,3]dioxol-4-yl)-5H-pyrrolo[3,2-d]pyrimidine-7-carboxylic acid (R)-pyrrolidin-3-ylamide hydrochloride (example A142) and acetic acid (S)-1-chlorocarbonyl-ethyl ester the title compound is obtained as colorless solid.

MS (ESI): m/z=494 (MH$^+$).
$^1$H-NMR (300 MHz, DMSO-d$_6$): 12.31 (br.s, 1H, —NH); 9.02 (s, 0.5H); 9.00 (s, 0.5H); 8.58 (d, J=7.1, 1H, —NH); 8.31 (s, 1H); 7.01 (d, J=8.6, 1H); 6.56 (d, J=8.6, 1H); 6.00 (s, 2H); 4.92 (d, J=6.7, 0.5H, —OH); 4.86 (d, J=6.7, 0.5H, —OH);

4.61 (m, 0.5H); 4.53 (m, 0.5H); 4.33 (m, 0.5H); 4.26 (m, 0.5H); 3.84 (m, 0.5H); 3.76 (d, J=6.7, 2H); 3.75-3.45 (m, 3H); 3.37 (m, 0.5H); 2.24 (m, 1H); 2.07 (m, 0.5H); 1.96 (m, 0.5H); 1.23 (d, J=6.6, 1.5H); 1.20 (d, J=6.6, 1.5H); 0.87 (m, 1H); 0.29 (m, 2H); 0.10 (m, 2H).

Example 182

4-(5-Cyclopropylmethoxy-benzo[1,3]dioxol-4-yl)-5H-pyrrolo[3,2-d]pyrimidine-7-carboxylic acid {(R)-1-[1-(1-hydroxy-cyclopropyl)-methanoyl]-pyrrolidin-3-yl}-amide Starting from 4-(5-cyclopropylmethoxy-benzo[1,3]dioxol-4-yl)-5H-pyrrolo[3,2-d]pyrimidine-7-carboxylic acid (R)-pyrrolidin-3-ylamide hydrochloride (example A142) and acetic acid 1-chlorocarbonyl-cyclopropyl ester the title compound is obtained as colorless solid.

Example 183

4-(5-Cyclopropylmethoxy-benzo[1,3]dioxol-4-yl)-5H-pyrrolo[3,2-d]pyrimidine-7-carboxylic acid [(S)-1-(2-hydroxy-ethanoyl)-pyrrolidin-3-yl]amide Starting from 4-(5-cyclopropylmethoxy-benzo[1,3]dioxol-4-yl)-5H-pyrrolo[3,2-d]pyrimidine-7-carboxylic acid (S)-pyrrolidin-3-ylamide hydrochloride (example A143) and acetic acid chlorocarbonyl-methyl ester the title compound is obtained as colorless solid.

MS (ESI): m/z=480.0 (MH$^+$).

$^1$H-NMR (300 MHz, DMSO-d$_6$): 12.31 (br.s, 1H, —NH); 9.03 (s, 1H); 8.57 (d, J=7.1, 0.5H, —NH); 8.54 (d, J=7.1, 0.5H, —NH); 8.31 (s, 1H); 7.01 (d, J=8.6, 1H); 6.56 (d, J=8.6, 1H); 6.00 (s, 2H); 4.62 (m, 0.5H); 4.56 (t, J=5.6, 1H, —OH & m, 0.5H); 4.06 (d, J=5.6, 1H); 4.01 (d, J=5.6, 1H); 3.76 (m, 1H); 3.53 (m, 2H); 3.37 (m, 1H); 2.32-2.18 (m, 1H); 2.07 (m, 0.5H); 1.94 (m, 0.5H); 0.87 (m, 1H); 0.29 (m, 2H); 0.10 (m, 2H).

Example 184

4-(5-Cyclopropylmethoxy-benzo[1,3]dioxol-4-yl)-5H-pyrrolo[3,2-d]pyrimidine-7-carboxylic acid [(S)-1-((S)-2-hydroxy-propanoyl)-pyrrolidin-3-yl]amide Starting from 4-(5-cyclopropylmethoxy-benzo[1,3]dioxol-4-yl)-5H-pyrrolo[3,2-d]pyrimidine-7-carboxylic acid (S)-pyrrolidin-3-ylamide hydrochloride (example A143) and acetic acid (S)-1-chlorocarbonyl-ethyl ester the title compound is obtained as colorless solid.

MS (ESI): m/z=494 (MH$^+$).

$^1$H-NMR (300 MHz, DMSO-d$_6$): 12.31 (br.s, 1H, —NH); 9.03 (s, 0.5H); 9.01 (s, 0.5H); 8.57 (d, J=7.0, 0.5H, —NH); 8.56 (d, J=6.7, 0.5H, —NH); 8.31 (s, 1H); 7.01 (d, J=8.6, 1H); 6.56 (d, J=8.6, 1H); 6.00 (s, 2H); 4.87 (d, J=6.8, 0.5H, —OH); 4.86 (d, J=6.8, 0.5H, —OH); 4.57 (m, 1H); 4.29 (m, 1H); 3.96 (m, 0.5H); 3.84-3.44 (m, 3H); 3.76 (d, J=6.8, 2H); 3.38 (m, 0.5H); 2.33-2.18 (m, 1H); 2.07 (m, 0.5H); 1.96 (m, 0.5H); 1.23 (d, J=6.5, 1.5H); 1.19 (d, J=6.5, 1.5H); 0.87 (m, 1H); 0.30 (m, 2H); 0.10 (m, 2H).

Example 185

4-(5-Cyclopropylmethoxy-benzo[1,3]dioxol-4-yl)-5H-pyrrolo[3,2-d]pyrimidine-7-carboxylic acid {(S)-1-[1-(1-hydroxy-cyclopropyl)-methanoyl]-pyrrolidin-3-yl}-amide Starting from 4-(5-cyclopropylmethoxy-benzo[1,3]dioxol-4-yl)-5H-pyrrolo[3,2-d]pyrimidine-7-carboxylic acid (S)-pyrrolidin-3-ylamide hydrochloride (example A143) and acetic acid 1-chlorocarbonyl-cyclopropyl ester the title compound is obtained as colorless solid.

Example 186

4-(5-Cyclopropylmethoxy-benzo[1,3]dioxol-4-yl)-5H-pyrrolo[3,2-d]pyrimidine-7-carboxylic acid [1-(2-hydroxy-ethanoyl)-piperidin-4-ylmethyl]-amide Starting from 4-(5-cyclopropylmethoxy-benzo[1,3]dioxol-4-yl)-5H-pyrrolo[3,2-d]pyrimidine-7-carboxylic acid (piperidin-4-ylmethyl)-amide (example A144) and acetic acid chlorocarbonyl-methyl ester the title compound is obtained as colorless solid.

MS (ESI): m/z=508 (MH$^+$).

$^1$H-NMR (400 MHz, DMSO-d$_6$): 12.27 (br.s, 1H, —NH); 9.03 (s, 1H); 8.51 (t, J=6.0, 1H, —NH); 8.27 (s, 1H); 7.01 (d, J=8.6, 1H); 6.56 (d, J=8.6, 1H); 6.00 (s, 2H); 4.41 (t, J=5.3, 1H, —OH); 4.35 (m, 1H); 4.07 (m, 2H); 3.77 (d, J=6.8, 2H); 3.69 (m, 1H); 3.34 (dd, J$_1$=J$_2$=5.8, 2H); 2.94 (m, 1H); 2.63 (m, 1H); 1.84 (m, 1H); 1.76 (m, 2H); 1.19 (m, 1H); 1.12 (m, 1H); 0.87 (m, 1H); 0.30 (m, 2H); 0.10 (m, 2H).

Example 187

4-(5-Cyclopropylmethoxy-benzo[1,3]dioxol-4-yl)-5H-pyrrolo[3,2-d]pyrimidine-7-carboxylic acid [1-((S)-2-hydroxy-propanoyl)piperidin-4-ylmethyl]-amide Starting from 4-(5-cyclopropylmethoxy-benzo[1,3]dioxol-4-yl)-5H-pyrrolo[3,2-d]pyrimidine-7-carboxylic acid (piperidin-4-ylmethyl)-amide (example A144) and acetic acid (S)-1-chlorocarbonyl-ethyl ester the title compound is obtained as colorless solid.

MS (ESI): m/z=522 (MH$^+$).

$^1$H-NMR (400 MHz, DMSO-d$_6$): 12.27 (br.s, 1H, —NH); 9.03 (s, 1H); 8.51 (t, J=6.0, 1H, —NH); 8.27 (s, 1H); 7.01 (d, J=8.5, 1H); 6.57 (d, J=8.5, 1H); 6.00 (s, 2H); 4.74 (br.s, 1H, —OH); 4.41 (m, 1H & 1H); 4.35 (m, 1H); 3.99 (m, 1H); 3.77 (d, J=6.7, 2H); 3.35 (dd, J$_1$=J$_2$=6.1, 2H); 2.98 (m, 1H); 2.60 (m, 1H); 1.86 (m, 1H); 1.76 (m, 2H); 1.19 (m, 1H); 1.17 (m, 3H); 1.12 (m, 1H); 0.88 (m, 1H); 0.30 (m, 2H); 0.10 (m, 2H).

Example 188

4-(5-Cyclopropylmethoxy-benzo[1,3]dioxol-4-yl)-5H-pyrrolo[3,2-d]pyrimidine-7-carboxylic acid {1-[1-(1-hydroxy-cyclopropyl)-methanoyl]-piperidin-4-ylmethyl}-amide Starting from 4-(5-cyclopropylmethoxy-benzo[1,3]dioxol-4-yl)-5H-pyrrolo[3,2-d]pyrimidine-7-carboxylic acid (piperidin-4-ylmethyl)-amide (example A144) and acetic acid 1-chlorocarbonyl-cyclopropyl ester the title compound is obtained as colorless solid.

MS (ESI): m/z=534 (MH$^+$).

$^1$H-NMR (400 MHz, DMSO-d$_6$): 12.27 (br.s, 1H, —NH); 9.04 (s, 1H); 8.51 (t, J=6.0, 1H, —NH); 8.27 (s, 1H); 7.01 (d, J=8.6, 1H); 6.57 (d, J=8.6, 1H); 6.23 (s, 1H, —OH); 6.00 (s, 2H); 4.42 (m, 2H); 3.77 (d, J=6.8, 2H); 3.35 (dd, J$_1$=J$_2$=6.3,

2H); 2.818 (m, 2H); 1.86 (m, 1H); 1.76 (m, 2H); 1.20 (m, 2H); 0.88 (m, 1H & 2H); 0.74 (m, 2H); 0.30 (m, 2H); 0.11 (m, 2H).

Example 189

4-(5-Cyclopropylmethoxy-benzo[1,3]dioxol-4-yl)-5H-pyrrolo[3,2-d]pyrimidine-7-carboxylic acid [1-(2-hydroxy-acetyl)piperidin-3-ylmethyl]-amide Starting from 4-(5-cyclopropylmethoxy-benzo[1,3]dioxol-4-yl)-5H-pyrrolo[3,2-d]pyrimidine-7-carboxylic acid (piperidin-3-ylmethyl)-amide (example A145) and acetic acid chlorocarbonyl-methyl ester the title compound is obtained as colorless solid.

MS (ESI): m/z=508 (MH+).

$^1$H-NMR (400 MHz, DMSO-$d_6$): 12.28 (br.s, 1H, —NH); 9.04 (s, 1H); 8.52 (br.s, 1H, —NH); 8.28 (s, 1H); 7.01 (d, J=8.6, 1H); 6.57 (d, J=8.6, 1H); 6.00 (s, 2H); 4.40 (br.s, 1H, —OH); 4.29 (m, 0.5H); 4.07 (m, 2.5H); 3.77 (d, J=6.7, 2H); 3.66 (m, 0.5H); 3.56 (m, 0.5H); 3.35 (m, 2H); 2.95 (m, 0.5H); 2.82 (m, 1H); 2.58 (m, 0.5H); 1.84 (m, 1.5H); 1.68 (m, 1.5H); 1.35 (m, 2H); 0.89 (m, 1H); 0.30 (m, 2H); 0.11 (m, 2H).

Example 190

4-(5-Cyclopropylmethoxy-benzo[1,3]dioxol-4-yl)-5H-pyrrolo[3,2-d]pyrimidine-7-carboxylic acid [1-((S)-2-hydroxy-propionyl)piperidin-3-ylmethyl]-amide Starting from 4-(5-cyclopropylmethoxy-benzo[1,3]dioxol-4-yl)-5H-pyrrolo[3,2-d]pyrimidine-7-carboxylic acid (piperidin-3-ylmethyl)-amide (example A145) and acetic acid (S)-1-chlorocarbonyl-ethyl ester the title compound is obtained as colorless solid.

MS (ESI): m/z=522 (MH+).

$^1$H-NMR (400 MHz, DMSO-$d_6$): 12.28 (br.s, 1H, —NH); 9.04 (s, 1H); 8.52 (br.s, 1H, —NH); 8.28 (s, 1H); 7.01 (d, J=8.6, 1H); 6.57 (d, J=8.6, 1H); 6.00 (s, 2H); 4.73 (m, 1H, —OH); 4.41 (m, 1H); 4.31 (m, 0.5H); 4.19 (m, 0.5H); 3.97 (m, 0.5H); 3.83 (m, 0.5H); 3.77 (d, J=6.7, 2H); 3.35 (m, 2H); 3.01 (m, 0.5H); 2.89 (m, 0.5H); 2.66 (m, 0.5H); 2.56 (m, 0.5H); 1.87 (m, 1H); 1.69 (m, 2H); 1.35 (m, 2H); 1.16 (m, 3H); 0.89 (m, 1H); 0.30 (m, 2H); 0.11 (m, 2H).

Example 191

4-(5-Cyclopropylmethoxy-benzo[1,3]dioxol-4-yl)-5H-pyrrolo[3,2-d]pyrimidine-7-carboxylic acid [1-(2-hydroxy-acetyl)pyrrolidin-3-ylmethyl]-amide Starting from 4-(5-cyclopropylmethoxy-benzo[1,3]dioxol-4-yl)-5H-pyrrolo[3,2-d]pyrimidine-7-carboxylic acid (pyrrolidin-3-ylmethyl)-amide (example A146) and acetic acid chlorocarbonyl-methyl ester the title compound is obtained as colorless solid.

MS (ESI): m/z=494 (MH+).

$^1$H-NMR (400 MHz, DMSO-$d_6$): 12.28 (br.s, 1H, —NH); 9.04 (s, 1H); 8.55 (m, 1H, —NH); 8.29 (s, 1H); 7.00 (d, J=8.6, 1H); 6.57 (d, J=8.6, 1H); 6.00 (s, 2H); 4.44 (t, J=5.4, 1H, —OH); 3.99 (m, 2H); 3.77 (d, J=6.7, 2H); 3.48 (m, 4H); 3.33 (m, 1H); 3.16 (m, 1H); 2.57 (m, 1H); 2.47 (m, 1H); 2.06 (, 0.5H); 1.97 (m, 0.5H); 1.76 (m, 0.5H); 1.66 (m, 0.5H); 0.88 (m, 1H); 0.29 (m, 2H); 0.10 (m, 2H).

Example 192

4-(5-Cyclopropylmethoxy-benzo[1,3]dioxol-4-yl)-5H-pyrrolo[3,2-d]pyrimidine-7-carboxylic acid [1-((S)-2-hydroxy-propionyl)pyrrolidin-3-ylmethyl]-amide Starting from 4-(5-cyclopropylmethoxy-benzo[1,3]dioxol-4-yl)-5H-pyrrolo[3,2-d]pyrimidine-7-carboxylic acid (pyrrolidin-3-ylmethyl)-amide (example A146) and acetic acid (S)-1-chlorocarbonyl-ethyl ester the title compound is obtained as colorless solid.

MS (ESI): m/z=508 (MH+).

$^1$H-NMR (400 MHz, DMSO-$d_6$): 12.28 (br.s, 1H, —NH); 9.05 (s, 0.5H); 9.04 (s, 0.5H); 8.54 (m, 1H, —NH); 8.29 (s, 1H); 7.01 (d, J=8.6, 1H); 6.57 (d, J=8.6, 1H); 6.00 (s, 2H); 4.77 (m, 1H, —OH); 4.24 (m, 1H); 3.77 (d, J=6.8, 2H); 3.75 (m, 0.5H); 3.64-3.38 (m, 4.5H); 3.29 (m, 0.5H); 3.13 (m, 0.5H); 2.55 (m, 0.5H); 2.47 (m, 0.5H); 2.05 (m, 0.5H); 1.97 (m, 0.5H); 1.77 (m, 0.5H); 1.66 (m, 0.5H); 1.16 (m, 3H); 0.88 (m, 1H); 0.30 (m, 2H); 0.10 (m, 2H).

Example 193

4-(5-Cyclopropylmethoxy-benzo[1,3]dioxol-4-yl)-5H-pyrrolo[3,2-d]pyrimidine-7-carboxylic acid [4-(2-hydroxy-acetyl)morpholin-2-ylmethyl]-amide Starting from 4-(5-cyclopropylmethoxy-benzo[1,3]dioxol-4-yl)-5H-pyrrolo[3,2-d]pyrimidine-7-carboxylic acid (morpholin-2-ylmethyl)-amide (example A147) and acetic acid chlorocarbonyl-methyl ester the title compound is obtained as colorless solid.

MS (ESI): m/z=510 (MH+).

$^1$H-NMR (400 MHz, DMSO-$d_6$): 12.29 (br.s, 1H, —NH); 9.04 (s, 1H); 8.58 (t, J=5.7, 1H, —NH); 8.30 (s, 1H); 7.01 (d, J=8.6, 1H); 6.56 (d, J=8.6, 1H); 6.00 (s, 2H); 4.59 (br.s, 1H, —OH); 4.28 (m, 0.5H); 4.14 (m, 1.5H); 4.05 (m, 1H); 3.91 (m, 1H); 3.76 (d, J=6.7, 2H & m, 0.5H); 3.59 (m, 2.5H); 3.23 (m, 2H); 3.11 (m, 0.5H); 2.95 (m, 0.5H); 2.80 (m, 0.5H); 2.60 (m, 0.5H); 0.88 (m, 1H); 0.29 (m, 2H): 0.10 (m, 2H).

Example 194

4-(5-Cyclopropylmethoxy-benzo[1,3]dioxol-4-yl)-5H-pyrrolo[3,2-d]pyrimidine-7-carboxylic acid [4-((S)-2-hydroxy-propionyl)-morpholin-2-ylmethyl]-amide Starting from 4-(5-cyclopropylmethoxy-benzo[1,3]dioxol-4-yl)-5H-pyrrolo[3,2-d]pyrimidine-7-carboxylic acid (morpholin-2-ylmethyl)-amide (example A147) and acetic acid (S)-1-chlorocarbonyl-ethyl ester the title compound is obtained as colorless solid.

MS (ESI): m/z=524 (MH+).

$^1$H-NMR (400 MHz, DMSO-$d_6$): 12.29 (br.s, 1H, —NH); 9.04 (s, 1H); 8.59 (t, J=5.6, 1H, —NH); 8.30 (s, 1H); 7.01 (d, J=8.6, 1H); 6.56 (d, J=8.6, 1H); 6.00 (s, 2H); 4.92 (br.s, 1H, —OH); 4.42 (m, 1H); 4.30 (m, 0.5H); 4.16 (m, 0.5H); 4.05 (m, 0.5H); 3.91 (m, 1.5H); 3.77 (d, J=6.7, 2H); 3.59 (m, 2H); 3.49 (m, 2H); 3.15 (m, 0.5H); 2.99 (m, 0.5H); 2.77 (m, 0.5H); 2.58 (m, 0.5H); 1.18 (br.s, 3H); 0.88 (m, 1H); 0.29 (M, 2H); 0.10 (m, 2H).

Example 195

4-(5-Cyclopropylmethoxy-benzo[1,3]dioxol-4-yl)-5H-pyrrolo[3,2-d]pyrimidine-7-carboxylic acid [1-(2-hydroxy-ethanoyl)-azetidin-3-yl]-amide Starting from 4-(5-cyclopropylmethoxy-benzo[1,3]dioxol-4-yl)-5H-pyrrolo[3,2-d]pyrimidine-7-carboxylic acid azetidin-3-ylamide (example A172) and acetic acid chlorocarbonyl-methyl ester the title compound is obtained as colorless solid.

MS (ESI): m/z=466 (MH$^+$).
$^1$H-NMR (400 MHz, DMSO-d$_6$): 12.32 (br.s, 1H, —NH); 9.06 (s, 1H); 8.86 (d, J=7.2, 1H, —NH); 8.32 (s, 1H); 7.01 (d, J=8.6, 1H); 6.57 (d, J=8.6, 1H); 6.01 (s, 2H); 4.90 (t, J=5.4, 1H, —OH); 4.82 (m, 1H); 4.54 (m, 1H); 4.28 (m, 1H); 4.21 (m, 1H); 3.94 (d, J=5.4, 2H); 3.90 (m, 1H); 3.76 (d, J=6.7, 2H); 0.87 (m, 1H); 0.29 (M, 2H); 0.09 (m, 2H).

Example 196

4-(5-Cyclopropylmethoxy-benzo[1,3]dioxol-4-yl)-5H-pyrrolo[3,2-d]pyrimidine-7-carboxylic acid [1-((S)-2-hydroxy-propanoyl)azetidin-3-yl]-amide Starting from 4-(5-cyclopropylmethoxy-benzo[1,3]dioxol-4-yl)-5H-pyrrolo[3,2-d]pyrimidine-7-carboxylic acid azetidin-3-ylamide (example A172) and acetic acid (S)-1-chlorocarbonyl-ethyl ester the title compound is obtained as colorless solid.

MS (ESI): m/z=480 (MH$^+$).
$^1$H-NMR (400 MHz, DMSO-d$_6$): 12.33 (br.s, 1H, —NH); 9.07 (s, 1H); 8.85 (d, J=7.2, 1H, —NH); 8.32 (s, 1H); 7.01 (d, J=8.6, 1H); 6.57 (d, J=8.6, 1H); 6.01 (s, 2H); 5.06 (m, 1H, —OH); 4.80 (m, 1H); 4.63 (m, 1H); 4.26 (m, 1H); 4.15 (m, 1H); 3.89 (d, J=5.4, 2H); 3.76 (d, J=6.7, 2H); 1.21 (d, J=6.7, 3H); 0.87 (m, 1H); 0.29 (M, 2H); 0.10 (m, 2H).

Example 197

4-(5-Cyclopropylmethoxy-benzo[1,3]dioxol-4-yl)-5H-pyrrolo[3,2-d]pyrimidine-7-carboxylic acid [(S)-1-((S)-2-hydroxy-propanoyl)piperidin-3-yl]-amide Starting from 4-(5-cyclopropylmethoxy-benzo[1,3]dioxol-4-yl)-5H-pyrrolo[3,2-d]pyrimidine-7-carboxylic acid (S)-piperidin-3-ylamide (example A148) and acetic acid (S)-1-chlorocarbonyl-ethyl ester the title compound is obtained as colorless solid.

MS (ESI): m/z=508.1 (MH$^+$).
$^1$H-NMR (400 MHz, DMSO-d$_6$): 11.86 (br.s, 1H, —NH); 9.01 (s, 0.5H); 8.98 (s, 0.5H); 8.52 (d, J=7.7, 1H, —NH); 8.30 (br.s, 1H); 7.01 (d, J=8.6, 1H); 6.56 (d, J=8.6, 1H); 6.00 (s, 2H); 4.76 (~d, 0.5H, —OH); 4.62 (~d, 0.5H, —OH); 4.46 (m, 1H); 4.06 (m, 0.5H); 3.92 (m, 2H); 3.76 (d, J=6.7, 2H); 3.59 (m, 0.5H); 3.38 (m, 1H); 3.20 (m, 1H); 2.96 (m, 1H); 1.99 (m, 1H); 1.76 (m, 2H); 1.52 (m, 1H); 1.24 (br.s, 3H); 0.87 (m, 1H); 0.29 (m, 2H); 0.10 (m, 2H).

Example 198

4-(5-Cyclopropylmethoxy-benzo[1,3]dioxol-4-yl)-5H-pyrrolo[3,2-d]pyrimidine-7-carboxylic acid [(R)-1-((S)-2-hydroxy-propanoyl)piperidin-3-yl]-amide Starting from 4-(5-cyclopropylmethoxy-benzo[1,3]dioxol-4-yl)-5H-pyrrolo[3,2-d]pyrimidine-7-carboxylic acid (R)-piperidin-3-ylamide (example A149) and acetic acid (S)-1-chlorocarbonyl-ethyl ester the title compound is obtained as colorless solid.

MS (ESI): m/z=508.1 (MH$^+$).
$^1$H-NMR (400 MHz, DMSO-d$_6$): 11.86 (br.s, 1H, —NH); 9.01 (s, 0.5H); 8.98 (s, 0.5H); 8.52 (d, J=7.7, 1H, —NH); 8.30 (br.s, 1H); 7.01 (d, J=8.6, 1H); 6.56 (d, J=8.6, 1H); 6.00 (s, 2H); 4.76 (~d, 0.5H, —OH); 4.62 (~d, 0.5H, —OH); 4.46 (m, 1H); 4.06 (m, 0.5H); 3.92 (m, 2H); 3.76 (d, J=6.7, 2H); 3.59 (m, 0.5H); 3.38 (m, 1H); 3.20 (m, 1H); 2.96 (m, 1H); 1.99 (m, 1H); 1.76 (m, 2H); 1.52 (m, 1H); 1.24 (br.s, 3H); 0.87 (m, 1H); 0.29 (m, 2H); 0.10 (m, 2H).

Example 199 trans-4-(2-Cyclopropylmethoxy-4-methoxy-phenyl)-5H-pyrrolo[3,2-d]pyrimidine-7-carboxylic acid [4-(2-hydroxy-acetylamino)-cyclohexyl]-amide Starting from trans-4-(2-cyclopropylmethoxy-4-methoxy-phenyl)-5H-pyrrolo[3,2-d]pyrimidine-7-carboxylic acid (4-amino-cyclohexyl)-amide (example A150) and acetic acid chlorocarbonyl-methyl ester the title compound is obtained as colorless solid.

MS (ESI): m/z=494 (MH$^+$, 100%).
$^1$H-NMR (400 MHz, DMSO-d$_6$): 11.90 (br.s, 1H, —NH); 9.01 (s, 1H); 8.39 (d, J=7.9, 1H, —NH); 8.21 (s, 1H); 7.62 (d, J=8.5, 1H); 7.49 (d, J=8.3, 1H, —NH); 6.73 (dd, J$_1$=8.5, J$_2$=2.1, 1H); 6.69 (d, J=2.1, 1H); 5.42 (t, J=5.8, 1H, —OH); 3.92 (d, J=6.9, 2H); 3.86 (s, 3H & m, 1H); 3.80 (d, J=5.8, 1H); 3.33 (m, 1H); 2.01 (m, 2H, 1.82 (m, 2H); 1.38 (m, 4H); 1.17 (t, J=7.0, 3H); 0.97 (m, 1H); 0.37 (m, 2H); 0.23 (m, 2H).

Example 200 trans-4-(2-Cyclopropylmethoxy-4-methoxy-phenyl)-5H-pyrrolo[3,2-d]pyrimidine-7-carboxylic acid [4-((S)-2-hydroxy-propionylamino)-cyclohexyl]-amide Starting from trans-4-(2-cyclopropylmethoxy-4-methoxy-phenyl)-5H-pyrrolo[3,2-d]pyrimidine-7-carboxylic acid (4-amino-cyclohexyl)-amide (example A150) and acetic acid (S)-1-chlorocarbonyl-ethyl ester the title compound is obtained as colorless solid.

MS (ESI): m/z=508 (MH$^+$, 100%).
$^1$H-NMR (400 MHz, DMSO-d$_6$): 11.90 (br.s, 1H, —NH); 9.01 (s, 1H); 8.39 (d, J=7.9, 1H, —NH); 8.21 (s, 1H); 7.62 (d, J=8.5, 1H); 7.43 (d, J=8.3, 1H, —NH); 6.73 (dd, J$_1$=8.5, J$_2$=2.1, 1H); 6.69 (d, J=2.1, 1H); 5.43 (d, J=5.2, 1H, —OH); 3.96 (m, 1H); 3.92 (d, J=6.9, 2H); 3.86 (s, 3H); 3.80 (m, 1H); 3.64 (m, 1H); 2.00 (m, 2H, 1.82 (m, 2H); 1.43 (m, 4H); 1.21 (d, J=6.7, 3H); 0.97 (m, 1H); 0.37 (m, 2H); 0.23 (m, 2H).

Example 201 trans-4-(2-Cyclopropylmethoxy-4-methoxy-phenyl)-5H-pyrrolo[3,2-d]pyrimidine-7-carboxylic acid {4-[(1-hydroxy-cyclopropanecarbonyl)-amino]-cyclohexyl}-amide Starting from trans-4-(2-cyclopropylmethoxy-4-methoxy-phenyl)-5H-pyrrolo[3,2-d]pyrimidine-7-carboxylic acid (4-amino-cyclohexyl)-amide (example A150) and acetic acid 1-chlorocarbonyl-cyclopropyl ester the title compound is obtained as colorless solid.

MS (ESI): m/z=520 (MH+, 100%).

¹H-NMR 300 MHz, DMSO-d₆): 11.89 (br.s, 1H, —NH); 9.00 (s, 1H); 8.37 (d, J=7.9, 1H, —NH); 8.20 (d, J=3.2, 1H); 7.61 (d, J=8.4, 1H); 7.56 (d, J=8.5, 1H, —NH); 6.72 (dd, J₁=8.4, J₂=2.2, 1H); 6.69 (d, J=2.2, 1H); 6.20 (s, 1H, —OH); 3.91 (d, J=6.9, 2H); 3.86 (s, 3H); 3.81 (m, 1H); 3.70 (m, 1H); 2.01 (m, 2H); 1.82 (m, 2H); 1.47 (m, 4H); 1.02 (m, 2H); 0.97 (m, 1H); 0.83 (m, 2H); 0.34 (m, 2H); 0.24 (m, 2H).

Example 202 cis-4-(2-Cyclopropylmethoxy-4-methoxy-phenyl)-5H-pyrrolo[3,2-d]pyrimidine-7-carboxylic acid [4-(2-hydroxy-acetylamino)-cyclohexyl]-amide Starting from cis-4-(2-cyclopropylmethoxy-4-methoxyphenyl)-5H-pyrrolo[3,2-d]pyrimidine-7-carboxylic acid (4-amino-cyclohexyl)-amide (example A151) and acetic acid chlorocarbonyl-methyl ester the title compound is obtained as colorless solid.

MS (ESI): m/z=(MH+, 100%).

¹H-NMR (400 MHz, DMSO-d₆): 11.91 (br.s, 1H, —NH); 9.03 (s, 1H); 8.68 (d, J=7.5, 1H, —NH); 8.21 (d, J=3.3, 1H); 7.62 (d, J=8.5, 1H); 7.56 (d, J=7.8, 1H, —NH); 6.72 (dd, J₁=8.5, J₂=2.2, 1H); 6.69 (d, J=2.2, 1H); 5.34 (t, J=5.9, 1H, —OH); 4.07 (m, 1H); 3.92 (d, J=6.9, 2H); 3.85 (s, 3H); 3.82 (d, J=5.9, 2H & m, 1H); 1.82-1.58 (m, 8H); 1.22 (d, J=6.7, 1H); 0.97 (m, 1H); 0.37 (m, 2H); 0.23 (m, 2H).

Example 203 cis-4-(2-Cyclopropylmethoxy-4-methoxy-phenyl)-5H-pyrrolo[3,2-d]pyrimidine-7-carboxylic acid [4-((S)-2-hydroxy-propionylamino)-cyclohexyl]-amide Starting from cis-4-(2-cyclopropylmethoxy-4-methoxyphenyl)-5H-pyrrolo[3,2-d]pyrimidine-7-carboxylic acid (4-amino-cyclohexyl)-amide (example A151) and acetic acid (S)-1-chlorocarbonyl-ethyl ester the title compound is obtained as colorless solid.

MS (ESI): m/z=508 (MH+, 100%).

¹H-NMR (400 MHz, DMSO-d₆): 11.90 (br.s, 1H, —NH); 9.03 (s, 1H); 8.67 (d, J=7.5, 1H, —NH); 8.21 (s, 1H); 7.62 (d, J=8.4, 1H); 7.51 (d, J=7.7, 1H, —NH); 6.72 (dd, J₁=8.4, J₂=2.2, 1H); 6.69 (d, J=2.2, 1H); 5.37 (d, J=5.4, 1H, —OH); 4.07 (m, 1H); 3.99 (m, 1H); 3.92 (d, J=7.0, 2H); 3.87 (s, 3H); 3.76 (m, 1H); 1.82-1.58 (m, 8H); 1.22 (d, J=6.7, 1H); 0.97 (m, 1H); 0.37 (m, 2H); 0.23 (m, 2H).

Example 204 cis-4-(2-Cyclopropylmethoxy-4-methoxy-phenyl)-5H-pyrrolo[3,2-d]pyrimidine-7-carboxylic acid {-[(1-hydroxy-cyclopropanecarbonyl)-amino]-cyclohexyl}-amide Starting from cis-4-(2-cyclopropylmethoxy-4-methoxyphenyl)-5H-pyrrolo[3,2-d]pyrimidine-7-carboxylic acid (4-amino-cyclohexyl)-amide (example A151) and acetic acid 1-chlorocarbonyl-cyclopropyl ester the title compound is obtained as colorless solid.

MS (ESI): m/z=520 (MH+, 100%).

¹H-NMR 400 MHz, DMSO-d₆): 11.90 (br.s, 1H, —NH); 9.04 (s, 1H); 8.37 (d, J=7.9, 1H, —NH); 8.20 (d, J=3.2, 1H); 7.61 (d, J=8.4, 1H); 7.56 (d, J=8.5, 1H, —NH); 6.72 (dd, J₁=8.4, J₂=2.2, 1H); 6.69 (d, J=2.2, 1H); 6.26 (s, 1H, —OH); 4.09 (m, 1H); 3.92 (d, J=7.0, 2H); 3.86 (s, 3H); 3.78 (m, 1H); 1.87-1.66 (m, 8H); 1.02 (m, 2H); 0.98 (m, 1H); 0.83 (m, 2H); 0.34 (m, 2H); 0.24 (m, 2H).

Example 205

4-(2-Cyclopropylmethoxy-4-methoxy-phenyl)-5H-pyrrolo[3,2-d]pyrimidine-7-carboxylic acid [1-(2-hydroxy-ethanoyl)-piperidin-4-yl]amide Starting from 4-(2-cyclopropylmethoxy-4-methoxy-phenyl)-5H-pyrrolo[3,2-d]pyrimidine-7-carboxylic acid piperidin-4-ylamide (example A152) and acetic acid chlorocarbonyl-methyl ester the title compound is obtained as colorless solid.

MS (ESI): m/z=480 (MH+, 100%).

¹H-NMR 400 MHz, DMSO-d₆): 11.92 (br.s, 1H, —NH); 9.00 (s, 1H); 8.53 (d, J=7.8, 1H, —NH); 8.22 (s, 1H); 7.62 (d, J=8.5, 1H); 6.73 (dd, J₁=8.5, J₂=2.1, 1H); 6.69 (d, J=2.1, 1H); 4.51 (t, J=5.4, 1H, —OH); 4.27-4.05 (m, 4H); 3.92 (d, J=6.9, 2H); 3.86 (s, 3H); 3.69 (m, 1H); 3.19 (m, 1H); 2.99 (m, 1H); 2.00 (m, 2H); 1.56 (m, 1H); 1.42 (m 1H); 1.21 (m, 3H); 0.98 (m, 1H); 0.36 (m, 2H); 0.23 (m, 2H).

Example 206

4-(2-Cyclopropylmethoxy-4-methoxy-phenyl)-5H-pyrrolo[3,2-d]pyrimidine-7-carboxylic acid [1-((S)-2-hydroxy-propanoyl)piperidin-4-yl]-amide Starting from 4-(2-cyclopropylmethoxy-4-methoxy-phenyl)-5H-pyrrolo[3,2-d]pyrimidine-7-carboxylic acid piperidin-4-ylamide (example A152) and acetic acid (S)-1-chlorocarbonyl-ethyl ester the title compound is obtained as colorless solid.

MS (ESI): m/z=494 (MH+, 100%).

¹H-NMR (400 MHz, DMSO-d₆): 11.94 (br.s, 1H, —NH); 9.00 (s, 1H); 8.53 (d, J=7.7, 1H, —NH); 8.23 (s, 1H); 7.62 (d, J=8.5, 1H); 6.73 (dd, J₁=8.5, J₂=2.1, 1H); 6.69 (d, J=2.1, 1H); 4.88 (d, J=6.9, 1H, —OH); 4.46 (m, 1H); 4.26 (m, 1H); 4.18 (m, 1H); 3.98 (m, 1H); 3.93 (d, J=6.9, 2H); 3.87 (s, 3H); 3.31 (m, 1H); 2.98 (m, 1H); 1.98 (m, 2H); 1.56 (m, 1H); 1.42 (m 1H); 0.97 (m, 1H); 0.36 (m, 2H); 0.23 (m, 2H).

Example 207

4-(2-Cyclopropylmethoxy-4-methoxy-phenyl)-5H-pyrrolo[3,2-d]pyrimidine-7-carboxylic acid {1-[1-(1-hydroxy-cyclopropyl)-methanoyl]-piperidin-4-yl}-amide Starting from 4-(2-cyclopropylmethoxy-4-methoxy-phenyl)-5H-pyrrolo[3,2-d]pyrimidine-7-carboxylic acid piperidin-4-ylamide (example A152) and acetic acid 1-chlorocarbonyl-cyclopropyl ester the title compound is obtained as colorless solid.

MS (ESI): m/z=506 (MH+, 100%).

¹H-NMR 400 MHz, DMSO-d₆): 11.92 (br.s, 1H, —NH); 9.00 (s, 1H); 8.54 (d, J=7.9, 1H, —NH); 8.23 (s, 1H); 7.62 (d, J=8.5, 1H); 6.72 (dd, J₁=8.5, J₂=2.2, 1H); 6.69 (d, J=2.2, 1H); 6.31 (s, 1H, —OH); 4.28 (m, 1H); 4.17 (m, 2H); 3.91 (d,

J=6.9, 2H); 3.86 (s, 3H); 3.16 (m, 2H); 1.99 (m, 2H); 1.51 (m, 2H); 0.97 (m, 1H); 0.94 (m, 2H); 0.77 (m, 2H); 0.36 (m, 2H); 0.23 (m, 2H).

Example 208 cis-4-(2-Cyclopropylmethoxy-5-methoxy-phenyl)-5H-pyrrolo[3,2-d]pyrimidine-7-carboxylic acid [4-(2-hydroxy-acetylamino)-cyclohexyl]-amide Starting from cis-4-(2-cyclopropylmethoxy-5-methoxy-phenyl)-5H-pyrrolo[3,2-d]pyrimidine-7-carboxylic acid (4-amino-cyclohexyl)-amide (example A154) and acetic acid chlorocarbonyl-methyl ester the title compound is obtained as colorless solid.

MS (ESI): m/z=494 (MH$^+$, 100%).

$^1$H-NMR 200 MHz, DMSO-d$_6$): 12.00 (br.s, 1H, —NH); 9.08 (s, 1H); 8.65 (d, J=7.8, 1H, —NH); 8.25 (s, 1H); 7.56 (d, J=7.7, 1H, —NH); 7.19 (t, J=1.7, 1H); 7.12 (d, J=1.7, 2H); 5.33 (t, J=5.9, 1H, —OH); 4.07 (m, 1H); 3.83 (d, J=6.8, 2H & d, J=5.9, 2H); 3.78 (s, 3H & m, 1H); 1.89-1.61 (m, 8H); 0.93 (m, 1H); 0.33 (m, 2H); 0.17 (m, 2H).

Example 209 cis-4-(2-Cyclopropylmethoxy-5-methoxy-phenyl)-5H-pyrrolo[3,2-d]pyrimidine-7-carboxylic acid {4-[(1-hydroxy-cyclopropanecarbonyl)-amino]-cyclohexyl}-amide Starting from cis-4-(2-cyclopropylmethoxy-5-methoxy-phenyl)-5H-pyrrolo[3,2-d]pyrimidine-7-carboxylic acid (4-amino-cyclohexyl)-amide (example A154) and acetic acid 1-chlorocarbonyl-cyclopropyl ester the title compound is obtained as colorless solid.

MS (ESI): m/z=520 (MH$^+$, 100%).

$^1$H-NMR 200 MHz, DMSO-d$_6$): 12.00 (br.s, 1H, —NH); 9.09 (s, 1H); 8.67 (d, J=7.4, 1H, —NH); 8.24 (s, 1H); 7.56 (d, J=7.8, 1H, —NH); 7.18 (t, J=1.6, 1H); 7.11 (d, J=1.6, 2H); 6.27 (s, 1H, —OH); 4.10 (m, 1H); 3.82 (d, J=6.8, 2H); 3.77 (s, 3H & m, 1H); 1.85-1.68 (m, 8H); 1.07 (m, 2H); 0.91 (m, 1H); 0.83 (m, 2H); 0.32 (m, 2H); 0.17 (m, 2H).

Example 210 trans-4-(2-Cyclopropylmethoxy-5-methoxy-phenyl)-5H-pyrrolo[3,2-d]pyrimidine-7-carboxylic acid {4-[(1-hydroxy-cyclopropanecarbonyl)-amino]-cyclohexyl}-amide Starting from trans-4-(2-cyclopropylmethoxy-5-methoxy-phenyl)-5H-pyrrolo[3,2-d]pyrimidine-7-carboxylic acid (4-amino-cyclohexyl)-amide (example A153) and acetic acid 1-chlorocarbonyl-cyclopropyl ester the title compound is obtained as colorless solid.

MS (ESI): m/z=520 (MH$^+$, 100%).

$^1$H-NMR 200 MHz, DMSO-d$_6$): 11.98 (br.s, 1H, —NH); 9.05 (s, 1H); 8.35 (d, J=7.8, 1H, —NH); 8.24 (s, 1H); 7.56 (d, J=8.4, 1H, —NH); 7.18 (t, J=1.6, 1H); 7.11 (d, J=1.6, 2H); 6.15 (s, 1H, —OH); 3.82 (d, J=6.8, 2H & m, 1H); 3.77 (s, 3H); 3.68 (m, 1H); 2.03 (m, 2H); 1.83 (m, 2H); 1.57-1.39 (m, 4H); 1.02 (m, 2H); 0.91 (m, 1H); 0.82 (m, 2H); 0.32 (m, 2H); 0.15 (m, 2H).

Example 211

4-(2-Cyclopropylmethoxy-5-methoxy-phenyl)-5H-pyrrolo[3,2-d]pyrimidine-7-carboxylic acid [1-(2-hydroxy-acetyl)piperidin-4-yl]-amide Starting from 4-(2-cyclopropylmethoxy-5-methoxy-phenyl)-5H-pyrrolo[3,2-d]pyrimidine-7-carboxylic acid piperidin-4-ylamide (example A155) and acetic acid chlorocarbonyl-methyl ester the title to compound is obtained as colorless solid.

MS (ESI): m/z=480 (MH$^+$, 100%).

$^1$H-NMR 400 MHz, DMSO-d$_6$): 12.03 (br.s, 1H, —NH); 9.05 (s, 1H); 8.51 (d, J=7.8, 1H, —NH); 8.27 (s, 1H); 7.19 (t, J=1.6, 1H); 7.11 (d, J=1.6, 2H); 4.52 (t, J=5.4, 1H, —OH); 4.27-4.08 (m, 4H); 3.82 (d, J=6.8, 2H); 3.77 (s, 3H); 3.69 (m, 1H); 3.20 (m, 1H); 3.00 (m, 1H); 1.99 (m, 2H); 1.58 (m, 1H); 1.43 (m, 1H); 0.91 (m, 1H); 0.32 (m, 2H); 0.17 (m, 2H).

Example 212

4-(2-Cyclopropylmethoxy-5-methoxy-phenyl)-5H-pyrrolo[3,2-d]pyrimidine-7-carboxylic acid [1-((S)-2-hydroxy-propionyl)piperidin-4-yl]-amide Starting from 4-(2-cyclopropylmethoxy-5-methoxy-phenyl)-5H-pyrrolo[3,2-d]pyrimidine-7-carboxylic acid piperidin-4-ylamide (example A155) and acetic acid (S)-1-chlorocarbonyl-ethyl ester the title compound is obtained as colorless solid.

MS (ESI): m/z=494 (MH$^+$, 100%).

$^1$H-NMR 400 MHz, DMSO-d$_6$): 12.03 (br.s, 1H, —NH); 9.05 (s, 1H); 8.51 (d, J=7.8, 1H, —NH); 8.27 (s, 1H); 7.19 (t, J=1.6, 1H); 7.11 (d, J=1.6, 2H); 488 (d, J=6.9, 1H, —OH); 447 (m, 1H); 4.30-4.20 (m, 2H); 3.97 (m, 1H); 3.82 (d, J=6.9, 2H); 3.78 (s, 3H); 3.28 (m, 1H); 2.96 (m, 1H); 1.99 (m, 2H); 1.57 (m, 1H); 1.42 (m, 1H); 1.21 (m, 3H); 0.91 (m, 1H); 0.32 (m, 2H); 0.17 (m, 2H).

Example 213

4-(2-Cyclopropylmethoxy-5-methoxy-phenyl)-5H-pyrrolo[3,2-d]pyrimidine-7-carboxylic acid [1-(1-hydroxy-cyclopropanecarbonyl)-piperidin-4-yl]-amide Starting from 4-(2-cyclopropylmethoxy-5-methoxy-phenyl)-5H-pyrrolo[3,2-d]pyrimidine-7-carboxylic acid piperidin-4-ylamide (example A155) and acetic acid 1-chlorocarbonyl-cyclopropyl ester the title compound is obtained as colorless solid.

MS (ESI): m/z=506 (MH$^+$, 100%).

$^1$H-NMR 400 MHz, DMSO-d$_6$): 12.01 (br.s, 1H, —NH); 9.06 (s, 1H); 8.52 (d, J=7.8, 1H, —NH); 8.27 (s, 1H); 7.19 (t, J=1.6, 1H); 7.11 (d, J=1.6, 2H); 6.31 (s, 1H, —OH); 4.29 (m, 2H); 4.18 (m, 1H); 3.83 (d, J=6.9, 2H); 3.77 (s, 3H); 3.17 (m, 2H); 2.00 (m, 2H); 1.51 (m, 2H); 0.92 (m, 3H); 0.78 (m, 2H); 0.32 (m, 2H); 0.17 (m, 2H).

Example 214 cis-4-(2-Cyclopropylmethoxy-4-fluoro-phenyl)-5H-pyrrolo[3,2-d]pyrimidine-7-carboxylic acid [4-(2-hydroxy-acetylamino)-cyclohexyl]-amide Starting from cis-4-(2-cyclopropylmethoxy-4-fluoro-phenyl)-5H-pyrrolo[3,2-d]pyrimidine-7-carboxylic acid (4-amino-cyclohexyl)-amide (example A156) and acetic acid chlorocarbonyl-methyl ester the title compound is obtained as colorless solid.

MS (ESI): m/z=482 (MH$^+$, 100%).

$^1$H-NMR (300 MHz, DMSO-d$_6$): 12.04 (br.s, 1H, —NH); 9.07 (s, 1H); 8.65 (d, J=7.5, 1H; —NH); 8.28 (s, 1H); 7.68 (dd, J$_1$=8.6, J$_2$=7.0, 1H); 7.55 (d, J=7.7, 1H, —NH); 7.09 (dd, J$_1$=11.6, J$_2$=2.4, 1H); 6.97 (ddd, J$_1$=J$_2$=8.5, J$_3$=2.4, 1H); 5.33 (t, J=5.9, 1H, —OH); 4.07 (m, 1H); 3.93 (d, J=7.0, 2H); 3.82 (d, J=5.9, 2H & m, 1H); 1.88-1.53 (m, 8H); 0.97 (m, 1H); 0.36 (m, 2H); 0.22 (m, 2H).

Example 215 cis-4-(2-Cyclopropylmethoxy-4-fluoro-phenyl)-5H-pyrrolo[3,2-d]pyrimidine-7-carboxylic acid [4-((S)-2-hydroxy-propionylamino)-cyclohexyl]-amide Starting from cis-4-(2-cyclopropylmethoxy-4-fluoro-phenyl)-5H-pyrrolo[3,2-d]pyrimidine-7-carboxylic acid (4-amino-cyclohexyl)-amide (example A156) and acetic acid (S)-1-chlorocarbonyl-ethyl ester the title compound is obtained as colorless solid.

MS (ESI): m/z=496 (MH$^+$, 100%).

$^1$H-NMR (300 MHz, DMSO-d$_6$): 11.95 (br.s, 1H, —NH); 9.08 (s, 1H); 8.64 (d, J=7.4, 1H; —NH); 8.28 (s, 1H); 7.68 (dd, J$_1$=8.4, J$_2$=7.1, 1H); 7.50 (d, J=7.7, 1H, —NH); 7.09 (dd, J$_1$=11.5, J$_2$=2.2, 1H); 6.97 (ddd, J$_1$=J$_2$=8.5, J$_3$=2.2, 1H); 5.37 (d, J=5.4, 1H, —OH); 4.07 (m, 1H); 3.99 (m, 1H); 3.93 (d, J=6.9, 2H); 3.76 (m, 1H); 1.82-1.59 (m, 8H); 0.97 (m, 1H); 0.37 (m, 2H); 0.22 (m, 2H).

Example 216 cis-4-(2-Cyclopropylmethoxy-4-fluoro-phenyl)-5H-pyrrolo[3,2-d]pyrimidine-7-carboxylic acid {4-[(1-hydroxy-cyclopropanecarbonyl)-amino]-cyclohexyl}-amide Starting from cis-4-(2-cyclopropylmethoxy-4-fluoro-phenyl)-5H-pyrrolo[3,2-d]pyrimidine-7-carboxylic acid (4-amino-cyclohexyl)-amide (example A156) and acetic acid 1-chlorocarbonyl-cyclopropyl ester the title compound is obtained as colorless solid.

MS (ESI): m/z=508 (MH$^+$, 100%).

$^1$H-NMR (300 MHz, DMSO-d$_6$): 12.03 (br.s, 1H, —NH); 9.09 (s, 1H); 8.67 (d, J=7.4, 1H; —NH); 8.28 (s, 1H); 7.68 (dd, J$_1$=8.4, J$_2$=7.0, 1H); 7.55 (d, J=7.8, 1H, —NH); 7.09 (dd, J$_1$=11.5, J$_2$=2.2, 1H); 6.97 (ddd, J$_1$=J$_2$=8.5, J$_3$=2.2, 1H); 6.25 (s, 1H, —OH); 4.09 (m, 1H); 3.93 (d, J=7.0, 2H); 3.78 (m, 1H); 1.85-1.64 (m, 8H); 1.03 (m, 2H); 0.97 (m, 1H); 0.83 (m, 2H); 0.37 (m, 2H); 0.22 (m, 2H).

Example 217 trans-4-(2-Cyclopropylmethoxy-4-fluoro-phenyl)-5H-pyrrolo[3,2-d]pyrimidine-7-carboxylic acid [4-(2-hydroxy-acetylamino)-cyclohexyl]-amide Starting from trans-4-(2-cyclopropylmethoxy-4-fluoro-phenyl)-5H-pyrrolo[3,2-d]pyrimidine-7-carboxylic acid (4-amino-cyclohexyl)-amide (example A157) acetic acid chlorocarbonyl-methyl ester the title compound is obtained as colorless solid.

MS (ESI): m/z=482 (MH$^+$, 100%).

$^1$H-NMR (400 MHz, DMSO-d$_6$): 12.05 (br.s, 1H, —NH); 9.04 (s, 1H); 8.35 (d, J=7.9, 1H; —NH); 8.27 (d, J=3.3, 1H); 7.67 (dd, J$_1$=8.4, J$_2$=7.2, 1H); 7.47 (d, J=8.2, 1H, —NH); 7.07 (dd, J$_1$=11.5, J$_2$=2.2, 1H); 6.96 (ddd, J$_1$=J$_2$=8.5, J$_3$=2.2, 1H); 5.41 (t, J=5.7, 1H, —OH); 3.92 (d, J=7.0, 2H); 3.79 (d, J=5.7, 2H & m, 1H); 2.02 (m, 2H); 1.83 (m, 2H); 1.46 (m, 4H); 0.96 (m, 1H); 0.36 (m, 2H); 0.22 (m, 2H).

Example 218 trans-4-(2-Cyclopropylmethoxy-4-fluoro-phenyl)-5H-pyrrolo[3,2-d]pyrimidine-7-carboxylic acid [4-((S)-2-hydroxy-propionylamino)-cyclohexyl]-amide Starting from trans-4-(2-cyclopropylmethoxy-4-fluoro-phenyl)-5H-pyrrolo[3,2-d]pyrimidine-7-carboxylic acid (4-amino-cyclohexyl)-amide (example A157) and acetic acid (S)-1-chlorocarbonyl-ethyl ester the title compound is obtained as colorless solid.

MS (ESI): m/z=496 (MH$^+$, 100%).

$^1$H-NMR (400 MHz, DMSO-d$_6$): 12.05 (br.s, 1H, —NH); 9.04 (s, 1H); 8.35 (d, J=7.8, 1H; —NH); 8.27 (d, J=3.3, 1H); 7.67 (dd, J$_1$=8.4, J$_2$=7.2, 1H); 7.41 (d, J=8.2, 1H, —NH); 7.07 (dd, J$_1$=11.5, J$_2$=2.2, 1H); 6.96 (ddd, J$_1$=J$_2$=8.5, J$_3$=2.2, 1H); 5.41 (d, J=5.2, 1H, —OH); 3.92 (d, J=7.0, 2H & m, 1H); 3.781 (m, 1H); 3.64 (m, 1H); 2.03 (m, 2H); 1.81 (m, 2H); 1.44 (m, 4H); 1.21 (d, J=6.7, 3H); 0.96 (m, 1H); 0.36 (m, 2H); 0.22 (m, 2H).

Example 219 trans-4-(2-Cyclopropylmethoxy-4-fluoro-phenyl)-5H-pyrrolo[3,2-d]pyrimidine-7-carboxylic acid {4-[(1-hydroxy-cyclopropanecarbonyl)-amino]-cyclohexyl}-amide Starting from trans-4-(2-cyclopropylmethoxy-4-fluoro-phenyl)-5H-pyrrolo[3,2-d]pyrimidine-7-carboxylic acid (4-amino-cyclohexyl)-amide (example A157) and acetic acid 1-chlorocarbonyl-cyclopropyl ester the title compound is obtained as colorless solid.

MS (ESI): m/z=508 (MH$^+$, 100%).

$^1$H-NMR (400 MHz, DMSO-d$_6$): 12.05 (br.s, 1H, —NH); 9.04 (s, 1H); 8.35 (d, J=7.9, 1H; —NH); 8.27 (s, 1H); 7.67 (dd, J$_1$=8.4, J$_2$=7.2, 1H); 7.56 (d, J=8.4, 1H, —NH); 7.07 (dd, J$_1$=11.5, J$_2$=2.2, 1H); 6.96 (ddd, J$_1$=J$_2$=8.5, J$_3$=2.2, 1H); 6.20 (s, 1H, —OH); 3.92 (d, J=7.0, 2H); 3.83 (m, 1H); 3.68 (m, 1H); 2.03 (m, 2H); 1.81 (m, 2H); 1.44 (m, 4H); 1.02 (m, 2H); 0.96 (m, 1H); 0.82 (m, 2H); 0.36 (m, 2H); 0.22 (m, 2H).

Example 220

4-(2-Cyclopropylmethoxy-5-fluoro-phenyl)-5H-pyrrolo[3,2-d]pyrimidine-7-carboxylic acid [1-(2-hydroxy-acetyl)piperidin-4-yl]-amide Starting from 4-(2-cyclopropylmethoxy-5-fluoro-phenyl)-5H-pyrrolo[3,2-d]pyrimidine-7-carboxylic acid piperidin-4-ylamide hydrochloride (example A159) and acetic acid chlorocarbonyl-methyl ester the title compound is obtained as colorless solid.

MS (ESI): m/z=468 (MH$^+$, 100%).

$^1$H-NMR (300 MHz, DMSO-d$_6$): 12.11 (br.s, 1H, —NH); 9.05 (s, 1H); 8.49 (d, J=7.7, 1H, —NH); 8.31 (s, 1H); 7.44 (dd, J$_1$=8.9, J$_2$=3.2, 1H); 7.38 (ddd, J$_1$=J$_2$=9.1, J$_3$=3.2, 1H); 7.19 (dd, J$_1$=9.1, J$_2$=4.4, 1H); 4.51 (t, J=5.4, 1H, —OH); 4.18 (m, 2H); 4.13 (d, J=5.4, 2H); 3.88 (d, J=6.9, 2H); 3.69 (m, 1H); 3.19 (m, 1H); 2.99 (m, 1H); 1.98 (m, 2H); 1.57 (m, 1H); 1.42 (m, 1H); 0.94 (m, 1H); 0.34 (m, 2H); 0.19 (m, 2H).

Example 221

4-(2-Cyclopropylmethoxy-5-fluoro-phenyl)-5H-pyrrolo[3,2-d]pyrimidine-7-carboxylic acid [1-((S)-2-hydroxy-propionyl)piperidin-4-yl]-amide Starting from 4-(2-cyclopropylmethoxy-5-fluoro-phenyl)-5H-pyrrolo[3,2-d]pyrimidine-7-carboxylic acid piperidin-4-ylamide hydrochloride (example A159) and acetic acid (S)-1-chlorocarbonyl-ethyl ester the title compound is obtained as colorless solid.

MS (ESI): m/z=482 (MH+, 100%).

$^1$H-NMR (300 MHz, DMSO-$d_6$): 12.11 (br.s, 1H, —NH); 9.05 (s, 1H); 8.49 (d, J=7.7, 1H, —NH); 8.31 (s, 1H); 7.44 (dd, $J_1$=8.9, $J_2$=3.2, 1H); 7.38 (ddd, $J_1$=$J_2$=9.1, $J_3$=3.2, 1H); 7.19 (dd, $J_1$=9.1, $J_2$=4.4, 1H); 4.86 (d, J=7.0, 1H, —OH); 4.47 (m, 1H); 4.31-4.10 (m, 2H); 3.97 (m, 1H); 3.88 (d, J=6.9, 2H); 3.28 (m, 1H); 2.97 (m, 1H); 1.99 (m, 2H); 1.55 (m, 1H); 1.44 (m, 1H); 1.20 (br.s, 3H); 0.94 (m, 1H); 0.34 (m, 2H); 0.19 (m, 2H).

Example 222 trans-4-(2-Cyclopropylmethoxy-5-fluoro-phenyl)-5H-pyrrolo[3,2-d]pyrimidine-7-carboxylic acid [4-(2-hydroxy-acetylamino)-cyclohexyl]-amide Starting from trans-4-(2-cyclopropylmethoxy-5-fluoro-phenyl)-5H-pyrrolo[3,2-d]pyrimidine-7-carboxylic acid (4-amino-cyclohexyl)-amide (example A160) acetic acid chlorocarbonyl-methyl ester the title compound is obtained as colorless solid.

MS (ESI): m/z=482 (MH+, 100%).

$^1$H-NMR (300 MHz, DMSO-$d_6$): 12.08 (br.s, 1H, —NH); 9.06 (s, 1H); 8.34 (d, J=7.9, 1H, —NH), 8.29 (d, J=3.3, 1H); 7.47 (d, J=8.9, 1H, —NH); 7.44 (dd, $J_1$=8.9, $J_2$=3.3, 1H); 7.38 (ddd, $J_1$=$J_2$=9.2, $J_3$=3.3, 1H); 7.19 (dd, $J_1$=9.2, $J_2$=4.4, 1H); 5.39 (br.s, 1H, —OH); 3.88 (d, J=6.9, 2H); 3.79 (m, 1H & s, 2H); 3.70 (m, 1H); 2.02 (m, 2H); 1.83 (m, 2H); 1.45 (m, 4H); 0.94 (m, 1H); 0.34 (m, 2H); 0.18 (m, 2H).

Example 223 trans-4-(2-Cyclopropylmethoxy-4-fluoro-phenyl)-5H-pyrrolo[3,2-d]pyrimidine-7-carboxylic acid [4-((S)-2-hydroxy-propionylamino)-cyclohexyl]-amide Starting from trans-4-(2-cyclopropylmethoxy-5-fluoro-phenyl)-5H-pyrrolo[3,2-d]pyrimidine-7-carboxylic acid (4-amino-cyclohexyl)-amide (example A160) and acetic acid (S)-1-chlorocarbonyl-ethyl ester the title compound is obtained as colorless solid.

MS (ESI): m/z=496 (MH+, 100%).

$^1$H-NMR (300 MHz, DMSO-$d_6$): 12.08 (br.s, 1H, —NH); 9.06 (s, 1H); 8.34 (d, J=7.8, 1H, —NH), 8.28 (s, 1H); 7.46-7.34 (m, 3H); 7.19 (dd, $J_1$=9.2, $J_2$=4.4, 1H); 5.41 (d, J=5.1, 1H, —OH); 3.95 (m, 1H); 3.88 (d, J=6.9, 2H); 3.86 (m, 1H); 3.64 (m, 1H); 2.01 (m, 2H); 1.83 (m, 2H); 1.44 (m, 4H); 1.21 (d, J=6.8, 3H); 0.94 (m, 1H); 0.34 (m, 2H); 0.18 (m, 2H).

Example 224 trans-4-(2-Cyclopropylmethoxy-phenyl)-5H-pyrrolo[3,2-d]pyrimidine-7-carboxylic acid [4-(2-hydroxy-acetylamino)-cyclohexyl]-amide Starting from trans-4-(2-cyclopropylmethoxy-phenyl)-5H-pyrrolo[3,2-d]pyrimidine-7-carboxylic acid (4-amino-cyclohexyl)-amide (example A161) acetic acid chlorocarbonyl-methyl ester the title compound is obtained as colorless solid.

MS (ESI): m/z=464 (MH+, 100%).

$^1$H-NMR (300 MHz, DMSO-$d_6$): 12.03 (s, 1H, —NH); 9.05 (s, 1H); 8.36 (d, J=7.8, 1H, —NH); 8.24 (s, 1H); 7.64 (dd, $J_1$=7.6, $J_2$=1.8, 1H); 7.53 (ddd, $J_1$=7.9, $J_2$=7.6, $J_3$=1.8, 1H); 7.48 (d, J=8.3, 1H, —NH); 7.17 (dd, $J_1$=7.9, $J_2$=0.9, 1H); 7.13 (ddd, $J_1$=$J_2$=7.6, $J_3$=0.9, 1H); 5.41 (t, J=5.7, 1H, —OH); 3.91 (d, J=6.9, 2H); 3.80 (d, J=5.7, 2H & m, 1H); 3.70 (m, 1H); 2.02 (m, 2H); 1.82 (m, 2H); 1.48 (m, 4H); 0.96 (m, 1H); 0.35 (m, 2H); 0.22 (m, 2H).

Example 225 trans-4-(2-Cyclopropylmethoxy-phenyl)-5H-pyrrolo[3,2-d]pyrimidine-7-carboxylic acid [4-((S)-2-hydroxy-propionylamino)-cyclohexyl]-amide Starting from trans-4-(2-cyclopropylmethoxy-phenyl)-5H-pyrrolo[3,2-d]pyrimidine-7-carboxylic acid (4-amino-cyclohexyl)-amide (example A161) and acetic acid (S)-1-chlorocarbonyl-ethyl ester the title compound is obtained as colorless solid.

MS (ESI): m/z=478 (MH+, 100%).

$^1$H-NMR (300 MHz, DMSO-$d_6$): 12.02 (s, 1H, —NH); 9.05 (s, 1H); 8.36 (d, J=7.9, 1H, —NH); 8.24 (s, 1H); 7.64 (dd, $J_1$=7.6, $J_2$=1.8, 1H); 7.53 (ddd, $J_1$=7.9, $J_2$=7.6, $J_3$=1.8, 1H); 7.24 (d, J=8.3, 1H, —NH); 7.17 (dd, $J_1$=7.9, $J_2$=0.9, 1H); 7.13 (ddd, $J_1$=$J_2$=7.6, $J_3$=0.9, 1H); 5.42 (d, J=5.2, 1H, —OH); 3.95 (m, 1H); 3.91 (d, J=6.9, 2H); 3.82 (m, 1H); 3.64 (m, 1H); 2.02 (m, 2H); 1.82 (m, 2H); 1.43 (m, 4H); 1.21 (d, J=6.8, 3H); 0.96 (m, 1H); 0.35 (m, 2H); 0.22 (m, 2H).

Example 226 trans-4-(2-Cyclopropylmethoxy-phenyl)-5H-pyrrolo[3,2-d]pyrimidine-7-carboxylic acid {4-[(1-hydroxy-cyclopropanecarbonyl)-amino]-cyclohexyl}-amide Starting from trans-4-(2-cyclopropylmethoxy-phenyl)-5H-pyrrolo[3,2-d]pyrimidine-7-carboxylic acid (4-amino-cyclohexyl)-amide (example A161) and acetic acid 1-chlorocarbonyl-cyclopropyl ester the title compound is obtained as colorless solid.

MS (ESI): m/z=490 (MH+, 100%).

$^1$H-NMR (300 MHz, DMSO-$d_6$): 12.02 (s, 1H, —NH); 9.05 (s, 1H); 8.36 (d, J=7.8, 1H, —NH); 8.24 (s, 1H); 7.63 (dd, $J_1$=7.6, $J_2$=1.8, 1H); 7.57 (, J=8.8, 1H, —NH); 7.53 (ddd, $J_1$=7.9, $J_2$=7.6, $J_3$=1.8, 1H); 7.17 (dd, $J_1$=7.9, $J_2$=0.9, 1H); 7.13 (ddd, $J_1$=$J_2$=7.6, $J_3$=0.9, 1H); 6.20 (s, 1H, —OH); 3.91 (d, J=6.9, 2H); 3.82 (m, 1H); 3.70 (m, 1H); 2.02 (m, 2H); 1.83 (m, 2H); 1.48 (m, 4H); 1.02 (m, 2H); 0.95 (m, 1H); 0.82 (m, 2H); 0.35 (m, 2H); 0.22 (m, 2H).

Example 227

4-(2-Cyclopropylmethoxy-phenyl)-5H-pyrrolo[3,2-d]pyrimidine-7-carboxylic acid [1-((S)-2-hydroxy-propionyl)-piperidin-4-yl]-amide Starting from 4-(2-cyclopropylmethoxy-phenyl)-5H-pyrrolo[3,2-d]pyrimidine-7-carboxylic acid piperidin-4-ylamide (example A162) and acetic acid (S)-1-chlorocarbonyl-ethyl ester the title compound is obtained as colorless solid.

MS (ESI): m/z=464 (MH$^+$, 100%).
$^1$H-NMR (300 MHz, DMSO-d$_6$): 12.05 (s, 1H, —NH); 9.05 (s, 1H); 8.52 (d, J=7.8, 1H, —NH); 8.26 (s, 1H); 7.64 (dd, J$_1$=7.6, J$_2$=1.7, 1H); 7.53 (ddd, J$_1$=8.0, J$_2$=7.6, J$_3$=1.7, 1H); 7.17 (dd, J$_1$=8.0, J$_2$=0.9, 1H); 7.13 (ddd, J$_1$=J$_2$=7.6, J$_3$=0.9, 1H); 4.87 (d, J=6.9, 1H, —OH); 4.47 (m, 1H); 4.21 (m, 1H); 4.17 (m, 1H); 3.98 (m, 1H); 3.91 (d, J=6.8, 2H); 3.28 (m, 1H); 2.98 (m, 1H); 1.99 (m, 2H); 1.53 (m, 1H); 1.44 (m, 1H); 1.21 (br.s, 3H); 0.96 (m, 1H); 0.36 (m, 2H); 0.22 (m, 2H).

Example 228

4-(2-Cyclopropylmethoxy-4-fluoro-5-methoxy-phenyl)-5H-pyrrolo[3,2-d]pyrimidine-7-carboxylic acid [1-((S)-2-hydroxy-propionyl)-piperidin-4-yl]-amide Starting from 4-(2-cyclopropylmethoxy-4-fluoro-5-methoxy-phenyl)-5H-pyrrolo[3,2-d]pyrimidine-7-carboxylic acid piperidin-4-ylamide (example A163) and acetic acid (S)-1-chlorocarbonyl-ethyl ester the title compound is obtained as colorless solid.

MS (ESI): m/z=512 (MH$^+$, 100%).
$^1$H-NMR (300 MHz, DMSO-d$_6$): 12.03 (br.s, 1H, —NH); 9.05 (s, 1H); 8.50 (d, J=7.8, 1H, —NH); 8.29 (s, 1H); 7.41 (d, J=9.8, 1H); 7.18 (d, J=13.4, 1H); 4.86 (d, J=7.0, 1H, —OH); 4.47 (m, 1H); 4.20 (m, 2H); 3.97 (m, 1H); 3.85 (s, 3H & d, J=6.8, 2H); 3.30 (m, 1H); 2.97 (m, 1H); 1.99 (m, 2H); 1.53 (m, 1H); 1.44 (m, 1H); 1.21 (br.s, 3H); 0.92 (m, 1H); 0.34 (m, 2H); 0.17 (m, 2H).

Example 229

4-(2-Cyclopropylmethoxy-4-fluoro-5-methoxy-phenyl)-5H-pyrrolo[3,2-d]pyrimidine-7-carboxylic acid [(R)-1-(2-hydroxy-acetyl)piperidin-3-yl]-amide Starting from 4-(2-Cyclopropylmethoxy-4-fluoro-5-methoxy-phenyl)-5H-pyrrolo[3,2-d]pyrimidine-7-carboxylic acid (R)-piperidin-3-ylamide hydrochloride (example A164) and acetic acid chlorocarbonyl-methyl ester the title compound is obtained as colorless solid.

MS (ESI): m/z=498 (MH$^+$, 100%).
$^1$H-NMR (300 MHz, DMSO-d$_6$): 11.87 (br.s, 1H, —NH); 9.02 (s, 1H); 8.61 (br.m, 1H, —NH); 8.30 (s, 1H); 7.41 (d, J=9.9, 1H); 7.18 (d, J=13.3, 1H); 4.46 (br.m, 1H, —OH); 4.15 (br.s, 1H); 4.08 (br.s, 1H); 4.02 (m, 1H); 3.85 (s, 3H & d, J=6.8, 2H); 3.69-3.40 (m, 2H); 3.40-3.19 (m, 2H); 1.98 (m, 1H); 1.76 (m, 2H); 1.58 (m, 1H); 0.93 (m, 1H); 0.33 (m, 2H); 0.18 (m, 2H).

Example 230

4-(2-Cyclopropylmethoxy-4-fluoro-5-methoxy-phenyl)-5H-pyrrolo[3,2-d]pyrimidine-7-carboxylic acid [(R)-1-((S)-2-hydroxy-propionyl)-piperidin-3-yl]-amide Starting from 4-(2-cyclopropylmethoxy-4-fluoro-5-methoxy-phenyl)-5H-pyrrolo[3,2-d]pyrimidine-7-carboxylic acid (R)-piperidin-3-ylamide hydrochloride (example A164) and acetic acid (S)-1-chlorocarbonyl-ethyl ester the title compound is obtained as colorless solid.

MS (ESI): m/z=512 (MH$^+$, 100%).
$^1$H-NMR (300 MHz, DMSO-d$_6$): 11.91 (br.s, 1H, —NH); 8.04 (s, 0.5H); 9.00 (s, 0.5H); 8.57 (d, J=7.7, 1H, —NH); 8.30 (br.s, 1H); 7.41 (d, J=9.8, 1H); 7.18 (d, J=13.3, 1H); 4.76 (~d, 0.5H, —OH); 4.62 (~d, 0.5H, —OH); 4.46 (m, 1H); 4.12-3.84 (m, 2.5H); 3.85 (s, 3H & d, J=6.8, 2H); 3.59 (m, 0.5H); 3.38 (m, 1H); 3.20 (m, 1H); 1.99 (m, 1H); 1.76 (m, 2H); 1.52 (m, 1H); 1.24 (br.s, 3H); 0.93 (m, 1H); 0.363 (m, 2H); 0.18 (m, 2H).

Example 231

4-(2-Cyclopropylmethoxy-4-fluoro-5-methoxy-phenyl)-5H-pyrrolo[3,2-d]pyrimidine-7-carboxylic acid [(R)-1-(2-hydroxy-acetyl)-pyrrolidin-3-yl]amide Starting from 4-(2-cyclopropylmethoxy-4-fluoro-5-methoxy-phenyl)-5H-pyrrolo[3,2-d]pyrimidine-7-carboxylic acid (R)-pyrrolidin-3-ylamide hydrochloride (example A165) and acetic acid chlorocarbonyl-methyl ester the title compound is obtained as colorless solid.

MS (ESI): m/z=484 (MH$^+$, 100%).
$^1$H-NMR (400 MHz, DMSO-d$_6$): 11.35 (br.s, 1H, —NH); 9.05 (s, 1H); 8.61 (d, J=7.0, 1H, —NH); 8.59 (d, J=7.0, 0.5H, —NH); 8.31 (s, 1H); 7.41 (d, J=9.8, 1H); 7.18 (d, J=13.4, 1H); 4.63 (m, 0.5H); 4.51 (m, 0.5H & br.s, 1H, —OH); 4.06 (s, 1H); 3.86 (s, 1H); 3.84 (s, 3H & d, J 0 4.4, 2H); 3.80-3.70 (m, 1H); 3.62-3.44 (m, 1.5H); 3.41-3.29 (m, 1.5H); 2.33-2.17 (m, 1H); 2.07 (m, 0.5H); 1.93 (m, 0.5H); 0.92 (m, 1H); 0.33 (m, 2H); 0.17 (m, 2H).

Example 232

4-(2-Cyclopropylmethoxy-4-fluoro-5-methoxy-phenyl)-5H-pyrrolo[3,2-d]pyrimidine-7-carboxylic acid [(R)-1-((S)-2-hydroxy-propionyl)-pyrrolidin-3-yl]amide Starting from 4-(2-cyclopropylmethoxy-4-fluoro-5-methoxy-phenyl)-5H-pyrrolo[3,2-d]pyrimidine-7-carboxylic acid (R)-pyrrolidin-3-ylamide hydrochloride (example A165) and acetic acid (S)-1-chlorocarbonyl-ethyl ester the title compound is obtained as colorless solid.

MS (ESI): m/z=498 (MH$^+$, 100%).
$^1$H-NMR (400 MHz, DMSO-d$_6$): 11.61 (br.s, 1H, —NH); 9.04 (s, 0.5H); 9.01 (s, 0.5H); 8.61 (d, J=6.9, 1H, —NH); 8.59 (d, J=7.0, 0.5H, —NH); 8.31 (s, 1H); 7.41 (d, J=9.8, 1H); 7.18 (d, J=13.4, 1H); 4.91 (d, J=6.8, 0.5H, —OH); 4.86 (d, J=6.8, 0.5H, —OH); 4.60 (m, 0.5H); 4.53 (m, 0.5H); 4.26 (m, 0.5H); 4.02 (m, 0.5H); 3.84 (s, 3H & d, J 0 4.4, 2H); 3.82-3.72 (m, 1H); 3.71-3.52 (m, 2.5H); 3.47 (m, 0.5H); 3.40-3.30 (m, 1H); 2.33-2.17 (m, 1H); 2.07 (m, 0.5H); 1.93 (m, 0.5H); 1.23 (d, J=6.6, 1.5H); 1.20 (d, J=6.6, 1.5H); 0.92 (m, 1H); 0.33 (m, 2H); 0.17 (m, 2H).

Example 233 trans-4-(2-Cyclopropylmethoxy-5-fluoro-4-methoxy-phenyl)-5H-pyrrolo[3,2-d]pyrimidine-7-carboxylic acid [4-(2-hydroxy-acetylamino)-cyclohexyl]-amide Starting from trans-4-(2-cyclopropylmethoxy-5-fluoro-4-methoxy-phenyl)-5H-pyrrolo[3,2-d]pyrimidine-7-carboxylic acid (4-amino-cyclohexyl)-amide (example A139) and acetic acid chlorocarbonyl-methyl ester the title compound is obtained as colorless solid.

MS (ESI): m/z=512.1 (MH$^+$, 100%)

$^1$H-NMR (300 MHz, DMSO-d$_6$): 11.95 (br.s, 1H, —NH); 9.01 (s, 1H); 8.36 (d, J=7.8, 1H, —NH); 8.24 (d, J=2.6, 1H); 7.50 (d, J=11.8, 1H); 7.47 (d, J=8.3, 1H, —NH); 6.93 (d, J=7.3, 1H); 5.41 (t, J=5.8, 1H, —OH); 3.97 (s, 3H); 3.95 (d, J=7.1, 2H); 3.79 (m, 1H & d, J=5.8, 2H); 3.69 (m, 1H); 2.03 (m, 2H); 1.82 (m, 2H); 1.46 (m, 4H); 0.96 (m, 1H); 0.35 (m, 2H); 0.21 (m, 2H).

Example 234 trans-4-(2-Cyclopropylmethoxy-5-fluoro-4-methoxy-phenyl)-5H-pyrrolo[3,2-d]pyrimidine-7-carboxylic acid [4-((S)-2-hydroxy-propionylamino)-cyclohexyl]-amide Starting from trans-4-(2-cyclopropylmethoxy-5-fluoro-4-methoxy-phenyl)-5H-pyrrolo[3,2-d]pyrimidine-7-carboxylic acid (4-amino-cyclohexyl)-amide (example A139) and acetic acid (S)-1-chlorocarbonyl-ethyl ester the title compound is obtained as colorless solid.

MS (ESI): m/z=526 (MH$^+$, 100%).

$^1$H-NMR (300 MHz, DMSO-d$_6$): 11.95 (br.s, 1H, —NH); 9.01 (s, 1H); 8.36 (d, J=7.9, 1H, —NH); 8.25 (s 1H); 7.50 (d, J=11.8, 1H); 7.42 (d, J=8.3, 1H, —NH); 6.93 (d, J=7.3, 1H); 5.41 (d, J=5.2, 1H, —OH); 3.97 (s, 3H); 3.94 (d, J=7.1, 2H & m, 1H); 3.81 (m, 1H); 3.64 (m, 1H); 2.03 (m, 2H); 1.81 (m, 2H); 1.44 (m, 4H); 1.21 (d, 3H); 0.97 (m, 1H); 0.36 (m, 2H); 0.21 (m, 2H).

Example 235 trans-4-(2-Cyclopropylmethoxy-5-fluoro-4-methoxy-phenyl)-5H-pyrrolo[3,2-d]pyrimidine-7-carboxylic acid {4-[(1-hydroxy-cyclopropanecarbonyl)-amino]-cyclohexyl}-amide Starting from trans-4-(2-cyclopropylmethoxy-5-fluoro-4-methoxy-phenyl)-5H-pyrrolo[3,2-d]pyrimidine-7-carboxylic acid (4-amino-cyclohexyl)-amide (example A139) and acetic acid 1-chlorocarbonyl-cyclopropyl ester the title compound is obtained as colorless solid.

MS (ESI): m/z=538 (MH$^+$, 100%).

$^1$H-NMR (300 MHz, DMSO-d$_6$): 11.95 (br.s, 1H, —NH); 9.01 (s, 1H); 8.36 (d, J=7.9, 1H, —NH); 8.25 (s, 1H); 7.57 (d, J=8.4, 1H, —NH); 7.49 (d, J=11.8, 1H); 6.93 (d, J=7.3, 1H); 6.20 (s, 1H, —OH); 3.97 (s, 3H); 3.95 (d, J=7.1, 2H); 3.81 (m, 1H); 3.69 (m, 1H); 2.02 (m, 2H); 1.83 (m, 2H); 1.48 (m, 4H); 1.02 (m, 1H); 0.97 (m, 1H); 0.82 (m, 2H); 0.36 (m, 2H); 0.21 (m, 2H).

Example 236

4-(2-Cyclopropylmethoxy-5-fluoro-4-methoxy-phenyl)-5H-pyrrolo[3,2-d]pyrimidine-7-carboxylic acid [1-(2-hydroxy-ethanoyl)-piperidin-4-yl]amide Starting from 4-(2-cyclopropylmethoxy-5-fluoro-4-methoxy-phenyl)-5H-pyrrolo[3,2-d]pyrimidine-7-carboxylic acid piperidin-4-ylamide hydrochloride (example A166) and acetic acid chlorocarbonyl-methyl ester the title compound is obtained as colorless solid.

MS (ESI): m/z=498 (MH$^+$, 100%).

$^1$H-NMR (300 MHz, DMSO-d$_6$): 11.97 (br.s, 1H, —NH); 9.01 (s, 1H); 8.52 (d, J=7.8, 1H, —NH); 8.27 (d, J=3.3, 1H); 7.48 (d, J=11.9, 1H); 6.93 (d, J=7.3, 1H); 4.51 (t, J=5.2, 1H, —OH); 4.18 (m, 2H); 4.13 (dd, J$_1$=J$_2$=5.2, 2H); 3.97 (m, 3H); 3.95 (d, J=7.2, 2H); 3.69 (m, 1H); 3.19 (m, 1H); 2.99 (m, 1H); 1.98 (m, 2H); 1.56 (m, 1H); 1.45 (m, 1H); 0.97 (m, 1H); 0.36 (m, 2H); 0.22 (m, 2H).

Example 237

4-(2-Cyclopropylmethoxy-5-fluoro-4-methoxy-phenyl)-5H-pyrrolo[3,2-d]pyrimidine-7-carboxylic acid [1-((S)-2-hydroxy-propanoyl)piperidin-4-yl]-amide Starting from 4-(2-cyclopropylmethoxy-5-fluoro-4-methoxy-phenyl)-5H-pyrrolo[3,2-d]pyrimidine-7-carboxylic acid piperidin-4-ylamide hydrochloride (example A166) and acetic acid (S)-1-chlorocarbonyl-ethyl ester the title compound is obtained as colorless solid.

MS (ESI): m/z=512 (MH$^+$, 100%).

$^1$H-NMR (300 MHz, DMSO-d$_6$): 11.98 (br.s, 1H, —NH); 9.01 (s, 1H); 8.52 (d, J=7.8, 1H, —NH); 8.27 (s, 1H); 7.50 (d, J=11.9, 1H); 6.93 (d, J=7.3, 1H); 4.86 (d, J=6.9, 1H, —OH); 4.47 (m, 1H); 4.20 (m, 2H); 3.97 (s, 3H & m, 1H); 3.95 (d, J=7.1, 2H); 3.29 (m, 1H); 2.97 (m, 1H); 1.98 (m, 2H); 1.53 (m, 1H); 1.43 (m, 1H); 1.21 (br.s, 3H); 0.97 (m, 1H); 0.36 (m, 2H); 0.22 (m, 2H).

Example 238

4-(2-Cyclopropylmethoxy-5-fluoro-4-methoxy-phenyl)-5H-pyrrolo[3,2-d]pyrimidine-7-carboxylic acid {1-[1-(1-hydroxy-cyclopropyl)methanoyl]-piperidin-4-yl}-amide Starting from 4-(2-cyclopropylmethoxy-5-fluoro-4-methoxy-phenyl)-5H-pyrrolo[3,2-d]pyrimidine-7-carboxylic acid piperidin-4-ylamide hydrochloride (example A166) and acetic acid 1-chlorocarbonyl-cyclopropyl ester the title compound is obtained as colorless solid.

MS (ESI): m/z=524 (MH$^+$, 100%).

$^1$H-NMR (300 MHz, DMSO-d$_6$): 11.98 (br.s, 1H, —NH); 9.02 (s, 1H); 8.53 (d, J=7.8, 1H, —NH); 8.27 (s, 1H); 7.50 (d, J=11.8, 1H); 6.93 (d, J=7.3, 1H); 6.31 (s, 1H, —OH); 4.28 (m, 1H); 4.18 (m, 2H); 3.97 (s, 3H); 3.95 (d, J=7.2, 2H); 3.16 (m, 2H); 1.99 (m, 2H); 1.52 (m, 2H); 0.95 (m, 1H & m, 2H); 0.77 (m, 2H); 0.37 (m, 2H); 0.22 (m, 2H).

Example 239

4-(2-cyclopropylmethoxy-5-fluoro-4-methoxy-phenyl)-5H-pyrrolo[3,2-d]pyrimidine-7-carboxylic acid [(S)-1-((S)-2-hydroxy-propanoyl)piperidin-3-yl]-amide Starting from 4-(2-Cyclopropylmethoxy-5-fluoro-4-methoxy-phenyl)-5H-pyrrolo[3,2-d]pyrimidine-7-carboxylic acid (S)-piperidin-3-ylamide hydrochloride (example A168) and acetic acid (S)-1-chlorocarbonyl-ethyl ester the title compound is obtained as colorless solid.

MS (ESI): m/z=512 (MH$^+$, 100%).

$^1$H-NMR (300 MHz, DMSO-d$_6$): 11.99 (br.s, 1H, —NH); 8.99 (s, 1H); 8.58 (d, J=7.7, 1H, —NH); 8.27 (br.s, 1H); 7.50 (d, J=11.9, 1H); 6.93 (d, J=7.3, 1H); 4.87 (~d, 0.5H, —OH); 4.81 (~d, 0.5H, —OH); 4.46 (m, 1H); 4.05 (m, 0.5H); 3.97 (s, 3H); 3.94 (d, J=7.2, 2H & m, 2H); 3.70 (m, 1H); 3.34 (m, 1H);

3.14 (m, 0.5H); 1.99 (m, 1H); 1.76 (m, 2H); 1.56 (m, 1H); 1.21 (~d, 1.5H); 1.13 (~d, 1.5H); 0.97 (m, 1H); 0.36 (m, 2H); 0.21 (m, 2H).

Example 240

4-(2-Cyclopropylmethoxy-5-fluoro-4-methoxy-phenyl)-5H-pyrrolo[3,2-d]pyrimidine-7-carboxylic acid [(R)-1-((S)-2-hydroxy-propanoyl)piperidin-3-yl]-amide Starting from 4-(2-cyclopropylmethoxy-5-fluoro-4-methoxy-phenyl)-5H-pyrrolo[3,2-d]pyrimidine-7-carboxylic acid (R)-piperidin-3-ylamide hydrochloride (example A167) and acetic acid (S)-1-chlorocarbonyl-ethyl ester the title compound is obtained as colorless solid.

MS (ESI): m/z=512 (MH$^+$; 100%).

$^1$H-NMR (300 MHz, DMSO-d$_6$): 11.98 (br.s, 1H, —NH); 8.99 (s, 0.5H); 8.96 (s, 0.5H); 8.57 (d, J=7.7, 1H, —NH); 8.27 (br.s, 1H); 7.50 (d, J=11.9, 1H); 6.93 (d, J=7.3, 1H); 4.76 (~d, 0.5H, —OH); 4.62 (~d, 0.5H, —OH); 4.46 (m, 1H); 4.06 (m, 0.5H); 3.97 (s, 3H); 3.94 (d, J=7.2, 2H & m, 2H); 3.59 (m, 0.5H); 3.38 (m, 1H); 3.20 (m, 1H); 1.98 (m, 1H); 1.76 (m, 2H); 1.52 (m, 1H); 1.24 (br.s, 3H); 0.97 (m, 1H); 0.36 (m, 2H); 0.22 (m, 2H).

Example 241

4-(2-Cyclopropylmethoxy-5-fluoro-4-methoxy-phenyl)-5H-pyrrolo[3,2-d]pyrimidine-7-carboxylic acid [(R)-1-(2-hydroxy-acetyl)pyrrolidin-3-yl]-amide Starting from 4-(2-cyclopropylmethoxy-5-fluoro-4-methoxy-phenyl)-5H-pyrrolo[3,2-d]pyrimidine-7-carboxylic acid (R)-pyrrolidin-3-ylamide hydrochloride (example A169) and acetic acid chlorocarbonyl-methyl ester the title compound is obtained as colorless solid.

MS (ESI): m/z=484 (MH$^+$, 100%).

$^1$H-NMR (300 MHz, DMSO-d$_6$/MeOH-d$_4$): 9.01 (s, 1H); 8.63 (d, J=7.3, 0.5H; —NH); 8.61 (d, J=7.3, 0.5H, —NH); 8.29 (s, 1H); 7.49 (d, J=11.8, 1H); 6.92 (d, J=7.3, 1H); 4.62 (m, 0.5H); 4.52 (m, 0.5H); 4.06 (s, 1H); 4.01 (s, 1H); 3.97 (s, 3H); 3.95 (d, J=7.0, 2H); 3.77 (m, 1H); 3.53 (m, 1.5H); 3.36 (m, 1.5H); 2.33-2.17 (m, 1H); 2.07 (m, 0.5H); 1.93 (m, 0.5H); 0.96 (m, 1H); 0.36 (m, 2H); 0.21 (m, 2H).

Example 242

4-(2-Cyclopropylmethoxy-5-fluoro-4-methoxy-phenyl)-5H-pyrrolo[3,2-d]pyrimidine-7-carboxylic acid [(R)-1-((S)-2-hydroxy-propionyl)pyrrolidin-3-yl]-amide Starting from 4-(2-cyclopropylmethoxy-5-fluoro-4-methoxy-phenyl)-5H-pyrrolo[3,2-d]pyrimidine-7-carboxylic acid (R)-pyrrolidin-3-ylamide hydrochloride (example A169) and acetic acid (S)-1-chlorocarbonyl-ethyl ester the title compound is obtained as colorless solid.

MS (ESI): m/z=498 (MH$^+$, 100%).

$^1$H-NMR (300 MHz, DMSO-d$_6$): 11.86 (br.s, 1H, —NH); 9.00 (s, 0.5H); 8.97 (s, 0.5H); 8.64 (d, J=7.0, 1H; —NH); 8.28 (s, 1H); 7.50 (d, J=11.8); 6.92 (d, J=7.2, 1H); 4.91 (d, J=6.8, 0.5H, —OH); 4.85 (d, J=6.8, 0.5H, —OH); 4.60 (m, 0.5H); 4.55 (m, 0.5H); 4.41 (m, 0.5H); 4.26 (m, 0.5H); 3.97 (s, 3H); 3.95 (d, J=7.0, 2H); 3.83 (m, 0.5H); 3.78 (m, 0.5H); 3.71-3.53 (m, 1.5H); 3.34 (m, 1H); 2.29 (m, 0.5H); 2.19 (m, 0.5H); 2.07 (m, 0.5H); 1.95 (m, 0.5H); 1.23 (d, J=6.5, 1.5H); 1.19 (d, J=6.5, 1.5H); 0.96 (m, 1H); 0.36 (m, 2H), 0.22 (m, 2H).

Example 243 trans-4-(2-Cyclopropylmethoxy-5-methyl-phenyl)-5H-pyrrolo[3,2-d]pyrimidine-7-carboxylic acid [4-(2-hydroxy-acetylamino)-cyclohexyl]-amide Starting from trans-4-(2-cyclopropylmethoxy-5-methyl-phenyl)-5H-pyrrolo[3,2-d]pyrimidine-7-carboxylic acid (4-amino-cyclohexyl)-amide (example A170) and acetic acid chlorocarbonyl-methyl to ester the title compound is obtained as colorless solid.

MS (ESI): m/z=478 (MH$^+$, 100%).

$^1$H-NMR 400 MHz, DMSO-d$_6$): 11.96 (br.s, 1H, —NH); 9.03 (s, 1H); 8.36 (d, J=7.8, 1H, —NH); 8.22 (s, 1H); 7.47 (d, J=8.2, 1H, —NH); 7.44 (s, 1H); 7.33 (d, J=8.4, 1H); 7.06 (d, J=8.4, 1H); 5.41 (t, J=5.6, 1H, —OH); 3.86 (d, J=6.8, 2H); 3.79 (d, J=5.6, 2H & m, 1H); 3.69 (m, 1H); 2.33 (s, 3H); 2.02 (m, 2H); 1.83 (m, 2H); 1.47 (m, 4H); 0.93 (m, 1H); 0.34 (m, 2H); 0.19 (m, 2H).

Example 244 trans-4-(2-Cyclopropylmethoxy-5-methyl-phenyl)-5H-pyrrolo[3,2-d]pyrimidine-7-carboxylic acid [4-((S)-2-hydroxy-propionylamino)-cyclohexyl]-amide Starting from trans-4-(2-cyclopropylmethoxy-5-methyl-phenyl)-5H-pyrrolo[3,2-d]pyrimidine-7-carboxylic acid (4-amino-cyclohexyl)-amide (example A170) and acetic acid (S)-1-chlorocarbonyl-ethyl ester the title compound is obtained as colorless solid.

MS (ESI): m/z=492 (MH$^+$, 100%).

$^1$H-NMR 300 MHz, DMSO-d$_6$): 11.96 (br.s, 1H, —NH); 9.03 (s, 1H); 8.36 (d, J=7.9, 1H, —NH); 8.22 (s, 1H); 7.44 (d, J=2.0, 1H); 7.42 (d, J=10.0, 1H, —NH); 7.33 (dd, J$_1$=8.4, J$_2$=2.0, 1H); 7.06 (d, J=8.4, 1H); 5.41 (d, J=6.1, 1H, —OH); 3.96 (m, 1H); 3.86 (d, J=6.8, 2H & m, 1H); 3.64 (m, 1H); 2.32 (s, 3H); 2.03 (m, 2H); 1.81 (m, 2H); 1.44 (m, 4H); 1.21 (d, J=6.8, 3H); 0.93 (m, 1H); 0.34 (m, 2H); 0.19 (m, 2H).

Example 245 trans-4-(2-Cyclopropylmethoxy-5-methyl-phenyl)-5H-pyrrolo[3,2-d]pyrimidine-7-carboxylic acid {4-[(1-hydroxy-cyclopropanecarbonyl)-amino]-cyclohexyl}-amide Starting from trans-4-(2-cyclopropylmethoxy-5-methyl-phenyl)-5H-pyrrolo[3,2-d]pyrimidine-7-carboxylic acid (4-amino-cyclohexyl)-amide (example A170) and acetic acid 1-chlorocarbonyl-cyclopropyl ester the title compound is obtained as colorless solid.

MS (ESI): m/z=504 (MH$^+$, 100%).

$^1$H-NMR 300 MHz, DMSO-d$_6$): 11.95 (br.s, 1H, —NH); 9.03 (s, 1H); 8.36 (d, J=7.9, 1H, —NH); 8.22 (d, J=3.4, 1H); 7.57 (d, J=8.4, 1H, —NH); 7.44 (d, J=2.1, 1H); 7.33 (dd, J$_1$=8.4, J$_2$=2.1, 1H); 7.06 (d, J=8.4, 1H); 6.20 (s, 1H, —OH); 3.86 (d, J=6.9, 2H & m, 1H); 3.70 (m, 1H); 2.32 (s, 3H); 2.03

(m, 2H); 1.82 (m, 2H); 1.59-1.38 (m, 4H); 1.03 (m, 2H); 0.93 (m, 1H); 0.83 (m, 2H); 0.34 (m, 2H); 0.19 (m, 2H).

Example 246

4-(2-Cyclopropylmethoxy-5-methyl-phenyl)-5H-pyrrolo[3,2-d]pyrimidine-7-carboxylic acid [1-(2-hydroxy-acetyl)piperidin-4-yl]-amide Starting from 4-(2-cyclopropylmethoxy-5-methyl-phenyl)-5H-pyrrolo[3,2-d]pyrimidine-7-carboxylic acid piperidin-4-ylamide (example A171) and acetic acid chlorocarbonyl-methyl ester the title compound is obtained as colorless solid.

MS (ESI): m/z=464 (MH$^+$, 100%).

$^1$H-NMR 400 MHz, DMSO-d$_6$): 11.99 (br.s, 1H, —NH); 9.03 (s, 1H); 8.52 (d, J=7.8, 1H, —NH); 8.25 (s, 1H); 7.44 (d, J=1.9, 1H); 7.33 (dd, J$_1$=8.5, J$_2$=1.9, 1H); 7.06 (d, J=8.5, 1H); 4.51 (t, J=5.4, 1H, —OH); 4.23-4.11 (m, 2H); 4.14 (d, J=5.4, 2H); 3.87 (d, J=6.9, 2H); 3.69 (m, 1H); 3.20 (m, 1H); 3.00 (m, 1H); 2.33 (s, 3H); 1.99 (m, 2H); 1.56 (m, 1H); 1.44 (m, 1H); 0.94 (m, 1H); 0.34 (m, 2H); 0.19 (m, 2H).

Example 247

4-(2-Cyclopropylmethoxy-5-methyl-phenyl)-5H-pyrrolo[3,2-d]pyrimidine-7-carboxylic acid [1-((S)-2-hydroxy-propionyl)piperidin-4-yl]-amide Starting from 4-(2-cyclopropylmethoxy-5-methyl-phenyl)-5H-pyrrolo[3,2-d]pyrimidine-7-carboxylic acid piperidin-4-ylamide (example A171) and acetic acid (S)-1-chlorocarbonyl-ethyl ester the title compound is obtained as colorless solid.

MS (ESI): m/z=478 (MH$^+$, 100%).

$^1$H-NMR 400 MHz, DMSO-d$_6$): 11.99 (br.s, 1H, —NH); 9.03 (s, 1H); 8.52 (d, J=7.8, 1H, —NH); 8.25 (s, 1H); 7.44 (d, J=1.9, 1H); 7.33 (dd, J$_1$=8.5, J$_2$=1.9, 1H); 7.06 (d, J=8.5, 1H); 4.86 (d, J=6.9, 1H, —OH); 4.47 (m, 1H); 4.29-4.10 (m, 2H); 3.97 (m, 1H); 3.86 (d, J=6.8, 2H); 3.29 (m, 1H); 3.97 (m, 1H); 2.33 (s, 3H); 1.99 (m, 2H); 1.57 (m, 1H); 1.43 (m, 1H); 1.21 (br.s, 3H); 0.94 (m, 1H); 0.34 (m, 2H); 0.19 (m, 2H).

Example 248

4-(2-Cyclopropylmethoxy-5-methyl-phenyl)-5H-pyrrolo[3,2-d]pyrimidine-7-carboxylic acid [1-(1-hydroxy-cyclopropanecarbonyl)-piperidin-4-yl]-amide Starting from 4-(2-cyclopropylmethoxy-5-methyl-phenyl)-5H-pyrrolo[3,2-d]pyrimidine-7-carboxylic acid piperidin-4-ylamide (example A171) and acetic acid 1-chlorocarbonyl-cyclopropyl ester the title compound is obtained as colorless solid.

MS (ESI): m/z=490 (MH$^+$, 100%).

$^1$H-NMR 400 MHz, DMSO-d$_6$): 11.99 (br.s, 1H, —NH); 9.03 (s, 1H); 8.53 (d, J=7.9, 1H, —NH); 8.25 (s, 1H); 7.44 (d, J=1.9, 1H); 7.33 (dd, J$_1$=8.5, J$_2$=1.9, 1H); 7.06 (d, J=8.5, 1H); 6.31 (s, 1H, —OH); 4.28 (m, 1H); 4.24-4.10 (m, 2H); 3.87 (d, J=6.9, 2H); 3.17 (m, 2H); 2.33 (s, 3H); 1.99 (m, 2H); 1.53 (m, 1H); 0.94 (m, 3H); 0.77 (m, 2H); 0.34 (m, 2H); 0.19 (m, 2H).

Example 249

4-(5-Ethoxy-benzo[1,3]dioxol-4-yl)-5H-pyrrolo[3,2-d]pyrimidine-7-carboxylic acid [1-((S)-2-hydroxy-propionyl)-piperidin-4-yl]-amide Starting from 4-(2-cyclopropylmethoxy-5-methyl-phenyl)-5H-pyrrolo[3,2-d]pyrimidine-7-carboxylic acid piperidin-4-ylamide (example A175) and acetic acid (S)-1-chlorocarbonyl-ethyl ester the title compound was obtained as colorless solid.

MS (ESI): m/z=482 (MH$^+$, 100%).

$^1$H-NMR (400 MHz, DMSO-d$_6$): 12.15 (s, 1H, —NH); 9.02 (s, 1H); 8.45 (d, J=7.7, 1H, —NH); 8.29 (s, 1H); 7.02 (d, J=8.6, 1H); 6.58 (d, J=8.6, 1H); 6.00 (s, 2H); 4.86 (d, J=6.7, 1H, —OH); 4.47 (m, 1H); 4.31-4.10 (m, 2H); 3.96 (qu, J=6.9, 2H & m, 1H); 3.27 (m, 1H); 2.97 (m, 1H); 1.99 (m, 2H); 1.62-1.31 (m, 2H); 1.20 (br.s, 3H); 1.03 (t, J=6.9, 3H).

Example 250

4-(5-Ethoxy-benzo[1,3]dioxol-4-yl)-5H-pyrrolo[3,2-d]pyrimidine-7-carboxylic acid [(R)-1-((S)-2-hydroxy-propionyl)-pyrrolidin-3-yl]amide Starting from 4-(5-ethoxy-benzo[1,3]dioxol-4-yl)-5H-pyrrolo[3,2-d]pyrimidine-7-carboxylic acid (R)-pyrrolidin-3-ylamide (example A176) and acetic acid (S)-1-chlorocarbonyl-ethyl ester the title compound was obtained as colorless solid.

MS (ESI): m/z=468 (MH$^+$, 100%).

$^1$H-NMR (300 MHz, DMSO-d$_6$): 11.72 (s, 1H, —NH); 9.01 (s, 0.5H); 8.99 (s, 0.5H); 8.57 (d, J=7.0, 1H, —NH); 8.31 (s, 1H); 7.02 (d, J=8.6, 1H); 6.58 (d, J=8.6, 1H); 6.00 (s, 2H); 4.90 (br.s, 1H, —OH); 4.60 (m, 0.5H); 4.53 (m, 0.5H); 4.33 (m, 0.5H); 4.27 (m, 0.5H); 3.95 (qu, J=6.9, 2H); 3.88-3.32 (m, 4H); 2.34-2.13 (m, 1H); 2.08 (m, 0.5H); 1.94 (m, 0.5H); 1.20 (m, 3H); 1.03 (t, J=6.9, 3H).

Example 251

4-(5-Propoxy-benzo[1,3]dioxol-4-yl)-5H-pyrrolo[3,2-d]pyrimidine-7-carboxylic acid [1-((S)-2-hydroxy-propionyl)piperidin-4-yl]-amide Starting from 4-(5-propoxy-benzo[1,3]dioxol-4-yl)-5H-pyrrolo[3,2-d]pyrimidine-7-carboxylic acid piperidin-4-ylamide (example A177) and acetic acid (S)-1-chlorocarbonyl-ethyl ester the title compound was obtained as colorless solid.

MS (ESI): m/z=496 (MH$^+$, 100%).

$^1$H-NMR (300 MHz, DMSO-d$_6$): 12.14 (s, 1H, —NH); 9.02 (s, 1H); 8.44 (d, J=7.8, 1H, —NH); 8.28 (s, 1H); 7.02 (d, J=8.6, 1H); 6.58 (d, J=8.6, 1H); 6.00 (s, 2H); 4.86 (d, J=6.3, 1H, —OH); 4.47 (m, 1H); 4.23 (m, 1H); 4.16 (m, 1H); 3.97 (m, 1H); 3.85 (t, J=6.4, 2H); 3.27 (m, 1H); 2.96 (m, 1H); 1.99 (m, 2H); 1.54 (m, 1H); 1.42 (m, 2H & m, 1H); 1.21 (br.s, 3H); 0.63 (t, J=7.4, 3H).

Example 252

4-(5-Propoxy-benzo[1,3]dioxol-4-yl)-5H-pyrrolo[3,2-d]pyrimidine-7-carboxylic acid [(R)-1-((S)-2-hydroxy-propionyl)-pyrrolidin-3-yl]amide Starting from 4-(5-propoxy-benzo[1,3]dioxol-4-yl)-5H-pyrrolo[3,2-d]pyrimidine-7-carboxylic acid (R)-pyrrolidin- 3-ylamide (example A178) and acetic acid (S)-1-chlorocarbonyl-ethyl ester the title compound was obtained as colorless solid.

MS (ESI): m/z=482 (MH$^+$, 100%).

$^1$H-NMR (300 MHz, DMSO-d$_6$): 11.99 (s, 1H, —NH); 9.01 (s, 0.5H); 8.99 (s, 0.5H); 8.57 (d, J=6.9, 1H, —NH); 8.30 (s, 1H); 7.03 (d, J=8.6, 1H); 6.58 (d, J=8.6, 1H); 6.00 (s, 2H); 4.90 (br.s, 1H, —OH); 4.60 (m, 0.5H); 4.52 (m, 0.5H); 4.32 (m, 0.5H); 4.27 (m, 0.5H); 3.86 (t, J=6.4, 2H); 3.80-3.34 (m, 4H); 2.33-2.14 (m, 1H); 2.08 (m, 0.5H); 1.97 (m, 0.5H); 1.42 (m, 2H); 1.23 (d, J=6.5, 1.5H); 1.20 (d, J=6.5, 1.5H); 0.62 (t, J=7.4, 3H).

Example 253

4-(5-Butoxy-benzo[1,3]dioxol-4-yl)-5H-pyrrolo[3,2-d]pyrimidine-7-carboxylic acid [1-((S)-2-hydroxy-propionyl)-piperidin-4-yl]-amide Starting from 4-(5-butoxy-benzo[1,3]dioxol-4-yl)-5H-pyrrolo[3,2-d]pyrimidine-7-carboxylic acid piperidin-4-ylamide (example A179) and acetic acid (S)-1-chlorocarbonyl-ethyl ester the title compound was obtained as colorless solid.

MS (ESI): m/z=510 (MH$^+$, 100%).

$^1$H-NMR (300 MHz, DMSO-d$_6$): 12.24 (s, 1H, —NH); 9.02 (s, 1H); 8.44 (d, J=7.7, 1H, —NH); 8.28 (s, 1H); 7.02 (d, J=8.6, 1H); 6.59 (d, J=8.6, 1H); 6.00 (s, 2H); 4.86 (d, J=6.9, 1H, —OH); 4.47 (m, 1H); 4.23 (m, 1H); 4.16 (m, 1H); 3.97 (m, 1H); 3.88 (t, J=6.4, 2H); 3.27 (m, 1H); 2.96 (m, 1H); 1.99 (m, 2H); 1.54 (m, 1H); 1.42 (m, 2H & m, 1H); 1.21 (br.s, 3H); 0.99 (m, 2H); 0.69 (t, J=7.4, 3H).

Example 254

4-(5-Butoxy-benzo[1,3]dioxol-4-yl)-5H-pyrrolo[3,2-d]pyrimidine-7-carboxylic acid [(R)-1-((S)-2-hydroxy-propionyl)-pyrrolidin-3-yl]amide Starting from 4-(5-butoxy-benzo[1,3]dioxol-4-yl)-5H-pyrrolo[3,2-d]pyrimidine-7-carboxylic acid (R)-pyrrolidin-3-ylamide (example A181) and acetic acid (S)-1-chlorocarbonyl-ethyl ester the title compound was obtained as colorless solid.

MS (ESI): m/z=496 (MH$^+$, 100%).

$^1$H-NMR 300 MHz, DMSO-d$_6$): 12.17 (br.s, 1H, —NH); 9.01 (s, 0.5H); 8.99 (s, 0.5H); 8.57 (d, J=7.0, 1H, —NH); 8.30 (s, 1H); 7.02 (d, J=8.6, 1H); 6.59 (d, J=8.6, 1H); 6.01 (s, 2H); 4.99-4.81 (m, 1H, —OH); 4.60 (m, 0.5H); 4.52 (m, 0.5H); 3.88 (t, J=6.4, 2H); 3.84-3.33 (m, 4H); 2.33-2.12 (m, 1H); 2.06 (m, 0.5H); 1.96 (m, 0.5H); 1.39 (m, 2H); 1.23 (d, J=6.5, 1.5H); 1.20 (d, J=6.5, 1.5H); 1.05 (m, 2H); 0.69 (t, J=7.4, 3H).

Example 255 trans-4-[4-Methoxy-2-(2-methoxy-ethoxy)-phenyl]-5H-pyrrolo[3,2-d]pyrimidine-7-carboxylic acid [4-(2-hydroxy-acetylamino)-cyclohexyl]-amide Starting from trans-4-[4-methoxy-2-(2-methoxy-ethoxy)-phenyl]-5H-pyrrolo[3,2-d]pyrimidine-7-carboxylic acid (4-amino-cyclohexyl)-amide (example A182) and acetic acid chlorocarbonyl-methyl ester the title compound was obtained as colorless solid.

MS (ESI): m/z=498 (MH$^+$).

$^1$H-NMR (400 MHz, DMSO-d$_6$): 11.73 (br.s, 1H, —NH); 9.00 (s, 1H); 8.39 (d, J=7.8, 1H, —NH); 8.22 (s, J=3.3, 1H); 7.69 (d, J=8.3, 1H); 7.48 (d, J=8.3, 1H, —NH); 6.77 (s, 1H); 6.76 (dd, J$_1$=8.3, J$_2$=2.2, 1H); 5.42 (t, J=5.7, 1H, —OH); 4.23 (t, J=4.6, 2H); 3.88 (s, 3H); 3.78 (d, J=5.7, 2H & m, 1H); 3.68 (m, 1H); 3.54 (t, J=4.6, 2H); 3.13 (s, 3H); 2.01 (m, 2H); 1.82 (m, 2H); 1.44 (m, 4H).

Example 256 trans-4-[4-Methoxy-2-(2-methoxy-ethoxy)-phenyl]-5H-pyrrolo[3,2-d]pyrimidine-7-carboxylic acid [4-((S)-2-hydroxy-propionylamino)-cyclohexyl]-amide Starting from trans-4-[4-methoxy-2-(2-methoxy-ethoxy)-phenyl]-5H-pyrrolo[3,2-d]pyrimidine-7-carboxylic acid (4-amino-cyclohexyl)-amide (example A182) and acetic acid (S)-1-chlorocarbonyl-ethyl ester the title compound was obtained as colorless solid.

MS (ESI): m/z=512 (MH$^+$).

$^1$H-NMR (400 MHz, DMSO-d$_6$): 11.73 (br.s, 1H, —NH); 9.00 (s, 1H); 8.39 (d, J=7.8, 1H, —NH); 8.22 (s, 1H); 7.69 (d, J=8.3, 1H); 7.43 (d, J=8.3, 1H, —NH); 6.77 (s, 1H); 6.76 (dd, J$_1$=8.3, J$_2$=2.2, 1H); 5.43 (d, J=5.1, 1H, —OH); 4.23 (t, J=4.6, 2H); 3.93 (m, 1H); 3.88 (s, 3H); 3.82 (m, 1H); 3.63 (m, 1H); 3.53 (t, J=4.6, 2H); 3.13 (s, 3H); 2.01 (m, 2H); 1.80 (m, 2H); 1.43 (m, 4H); 1.20 (d, J=6.7, 3H).

Example 257 trans-4-[4-Methoxy-2-(2-methoxy-ethoxy)-phenyl]-5H-pyrrolo[3,2-d]pyrimidine-7-carboxylic acid {-[(1-hydroxy-cyclopropanecarbonyl)-amino]-cyclohexyl}-amide Starting from trans-4-[4-methoxy-2-(2-methoxy-ethoxy)-phenyl]-5H-pyrrolo[3,2-d]pyrimidine-7-carboxylic acid (4-amino-cyclohexyl)-amide (example A182) and acetic acid 1-chlorocarbonyl-cyclopropyl ester the title compound was obtained as colorless solid.

MS (ESI): m/z=524 (MH$^+$).

$^1$H-NMR (400 MHz, DMSO-d$_6$): 11.72 (br.s, 1H, —NH); 9.00 (s, 1H); 8.39 (d, J=7.8, 1H, —NH); 8.22 (s, 1H); 7.69 (d, J=8.5, 1H); 7.57 (d, J=8.5, 1H, —NH); 6.77 (s, 1H); 6.76 (dd, J$_1$=8.5, J$_2$=2.2, 1H); 6.20 (s, 1H, —OH); 4.23 (t, J=4.6, 2H); 3.87 (s, 3H); 3.84 (m, 1H); 3.68 (m, 1H); 3.54 (t, J=4.6, 2H); 3.13 (s, 3H); 2.01 (m, 2H); 1.82 (m, 2H); 1.48 (m, 4H); 1.01 (m, 2H); 0.81 (m, 2H).

Example 258 cis-4-[4-Methoxy-2-(2-methoxy-ethoxy)-phenyl]-5H-pyrrolo[3,2-d]pyrimidine-7-carboxylic acid {-[(1-hydroxy-cyclopropanecarbonyl)-amino]-cyclohexyl}-amide Starting from cis-4-[4-methoxy-2-(2-methoxy-ethoxy)-phenyl]-5H-pyrrolo[3,2-d]pyrimidine-7-carboxylic acid (4-amino-cyclohexyl)-amide (example A183) and acetic acid 1-chlorocarbonyl-cyclopropyl ester the title compound was obtained as colorless solid.

MS (ESI): m/z=524 (MH$^+$).

$^1$H-NMR (400 MHz, DMSO-d$_6$): 11.73 (br.s, 1H, —NH); 9.04 (s, 1H); 8.71 (d, J=7.8, 1H, —NH); 8.23 (s, 1H); 7.70 (d, J=8.3, 1H); 7.56 (d, J=7.8, 1H, —NH); 6.77 (s, 1H); 6.76 (dd, J$_1$=8.3, J$_2$=2.2, 1H); 6.25 (s, 1H, —OH); 4.24 (t, J=4.6, 2H); 4.08 (m, 1H); 3.88 (s, 3H); 3.78 (m, 1H); 3.55 (t, J=4.6, 2H); 3.14 (s, 3H); 1.85-1.67 (m, 8H); 1.82 (m, 2H); 1.03 (m, 2H); 0.83 (m, 2H).

Example 259

4-[4-Methoxy-2-(2-methoxy-ethoxy)-phenyl]-5H-pyrrolo[3,2-d]pyrimidine-7-carboxylic acid [1-(1-hydroxy-cyclopropanecarbonyl)-piperidin-4-yl]-amide Starting from 4-[4-methoxy-2-(2-methoxy-ethoxy)-phenyl]-5H-pyrrolo[3,2-d]pyrimidine-7-carboxylic acid piperidin-4-ylamide (example A184) and acetic acid 1-chlorocarbonyl-cyclopropyl ester the title compound was obtained as colorless solid.

MS (ESI): m/z=510 (MH$^+$).
$^1$H-NMR (400 MHz, DMSO-d$_6$): 11.74 (br.s, 1H, —NH); 9.00 (s, 1H); 8.56 (d, J=7.8, 1H, —NH); 8.24 (s, 1H); 7.70 (d, J=8.3, 1H); 6.77 (s, 1H); 6.76 (dd, J$_1$=8.3, J$_2$=2.1, 1H); 6.30 (s, 1H, —OH); 4.30 (m, 1H); 4.24 (t, J=4.6, 2H); 4.18 (m, 2H); 3.87 (s, 3H); 3.54 (t, J=4.6, 2H); 3.13 (s, 3H & m, 2H); 2.00 (m, 2H); 1.51 (m, 2H); 0.94 (m, 2H); 0.77 (m, 2H).

Example 260 trans-4-[5-(2-Methoxy-ethoxy)-benzo[1,3]dioxol-4-yl]-5H-pyrrolo[3,2-d]pyrimidine-7-carboxylic acid [4-(2-hydroxy-acetylamino)-cyclohexyl]-amide Starting from trans-4-[5-(2-methoxy-ethoxy)-benzo[1,3]dioxol-4-yl]-5H-pyrrolo[3,2-d]pyrimidine-7-carboxylic acid (4-amino-cyclohexyl)-amide (example A185) and acetic acid chlorocarbonyl-methyl ester the title compound was obtained as colorless solid.

MS (ESI): m/z=512 (MH$^+$).
$^1$H-NMR (200 MHz, DMSO-d$_6$): 12.12 (br. s, 1H, —NH); 9.02 (s, 1H); 8.33 (d, J=7.8, 1H, —NH); 8.23 (s, 1H); 7.47 (d, J=8.2, —NH); 7.02 (d, J=8.6, 1H); 6.61 (d, J=8.6, 1H); 6.01 (s, 2H); 5.42 (br.s, 1H, —OH); 4.03 (t, J=4.7, 2H); 3.79 (s, 2H & m, 2H); 3.39 (t, J=4.7, 2H); 3.02 (s, 3H); 2.04 (m, 2H); 1.81 (m, 2H); 1.45 (m, 4H).

Example 261 cis-4-[5-(2-Methoxy-ethoxy)-benzo[1,3]dioxol-4-yl]-5H-pyrrolo[3,2-d]pyrimidine-7-carboxylic acid [4-(2-hydroxy-acetylamino)-cyclohexyl]-amide Starting from cis-4-[5-(2-methoxy-ethoxy)-benzo[1,3]dioxol-4-yl]-5H-pyrrolo[3,2-d]pyrimidine-7-carboxylic acid (4-amino-cyclohexyl)-amide (example A186) and acetic acid chlorocarbonyl-methyl ester the title compound was obtained as colorless solid.

MS (ESI): m/z=512 (MH$^+$).
$^1$H-NMR (200 MHz, DMSO-d$_6$): 11.20 (br.s, 1H, —NH); 9.05 (s, 1H); 8.59 (d, J=7.5, 1H; —NH); 8.28 (s, 1H); 7.56 (d, J=7.7, 1H, —NH); 7.03 (d, J=8.6, 1H); 6.62 (d, J=8.6, 1H); 6.02 (s, 2H); 5.40 (br.s, 1H, —OH); 4.04 (t, J=4.7, 2H & m, 1H); 3.82 (s, 2H & m, 1H); 3.39 (t, J=4.7, 2H); 3.03 (s, 3H); 1.72 (m. 8H).

Example 262 cis-4-[5-(2-Methoxy-ethoxy)-benzo[1,3]dioxol-4-yl]-5H-pyrrolo[3,2-d]pyrimidine-7-carboxylic acid [4-((S)-2-hydroxy-propionylamino)-cyclohexyl]-amide Starting from cis-4-[5-(2-methoxy-ethoxy)-benzo[1,3]dioxol-4-yl]-5H-pyrrolo[3,2-d]pyrimidine-7-carboxylic acid (4-amino-cyclohexyl)-amide (example A186) and acetic acid (S)-1-chlorocarbonyl-ethyl ester the title compound was obtained as colorless solid.

MS (ESI): m/z=526 (MH$^+$).
$^1$H-NMR (200 MHz, DMSO-d$_6$): 11.82 (br.s, 1H, —NH); 9.05 (s, 1H); 8.57 (d, J=7.4, 1H; —NH); 8.28 (s, 1H); 7.50 (d, J=7.7, 1H, —NH); 7.03 (d, J=8.6, 1H); 6.62 (d, J=8.6, 1H); 6.02 (s, 2H); 5.37 (br.s, 1H, —OH); 4.04 (t, J=4.7, 2H & m, 1H); 3.99 (m, 1H); 3.76 (m, 1H); 3.39 (t, J=4.7, 2H); 3.03 (s, 3H); 1.74 (m. 8H); 1.22 (d, J=6.7, 3H).

Example 263

4-[5-(2-Methoxy-ethoxy)-benzo[1,3]dioxol-4-yl]-5H-pyrrolo[3,2-d]pyrimidine-7-carboxylic acid [1-((S)-2-hydroxy-propionyl)piperidin-4-yl]-amide Starting from 4-[5-(2-methoxy-ethoxy)-benzo[1,3]dioxol-4-yl]-5H-pyrrolo[3,2-d]pyrimidine-7-carboxylic acid piperidin-4-ylamide (example A187) and acetic acid (S)-1-chlorocarbonyl-ethyl ester the title compound was obtained as colorless solid.

MS (ESI): m/z=512 (MH$^+$).
$^1$H-NMR (200 MHz, DMSO-d$_6$): 12.19 (br.s, 1H, —NH); 9.02 (s, 1H); 8.45 (d, J=7.7, 1H; —NH); 8.30 (s, 1H); 7.02 (d, J=8.6, 1H); 6.61 (d, J=8.6, 1H); 6.01 (s, 2H); 4.87 (d, J=6.9, 1H, —OH); 4.47 (m, 1H); 4.18 (m, 2H); 4.03 (t, J=4.7, 2H); 3.92 (m, 1H); 3.39 (t, J=4.7, 2H); 3.30 (s, 1H); 3.02 (s, 3H); 2.94 (m, 1H); 1.99 (m, 2H); 1.51 (m, 2H); 1.21 (d, J=6.3, 3H).

Example 264

4-(5-Acetyl-2-cyclopropylmethoxy-phenyl)-5H-pyrrolo[3,2-d]pyrimidine-7-carboxylic acid [1-((S)-2-hydroxy-propanoyl)piperidin-4-yl]-amide To a solution of 4-(5-acetyl-2-cyclopropylmethoxy-phenyl)-5H-pyrrolo[3,2-d]pyrimidine-7-carboxylic acid from example A81 (43 mg; 0.12 mmol) in dichloromethane (2 mL) is added 1-(3-dimethylaminopropyl)-3-ethylcarbodiimide hydrochloride (0.16 mmol), triethylamine (0.24 mmol) and 1-hydroxybenzotriazole (0.12 mmol). The suspension is stirred for 20 min at ambient temperature and then (S)-1-(4-amino-piperidin-1-yl)-2-hydroxy-propan-1-one hydrochloride from example A190 (0.16 mmol) is added. The reaction mixture is stirred overnight at ambient temperature. The volatiles are evaporated and the crude is distributed between ethyl acetate and aqueous phosphate buffer (1M, pH=7). The organic phase is separated, washed with aqueous phosphate buffer and evaporated to dryness. The obtained crude product is purified by preparative HPLC yielding 38 mg of the title compound as white solid.

MS (ESI): m/z=506 (MH$^+$, 100%).
$^1$H-NMR (400 MHz, DMSO-d$_6$): 12.15 (s, 1H, —NH), 9.10 (s, 1H), 8.52 (d, 1H, J=7 Hz, NH), 8.30 (s, 1H), 8.21 (d, 1H, J=1.5 Hz), 8.12 (dd, 1H, J=9, 1.5 Hz), 7.28 (d, 1H, J=9 Hz), 4.45 (m, 1H), 4.18 (m, 2H), 4.02 (d, 2H, J=7 Hz), 3.28 (m, 1H), 2.98 (m, 1H), 2.60 (s, 3H), 1.98 (m, 2H), 1.50 (m, 2H), 1.20 (m, 3H), 1.00 (m, 1H), 0.35 (m, 2H), 0.24 (m, 2H).

The following compounds are obtained analogously to the procedure described in above example 264.

Example 265

4-(5-Acetyl-2-cyclopropylmethoxy-phenyl)-5H-pyrrolo[3,2-d]pyrimidine-7-carboxylic acid [1-(2-methoxy-acetyl)piperidin-4-yl]-amide Starting from 4-(5-acetyl-2-cyclopropylmethoxy-phenyl)-5H-pyrrolo[3,2-d]pyrimidine-7-carboxylic acid (example A81) and 1-(4-amino-piperidin-1-yl)-2-methoxy-ethanone (A192) the title compound is obtained as colorless solid.

MS (ESI): m/z=506 (MH+, 100%).

¹H-NMR (400 MHz, DMSO-d₆) 12.15 (s, 1H, —NH); 9.10 (s, 1H); 8.50 (d, J=7.0, 1H, —NH); 8.32 (s, 1H); 8.20 (d, J=1.5, 1H); 8.12 (dd, J₁=9.0, J₂=1.5, 1H); 7.25 (d, J=9.0, 1H); 4.22 (m, 2H); 4.03 (m, 2H); 4.02 (d, J=7.0, 2H); 3.75 (m, 1H); 3.20 (m, 1H); 2.93 (m, 1H); 2.60 (s, 3H); 1.95 (m, 2H); 1.75 (m, 2H); 1.00 (m, 1H); 0.35 (m, 2H); 0.24 (m, 2H).

Example 266

4-(5-Acetyl-2-cyclopropylmethoxy-phenyl)-5H-pyrrolo[3,2-d]pyrimidine-7-carboxylic acid (1-acetyl-piperidin-4-yl)-amide Starting from 4-(5-acetyl-2-cyclopropylmethoxy-phenyl)-5H-pyrrolo[3,2-d]pyrimidine-7-carboxylic acid (example A81) and 1-(4-Amino-piperidin-1-yl)-ethanone (A191) the title compound is obtained as colorless solid.

MS (ESI): m/z=476.0 (MH+, 100%).

¹H-NMR (400 MHz, DMSO-d₆) 12.15 (s, 1H, —NH); 9.10 (s, 1H); 8.52 (d, J=7.0, 1H); 8.32 (s, 1H); 8.20 (d, J=1.5, 1H); 8.12 (dd, J₁=9.0, J₂=1.5, 1H); 7.25 (d, J=9.0, 1H); 4.18 (m, 2H); 4.02 (d, J=7.0, 2H); 3.80 (m, 1H); 3.30 (m, 1H); 2.93 (m, 1H); 2.60 (s, 3H); 2.05 (s, 3H); 1.96 (m, 2H); 1.45 (m, 2H); 1.00 (m, 1H); 0.35 (m, 2H); 0.24 (m, 2H).

Example 267

4-(5-Acetyl-2-cyclopropylmethoxy-4-methyl-phenyl)-5H-pyrrolo[3,2-d]pyrimidine-7-carboxylic acid [1-((S)-2-hydroxy-propionyl)piperidin-4-yl]-amide Starting from 4-(5-acetyl-2-cyclopropylmethoxy-4-methyl-phenyl)-5H-pyrrolo[3,2-d]pyrimidine-7-carboxylic acid (example A82) and (S)-1-(4-amino-piperidin-1-yl)-2-hydroxy-propan-1-one; hydrochloride (A190) the title compound is obtained as colorless solid.

MS (ESI): m/z=520 (MH+, 100%).

¹H-NMR (400 MHz, DMSO-d₆): 12.10 (s, 1H, —NH); 9.08 (s, 1H); 8.52 (d, 1H, J=8.0, —NH); 8.30 (s, 1H); 8.13 (s, 1H); 7.10 (m, 1H); 4.87 (d, 1H, J=7.0, —OH); 4.45 (m, 1H); 4.20 (m, 2H); 4.02 (d, 2H, J=7.0); 3.98 (m, 1H); 3.30 (m, 1H); 3.00 (m, 1H); 2.60 (s, 3H); 2.55 (s, 3H); 1.98 (m, 2H); 1.40 (m, 2H); 1.23 (m, 3H); 1.00 (m, 1H); 0.35 (m, 2H); 0.24 (m, 2H).

Example 268

4-(5-Acetyl-2-cyclopropylmethoxy-4-methyl-phenyl)-5H-pyrrolo[3,2-d]pyrimidine-7-carboxylic acid (1-acetyl-piperidin-4-yl)-amide Starting from 4-(5-acetyl-2-cyclopropylmethoxy-4-methyl-phenyl)-5H-pyrrolo[3,2-d]pyrimidine-7-carboxylic acid (example A82) and 1-(4-amino-piperidin-1-yl)-ethanone (A191) the title compound is obtained as colorless solid.

MS (ESI): m/z=490 (MH+, 100%).

¹H-NMR (400 MHz, DMSO-d₆): 12.10 (s, 1H, —NH); 9.05 (s, 1H); 8.36 (d, J=3.0, 1H); 8.10 (s, 1H); 7.10 (s, 1H); 4.00 (d, J=7.0, 2H); 2.60 (s, 3H); 2.55 (s, 3H); 1.00 (m, 1H); 0.37 (m, 2H); 0.24 (m, 2H).

Example 269 trans-4-(5-Cyclopropylmethoxy-benzo[1,3]dioxol-4-yl)-5H-pyrrolo[3,2-d]pyrimidine-7-carboxylic acid [4-(2-methoxy-ethylcarbamoyl)-cyclohexyl]-amide Starting from 4-(5-cyclopropylmethoxy-benzo[1,3]dioxol-4-yl)-5H-pyrrolo[3,2-d]pyrimidine-7-carboxylic acid (example A67) and trans-4-amino-cyclohexanecarboxylic acid (2-methoxy-ethyl)-amide hydrochloride (A196) the title compound is obtained as colorless solid.

MS (ESI): m/z=536 (MH+).

¹H-NMR (400 MHz, DMSO-d₆): 12.25 (br.s, 1H, —NH); 9.03 (s, 1H); 8.29 (d, J=7.8, 1H, —NH); 8.26 (s, 1H); 7.99 (t, J=5.6, 1H, —NH); 7.01 (d, J=8.6, 1H); 6.56 (d, J=8.6, 1H); 6.00 (s, 2H); 3.80 (m, 1H); 3.76 (d, J=6.8, 2H); 3.34 (m, 2H); 3.25 (s, 3H); 3.20 (m, 2H); 2.18 (m, 1H); 2.05 (m, 2H); 1.80 (m, 2H); 1.50 (m, 2H); 1.34 (m, 2H)); 0.87 (m, 1H); 0.29 (m, 2H); 0.10 (m, 2H).

Example 270 trans-4-(5-Cyclopropylmethoxy-benzo[1,3]dioxol-4-yl)-5H-pyrrolo[3,2-d]pyrimidine-7-carboxylic acid (4-cyclopropylcarbamoyl-cyclohexyl)-amide Starting from 4-(5-cyclopropylmethoxy-benzo[1,3]dioxol-4-yl)-5H-pyrrolo[3,2-d]pyrimidine-7-carboxylic acid (example A67) and trans-(4-cyclopropylcarbamoyl-cyclohexyl)-carbamic acid tart-butyl ester (A195) the title compound is obtained as colorless solid.

MS (ESI): m/z=518 (MH+).

¹H-NMR (400 MHz, DMSO-d₆): 12.25 (br.s, 1H, —NH); 9.02 (s, 1H); 8.28 (d, J=7.9, 1H, —NH); 8.26 (s, 1H); 7.77 (d, J=4.3, 1H, —NH); 7.01 (d, J=8.6, 1H); 6.56 (d, J=8.6, 1H); 6.00 (s, 2H); 3.79 (m, 1H); 3.76 (d, J=6.7, 2H); 2.62 (m, 1H); 2.11-2.04 (m, 3H); 1.78 (m, 2H); 1.49 (m, 2H); 1.32 (m, 2H)); 0.87 (m, 1H); 0.59 (m, 2H); 0.38 (m, 2H); 0.29 (m, 2H); 0.10 (m, 2H).

Example 271 trans-4-(2-Cyclopropylmethoxy-4-methoxy-phenyl)-5H-pyrrolo[3,2-d]pyrimidine-7-carboxylic acid (4-cyclopropylcarbamoyl-cyclohexyl)-amide Starting from 4-(2-cyclopropylmethoxy-4-methoxy-phenyl)-5H-pyrrolo[3,2-d]pyrimidine-7-carboxylic acid (example A73) and trans-(4-cyclopropylcarbamoyl-cyclohexyl)-carbamic acid tert-butyl ester (A195) the title compound is obtained as colorless solid.

MS (ESI): m/z=504 (MH+, 100%).

¹H-NMR (400 MHz, DMSO-d₆): 11.88 (br.s, 1H, —NH); 8.99 (s, 1H); 8.36 (d, J=7.9, 1H, —NH); 8.19 (s, 1H); 7.77 (d, J=4.3, 1H, —NH); 7.61 (d, J=8.5, 1H); 6.72 (dd, J₁=8.5, J₂=2.2, 1H); 6.69 (d, J=2.2, 1H); 3.91 (d, J=6.9, 2H); 3.86 (s, 3H); 3.79 (m, 1H); 2.62 (m, 1H); 2.11-2.03 (m, 3H); 1.78 (m, 2H); 1.49 (m, 2H); 1.32 (m, 2H); 0.97 (m, 1H); 0.37 (m, 2H); 0.23 (m, 2H).

Example 272 trans-4-(2-Cyclopropylmethoxy-4-methoxy-phenyl)-5H-pyrrolo[3,2-d]pyrimidine-7-carboxylic acid [4-(2-methoxy-ethylcarbamoyl)-cyclohexyl]-amide Starting from 4-(2-cyclopropylmethoxy-4-methoxy-phenyl)-5H-pyrrolo[3,2-d]pyrimidine-7-carboxylic acid (example A73) and trans-4-amino-cyclohexanecarboxylic acid (2-methoxy-ethyl)-amide hydrochloride (A196) the title compound is obtained as colorless solid.

MS (ESI): m/z=522 (MH+, 100%).

$^1$H-NMR (400 MHz, DMSO-$d_6$): 11.89 (br.s, 1H, —NH); 9.00 (s, 1H); 8.37 (d, J=7.9, 1H, —NH); 8.19 (s, 1H); 7.78 (t, J=5.6, 1H, —NH); 7.61 (d, J=8.5, 1H); 6.72 (dd, $J_1$=8.5, $J_2$=2.3, 1H); 6.69 (d, J=2.3, 1H); 3.92 (d, J=7.0, 2H); 3.86 (s, 3H); 3.80 (m, 1H); 3.34 (m, 2H); 3.25 (s, 3H); 3.20 (m, 2H); 2.18 (m, 1H); 2.05 (m, 2H); 1.80 (m, 2H); 1.50 (m, 2H); 1.33 (m, 2H); 0.97 (m, 1H); 0.36 (m, 2H); 0.23 (m, 2H).

Example 273 trans-4-(2-Cyclopropylmethoxy-5-fluoro-phenyl)-5H-pyrrolo[3,2-d]pyrimidine-7-carboxylic acid (4-cyclopropylcarbamoyl-cyclohexyl)-amide Starting from 4-(2-cyclopropylmethoxy-5-fluoro-phenyl)-5H-pyrrolo[3,2-d]pyrimidine-7-carboxylic acid (example A77) and trans-(4-cyclopropylcarbamoyl-cyclohexyl)-carbamic acid tert-butyl ester (A195) the title compound is obtained as colorless solid.

MS (ESI): m/z=492 (MH+, 100%).

$^1$H-NMR (400 MHz, DMSO-$d_6$): 12.08 (br.s, 1H, —NH); 9.05 (s, 1H); 8.32 (d, J=7.9, 1H, —NH); 8.28 (s, 1H); 7.77 (d, J=4.3, 1H, —NH); 7.43 (dd, $J_1$=8.9, $J_2$=3.3, 1H); 7.38 (ddd, $J_1$=$J_2$=9.2, $J_3$=3.3, 1H); 7.19 (dd, J1=9.2, $J_2$=4.4, 1H); 3.88 (d, J=6.9, 2H); 3.80 (m, 1H); 2.61 (m, 1H); 2.11-2.04 (m, 3H); 1.79 (m, 2H); 1.50 (m, 2H); 1.32 (m, 2H); 0.94 (m, 1H); 0.59 (m, 2H); 0.38 (m, 2H); 0.33 (m, 2H); 0.19 (m, 2H).

Example 274 trans-4-(2-Cyclopropylmethoxy-5-fluoro-phenyl)-5H-pyrrolo[3,2-d]pyrimidine-7-carboxylic acid [4-(2-methoxy-ethylcarbamoyl)-cyclohexyl]-amide Starting from 4-(2-cyclopropylmethoxy-5-fluoro-phenyl)-5H-pyrrolo[3,2-d]pyrimidine-7-carboxylic acid (example A77) and trans-4-amino-cyclohexanecarboxylic acid (2-methoxy-ethyl)-amide hydrochloride (A196) the title compound is obtained as colorless solid.

MS (ESI): m/z=510 (MH+, 100%).

$^1$H-NMR (400 MHz, DMSO-$d_6$): 12.08 (br.s, 1H, —NH); 9.06 (s, 1H); 8.33 (d, J=7.9, 1H, —NH); 8.28 (s, 1H); 7.79 (d, J=5.5, 1H, —NH); 7.43 (dd, $J_1$=9.0, $J_2$=3.3, 1H); 7.38 (ddd, $J_1$=$J_2$=9.1, $J_3$=3.3, 1H); 7.19 (dd, $J_1$=9.1, $J_2$=4.4, 1H); 3.88 (d, J=6.9, 2H); 3.79 (m, 1H); 3.34 (m, 2H); 3.25 (s, 3H); 3.20 (m, 2H); 2.17 (m, 1H); 2.06 (m, 2H); 1.80 (m, 2H); 1.50 (m, 2H); 1.33 (m, 2H); 0.94 (m, 1H); 0.34 (m, 2H); 0.18 (m, 2H).

Example 275 trans-4-(5-Cyclobutylmethoxy-benzo[1,3]dioxol-4-yl)-5H-pyrrolo[3,2-d]pyrimidine-7-carboxylic acid [4-(2-methoxy-ethylcarbamoyl)-cyclohexyl]-amide Starting 4-(5-cyclobutylmethoxy-benzo[1,3]dioxol-4-yl)-5H-pyrrolo[3,2-d]pyrimidine-7-carboxylic acid (example A68) and trans-4-amino-cyclohexanecarboxylic acid (2-methoxy-ethyl)-amide hydrochloride (A196) the title compound is obtained as colorless solid.

MS (ESI): m/z=550 (MH+, 100%).

$^1$H-NMR (400 MHz, DMSO-$d_6$): 12.28 (br.s, 1H, —NH); 9.01 (s, 1H); 8.28 (d, J=7.8, 1H, —NH); 8.24 (s, 1H); 7.78 (t, J=5.6, 1H, —NH); 7.01 (d, J=8.6, 1H); 6.59 (d, J=8.6, 1H); 6.00 (s, 2H); 3.84 (d, J=6.2, 1H); 3.79 (m, 1H); 3.33 (m, 2H); 3.25 (s, 3H); 3.20 (m, 2H); 2.36 (m, 1H); 2.17 (m, 2H); 2.05 (m, 2H); 1.80 (m, 2H); 1.68 (m, 3H); 1.57-1.44 (m, 5H); 1.33 (m, 2H).

Example 276 trans-4-(5-Cyclobutylmethoxy-benzo[1,3]dioxol-4-yl)-5H-pyrrolo[3,2-d]pyrimidine-7-carboxylic acid (4-cyclopropylcarbamoyl-cyclohexyl)-amide Starting from 4-(5-cyclobutylmethoxy-benzo[1,3]dioxol-4-yl)-5H-pyrrolo[3,2-d]pyrimidine-7-carboxylic acid (example A68) and trans-(4-cyclopropylcarbamoyl-cyclohexyl)-carbamic acid tert-butyl ester (A195) the title compound is obtained as colorless solid.

MS (ESI): m/z=532 (MH+, 100%).

$^1$H-NMR (400 MHz, DMSO-$d_6$): 12.28 (br.s, 1H, —NH); 9.01 (s, 1H); 8.27 (d, J=7.8, 1H, —NH); 8.24 (s, 1H); 7.77 (d, J=4.3, 1H, —NH); 7.01 (d, J=8.6, 1H); 6.59 (d, J=8.6, 1H); 6.00 (s, 2H); 3.84 (d, J=6.2, 1H); 3.79 (m, 1H); 3.25 (s, 3H); 2.61 (m, 1H); 2.36 (m, 1H); 2.10-2.02 (m, 2H); 1.79 (m, 2H); 1.68 (m, 3H); 1.57-1.44 (m, 5H); 1.32 (m, 2H); 0.59 (m, 2H); 0.39 (m, 2H).

The following compounds are obtained analogously to the procedure described in above example 1.

Example 277

4-(2-Cyclopropylmethoxy-5-fluoro-4-hydroxy-phenyl)-5H-pyrrolo[3,2-d]pyrimidine-7-carboxylic acid (1-acetyl-piperidin-4-yl)-amide Starting from 4-(2-cyclopropylmethoxy-5-fluoro-4-hydroxy-phenyl)-5H-pyrrolo[3,2-d]pyrimidine-7-carboxylic acid piperidin-4-ylamide hydrochloride (example A188) and acetyl chloride the title compound is obtained as colorless solid MS (ESI): m/z=468 (MH+, 100%).

$^1$H-NMR (300 MHz, DMSO-$d_6$): 11.90 (br.d, J=3.5, 1H, —NH); 10.43 (s, 1H, —OH); 8.99 (s, 1H); 8.52 (d, J=7.9, 1H, —NH); 8.29 (d, J=3.5, 1H); 7.45 (d, J=11.5, 1H); 6.70 (d, J=7.5, 1H); 4.27-4.06 (m, 2H); 3.81 (d, J=6.9, 2H); 3.80 (m, 1H); 3.27 (m, 1H); 2.92 (m, 1H); 2.04 (s, 3H); 1.96 (m, 2H); 1.55 (m, 1H); 1.39 (m, 1H); 0.96 (m, 1H); 0.35 (m, 2H); 0.22 (m, 2H).

Example 278

4-(2-Cyclopropylmethoxy-5-fluoro-4-hydroxy-phenyl)-5H-pyrrolo[3,2-d]pyrimidine-7-carboxylic acid (1-propionyl-piperidin-4-yl)-amide Starting from 4-(2-cyclopropylmethoxy-5-fluoro-4-hydroxy-phenyl)-5H-pyrrolo[3,2-d]pyrimidine-7-carboxylic acid piperidin-4-ylamide hydrochloride (example A188) and propionyl chloride the title compound is obtained as colorless solid MS (ESI): m/z=482 (MH+, 100%).

$^1$H-NMR (300 MHz, DMSO-$d_6$): 11.90 (br.d, J=3.1, 1H, —NH); 10.43 (br.s, 1H, —OH); 8.99 (s, 1H); 8.52 (d, J=7.8, 1H, —NH); 8.25 (d, J=3.1, 1H); 7.44 (d, J=11.5, 1H); 6.70 (d, J=7.3, 1H); 4.23 (m, 1H); 4.13 (m, 1H); 3.83 (m, 1H); 3.81 (d, J=6.8, 2H); 3.24 (m, 1H); 2.93 (m, 1H); 2.36 (qu, J=7.3, 2H); 1.96 (m, 2H); 1.53 (m, 1H); 1.39 (m, 1H); 1.01 (t, J=7.3, 3H); 0.96 (m, 1H); 0.35 (m, 2H); 0.22 (m, 2H).

Example 279

4-[2-Cyclopropylmethoxy-4-(1,1-difluoro-methoxy)-5-fluoro-phenyl]-5H-pyrrolo[3,2-d]pyrimidine-7-carboxylic acid (1-acetyl-piperidin-4-yl)-amide Starting from 4-[2-cyclopropylmethoxy-4-(1,1-difluoro-methoxy)-5-fluoro-phenyl]-5H-pyrrolo[3,2-d]pyrimidine-7-carboxylic acid piperidin-4-ylamide hydrochloride (example A189) and acetyl chloride the title compound is obtained as colorless solid.

MS (ESI): m/z=518 (MH$^+$, 100%).
$^1$H-NMR (300 MHz, DMSO-d$_6$): 12.16 (br.s, 1H, —NH); 9.05 (s, 1H); 8.48 (d, J=7.9, 1H, —NH); 8.35 (s, 1H); 7.64 (d, J=10.8, 1H); 7.40 (t, J=73.2, 1H); 7.18 (d, J=6.8, 1H); 4.21 (m, 1H); 4.14 (m, 1H); 3.91 (d, J=6.9, 2H); 3.80 (m, 1H); 3.27 (m, 1H); 2.92 (m, 1H); 2.04 (s, 3H); 1.96 (m, 2H); 1.56 (m, 1H); 1.40 (m, 1H); 0.95 (m, 1H); 0.35 (m, 2H); 0.21 (m, 2H).

Example 280

4-[2-Cyclopropylmethoxy-4-(1,1-difluoro-methoxy)-5-fluoro-phenyl]-5H-pyrrolo[3,2-d]pyrimidine-7-carboxylic acid [1-(2-methoxy-ethanoyl)-piperidin-4-yl]amide Starting from 4-[2-cyclopropylmethoxy-4-(1,1-difluoro-methoxy)-5-fluoro-phenyl]-5H-pyrrolo[3,2-d]pyrimidine-7-carboxylic acid piperidin-4-ylamide hydrochloride (example A189) and methoxy-acetyl chloride the title compound is obtained as colorless solid MS (ESI): m/z=548 (MH$^+$, 100%).
$^1$H-NMR (300 MHz, DMSO-d$_6$): 12.01 (br.s, 1H, —NH); 9.05 (s, 1H); 8.48 (d, J=7.9, 1H, —NH); 8.34 (s, 1H); 7.64 (d, J=10.9, 1H); 7.41 (t, J=77.6, 1H); 7.18 (d, J=6.6, 1H); 4.16 (m, 2H); 4.12 (d J=2.6, 1H); 3.91 (d, J=7.1, 2H); 3.76 (m, 1H); 3.31 (s, 3H); 3.22 (m, 1H); 2.95 (m, 1H); 1.98 (m, 2H); 1.56 (m, 1H); 1.43 (m, 1H); 0.95 (m, 1H); 0.36 (m, 2H); 0.21 (m, 2H).

The following compounds are obtained analogously to the procedure described in above example 171.

Example 281

4-(2-Cyclopropylmethoxy-5-fluoro-4-hydroxy-phenyl)-5H-pyrrolo[3,2-d]pyrimidine-7-carboxylic acid [1-(2-hydroxy-acetyl)piperidin-4-yl]-amide Starting from 4-(2-cyclopropylmethoxy-5-fluoro-4-hydroxy-phenyl)-5H-pyrrolo[3,2-d]pyrimidine-7-carboxylic acid piperidin-4-ylamide hydrochloride (example A188) and acetic acid chlorocarbonyl-methyl ester the title compound is obtained as colorless solid MS (ESI): m/z=484 (MH$^+$, 100%).
$^1$H-NMR (300 MHz, DMSO-d$_6$): 11.91 (br.d, J=3.3, 1H, —NH); 10.43 (br.s, 1H, —OH); 8.99 (s, 1H); 8.52 (d, J=7.7, 1H, —NH); 8.25 (d, J=3.3, 1H); 7.44 (d, J=11.5, 1H); 6.70 (d, J=7.3, 1H); 4.51 (t, J=5.3, 1H, —OH); 4.28 (m, 2H); 4.13 (m, 2H); 3.81 (d, J=6.8, 2H); 3.69 (m, 1H); 3.19 (m, 1H); 3.00 (m, 1H); 1.97 (m, 2H); 1.56 (m, 1H); 1.42 (m, 1H); 0.96 (m, 1H); 0.35 (m, 2H); 0.22 (m, 2H).

Example 282

4-(2-Cyclopropylmethoxy-5-fluoro-4-hydroxy-phenyl)-5H-pyrrolo[3,2-d]pyrimidine-7-carboxylic acid [1-((S)-2-hydroxy-propionyl)piperidin-4-yl]-amide Starting from 4-(2-cyclopropylmethoxy-5-fluoro-4-hydroxy-phenyl)-5H-pyrrolo[3,2-d]pyrimidine-7-carboxylic acid piperidin-4-ylamide hydrochloride (example A188) and acetic acid (S)-1-chlorocarbonyl-ethyl ester the title compound is obtained as colorless solid MS (ESI): m/z=498 (MH$^+$, 100%).
$^1$H-NMR (300 MHz, DMSO-d$_6$): 11.99 (br.d, J=3.5, 1H, —NH); 10.48 (br.s, 1H, —OH); 9.01 (s, 1H); 8.51 (d, J=7.7, 1H, —NH); 8.29 (d, J=3.5, 1H); 7.54 (d, J=11.5, 1H); 6.71 (d, J=7.5, 1H); 4.46 (m, 1H); 4.32-3.87 (m, 4H); 3.82 (d, J=6.9, 2H); 3.27 (m, 1H); 2.97 (m, 1H); 1.98 (m, 2H); 1.55 (m, 1H); 1.42 (m, 1H); 1.21 (br.s, 3H); 0.96 (m, 1H); 0.35 (m, 2H); 0.22 (m, 2H).

Example 283

4-[2-Cyclopropylmethoxy-4-(1,1-difluoro-methoxy)-5-fluoro-phenyl]-5H-pyrrolo[3,2-d]pyrimidine-7-carboxylic acid [1-(2-hydroxy-acetyl)piperidin-4-yl]-amide Starting from 4-(2-cyclopropylmethoxy-5-fluoro-4-hydroxy-phenyl)-5H-pyrrolo[3,2-d]pyrimidine-7-carboxylic acid piperidin-4-ylamide hydrochloride (example A188) and acetic acid chlorocarbonyl-methyl ester the title compound is obtained as colorless solid MS (ESI): m/z=534 (MH$^+$, 100%).
$^1$H-NMR (300 MHz, DMSO-d$_6$): 12.16 (br.s, 1H, —NH); 9.05 (s, 1H); 8.48 (d, J=7.9, 1H, —NH); 8.34 (d, J=3.5, 1H); 7.64 (d, J=10.9, 1H); 7.40 (t, J=73.2, 1H); 7.18 (d, J=6.6, 1H); 4.51 (br.s, 1H, —OH); 4.18 (m, 1H); 4.13 (m, 1H & d, J=4.6, 2H); 3.91 (d, J=7.1, 2H); 3.70 (m, 1H); 3.20 (m, 1H); 2.99 (m, 1H); 1.98 (m, 2H); 1.56 (m, 1H); 1.43 (m, 1H); 0.95 (m, 1H); 0.35 (m, 2H); 0.21 (m, 2H).

Example 284

4-[2-Cyclopropylmethoxy-4-(1,1-difluoro-methoxy)-5-fluoro-phenyl]-5H-pyrrolo[3,2-d]pyrimidine-7-carboxylic acid [1-((S)-2-hydroxy-propionyl)-piperidin-4-yl]-amide Starting from 4-(2-cyclopropylmethoxy-5-fluoro-4-hydroxy-phenyl)-5H-pyrrolo[3,2-d]pyrimidine-7-carboxylic acid piperidin-4-ylamide hydrochloride (example A188) and acetic acid (S)-1-chlorocarbonyl-ethyl ester the title compound is obtained as colorless solid MS (ESI): m/z=548 (MH$^+$, 100%).
$^1$H-NMR (300 MHz, DMSO-d$_6$): 12.16 (br.s, 1H, —NH); 9.06 (s, 1H); 8.49 (d, J=7.9, 1H, —NH); 8.34 (d, J=3.1, 1H); 7.65 (d, J=10.8, 1H); 7.41 (t, J=73.2, 1H); 7.18 (d, J=6.6, 1H); 4.87 (d, J=6.9, 1H, —OH); 4.47 (m, 1H); 4.23 (m, 1H); 4.17 (m, 1H) 3.95 (m, 1H); 3.91 (d, J=6.9, 2H); 3.26 (m, 1H); 2.97 (m, 1H); 1.99 (m, 2H); 1.56 (m, 1H); 1.44 (m, 1H); 1.22 (br.s, 3H); 0.94 (m, 1H); 0.35 (m, 2H); 0.21 (m, 2H).

Commercial Utility

The compounds of formula (I), the salts thereof, N-oxides of the compounds and the salts thereof, and the stereoisomers of the compounds, the salts, the N-oxides of the compounds and the N-oxides of the salts thereof are hereinafter referred to as the compounds of the invention. In particular, the compounds of the invention are pharmaceutically acceptable.

The compounds of the invention have valuable pharmaceutical properties which make them commercially utilizable. In particular, as type 5 phosphodiesterase (PDE5) inhibitors, they are able to influence the physiological and pathophysiological function of various cells, e.g., but not limited to, smooth muscle cells, fibroblasts, myofibroblasts and platelets, which are involved in a great variety of physiological and pathophysiological mechanisms. In particular, the PDE5 inhibiting compounds of the invention can effect relaxation of the vasculature, thus increasing blood flow, improve the spatial balance between blood perfusion and ventilation within the lung ("re-matching" effect) thereby reducing the amount of so-called low V/Q-areas [areas within the lung with high perfusion (Q) but no or reduced ventilation (V)] and high V/Q-areas (areas within the lung with low perfusion but high ventilation), induce neurogenesis, inhibit platelet function, such as aggregation, adhesion and mediator release and, thus, have an anti-inflammatory effect. The compounds of the invention are distinguished by valuable and desirable properties, such as, for example, high efficacy, high selectivity, low toxicity, superior bioavailability in general (e.g. good enteral absorption), superior therapeutic window, superior pharmacokinetics (e.g. half-life), absence of significant side effects, and further beneficial effects related with their therapeutic and pharmaceutical suitability.

Accordingly, the invention further relates to the compounds of the invention for the treatment or prophylaxis of diseases, especially diseases alleviated by inhibition of the type 5 phospho-diesterase. In particular, the invention relates to the compounds of the invention for the treatment or prophylaxis of the following diseases:

male and female sexual dysfunction, such as, but not limited to, male erectile dysfunction, premature ejaculation, Peyronie's disease;

acute and chronic airway diseases, such as, but not limited to, COPD (chronic obstructive pulmonary disease), bronchitis, emphysema, pulmonary vascular remodeling, pulmonary hypertension, lung fibrosis, asthma, cystic fibrosis, bronchiectasis, bronchiolitis obliterans, connective tissue diseases, sarcoidosis, kyphoscoliosis, pneumoconiosis, amyotrophic lateral sclerosis, thoracoplasty, extrinsic allergic alveolitis;

inflammatory diseases, such as, but not limited to, vasculature inflammation, acute respiratory distress syndrome, mesangial glomerulonephritis, chronic inflammatory bowel disease, disseminated intravascular inflammation, allergic vasculitis, dermatoses (e.g., but not limited to, psoriasis, toxic and allergic contact eczema, atopic eczema, seborrhoeic eczema, Lichen simplex, sunburn, pruritus in the anogenital area, alopecia greata, hypertrophic scars, discoid lupus erythematosus, follicular and widespread pyodermias, endogenous and exogenous acne, acne rosacea), disorders of the arthritis type (e.g., but not limited to, rheumatoid arthritis, rheumatoid spondylitis, osteoarthritis), disorders of the immune system [e.g., but not limited to, AIDS (acquired immunodeficiency syndrome), multiple sclerosis], graft versus host reaction, allograft rejections, shock [e.g., but not limited to, septic shock, endotoxin shock, gram-negative sepsis shock, toxic shock syndrome and ARDS (adult respiratory distress syndrome)], gastrointestinal inflammations (e.g., but not limited to, Crohn's disease and ulcerative colitis); disorders which are based on to allergic and/or chronic, immunological false reactions (e.g., but not limited to, allergic rhinitis, allergic sinusitis, chronic rhinitis, chronic sinusitis, allergic conjunctivitis, nasal polyps);

pain, such as, but not limited to, inflammatory pain;

right-heart failure, right heart hypertrophy (car pulmonale), hypertension, hypercholesterolemia, hypertriglyceridemia;

ischaemic diseases, such as, but not limited to, diabetes mellitus, stroke, coronary artery disease, angina (including, but not limited to, vasospastic angina), myocardial infarction, peripheral artery disease, cerebrovascular obstruction, sleep apnea, macular ischaemia, arterial and venous occlusion, congestive heart failure;

diabetic gastroparesis and diseases with symptoms of gastroparesis;

diseases or conditions in which it is desirable to suppress platelet function, for example, but not limited to, after stent implantations (e.g., but not limited to, coronary stenting), after bypass operations, in pulmonary hypertension, thrombotic diseases, post-angioplasty stenosis, coronary artery disease, infarction (e.g., but not limited to, myocardial infarction), instable angina pectoris, stroke, and arterial and venous occlusion diseases (e.g., but not limited to, claudicatio intermittens);

diseases or conditions with an impairment or dysfunction of cerebral vascular reactivity and/or neurovascular coupling, such as, but not limited to, arteriosclerotic dementia, multi-infarct dementia, cerebral senility;

diseases which are based on neuronal damage or degradation, such as but not limited to, stroke, spinal cord injury, brain injury, morbus parkinson, amyotrophic lateral sclerosis, morbus alzheimer, amyloidosis, prion diseases and neuropathy;

peripheral arterial diseases, chronic renal failure, chronic heart failure, sepsis, senile dementia (Alzheimer's disease), Creutzfeld-Jacob disease, septic encephalopathy, arteriosclerotic encephalopathy, diabetes associated encephalopathy, toxic encephalopathy, vascular and neuronal dementia, Huntington's disease, Parkinson's disease, multiple sclerosis and preeclampsia;

portal hypertension, liver cirrhosis, toxic liver damage (e.g., but not limited to, alcohol-induced liver damage), hepatitis, thrombosis of the portal vein, Budd-Chiari syndrome, malformation of liver veins, compression of liver veins (e.g., but without limitation, due to tumors), arteriovenous fistula, diseases associated with an enlarged spleen, schistosomiasis (bilharziosis), sarcoidosis and other granulomatous diseases, primary biliary cirrhosis, myeloproliferative disorders (e.g., but not limited to, chronic myeloid leukemia, osteomyelofibrosis), lymphatic systemic diseases, collagenosis (e.g., but not limited to, systemic lupus erythematodes, sclerodermia), morbus Osler (congenital arteriovenous malformations, inter alia in the liver), nodular regenerative hyperplasia, tricuspid insufficiency, pericarditis constrictive, veno-occlusive disease (VOD), non-alcoholic steatohepatitis (NASH), liver fibrosis;

benign prostatic hyperplasia;

insufficient uteroplacental blood flow in pregnancies with fetal growth restriction;

insufficient brain skills, such as but not limited to, verbal attainment, attention, concentration, deductive thinking, central auditory processing, cognition, learning, vigilance, apprehension and reagibility;

Overactive Bladder; LUTS=lower urinary tract symptoms; Raynauds syndrome/phenomenon.

In this respect, the term "pulmonary hypertension" in particular embraces pulmonary arterial hypertension including primary pulmonary hypertension (e.g. sporadic or familial) and pulmonary arterial hypertension related, for example, but without limitation, to collagen vascular disease, congenital systemic-to-pulmonary shunts, portal hypertension, human immunodeficiency virus infection, drugs or toxins (e.g., but not limited to, anorexigens), persistent pulmonary hypertension of the newborn;

pulmonary venous hypertension due to, for example, but without limitation, left-sided atrial or ventricular heart disease, left-sided valvular heart disease, extrinsic compression of central pulmonary veins (e.g. fibrosing mediastinitis, adenopathy in relation to tumors), pulmonary veno-occlusive disease;

pulmonary hypertension associated with disorders of the respiratory system or hypoxemia including, for example, but without limitation, chronic obstructive pulmonary disease (COPD), interstitial lung disease, sleep-disordered breathing, alveolar hypoventilation disorders, chronic exposure to high altitude, neonatal lung disease, alveolar-capillary dysplasia;

pulmonary hypertension caused by chronic thrombotic or embolic diseases including thromboembolic obstruction of proximal pulmonary arteries and obstruction of distal pulmonary arteries, such as pulmonary embolism (due to thrombus, tumor, ova, parasites, or foreign material), in situ thrombosis and sickle-cell disease, in particular chronic thromboembolic pulmonary hypertension (CTEPH);

pulmonary hypertension caused by disorders directly affecting the pulmonary vasculature including inflammatory disorders (e.g., but not limited to, schistosomiasis, sarcoidosis) and pulmonary capillary hemangiomatosis.

Preferably, the invention further relates to the compounds of the invention for the treatment or prophylaxis of the following diseases: acute and chronic airway diseases, such as pulmonary hypertension, in particular chronic thromboembolic pulmonary hypertension, lung fibrosis, asthma, bronchitis, emphysema and chronic obstructive pulmonary disease.

The invention also relates to the use of a compound of the invention in the manufacture of a pharmaceutical composition inhibiting the type 5 phosphodiesterase, in particular a pharmaceutical composition for the treatment or prophylaxis of diseases alleviated by inhibition of the type 5 phosphodiesterase, preferably, a pharmaceutical composition for the treatment or prophylaxis of to the diseases exemplified above.

Preferably, the invention relates to the use of a compound of the invention in the manufacture of a pharmaceutical composition for the treatment or prophylaxis of an acute or chronic airway disease, such as, but not limited to, pulmonary hypertension, lung fibrosis, asthma, bronchitis, emphysema and chronic obstructive pulmonary disease.

In a particularly preferred embodiment of the invention, the invention relates to the use of a compound of the above examples in the manufacture of a pharmaceutical composition for the treatment or prophylaxis of an acute or chronic airway disease, such as, but not limited to, pulmonary hypertension, lung fibrosis, asthma, bronchitis, emphysema and chronic obstructive pulmonary disease.

The invention further relates to a method of treating or preventing a disease comprising administering to a patient in need thereof a therapeutically effective amount of at least one of the compounds of the invention.

In particular, the invention relates to a method of treating or preventing one of the above mentioned diseases comprising administering to a patient in need thereof a therapeutically effective amount of at least one of the compounds of the invention.

Especially, the invention relates to a method of treating or preventing a disease which is alleviated by inhibition of the type 5 phosphodiesterase comprising administering to a patient in need thereof a therapeutically effective amount of at least one of the compounds of the invention.

Preferably, the invention relates to a method of treating or preventing an acute or chronic airway disease, for example, but not limited to, pulmonary hypertension, lung fibrosis, asthma, bronchitis, emphysema and chronic obstructive pulmonary disease, comprising administering to a patient in need thereof a therapeutically effective amount of at least one of the compounds of the invention.

In the above methods, the patient is preferably a mammal, more preferably a human. Furthermore, in the above methods, at least one of the compounds of the invention can be used. Preferably, one or two of the compounds of the invention are used, more preferably, one of the compounds of the invention is used.

In a particularly preferred embodiment of the invention, the above methods of treating or preventing one of the above mentioned diseases comprise administering to a patient in need thereof a therapeutically effective amount of one compound of the examples according to the present to invention.

The invention furthermore relates to a pharmaceutical composition which comprises at least one of the compounds of the invention together with at least one pharmaceutically acceptable auxiliary.

The invention additionally relates to a pharmaceutical composition for the treatment or prophylaxis of an acute or chronic airway disease, in particular for the treatment or prophylaxis of pulmonary hypertension, lung fibrosis, asthma, bronchitis, emphysema and chronic obstructive pulmonary disease.

Preferably, the pharmaceutical composition comprises one or two of the compounds of the invention. More preferably, the pharmaceutical composition comprises one of the compounds of the invention.

In a particularly preferred embodiment of the invention, the pharmaceutical composition comprises a compound of the examples according to the present invention together with at least one pharmaceutically acceptable auxiliary.

The invention additionally relates to a pharmaceutical composition comprising at least one of the compounds of the invention, at least one pharmaceutically acceptable auxiliary and at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, antidepressants, antibiotics, anticoagulants, diuretics and digitalis glycosides.

In this respect, the therapeutic agent includes the corticosteroids, anticholinergics, beta-mimetics, lung surfactants, endothelin antagonists, prostacyclins, calcium channel blockers, beta-blockers, type 4 phosphodiesterase inhibitors, antidepressants, antibiotics, anticoagulants, diuretics and digitalis glycosides in form of the free compounds, the pharmaceutically acceptable salts thereof, the pharmaceutically acceptable derivatives thereof (e.g., but not limited to, ester derivatives), the solvates thereof and the stereoisomers of the compounds, salts, derivatives and solvates.

Examples of corticosteroids include without limitation budesonide, fluticasone such as fluticasone propionate, beclometasone such as beclometasone dipropionate, triamcinolone such as triamcinolone acetonide, and ciclesonide. Examples of anticholinergics include without limitation indacaterol, tiotropium such as tiotropium bromide, and ipratropium such as ipratropium bromide. Examples of beta-mimetics include without limitation formoterol such as formoterol fumarate, and salmeterol such as salmeterol xinafoate. Examples of lung surfactants include without limitation lusupultide, poractant alfa, sinapultide, beractant, bovactant, colfosceril such as colfosceril palmitate, surfactant-TA, and calfactant. Examples of endothelin antagonists include without limitation bosentan, ambrisentan and sitaxsentan such as sitaxsentan sodium. Examples of prostacyclins include without limitation iloprost such as iloprost tromethamine, epoprostenol such as epoprostenol sodium and treprostinil such as treprostinil sodium. Examples of calcium channel blockers include without limitation amlodipine such as amlodipine besylate and amlodipine maleate, nifedipine, diltiazem such as diltiazem hydrochloride, verapamil such as verapamil hydrochloride, and felodipine. Examples of beta-blockers include without limitation bisoprolol such as bisoprolol fumarate, nebivolol, metoprolol such as metoprolol succinate and metoprolol tartrate, carvedilol, atenolol and nadolol. Examples of type 4 phosphodiesterase inhibitors include without limitation roflumilast, roflumilast N-oxide, cilomilast, tetomilast and oglemilast. Examples of antidepressants include without limitation bupropion such as bupropion hydrochloride. Examples of antibiotics include without limitation amoxicillin, ampicillin, levofloxacin, clarithromycin, ciprofloxacin such as ciprofloxacin hydrochloride, telithromycin and azithromycin. Examples of anticoagulants include without limitation clopidogrel, enoxaparin, cilostazol, nadroparin, warfarin and abciximab. Examples of diuretics include without limitation furosemide, bumetanide and torsemide. Examples of digitalis glycosides include without limitation digoxin and digitoxin.

In a preferred embodiment, the pharmaceutical composition comprises a compound of the invention in combination with a corticosteroid. In a particularly preferred embodiment, the pharmaceutical composition comprises:
a compound of the invention and budesonide,
a compound of the invention and fluticasone,
a compound of the invention and beclometasone,
a compound of the invention and triamcinolone, or
a compound of the invention and ciclesonide.

In a further preferred embodiment, the pharmaceutical composition comprises a compound of the invention in combination with an anticholinergic. In a particularly preferred embodiment, the pharmaceutical composition comprises:
a compound of the invention and indacaterol,
a compound of the invention and tiotropium, or
a compound of the invention and ipratropium.

In a further preferred embodiment, the pharmaceutical composition comprises a compound of the invention in combination with a beta-mimetic. In a particularly preferred embodiment, the pharmaceutical composition comprises:
a compound of the invention and formoterol, or
a compound of the invention and salmeterol.

In a further preferred embodiment, the pharmaceutical composition comprises a compound of the to invention in combination with a lung surfactant. In a particularly preferred embodiment, the pharmaceutical composition comprises:
a compound of the invention and lusupultide,
a compound of the invention and poractant alfa,
a compound of the invention and sinapultide,
a compound of the invention and beractant,
a compound of the invention and bovactant,
a compound of the invention and colfosceril,
a compound of the invention and surfactant-TA, or
a compound of the invention and calfactant.

In a further preferred embodiment, the pharmaceutical composition comprises a compound of the invention in combination with an endothelin antagonist. In a particularly preferred embodiment, the pharmaceutical composition comprises:
a compound of the invention and bosentan,
a compound of the invention and ambrisentan, or
a compound of the invention and sitaxsentan.

In a further preferred embodiment, the pharmaceutical composition comprises a compound of the invention in combination with a prostacyclin. In a particularly preferred embodiment, the pharmaceutical composition comprises:
a compound of the invention and iloprost,
a compound of the invention and epoprostenol,
a compound of the invention and triprostinil.

In a further preferred embodiment, the pharmaceutical composition comprises a compound of the invention in combination with a calcium channel blocker. In a particularly preferred embodiment, the pharmaceutical composition comprises:
a compound of the invention and amlodipine,
a compound of the invention and nifedipine,
a compound of the invention and diltiazem,
a compound of the invention and verapamil, or
a compound of the invention and felodipine.

In a further preferred embodiment, the pharmaceutical composition comprises a compound of the invention in combination with a beta-blocker. In a particularly preferred embodiment, the pharmaceutical composition comprises:
a compound of the invention and bisoprolol,
a compound of the invention and nebivolol,
a compound of the invention and metoprolol,
a compound of the invention and carvedilol,
a compound of the invention and atenolol, or
a compound of the invention and nadolol.

In a further preferred embodiment, the pharmaceutical composition comprises a compound of the invention in combination with a type 4 phosphodiesterase inhibitor. In a particularly preferred embodiment, the pharmaceutical composition comprises:
a compound of the invention and roflumilast,
a compound of the invention and roflumilast N-oxide,
a compound of the invention and cilomilast,
a compound of the invention and tetomilast, or
a compound of the invention and oglemilast.

In a further preferred embodiment, the pharmaceutical composition comprises a compound of the invention in combination with an antidepressant. In a particularly preferred embodiment, the pharmaceutical composition comprises:
a compound of the invention and bupropion.

In a further preferred embodiment, the pharmaceutical composition comprises a compound of the invention in combination with an antibiotic. In a particularly preferred embodiment, the pharmaceutical composition comprises:
a compound of the invention and amoxicillin,
a compound of the invention and ampicillin,
a compound of the invention and levofloxacin,
a compound of the invention and clarithromycin,
a compound of the invention and ciprofloxacin,
a compound of the invention and telithromycin, or
a compound of the invention and azithromycin.

In a further preferred embodiment, the pharmaceutical composition comprises a compound of the invention in combination with an anticoagulant. In a particularly preferred embodiment, the pharmaceutical composition comprises:
a compound of the invention and clopidogrel,
a compound of the invention and enoxaparin,
a compound of the invention and cilostazol,
a compound of the invention and nadroparin,
a compound of the invention and warfarin, or
a compound of the invention and abciximab.

In a further preferred embodiment, the pharmaceutical composition comprises a compound of the invention in combination with a diuretic. In a particularly preferred embodiment, the pharmaceutical composition comprises:
a compound of the invention and furosemide,
a compound of the invention and bumetanide, or
a compound of the invention and torsemide.

In a further preferred embodiment, the pharmaceutical composition comprises a compound of the invention in combination with a digitalis glycoside. In a particularly preferred embodiment, the pharmaceutical composition comprises:
a compound of the invention and digoxin, or
a compound of the invention and digitoxin.

In a further preferred embodiment, the pharmaceutical composition comprises a compound of the invention in combination with a corticosteroid and a beta-mimetic. In a particularly preferred embodiment, the pharmaceutical composition comprises:
a compound of the invention, budesonide and indacaterol,
a compound of the invention, budesonide and formoterol,
a compound of the invention, budesonide and salmeterol,
a compound of the invention, fluticasone and indacaterol,
a compound of the invention, fluticasone and formoterol,
a compound of the invention, fluticasone and salmeterol,
a compound of the invention, beclometasone and indacaterol,
a compound of the invention, beclometasone and formoterol,
a compound of the invention, beclometasone and salmeterol,
a compound of the invention, triamcinolone and indacaterol,
a compound of the invention, triamcinolone and formoterol,
a compound of the invention, triamcinolone and salmeterol,
a compound of the invention, ciclesonide and indacaterol,
a compound of the invention, ciclesonide and formoterol, or
a compound of the invention, ciclesonide and salmeterol.

In a further preferred embodiment, the pharmaceutical composition comprises a compound of the invention in combination with a corticosteroid and an anticholinergic. In a particularly preferred embodiment, the pharmaceutical composition comprises:
a compound of the invention, budesonide and tiotropium,
a compound of the invention, budesonide and ipratropium,
a compound of the invention, fluticasone and tiotropium,
a compound of the invention, fluticasone and ipratropium,
a compound of the invention, beclometasone and tiotropium,
a compound of the invention, beclometasone and ipratropium,
a compound of the invention, triamcinolone and tiotropium,
a compound of the invention, triamcinolone and ipratropium,
a compound of the invention, ciclesonide and tiotropium, or
a compound of the invention, ciclesonide and ipratropium.

The above mentioned compound of the invention is preferably a compound according to the examples.

The invention furthermore relates to pharmaceutical compositions according to the invention, as defined above, inhibiting the type 5 phosphodiesterase, especially for the treatment or prophylaxis of diseases alleviated by inhibition of type 5 phosphodiesterase, in particular for the treatment or prophylaxis of the diseases exemplified above.

The invention also encompasses pharmaceutical compositions according to the invention, as defined above, for the treatment or prophylaxis of the following diseases: acute and chronic airway diseases, such as pulmonary hypertension, lung fibrosis, asthma, bronchitis, emphysema and chronic obstructive pulmonary disease.

The pharmaceutical compositions according to the invention preferably contain the compound or compounds of the invention in a total amount of from 0.1 to 99.9 wt %, more preferably 5 to 95 wt %, in particular 20 to 80 wt %. In case at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, antidepressants, antibiotics, anticoagulants, diuretics and digitalis glycosides is present in the pharmaceutical compositions of the invention, the total amount of said therapeutic agent or therapeutic agents in the pharmaceutical compositions is preferably in the range of from 0.1 to 99.9 wt %, more preferably 5 to 95 wt %, in particular 20 to 80 wt %, under the provision that the total amount of the compound or compounds of the invention and the therapeutic agent or therapeutic agents is less than 100 wt %. Preferably, the at least one compound of the invention and the at least one therapeutic agent are present in the pharmaceutical composition in a weight ratio of from 1000:1 to 1:1000, more preferably 500:1 to 1:500.

As pharmaceutically acceptable auxiliaries, any auxiliaries known to be suitable for preparing pharmaceutical compositions can be used. Examples thereof include, but are not limited to, solvents, excipients, dispersants, emulsifiers, solubilizers, gel formers, ointment bases, antioxidants, preservatives, stabilizers, carriers, fillers, binders, thickeners, complexing agents, disintegrating agents, buffers, permeation promoters, polymers, lubricants, coating agents, propellants, tonicity adjusting agents, surfactants, colorants, flavorings, sweeteners and dyes. In particular, auxiliaries of a type appropriate to the desired formulation and the desired mode of administration are used.

The pharmaceutical compositions can be formulated, for example, into tablets, coated tablets (dragees), pills, cachets, capsules (caplets), granules, powders, suppositories, solutions (e.g., but not limited to, sterile solutions), emulsions, suspensions, ointments, creams, lotions, pastes, oils, to gels, sprays and patches (e.g., but not limited to, transdermal therapeutic systems). Additionally, the pharmaceutical compositions can be prepared as e.g. liposome delivery systems, systems in which the compound of the invention is coupled to monoclonal antibodies and systems in which the compound of the invention is coupled to polymers (e.g., but not limited to, soluble or biodegradable polymers).

In case of pharmaceutical compositions comprising at least one of the compounds of the invention and at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, antidepressants, antibiotics, anticoagulants, diuretics and digitalis glycosides, the compound of the invention and the therapeutic agent may be formulated together into the same dosage form (e.g., but not limited to, tablets), separately into the same dosage form (e.g., but not limited to, tablets), or into different dosage forms (without limitation e.g. the compound of the invention may be formulated as tablet and the therapeutic agent may be formulated as powder, solution or suspension).

The pharmaceutical compositions can be manufactured in a manner known to a person skilled in the art, e.g. by dissolving, mixing, granulating, dragee-making, levigating, emulsifying, encapsulating, entrapping or lyophilizing processes.

The selected formulation depends inter alia on the route of administering the pharmaceutical composition. The pharmaceutical compositions of the invention can be administered by any suitable route, for example, by the oral, sublingual, buccal, intravenous, intraarterial, intramuscular, subcutaneous, intracutaneous, topical, transdermal, intranasal, intraocular, intraperitoneal, intrasternal, intracoronary, transurethral, rectal or vaginal route, by inhalation or by insufflation. Oral administration is preferred.

In case of pharmaceutical compositions comprising at least one of the compounds of the invention and at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, antidepressants, antibiotics, anticoagulants, diuretics and digitalis glycosides, the compound of the invention and the therapeutic agent may be administered by the same route, e.g., without limitation, orally, or by different routes, e.g., without limitation, the compound of the invention can be administered orally and the therapeutic agent can be administered by inhalation or instillation.

Tablets, coated tablets (dragees), pills, cachets, capsules (caplets), granules, solutions, emulsions and suspensions are e.g. suitable for oral administration. In particular, said formulations can be adapted so as to represent, for example, an enteric form, an immediate release form, a delayed release form, a repeated dose release form, a prolonged release form or a sustained release form. Said forms can be obtained, for example, by coating tablets, by dividing tablets into several compartments separated by layers disintegrating under different conditions (e.g. pH conditions) or by coupling the compound of the invention to a biodegradable polymer.

Administration by inhalation or instillation is preferably made by using an aerosol. The aerosol is a liquid-gaseous dispersion, a solid-gaseous dispersion or a mixed liquid/solid-gaseous dispersion.

The aerosol may be generated by means of aerosol-producing devices such as dry powder inhalers (DPIs), pressurized metered dose inhalers (PMDIs) and nebulizers. Depending on the kind of the compound of the invention, and optionally the therapeutic agent, to be administered, the aerosol-producing device can contain the compound and, optionally, the therapeutic agent in form of a powder, a solution or a dispersion. The powder may contain, for example, one or more of the following auxiliaries: carriers, stabilizers and fillers. The solution may contain in addition to the solvent, for example, one or more of the following auxiliaries: propellants, solubilizers (co-solvents), surfactants, stabilizers, buffers, tonicity adjusting agents, preservatives and flavorings. The dispersion may contain in addition to the dispersant, for example, one or more of the following auxiliaries: propellants, surfactants, stabilizers, buffers, preservatives and flavorings. Examples of carriers include, but are not limited to, saccharides, e.g. lactose and glucose. Examples of propellants include, but are not limited to, fluorohydrocarbons, e.g. 1,1,1,2-tetrafluoroethane and 1,1,1,2,3,3,3-heptafluoropropane.

The particle size of the aerosol particles (solid, liquid or solid/liquid particles) is preferably less than 100 μm, more preferably it is in the range of from 0.5 to 10 μm, in particular in the range of from 2 to 6 μm (D50 value, measured by laser diffraction).

Specific aerosol-producing devices which may be used for inhaled administration include, but are not limited to, Cyclohaler®, Diskhaler®, Rotadisk®, Turbohaler®, Autohaler®, Turbohaler®, Novolizer®, Easyhaler®, Aerolizer®, Jethaler®, Diskus®, Ultrahaler® and Mystic® inhalers. The aerosol-producing devices may be combined with spacers or expanders, e.g. Aerochamber®, Nebulator®, Volumatic® and Rondo®, for improving inhalation efficiency.

In case of topical administration, suitable pharmaceutical formulations are, for example, ointments, creams, lotions, pastes, gels, powders, solutions, emulsions, suspensions, oils, sprays and patches (e.g., but not limited to, transdermal therapeutic systems).

For parenteral modes of administration such as, for example, intravenous, intraarterial, to intramuscular, subcutaneous, intracutaneous, intraperitoneal and intrasternal administration, preferably solutions (e.g., but not limited to, sterile solutions, isotonic solutions) are used. They are preferably administered by injection or infusion techniques.

In case of intranasal administration, for example, sprays and solutions to be applied in drop form are preferred formulations.

For intraocular administration, solutions to be applied in drop form, gels and ointments are exemplified formulations.

Generally, the pharmaceutical compositions according to the invention can be administered such that the dose of the compound of the invention is in the range customary for type 5 phosphodiesterase inhibitors. In particular, a dose in the range of from 0.01 to 4000 mg of the compound of the invention per day is preferred. In this respect, it is to be noted that the dose is dependent, for example, on the specific compound used, the species treated, age, body weight, general health, sex and diet of the subject treated, mode and time of administration, rate of excretion, severity of the disease to be treated and drug combination. In case the pharmaceutical composition of the invention comprises at least one of the compounds of the invention and at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, antidepressants, antibiotics, anticoagulants, diuretics and digitalis glycosides, the same dose ranges apply to the therapeutic agent.

The pharmaceutical compositions according to the invention can be administered in a single dose per day or in multiple subdoses, for example, 2 to 4 doses per day. A single dose unit of the pharmaceutical composition can contain e.g. from 0.01 mg to 4000 mg, preferably 0.1 mg to 2000 mg, more preferably 0.5 to 1000 mg, most preferably 1 to 500 mg, of the compound of the invention. In case the pharmaceutical composition of the invention comprises at least one of the compounds of the invention and at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, antidepressants, antibiotics, anticoagulants, diuretics and digitalis glycosides, a single dose unit of the pharmaceutical composition can contain e.g. from 0.01 mg to 4000 mg, preferably 0.1 mg to 2000 mg, more preferably 0.5 to 1000 mg, most preferably 1 to 500 mg, of the therapeutic agent. Furthermore, the pharmaceutical composition can be adapted to weekly, monthly or even more infrequent administration, for example by using an implant, e.g. a subcutaneous or intramuscular implant, by using the compound of the invention in form of a sparingly soluble salt or by using the compound of the invention coupled to a polymer. Administration of the pharmaceutical composition in a single dose per day is preferred.

In case the pharmaceutical composition of the invention comprises at least one of the compounds of the invention and at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, antidepressants, antibiotics, anticoagulants, diuretics and digitalis glycosides, administration of the compound of the invention and administration of the therapeutic agent can be made simultaneously or sequentially. In case of sequential administration, the compound of the invention can be administered before or after administration of the therapeutic agent.

Biological Investigations

Method for Measuring Inhibition of the Type 5 Phosphodiesterase (PDE5) Activity:

As a source for human PDE5, platelets are used. For that purpose, 150 ml fresh blood from human donors anticoagulated with citrate [final concentration 0.3% (w/v)] is centrifuged at 200 g for 10 min to obtain the so-called platelet-rich-plasma (PRP) as a supernatant. 1/10 volume of ACD solution (85 mM $Na_3$-citrate, 111 mM D-glucose, 71 mM citric acid, pH 4.4) is added to 9/10 volume of PRP. After centrifugation (1,400 g, 10 min) the cell pellet is resuspended in 3 ml homogenization buffer (NaCl 140 mM, KCl 3.8 mM, EGTA (ethylene glycol tetraacetic acid) 1 mM, $MgCl_2$ 1 mM, Tris-HCl 20 mM, beta-mercaptoethanol 1 mM, pH 8.2) plus protease-inhibitor mix giving rise to the final concentrations of 0.5 mM Pefablock (Roche), 10 μM Leupeptin, 5 μM Trypsininhibitor, 2 mM Benzamidin and 10 μM Pepstatin A. The suspension is sonified and thereafter centrifuged for 15 min at 10,000 g. The resulting supernatant (platelet lysate) is used for enzymatic testings.

PDE5A1 activity is inhibited by the compounds of the invention in a modified SPA (scintillation proximity assay) test, supplied by Amersham Biosciences (see procedural instructions "phosphodiesterase [3H]cAMP SPA enzyme assay, code TRKQ 7090"), carried out in 96-well microtitre plates (MTP's). The test volume is 100 μl and contains 20 mM Tris buffer (pH 7.4), 0.1 mg of BSA (bovine serum albumin)/ml, 5 mM $Mg^{2+}$, 1 μM motapizone, 10 nM PDE2 inhibitor 2-(3,4-dimethoxybenzyl)-7-[(1R,2R)-2-hydroxy-1-(2-phenylethyl)propyl]-5-methylimidazo[5,1-f][1,2,4]triazin-4 (3H)-one, 0.5 μM cGMP (cyclic guanosine monophosphate) (including about 50,000 cpm of [3H]cGMP as a tracer), 1 μl of the respective compound dilution in dimethylsulfoxide (DMSO) and sufficient PDE5-containing platelet lysat (10,000×g supernatant, see above) to ensure that 10-20 wt % of the cGMP is converted under the said experimental conditions. The final concentration of DMSO in the assay (1% v/v) does not substantially affect the activity of the PDE investigated. After a preincubation of 5 min at 37° C., the reaction is started by adding the substrate (cGMP) and the assay is incubated for a further 15 min; after that, it is stopped by adding SPA beads (50 μl). In accordance with the manufacturer's instructions, the SPA beads had previously been resuspended in water, but are then diluted 1:3 (v/v) in water; the diluted solution also contains 3 mM 8-methoxymethyl-3-isobutyl-1-methylxanthine (IBMX) to ensure a complete PDE activity stop. After the beads have been sedimented (>30 min), the MTP's are analyzed in commercially available luminescence detection de-vices. The corresponding $IC_{50}$ values of the compounds for the inhibition of PDE activity are deter-mined from the concentration-effect curves by means of non-linear regression.

Representative inhibitory values determined for the compounds of the invention are given in the following table:

| Example | -log $IC_{50}$ (mol/l) |
|---|---|
| 1 | 10.11 |
| 2 | 10.01 |
| 3 | 9.40 |
| 4 | 9.79 |
| 5 | 9.91 |
| 6 | 10.07 |
| 7 | 9.67 |
| 8 | 9.65 |
| 9 | 8.94 |
| 10 | 9.70 |
| 11 | 9.84 |
| 12 | 10.16 |
| 13 | 9.11 |
| 14 | 8.86 |
| 15 | 9.00 |
| 16 | 9.41 |
| 17 | 9.47 |
| 18 | 8.74 |
| 19 | 8.61 |
| 20 | 9.27 |
| 21 | 8.74 |
| 22 | 9.31 |
| 23 | 9.35 |
| 24 | 9.52 |
| 25 | 9.62 |
| 26 | 9.34 |
| 27 | 9.43 |
| 28 | 9.16 |
| 29 | 9.56 |
| 30 | 9.32 |
| 31 | 9.65 |
| 32 | 8.96 |
| 33 | 8.82 |
| 34 | 9.46 |
| 35 | 9.15 |
| 36 | 9.31 |
| 37 | 9.04 |
| 38 | 9.40 |
| 39 | 9.11 |
| 40 | 9.37 |
| 41 | 9.05 |
| 42 | 9.72 |
| 43 | 9.55 |
| 44 | 9.10 |
| 45 | 8.81 |
| 46 | 8.86 |
| 47 | 9.64 |
| 48 | 9.37 |
| 49 | 9.47 |
| 50 | 9.85 |
| 51 | 9.31 |
| 52 | 9.52 |
| 53 | 9.43 |
| 54 | 9.38 |
| 55 | 9.43 |
| 56 | 9.55 |
| 57 | 9.33 |
| 58 | 9.47 |
| 59 | 9.13 |
| 60 | 9.58 |
| 61 | 9.28 |
| 62 | 9.51 |
| 63 | 9.04 |
| 64 | 9.22 |
| 65 | 8.94 |
| 66 | 9.20 |
| 67 | 8.86 |
| 68 | 9.04 |
| 69 | 8.75 |
| 70 | 8.97 |
| 71 | 8.87 |
| 72 | 9.36 |
| 73 | 8.73 |
| 74 | 9.26 |
| 75 | 8.80 |
| 76 | 8.62 |
| 77 | 8.67 |
| 78 | 8.64 |
| 79 | 8.81 |
| 80 | 8.85 |
| 81 | 8.83 |
| 82 | 8.96 |
| 83 | 8.29 |
| 84 | 8.53 |
| 85 | 8.80 |
| 86 | 8.40 |
| 87 | 8.95 |
| 88 | 8.78 |
| 89 | 8.89 |
| 90 | 8.25 |
| 91 | 8.20 |
| 92 | 8.47 |
| 93 | 8.60 |

| Example | -log IC$_{50}$ (mol/l) |
|---|---|
| 94 | 8.06 |
| 95 | 8.48 |
| 96 | 8.67 |
| 97 | 9.93 |
| 98 | 9.66 |
| 99 | 9.75 |
| 100 | 9.90 |
| 101 | 9.79 |
| 102 | 9.94 |
| 103 | 9.33 |
| 104 | 9.63 |
| 105 | 9.43 |
| 106 | 9.05 |
| 107 | 9.27 |
| 108 | 9.18 |
| 109 | 9.16 |
| 110 | 9.67 |
| 111 | 9.98 |
| 112 | 9.86 |
| 113 | 9.70 |
| 114 | 8.65 |
| 115 | 8.42 |
| 116 | 8.51 |
| 117 | 8.96 |
| 118 | 9.30 |
| 119 | 8.92 |
| 120 | 8.92 |
| 121 | 8.75 |
| 122 | 8.86 |
| 123 | 8.74 |
| 124 | 8.66 |
| 125 | 8.93 |
| 126 | 9.33 |
| 128 | 9.68 |
| 129 | 9.41 |
| 130 | 9.90 |
| 131 | 9.31 |
| 132 | 9.53 |
| 133 | 9.20 |
| 134 | 9.46 |
| 135 | 8.70 |
| 136 | 8.43 |
| 137 | 8.65 |
| 138 | 8.22 |
| 139 | 9.69 |
| 140 | 9.83 |
| 141 | 9.03 |
| 142 | 9.21 |
| 143 | 8.82 |
| 144 | 9.94 |
| 145 | 10.00 |
| 146 | 9.64 |
| 147 | 9.62 |
| 148 | 9.39 |
| 149 | 9.53 |
| 150 | 9.41 |
| 151 | 9.53 |
| 152 | 7.84 |
| 153 | 8.21 |
| 154 | 7.77 |
| 155 | 8.02 |
| 156 | 8.18 |
| 157 | 7.81 |
| 158 | 7.62 |
| 159 | 8.22 |
| 160 | 7.63 |
| 161 | 8.28 |
| 162 | 7.96 |
| 164 | 8.11 |
| 165 | 8.23 |
| 166 | 7.99 |
| 167 | 8.28 |
| 168 | 8.10 |
| 169 | 8.76 |
| 170 | 7.86 |
| 171 | 9.52 |
| 172 | 9.95 |
| 173 | 9.73 |
| 174 | 9.41 |
| 175 | 9.61 |
| 176 | 9.61 |
| 177 | 9.91 |
| 178 | 9.64 |
| 179 | 9.74 |
| 180 | 8.92 |
| 181 | 9.23 |
| 182 | 9.32 |
| 183 | 8.73 |
| 184 | 8.50 |
| 185 | 8.69 |
| 186 | 9.26 |
| 187 | 9.34 |
| 188 | 9.29 |
| 189 | 9.41 |
| 190 | 9.60 |
| 191 | 8.99 |
| 192 | 9.08 |
| 193 | 8.97 |
| 194 | 9.08 |
| 195 | 8.88 |
| 196 | 9.12 |
| 197 | 9.07 |
| 198 | 9.21 |
| 199 | 9.23 |
| 200 | 9.32 |
| 201 | 9.39 |
| 202 | 9.13 |
| 203 | 9.41 |
| 204 | 9.59 |
| 205 | 9.08 |
| 206 | 9.18 |
| 207 | 9.61 |
| 208 | 8.73 |
| 209 | 9.16 |
| 210 | 9.19 |
| 211 | 8.63 |
| 212 | 8.97 |
| 213 | 9.26 |
| 214 | 8.58 |
| 215 | 8.59 |
| 216 | 8.82 |
| 217 | 8.65 |
| 218 | 8.60 |
| 219 | 8.70 |
| 220 | 8.13 |
| 221 | 8.19 |
| 222 | 8.72 |
| 223 | 8.46 |
| 224 | 8.16 |
| 225 | 8.15 |
| 226 | 8.47 |
| 227 | 7.85 |
| 228 | 9.79 |
| 229 | 9.70 |
| 230 | 9.62 |
| 231 | 9.16 |
| 232 | 9.45 |
| 233 | 9.12 |
| 234 | 9.01 |
| 235 | 9.34 |
| 236 | 8.78 |
| 237 | 9.21 |
| 238 | 9.50 |
| 239 | 8.60 |
| 240 | 9.30 |
| 241 | 8.87 |
| 242 | 9.01 |
| 243 | 8.64 |
| 244 | 8.71 |
| 245 | 8.94 |
| 246 | 8.44 |
| 247 | 8.63 |
| 248 | 8.96 |
| 249 | 8.67 |
| 250 | 8.32 |
| 251 | 9.44 |

| Example | -log IC$_{50}$ (mol/l) |
|---|---|
| 252 | 8.92 |
| 253 | 9.77 |
| 254 | 9.23 |
| 255 | 7.87 |
| 256 | 7.92 |
| 257 | 8.03 |
| 258 | 8.20 |
| 259 | 8.07 |
| 260 | 8.32 |
| 261 | 7.96 |
| 262 | 8.03 |
| 263 | 8.00 |
| 264 | 9.66 |
| 265 | 9.54 |
| 266 | 10.10 |
| 267 | 9.49 |
| 268 | 9.10 |
| 269 | 9.24 |
| 270 | 9.72 |
| 271 | 9.26 |
| 272 | 9.15 |
| 273 | 8.66 |
| 274 | 8.28 |
| 275 | 9.46 |
| 276 | 9.78 |
| 277 | 7.03 |
| 278 | 7.24 |
| 279 | 8.63 |
| 280 | 8.76 |
| 281 | 6.07 |
| 282 | 6.60 |
| 283 | 8.29 |
| 284 | 8.54 |

Animal Pharmacological Testing

Nitric oxide regulates smooth muscle tone by elevation of cGMP via activation of guanylate cyclase and subsequent activation of cyclic GMP-dependent protein kinase. The amplitude and duration of the cGMP signal in smooth muscle is largely regulated by cGMP-specific cyclic nucleotide phosphodiesterase 5 (PDE5). Therefore, inhibition of PDE5 or activation of guanylate cyclase causes altered arterial blood pressure response, which is more pronounced under conditions of acute arterial hypertension, which can be easily induced by continuous intravenous (i.v.) phenylephrine (PE)-infusion. The aim of the study was to evaluate the effects of the selective PDE5 inhibitors described in this invention on phenylephrine-induced acute arterial hypertension and sodium-nitroprusside (SNP) induced blood pressure response in anaesthetised male Sprague Dawley rats.

Method

The test compound (suspended in a 4% w/v aqueous methylcellulose solution either 3 or 10 mg/kg) or placebo (i.e. 4% aqueous methylcellulose solution) is administered orally to conscious Sprague Dawley rats 90 min prior to SNP administration. 40 min later, rats are anaesthetised by intramuscular administration of 80 mg/kg ketamine-HCl+4 mg/kg xylazin-HCl and ventilated with ~1.5% isoflurane in a mixture of ambient air and 40% oxygen. Catheters for i.v. PE- and SNP-administration and recording of mean arterial blood pressure (MAP) are inserted. One hour after compound or placebo administration, a continuous i.v. (V. femoralis) PE-infusion (3 µg/kg/min at an infusion rate of 0.06 ml/min) is started and maintained till the end of the experiment. 30 min after start of the PE-infusion, an i.v.-bolus of the NO-donor sodium nitroprusside (SNP, 30 µg/kg at a volume of 1.0 ml/kg) is administered. To assess the effect of test compounds (PDE5 inhibitory activity) in comparison to placebo, MAP response is analysed. MAP prior to SNP-administration and area under the curve of MAP within 180 s following SNP-administration, corrected for initial MAP (corr. AUC$_{MAP\ 0\text{-}180s}$) is used, to describe altered arterial vascular response and thus in vivo PDE5-inhibitory activity. The efficacy (% change vs. control) achievable in this model is approximately between −13% and −45% effect for the examples 2, 3, 4, 6, 7, 8, 10, 11, 15, 16, 23, 24, 26, 50, 98, 99, 112, 113, 132, 171, 172, 173, 176, 177, 178, 179, 181, 182, 187, 228, 237, 269 and 272.

The invention claimed is:

1. A compound of formula (I)

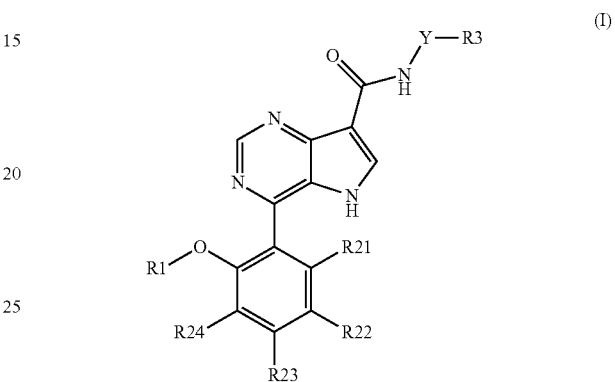

wherein
R1 is —CH$_2$-3-6C-cycloalkyl or 1-4C-alkyl which is optionally substituted by R11,
R11 is 1-4C-alkoxy or hydroxy,
R21 is hydrogen,
R22 is hydrogen, halogen, 1-4C-alkyl, 1-4C-alkoxy, hydroxy, 1-4C-fluoroalkoxy or —C(O)-1-4C-alkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R6 is —NH—C(O)—R7, —C(O)—NR8R9 or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen, R9 is 1-4C-alkyl, which is optionally substituted by R91, or 3-6C-cycloalkyl, which is optionally substituted by R92, R91 is 1-4C-alkoxy or hydroxy, R92 is 1-4C-alkoxy or hydroxy, or a salt thereof, a stereoisomer thereof or a salt of a stereoisomer thereof.

2. The compound according to claim 1, wherein

R1 is —CH$_2$-3-4C-cycloalkyl or 2-4C-alkyl which is optionally substituted by R11, R11 is 1-4C-alkoxy or hydroxy, R21 is hydrogen, R22 is hydrogen, halogen, 1-4C-alkyl, 1-4C-alkoxy, hydroxy, 1-4C-fluoroalkoxy or —C(O)-1-4C-alkyl, or R21 and R22 combine to form a group —O—CH$_2$—O—, R23 is hydrogen, halogen, 1-4C-alkyl, 1-4C-alkoxy, hydroxy or 1-4C-fluoroalkoxy, R24 is hydrogen, Y is —(CH$_2$)$_n$—, n is 0 or 1, R3 is a 4- to 6-membered saturated heterocyclic ring containing one nitrogen atom and optionally one oxygen atom, said heterocyclic ring being optionally substituted by R4, R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43, R41 is 1-4C-alkoxy or hydroxy, R42 is 1-4C-alkoxy or hydroxy, R43 is 1-4C-alkoxy or hydroxy, or a salt thereof, a stereoisomer thereof or a salt of a stereoisomer thereof.

3. The compound according to claim 1, wherein

R1 is —CH$_2$-3-4C-cycloalkyl or 2-4C-alkyl which is optionally substituted by R11, R11 is 1-4C-alkoxy or hydroxy, R21 is hydrogen, R22 is hydrogen, halogen, 1-4C-alkyl, 1-4C-alkoxy, hydroxy, 1-4C-fluoroalkoxy or —C(O)-1-4C-alkyl, or R21 and R22 combine to form a group —O—CH$_2$—O—, R23 is hydrogen, halogen, 1-4C-alkyl, 1-4C-alkoxy, hydroxy or 1-4C-fluoroalkoxy, R24 is hydrogen, Y is —(CH$_2$)$_n$—, n is 0 or 1, R3 is a cyclohexyl group substituted by R6, R6 is —NH—C(O)—R7, —C(O)—NR8R9 or NH$_2$, R7 is hydrogen, 1-4C-alkyl, which is optionally substituted by R71, 3-6C-cycloalkyl, which is optionally substituted by R72, or 1-4C-alkoxy, which is optionally substituted by R73, R71 is 1-4C-alkoxy or hydroxy, R72 is 1-4C-alkoxy or hydroxy, R73 is 1-4C-alkoxy or hydroxy, R8 is hydrogen, R9 is 1-4C-alkyl, which is optionally substituted by R91, or 3-6C-cycloalkyl, R91 is 1-4C-alkoxy or hydroxy, or a salt thereof, a stereoisomer thereof or a salt of a stereoisomer thereof.

4. The compound according to claim 1, wherein

R1 is —CH$_2$-3-6C-cycloalkyl or 1-4C-alkyl which is optionally substituted by R11, R11 is 1-4C-alkoxy or hydroxy, R21 and R22 combine to form a group —O—CH$_2$—O—, R23 is hydrogen, halogen, 1-4C-alkyl, 1-4C-alkoxy, hydroxy or 1-4C-fluoroalkoxy, R24 is hydrogen, Y is —(CH$_2$)$_n$—, n is 0 or 1, R3 is a 4- to 7-membered saturated heterocyclic ring containing one nitrogen atom and optionally one oxygen atom, said heterocyclic ring being optionally substituted by R4, or a 3-6C-cycloalkyl group substituted by R6, R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43, R41 is 1-4C-alkoxy or hydroxy, R42 is 1-4C-alkoxy or hydroxy, R43 is 1-4C-alkoxy or hydroxy, R6 is —NH—C(O)—R7, —C(O)—NR8R9 or NH$_2$, R7 is hydrogen, 1-4C-alkyl, which is optionally substituted by R71, 3-6C-cycloalkyl, which is optionally substituted by R72, or 1-4C-alkoxy, which is optionally substituted by R73, R71 is 1-4C-alkoxy or hydroxy, R72 is 1-4C-alkoxy or hydroxy, R73 is 1-4C-alkoxy or hydroxy, R8 is hydrogen, R9 is 1-4C-alkyl, which is optionally substituted by R91, or 3-6C-cycloalkyl, R91 is 1-4C-alkoxy or hydroxy, or a salt thereof, a stereoisomer thereof or a salt of a stereoisomer thereof.

5. The compound according to claim 1 selected from the group consisting of 4-(5-Cyclopropylmethoxy-1,3-benzodioxol-4-yl)-5H-pyrrolo[3,2-d]pyrimidine-7-carboxylic acid (1-propionyl-piperidin-4-yl)-amide 4-({1-[4-(5-Cyclopropylmethoxy-benzo[1,3]dioxol-4-yl)-5H-pyrrolo[3,2-d]pyrimidin-7-yl]-methanoyl}-amino)-piperidine-1-carboxylic acid ethyl ester;

4-(5-Cyclopropylmethoxy-benzo[1,3]dioxol-4-yl)-5H-pyrrolo[3,2-d]pyrimidine-7-carboxylic acid [1-(2-methoxy-acetyl)-piperidin-4-yl]-amide;

trans-4-(5-Cyclopropylmethoxy-benzo[1,3]dioxol-4-yl)-5H-pyrrolo[3,2-d]pyrimidine-7-carboxylic acid (4-acetylamino-cyclohexyl)-amide;

trans-4-(5-Cyclopropylmethoxy-benzo[1,3]dioxol-4-yl)-5H-pyrrolo[3,2-d]pyrimidine-7-carboxylic acid {4-[(1-cyclopropyl-methanoyl)-amino]-cyclohexyl}-amide;

trans-[4-({1-[4-(5-Cyclopropylmethoxy-benzo[1,3]dioxol-4-yl)-5H-pyrrolo[3,2-d]pyrimidin-7-yl]-methanoyl}-amino)-cyclohexyl]-carbamic acid ethyl ester;

cis-4-(5-Cyclopropylmethoxy-benzo[1,3]dioxol-4-yl)-5H-pyrrolo[3,2-d]pyrimidine-7-carboxylic acid (4-acetylamino-cyclohexyl)-amide;

cis-4-(5-Cyclopropylmethoxy-benzo[1,3]dioxol-4-yl)-5H-pyrrolo[3,2-d]pyrimidine-7-carboxylic acid {4-[(1-cyclopropyl-methanoyl)-amino]-cyclohexyl}-amide;

cis-4-(5-Cyclopropylmethoxy-benzo[1,3]dioxol-4-yl)-5H-pyrrolo[3,2-d]pyrimidine-7-carboxylic acid [4-(2-methoxy-ethanoylamino)-cyclohexyl]-amide;

cis-[4-({1-[4-(5-Cyclopropylmethoxy-benzo[1,3]dioxol-4-yl)-5H-pyrrolo[3,2-d]pyrimidin-7-yl]-methanoyl}-amino)-cyclohexyl]-carbamic acid ethyl ester;
4-(5-Cyclopropylmethoxy-benzo[1,3]dioxol-4-yl)-5H-pyrrolo[3,2-d]pyrimidine-7-carboxylic acid (1-acetyl-piperidin-4-yl)-amide;
4-(5-Cyclopropylmethoxy-benzo[1,3]dioxol-4-yl)-5H-pyrrolo[3,2-d]pyrimidine-7-carboxylic acid [1-(1-cyclopropyl-methanoyl)-piperidin-4-yl]-amide;
4-(5-Cyclopropylmethoxy-benzo[1,3]dioxol-4-yl)-5H-pyrrolo[3,2-d]pyrimidine-7-carboxylic acid [(R)-1-(2-methoxy-acetyl)-pyrrolidin-3-yl]-amide;
4-(5-Cyclopropylmethoxy-benzo[1,3]dioxol-4-yl)-5H-pyrrolo[3,2-d]pyrimidine-7-carboxylic acid ((R)-1-formyl-pyrrolidin-3-yl)-amide;
4-(5-Cyclopropylmethoxy-benzo[1,3]dioxol-4-yl)-5H-pyrrolo[3,2-d]pyrimidine-7-carboxylic acid ((R)-1-acetyl-pyrrolidin-3-yl)-amide;
4-(5-Cyclopropylmethoxy-benzo[1,3]dioxol-4-yl)-5H-pyrrolo[3,2-d]pyrimidine-7-carboxylic acid [(R)-1-(1-cyclopropyl-methanoyl)-pyrrolidin-3-yl]-amide;
(R)-3-({1-[4-(5-Cyclopropylmethoxy-benzo[1,3]dioxol-4-yl)-5H-pyrrolo[3,2-d]pyrimidin-7-yl]-methanoyl}-amino)-pyrrolidine-1-carboxylic acid ethyl ester;
4-(5-Cyclopropylmethoxy-benzo[1,3]dioxol-4-yl)-5H-pyrrolo[3,2-d]pyrimidine-7-carboxylic acid ((S)-1-formyl-pyrrolidin-3-yl)-amide;
4-(5-Cyclopropylmethoxy-benzo[1,3]dioxol-4-yl)-5H-pyrrolo[3,2-d]pyrimidine-7-carboxylic acid ((S)-1-acetyl-pyrrolidin-3-yl)-amide;
4-(5-Cyclopropylmethoxy-benzo[1,3]dioxol-4-yl)-5H-pyrrolo[3,2-d]pyrimidine-7-carboxylic acid [(S)-1-(1-cyclopropyl-methanoyl)-pyrrolidin-3-yl]-amide;
4-(5-Cyclopropylmethoxy-benzo[1,3]dioxol-4-yl)-5H-pyrrolo[3,2-d]pyrimidine-7-carboxylic acid [(S)-1-(2-methoxy-ethanoyl)-pyrrolidin-3-yl]-amide;
(S)-3-({1-[4-(5-Cyclopropylmethoxy-benzo[1,3]dioxol-4-yl)-5H-pyrrolo[3,2-d]pyrimidin-7-yl]-methanoyl}-amino)-pyrrolidine-1-carboxylic acid ethyl ester;
4-(5-Cyclopropylmethoxy-benzo[1,3]dioxol-4-yl)-5H-pyrrolo[3,2-d]pyrimidine-7-carboxylic acid (1-formyl-piperidin-4-ylmethyl)-amide;
4-(5-Cyclopropylmethoxy-benzo[1,3]dioxol-4-yl)-5H-pyrrolo[3,2-d]pyrimidine-7-carboxylic acid (1-acetyl-piperidin-4-ylmethyl)-amide;
4-(5-Cyclopropylmethoxy-benzo[1,3]dioxol-4-yl)-5H-pyrrolo[3,2-d]pyrimidine-7-carboxylic acid [1-(1-cyclopropyl-methanoyl)-piperidin-4-ylmethyl]-amide;
4-(5-Cyclopropylmethoxy-benzo[1,3]dioxol-4-yl)-5H-pyrrolo[3,2-d]pyrimidine-7-carboxylic acid [1-(2-methoxy-ethanoyl)-piperidin-4-ylmethyl]-amide;
4-[({1-[4-(5-Cyclopropylmethoxy-benzo[1,3]dioxol-4-yl)-5H-pyrrolo[3,2-d]pyrimidin-7-yl]-methanoyl}-amino)-methyl]-piperidine-1-carboxylic acid ethyl ester;
4-(5-Cyclopropylmethoxy-benzo[1,3]dioxol-4-yl)-5H-pyrrolo[3,2-d]pyrimidine-7-carboxylic acid (1-formyl-piperidin-3-ylmethyl)-amide;
4-(5-Cyclopropylmethoxy-benzo[1,3]dioxol-4-yl)-5H-pyrrolo[3,2-d]pyrimidine-7-carboxylic acid (1-propionyl-piperidin-3-ylmethyl)-amide;
4-(5-Cyclopropylmethoxy-benzo[1,3dioxol-4-yl)-5H-pyrrolo[3,2-d]pyrimidine-7-carboxylic acid [1-(2-methoxy-acetyl)-piperidin-3-ylmethyl]-amide;
3-({[4-(5-Cyclopropylmethoxy-benzo[1,3]dioxol-4-yl)-5H-pyrrolo[3,2-d]pyrimidine-7-carbonyl]-amino}-methyl)-piperidine-1-carboxylic acid ethyl ester;
4-(5-Cyclopropylmethoxy-benzo[1,3]dioxol-4-yl)-5H-pyrrolo[3,2-d]pyrimidine-7-carboxylic acid (1-formyl-pyrrolidin-3-ylmethyl)-amide;
4-(5-Cyclopropylmethoxy-benzo[1,3]dioxol-4-yl)-5H-pyrrolo[3,2-d]pyrimidine-7-carboxylic acid [1-(2-methoxy-acetyl)-pyrrolidin-3-ylmethyl]-amide;
3-({[4-(5-Cyclopropylmethoxy-benzo[1,3]dioxol-4-yl)-5H-pyrrolo[3,2-d]pyrimidine-7-carbonyl]-amino}-methyl)-pyrrolidine-1-carboxylic acid ethyl ester;
4-(5-Cyclopropylmethoxy-benzo[1,3]dioxol-4-yl)-5H-pyrrolo[3,2-d]pyrimidine-7-carboxylic acid (4-formyl-morpholin-2-ylmethyl)-amide;
4-(5-Cyclopropylmethoxy-benzo[1,3]dioxol-4-yl)-5H-pyrrolo[3,2-d]pyrimidine-7-carboxylic acid (4-propionyl-morpholin-2-ylmethyl)-amide;
4-(5-Cyclopropylmethoxy-benzo[1,3]dioxol-4-yl)-5H-pyrrolo[3,2-d]pyrimidine-7-carboxylic acid [4-(2-methoxy-acetyl)-morpholin-2-ylmethyl]-amide;
2-({[4-(5-Cyclopropylmethoxy-benzo[1,3]dioxol-4-yl)-5H-pyrrolo[3,2-d]pyrimidine-7-carbonyl]-amino}-methyl)-morpholine-4-carboxylic acid ethyl ester;
4-(5-Cyclopropylmethoxy-benzo[1,3]dioxol-4-yl)-5H-pyrrolo[3,2-d]pyrimidine-7-carboxylic acid (1-acetyl-azetidin-3-yl)-amide;
4-(5-Cyclopropylmethoxy-benzo[1,3]dioxol-4-yl)-5H-pyrrolo[3,2-d]pyrimidine-7-carboxylic acid (1-propionyl-azetidin-3-yl)-amide;
4-(5-Cyclopropylmethoxy-benzo[1,3]dioxol-4-yl)-5H-pyrrolo[3,2-d]pyrimidine-7-carboxylic acid [1-(2-methoxy-ethanoyl)-azetidin-3-yl]-amide;
3-({1-[4-(5-Cyclopropyl methoxy-benzo[1,3]dioxol-4-yl)-5H-pyrrolo[3,2-d]pyrimidin-7-yl]-methanoyl}-amino)-azetidine-1-carboxylic acid ethyl ester;
4-(5-Cyclopropylmethoxy-benzo[1,3]dioxol-4-yl)-5H-pyrrolo[3,2-d]pyrimidine-7-carboxylic acid (1-formyl-piperidin-4-yl)-amide;
4-(5-Cyclopropylmethoxy-benzo[1,3]dioxol-4-yl)-5H-pyrrolo[3,2-d]pyrimidine-7-carboxylic acid ((S)-1-propionyl-piperidin-3-yl)-amide;
4-(5-Cyclopropylmethoxy-benzo[1,3]dioxol-4-yl)-5H-pyrrolo[3,2-d]pyrimidine-7-carboxylic acid [(S)-1-(2-methoxy-ethanoyl)-piperidin-3-yl]-amide;
4-(5-Cyclopropylmethoxy-benzo[1,3]dioxol-4-yl)-5H-pyrrolo[3,2-d]pyrimidine-7-carboxylic acid ((S)-1-acetyl-piperidin-3-yl)-amide;
4-(5-Cyclopropylmethoxy-benzo[1,3]dioxol-4-yl)-5H-pyrrolo[3,2-d]pyrimidine-7-carboxylic acid ((R)-1-propionyl-piperidin-3-yl)-amide;
4-(5-Cyclopropylmethoxy-benzo[1,3]dioxol-4-yl)-5H-pyrrolo[3,2-d]pyrimidine-7-carboxylic acid [(R)-1-(2-methoxy-ethanoyl)-piperidin-3-yl]-amide;
4-(5-Cyclopropylmethoxy-benzo[1,3]dioxol-4-yl)-5H-pyrrolo[3,2-d]pyrimidine-7-carboxylic acid ((R)-1-acetyl-piperidin-3-yl)-amide;
trans-4-(5-Cyclopropylmethoxy-benzo[1,3]dioxol-4-yl)-5H-pyrrolo[3,2-d]pyrimidine-7-carboxylic acid [4-(2-methoxy-acetylamino)-cyclohexyl]-amide;
trans-4-(2-Cyclopropylmethoxy-4-methoxy-phenyl)-5H-pyrrolo[3,2-d]pyrimidine-7-carboxylic acid (4-acetylamino-cyclohexyl)-amide;
trans-4-(2-Cyclopropylmethoxy-4-methoxy-phenyl)-5H-pyrrolo[3,2-d]pyrimidine-7-carboxylic acid [4-(cyclopropanecarbonyl-amino)-cyclohexyl]-amide;
trans-4-(2-Cyclopropylmethoxy-4-methoxy-phenyl)-5H-pyrrolo[3,2-d]pyrimidine-7-carboxylic acid [4-(2-methoxy-acetylamino)-cyclohexyl]-amide;

trans-(4-{[4-(2-Cyclopropylmethoxy-4-methoxy-phenyl)-5H-pyrrolo[3,2-d]pyrimidine-7-carbonyl]-amino}-cyclohexyl)-carbamic acid ethyl ester;

cis-4-(2-Cyclopropylmethoxy-4-methoxy-phenyl)-5H-pyrrolo[3,2-d]pyrimidine-7-carboxylic acid (4-acetylamino-cyclohexyl)-amide;

cis-4-(2-Cyclopropylmethoxy-4-methoxy-phenyl)-5H-pyrrolo[3,2-d]pyrimidine-7-carboxylic acid [4-(cyclopropanecarbonyl-amino)-cyclohexyl]-amide;

cis-4-(2-Cyclopropylmethoxy-4-methoxy-phenyl)-5H-pyrrolo[3,2-d]pyrimidine-7-carboxylic acid [4-(2-methoxy-acetylamino)-cyclohexyl]-amide;

cis-(4-{[4-(2-Cyclopropylmethoxy-4-methoxy-phenyl)-5H-pyrrolo[3,2-d]pyrimidine-7-carbonyl]-amino}-cyclohexyl)-carbamic acid ethyl ester;

4-(2-Cyclopropylmethoxy-4-methoxy-phenyl)-5H-pyrrolo[3,2-d]pyrimidine-7-carboxylic acid (1-acetyl-piperidin-4-yl)-amide;

4-(2-Cyclopropylmethoxy-4-methoxy-phenyl)-5H-pyrrolo[3,2-d]pyrimidine-7-carboxylic acid [1-(1-cyclopropyl-methanoyl)-piperidin-4-yl]-amide;

4-(2-Cyclopropylmethoxy-4-methoxy-phenyl)-5H-pyrrolo[3,2-d]pyrimidine-7-carboxylic acid [1-(2-methoxy-ethanoyl)-piperidin-4-yl]-amide;

4-({1-[4-(2-Cyclopropylmethoxy-4-methoxy-phenyl)-5H-pyrrolo[3,2-d]pyrimidin-7-yl]-methanoyl}-amino)-piperidine-1-carboxylic acid ethyl ester;

trans-4-(2-Cyclopropylmethoxy-5-methoxy-phenyl)-5H-pyrrolo[3,2-d]pyrimidine-7-carboxylic acid (4-acetylamino-cyclohexyl)-amide;

trans-4-(2-Cyclopropylmethoxy-5-methoxy-phenyl)-5H-pyrrolo[3,2-d]pyrimidine-7-carboxylic acid [4-(cyclopropanecarbonyl-amino)-cyclohexyl]-amide;

trans-4-(2-Cyclopropylmethoxy-5-methoxy-phenyl)-5H-pyrrolo[3,2-d]pyrimidine-7-carboxylic acid [4-(2-methoxy-acetylamino)-cyclohexyl]-amide;

trans-(4-{[4-(2-Cyclopropylmethoxy-5-methoxy-phenyl)-5H-pyrrolo[3,2-d]pyrimidine-7-carbonyl]-amino}-cyclohexyl)-carbamic acid ethyl ester;

cis-4-(2-Cyclopropylmethoxy-5-methoxy-phenyl)-5H-pyrrolo[3,2-d]pyrimidine-7-carboxylic acid (4-acetylamino-cyclohexyl)-amide;

cis-4-(2-Cyclopropylmethoxy-5-methoxy-phenyl)-5H-pyrrolo[3,2-d]pyrimidine-7-carboxylic acid [4-(cyclopropanecarbonyl-amino)-cyclohexyl]-amide;

cis-4-(2-Cyclopropylmethoxy-5-methoxy-phenyl)-5H-pyrrolo[3,2-d]pyrimidine-7-carboxylic acid [4-(2-methoxy-acetylamino)-cyclohexyl]-amide;

cis-(4-{[4-(2-Cyclopropylmethoxy-5-methoxy-phenyl)-5H-pyrrolo[3,2-d]pyrimidine-7-carbonyl]-amino}-cyclohexyl)-carbamic acid ethyl ester;

4-(2-Cyclopropylmethoxy-5-methoxy-phenyl)-5H-pyrrolo[3,2-d]pyrimidine-7-carboxylic acid (1-acetyl-piperidin-4-yl)-amide;

4-(2-Cyclopropylmethoxy-5-methoxy-phenyl)-5H-pyrrolo[3,2-d]pyrimidine-7-carboxylic acid (1-cyclopropanecarbonyl-piperidin-4-yl)-amide;

4-(2-Cyclopropylmethoxy-5-methoxy-phenyl)-5H-pyrrolo[3,2-d]pyrimidine-7-carboxylic acid [1-(2-methoxy-acetyl)piperidin-4-yl]-amide;

4-{[4-(2-Cyclopropylmethoxy-5-methoxy-phenyl)-5H-pyrrolo[3,2-d]pyrimidine-7-carbonyl]-amino}-piperidine-1-carboxylic acid ethyl ester;

cis-4-(2-Cyclopropylmethoxy-4-fluoro-phenyl)-5H-pyrrolo[3,2-d]pyrimidine-7-carboxylic acid (4-acetylamino-cyclohexyl)-amide;

cis-4-(2-Cyclopropylmethoxy-4-fluoro-phenyl)-5H-pyrrolo[3,2-d]pyrimidine-7-carboxylic acid [4-(2-methoxy-acetylamino)-cyclohexyl]-amide;

cis-(4-{[4-(2-Cyclopropylmethoxy-4-fluoro-phenyl)-5H-pyrrolo[3,2-d]pyrimidine-7-carbonyl]-amino}-cyclohexyl)-carbamic acid ethyl ester;

trans-4-(2-Cyclopropylmethoxy-4-fluoro-phenyl)-5H-pyrrolo[3,2-d]pyrimidine-7-carboxylic acid (4-acetylamino-cyclohexyl)-amide;

trans-4-(2-Cyclopropylmethoxy-4-fluoro-phenyl)-5H-pyrrolo[3,2-d]pyrimidine-7-carboxylic acid [4-(2-methoxy-acetylamino)-cyclohexyl]-amide;

trans-(4-{[4-(2-Cyclopropylmethoxy-4-fluoro-phenyl)-5H-pyrrolo[3,2-d]pyrimidine-7-carbonyl]-amino}-cyclohexyl)-carbamic acid ethyl ester;

4-(2-Cyclopropylmethoxy-4-fluoro-phenyl)-5H-pyrrolo[3,2-d]pyrimidine-7-carboxylic acid (1-acetyl-piperidin-4-yl)-amideter;

4-(2-Cyclopropylmethoxy-4-fluoro-phenyl)-5H-pyrrolo[3,2-d]pyrimidine-7-carboxylic acid (1-propionyl-piperidin-4-yl)-amide;

4-(2-Cyclopropylmethoxy-4-fluoro-phenyl)-5H-pyrrolo[3,2-d]pyrimidine-7-carboxylic acid [1-(2-methoxyacetyl)piperidin-4-yl]-amide;

4-(2-Cyclopropylmethoxy-5-fluoro-phenyl)-5H-pyrrolo[3,2-d]pyrimidine-7-carboxylic acid (1-acetyl-piperidin-4-yl)-amide;

4-(2-Cyclopropylmethoxy-5-fluoro-phenyl)-5H-pyrrolo[3,2-d]pyrimidine-7-carboxylic acid (1-propionyl-piperidin-4-yl)-amide;

4-(2-Cyclopropylmethoxy-5-fluoro-phenyl)-5H-pyrrolo[3,2-d]pyrimidine-7-carboxylic acid [1-(2-methoxyacetyl)piperidin-4-yl]-amide;

trans-4-(2-Cyclopropylmethoxy-5-fluoro-phenyl)-5H-pyrrolo[3,2-d]pyrimidine-7-carboxylic acid (4-acetylamino-cyclohexyl)-amide;

trans-4-(2-Cyclopropylmethoxy-5-fluoro-phenyl)-5H-pyrrolo[3,2-d]pyrimidine-7-carboxylic acid (4-propionylamino-cyclohexyl)-amide;

trans-4-(2-Cyclopropylmethoxy-5-fluoro-phenyl)-5H-pyrrolo[3,2-d]pyrimidine-7-carboxylic acid [4-(2-methoxy-acetylamino)-cyclohexyl]-amide;

trans-4-(2-Cyclopropylmethoxy-phenyl)-5H-pyrrolo[3,2-d]pyrimidine-7-carboxylic acid (4-acetylamino-cyclohexyl)-amide;

trans-4-(2-Cyclopropylmethoxy-phenyl)-5H-pyrrolo[3,2-d]pyrimidine-7-carboxylic acid [4-(2-methoxy-acetylamino)-cyclohexyl]-amide;

trans-(4-{[4-(2-Cyclopropylmethoxy-phenyl)-5H-pyrrolo[3,2-d]pyrimidine-7-carbonyl]-amino}-cyclohexyl)-carbamic acid ethyl ester;

trans-4-(2-Cyclopropylmethoxy-phenyl)-5H-pyrrolo[3,2-d]pyrimidine-7-carboxylic acid [4-(cyclopropanecarbonyl-amino)-cyclohexyl]-amide;

4-(2-Cyclopropylmethoxy-phenyl)-5H-pyrrolo[3,2-d]pyrimidine-7-carboxylic acid (1-acetyl-piperidin-4-yl)-amide;

4-{[4-(2-Cyclopropylmethoxy-phenyl)-5H-pyrrolo[3,2-d]pyrimidine-7-carbonyl]-amino}-piperidine-1-carboxylic acid ethyl ester;

4-(2-Cyclopropylmethoxy-phenyl)-5H-pyrrolo[3,2-d]pyrimidine-7-carboxylic acid (1-cyclopropanecarbonyl-piperidin-4-yl)-amide;

4-(2-Cyclopropyl methoxy-4-fluoro-5-methoxy-phenyl)-5H-pyrrolo[3,2-d]pyrimidine-7-carboxylic acid (1-propionyl-piperidin-4-yl)-amide;

4-(2-Cyclopropyl methoxy-4-fluoro-5-methoxy-phenyl)-5H-pyrrolo[3,2-d]pyrimidine-7-carboxylic acid [1-(2-methoxy-ethanoyl)-piperidin-4-yl]-amide;

4-(2-Cyclopropyl methoxy-4-fluoro-5-methoxy-phenyl)-5H-pyrrolo[3,2-d]pyrimidine-7-carboxylic acid (1-acetyl-piperidin-4-yl)-amide;

4-(2-Cyclopropyl methoxy-4-fluoro-5-methoxy-phenyl)-5H-pyrrolo[3,2-d]pyrimidine-7-carboxylic acid ((R)-1-acetyl-piperidin-3-yl)-amide;

4-(2-Cyclopropyl methoxy-4-fluoro-5-methoxy-phenyl)-5H-pyrrolo[3,2-d]pyrimidine-7-carboxylic acid ((R)-1-propionyl-piperidin-3-yl)-amide;

4-(2-Cyclopropylmethoxy-4-fluoro-5-methoxy-phenyl)-5H-pyrrolo[3,2-d]pyrimidine-7-carboxylic acid [(R)-1-(2-methoxy-acetyl)piperidin-3-yl]-amide;

4-(2-Cyclopropyl methoxy-4-fluoro-5-methoxy-phenyl)-5H-pyrrolo[3,2-d]pyrimidine-7-carboxylic acid ((R)-1-acetyl-pyrrolidin-3-yl)-amide;

4-(2-Cyclopropyl methoxy-4-fluoro-5-methoxy-phenyl)-5H-pyrrolo[3,2-d]pyrimidine-7-carboxylic acid ((R)-1-propionyl-pyrrolidin-3-yl)-amide;

4-(2-Cyclopropyl methoxy-4-fluoro-5-methoxy-phenyl)-5H-pyrrolo[3,2-d]pyrimidine-7-carboxylic acid [(R)-1-(2-methoxy-acetyl)-pyrrolidin-3-yl]-amide;

trans-4-(2-Cyclopropyl methoxy-5-fluoro-4-methoxy-phenyl)-5H-pyrrolo[3,2-d]pyrimidine-7-carboxylic acid (4-acetylamino-cyclohexyl)-amide;

trans-4-(2-Cyclopropyl methoxy-5-fluoro-4-methoxy-phenyl)-5H-pyrrolo[3,2-d]pyrimidine-7-carboxylic acid [4-(2-methoxy-acetylamino)-cyclohexyl]-amide;

4-(2-Cyclopropyl methoxy-5-fluoro-4-methoxy-phenyl)-5H-pyrrolo[3,2-d]pyrimidine-7-carboxylic acid (1-acetyl-piperidin-4-yl)-amide;

4-(2-Cyclopropyl methoxy-5-fluoro-4-methoxy-phenyl)-5H-pyrrolo[3,2-d]pyrimidine-7-carboxylic acid [1-(2-methoxy-ethanoyl)-piperidin-4-yl]-amide;

4-(2-Cyclopropyl methoxy-5-fluoro-4-methoxy-phenyl)-5H-pyrrolo[3,2-d]pyrimidine-7-carboxylic acid (1-propionyl-piperidin-4-yl)-amide;

4-(2-Cyclopropyl methoxy-5-fluoro-4-methoxy-phenyl)-5H-pyrrolo[3,2-d]pyrimidine-7-carboxylic acid ((R)-1-propionyl-piperidin-3-yl)-amide;

4-(2-Cyclopropyl methoxy-5-fluoro-4-methoxy-phenyl)-5H-pyrrolo[3,2-d]pyrimidine-7-carboxylic acid [(R)-1-(2-methoxy-ethanoyl)-piperidin-3-yl]-amide;

4-(2-Cyclopropyl methoxy-5-fluoro-4-methoxy-phenyl)-5H-pyrrolo[3,2-d]pyrimidine-7-carboxylic acid ((R)-1-acetyl-piperidin-3-yl)-amide;

4-(2-Cyclopropyl methoxy-5-fluoro-4-methoxy-phenyl)-5H-pyrrolo[3,2-d]pyrimidine-7-carboxylic acid ((S)-1-propionyl-piperidin-3-yl)-amide;

4-(2-Cyclopropyl methoxy-5-fluoro-4-methoxy-phenyl)-5H-pyrrolo[3,2-d]pyrimidine-7-carboxylic acid [(S)-1-(2-methoxy-ethanoyl)-piperidin-3-yl]-amide;

4-(2-Cyclopropyl methoxy-5-fluoro-4-methoxy-phenyl)-5H-pyrrolo[3,2-d]pyrimidine-7-carboxylic acid ((S)-1-acetyl-piperidin-3-yl)-amide;

4-(2-Cyclopropyl methoxy-5-fluoro-4-methoxy-phenyl)-5H-pyrrolo[3,2-d]pyrimidine-7-carboxylic acid ((R)-1-acetyl-pyrrolidin-3-yl)-amide;

4-(2-Cyclopropyl methoxy-5-fluoro-4-methoxy-phenyl)-5H-pyrrolo[3,2-d]pyrimidine-7-carboxylic acid ((R)-1-propionyl-pyrrolidin-3-yl)-amide;

4-(2-Cyclopropylmethoxy-5-fluoro-4-methoxy-phenyl)-5H-pyrrolo[3,2-d]pyrimidine-7-carboxylic acid [(R)-1-(2-methoxy-acetyl)-pyrrolidin-3-yl]-amide;

trans-4-(2-Cyclopropylmethoxy-5-methyl-phenyl)-5H-pyrrolo[3,2-d]pyrimidine-7-carboxylic acid (4-acetylamino-cyclohexyl)-amide;

trans-4-(2-Cyclopropylmethoxy-5-methyl-phenyl)-5H-pyrrolo[3,2-d]pyrimidine-7-carboxylic acid [4-(2-methoxy-acetylamino)-cyclohexyl]-amide;

trans-(4-{[4-(2-Cyclopropylmethoxy-5-methyl-phenyl)-5H-pyrrolo[3,2-d]pyrimidine-7-carbonyl]-amino}-cyclohexyl)-carbamic acid ethyl ester;

4-(2-Cyclopropylmethoxy-5-methyl-phenyl)-5H-pyrrolo[3,2-d]pyrimidine-7-carboxylic acid (1-acetyl-piperidin-4-yl)-amide;

4-(2-Cyclopropylmethoxy-5-methyl-phenyl)-5H-pyrrolo[3,2-d]pyrimidine-7-carboxylic acid [1-(2-methoxy-acetyl)piperidin-4-yl]-amide;

4-{[4-(2-Cyclopropylmethoxy-5-methyl-phenyl)-5H-pyrrolo[3,2-d]pyrimidine-7-carbonyl]-amino}-piperidine-1-carboxylic acid ethyl ester;

trans-4-(5-Cyclobutylmethoxy-benzo[1,3]dioxol-4-yl)-5H-pyrrolo[3,2-d]pyrimidine-7-carboxylic acid (4-acetylamino-cyclohexyl)-amide;

trans-4-(5-Cyclobutylmethoxy-benzo[1,3]dioxol-4-yl)-5H-pyrrolo[3,2-d]pyrimidine-7-carboxylic acid [4-(cyclopropanecarbonyl-amino)-cyclohexyl]-amide;

trans-4-(5-Cyclobutylmethoxy-benzo[1,3]dioxol-4-yl)-5H-pyrrolo[3,2-d]pyrimidine-7-carboxylic acid [4-(2-methoxy-ethanoylamino)-cyclohexyl]-amide;

4-(5-Cyclobutylmethoxy-benzo[1,3]dioxol-4-yl)-5H-pyrrolo[3,2-d]pyrimidine-7-carboxylic acid (1-acetyl-piperidin-4-yl)-amide;

4-(5-Cyclobutylmethoxy-benzo[1,3]dioxol-4-yl)-5H-pyrrolo[3,2-d]pyrimidine-7-carboxylic acid [1-(1-cyclopropyl-methanoyl)-piperidin-4-yl]-amide;

4-(5-Cyclobutylmethoxy-benzo[1,3]dioxol-4-yl)-5H-pyrrolo[3,2-d]pyrimidine-7-carboxylic acid [1-(2-methoxy-ethanoyl)-piperidin-4-yl]-amide;

4-({1-[4-(5-Cyclobutylmethoxy-benzo[1,3]dioxol-4-yl)-5H-pyrrolo[3,2-d]pyrimidine-7-yl]-methanoyl}-amino)-piperidine-1-carboxylic acid ethyl ester;

4-(5-Ethoxy-benzo[1,3]dioxol-4-yl)-5H-pyrrolo[3,2-d]pyrimidine-7-carboxylic acid (1-propionyl-piperidin-4-yl)-amide;

4-{[4-(5-Ethoxy-benzo[1,3]dioxol-4-yl)-5H-pyrrolo[3,2-d]pyrimidine-7-carbonyl]-amino}-piperidine-1-carboxylic acid ethyl ester;

4-(5-Ethoxy-benzo[1,3]dioxol-4-yl)-5H-pyrrolo[3,2-d]pyrimidine-7-carboxylic acid [1-(2-methoxy-acetyl)-piperidin-4-yl]-amide;

4-(5-Ethoxy-benzo[1,3]dioxol-4-yl)-5H-pyrrolo[3,2-d]pyrimidine-7-carboxylic acid ((R)-1-propionyl-pyrrolidin-3-yl)-amide;

(R)-3-{[4-(5-Ethoxy-benzo[1,3]dioxol-4-yl)-5H-pyrrolo[3,2-d]pyrimidine-7-carbonyl]-amino}-pyrrolidine-1-carboxylic acid ethyl ester;

4-(5-Ethoxy-benzo[1,3]dioxol-4-yl)-5H-pyrrolo[3,2-d]pyrimidine-7-carboxylic acid [(R)-1-(2-methoxy-acetyl)-pyrrolidin-amide;

4-(5-Propoxy-benzo[1,3]dioxol-4-yl)-5H-pyrrolo[3,2-d]pyrimidine-7-carboxylic acid (1-propionyl-piperidin-4-yl)-amide;

4-{[4-(5-Propoxy-benzo[1,3]dioxol-4-yl)-5H-pyrrolo[3,2-d]pyrimidine-7-carbonyl]-amino}-piperidine-1-carboxylic acid ethyl ester;

4-(5-Propoxy-benzo[1,3]dioxol-4-yl)-5H-pyrrolo[3,2-d]pyrimidine-7-carboxylic acid ((R)-1-propionyl-pyrrolidin-3-yl)-amide;

(R)-3-{[4-(5-Propoxy-benzo[1,3]dioxol-4-yl)-5H-pyrrolo[3,2-d]pyrimidine-7-carbonyl]-amino}-pyrrolidine-1-carboxylic acid ethyl ester;
4-(5-Propoxy-benzo[1,3]dioxol-4-yl)-5H-pyrrolo[3,2-d]pyrimidine-7-carboxylic acid [(R)-1-(2-methoxy-acetyl)-pyrrolidin-3-yl]-amide;
4-(5-Butoxy-benzo[1,3]dioxol-4-yl)-5H-pyrrolo[3,2-d]pyrimidine-7-carboxylic acid (1-propionyl-piperidin-4-yl)-amide;
4-{[4-(5-Butoxy-benzo[1,3]dioxol-4-yl)-5H-pyrrolo[3,2-d]pyrimidine-7-carbonyl]-amino}-piperidine-1-carboxylic acid ethyl ester;
4-(5-Butoxy-benzo[1,3]dioxol-4-yl)-5H-pyrrolo[3,2-d]pyrimidine-7-carboxylic acid (1-formyl-piperidin-4-yl)-amide;
4-(5-Butoxy-benzo[1,3]dioxol-4-yl)-5H-pyrrolo[3,2-d]pyrimidine-7-carboxylic acid (1-propionyl-piperidin-3-yl)-amide;
3-{[4-(5-Butoxy-benzo[1,3]dioxol-4-yl)-5H-pyrrolo[3,2-d]pyrimidine-7-carbonyl]-amino}-piperidine-1-carboxylic acid ethyl ester;
4-(5-Butoxy-benzo[1,3]dioxol-4-yl)-5H-pyrrolo[3,2-d]pyrimidine-7-carboxylic acid [1-(2-methoxy-acetyl)-piperidin-3-yl]-amide;
4-(5-Butoxy-benzo[1,3]dioxol-4-yl)-5H-pyrrolo[3,2-d]pyrimidine-7-carboxylic acid ((R)-1-propionyl-pyrrolidin-3-yl)-amide;
(R)-3-{[4-(5-Butoxy-benzo[1,3]dioxol-4-yl)-5H-pyrrolo[3,2-d]pyrimidine-7-carbonyl]-amino}-pyrrolidine-1-carboxylic acid ethyl ester;
cis-4-[4-Methoxy-2-(2-methoxy-ethoxy)-phenyl]-5H-pyrrolo[3,2-d]pyrimidine-7-carboxylic acid (4-acetylamino-cyclohexyl)-amide;
cis-4-[4-Methoxy-2-(2-methoxy-ethoxy)-phenyl]-5H-pyrrolo[3,2-d]pyrimidine-7-carboxylic acid [4-(cyclopropanecarbonyl-amino)-cyclohexyl]-amide;
cis-4-[4-Methoxy-2-(2-methoxy-ethoxy)-phenyl]-5H-pyrrolo[3,2-d]pyrimidine-7-carboxylic acid [4-(2-methoxy-acetylamino)-cyclohexyl]-amide;
trans-4-[4-Methoxy-2-(2-methoxy-ethoxy)-phenyl]-5H-pyrrolo[3,2-d]pyrimidine-7-carboxylic acid (4-acetylamino-cyclohexyl)-amide;
trans-4-[4-Methoxy-2-(2-methoxy-ethoxy)-phenyl]-5H-pyrrolo[3,2-d]pyrimidine-7-carboxylic acid [4-(cyclopropanecarbonyl-amino)-cyclohexyl]-amide;
trans-4-[4-Methoxy-2-(2-methoxy-ethoxy)-phenyl]-5H-pyrrolo[3,2-d]pyrimidine-7-carboxylic acid [4-(2-methoxy-acetylamino)-cyclohexyl]-amide;
4-[4-Methoxy-2-(2-methoxy-ethoxy)-phenyl]-5H-pyrrolo[3,2-d]pyrimidine-7-carboxylic acid (1-acetyl-piperidin-4-yl)-amide;
4-[4-Methoxy-2-(2-methoxy-ethoxy)-phenyl]-5H-pyrrolo[3,2-d]pyrimidine-7-carboxylic acid (1-cyclopropanecarbonyl-piperidin-4-yl)-amide;
4-[4-Methoxy-2-(2-methoxy-ethoxy)-phenyl]-5H-pyrrolo[3,2-d]pyrimidine-7-carboxylic acid [1-(2-methoxy-acetyl)piperidin-4-yl]-amide;
trans-4-[5-(2-Methoxy-ethoxy)-benzo[1,3]dioxol-4-yl]-5H-pyrrolo[3,2-d]pyrimidine-7-carboxylic acid (4-acetylamino-cyclohexyl)-amide;
trans-4-[5-(2-Methoxy-ethoxy)-benzo[1,3]dioxol-4-yl]-5H-pyrrolo[3,2-d]pyrimidine-7-carboxylic acid (4-(cyclopropanecarbonyl-amino)-cyclohexyl]-amide
trans-4-[5-(2-Methoxy-ethoxy)-benzo[1,3]dioxol-4-yl]-5H-pyrrolo[3,2-d]pyrimidine-7-carboxylic acid [4-(2-methoxy-acetylamino)-cyclohexyl]-amide;
cis-4-[5-(2-Methoxy-ethoxy)-benzo[1,3]dioxol-4-yl]-5H-pyrrolo[3,2-d]pyrimidine-7-carboxylic acid (4-acetylamino-cyclohexyl)-amide;
cis-4-[5-(2-Methoxy-ethoxy)-benzo[1,3]-dioxol-4-yl]-5H-pyrrolo[3,2-d]pyrimidine-7-carboxylic acid [4-(cyclopropanecarbonyl-amino)-cyclohexyl]-amide; cis-4-[5-(2-Methoxy-ethoxy)-benzo[1,3]dioxol-4-yl]-5H-pyrrolo[3,2-d]pyrimidine-7-carboxylic acid [4-(2-methoxy-acetylamino)-cyclohexyl]-amide;
cis-[4-({4-[5-(2-Methoxy-ethoxy)-benzo[1,3]dioxol-4-yl]-5H-pyrrolo[3,2-d]pyrimidine-7-carbonyl}-amino)-cyclohexyl]-carbamic acid ethyl ester;
4-[5-(2-Methoxy-ethoxy)-benzo[1,3]dioxol-4-yl]-5H-pyrrolo[3,2-d]pyrimidine-7-carboxylic acid (1-acetyl-piperidin-4-yl)-amide;
4-[5-(2-Methoxy-ethoxy)-benzo[1,3]dioxol-4-yl]-5H-pyrrolo[3,2-d]pyrimidine-7-carboxylic acid (1-cyclopropanecarbonyl-piperidin-4-yl)-amide;
4-[5-(2-Methoxy-ethoxy)-benzo[1,3]dioxol-4-yl]-5H-pyrrolo[3,2-d]pyrimidine-7-carboxylic acid [1-(2-methoxy-acetyl)piperidin-4-yl]-amide;
4-(5-Cyclopropylmethoxy-benzo[1,3]dioxol-4-yl)-5H-pyrrolo[3,2-d]pyrimidine-7-carboxylic acid [1-(2-hydroxy-ethanoyl)-piperidin-4-yl]-amide;
trans-[4-({1-[4-(5-Cyclopropylmethoxy-benzo[1,3]dioxol-4-yl)-5H-pyrrolo[3,2-d]pyrimidine-7-carboxylic acid [4-(2-hydroxy-ethanoylamino)-cyclohexyl]-amide;
trans-[4-({1-[4-(5-Cyclopropylmethoxy-benzo[1,3]dioxol-4-yl)-5H-pyrrolo[3,2-d]pyrimidine-7-carboxylic acid [4-((S)-2-hydroxy-propanoylamino)-cyclohexyl]-amide;
cis-[4-({1-[4-(5-Cyclopropylmethoxy-benzo[1,3]dioxol-4-yl)-5H-pyrrolo[3,2-d]pyrimidine-7-carboxylic acid [4-(2-hydroxy-ethanoylamino)-cyclohexyl]-amide;
cis-[4-({1-[4-(5-Cyclopropylmethoxy-benzo[1,3]dioxol-4-yl)-5H-pyrrolo[3,2-d]pyrimidine-7-carboxylic acid [4-((S)-2-hydroxy-propanoylamino)-cyclohexyl]-amide;
4-(5-Cyclopropylmethoxy-benzo[1,3]dioxol-4-yl)-5H-pyrrolo[3,2-d]pyrimidine-7-carboxylic acid [1-((S)-2-hydroxy-propanoyl)-piperidin-4-yl]-amide;
trans-4-(5-Cyclopropylmethoxy-benzo[1,3]dioxol-4-yl)-5H-pyrrolo[3,2-d]pyrimidine-7-carboxylic acid {4-[(1-hydroxy-cyclopropanecarbonyl)-amino]-cyclohexyl}-amide;
cis-4-(5-Cyclopropylmethoxy-benzo[1,3]dioxol-4-yl)-5H-pyrrolo[3,2-d]pyrimidine-7-carboxylic acid {4-[(1-hydroxy-cyclopropanecarbonyl)-amino]-cyclohexyl}-amide;
4-(5-Cyclopropylmethoxy-benzo[1,3]dioxol-4-yl)-5H-pyrrolo[3,2-d]pyrimidine-7-carboxylic acid {1-[1-(1-hydroxy-cyclopropyl)-methanoyl]-piperidin-4-yl}-amide;
4-(5-Cyclopropylmethoxy-benzo[1,3]dioxol-4-yl)-5H-pyrrolo[3,2-d]pyrimidine-7-carboxylic acid [(R)-1-(2-hydroxy-ethanoyl)-pyrrolidin-3-yl]-amide;
4-(5-Cyclopropylmethoxy-benzo[1,3]dioxol-4-yl)-5H-pyrrolo[3,2-d]pyrimidine-7-carboxylic acid [(R)-1-((S)-2-hydroxy-propanoyl)-pyrrolidin-3-yl]-amide;
4-(5-Cyclopropylmethoxy-benzo[1,3]dioxol-4-yl)-5H-pyrrolo[3,2-d]pyrimidine-7-carboxylic acid {(R)-1-[1-(1-hydroxy-cyclopropyl)-methanoyl]-pyrrolidin-3-yl}-amide;
4-(5-Cyclopropylmethoxy-benzo[1,3]dioxol-4-yl)-5H-pyrrolo[3,2-d]pyrimidine-7-carboxylic acid [(S)-1-(2-hydroxy-ethanoyl)-pyrrolidin-3-yl]-amide;

4-(5-Cyclopropylmethoxy-benzo[1,3]dioxol-4-yl)-5H-pyrrolo[3,2-d]pyrimidine-7-carboxylic acid [(S)-1-((S)-2-hydroxy-propanoyl)-pyrrolidin-3-yl]-amide;

4-(5-Cyclopropylmethoxy-benzo[1,3]dioxol-4-yl)-5H-pyrrolo[3,2-d]pyrimidine-7-carboxylic acid {(S)-1-[1-(1-hydroxy-cyclopropyl)-methanoyl]-pyrrolidin-3-yl}-amide;

4-(5-Cyclopropylmethoxy-benzo[1,3]dioxol-4-yl)-5H-pyrrolo[3,2-d]pyrimidine-7-carboxylic acid [1-(2-hydroxy-ethanoyl)-piperidin-4-ylmethyl]-amide;

4-(5-Cyclopropylmethoxy-benzo[1,3]dioxol-4-yl)-5H-pyrrolo[3,2-d]pyrimidine-7-carboxylic acid [1-((S)-2-hydroxy-propanoyl)-piperidin-4-ylmethyl]-amide;

4-(5-Cyclopropylmethoxy-benzo[1,3]dioxol-4-yl)-5H-pyrrolo[3,2-d]pyrimidine-7-carboxylic acid {1-[1-(1-hydroxy-cyclopropyl)-methanoyl]-piperidin-4-ylmethyl}-amide;

4-(5-Cyclopropylmethoxy-benzo[1,3]dioxol-4-yl)-5H-pyrrolo[3,2-d]pyrimidine-7-carboxylic acid [1-(2-hydroxy-acetyl)-piperidin-3-ylmethyl]-amide;

4-(5-Cyclopropylmethoxy-benzo[1,3]dioxol-4-yl)-5H-pyrrolo[3,2-d]pyrimidine-7-carboxylic acid [1-((S)-2-hydroxy-propionyl)-piperidin-3-ylmethyl]-amide;

4-(5-Cyclopropylmethoxy-benzo[1,3]dioxol-4-yl)-5H-pyrrolo[3,2-d]pyrimidine-7-carboxylic acid [1-(2-hydroxy-acetyl)-pyrrolidin-3-ylmethyl]-amide;

4-(5-Cyclopropylmethoxy-benzo[1,3]dioxol-4-yl)-5H-pyrrolo[3,2-d]pyrimidine-7-carboxylic acid [1-((S)-2-hydroxy-propionyl)-pyrrolidin-3-ylmethyl]-amide;

4-(5-Cyclopropylmethoxy-benzo[1,3]dioxol-4-yl)-5H-pyrrolo[3,2-d]pyrimidine-7-carboxylic acid [4-(2-hydroxy-acetyl)-morpholin-2-ylmethyl]-amide;

4-(5-Cyclopropylmethoxy-benzo[1,3]dioxol-4-yl)-5H-pyrrolo[3,2-d]pyrimidine-7-carboxylic acid [4-((S)-2-hydroxy-propionyl)-morpholin-2-ylmethyl]-amide;

4-(5-Cyclopropylmethoxy-benzo[1,3]dioxol-4-yl)-5H-pyrrolo[3,2-d]pyrimidine-7-carboxylic acid [1-(2-hydroxy-ethanoyl)-azetidin-3-yl]-amide;

4-(5-Cyclopropylmethoxy-benzo[1,3]dioxol-4-yl)-5H-pyrrolo[3,2-d]pyrimidine-7-carboxylic acid [1-((S)-2-hydroxy-propanoyl]-azetidin-3-yl]-amide;

4-(5-Cyclopropylmethoxy-benzo[1,3]dioxol-4-yl)-5H-pyrrolo[3,2-d]pyrimidine-7-carboxylic acid [(S)-1-((S)-2-hydroxy-propanoyl)piperidin-3-yl]-amide;

4-(5-Cyclopropylmethoxy-benzo[1,3]dioxol-4-yl)-5H-pyrrolo[3,2-d]pyrimidine-7-carboxylic acid [(R)-1-((S)-2-hydroxy-propanoyl)piperidin-3-yl]-amide;

trans-4-(2-Cyclopropylmethoxy-4-methoxy-phenyl)-5H-pyrrolo[3,2-d]pyrimidine-7-carboxylic acid [4-(2-hydroxy-acetylamino)-cyclohexyl]-amide;

trans-4-(2-Cyclopropylmethoxy-4-methoxy-phenyl)-5H-pyrrolo[3,2-d]pyrimidine-7-carboxylic acid [4-((S)-2-hydroxy-propionylamino)-cyclohexyl]-amide;

trans-4-(2-Cyclopropylmethoxy-4-methoxy-phenyl)-5H-pyrrolo[3,2-d]pyrimidine-7-carboxylic acid {4-[(1-hydroxy-cyclopropanecarbonyl)-amino]-cyclohexyl}-amide;

cis-4-(2-Cyclopropylmethoxy-4-methoxy-phenyl)-5H-pyrrolo[3,2-d]pyrimidine-7-carboxylic acid [4-(2-hydroxy-acetylamino)-cyclohexyl]-amide;

cis-4-(2-Cyclopropylmethoxy-4-methoxy-phenyl)-5H-pyrrolo[3,2-d]pyrimidine-7-carboxylic acid [4-((S)-2-hydroxy-propionylamino)-cyclohexyl]-amide;

cis-4-(2-Cyclopropylmethoxy-4-methoxy-phenyl)-5H-pyrrolo[3,2-d]pyrimidine-7-carboxylic acid {4-[(1-hydroxy-cyclopropanecarbonyl)-amino]-cyclohexyl}-amide;

4-(2-Cyclopropylmethoxy-4-methoxy-phenyl)-5H-pyrrolo[3,2-d]pyrimidine-7-carboxylic acid [1-(2-hydroxy-ethanoyl)-piperidin-4-yl]-amide;

4-(2-Cyclopropylmethoxy-4-methoxy-phenyl)-5H-pyrrolo[3,2-d]pyrimidine-7-carboxylic acid [1-((S)-2-hydroxy-propanoyl)piperidin-4-yl]-amide;

4-(2-Cyclopropylmethoxy-4-methoxy-phenyl)-5H-pyrrolo[3,2-d]pyrimidine-7-carboxylic acid {1-[1-(1-hydroxy-cyclopropyl)-methanoyl]-piperidin-4-yl}-amide;

cis-4-(2-Cyclopropylmethoxy-5-methoxy-phenyl)-5H-pyrrolo[3,2-d]pyrimidine-7-carboxylic acid [4-(2-hydroxy-acetylamino)-cyclohexyl]-amide;

cis-4-(2-Cyclopropylmethoxy-5-methoxy-phenyl)-5H-pyrrolo[3,2-d]pyrimidine-7-carboxylic acid {4-[(1-hydroxy-cyclopropanecarbonyl)-amino]-cyclohexyl}-amide;

trans-4-(2-Cyclopropylmethoxy-5-methoxy-phenyl)-5H-pyrrolo[3,2-d]pyrimidine-7-carboxylic acid {4-[(1-hydroxy-cyclopropanecarbonyl)-amino]-cyclohexyl}-amide;

4-(2-Cyclopropylmethoxy-5-methoxy-phenyl)-5H-pyrrolo[3,2-d]pyrimidine-7-carboxylic acid [1-(2-hydroxy-acetyl)piperidin-4-yl]-amide;

4-(2-Cyclopropylmethoxy-5-methoxy-phenyl)-5H-pyrrolo[3,2-d]pyrimidine-7-carboxylic acid [1-((S)-2-hydroxy-propionyl)piperidin-4-yl]-amide;

4-(2-Cyclopropylmethoxy-5-methoxy-phenyl)-5H-pyrrolo[3,2-d]pyrimidine-7-carboxylic acid [1-(1-hydroxy-cyclopropanecarbonyl)-piperidin-4-yl]-amide;

cis-4-(2-Cyclopropylmethoxy-4-fluoro-phenyl)-5H-pyrrolo[3,2-d]pyrimidine-7-carboxylic acid [4-(2-hydroxy-acetylamino)-cyclohexyl]-amide;

cis-4-(2-Cyclopropylmethoxy-4-fluoro-phenyl)-5H-pyrrolo[3,2-d]pyrimidine-7-carboxylic acid [4-((S)-2-hydroxy-propionylamino)-cyclohexyl]-amide;

cis-4-(2-Cyclopropylmethoxy-4-fluoro-phenyl)-5H-pyrrolo[3,2-d]pyrimidine-7-carboxylic acid {4-[(1-hydroxy-cyclopropanecarbonyl)-amino]-cyclohexyl}-amide;

trans-4-(2-Cyclopropylmethoxy-4-fluoro-phenyl)-5H-pyrrolo[3,2-d]pyrimidine-7-carboxylic acid [4-(2-hydroxy-acetylamino)-cyclohexyl]-amide;

trans-4-(2-Cyclopropylmethoxy-4-fluoro-phenyl)-5H-pyrrolo[3,2-d]pyrimidine-7-carboxylic acid [4-((S)-2-hydroxy-propionylamino)-cyclohexyl]-amide;

trans-4-(2-Cyclopropylmethoxy-4-fluoro-phenyl)-5H-pyrrolo[3,2-d]pyrimidine-7-carboxylic acid {4-[(1-hydroxy-cyclopropanecarbonyl)-amino]-cyclohexyl}-amide;

4-(2-Cyclopropylmethoxy-5-fluoro-phenyl)-5H-pyrrolo[3,2-d]pyrimidine-7-carboxylic acid [1-(2-hydroxy-acetyl)piperidin-4-yl]-amide;

4-(2-Cyclopropylmethoxy-5-fluoro-phenyl)-5H-pyrrolo[3,2-d]pyrimidine-7-carboxylic acid [1-((S)-2-hydroxy-propionyl)-piperidin-4-yl]-amide;

trans-4-(2-Cyclopropylmethoxy-5-fluoro-phenyl)-5H-pyrrolo[3,2-d]pyrimidine-7-carboxylic acid [4-(2-hydroxy-acetylamino)-cyclohexyl]-amide;

trans-4-(2-Cyclopropylmethoxy-5-fluoro-phenyl)-5H-pyrrolo[3,2-d]pyrimidine-7-carboxylic acid [4-((S)-2-hydroxy-propionylamino)-cyclohexyl]-amide;

trans-4-(2-Cyclopropylmethoxy-phenyl)-5H-pyrrolo[3,2-d]pyrimidine-7-carboxylic acid [4-(2-hydroxy-acetylamino)-cyclohexyl]-amide;

trans-4-(2-Cyclopropylmethoxy-phenyl)-5H-pyrrolo[3,2-d]pyrimidine-7-carboxylic acid [4-((S)-2-hydroxy-propionylamino)-cyclohexyl]-amide;

trans-4-(2-Cyclopropylmethoxy-phenyl)-5H-pyrrolo[3,2-d]pyrimidine-7-carboxylic acid {4-[(1-hydroxy-cyclopropanecarbonyl)-amino]-cyclohexyl}-amide;

4-(2-Cyclopropylmethoxy-phenyl)-5H-pyrrolo[3,2-d]pyrimidine-7-carboxylic acid [1-((S)-2-hydroxy-propionyl)-piperidin-4-yl]-amide;

4-(2-Cyclopropylmethoxy-4-fluoro-5-methoxy-phenyl)-5H-pyrrolo[3,2-d]pyrimidine-7-carboxylic acid [1-((S)-2-hydroxy-propionyl)-piperidin-4-yl]-amide;

4-(2-Cyclopropylmethoxy-4-fluoro-5-methoxy-phenyl)-5H-pyrrolo[3,2-d]pyrimidine-7-carboxylic acid [(R)-1-(2-hydroxy-acetyl)piperidin-3-yl]-amide;

4-(2-Cyclopropylmethoxy-4-fluoro-5-methoxy-phenyl)-5H-pyrrolo[3,2-d]pyrimidine-7-carboxylic acid [(R)-1-((S)-2-hydroxy-propionyl)-piperidin-3-yl]-amide;

4-(2-Cyclopropylmethoxy-4-fluoro-5-methoxy-phenyl)-5H-pyrrolo[3,2-d]pyrimidine-7-carboxylic acid [(R)-1-(2-hydroxy-acetyl)-pyrrolidin-3-yl]-amide;

4-(2-Cyclopropylmethoxy-4-fluoro-5-methoxy-phenyl)-5H-pyrrolo[3,2-d]pyrimidine-7-carboxylic acid [(R)-1-((S)-2-hydroxy-propionyl)-pyrrolidin-3-yl]-amide;

trans-4-(2-Cyclopropylmethoxy-5-fluoro-4-methoxy-phenyl)-5H-pyrrolo[3,2-d]pyrimidine-7-carboxylic acid [4-(2-hydroxy-acetylamino)-cyclohexyl]-amide;

trans-4-(2-Cyclopropylmethoxy-5-fluoro-4-methoxy-phenyl)-5H-pyrrolo[3,2-d]pyrimidine-7-carboxylic acid [4-((S)-2-hydroxy-propionylamino)-cyclohexyl]-amide;

trans-4-(2-Cyclopropylmethoxy-5-fluoro-4-methoxy-phenyl)-5H-pyrrolo[3,2-d]pyrimidine-7-carboxylic acid {4-[(1-hydroxy-cyclopropanecarbonyl)-amino]-cyclohexyl}-amide;

4-(2-Cyclopropylmethoxy-5-fluoro-4-methoxy-phenyl)-5H-pyrrolo[3,2-d]pyrimidine-7-carboxylic acid [1-(2-hydroxy-ethanoyl)-piperidin-4-yl]-amide;

4-(2-Cyclopropylmethoxy-5-fluoro-4-methoxy-phenyl)-5H-pyrrolo[3,2-d]pyrimidine-7-carboxylic acid [1-((S)-2-hydroxy-propanoyl)-piperidin-4-yl]-amide;

4-(2-Cyclopropylmethoxy-5-fluoro-4-methoxy-phenyl)-5H-pyrrolo[3,2-d]pyrimidine-7-carboxylic acid {1-[1-(1-hydroxy-cyclopropyl)-methanoyl]-piperidin-4-yl}-amide;

4-(2-cyclopropylmethoxy-5-fluoro-4-methoxy-phenyl)-5H-pyrrolo[3,2-d]pyrimidine-7-carboxylic acid [(S)-1-((S)-2-hydroxy-propanoyl)-piperidin-3-yl]-amide;

4-(2-Cyclopropylmethoxy-5-fluoro-4-methoxy-phenyl)-5H-pyrrolo[3,2-d]pyrimidine-7-carboxylic acid [(R)-1-((S)-2-hydroxy-propanoyl)-piperidin-3-yl]-amide;

4-(2-Cyclopropylmethoxy-5-fluoro-4-methoxy-phenyl)-5H-pyrrolo[3,2-d]pyrimidine-7-carboxylic acid [(R)-1-(2-hydroxy-acetyl)-pyrrolidin-3-yl]-amide;

4-(2-Cyclopropylmethoxy-5-fluoro-4-methoxy-phenyl)-5H-pyrrolo[3,2-d]pyrimidine-7-carboxylic acid [(R)-1-((S)-2-hydroxy-propionyl)-pyrrolidin-3-yl]-amide;

trans-4-(2-Cyclopropylmethoxy-5-methyl-phenyl)-5H-pyrrolo[3,2-d]pyrimidine-7-carboxylic acid [4-(2-hydroxy-acetylamino)-cyclohexyl]-amide;

trans-4-(2-Cyclopropylmethoxy-5-methyl-phenyl)-5H-pyrrolo[3,2-d]pyrimidine-7-carboxylic acid [4-((S)-2-hydroxy-propionylamino)-cyclohexyl]-amide;

trans-4-(2-Cyclopropylmethoxy-5-methyl-phenyl)-5H-pyrrolo[3,2-d]pyrimidine-7-carboxylic acid {4-[(1-hydroxy-cyclopropanecarbonyl)-amino]-cyclohexyl}-amide;

4-(2-Cyclopropylmethoxy-5-methyl-phenyl)-5H-pyrrolo[3,2-d]pyrimidine-7-carboxylic acid [1-(2-hydroxy-acetyl)piperidin-4-yl]-amide;

4-(2-Cyclopropylmethoxy-5-methyl-phenyl)-5H-pyrrolo[3,2-d]pyrimidine-7-carboxylic acid [1-((S)-2-hydroxy-propionyl)piperidin-4-yl]-amide;

4-(2-Cyclopropylmethoxy-5-methyl-phenyl)-5H-pyrrolo[3,2-d]pyrimidine-7-carboxylic acid [1-(1-hydroxy-cyclopropanecarbonyl)-piperidin-4-yl]-amide;

4-(5-Ethoxy-benzo[1,3]dioxol-4-yl)-5H-pyrrolo[3,2-d]pyrimidine-7-carboxylic acid [1-((S)-2-hydroxy-propionyl)-piperidin-4-yl]-amide;

4-(5-Ethoxy-benzo[1,3]dioxol-4-yl)-5H-pyrrolo[3,2-d]pyrimidine-7-carboxylic acid [(R)-1-((S)-2-hydroxy-propionyl)-pyrrolidin-3-yl]-amide;

4-(5-Propoxy-benzo[1,3]dioxol-4-yl)-5H-pyrrolo[3,2-d]pyrimidine-7-carboxylic acid [1-((S)-2-hydroxy-propionyl)-piperidin-4-yl]-amide;

4-(5-Propoxy-benzo[1,3]dioxol-4-yl)-5H-pyrrolo[3,2-d]pyrimidine-7-carboxylic acid [(R)-1-((S)-2-hydroxy-propionyl)pyrrolidin-3-yl]-amide;

4-(5-Butoxy-benzo[1,3]dioxol-4-yl)-5H-pyrrolo[3,2-d]pyrimidine-7-carboxylic acid [1-((S)-2-hydroxy-propionyl)-piperidin-4-yl]-amide;

4-(5-Butoxy-benzo[1,3]dioxol-4-yl)-5H-pyrrolo[3,2-d]pyrimidine-7-carboxylic acid [(R)-1-((S)-2-hydroxy-propionyl)-pyrrolidin-3-yl]-amide;

trans-4-[4-Methoxy-2-(2-methoxy-ethoxy)-phenyl]-5H-pyrrolo[3,2-d]pyrimidine-7-carboxylic acid [4-(2-hydroxy-acetylamino)-cyclohexyl]-amide;

trans-4-[4-Methoxy-2-(2-methoxy-ethoxy)-phenyl]-5H-pyrrolo[3,2-d]pyrimidine-7-carboxylic acid [4-((S)-2-hydroxy-propionylamino)-cyclohexyl]-amide;

trans-4-[4-Methoxy-2-(2-methoxy-ethoxy)-phenyl]-5H-pyrrolo[3,2-d]pyrimidine-7-carboxylic acid {4-[(1-hydroxy-cyclopropanecarbonyl)-amino]-cyclohexyl}-amide;

cis-4-[4-Methoxy-2-(2-methoxy-ethoxy)-phenyl]-5H-pyrrolo[3,2-d]pyrimidine-7-carboxylic acid {4-[(1-hydroxy-cyclopropanecarbonyl)-amino]-cyclohexyl}-amide;

4-[4-Methoxy-2-(2-methoxy-ethoxy)-phenyl]-5H-pyrrolo[3,2-d]pyrimidine-7-carboxylic acid [1-(1-hydroxy-cyclopropanecarbonyl)-piperidin-4-yl]-amide;

trans-4-[5-(2-Methoxy-ethoxy)-benzo[1,3]dioxol-4-yl]-5H-pyrrolo[3,2-d]pyrimidine-7-carboxylic acid [4-(2-hydroxy-acetylamino)-cyclohexyl]-amide;

cis-4-[5-(2-Methoxy-ethoxy)-benzo[1,3]dioxol-4-yl]-5H-pyrrolo[3,2-d]pyrimidine-7-carboxylic acid [4-(2-hydroxy-acetylamino)-cyclohexyl]-amide;

cis-4-[5-(2-Methoxy-ethoxy)-benzo[1,3]dioxol-4-yl]-5H-pyrrolo[3,2-d]pyrimidine-7-carboxylic acid [4-((S)-2-hydroxy-propionylamino)-cyclohexyl]-amide;

4-[5-(2-Methoxy-ethoxy)-benzo[1,3]dioxol-4-yl]-5H-pyrrolo[3,2-d]pyrimidine-7-carboxylic acid [1-((S)-2-hydroxy-propionyl)piperidin-4-yl]-amide;

4-(5-Acetyl-2-cyclopropylmethoxy-phenyl)-5H-pyrrolo[3,2-d]pyrimidine-7-carboxylic acid [1-((S)-2-hydroxy-propanoyl)-piperidin-4-yl]-amide;

4-(5-Acetyl-2-cyclopropylmethoxy-phenyl)-5H-pyrrolo[3,2-d]pyrimidine-7-carboxylic acid [1-(2-methoxy-acetyl)-piperidin-4-yl]-amide;

4-(5-Acetyl-2-cyclopropylmethoxy-phenyl)-5H-pyrrolo[3,2-d]pyrimidine-7-carboxylic acid (1-acetyl-piperidin-4-yl)-amide;

4-(5-Acetyl-2-cyclopropylmethoxy-4-methyl-phenyl)-5H-pyrrolo[3,2-d]pyrimidine-7-carboxylic acid [1-((S)-2-hydroxy-propionyl)-piperidin-4-yl]-amide;

4-(5-Acetyl-2-cyclopropylmethoxy-4-methyl-phenyl)-5H-pyrrolo[3,2-d]pyrimidine-7-carboxylic acid (1-acetyl-piperidin-4-yl)-amide;

trans-4-(5-Cyclopropylmethoxy-benzo[1,3]dioxol-4-yl)-5H-pyrrolo[3,2-d]pyrimidine-7-carboxylic acid [4-(2-methoxy-ethylcarbamoyl)-cyclohexyl]-amide;

trans-4-(5-Cyclopropylmethoxy-benzo[1,3]dioxol-4-yl)-5H-pyrrolo[3,2-d]pyrimidine-7-carboxylic acid (4-cyclopropylcarbamoyl-cyclohexyl)-amide;

trans-4-(2-Cyclopropylmethoxy-4-methoxy-phenyl)-5H-pyrrolo[3,2-d]pyrimidine-7-carboxylic acid (4-cyclopropylcarbamoyl-cyclohexyl)-amide;

trans-4-(2-Cyclopropylmethoxy-4-methoxy-phenyl)-5H-pyrrolo[3,2-d]pyrimidine-7-carboxylic acid [4-(2-methoxy-ethylcarbamoyl)-cyclohexyl]-amide;

trans-4-(2-Cyclopropylmethoxy-5-fluoro-phenyl)-5H-pyrrolo[3,2-d]pyrimidine-7-carboxylic acid (4-cyclopropylcarbamoyl-cyclohexyl)-amide;

trans-4-(2-Cyclopropylmethoxy-5-fluoro-phenyl)-5H-pyrrolo[3,2-d]pyrimidine-7-carboxylic acid [4-(2-methoxy-ethylcarbamoyl)-cyclohexyl]-amide;

trans-4-(5-Cyclobutylmethoxy-benzo[1,3]dioxol-4-yl)-5H-pyrrolo[3,2-d]pyrimidine-7-carboxylic acid [4-(2-methoxy-ethylcarbamoyl)-cyclohexyl]-amide;

trans-4-(5-Cyclobutylmethoxy-benzo[1,3]dioxol-4-yl)-5H-pyrrolo[3,2-d]pyrimidine-7-carboxylic acid (4-cyclopropylcarbamoyl-cyclohexyl)-amide;

4-(2-Cyclopropylmethoxy-5-fluoro-4-hydroxy-phenyl)-5H-pyrrolo[3,2-d]pyrimidine-7-carboxylic acid (1-acetyl-piperidin-4-yl)-amide;

4-(2-Cyclopropylmethoxy-5-fluoro-4-hydroxy-phenyl)-5H-pyrrolo[3,2-d]pyrimidine-7-carboxylic acid (1-propionyl-piperidin-4-yl)-amide;

4-[2-Cyclopropylmethoxy-4-(1,1-difluoro-methoxy)-5-fluoro-phenyl]-5H-pyrrolo[3,2-d]pyrimidine-7-carboxylic acid (1-acetyl-piperidin-4-yl)-amide;

4-[2-Cyclopropylmethoxy-4-(1,1-difluoro-methoxy)-5-fluoro-phenyl]-5H-pyrrolo[3,2-d]pyrimidine-7-carboxylic acid [1-(2-methoxy-ethanoyl)-piperidin-4-yl]-amide;

4-(2-Cyclopropylmethoxy-5-fluoro-4-hydroxy-phenyl)-5H-pyrrolo[3,2-d]pyrimidine-7-carboxylic acid [1-(2-hydroxy-acetyl)piperidin-4-yl]-amide;

4-(2-Cyclopropylmethoxy-5-fluoro-4-hydroxy-phenyl)-5H-pyrrolo[3,2-d]pyrimidine-7-carboxylic acid [1-((S)-2-hydroxy-propionyl)-piperidin-4-yl]-amide;

4-[2-Cyclopropylmethoxy-4-(1,1-difluoro-methoxy)-5-fluoro-phenyl]-5H-pyrrolo[3,2-d]pyrimidine-7-carboxylic acid [1-(2-hydroxy-acetyl)piperidin-4-yl]-amide;

4-[2-Cyclopropylmethoxy-4-(1,1-difluoro-methoxy)-5-fluoro-phenyl]-5H-pyrrolo[3,2-d]pyrimidine-7-carboxylic acid [1-((S)-2-hydroxy-propionyl)piperidin-4-yl]-amide;

and salts thereof, stereoisomers thereof and salts of the stereoisomers thereof.

6. A pharmaceutical composition comprising at least one of the compounds, or pharmaceutically acceptable salts, stereoisomers or salts of the stereoisomers thereof according to claim 1, together with at least one pharmaceutically acceptable auxiliary.

7. The pharmaceutical composition according to claim 6 further comprising at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, antidepressants and antibiotics.

8. A method for treating portal hypertension, pulmonary hypertension, chronic obstructive pulmonary disease or lung fibrosis in a patient comprising administering to a patient in need thereof a therapeutically effective amount of a compound, or a pharmaceutically acceptable salt, stereoisomer or salt of a stereoisomer thereof according to claim 1.

9. A compound according to claim 1 selected from the group consisting of trans-4-(5-Cyclopropylmethoxy-benzo[1,3]dioxol-4-yl)-5H-pyrrolo[3,2-d]pyrimidine-7-carboxylic acid (4-acetylamino-cyclohexyl)-amide, a salt thereof, a stereoisomer of the compound and a salt of the stereoisomer thereof.

10. A compound according to claim 1 selected from the group consisting of 4-(5-Cyclopropyl methoxy-benzo[1,3]dioxol-4-yl)-5H-pyrrolo[3,2-d]pyrimidine-7-carboxyl is acid [1-((S)-2-hydroxy-propanoyl)-piperidin-4-yl]-amide, a salt thereof, a stereoisomer of the compound and a salt of the stereoisomer thereof.

11. A compound according to claim 1 selected from the group consisting of 4-(2-Cyclopropyl methoxy-4-fluoro-5-methoxy-phenyl)-5H-pyrrolo[3,2-d]pyrimidine-7-carboxylic acid [1-((S)-2-hydroxy-propionyl)piperidin-4-yl]-amide, a salt thereof, a stereoisomer of the compound and a salt of the stereoisomer thereof.

12. A compound according to claim 1 selected from the group consisting of 4-(2-Cyclopropyl methoxy-5-fluoro-4-methoxy-phenyl)-5H-pyrrolo[3,2-d]pyrimidine-7-carboxylic acid [1-((S)-2-hydroxy-propanoyl-piperidin-4-yl]-amide, a salt thereof, a stereoisomer of the compound and a salt of the stereoisomer thereof.

13. A method for treating portal hypertension, pulmonary hypertension, chronic obstructive pulmonary disease or lung fibrosis in a patient comprising administering to a patient in need thereof a therapeutically effective amount of a compound, or a pharmaceutically acceptable salt, stereoisomer or salt of a stereoisomer thereof according to claim 9.

14. A method for treating portal hypertension, pulmonary hypertension, chronic obstructive pulmonary disease or lung fibrosis in a patient comprising administering to a patient in need thereof a therapeutically effective amount of a compound, or a pharmaceutically acceptable salt, stereoisomer or salt of a stereoisomer thereof according to claim 10.

15. A method for treating portal hypertension, pulmonary hypertension, chronic obstructive pulmonary disease or lung fibrosis in a patient comprising administering to a patient in need thereof a therapeutically effective amount of a compound, or a pharmaceutically acceptable salt, stereoisomer or salt of a stereoisomer thereof according to claim 11.

16. A method for treating portal hypertension, pulmonary hypertension, chronic obstructive pulmonary disease or lung fibrosis in a patient comprising administering to a patient in need thereof a therapeutically effective amount of a compound, or a pharmaceutically acceptable salt, stereoisomer or salt of a stereoisomer thereof according to claim 12.

* * * * *

UNITED STATES PATENT AND TRADEMARK OFFICE
CERTIFICATE OF CORRECTION

PATENT NO.        : 8,445,501 B2
APPLICATION NO.   : 12/918740
DATED             : May 21, 2013
INVENTOR(S)       : Stadlwieser et al.

It is certified that error appears in the above-identified patent and that said Letters Patent is hereby corrected as shown below:

In the Claims:

Claim 5, Col. 301, lines 62-64 should read as follows:

-- 4-(5-Cyclopropylmethoxy-benzo[1,3]dioxol-4-yl)-5H-pyrrolo[3,2-d]pyrimidine-7-carboxylic acid [1-(2-methoxy-acetyl)-piperidin-3-ylmethyl]-amide; --

Claim 10, Col. 314, lines 21-26 should read as follows:

-- A compound according to claim 1 selected from the group consisting of 4-(5-Cyclopropylmethoxy-benzo[1,3]dioxol-4-yl)-5H-pyrrolo[3,2-d]pyrimidine-7-carboxylic acid [1-((S)-2-hydroxy-propanoyl)-piperidin-4-yl]-amide, a salt thereof, a stereoisomer of the compound and a salt of the stereoisomer thereof. --

Signed and Sealed this
Twenty-third Day of July, 2013

Teresa Stanek Rea
*Acting Director of the United States Patent and Trademark Office*